US008846369B2

(12) United States Patent
Piven et al.

(10) Patent No.: US 8,846,369 B2
(45) Date of Patent: Sep. 30, 2014

(54) ***CYANOBACTERIUM* SP. HOST CELL AND VECTOR FOR PRODUCTION OF CHEMICAL COMPOUNDS IN CYANOBACTERIAL CULTURES**

(71) Applicant: Algenol Biofuels Inc., Fort Myers, FL (US)

(72) Inventors: Irina Piven, Berlin (DE); Alexandra Friedrich, Berlin (DE); Ulf Dühring, Berlin (DE); Frank Uliczka, Berlin (DE); Kerstin Baier, Kleinmachnow (DE); Masami Inaba, Berlin (DE); Tuo Shi, San Diego, CA (US); Kui Wang, Fort Meyers, FL (US); Heike Enke, Berlin (DE); Dan Kramer, Berlin (DE)

(73) Assignee: Algenol Biofuels Inc., Ft. Myers, FL (US)

( * ) Notice: Subject to any disclaimer, the term of this patent is extended or adjusted under 35 U.S.C. 154(b) by 0 days.

(21) Appl. No.: 14/041,122

(22) Filed: Sep. 30, 2013

(65) Prior Publication Data

US 2014/0178973 A1 Jun. 26, 2014

Related U.S. Application Data

(60) Provisional application No. 61/741,000, filed on Dec. 21, 2012.

(51) Int. Cl.

| | |
|---|---|
| ***C12N 1/00*** | (2006.01) |
| ***C12N 1/20*** | (2006.01) |
| ***C12N 15/00*** | (2006.01) |
| ***C12P 21/06*** | (2006.01) |
| ***C12P 19/34*** | (2006.01) |
| ***C12P 7/06*** | (2006.01) |
| ***C07H 21/04*** | (2006.01) |

(52) U.S. Cl.
USPC ..................... 435/243; 435/252.3; 435/320.1; 435/69.1; 435/91.1; 435/161; 536/23.1; 536/23.2; 536/24.1

(58) Field of Classification Search
USPC ......... 435/243, 252.3, 320.1, 69.1, 91.1, 161; 536/23.1, 23.2, 24.1
See application file for complete search history.

(56) References Cited

U.S. PATENT DOCUMENTS

| | | | |
|---|---|---|---|
| 6,306,639 | B1 | 10/2001 | Woods et al. |
| 6,699,696 | B2 | 3/2004 | Woods et al. |
| 7,794,969 | B1 | 9/2010 | Reppas et al. |
| 8,183,027 | B2 | 5/2012 | Reppas et al. |
| 2010/0304456 | A1 | 12/2010 | Huntley et al. |
| 2011/0217692 | A1 | 9/2011 | Morgan et al. |
| 2011/0287541 | A1 | 11/2011 | Cuello et al. |

FOREIGN PATENT DOCUMENTS

| | | |
|---|---|---|
| WO | WO/2011/094457 | 8/2011 |
| WO | WO/2012/000057 | 1/2012 |
| WO | WO/2012/101459 | 8/2012 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Deng, M.D. et al., (1999), "Ethanol Synthesis by Genetic Engineering in Cyanobacteria," Applied and Environmental Microbiology, 65:523-528.
Blanch, H.W., (2012), "Bioprocessing for Biofuels," Current Opinion in Biotechnology, 23:390-395.
Wang, B. "Application of synthetic biology in cyanobacteria and algae", Frontiers in Microbiology, 2012, vol. 3, article 344, pp. 1-15.
Shih, PM. "Improving the coverage of the cyanobacterial phylum using diversity-driven genome sequencing", PNAS, 2013, vol. 110, pp. 1053-1058.
Rippka, R. "Generic assignments, strain histories and properties of pure cultures of cyanobacteria", Journal of General Microbiology, 1979, vol. 111, pp. 1-61.

* cited by examiner

*Primary Examiner* — Ganapathirama Raghu
(74) *Attorney, Agent, or Firm* — Sam J. Barkley; Lawrence B. Ebert; David J. Lorenz

(57) ABSTRACT

A cyanobacterial host cell, *Cyanobacterium* sp., that harbors at least one recombinant gene for the production of a chemical compounds is provided, as well as vectors derived from an endogenous plasmid isolated from the cell.

10 Claims, 177 Drawing Sheets

A. B.

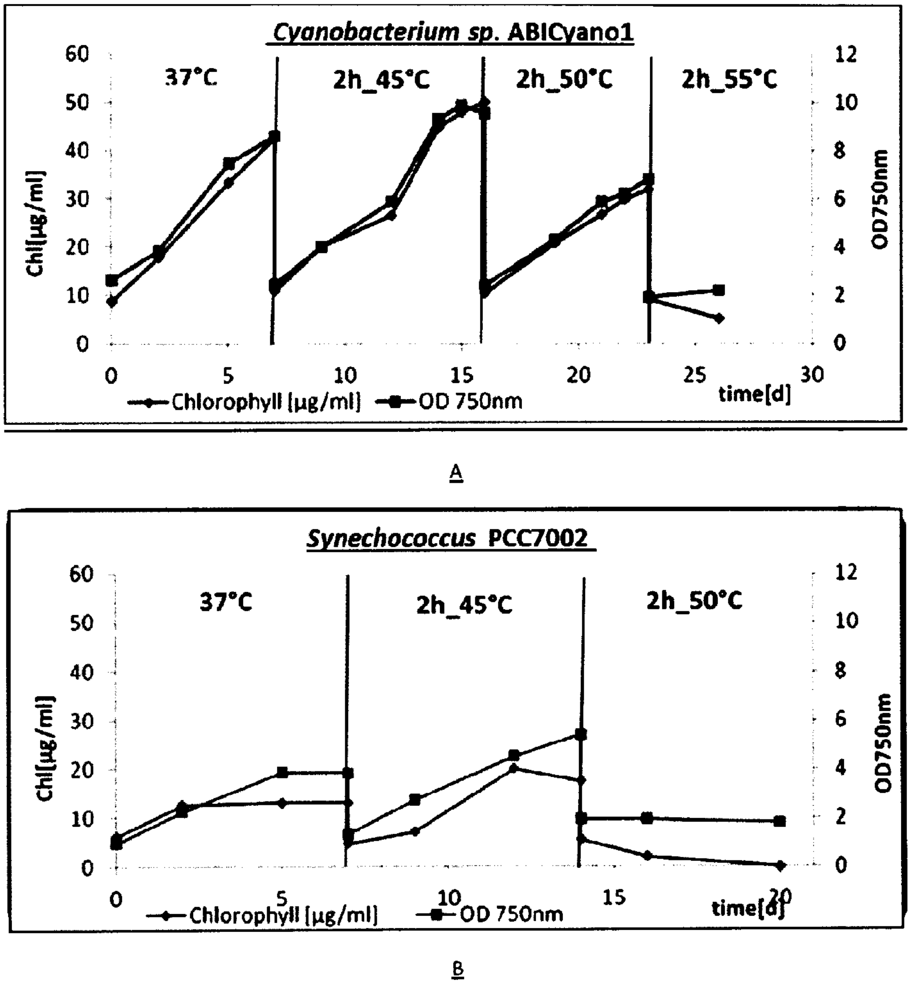
FIG. 2 A and 2 B

```
ID   pABICyanol-6.8  standard; circular DNA;    ; 6828 BP.
DE   Complementary copy of pABICyanol-6.8 ano rc
CC   This file is created by Vector NTI
CC   http://www.invitrogen.com/
CC   ORIGDB|GenBank
CC   VNTDATE|640865706|
CC   VNTDBDATE|640865706|
CC   LSOWNER|
CC   VNTAUTHORNAME|Irina Piven|
FH   Key             Location/Qualifiers
FH
FT   primer          complement(1859..1883)
FT                   /vntifkey="27"
FT                   /label=FB3
FT   CDS             594..3779
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   CDS             5350..6036
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             3815..4000
FT                   /vntifkey="4"
FT                   /label=ORF\2
FT                   /note="orf2"
FT   CDS             complement(4260..5024)
FT                   /vntifkey="4"
FT                   /label=ORF\3
FT                   /note="orf3"
FT   CDS             6078..6341
FT                   /vntifkey="4"
FT                   /label=ORF\5
FT                   /note="orf5"
FT   CDS             6338..6586
FT                   /vntifkey="4"
FT                   /label=ORF\6
FT                   /note="orf6"
FT   rep_origin      3375..3408
FT                   /vntifkey="33"
FT                   /label=Rep_Origin_1
FT                   /note="active site motif of Rep protein"
SQ   Sequence 6828 BP; 2360 A; 1153 C; 1212 G; 2103 t;
     aatatttttc gtcagatacg caaaccttac aaacataatt aacaactgaa actattgata        60
     tgtctaggtt ttagctctat cacaggttgt tagacaccct gtcatgtatt ttatattatt       120
     tatttcacca tacggattaa gtgaaaccta atgaaaatag tactttcgga gctttaactt       180
     taatgaaggt atgttttttt atagacatcg atgtctggtt taacaatagg aaaaagtagc       240
     taaaactccc atgaattaaa gaaataacaa ggtgtctaac aacctgttat taagaatgtt       300
     agaaaagact taacatttgt gttgagtttt tatagacatt ggtgtctaga catacggtag       360
     ataaggtttg ctcaaaaata aaataaaaaa agattggact aaaaaacatt taatttagta       420
```

FIG. 4A

```
caatttaatt agttattttt tcgtctcaaa ttttgctttg ttgagcagaa atttagataa     480
aaaaatcccc gtgatcagat tacaatgtcg ttcattgtac gatgtgtcga aaaatcttta     540
cgacactcta aactgaccac acgggggaaa aagaaaactg aactaataac atcatgatac     600
tcggaaaacc tagcaattct caacccctaa acaaaagaaa cttccaaaac cctgaccata     660
taaaggagtg gcaacaatca gcaatcagtc aagatttgat agcagaaaat cttgtatcgg     720
ttgctaatgg ttttgatgta ctatttatcg gcaataaata ccgaactaac acgggtgttc     780
tgtcacggca catattaaac tcctattctc atttagaaga tggtggttcg tatggtagaa     840
catttgaccc atttaccaat aaagaaatgc agtgggttca atttaaaccg aatagaccaa     900
gaaaaggttc tactggtaag gtaatcaaat atgaatcgcc aaaaggtgaa cctacaagag     960
ttctaatgcc gtttgtgcct atgaaaatat ggcaacggat tagcgataag ttcggagtac    1020
cgattaatcc gaaaaaagat actcactttt gggaatgggt aaagaataat ccatcgatac    1080
cgattgccat tacagaagga aataaaaaag ctaattgcct attatcctat ggctatcctg    1140
ctattgcctt tgtaggcatt tggaacggat tagagaaaat aaatgatttc tcgaaggaaa    1200
agcagttaaa agaggatttg aaatggttgt tatccaacgg caaccgaaat attaatatca    1260
tctttgacca agaccagaaa caaaaaactg taattaatgt aaacaaagct attttcgctt    1320
tatcttctct aataagtaga aatggtcata aagttaatat tgtgcaatgg ttgccgtcaa    1380
aaggtaaagg aatagatgat tatttggtag ctttaccttt tgagaaaaga gaaaatcatt    1440
tagacaactt aattaaaatt gcaccatcat ttaatttttg gtcaactaaa tacttattca    1500
agtgtcgtaa accagattta accgtaaatt gccgttattt gagcgatgca gtaaaagaat    1560
tacctcaaga ggatatagca ttaatagcac ctcacggcac gggtaaaact tcattagtag    1620
ctactcacgt taagaatcgg agttatcacg gaaggaaaac tatttcattg gtgcatcttg    1680
aaagtttagc caaagctaat ggcaacgcac ttggattata ttaccgaacc gaaaataata    1740
ttgaaaagca atatcttgga tttagcttat gtgtagatag ttgccgtgat aagattaacg    1800
gcattacaac tgatattatt tcaggtcaag attattgcct tttcattgat gaaattgacc    1860
aagtaattcc acacatcctt aacagtgaaa ctgaagtaag taagtataga tgcaccatca    1920
ttgacacttt ttctgaactg gtgagaaatg ctgaacaggt cattattgct gatgctgatt    1980
tatccgatgt gacgattgac ctaatagaaa acatcagagg taaaaaacta tatgtaatca    2040
agaatgaata tcagtatcag ggaatgactt ttaacgccgt tggttcacca ttagaaatga    2100
tggcaatgat gggaaaatcg gtgtcagaag gcaagaaatt atttattaac accacatccc    2160
aaaaggcaaa aagtaagtac ggcacaatcg ctcttgagtc ttatattttt ggtctaaata    2220
aagaagcaaa gatattaaga atagactctg aaaccactaa aaaccctgaa catccagcct    2280
ataaaatcat tgaccaagac ttaaataata tcctcaaaga ttatgattat gtcattgcct    2340
caccttgcct tcaaacaggt gtcagtatta ccttaaaagg gcattttgac cagcaattta    2400
acttttccag tggaaacatt acacctcatt gctttttaca gcaaatgtgg cggttgaggg    2460
atgcagaaat tgaaagattc tattatgtgc cgaactcatc taacctcaat ctcattggga    2520
ataagtcaag ttcaccatca gaccttctaa agagcaataa caagatggca acggcaacgg    2580
ttaacctttt gggtagaatc gactccgaat attccctaga gtatgaatcg cacggcattt    2640
ggcttgagac gtgggcaaaa ttatcagcac ggcataacag ttcaatgcgt tgttactctg    2700
aaattcttac ctatctaatt acgtctcaag ggcataaatt aaatatcaac attccctcac    2760
ctcttgcaga tattaagaag ctaaatgatg aggtaagtag taacagggaa aaggtaaaaa    2820
atgagagata ctctcagagg ttaaactcac cagatattaa cgatgcagaa gctaccatac    2880
tcgaatctaa agagcaaaaa atcggattga ctctcaatga gagatgcacc ctagaaaagc    2940
ataaagttaa gaagcggtat gggaatgtaa agatggatat tctcaccttt gatgatgatg    3000
gactataccc caaactcaga ctattttatt acctcaccat cggtaaacct catctcaagg    3060
ctaatgacag aaaagctatt gccaaaatgg gcaatgacaa taaaggcaag attctatcaa    3120
aagacttagt taataaaact tactccgctc gtgtgaaggt cttagagatt cttaaactaa    3180
ctgactttat cgacaatctt agagatgaac tcttaataac tcccaataat ccagctatca    3240
ccgattttaa taatcttctg ctaagagcta agaaggattt aagagtatta ggagtcaaca    3300
tcggaaaata tccaatggcc aacattaatg ccgtacttac tctcattggt cacaaacttt    3360
ctgtaatgag agatgagttc ggaaaagaga aaaggataaa agtagatggt aaatcatacc    3420
gatgttatca acttgaaaca ttaccagatt ttaccaatga tactcttgac tactggttag    3480
```

FIG. 4A (continued)

```
aaaatgatag ccaaaaagaa gtaacagcaa cagaaaatta ctccgaaaat tttaaccctt 3540
caaatagcta caatccagac agtaagacac tttcagaggg tgcaaatttc ctatatataa 3600
ataaagaaga attgcatcca aataaattgc acctagaaat aaaagaaggt gctgaacttt 3660
ttttattcgg ggtaaaggtg attgtgaaag gaatcttgga cggggcagta actatattct 3720
ctatgggtca agaatacgat ttatccctca atgaactaga ggggatgtta acatcatgaa 3780
ctttacaaga atctttttaa agggcgatcg caccatgtta aatgatggta catttgttca 3840
gatatttgat atttaccatg accacgcatt gggagtgacc cttgacctta agacagaaaa 3900
aattatttcc gatgatgtta gggtaattac tgtcaaagac ttattgttcg atggcactta 3960
taaaggggta aaatctttta tgcccgataa tgcccgataa tgcccgattg atgctacaaa 4020
atcccataat cataagcgat aatcccctaa tagcttgtaa ttcttgaacc gtagcgattt 4080
tagagtattc caaaaagaag aaataaacac cgcaaaatgt cgtatttcac atatataaac 4140
caaggttttt tgccctaaaa tctttatgtt tgtagtgtga tgttgggtca aaatggtcag 4200
aaaagttgca aggtttttat ggatgcttac gcgcgcgagg ggtaagcatc cccaaatagt 4260
tactttatcc tagtccatgc ccatttattg ccgtcccgtt cggctttaaa aaagtgccaa 4320
aactcacaag gtgcaataaa aagttctgta cctttcgcaa ccctagataa tctttcaaca 4380
gttacttttt ttcctattat ctcggtacaa agtttggcta gtttctcttt tccctctttt 4440
tcaatcaagc cttcttgtat gcccaactca ttgattaatc tctctatttt taccattatt 4500
tcccgttcag gtagtttatc ccctaaatct tcatcggggg gcaatgtagg gcattctgaa 4560
ggggcttttt cttctgtctg gacattatct aatattgaag taaccaaact atcttcagtt 4620
ttttctattc ctattaattc atattcggtt actgtatccg tatcaatatc cgaataacta 4680
tctttatccg tattagctat tcggttaagt ttatccgtta actcagaaac aagactatat 4740
agcggtttta gcttttcttc tatcctgtta tctaatacgg ataagtttat acggttatca 4800
ttatccgtat tagtatcatt gggctttttt ggtagttcta ccccctcata aaccgctttt 4860
attcccaatt ccaacagact gataacagta tcctttataa tgggtttttt gctgatatgg 4920
tgaacttttg ccccttccat cattgcgata ctttctatct cactcatcaa cttatcgctt 4980
aagtgaatct cgtatctgtt taatccctta ctggttttat tcatatccgt ttactttatt 5040
cggttaacaa ttctatttta tacgaataaa atattatacg gttaacttta tacgtttaac 5100
tattttatct atacggataa cagtaataag ttattcgtat tagttatacg tttactttta 5160
tccaaataaa attagtgcat ttaaactaaa agaatgattt tatcggagtt gatagcattg 5220
gattaaccta aagatgttta taagctatat ctgataagta tttaaggtta ttttgttatt 5280
ctgtttattg acattatcag aataaaagaa tagaatataa ttgttgagag ataagaggtt 5340
taagtgatta tggttaagaa gttagttggt tatgtcaggg tcagtagtga atcgcaagag 5400
gataacacta gcttacagaa tcagatagag agaattgaag catattgtat ggcttttggt 5460
tatgagttgg taaaaatatt caaagaggtt gccactggta caaaagcaga tattgaaacc 5520
cgtcctattt ttaatgaagc tatagaatac ttgaaacagg ataatgctaa tggaattatt 5580
gccttgaagc tagaccgaat cgcacggaat gctttagatg tattgcgttt ggttcgtgaa 5640
accttagaac cacaaaataa aatgttagtg ttactagata ttcaggtaga tacttcgaca 5700
ccttcaggaa aaatgatttt aactgtaatg agtgccgttg ctgaactcga aagagacatg 5760
atctatgatc gcactcaggg gggtagaaag actaaagccc aaaagggcgg gtatgcctac 5820
gggaaaccta aatttggcta taagactgaa gaaaaggaac taaaagaaga ttcagcacaa 5880
caggaaacta ttaaactaat taagagacac cgtaggtcag ggaaaagcta ccagaaaata 5940
gctgattatc tcaatgccca aagtattccc actaaacaag gtaagaaatg gagttctagc 6000
gtcgtctatc gaatctgtca ggaaaaagct ggttaagtct gtttatagat atttagaatt 6060
tattgaataa aaatagtatg aacaataaat atttatggac taaccacgct cggaaacgtt 6120
taactgaacg atgggaaata aaagaatcat gggttattga taccatcgaa aatcctgaac 6180
gttcagaatt tattgttgat gagtcagggg aaaaatatca ttactataaa agaatagcta 6240
agtttaagaa tagagtgtta gaagtgataa cttctgccaa ctcaacaccc acaagaataa 6300
taacctttta ctttaaccgt aacatgagga aaaatttatg attgttactt acgataatga 6360
agttgacgca atttatttta agttaacgga aaataaaatt gatagcaccg aacctcaaac 6420
agacaggatt atcattgatt acgatgaaag taataatatt gttggcattg aggtattaga 6480
```

FIG. 4A (continued)

```
ttttaattat cttgtcaaga aaggtttaac cgttgctgat ttaccttttt ctgaagatga      6540
aagattaaca gcttctcaat attttaattt tcctgttgct atctaatcca gaaggggcaa      6600
taatcccctt ctttcatcga gttagactta atatcacaaa agtcattttc attttaccgt      6660
ttcttttcca cagcgtccgt acgcccctcg ttaaatctca aaaccgacaa tttatgatgt      6720
ttataaaaag ttactcactt taataagtat ttatactcat taaagggtta ttcttttttt      6780
gtagcctgat aggttgggaa ggaatatttc agattatcag atttgttg
```

FIG. 4A (continued)

orf1 rep ori binding protein

MILGKPSNSQPLNKRNFQNPDHIKEWQQSAISQDLIAENLVSVANGFDVLFIGNKYRTNTGVLSRHILNS
YSHLEDGGSYGRTFDPFTNKEMQWVQFKPNRPRKGSTGKVIKYESPKGEPTRVLMPFVPMKIWQRISDKF
GVPINPKKDTHFWEWVKNNPSIPIAITEGNKKANCLLSYGYPAIAFVGIWNGLEKINDFSKEKQLKEDLK
WLLSNGNRNINIIFDQDQKQKTVINVNKAIFALSSLISRNGHKVNIVQWLPSKGKGIDDYLVALPFEKRE
NHLDNLIKIAPSFNFWSTKYLFKCRKPDLTVNCRYLSDAVKELPQEDIALIAPHGTGKTSLVATHVKNRS
YHGRKTISLVHLESLAKANGNALGLYYRTENNIEKQYLGFSLCVDSCRDKINGITTDIISGQDYCLFIDE
IDQVIPHILNSETEVSKYRCTIIDTFSELVRNAEQVIIADADLSDVTIDLIENIRGKKLYVIKNEYQYQG
MTFNAVGSPLEMMAMMGKSVSEGKKLFINTTSQKAKSKYGTIALESYIFGLNKEAKILRIDSETTKNPEH
PAYKIIDQDLNNILKDYDYVIASPCLQTGVSITLKGHFDQQFNFSSGNITPHCFLQQMWRLRDAEIERFY
YVPNSSNLNLIGNKSSSPSDLLKSNNKMATATVNLLGRIDSEYSLEYESHGIWLETWAKLSARHNSSMRC
YSEILTYLITSQGHKLNINIPSPLADIKKLNDEVSSNREKVKNERYSQRLNSPDINDAEATILESKEQKI
GLTLNERCTLEKHKVKKRYGNVKMDILTFDDDGLYPKLRLFYYLTIGKPHLKANDRKAIAKMGNDNKGKI
LSKDLVNKTYSARVKVLEILKLTDFIDNLRDELLITPNNPAITDFNNLLLRAKKDLRVLGVNIGKYPMAN
INAVLTLIGHKLSVMRDEFGKEKRIKVDGKSYRCYQLETLPDFTNDTLDYWLENDSQKEVTATENYSENF
NPSNSYNPDSKTLSEGANFLYINKEELHPNKLHLEIKEGAELFLFGVKVIVKGILDGAVTIFSMGQEYDL
SLNELEGMLTS*

Fig. 4B orf2

MLNDGTFVQIFDIYHDHALGVTLDLKTEKIISDDVRVITVKDLLFDGTYKGVKSFMPDNAR

Fig. 4C orf3

MNKTSKGLNRYEIHLSDKLMSEIESIAMMEGAKVHHISKKPIIKDTVISLLELGIKAVYEGVELPKKPNDTNTDNDNRINLS
VLDNRIEEKLKPLYSLVSELTDKLNRIANTDKDSYSDIDTDTVTEYELIGIEKTEDSLVTSILDNVQTEEKAPSECPTLPPDEDL
GDKLPEREIMVKIERLINELGIQEGLIEKEGKEKLAKLCTEIIGKKVTVERLSRVAKGTELFIAPCEFWHFFKAERDGNKWA
WTRIK

Fig. 4D orf4

MVKKLVGYVRVSSESQEDNTSLQNQIERIEAYCMAFGYELVKIFKEVATGTKADIETRPIFNEAIEYLKQDNANGIIALKLD
RIARNALDVLRLVRETLEPQNKMLVLLDIQVDTSTPSGKMILTVMSAVAELERDMIYDRTQGGRKTKAQKGGYAYGKP
KFGYKTEEKELKEDSAQQETIKLIKRHRRSGKSYQKIADYLNAQSIPTKQGKKWSSSVVYRICQEKAG

Fig. 4E orf5

MNNKYLWTNHARKRLTERWEIKESWVIDTIENPERSEFIVDESGEKYHYYKRIAKFKNRVLEVITSANSTPTRIITFYFNRN
MRKNL

Fig. 4F orf6

MIVTYDNEVDAIYFKLTENKIDSTEPQTDRIIIDYDESNNIVGIEVLDFNYLVKKGLTVADLPFSEDERLTASQYFNFPV
AI

Fig. 4G

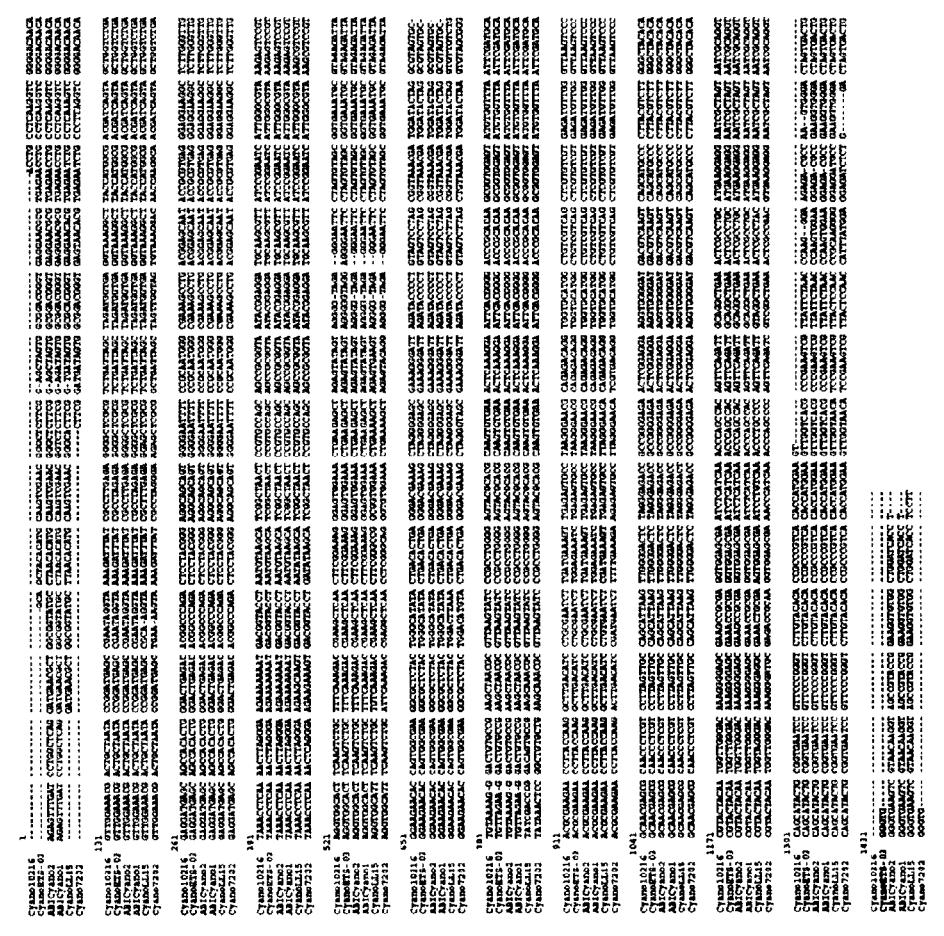

```
            1
Cyano10216  ---------- ---------- ---------- ---------- ---------- ---------- ---------- ---------- ---------- ---------- -----ACCTG CCTCAAGGTC GGGGACAACA
CyanoETS-03 ---------- ---------- ---------- -------GCA GCTACACATG CAAGTCGAAC GGGCTCTTCG G-AGCTAGTG GCGGACGGGT GAGGAACGCG TGAGAACCTG CCTCAAGGTC GGGGACAACA
ABICyano2   AGAGTTTGAT CCTGGCTCAG GATGAACGCT GGCGGTATGC CTAACACATG CAAGTCGAAC GGGCTCTTCG G-AGCTAGTG GCGGACGGGT GAGGAACGCG TGAGAACCTG CCTCAAGGTC GGGGACAACA
ABICyano1   AGAGTTTGAT CCTGGCTCAG GATGAACGCT GGCGGTATGC CTAACACATG CAAGTCGAAC GGTCTCTTCG G-AGATAGTG GCGGACGGGT GAGGAACGCG TGAGAACCTG CCTCAAGGTC GGGGACAACA
CyanoLL15   ---------- ---------- GATGAACGCT GGCGGTATGC TTAACACATG CAAGTCGAAC GGGCACTTCG G-TGATAGTG GCGGACGGGT GAGGAACACG TGAGAATCTG CCTCAAGGTC GGGGACAACA
Cyano7202   ---------- ---------- ---------- ---------- ---------- ---------- -----CTTCG GATGATAGTG GCGGACGGGT GAGTAACACG TGAGAATCTG CCCTTAGGTC GGGGACAACA

            131
Cyano10216  GTTGGAAACG ACTGCTAATA CCGGATGAGC CGAATAGGTA AAAGATTTAT CGCCTTGAGA GGGGCTCGCG TCTGATTAGC TAGATGGTGA GGTAAAGGCT TACCATGGCG ACGATCAGTA GCTGGTCTGA
CyanoETS-03 GTTGGAAACG ACTGCTAATA CCGGATGAGC CGAATAGGTA AAAGATTTAT CGCCTAGAGA GGGGCTCGCG TCTGATTAGC TAGATGGTGA GGTAAAGGCT TACCATGGCG ACGATCAGTA GCTGGTCTGA
ABICyano2   GTTGGAAACG ACTGCTAATA CCGGATGAGC CGAATAGGTA AAAGATTTAT CGCCTTGAGA GGGGCTCGCG TCTGATTAGC TAGATGGTGA GGTAAAGGCT TACCATGGCG ACGATCAGTA GCTGGTCTGA
ABICyano1   GTTGGAAACG ACTGCTAATA CCGGATGAGC CGAATAGGTA AAAGATTTAT CGCCTAGAGA GGGGCTCGCG TCTGATTAGC TAGATGGTGA GGTAAAGGCT TACCATGGCG ACGATCAGTA GCTGGTCTGA
CyanoLL15   GTTGGAAACG ACTGCTAATA CCGGATGAGC CGCA-AGGTA AAAGATTTAT CGCTTTGAGA GGAGCTCGCG TCTGATTAGC TAGATGGTGA GGTAAAGGCT TACCATGGCG ACGATCAGTA GCTGGTCTGA
Cyano7202   GTTGGAAACG ACTGCTAATA CCGGATGAGC TGAA-AAGTA AAAGATTTAT CGCCTAGGGA AGAGCTCGCG GCTGATTAGC TAGTTGGTAG TGTAAAGGAC AACCAAGGCA ACGATCAGTA GCTGGTCTGA

            261
Cyano10216  GAGGATGAGC AGCCACACTG GGACTGAGAC ACGGCCCAGA CTCCTACGGG AGGCAGCAGT GGGGAATTTT CCGCAATGGG CGAAAGCCTG ACGGAGCAAT ACCGCGTGAG GGAGGAAGGC TCTTGGGTTG
CyanoETS-03 GAGGATGAGC AGCCACACTG GGACTGAGAC ACGGCCCAGA CTCCTACGGG AGGCAGCAGT GGGGAATTTT CCGCAATGGG CGAAAGCCTG ACGGAGCAAT ACCGCGTGAG GGAGGAAGGC TCTTGGGTTG
ABICyano2   GAGGATGAGC AGCCACACTG GGACTGAGAC ACGGCCCAGA CTCCTACGGG AGGCAGCAGT GGGGAATTTT CCGCAATGGG CGAAAGCCTG ACGGAGCAAT ACCGCGTGAG GGAGGAAGGC TCTTGGGTTG
ABICyano1   GAGGATGAGC AGCCACACTG GGACTGAGAC ACGGCCCAGA CTCCTACGGG AGGCAGCAGT GGGGAATTTT CCGCAATGGG CGAAAGCCTG ACGGAGCAAT ACCGCGTGAG GGAGGAAGGC TCTTGGGTTG
CyanoLL15   GAGGATGAGC AGCCACACTG GGACTGAGAC ACGGCCCAGA CTCCTACGGG AGGCAGCAGT GGGGAATTTT CCGCAATGGG CGAAAGCCTG ACGGAGCAAT ACCGCGTGAG GGAGGAAGGC TCTTGGGTTG
Cyano7202   GAGGATGAGC AGCCACACTG GGACTGAGAC ACGGCCCAGA CTCCTACGGG AGGCAGCAGT GGGGAATTTT CCGCAATGGG CGAAAGCCTG ACGGAGCAAT ACCGCGTGAG GGAGGAAGGC TCTTGGGTTG

            391
Cyano10216  TAAACCTCAA AACTTAGGGA AGAAAAAAAT GACGGTACCT AATGTAAGCA TCGGCTAACT CCGTGCCAGC AGCCGCGGTA ATACGGAGGA TGCAAGCGTT ATCCGGAATC ATTGGGCGTA AAGAGTCCGT
CyanoETS-03 TAAACCTCAA AACTTAGGGA AGAAAAAAAT GACGGTACCT AATGTAAGCA TCGGCTAACT CCGTGCCAGC AGCCGCGGTA ATACGGAGGA TGCAAGCGTT ATCCGGAATC ATTGGGCGTA AAGAGTCCGT
ABICyano2   TAAACCTCAA AACTTAGGGA AGAAAAAAAT GACGGTACCT AATGTAAGCA TCGGCTAACT CCGTGCCAGC AGCCGCGGTA ATACGGAGGA TGCAAGCGTT ATCCGGAATC ATTGGGCGTA AAGAGTCCGT
ABICyano1   TAAACCTCAA AACTTAGGGA AGAAAAAAAT GACGGTACCT AATGTAAGCA TCGGCTAACT CCGTGCCAGC AGCCGCGGTA ATACGGAGGA TGCAAGCGTT ATCCGGAATC ATTGGGCGTA AAGAGTCCGT
CyanoLL15   TAAACCTCAA AACTTAGGGA AGAAGCAAGT GACGGTACCT AATATAAGCA TCGGCTAACT CCGTGCCAGC AGCCGCGGTA ATACGGAGGA TGCAAGCGTT ATCCGGAATC ATTGGGCGTA AAGCGTCCGT
Cyano7202   TAAACCTCAA AACTCAGGGA AGAAGAAAGT GACGGTACCT GATATAAGCA TCGGCTAACT CCGTGCCAGC AGCCGCGGTA ATACGGAGGA TGCAAGCGTT ATCCGGAATC ATTGGGCGTA AAGCGTCCGT

            521
Cyano10216  AGGTGGCACT TCAAGTCTGC TTTCAAAGAC CGAAGCTCAA CTTCGGAAAG GGAGTGGAAA CTGAAGAGCT AGAGTATAGT AGGGG-TAGA --GGGAATTC CTAGTGTAGC GGTGAAATGC GTAGAGATTA
CyanoETS-03 AGGTGGCACT TCAAGTCTGC TTTCAAAGAC CGAAGCTCAA CTTCGGAAAG GGAGTGGAAA CTGAAGAGCT AGAGTATAGT AGGGGGTAGG AGGGGAATTC CTAGTGTAGC GGTGAAATGC GTAGAGATTA
ABICyano2   AGGTGGCACT TCAAGTCTGC TTTCAAAGAC CGAAGCTCAA CTTCGGAAAG GGAGTGGAAA CTGAAGAGCT AGAGTATAGT AGGGG-TAGA --GGGAATTC CTAGTGTAGC GGTGAAATGC GTAGAGATTA
ABICyano1   AGGTGGCACT TCAAGTCTGC TTTCAAAGAC CGAAGCTCAA CTTCGGAAAG GGAGTGGAAA CTGAAGAGCT AGAGTATAGT AGGGG-TAGA --GGGAATTC CTAGTGTAGC GGTGAAATGC GTAGAGATTA
CyanoLL15   AGGTGGCATT TCAAGTCTGC TGTCAAAGAC CGAAGCTCAA CTTCGGCCCG GCGGTGGAAA CTGAAAAGCT AGAGTGAAGT AGGGG-TAGA --GGGAATTC CTAGTGTAGC GGTGAAATGC GTAGAGATTA
Cyano7202   AGGTGGCATT TCAAGTCTGC ATTCAAAGAC CGAGGCTCAA CCTCGGGCAG GGTGTGGAAA CTGAAAAGCT AGAGTACAGG AGGGG-TAGA --GGGAATTC CTAGTGTAGC GGTGAAATGC GTAGAGATTA

            651
Cyano10216  GGAAGAACAC CAGTGGCGAA GGCGCTCTAC TGGGCATATA CTGACACTGA GGGACGAAAG CTAGGGGAGC GAAAGGGATT AGATACCCCT GTAGTCCTAG CGGTAAACGA TGGATACTAG GCGTAGTGC-
CyanoETS-03 GGAAGAACAC CAGTGGCGAA GGCGCTCTAC TGGGCATATA CTGACACTGA GGGACGAAAG CTAGGGGAGC GAAAGGGATT AGATACCCCT GTAGTCCTAG CGGTAAACGA TGGATACTAG GCGTAGTGC-
ABICyano2   GGAAGAACAC CAGTGGCGAA GGCGCTCTAC TGGGCATATA CTGACACTGA GGGACGAAAG CTAGGGGAGC GAAAGGGATT AGATACCCCT GTAGTCCTAG CGGTAAACGA TGGATACTAG GCGTAGTGC-
ABICyano1   GGAAGAACAC CAGTGGCGAA GGCGCTCTAC TGGGCATATA CTGACACTGA GGGACGAAAG CTAGGGGAGC GAAAGGGATT AGATACCCCT GTAGTCCTAG CGGTAAACGA TGGATACTAG GCGTAGTGC-
CyanoLL15   GGAAGAACAC CAGTGGCGAA GGCGCTCTAC TGGACTTAAA CTGACACTGA GGGACGAAAG CTAGGGGAGC GAAAGGGATT AGATACCCCT GTAGTCTTAG CGGTAAACGA TGGATACTAG GTGTTGTCTG
Cyano7202   GGAAGAACAC CAGTGGCGAA GGCGCTCTAC TGGACATGTA CTGACACTGA GGGACGAAAG CTAGGGTAGC GAAAGGGATT AGATACCCCT GTAGTCTTAG CTGTAAACGA TGGATACTAA GTGTAGCGGG

            781
Cyano10216  TGTAAAAG-G GACTGTGCCG AAGCTAACGC GTTAAGTATC CCGCCTGGGG AGTACGCACG CAAGTGTGAA ACTCAAAGGA ATTGACGGGG ACCCGCACAA GCGGTGGAGT ATGTGGTTTA ATTCGATGCA
CyanoETS-03 TGTTAGAA-G GACTGTGCCG AAGCTAACGC GTTAAGTATC CCGCCTGGGG AGTACGCACG CAAGTGTGAA ACTCAAAGGA ATTGACGGGG ACCCGCACAA GCGGTGGAGT ATGTGGTTTA ATTCGATGCA
ABICyano2   TGTAAAAG-G GACTGTGCCG AAGCTAACGC GTTAAGTATC CCGCCTGGGG AGTACGCACG CAAGTGTGAA ACTCAAAGGA ATTGACGGGG ACCCGCACAA GCGGTGGAGT ATGTGGTTTA ATTCGATGCA
ABICyano1   TGTTAGAA-G GACTGTGCCG AAGCTAACGC GTTAAGTATC CCGCCTGGGG AGTACGCACG CAAGTGTGAA ACTCAAAGGA ATTGACGGGG ACCCGCACAA GCGGTGGAGT ATGTGGTTTA ATTCGATGCA
CyanoLL15   TATCGACCCG GACAGTGCCG AAGCAAACGC GTTAAGTATC CCGCCTGGGG AGTACGCACG CAAGTGTGAA ACTCAAAGGA ATTGACGGGG ACCCGCACAA GCGGTGGAGT ATGTGGTTTA ATTCGATGCA
Cyano7202   TATAAACTCC GGCTGTGCTG AAGCAAACGC GTTAAGTATC CCGCCTGGGG AGTACGCACG CAAGTGTGAA ACTCAAAGGA ATTGACGGGG ACCCGCACAA GCGGTGGAGT ATGTGGTTTA ATTCGATGCA

            911
Cyano10216  ACGCGAAGAA CCTTACCAAG GCTTGACATC CTGCGAATCT TGATGAAAGT TGAGAGTGCC TAAGGGAACG CAGAGACAGG TGGTGCATGG CTGTCGTCAG CTCGTGTCGT GAGATGTTGG GTTAAGTCCC
CyanoETS-03 ACGCGAAGAA CCTTACCAAG GCTTGACATC CTGCGAATCT TGGAGAAATC TGAGAGTGCC TAAGGGAACG CAGAGACAGG TGGTGCATGG CTGTCGTCAG CTCGTGTCGT GAGATGTTGG GTTAAGTCCC
ABICyano2   ACGCGAAGAA CCTTACCAAG GCTTGACATC CTGCGAATCT TGATGAAAGT TGAGAGTGCC TAAGGGAACG CAGAGACAGG TGGTGCATGG CTGTCGTCAG CTCGTGTCGT GAGATGTTGG GTTAAGTCCC
ABICyano1   ACGCGAAGAA CCTTACCAAG GCTTGACATC CTGCGAATCT TGGAGAAATC TGAGAGTGCC TAAGGGAACG CAGAGACAGG TGGTGCATGG CTGTCGTCAG CTCGTGTCGT GAGATGTTGG GTTAAGTCCC
CyanoLL15   ACGCGAAGAA CCTTACCAAG GCTTGACATC CTGTGAATCT CGATGAAAGT TGAGAGTGCC TTAGGGAACA CAGAGACAGG TGGTGCATGG CTGTCGTCAG CTCGTGTCGT GAGATGTTGG GTTAAGTCCC
Cyano7202   ACGCGAAGAA CCTTACCAAG ACTTGACATC CGATGAATCT TTTTGAAAGA AGAGAGTGCC TTAGGGAACA TCGTGACAGG TGGTGCATGG CTGTCGTCAG CTCGTGTCGT GAGATGTTGG GTTAAGTCCC

            1041
Cyano10216  GCAACGAGCG CAACCCTCGT CCTTAGTTGC CAGCATTAAG TTGGGGACTC TAGGGAGACC GCCGGGGAGA ACTCGGAGGA AGGTGGGGAT GACGTCAAGT CAGCATGCCC CTTACGTCTT GGGCTACACA
CyanoETS-03 GCAACGAGCG CAACCCTCGT CCTTAGTTGC CAGCATTAAG TTGGGGACTC TAGGGAGACC GCCGGGGAGA ACTCGGAGGA AGGTGGGGAT GACGTCAAGT CAGCATGCCC CTTACGTCTT GGGCTACACA
ABICyano2   GCAACGAGCG CAACCCTCGT CCTTAGTTGC CAGCATTAAG TTGGGGACTC TAGGGAGACC GCCGGGGAGA ACTCGGAGGA AGGTGGGGAT GACGTCAAGT CAGCATGCCC CTTACGTCTT GGGCTACACA
ABICyano1   GCAACGAGCG CAACCCTCGT CCTTAGTTGC CAGCATTAAG TTGGGGACTC TAGGGAGACC GCCGGGGAGA ACTCGGAGGA AGGTGGGGAT GACGTCAAGT CAGCATGCCC CTTACGTCTT GGGCTACACA
CyanoLL15   GCAACGAGCG CAACCCTCGT CCTTAGTTGC CAGCATTAAG TTGGGGACTC TAGGGAGACT GCCGGGGAGA ACTCGGAGGA AGGTGGGGAT GACGTCAAGT CAGCATGCCC CTTACGTCTT GGGCTACACA
Cyano7202   GCAACGAGCG CAACCCTCGT CCTTAGTTGC CAGCATTAAG TTGGGGACTC TAGGGAGACC GCCGGGGAGA ACTCGGAGGA AGGTGGGGAT GACGTCAAGT CAGCATGCCC CTTACGTCTT GGGCTACACA

            1171
Cyano10216  CGTACTACAA TGGTTGGGAC AAAGGGGAGC GAAGCCGCGA GGTGGAGCGA ATCTCATCAA ACCCAGCCAC AGTTCAGATT GCAGGCTGAA ACTCGCCTGC ATGAAGGAGG AATCGCTAGT AATCGCAGGT
CyanoETS-03 CGTACTACAA TGGTTGGGAC AAAGGGGAGC GAAACCGCGA GGTGGAGCGA ATCTCATCAA ACCCAGCCAC AGTTCAGATT GCAGGCTGAA ACTCGCCTGC ATGAAGGAGG AATCGCTAGT AATCGCAGGT
ABICyano2   CGTACTACAA TGGTTGGGAC AAAGGGGAGC GAAGCCGCGA GGTGGAGCGA ATCTCATCAA ACCCAGCCAC AGTTCAGATT GCAGGCTGAA ACTCGCCTGC ATGAAGGAGG AATCGCTAGT AATCGCAGGT
ABICyano1   CGTACTACAA TGGTTGGGAC AAAGGGGAGC GAAACCGCGA GGTGGAGCGA ATCTCATCAA ACCCAGCCAC AGTTCAGATT GCAGGCTGAA ACTCGCCTGC ATGAAGGAGG AATCGCTAGT AATCGCAGGT
CyanoLL15   CGTACTACAA TGGTAGGGAC AAAGGGAGGC GAAACTGCGA AGTGGAGCGA ATCCTGTCAA ACCCTGCCCC AGTTCAGATT GTAGGCTGAA ACTCGCCTAC ATGAAGGAGG AATCGCTAGT AATCGCAGGT
Cyano7202   CGTACTACAA TGGTTGGGAC AAAGGGATGC GAGACCGCAA GGTGGAGCGA AACCCATCAA ACCCAGCCCC AGTTCAGATC GTCGGCTGAA ACTCGCCGAC GTGAAGGAGG AATCGCTAGT AATCGCAGGT

            1301
Cyano10216  CAGCATACTG CGGTGAATCC GTTCCCGGGT CTTGTACACA CCGCCCGTCA CACCATGGAA GT-------- ---------- ---------- ---------- ---------- ---------- ----------
CyanoETS-03 CAGCATACTG CGGTGAATCC GTTCCCGGGT CTTGTACACA CCGCCCGTCA CACCATGGAA GTTGGTCACG CCCGAAGTCG TTATTCTAAC CCAAG--GGA AGAGA-CGCC AA--GTGGGA CTAGTGACTG
ABICyano2   CAGCATACTG CGGTGAATCC GTTCCCGGGT CTTGTACACA CCGCCCGTCA CACCATGGAA GTTGGTCACG CCCGAAGTCG TTATTCTAAC CCAAGTGGAA GGAGA-CGCC GAAGGTGGGA CTAGTGACTG
ABICyano1   CAGCATACTG CGGTGAATCC GTTCCCGGGT CTTGTACACA CCGCCCGTCA CACCATGGAA GTTGGTCACG CCCGAAGTCG TTATTCTAAC CCAAGTGGAA GGAGA-CGCC GAAGGTGGGA CTAGTGACTG
CyanoLL15   CAGCATACTG CGGTGAATCC GTTCCCGGGT CTTGTACACA CCGCCCGTCA CACCATGGAA GTTGGTAACA TCCGAAGTCG TTACTCCAAC CCGCAAGGGG GGAGGATGCC GAAGGTGGGA CTAGTGACTG
Cyano7202   CAGCATACTG CGGTGAATCC GTTCCCGGGT CTTGTACACA CCGCCCGTCA CACCATGGAA GTTGGTAACA TCCGAAGTCG TTACTCCAAC CATTTATGGA GGAGATCTCT G-------GA CTAGTGACTG

            1431
Cyano10216  ---------- ---------- ---------- ---------- ---------- -----
CyanoETS-03 GGGTG----- ---------- ---------- ---------- ---------- -----
ABICyano2   GGGTGAAGTC GTAACAAGGT AGCCGTACCG GAAGGTGTGG CTGGATCACC T----
ABICyano1   GGGTGAAGTC GTAACAAGGT AGCCGTACCG GAAGGTGTGG CTGGATCACC T----
CyanoLL15   GGGTGAAGTC GTAACAAGGT AGCCGTACCG GAAGGTGTGG CTGGATCACC TCCTT
Cyano7202   GGGTG----- ---------- ---------- ---------- ---------- -----
```

Fig. 5B

```
ID   pRL528    standard; circular DNA;    ; 16301 BP.
CC   This file is created by Vector NTI
CC   http://www.invitrogen.com/
CC   VNTDATE|584889451|
CC   VNTDBDATE|584895165|
CC   LSOWNER|
FH   Key              Location/Qualifiers
FH
FT   CDS              548..1996
FT                    /vntifkey="4"
FT                    /label=M.AvaI
FT   CDS              3006..4259
FT                    /vntifkey="4"
FT                    /label=M.Eco47II
FT   CDS              complement(15314..15955)
FT                    /vntifkey="4"
FT                    /label=Cm
SQ   Sequence 16301 BP; 4386 A; 3985 C; 3477 G; 4453 t;
     aagtcacggt actctccgga ggccttttc atatccggcg ggcctgacac ttccggatgc        60
     agcacacgaa aacagaagtc accggaacac gccattctga gaaaactgtc actaatctgt       120
     tttattccgc aaacagaaaa ccaccggata accggggtat aggaagtata aaccaccttt       180
     ttgggtatag gaagtataaa ccaccttttt gctcctcatc cgaagtatct tacctgaaat       240
     tccctcactc gtttaccgct caagccccaa ttttaactgc cggtccagcc taaaccgctc       300
     taataaggtt cgatttggcg gtaaaatctc tagcctgata gctcgagatc tagatatcga       360
     tgaattcgag ctcggtaccc tattcaatat ttaacttgat tactgtagaa gtataacaaa       420
     gtataatcag gttctaactg ttgtcaatta gtctataaaa aatagggttc aaatcttaag       480
     tgatagacga tagtgctttg tcctgataga atcttaagtt acctctttgt tacaagaaaa       540
     atataaaatg acttcatttg agcttgagag tccaatagaa ataaagactg acccgactga       600
     tcttgatcaa gagagtgatt cctttgtaca agaaatttct cgattcaata aagcacttga       660
     gcaacgtttt agagataaga tgcgattgca tgaaagttta agtcgaaaaa tagttagttt       720
     tcaagctaat aagtcaaaac ctcagtatcg ctggtttaaa tataaagaag ctttttcagt       780
     tgatttggta aatcagttaa tattcgagta cgagaaaaaa tcatttgaga ggattcttga       840
     ccccttcgca ggagcaggaa caatgctatt tgcctgtagt gatgccggta ttcaagcaga       900
     tggtatagaa gtgttaccta ttggtcaaga gattattgaa gtaaggaaaa taatccagcg       960
     acaattccgt cgagaagatt ttttgagatt gattgaatgg tacaaacaaa aaccttggaa      1020
     tcagcataat aatagaaaat atcttaatcg tttaagaatt actgacggag cttatcctcc      1080
     tgaaacagaa gcatcaatag agagattttt attttctata gaaaaagaga atattcttgt      1140
     gaaacaagtt ctccgttttg ctctattgtg tattcttgaa tctatcagct atacccgtaa      1200
     agatggacag tatctacgtt gggataaaag agcatttagg aaaagtggat cagataaatt      1260
     tgataaaggt aaaattctgg atttcgatga agcaattact gagcaaataa aattaatttt      1320
     gaatgattcc tttgacttaa taagtaatac attattttgt tatgggactc aaagaagtgg      1380
     aattaattta tttaatgctt catgtcttaa aattctgcct gaatttgagc aagattttta      1440
     cgactgtatc attacctctc caccctattg taatcgttat gactatacac gtacatacgc      1500
     tctagaatta gctctattag gtgtgggaga aagagatata gtacaactta ggcaagatat      1560
     gctgagttgt actgttgaaa acaaagaaaa gtctcttatt cacaattggc aggaagcatt      1620
     acgcatactt gataaacaag aattgttaca aagtatcttg cgctttcttg agcgagagct      1680
     tgaaagaaaa aaacttaata ataacggtat tcctcgtatg ataaaaggat atttctatga      1740
     aatggcttgc gttattatag aatgctttag agttttaaaa aatggctcac ctttatttat      1800
     ggtaaatgat aatgttcgct atgcaggtat tgatatttcg gttgatttaa ttctttctaa      1860
     tattgcagaa gaaattggtt ttaatgtgga gaaaattctt gtcttaccta ctggcaaagg      1920
     taacagtagc caacaaatgg ggacacatgg aagaaagaca cttcgcaaat gtgtgtatgt      1980
     ttggagaaaa ccctagtgcc atatcaatat catattcaaa gcaatgatga tcttgtgact      2040
```

FIG. 7

```
ccatatcaag aagtccgagc aggatttgtt gctttagctt tagaaagaaa tcgaaaagca 2100
acaccatttg ttgagcaggc aagagcatta aagatccgag taagccaaat tgaaaggggg 2160
gatcctctag aagctttaat gcggtagttt atcacagtta aattgctaac gcagtcaggc 2220
accgtgtatg aaatctaaca atgcgctcat cgtcatcctc ggcaccgtca ccctggatgc 2280
tgtaggcata ggcttggtta tgccggtact gccgggcctc ttgcgggata tcgtccattc 2340
cgacagcatc gccagtcact atggcgtgct gctagcgcta tatgcgttga tgcaatttct 2400
atgcgcaccc gttctcggag cactgtccga ccgctttggc cgccgcccag tcctgctcgc 2460
ttcgctactt ggagccacta tcgactacgc gatcatggcg accacacccg tcctgtggat 2520
cttctcaacg aagaaagaag aatcatcgct gaggtgaaaa ataaatactc aacggttact 2580
ggcggggatt tagcagataa atataaaggc ttagatgagt tggtatcacc gaaacatagc 2640
cgatttaagg attactgtgc gtactttgtt aatataatcc ctcgtaaacc tatcagatat 2700
aacagcccct ttactccttc caataaaggt agtggtactc tgtgtccttc gaaccctaac 2760
attagaatca ttgatggtgc gagtttctat gagcttgtca ctggcagacc agatgctctg 2820
caagaactcc atagtgctct ccctcacgca attgagtata ttttgagcga acgtcttggg 2880
cagcaaggtt tttccatccc tgataaagat agttttatta agtattttgg gctcgcttac 2940
ggctgataac catgatcaat gtttgacaaa gcacatgtaa acccatacag tagtaaccat 3000
gactaatgtt ggcatggtta ctaaatatgt taaaggaaga gttttcactt tcagaagttg 3060
cagacatttt gggcgtttca aaagaaactt taaggcgttg ggatactgct ggaaaattag 3120
tttctcaaag aaatgacgaa aacaactatc gattttataa aaaagagcaa cttaaaaatt 3180
ttgaacaagc tcagttttta tttaaaagcc agtggcctga tgagactaaa ataagcaata 3240
atgtttatac tgtattagag ttatttgctg gcgcaggggg gatggcttta ggtttagaaa 3300
aagccggttt aaaatctgtt ttactaaatg aaattgactc ccatgcttgt aagacgttac 3360
gaaaaaatag gcctgaatgg aatgtggttg aaggtgatgt gagccaagta gacttcaccc 3420
cttataggaa taccgttgat gtgctggctg gtggctttcc ttgccaggca ttctcttatg 3480
caggcaaaaa acttggtttt gaagatacac ggggcaccct ttctttgaa ttcgcccgag 3540
ccgctaaaga aatcaatccg aaagttcttt tagcagagaa tgttcgaggg ttgctaaatc 3600
atgatgctgg acgaacttta gaaacaataa aaaatattat cacagacttg ggctacactt 3660
tatttgagcc aagagtgctt aaggctattt tctacaaagt gccgcaaaaa cgcgagcgtt 3720
tgatcattgt agctgtaaga aatgatcttg ctgatggcat cgattatgag tggccttctt 3780
cttacaataa aatattaacc cttaaagatg cattaaaaaa gggagagctg tatgatagcg 3840
acgtgccaga atctgaagga caaaaatatc ccaaaagaaa agcagagatc ctaagtatgg 3900
ttcctcccgg tggctactgg agagatcttc ctgaagatat tcaaaaagaa tacatgctca 3960
agagttttta cttaggtggg ggcaaaactg gtatggctcg tcgtttgtca tgggatgaac 4020
caagcctaac attaacatgc gccccagcac agaaacaaac agagcgttgc cacccagaag 4080
aaacaagacc attaactgtg cgtgagtatg caagaataca gaccttcccc gatgaatggg 4140
tatttgaagg cccaatgtca gcgaaatata agcaaatagg aaacgctgtt cctgttaatc 4200
tgtcatttgc tgttggcaaa tctgtggtac atcttttaga taagataaat aaaagataga 4260
ccctgtaaat aattctgtgt aattgctgcc atattaaagg tgatcgctca ggcggtcacc 4320
gaactcgata ataaagcgac tcatcgccag ccgccagctc tggattggca tattccattt 4380
ttttgatgca tccttgatcg ccagagaaat gaccttccgc agcgagtcgt cagtcgggaa 4440
cactttacgc ttcttaatgg ccgcacggat cacgctgttc agcgattcga tagcgttcgt 4500
ggtgtagatg gccttgcgga tatcgggcga atagccgaag aacgtgttga tattttccca 4560
gtgcgcacgc cagcttttgc tgatttgcgg gtatttatcg tcccagacat tcgggaactg 4620
ctccggtgcc actagcgccg cctcttctgt tggcgcctga tacaccgttt ttaacccgcc 4680
agtgacggct ttgtagtcct tccacgatac gtatttcagg ctgttgcgca ccatatgaat 4740
gatgcacaac tggatgtgcg tctacggata cacgctgttt atcgcatccg gaaagccttt 4800
cagaccgtcc atgcaggcaa taaggatatc ctgaagcccc cgattcttaa gctctgtcag 4860
cccccccagc cagaacttcg ccccttcgtt ctcggccagc cacatgccca gcaactcttt 4920
ctggcctcca gtattaatac cgagtgcaag gaacaccgct ttgttaatta cggtgccacc 4980
ttgacgaact ttcaccacga tacagtcaag gtaaacaatg ggatacagtg catccagagg 5040
tcgattttgc cattctgcaa cctgctcttt gaccgcatca gtgactttac atatcagcgt 5100
```

FIG. 7 (continued)

```
gggtgacaca tctgcgtcgt acatctcttt gaaggtggcg acaatttcgc gggtagtcat 5160
atctttggcg tagagggata aaatctggct gtccatctgc gtaatgcgcg tctggtgctt 5220
cttaatcaac tgcggttcga aggtgttttc acggtcacgc gacgtgttca gttcgatcct 5280
ctacgccgga cgcatcgtgg ccggcatcac cggcgccaca ggtgcggttg ctggcgccta 5340
tatcgccgac atcaccgatg gggaagatcg ggctcgccac ttcgggctca tgagcgcttg 5400
tttcggcgtg ggtatggtgg caggccccgt ggccggggga ctgttgggcg ccatctcctt 5460
gcatgcacca ttccttgcgg cggcggtgct caacggcctc aacctactac tgggctgctt 5520
cctaatgcag gagtcgcata agggagagcg tcgactctag agtcgacctg cagcaatggc 5580
aacaacgttg cgcaaactat taactggcga actacttact ctagcttccc ggcaacaatt 5640
aatagactgg atggaggcgg ataaagttgc aggaccactt ctgcgctcgg cccttccggc 5700
tggctggttt attgctgata aatctggagc cggtgagcgt ggatctcgcg gtatcattgc 5760
agcactgggg ccagatggta agccctcccg tatcgtagtt atctacacga cggggagtca 5820
ggcaactatg gatgaacgaa atagacagat cgctgagata ggtgcctcac tgattaagca 5880
ttggtaactg tcagaccaag tttactcata tatactttag attgatttaa aacttcattt 5940
ttaatttaaa aggatctagg tgaagatcct ttttgataat ctcatgacca aaatccctta 6000
acgtgagttt tcgttccact gagcgtcaga ccccgtacat cacgaatata gtttgcttga 6060
catcctgaca agaataatat tgtaattaga aaaattatta ttttcatatt tctttccaac 6120
aaaagtaaaa atacttatgc atttaaaata ctacctacat aatttacctg aatcacttat 6180
accatggatt cttattttaa tatttaacga caatgataac actcctttgt tatttatatt 6240
tatatcatca atacatgtat tgctatatcc atactctaaa ttaaccatat ctagatatat 6300
caaagaaaat acaaagttaa aaaaagaacc ctggtactta tgcaagttat ctgcattgtt 6360
ttatttatta atggcaatcc cagtaggatt gccaagtttc atatattaca ctctaaagag 6420
aaattaaatc cctaacaact cattaagttt gctcaactca tcatccccta tgtaagaaga 6480
aacaatacct gtgacaattg caatccccca gaaaccaaga ggcacaccaa caataaaact 6540
aaacattaat gccacaattt ttgccacacc tacatcgacc gcacttttct ccagcgtgac 6600
aaacaaaggt cgccagttac cagtttctat tgcattttta aaatcagaac caacatcata 6660
tagaaaagat actcgactgg tgattttaag cgactttgat atcttcgtta aattcttaga 6720
taactcatca taattaacag actctaacgc attaaaaata gcatcccgat caaccttact 6780
gaatttctta tccagtacat tcttatactt ttcaaatgct gccagagctt catcaacacc 6840
ttgaattttc tttcctttag acttttccgc taaatcctga gcaatttttg cgtatttttc 6900
tccatattgt tcggttatat attgataaaa tccaaccata gtttcaacag catcttttat 6960
ctggctcttt tcaagagcat cctgagcttc ttttaatttc tgctctgcct ctttaacctc 7020
agcggcctta ccatccctga cactaacagc attcttaatt tcattttcaa ctgcggagta 7080
ctcagcctgc ttagcttcaa gctgacgctg tagtttttcc tgaacgtcac gccatcccgg 7140
aaatccggag accttcacgt caacactctt ctgagcgttt tcaagctctc ctgcaactct 7200
ggaaacagta gcttgcttac tctgtacatc actttcagcc ttcgccagtt cagctttcgc 7260
ctcagctaaa cgcttctctg cttccgccac cgcctgtttc tcttcattaa gagtttcatg 7320
ttcagcgacc tctgcatttt cacgagcctt ttcttcagct tccttctgtt tattcacatc 7380
accaatttta ctttgcaatg tatttttata agaattaagt ttgctaatat ctgcatcaag 7440
ctgatttgat ttttttgca actcatcaac atccctctca agatcagtga taccatgata 7500
agaatgatgc ttgaatactt ttttcatctc ctcgatttct ttctgttttt cactaatctg 7560
tgtagcaatt ttattcttct gcttttgttt ttcattaatt acattactca ccaccttcga 7620
actcttatcc atatcactga cctgagcatt cgttggtgca gtattaactg aagcagtgtt 7680
attgttgtta tttcctgagc tttctgcaaa aagtgatggc atatcactaa ttaaagaatt 7740
aagaactctg gagacccctc caaatggatt atcaaccaga gttgaattct cttctgtcat 7800
aacaatacca ttcatcaccg gaaggccatc attattaatg acaacatcac cccacggagt 7860
cagatatgac tcaccggttt tcatcacagt tgatgtagaa ccagatgaat ttgaatttcc 7920
ctgaccacca ttattaccat gcccagagcc accaccccag tgaaccccac tattactatt 7980
attatttcca ccttgctgat tcagattcgc ccctgttccc cccatagact caccagcagt 8040
tggtccatat ccacttagtt ctttagccat aaattcctct ttgataatta aaacaataaa 8100
ttaaaaacaa tatactgtac atataaccac tggttttatg tacagtaaaa acctactact 8160
```

FIG. 7 (continued)

```
cagcattgtc catgtcaaga gcatggattt tcatttttgc aataaggatc acactatggg    8220
gaggcaggca ttgagaacgt cgaaacagaa caccggagca aatcaggatg agatataaaa    8280
ctgttggatc atgaaaaaac ggagaacgat gtgagcaaat caccccgcca taaactgaac    8340
aaaacagaca aacgacttct cgacacccct gttgctgccg gatatgagca tgacaaagcc    8400
cgtgacctca tccagaaaca ggtttacacg ctgacactgg ctgatcagcg tcatgtggtc    8460
agtgaaatca gtaatggtgt gaatcccacc caggcttact cggcggtata ccaggcaaga    8520
cgcattcgcc tcgccccgtaa atatctgaac ggtaaaaagg ttatggaaga aaccggggaa    8580
aatacgcccc catcagcgta aggatttctt ttgccgctcc agagactcca gtttttttacg    8640
caaatcctct ctttttgggg catctctggt gccagccagc tctgctctca actcatcgat    8700
ctgaagttgt atcttcagtc tattactgaa cattttctgt ctggcattaa catccgcaac    8760
aatgccgttt tttgtcttct cggccttttg ttgaaaaaca ttgctgtccg catgactggc    8820
aaccgaagca gaaagaacac taaaaagcag gactggcaca catttttttca cgggattatt    8880
cctgactcat tgaccatcaa atcacattgg gagtaaaccg acgtatgata agagatactc    8940
ttcggagata taactccctg agtatcaaga ttaaaaacgc aaggagatgt ttatgagatc    9000
tgccgctgcc aggctgcttc tgatacctct gataacagca acaatagctc ttacaggatg    9060
cacaccaaag accagcctgg aacgacatac ccggcattat gtttatgctt cagatgatgg    9120
atttgatcct aacttctaca cccagaaagc agacaccata cgtatgatgc tcccgttctt    9180
tcagcagttc cgggatatgg ggatgaaaga caaagcagcc ggagtatcag cagaaacggc    9240
acagcaacgt gtaaaagaat tccactcaga aaaatttttt cactcactcc ggagcacaac    9300
agcctttgct ggcagaaaat acacaaacag cgatatgcct tcgccgaaaa aaatgaaact    9360
aatggcagac accatttctg cggtttatct cgatggatac gagggcagac agtaagggat    9420
ttaccataat cccttaattg tacgcaccgc tgaaatgcgt tcagcgcgat cacggctgct    9480
gacaggtaaa aatggcaaca aaccacccga aaagctgccg cgatcgcacc tgataaattt    9540
taaccgtatg catagctatt cagccatgtg aataacgctg gttttgcctg cgtaaacctc    9600
atgacactgt ttttttttcca tcttttcagt tgatgacata cgcagacatc gcgggatgag    9660
gctgaggaat gagcgcgatc tggcaaagag gcaaaacaca gcaacaaaaa cgacacgcca    9720
gaatcgcgcc cggatgcgtt tttaacgcgt tccggtacca tctggcaacc tcccggaaca    9780
actcaccgtc acatacctat tgacgggcca cgccataccc gtgcttcccg ttcctgctct    9840
tcatgccagg accgcgcacg ctcccgttcc aggcgtgcct gcctttcctg ttcatccctt    9900
atctgctgtt cgtgataaat aaccgactca agtggtccac ctgcccggct aatctctgca    9960
cctgctgact caagtcgtcg cactgttccc tcagttgccc gttctcctgt cgtgtcagct   10020
cgaacatatg ctgcaaatcc gtgaaggcgc tctcccagtc tttcagccgc tgcatatagt   10080
cctgctgcaa ttgctctaag gcgttcagta agtgcatttc cagctctgtc atactcactt   10140
actccctgac cagtcttact gcgttcttct tctccaccgt ccagttgttt tcccccttca   10200
ccccggacgg caacactaga aatttcccgt tcctgccctc gtgatacgtc acaccccatg   10260
tttttttcccg gagtttcgcc agcgtctctt cctggtccct gatagccagg atgttcgccg   10320
caatccggct ttcctgccac tgaatcagcc ccccatgacg ccagaaaaat cccgcccgtg   10380
acgcagagcg ccgtcagcga cgggtacagt atccgccctt tgaccagctt ccagagcagc   10440
tcttcctgcc gccgggccag ttcgttctct gtggcgctga actgcgcgtt cacggcactg   10500
ttcagcgtct ccagttgttc tttcaccgct gctgtgtgtg cgctgatagc gtctctgatt   10560
ttctgcccgt ttaagttcag ttccctgtct acagacgctt cgagcttcct gaactcgctg   10620
ttcagcatgt tctctgtaga gacggcacgc tctttcagtt tcttctcgaa gtctgtcccc   10680
atttgtaaaa gattgctcat acagcgcccc tttcagcctg agattacgcc caccctccgg   10740
gtcggcgata ctgatactgc tcctggttgt cctcacaacc tcaaaacctg ccgctgtaag   10800
cgcctcagtg acatcctgac gcgtttttag cgctccggca tggtaaagag cctccagtcc   10860
cctcgtaatc gcttctgcgg cctcctgttt cgctttcggc agattattcg ggtgacaag    10920
tgtccgcctg ttctccggtg cgttcgggtc gtgcagcccg taatggtgat tcaccagtgt   10980
ctgccaggca ttgattcgcg gacggtccgc tcggtcgtaa tagggctgga gccgttttcc   11040
gctcgccagc tccatattcg ggatgacaaa attcagctca agacgcccct tgtcctggtg   11100
ctccacccac aggatgctgt actgattttt ttcaagaccg ggcatcagta cccgctcaaa   11160
gctctccatc accctttcac gctctcccgg tggcagggtc tgctctgcaa aagacagaac   11220
ccccgaggtg tattttttcg caaacggcgt ggcatcgatg agttcccgca cctcttcggg   11280
```

FIG. 7 (continued)

```
agcaccccgc agaactctcg ccccttcccg gttacgctcc cggcccagca ggtaatcaac     11340
cggaccactg ccaccgcctt ttcccctggc atgaaactta actatcatcc cgttctccct     11400
gtttacggac ctcatccctc agctcactca gttcacgtcc gatggccatc agtgcagcca     11460
ccacatgaac ccggtcatgc cccgaccact gtccgctgtt tatcttccgg gctatctgat     11520
tcaggttatt gccgaccgaa gcgaactggc gcaacagcgg cggtgccagt gtcggaagac     11580
ctgacgtttt cgatggcggt gcccccaggc agaccttacg catccatgac gcaagttgtt     11640
ttccctcaca acgtgccagc agccgcgcat gttcctcatc cgtgacccgt atcgtgagca     11700
tcctttcgcg tttcaccggt atcattaaaa acctccgaca gactccccac acatggagaa     11760
acagaactgt gactaaacag gaaaaaaccg cccttaacat ggcccgcttc atcagaagcc     11820
agacgctgac cctgctggaa aaactgaatg aactggacgc cgacgaccag gctgacatct     11880
gcgaagcgct tcacgatcac gctgacgagc tttaccgcag ctgcctcgca cgcttcgggg     11940
ataacggtga aaacctctga cacatgcagc tcccggagac ggtcacagct ggcctgtgag     12000
cggatgccgg gagcagacaa gcccgtcagg gcgcgtcagc gggttttagc gggtgtcggg     12060
gcgcagccat gacccagtca cgtagcgata gcggagtgta tactggctta atcatttggc     12120
atcagtgagg attgtatgaa aagtgcacca tgccgggtgt gaaatgccgc acagatgcgt     12180
aaggagaaaa tgctcgtcca ggcgcttttc cgcttcctcg ctcactgact cgctccgctc     12240
ggtcgttcgg ctgcggcgag cggtatcagc tcactcaaag acggtaatgc ggttatccac     12300
agaatcaggg gataacacca aaagaaacat gtgagcaaaa aacaagaacc cggaaaaggc     12360
cacgcagctg gcgtttttcc ataggctccg ccccccttga cgagcatcac aaaaaaccga     12420
cgctcaagtc agaggtggcg aaacccgaca ggacttaaag ataccaggcg tttccccctg     12480
gtggctccct cgtgcgctct cctgttccga ccctgccgct taccggatac ctgtccgcct     12540
ttctcccttt gggaagcgtg gcgctttctc atagctcacg ctgttggtat ctcagttcgg     12600
tgtaggtcgt tcgctccaag ctgggctgtg tgcacgaacc ccccgttcag cccgaccgct     12660
gcgccttatc cggtaactat cgtcttgagt ccaacccggt aagacacgac ttaacgccac     12720
tggcagcagc cattggtaac tggatagtgg atttagatac gcagaactct tgaagttgaa     12780
gccttatagc ggctacactg gaaggacagc atttggtatc tgtgctccac taaagccagt     12840
tacccggtta agcagtcccc aactgactta accttcgact aaaccgcctc cccaggcggt     12900
tttttcgttt acaggcagca gattacgcgc agaaaaaaag gatctcaaga agatcctttg     12960
atcttttcta ctgaaccgcg atccccgtca gttcagaaga cgaagatggt gcaacggttc     13020
ctccttgtac aggggtctga cgctcagtgg aacgaaaact cacgttaagc aacgttttct     13080
acctctgacg cctcttttaa tggtctcaga tgtcctttgg tcaccagttc tgccagcgtg     13140
aaggaataat ggccgagcat attgatatgt ccgtggcaaa gcggggagag gcgtgcgata     13200
tcttcatcat tcagtgtttc accttgcgcc cggagatgat ccagggctgc ctgcatatac     13260
atagtgttcc ataacacgac ggcgttagtg accagcccca gtgcgcccag ttgatcttcc     13320
tgaccgtcgg tatatcgttt tcttatctca cctttttgac cgtgacagat ggctctggca     13380
acggcatggc ggctttctcc ccgattaagc tgggtcagaa tgcgccggcg gtaatcttca     13440
tcatcaatat aattaagcag atacagcgtt ttgttgatgc gccccacttc aatgattgcc     13500
tgagtcagtc cggaaggacg ttcacttttc agcaatgaac ggaccagcac tgaagcctgt     13560
actttgccca gtttcaggga gccagcggtc cggatcattt cgtcccactg aaggactatt     13620
tttcggggat ctgattgccc tctggcaata tcattcagca cgccatagtt ggcatcatgg     13680
cccattcgcc agaaaaccga agcaccggca tcagccaggc gtggagaaaa ctggtatccc     13740
agcagccaga aaaggccaaa gacaagttcg ctggtacctg ctgtatcggt cataatttcg     13800
gttggattca gcccggtctc ctgttccaga aggccttcca gcacaaagat agagtccctc     13860
agcgtccccg gtataacgat gccatgaaag ccggaatact gatcggacac aaagttgtac     13920
caggtgatcc ctctgttatt accaaagtat ttgcggttcg gtccggcatt gattgttctg     13980
actggcgtaa caaagcgcat tccatctgca gtccgcctca gcaatatcgg gatagagcgc     14040
agggtcagga aatccttgga tatcgttcag gtagcccacg ccgcgcttga gcgcatagcg     14100
ctgggtttcc ggttggaagc tgtcgattga aacacggtgc atctgatcgg acagggcgtc     14160
taagagcggc gcaatacgtc tgatctcatc ggccggcgat acaggcctcg cgtccggatg     14220
gctggcggcc ggtccgacat ccacgacgtc tgatccgact cgcagcattt cgatcgccgc     14280
ggtgacagcg ccggcggggt ctagccgccg gctctcatcg aagaaggagt cctcggtgag     14340
```

FIG. 7 (continued)

```
attcagaatg ccgaacaccg tcaccatggc gtcggcctcc gcagcgactt ccacgatggg    14400
gatcgggcga gcaaaaaggc agcaattatg agccccatac ctacaaagcc ccacgcatca    14460
agcttttgcc catgaagcaa ccaggcaatg gctgtaatta tgacgacgcc gagtcccgac    14520
cagactgcat aagcaacacc gacagggatg gatttcagaa ccagagaaca tgtcattgta    14580
ctggaaggcg cattacaact gcggctgggg gatgagtggc acaccgtttc tgccggggaa    14640
tccctgcgct tccatgcgga tatcccgcac gcttacgcca atcccggtaa ggccattgtg    14700
acactgcata atctgatcca ttatccgcgc ccggcggaca aataaaaaag cagggtataa    14760
taaatatacc ccgctttgac ttaacggatc gtcttacttt atttgtaaaa taaaaccaaa    14820
ataaatatgt gttcagctta acttattata tatcatcctt ataccaaccg ggatgatatg    14880
tttatactga acagaaaagc atgccattca gaatactatc ttctgttata tatggcggtt    14940
tatttattgt ttaattacac acactcaggc atatcactat gctatcgtga tgttttcact    15000
ggtgttgtta ctactgcctt tacggcattt tggtgttgtt caaaatgact gtcgcagcag    15060
tctttctggt gtcttaaata ctattattat aactgcatct ggtgttgtta atattattgt    15120
tactgcttac tttattatta ttgctgtcag tctttgctgt ttctttttta ttaagggtat    15180
taccaaactg cgggggcatt atcgtacagt gatcctgaac cagtctgaaa cgaaattaca    15240
gattacggtt aaaatataaa aaaaagccac cattcctgcc ggatacggtg gcttaaatac    15300
agaattaatt aatttatttc agtatgttat cacacatcag ctgaagtgta ttaataaacc    15360
gtgctgcatg aaagccatca cagactgcat gatgaacctg tacagaaaca ggtaataata    15420
cgcggtcacc ttcctgctga aactttgcca tcgtaaaaac cggggcaaaa taatcatcat    15480
ttccggtgat gttcaggtta aatccgtcaa aactcaccca cggtaatgat gatatattca    15540
ggtgattctc cggtaaattt ccctgcggaa acaatctggt atcatgctga tattctgccg    15600
ttaccgcatt ataacctgcc ataaactcac tgagatccgg aaaataacgg caggacagtg    15660
cagagaatgt ttcggtttct ttatgaaaga cagtaaagac cgggtctgac tggtcccagt    15720
aaataagttc attgtctttc agtgccatcc ggaactccgg aaactgatta acagcccggg    15780
agatcaggta aatcatcagc ggataaaact tataacctgt ctccgccagt gcggtacgca    15840
aagcggtaat atcgagtttg gtggtcaggc tgaatccgca tttaatctgc tgacgataaa    15900
gggcaaagtg ttccctgcga ttccaggtat tcaggtcaat ccgggtaaaa ttcatggtta    15960
ttccttctga ttaatagtga aaaatattaa taatcagaag gcagtctggt tgtctcaatg    16020
ggtaacattc cgtcctccgt aagctgtttg gtattcagta ataataccct atacgggctt    16080
aatctgtatt aagcccggct ttatttattc cggccaatca tccgcaaaca catagcggat    16140
cagttctgcg gattcacggg gcggtgctct cagcacatcc gccattaaat caatctccat    16200
ctgacaggtt tgcagcttgt cttccgccgg tacatacgga tcatccgtca ggaaactatc    16260
gccgtattta tccatcgacc cctgtatttg tgccgaaaat a                        16301
```

FIG. 7 (continued)

TK225 pABICyano1-6.8 PnirAABICyano1-PDCmax-synADHmax-PrbcABICyano1-Km**-oriVT

```
ID   TK225\pABICyano1-6.8_PnirAABICyano1-PDCmax-synADHmax-PrbcABICyano1-Km**-oriVT
standard; circular DNA;    ; 12968 BP.
CC   This file is created by Vector NTI
CC   http://www.invitrogen.com/
CC   VNTDATE|625138593|
CC   VNTDBDATE|625140543|
CC   LSOWNER|
CC   VNTAUTHORNAME|Frank Uliczka|
FH   Key             Location/Qualifiers
FT   promoter        3574..4099
FT                   /vntifkey="30"
FT                   /label=PrbcLABICyano1
FT   CDS             4101..4916
FT                   /vntifkey="4"
FT                   /label=Km**
FT                   /note="maximal codon optimized kanamycin resistance gene"
FT   CDS             12478..12726
FT                   /vntifkey="4"
FT                   /label=ORF\6
FT                   /note="orf6"
FT   CDS             12218..12481
FT                   /vntifkey="4"
FT                   /label=ORF\5
FT                   /note="orf5"
FT   CDS             11490..12176
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(10400..11164)
FT                   /vntifkey="4"
FT                   /label=ORF\3
FT                   /note="orf3"
FT   CDS             9955..10140
FT                   /vntifkey="4"
FT                   /label=ORF\2
FT                   /note="orf2"
FT   rep_origin      complement(9255..9272)
FT                   /vntifkey="33"
FT                   /label=Rep_Origin_1\(potential)
FT                   /note="potential rep origin; match pNostoc (Acc# M81381) nick
site (358-375); on reserse strand"
FT   misc_feature    9515..9548
FT                   /vntifkey="21"
FT                   /label=Rep\motif
FT                   /note="Rep protein active site motig EXXKYXVKXXD"
FT   CDS             6734..9919
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   rep_origin      complement(5159..6217)
FT                   /vntifkey="33"
FT                   /label=OriVT
FT   insertion_seq   6224..89
FT                   /source="pABICyano1-6HindIIIBamHI"
FT                   /type="Custom cloned insert"
FT                   /vntifkey="14"
FT                   /label=pABICyano1-6HindIIIBamHI
FT                   /note="Unknown feature type:insert"
```

FIG. 9

```
FT   terminator      3214..3369
FT                   /vntifkey="43"
FT                   /label=TrbcSABICyanol
FT   promoter        96..378
FT                   /vntifkey="30"
FT                   /label=PnirAABICyanol
FT   CDS             2203..3210
FT                   /vntifkey="4"
FT                   /label=synADHmax
FT   CDS             379..2085
FT                   /vntifkey="4"
FT                   /label=PDCmax
FT   gene            2203..3213
FT                   /vntifkey="60"
FT                   /note="ADH"
FT   gene            379..2088
FT                   /vntifkey="60"
FT                   /note="PDC"
SQ   Sequence 12968 BP; 4008 A; 2277 C; 2560 G; 4123 t;
     aatatttttc gtcagatacg caaaccttac aaacataatt aacaactgaa actattgata        60
     tgtctaggtt ttagctctat cacaggttgg atctgtcgac aattaataac ttcttcctgt       120
     acgggcgaat ggccatttgc tcctaactaa ctccgtactg ctttgcggaa cgagcgtagc       180
     gaactctccg aattactaag ccttcatccc tgatagatgc aaaaaacgaa ttaaaattat       240
     gtgtaaaaag aaaatgtgtc tttatttagt agtcaaagtt acaaaatatt aagaatcaaa       300
     ttaataatgt attgggcagt taagtatata agtctttaaa tatttatttg tattcaatat       360
     attaaccgag gacaaattat gaattcttat accgtgggta cttatttagc cgaacgctta       420
     gtgcaaattg gtttaaaaca tcattttgcc gtggctgggg actataattt agtgttattg       480
     gataacttat tattaaataa aaacatggaa caagtgtatt gttgtaatga attaaattgt       540
     ggtttttctg ctgaaggtta tgctagagct aaaggtgcag ctgctgctgt tgttacttat       600
     tctgtgggtg ctttatctgc ttttgatgct attggtggtg cttatgccga aaatttaccc       660
     gtgattttaa tttctggtgc ccctaataat aatgatcatg ccgctggaca tgttttacat       720
     catgccttag gtaaaaccga ttatcattat caattagaaa tggccaaaaa tattactgct       780
     gctgccgaag ctatttatac tcctgaagaa gcccctgcca aaattgatca tgtgattaaa       840
     accgccttac gcgaaaaaaa acccgtgtat ttagaaattg cctgtaatat tgcttctatg       900
     ccttgtgctg ctcctgggcc tgcttctgct ttatttaatg atgaagcctc tgatgaagct       960
     agtttaaatg ctgccgtgga agaaacctta aaatttattg ccaatcgcga taaagttgcc      1020
     gtgttagttg gttctaaatt aagagctgct ggtgctgaag aagctgctgt taaatttgct      1080
     gatgctttag gtggtgcagt tgctactatg gctgctgcca aatctttttt tcccgaagaa      1140
     aatccccatt atattggaac tagttgggga gaagtttctt atcctggtgt ggaaaaaact      1200
     atgaaagaag ccgacgctgt tattgcttta gcccctgtgt ttaatgatta ttctaccact      1260
     ggttggactg atattcccga tcccaaaaaa ttagttttag ccgaacctcg ttctgttgtt      1320
     gttaatggtg ttcgctttcc ctctgtgcat ttaaaagatt atttaacccg cttagcccaa      1380
     aaagtttcta aaaaaactgg tgccttagat tttttaaat ctttaaatgc gggtgaatta       1440
     aaaaaagctg ctcctgctga tccttctgct cctttagtta atgctgaaat tgcccgtcaa      1500
     gttgaagcct tattaacccc taatactacc gttattgccg aaactggtga ttcttggttt      1560
     aatgcccaac gcatgaaatt acctaatggt gcccgtgttg aatatgaaat gcaatggggt      1620
     catattggtt ggtctgtacc tgctgctttt ggttatgctg ttggtgctcc tgaacgtcgt      1680
     aatattttaa tggtgggtga tggttctttt caattaactg cccaagaagt tgcccaaatg      1740
     gttcgcttaa aattacccgt tattattttt ttaataaata attatggtta taccattgaa      1800
     gtgatgattc atgatgggcc atataataat attaaaaatt gggattatgc gggtttaatg      1860
     gaagtgttta atggtaatgg tggttatgat tctggtgctg gtaaaggttt aaaagccaaa      1920
     actggtggtg aattagctga agctattaaa gttgccttag ccaatactga tggcccaacc      1980
     ttaattgaat gttttattgg tcgcgaagat tgtaccgaag aattagttaa atggggtaaa      2040
     cgtgttgctg ctgctaattc tcgcaaaccc gtgaataaat tattgtaatt tttggggatc      2100
     aattcgagct cggtacccaa actagtatgt agggtgaggt tatagctagc gcttttaatt      2160
     aatccgcgga tttgtattca atatattaac cgaggacaac atatgattaa agcctatgct      2220
     gccttagaag ccaatggtaa attacaaccc tttgaatatg atcctggtgc tttaggtgcc      2280
     aatgaagtgg aaattgaagt gcaatattgt ggtgtgtgtc attctgattt atctatgatt      2340
```

FIG. 9 (continued)

```
aataatgaat ggggtatttc taattatccc ttagttcctg gtcatgaagt tgttggtact    2400
gttgctgcta tgggtgaagg tgttaatcat gtggaagtgg gtgatttagt tggtttaggt    2460
tggcattctg gttattgtat gacctgtcat tcttgtttat ctggttatca taatttatgt    2520
gccactgccg aatctactat tgtgggtcat tatggtggtt ttggtgatag agttcgtgct    2580
aaaggtgttt ctgtggtgaa attacccaaa ggtattgatt tagcctctgc tgggccttta    2640
ttttgtggtg gtattaccgt tttttctccc atggtggaat tatctttaaa acctaccgcc    2700
aaagttgctg ttattggtat tggtggttta ggtcatttag ccgttcaatt tttaagagcc    2760
tggggttgtg aagttactgc ttttacctct tctgcccgta aacaaaccga agttttagaa    2820
ttaggtgccc atcatatttt agattctacc aatcctgaag ctattgcttc tgccgaaggt    2880
aaatttgatt atattatttc taccgtgaat ttaaaattag attggaattt atatatcagt    2940
accttagccc ctcaaggtca ttttcatttt gttggtgtgg tgttagaacc cttggactta    3000
aacttatttc ccttattaat gggacaacgt tctgtttctg cttctcctgt tggttctcct    3060
gctactattg ccactatgtt agattttgcc gtgcgtcatg atattaaacc cgtggtggaa    3120
caattttctt ttgatcaaat taatgaagcc attgcccatt tagaatctgg taaagcccat    3180
tatcgcgtgg tgttatctca ttctaaaaat taataagatt aacttctaaa ctgaaacaaa    3240
tttgagggta ggcttcattg tctgccctta ttttttttatt taggaaaagt gaacagacta    3300
aagagtgttg gctctattgc tttgagtatg taaattaggc gttgctgaat taaggtatga    3360
tttttgaccc cttctctctt ctgcagttac ctaggatttc tggcgaaagg gggatgtgct    3420
gcaaggcgat taagttgggt aacgccaggg ttttcccagt cacgacgttg taaaacgacg    3480
gccagtgagc gcgacgtaat acgactcact atagggcgaa ttggcggaag gccgtcaagg    3540
ccgcatggcg cgcctacgta gacaattgtc gatgtaatta ttaactatct tattatagat    3600
gaggggagag ggagaaatta gttcggagag aacgctcgag cgctcgttcc gcaaagcggt    3660
acggagttag ttaggggcta atgggcattc tcccgtacag gaaagagtta gaagttatta    3720
attatcaaca attctccttt gcctagtgca tcgttacctt tttaattaaa acataaggaa    3780
aactaataat cgtaataatt taacctcaaa gtgtaaagaa atgtgaaatt ctgactttta    3840
taacgttaaa gagggaaaaa ttagcagttt aaaataccta gagaatagtc tggggtaagc    3900
atagagaatt agattagtta agttaatcaa attcagaaaa aataataatc gtaaatagtt    3960
aatctgggtg tatagaaaat gatccccttc atgataagat ttaaactcga aaagcaaaag    4020
ccaaaaaact aacttccatt aaaagaagtt gttacatata acgctataaa gaaaatttat    4080
atatttggag gataccaacc atgtctcata ttcaacgtga aactagttgt tctcgtcctc    4140
gtttaaattc taatatggat gccgatttat atggttataa atgggctcgt gataatgttg    4200
gtcaatctgg tgctactatt tatcgtttat atggtaaacc tgatgctcct gaattattct    4260
tgaaacatgg taaaggttct gttgctaatg atgttactga tgaaatggtt cgtttaaact    4320
ggttgactga atttatgcct ttacctacta ttaaacattt tattcgtact cccgatgatg    4380
cttggttatt aactactgct attcctggta aaactgcttt tcaagtttta gaagaatatc    4440
ctgattctgg tgaaaatatt gttgatgctt tagctgtttt tttacgtcgt ttacattcta    4500
ttcccgtttg taattgtcct tttaattctg atcgtgtttt tcgtttagct caagctcaat    4560
ctcgtatgaa taatggttta gttgatgctt ctgattttga tgatgaacgt aatggttggc    4620
ctgttgaaca agtttggaaa gaaatgcaca aattgttacc tttttctcct gattctgttg    4680
ttactcatgg tgattttttct ttagataatt tgatctttga tgaaggtaaa ttgattggtt    4740
gtattgatgt tggtcgtgtt ggtattgctg atcgttatca agatttagct attttatgga    4800
attgtttagg tgaattttct ccttctttac agaaacgttt atttcagaaa tatggtattg    4860
ataatcctga tatgaacaag ttacaatttc atttaatgtt ggacgagttc ttttaagaat    4920
taattcatga ccaaaatccc ttaacgtgag ttttcgttcc actgagcgtc agaccccgta    4980
gaaaagatca aaggatcttc ttgagatcct ttttttctgc gcgtaatctg ctgctattta    5040
aattacgtac acgtgttatt actttgttaa cgacaattgt cttaattaac tgggcctcat    5100
gggccttccg ctcactgccc gctttccagt cgggaaacct gtcgtgccag ctctgcagat    5160
gacggtgaaa acctctgaca catgcagctc ccggagacgg tcacagcttg tctgtaagcg    5220
gatgccggga gcagacaagc ccgtcagggc gcgtcagcgg gtgttggcgg gtgtcggggc    5280
gcagccatga cccagtcacg tagcgatagc ggagtgtata ctggcttaac tatgcggcat    5340
cagagcagat tgtactgaga gtgcaccata tgcggtgtga aataccgcac agatgcgtaa    5400
ggagaaaata ccgcatcagg cgctcttccg cttcctcgct cactgactcg ctgcgctcgg    5460
tcgttcggct gcggcgagcg gtatcagctc actcaaaggc ggtaatacgg ttatccacag    5520
aatcagggga taacgcagga aagaacatgt gagcaaaagg ccagcaaaag gccaggaacc    5580
gtaaaaaggc cgcgttgctg gcgtttttcc ataggctccg cccccctgac gagcatcaca    5640
aaaatcgacg ctcaagtcag aggtggcgaa acccgacagg actataaaga taccaggcgt    5700
ttccccctgg aagctccctc gtgcgctctc ctgttccgac cctgccgctt accggatacc    5760
tgtccgcctt tctcccttcg ggaagcgtgg cgctttctca tagctcacgc tgtaggtatc    5820
tcagttcggt gtaggtcgtt cgctccaagc tgggctgtgt gcacgaaccc cccgttcagc    5880
ccgaccgctg cgccttatcc ggtaactatc gtcttgagtc caacccggta agacacgact    5940
```

FIG. 9 (continued)

```
tatcgccact ggcagcagcc actggtaaca ggattagcag agcgaggtat gtaggcggtg      6000
ctacagagtt cttgaagtgg tggcctaact acggctacac tagaaggaca gtatttggta      6060
tctgcgctct gctgaagcca gttaccttcg gaaaaagagt tggtagctct tgatccggca      6120
aacaaaccac cgctggtagc ggtggttttt ttgtttgcaa gcagcagatt acgcgcagaa      6180
aaaaaggatc tcaagaagat cctttgatct tttctactgc agaagcttgt tagacaccct      6240
gtcatgtatt ttatattatt tatttcacca tacggattaa gtgaaaccta atgaaaatag      6300
tactttcgga gctttaactt taatgaaggt atgttttttt atagacatcg atgtctggtt      6360
taacaatagg aaaaagtagc taaaactccc atgaattaaa gaaataacaa ggtgtctaac      6420
aacctgttat taagaatgtt agaaaagact taacatttgt gttgagtttt tatagacatt      6480
ggtgtctaga catacggtag ataaggtttg ctcaaaaata aaataaaaaa agattggact      6540
aaaaaacatt taatttagta caatttaatt agttattttt tcgtctcaaa ttttgctttg      6600
ttgagcagaa atttagataa aaaaatcccc gtgatcagat tacaatgtcg ttcattgtac      6660
gatgtgtcga aaaatcttta cgacactcta aactgaccac acgggggaaa aagaaaactg      6720
aactaataac atcatgatac tcggaaaacc tagcaattct caacccctaa acaaaagaaa      6780
cttccaaaac cctgaccata taaaggagtg gcaacaatca gcaatcagtc aagatttgat      6840
agcagaaaat cttgtatcgg ttgctaatgg ttttgatgta ctatttatcg gcaataaata      6900
ccgaactaac acgggtgttc tgtcacggca catattaaac tcctattctc atttagaaga      6960
tggtggttcg tatggtagaa catttgaccc atttaccaat aaagaaatgc agtgggttca      7020
atttaaaccg aatagaccaa gaaaaggttc tactggtaag gtaatcaaat atgaatcgcc      7080
aaaaggtgaa cctacaagag ttctaatgcc gtttgtgcct atgaaaatat ggcaacggat      7140
tagcgataag ttcggagtac cgattaatcc gaaaaaagat actcactttt gggaatgggt      7200
aaagaataat ccatcgatac cgattgccat tacagaagga aataaaaaag ctaattgcct      7260
attatcctat ggctatcctg ctattgcctt tgtaggcatt tggaacggat tagagaaaat      7320
aaatgatttc tcgaaggaaa agcagttaaa agaggatttg aaatggttgt tatccaacgg      7380
caaccgaaat attaatatca tctttgacca agaccagaaa caaaaaactg taattaatgt      7440
aaacaaagct attttcgctt tatcttctct aataagtaga aatggtcata aagttaatat      7500
tgtgcaatgg ttgccgtcaa aaggtaaagg aatagatgat tatttggtag ctttaccttt      7560
tgagaaaaga gaaaatcatt tagacaactt aattaaaatt gcaccatcat ttaatttttg      7620
gtcaactaaa tacttattca agtgtcgtaa accagattta accgtaaatt gccgttattt      7680
gagcgatgca gtaaaagaat tacctcaaga ggatatagca ttaatagcac ctcacggcac      7740
gggtaaaact tcattagtag ctactcacgt taagaatcgg agttatcacg gaaggaaaac      7800
tatttcattg gtgcatcttg aaagtttagc caaagctaat ggcaacgcac ttggattata      7860
ttaccgaacc gaaaataata ttgaaaagca atatcttgga tttagcttat gtgtagatag      7920
ttgccgtgat aagattaacg gcattacaac tgatattatt tcaggtcaag attattgcct      7980
tttcattgat gaaattgacc aagtaattcc acacatcctt aacagtgaaa ctgaagtaag      8040
taagtataga tgcaccatca ttgacacttt ttctgaactg gtgagaaatg ctgaacaggt      8100
cattattgct gatgctgatt tatccgatgt gacgattgac ctaatagaaa acatcagagg      8160
taaaaaacta tatgtaatca agaatgaata tcagtatcag ggaatgactt ttaacgccgt      8220
tggttcacca ttagaaatga tggcaatgat gggaaaatcg gtgtcagaag gcaagaaatt      8280
atttattaac accacatccc aaaaggcaaa aagtaagtac ggcacaatcg ctcttgagtc      8340
ttatattttt ggtctaaata aagaagcaaa gatattaaga atagactctg aaaccactaa      8400
aaaccctgaa catccagcct ataaaatcat tgaccaagac ttaaataata tcctcaaaga      8460
ttatgattat gtcattgcct caccttgcct tcaaacaggt gtcagtatta ccttaaaagg      8520
gcattttgac cagcaattta acttttccag tggaaacatt acacctcatt gctttttaca      8580
gcaaatgtgg cggttgaggg atgcagaaat tgaaagattc tattatgtgc cgaactcatc      8640
taacctcaat ctcattggga ataagtcaag ttcaccatca gaccttctaa agagcaataa      8700
caagatggca acggcaacgg ttaacctttt gggtagaatc gactccgaat attccctaga      8760
gtatgaatcg cacggcattt ggcttgagac gtgggcaaaa ttatcagcac ggcataacag      8820
ttcaatgcgt tgttactctg aaattcttac ctatctaatt acgtctcaag ggcataaatt      8880
aaatatcaac attccctcac ctcttgcaga tattaagaag ctaaatgatg aggtaagtag      8940
taacagggaa aaggtaaaaa atgagagata ctctcagagg ttaaactcac cagatattaa      9000
cgatgcagaa gctaccatac tcgaatctaa agagcaaaaa atcggattga ctctcaatga      9060
gagatgcacc ctagaaaagc ataaagttaa gaagcggtat gggaatgtaa agatggatat      9120
tctcaccttt gatgatgatg gactataccc caaactcaga ctattttatt acctcaccat      9180
cggtaaacct catctcaagg ctaatgacag aaaagctatt gccaaaatgg gcaatgacaa      9240
taaaggcaag attctatcaa aagacttagt taataaaact tactccgctc gtgtgaaggt      9300
cttagagatt cttaaactaa ctgactttat cgacaatctt agagatgaac tcttaataac      9360
tcccaataat ccagctatca ccgattttaa taatcttctg ctaagagcta agaaggattt      9420
aagagtatta ggagtcaaca tcggaaaata tccaatggcc aacattaatg ccgtacttac      9480
```

FIG. 9 (continued)

```
tctcattggt cacaaacttt ctgtaatgag agatgagttc ggaaaagaga aaaggataaa      9540
agtagatggt aaatcatacc gatgttatca acttgaaaca ttaccagatt ttaccaatga      9600
tactcttgac tactggttag aaaatgatag ccaaaaagaa gtaacagcaa cagaaaatta      9660
ctccgaaaat tttaaccctt caaatagcta caatccagac agtaagacac tttcagaggg      9720
tgcaaatttc ctatatataa ataaagaaga attgcatcca aataaattgc acctagaaat      9780
aaaagaaggt gctgaacttt ttttattcgg ggtaaaggtg attgtgaaag gaatcttgga      9840
cggggcagta actatattct ctatgggtca agaatacgat ttatccctca atgaactaga      9900
ggggatgtta acatcatgaa ctttacaaga atctttttaa agggcgatcg caccatgtta      9960
aatgatggta catttgttca gatatttgat atttaccatg accacgcatt gggagtgacc     10020
cttgacctta agacagaaaa aattatttcc gatgatgtta gggtaattac tgtcaaagac     10080
ttattgttcg atggcactta taaaggggta aaatctttta tgcccgataa tgcccgataa     10140
tgcccgattg atgctacaaa atcccataat cataagcgat aatcccctaa tagcttgtaa     10200
ttcttgaacc gtagcgattt tagagtattc caaaaagaag aaataaacac cgcaaaatgt     10260
cgtatttcac atatataaac caaggttttt tgccctaaaa tctttatgtt tgtagtgtga     10320
tgttgggtca aaatggtcag aaaagttgca aggtttttat ggatgcttac gcgcgcgagg     10380
ggtaagcatc cccaaatagt tactttatcc tagtccatgc ccatttattg ccgtcccgtt     10440
cggctttaaa aaagtgccaa aactcacaag gtgcaataaa aagttctgta cctttcgcaa     10500
ccctagataa tctttcaaca gttacttttt ttcctattat ctcggtacaa agtttggcta     10560
gtttctcttt tccctctttt tcaatcaagc cttcttgtat gcccaactca ttgattaatc     10620
tctctatttt taccattatt tcccgttcag gtagtttatc ccctaaatct tcatcggggg     10680
gcaatgtagg gcattctgaa ggggcttttt cttctgtctg gacattatct aatattgaag     10740
taaccaaact atcttcagtt ttttctattc ctattaattc atattcggtt actgtatccg     10800
tatcaatatc cgaataacta tctttatccg tattagctat tcggttaagt ttatccgtta     10860
actcagaaac aagactatat agcggtttta gcttttcttc tatcctgtta tctaatacgg     10920
ataagtttat acggttatca ttatccgtat tagtatcatt gggctttttt ggtagttcta     10980
ccccctcata aaccgctttt attcccaatt ccaacagact gataacagta tcctttataa     11040
tgggtttttt gctgatatgg tgaacttttg ccccttccat cattgcgata ctttctatct     11100
cactcatcaa cttatcgctt aagtgaatct cgtatctgtt taatccctta ctggttttat     11160
tcatatccgt ttactttatt cggttaacaa ttctatttta tacgaataaa atattatacg     11220
gttaacttta tacgtttaac tattttatct atacggataa cagtaataag ttattcgtat     11280
tagttatacg tttactttta tccaaataaa attagtgcat ttaaactaaa agaatgattt     11340
tatcggagtt gatagcattg gattaaccta aagatgttta taagctatat ctgataagta     11400
tttaaggtta ttttgttatt ctgtttattg acattatcag aataaaagaa tagaatataa     11460
ttgttgagag ataagaggtt taagtgatta tggttaagaa gttagttggt tatgtcaggg     11520
tcagtagtga atcgcaagag gataacacta gcttacagaa tcagatagag agaattgaag     11580
catattgtat ggcttttggt tatgagttgg taaaaatatt caaagaggtt gccactggta     11640
caaaagcaga tattgaaacc cgtcctattt ttaatgaagc tatagaatac ttgaaacagg     11700
ataatgctaa tggaattatt gccttgaagc tagaccgaat cgcacggaat gctttagatg     11760
tattgcgttt ggttcgtgaa accttagaac cacaaaataa aatgttagtg ttactagata     11820
ttcaggtaga tacttcgaca ccttcaggaa aaatgatttt aactgtaatg agtgccgttg     11880
ctgaactcga aagagacatg atctatgatc gcactcaggg gggtagaaag actaaagccc     11940
aaaagggcgg gtatgcctac gggaaaccta aatttggcta taagactgaa gaaaaggaac     12000
taaaagaaga ttcagcacaa caggaaacta ttaaactaat taagagacac cgtaggtcag     12060
ggaaaagcta ccagaaaata gctgattatc tcaatgccca aagtattccc actaaacaag     12120
gtaagaaatg gagttctagc gtcgtctatc gaatctgtca ggaaaaagct ggttaagtct     12180
gtttatagat atttagaatt tattgaataa aaatagtatg aacaataaat atttatggac     12240
taaccacgct cggaaacgtt taactgaacg atgggaaata aaagaatcat gggttattga     12300
taccatcgaa aatcctgaac gttcagaatt tattgttgat gagtcagggg aaaaatatca     12360
ttactataaa agaatagcta agtttaagaa tagagtgtta gaagtgataa cttctgccaa     12420
ctcaacaccc acaagaataa taacctttta ctttaaccgt aacatgagga aaaatttatg     12480
attgttactt acgataatga agttgacgca atttatttta agttaacgga aaataaaatt     12540
gatagcaccg aacctcaaac agacaggatt atcattgatt acgatgaaag taataatatt     12600
gttggcattg aggtattaga ttttaattat cttgtcaaga aaggtttaac cgttgctgat     12660
ttaccttttt ctgaagatga aagattaaca gcttctcaat attttaattt tcctgttgct     12720
atctaatcca gaagggcaa taatcccctt ctttcatcga gttagactta atatcacaaa     12780
agtcattttc attttaccgt ttcttttcca cagcgtccgt acgcccctcg ttaaatctca     12840
aaaccgacaa tttatgatgt ttataaaaag ttactcactt taataagtat ttatactcat     12900
taaagggtta ttcttttttt gtagcctgat aggttgggaa ggaatatttc agattatcag     12960
atttgttg                                                              12968
```

FIG. 9 (continued)

TK293 pABICyano1-6.8 PnirAABICyano1-PDCmax-PrpsLABICyano1-synADHmax-PrbcABICyano1-Km**-oriVT

```
ID   TK293\pABICyano1-6.8_PnirAABICyano1-PDCmax-PrpsLABICyano1-synADHmax-
PrbcABICyano1-Km**-oriVT standard; circular DNA;    ; 13449 BP.
CC   This file is created by Vector NTI
CC   http://www.invitrogen.com/
CC   VNTDATE|620148318|
CC   VNTDBDATE|629812662|
CC   LSOWNER|
CC   VNTAUTHORNAME|Frank Uliczka|
FH   Key             Location/Qualifiers
FH
FT   promoter        4055..4580
FT                   /vntifkey="30"
FT                   /label=PrbcABICyano1
FT   CDS             4582..5397
FT                   /vntifkey="4"
FT                   /label=Km**
FT                   /note=" maximal codon optimized kanamycin resistance gene "
FT   CDS             12959..13207
FT                   /vntifkey="4"
FT                   /label=ORF\6
FT                   /note="orf6"
FT   CDS             12699..12962
FT                   /vntifkey="4"
FT                   /label=ORF\5
FT                   /note="orf5"
FT   CDS             11971..12657
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(10881..11645)
FT                   /vntifkey="4"
FT                   /label=ORF\3
FT                   /note="orf3"
FT   CDS             10436..10621
FT                   /vntifkey="4"
FT                   /label=ORF\2
FT                   /note="orf2"
FT   rep_origin      complement(9736..9753)
FT                   /vntifkey="33"
FT                   /label=Rep_Origin_1\(potential)
FT                   /note="potential rep origin; match pNostoc (Acc# M81381) nick
site (358-375); on reserse strand"
FT   misc_feature    9996..10029
FT                   /vntifkey="21"
FT                   /label=Rep\motif
FT                   /note="Rep protein active site motig EXXKYXVKXXD"
FT   CDS             7215..10400
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
```

FIG. 11

```
FT   rep_origin      complement(5640..6698)
FT                   /vntifkey="33"
FT                   /label=OriVT
FT   insertion_seq   6705..89
FT                   /source="pABICyanol-6HindIIIBamHI"
FT                   /type="Custom cloned insert"
FT                   /vntifkey="14"
FT                   /label=pABICyanol-6HindIIIBamHI
FT                   /note="Unknown feature type:insert"
FT   promoter        2112..2680
FT                   /vntifkey="30"
FT                   /label=PrpsLABICyanol
FT   gene            379..2088
FT                   /vntifkey="60"
FT                   /note="PDC"
FT   gene            2684..3694
FT                   /vntifkey="60"
FT                   /note="ADH"
FT   CDS             379..2085
FT                   /vntifkey="4"
FT                   /label=PDCmax
FT   CDS             2684..3691
FT                   /vntifkey="4"
FT                   /label=synADHmax
FT   promoter        96..378
FT                   /vntifkey="30"
FT                   /label=PnirAABICyanol
FT   terminator      3695..3850
FT                   /vntifkey="43"
FT                   /label=TrbcABICyanol
SQ   Sequence 13449 BP; 4193 A; 2336 C; 2598 G; 4322 t;
     aatattttc gtcagatacg caaaccttac aaacataatt aacaactgaa actattgata        60
     tgtctaggtt ttagctctat cacaggttgg atctgtcgac aattaataac ttcttcctgt       120
     acgggcgaat ggccatttgc tcctaactaa ctccgtactg ctttgcggaa cgagcgtagc       180
     gaactctccg aattactaag ccttcatccc tgatagatgc aaaaaacgaa ttaaaattat       240
     gtgtaaaaag aaaatgtgtc tttatttagt agtcaaagtt acaaaatatt aagaatcaaa       300
     ttaataatgt attgggcagt taagtatata agtctttaaa tatttatttg tattcaatat       360
     attaaccgag gacaaattat gaattcttat accgtgggta cttatttagc cgaacgctta       420
     gtgcaaattg gtttaaaaca tcattttgcc gtggctgggg actataattt agtgttattg       480
     gataacttat tattaaataa aaacatggaa caagtgtatt gttgtaatga attaaattgt       540
     ggtttttctg ctgaaggtta tgctagagct aaaggtgcag ctgctgctgt tgttacttat       600
     tctgtgggtg ctttatctgc ttttgatgct attggtggtg cttatgccga aaatttaccc       660
     gtgattttaa tttctggtgc ccctaataat aatgatcatg ccgctggaca tgttttacat       720
     catgccttag gtaaaaccga ttatcattat caattagaaa tggccaaaaa tattactgct       780
     gctgccgaag ctatttatac tcctgaagaa gcccctgcca aaattgatca tgtgattaaa       840
     accgccttac gcgaaaaaaa acccgtgtat ttagaaattg cctgtaatat tgcttctatg       900
     ccttgtgctg ctcctgggcc tgcttctgct ttatttaatg atgaagcctc tgatgaagct       960
     agtttaaatg ctgccgtgga agaaacctta aaatttattg ccaatcgcga taaagttgcc      1020
     gtgttagttg gttctaaatt aagagctgct ggtgctgaag aagctgctgt taaatttgct      1080
     gatgctttag gtggtgcagt tgctactatg gctgctgcca aatctttttt tcccgaagaa      1140
     aatccccatt atattggaac tagttgggga gaagtttctt atcctggtgt ggaaaaaact      1200
     atgaaagaag ccgacgctgt tattgcttta gcccctgtgt ttaatgatta ttctaccact      1260
```

FIG. 11(continued)

```
ggttggactg atattcccga tcccaaaaaa ttagttttag ccgaacctcg ttctgttgtt    1320
gttaatggtg ttcgctttcc ctctgtgcat ttaaaagatt atttaacccg cttagcccaa    1380
aaagtttcta aaaaaactgg tgccttagat ttttttaaat ctttaaatgc gggtgaatta    1440
aaaaaagctg ctcctgctga tccttctgct cctttagtta atgctgaaat tgcccgtcaa    1500
gttgaagcct tattaacccc taatactacc gttattgccg aaactggtga ttcttggttt    1560
aatgcccaac gcatgaaatt acctaatggt gcccgtgttg aatatgaaat gcaatggggt    1620
catattggtt ggtctgtacc tgctgctttt ggttatgctg ttggtgctcc tgaacgtcgt    1680
aatattttaa tggtgggtga tggttctttt caattaactg cccaagaagt tgcccaaatg    1740
gttcgcttaa aattacccgt tattattttt ttaataaata attatggtta taccattgaa    1800
gtgatgattc atgatgggcc atataataat attaaaaatt gggattatgc gggtttaatg    1860
gaagtgttta atggtaatgg tggttatgat tctggtgctg gtaaaggttt aaaagccaaa    1920
actggtggtg aattagctga agctattaaa gttgccttag ccaatactga tgggccaacc    1980
ttaattgaat gttttattgg tcgcgaagat tgtaccgaag aattagttaa atggggtaaa    2040
cgtgttgctg ctgctaattc tcgcaaaccc gtgaataaat tattgtaatt tttgggggatc   2100
aattcgagct cctccgctta aaaaatttca tttttcgatc aaaaaagaca aattattact    2160
aattagctca tggcaataaa taatcagtag taatctgttt tcacatttta ttgttaattt    2220
ttattattgc taatatcaac cttttctact tctgcttaat atttttattta tgctcaatgg   2280
gaaaatctga aataagattg agaacagtgt taccaataga agtatttaag gtttaaagca    2340
taccttaaag ataacatttt tttttgaaaa gagtcaaatt atttttgaaa ggctgatatt    2400
tttgatattt actaatattt tatttatttc tttttccctt aaaataagag ctaaatctgt    2460
ttttattatc atttatcaag ctctattaat acctcaactt tttcaagaaa aaataataat    2520
aatttttccc tctattctca tgacctttta ggaaaattaa ttttagaaaa actattgaca    2580
aacccataaa aaatgagata agattataga ttgtcactgg tattttatac tagaggcaaa    2640
ttatatttat atatacaaaa atgctgtata aaaaacatct catatgatta aagcctatgc    2700
tgccttagaa gccaatggta aattacaacc ctttgaatat gatcctggtg ctttaggtgc    2760
caatgaagtg gaaattgaag tgcaatattg tggtgtgtgt cattctgatt tatctatgat    2820
taataatgaa tggggtattt ctaattatcc cttagttcct ggtcatgaag ttgttggtac    2880
tgttgctgct atgggtgaag gtgttaatca tgtggaagtg ggtgatttag ttggtttagg    2940
ttggcattct ggttattgta tgacctgtca ttcttgttta tctggttatc ataatttatg    3000
tgccactgcc gaatctacta ttgtgggtca ttatggtggt tttggtgata gagttcgtgc    3060
taaaggtgtt tctgtggtga aattacccaa aggtattgat ttagcctctg ctgggccttt    3120
attttgtggt ggtattaccg tttttctccc catggtggaa ttatctttaa aacctaccgc    3180
caaagttgct gttattggta ttggtggttt aggtcattta gccgttcaat ttttaagagc    3240
ctggggttgt gaagttactg cttttacctc ttctgcccgt aaacaaaccg aagttttaga    3300
attaggtgcc catcatattt tagattctac caatcctgaa gctattgctt ctgccgaagg    3360
taaatttgat tatattattt ctaccgtgaa tttaaaatta gattggaatt tatatatcag    3420
taccttagcc cctcaaggtc attttcattt tgttggtgtg gtgttagaac ccttggactt    3480
aaacttattt cccttattaa tgggacaacg ttctgtttct gcttctcctg ttggttctcc    3540
tgctactatt gccactatgt tagattttgc cgtgcgtcat gatattaaac ccgtggtgga    3600
acaattttct tttgatcaaa ttaatgaagc cattgcccat ttagaatctg gtaaagccca    3660
ttatcgcgtg gtgttatctc attctaaaaa ttaataagat taacttctaa actgaaacaa    3720
atttgagggt aggcttcatt gtctgccctt atttttttat ttaggaaaag tgaacagact    3780
aaagagtgtt ggctctattg ctttgagtat gtaaattagg cgttgctgaa ttaaggtatg    3840
atttttgacc ccttctctct tctgcagtta cctaggattt ctggcgaaag gggatgtgc     3900
tgcaaggcga ttaagttggg taacgccagg gttttcccag tcacgacgtt gtaaaacgac    3960
ggccagtgag cgcgacgtaa tacgactcac tatagggcga attggcggaa ggccgtcaag    4020
gccgcatggc gcgcctacgt agacaattgt cgatgtaatt attaactatc ttattataga    4080
tgaggggaga gggagaaatt agttcggaga gaacgctcga gcgctcgttc cgcaaagcgg    4140
tacggagtta gttaggggct aatgggcatt ctcccgtaca ggaaagagtt agaagttatt    4200
aattatcaac aattctcctt tgcctagtgc atcgttacct ttttaattaa aacataagga    4260
aaactaataa tcgtaataat ttaacctcaa agtgtaaaga aatgtgaaat tctgactttt    4320
```

FIG. 11(continued)

```
ataacgttaa agagggaaaa attagcagtt taaaatacct agagaatagt ctggggtaag      4380
catagagaat tagattagtt aagttaatca aattcagaaa aaataataat cgtaaatagt      4440
taatctgggt gtatagaaaa tgatcccctt catgataaga tttaaactcg aaaagcaaaa      4500
gccaaaaaac taacttccat taaaagaagt tgttacatat aacgctataa agaaaattta      4560
tatatttgga ggataccaac catgtctcat attcaacgtg aaactagttg ttctcgtcct      4620
cgtttaaatt ctaatatgga tgccgattta tatggttata aatgggctcg tgataatgtt      4680
ggtcaatctg gtgctactat ttatcgttta tatggtaaac ctgatgctcc tgaattattc      4740
ttgaaacatg gtaaaggttc tgttgctaat gatgttactg atgaaatggt tcgtttaaac      4800
tggttgactg aatttatgcc tttacctact attaaacatt ttattcgtac tcccgatgat      4860
gcttggttat taactactgc tattcctggt aaaactgctt ttcaagtttt agaagaatat      4920
cctgattctg gtgaaaatat tgttgatgct ttagctgttt ttttacgtcg tttacattct      4980
attcccgttt gtaattgtcc ttttaattct gatcgtgttt ttcgtttagc tcaagctcaa      5040
tctcgtatga ataatggttt agttgatgct tctgattttg atgatgaacg taatggttgg      5100
cctgttgaac aagtttggaa agaaatgcac aaattgttac ctttttctcc tgattctgtt      5160
gttactcatg gtgatttttc tttagataat ttgatctttg atgaaggtaa attgattggt      5220
tgtattgatg ttggtcgtgt tggtattgct gatcgttatc aagatttagc tattttatgg      5280
aattgtttag gtgaattttc tccttcttta cagaaacgtt tatttcagaa atatggtatt      5340
gataatcctg atatgaacaa gttacaattt catttaatgt tggacgagtt cttttaagaa      5400
ttaattcatg accaaaatcc cttaacgtga gttttcgttc cactgagcgt cagaccccgt      5460
agaaaagatc aaaggatctt cttgagatcc tttttttctg cgcgtaatct gctgctattt      5520
aaattacgta cacgtgttat tactttgtta acgacaattg tcttaattaa ctgggcctca      5580
tgggccttcc gctcactgcc cgctttccag tcgggaaacc tgtcgtgcca gctctgcaga      5640
tgacggtgaa aacctctgac acatgcagct cccggagacg gtcacagctt gtctgtaagc      5700
ggatgccggg agcagacaag cccgtcaggg cgcgtcagcg ggtgttggcg ggtgtcgggg      5760
cgcagccatg acccagtcac gtagcgatag cggagtgtat actggcttaa ctatgcggca      5820
tcagagcaga ttgtactgag agtgcaccat atgcggtgtg aaataccgca cagatgcgta      5880
aggagaaaat accgcatcag gcgctcttcc gcttcctcgc tcactgactc gctgcgctcg      5940
gtcgttcggc tgcggcgagc ggtatcagct cactcaaagg cggtaatacg gttatccaca      6000
gaatcagggg ataacgcagg aaagaacatg tgagcaaaag gccagcaaaa ggccaggaac      6060
cgtaaaaagg ccgcgttgct ggcgtttttc cataggctcc gcccccctga cgagcatcac      6120
aaaaatcgac gctcaagtca gaggtggcga aacccgacag gactataaag ataccaggcg      6180
tttccccctg gaagctccct cgtgcgctct cctgttccga ccctgccgct taccggatac      6240
ctgtccgcct ttctcccttc gggaagcgtg gcgctttctc atagctcacg ctgtaggtat      6300
ctcagttcgg tgtaggtcgt tcgctccaag ctgggctgtg tgcacgaacc ccccgttcag      6360
cccgaccgct gcgccttatc cggtaactat cgtcttgagt ccaacccggt aagacacgac      6420
ttatcgccac tggcagcagc cactggtaac aggattagca gagcgaggta tgtaggcggt      6480
gctacagagt tcttgaagtg gtggcctaac tacggctaca ctagaaggac agtatttggt      6540
atctgcgctc tgctgaagcc agttaccttc ggaaaaagag ttggtagctc ttgatccggc      6600
aaacaaacca ccgctggtag cggtggtttt tttgtttgca agcagcagat tacgcgcaga      6660
aaaaaaggat ctcaagaaga tcctttgatc ttttctactg cagaagcttg ttagacaccc      6720
tgtcatgtat tttatattat ttatttcacc atacggatta agtgaaacct aatgaaaata      6780
gtactttcgg agctttaact ttaatgaagg tatgtttttt tatagacatc gatgtctggt      6840
ttaacaatag gaaaaagtag ctaaaactcc catgaattaa agaaataaca aggtgtctaa      6900
caacctgtta ttaagaatgt tagaaaagac ttaacatttg tgttgagttt ttatagacat      6960
tggtgtctag acatacggta gataaggttt gctcaaaaat aaaataaaaa aagattggac      7020
taaaaaacat ttaatttagt acaatttaat tagttatttt ttcgtctcaa attttgcttt      7080
gttgagcaga aatttagata aaaaaatccc cgtgatcaga ttacaatgtc gttcattgta      7140
cgatgtgtcg aaaaatcttt acgacactct aaactgacca cacgggggaa aaagaaaact      7200
gaactaataa catcatgata ctcggaaaac ctagcaattc tcaaccccta aacaaaagaa      7260
acttccaaaa ccctgaccat ataaaggagt ggcaacaatc agcaatcagt caagatttga      7320
tagcagaaaa tcttgtatcg gttgctaatg gttttgatgt actatttatc ggcaataaat      7380
```

FIG. 11(continued)

```
accgaactaa cacgggtgtt ctgtcacggc acatattaaa ctcctattct catttagaag     7440
atggtggttc gtatggtaga acatttgacc catttaccaa taaagaaatg cagtgggttc     7500
aatttaaacc gaatagacca agaaaaggtt ctactggtaa ggtaatcaaa tatgaatcgc     7560
caaaaggtga acctacaaga gttctaatgc cgtttgtgcc tatgaaaata tggcaacgga     7620
ttagcgataa gttcggagta ccgattaatc cgaaaaaaga tactcacttt tgggaatggg     7680
taaagaataa tccatcgata ccgattgcca ttacagaagg aaataaaaaa gctaattgcc     7740
tattatccta tggctatcct gctattgcct ttgtaggcat ttggaacgga ttagagaaaa     7800
taaatgattt ctcgaaggaa aagcagttaa aagaggattt gaaatggttg ttatccaacg     7860
gcaaccgaaa tattaatatc atctttgacc aagaccagaa acaaaaaact gtaattaatg     7920
taaacaaagc tattttcgct ttatcttctc taataagtag aaatggtcat aaagttaata     7980
ttgtgcaatg gttgccgtca aaaggtaaag gaatagatga ttatttggta gctttacctt     8040
ttgagaaaag agaaaatcat ttagacaact taattaaaat tgcaccatca tttaattttt     8100
ggtcaactaa atacttattc aagtgtcgta aaccagattt aaccgtaaat tgccgttatt     8160
tgagcgatgc agtaaaagaa ttacctcaag aggatatagc attaatagca cctcacggca     8220
cgggtaaaac ttcattagta gctactcacg ttaagaatcg gagttatcac ggaaggaaaa     8280
ctatttcatt ggtgcatctt gaaagtttag ccaaagctaa tggcaacgca cttggattat     8340
attaccgaac cgaaaataat attgaaaagc aatatcttgg atttagctta tgtgtagata     8400
gttgccgtga taagattaac ggcattacaa ctgatattat ttcaggtcaa gattattgcc     8460
ttttcattga tgaaattgac caagtaattc cacacatcct taacagtgaa actgaagtaa     8520
gtaagtatag atgcaccatc attgacactt tttctgaact ggtgagaaat gctgaacagg     8580
tcattattgc tgatgctgat ttatccgatg tgacgattga cctaatagaa aacatcagag     8640
gtaaaaaact atatgtaatc aagaatgaat atcagtatca gggaatgact tttaacgccg     8700
ttggttcacc attagaaatg atggcaatga tgggaaaatc ggtgtcagaa ggcaagaaat     8760
tatttattaa caccacatcc caaaaggcaa aaagtaagta cggcacaatc gctcttgagt     8820
cttatatttt tggtctaaat aaagaagcaa agatattaag aatagactct gaaaccacta     8880
aaaaccctga acatccagcc tataaaatca ttgaccaaga cttaaataat atcctcaaag     8940
attatgatta tgtcattgcc tcaccttgcc ttcaaacagg tgtcagtatt accttaaaag     9000
ggcattttga ccagcaattt aacttttcca gtggaaacat tacacctcat tgctttttac     9060
agcaaatgtg gcggttgagg gatgcagaaa ttgaaagatt ctattatgtg ccgaactcat     9120
ctaacctcaa tctcattggg aataagtcaa gttcaccatc agaccttcta aagagcaata     9180
acaagatggc aacggcaacg gttaaccttt tgggtagaat cgactccgaa tattccctag     9240
agtatgaatc gcacggcatt tggcttgaga cgtgggcaaa attatcagca cggcataaca     9300
gttcaatgcg ttgttactct gaaattctta cctatctaat tacgtctcaa gggcataaat     9360
taaatatcaa cattccctca cctcttgcag atattaagaa gctaaatgat gaggtaagta     9420
gtaacaggga aaaggtaaaa aatgagagat actctcagag gttaaactca ccagatatta     9480
acgatgcaga agctaccata ctcgaatcta aagagcaaaa aatcggattg actctcaatg     9540
agagatgcac cctagaaaag cataaagtta agaagcggta tgggaatgta aagatggata     9600
ttctcacctt tgatgatgat ggactatacc ccaaactcag actattttat tacctcacca     9660
tcggtaaacc tcatctcaag gctaatgaca gaaaagctat tgccaaaatg ggcaatgaca     9720
ataaaggcaa gattctatca aaagacttag ttaataaaac ttactccgct cgtgtgaagg     9780
tcttagagat tcttaaacta actgacttta tcgacaatct tagagatgaa ctcttaataa     9840
ctcccaataa tccagctatc accgatttta ataatcttct gctaagagct aagaaggatt     9900
taagagtatt aggagtcaac atcggaaaat atccaatggc caacattaat gccgtactta     9960
ctctcattgg tcacaaactt tctgtaatga gagatgagtt cggaaaagag aaaaggataa    10020
aagtagatgg taaatcatac cgatgttatc aacttgaaac attaccagat tttaccaatg    10080
atactcttga ctactggtta gaaaatgata gccaaaaaga agtaacagca acagaaaatt    10140
actccgaaaa ttttaaccct tcaaatagct acaatccaga cagtaagaca ctttcagagg    10200
gtgcaaattt cctatatata aataaagaag aattgcatcc aaataaattg cacctagaaa    10260
taaaagaagg tgctgaactt tttttattcg ggtaaaggt gattgtgaaa ggaatcttgg     10320
acggggcagt aactatattc tctatgggtc aagaatacga tttatccctc aatgaactag    10380
aggggatgtt aacatcatga actttacaag aatcttttta aagggcgatc gcaccatgtt    10440
```

FIG. 11(continued)

```
aaatgatggt acatttgttc agatatttga tatttaccat gaccacgcat tgggagtgac    10500
ccttgacctt aagacagaaa aaattatttc cgatgatgtt agggtaatta ctgtcaaaga    10560
cttattgttc gatggcactt ataaaggggt aaaatctttt atgcccgata atgcccgata    10620
atgcccgatt gatgctacaa aatcccataa tcataagcga taatccccta atagcttgta    10680
attcttgaac cgtagcgatt ttagagtatt ccaaaaagaa gaaataaaca ccgcaaaatg    10740
tcgtatttca catatataaa ccaaggtttt ttgccctaaa atctttatgt ttgtagtgtg    10800
atgttgggtc aaaatggtca gaaaagttgc aaggttttta tggatgctta cgcgcgcgag    10860
gggtaagcat ccccaaatag ttactttatc ctagtccatg cccatttatt gccgtcccgt    10920
tcggctttaa aaaagtgcca aaactcacaa ggtgcaataa aaagttctgt acctttcgca    10980
accctagata atctttcaac agttactttt tttcctatta tctcggtaca aagtttggct    11040
agtttctctt ttccctcttt ttcaatcaag ccttcttgta tgcccaactc attgattaat    11100
ctctctattt ttaccattat ttcccgttca ggtagtttat cccctaaatc ttcatcgggg    11160
ggcaatgtag ggcattctga aggggctttt tcttctgtct ggacattatc taatattgaa    11220
gtaaccaaac tatcttcagt tttttctatt cctattaatt catattcggt tactgtatcc    11280
gtatcaatat ccgaataact atctttatcc gtattagcta ttcggttaag tttatccgtt    11340
aactcagaaa caagactata tagcggtttt agcttttctt ctatcctgtt atctaatacg    11400
gataagttta tacggttatc attatccgta ttagtatcat tgggcttttt tggtagttct    11460
accccctcat aaaccgcttt tattcccaat tccaacagac tgataacagt atcctttata    11520
atgggttttt tgctgatatg gtgaactttt gccccttcca tcattgcgat actttctatc    11580
tcactcatca acttatcgct taagtgaatc tcgtatctgt ttaatccctt actggtttta    11640
ttcatatccg tttactttat tcggttaaca attctatttt atacgaataa aatattatac    11700
ggttaacttt atacgtttaa ctattttatc tatacggata acagtaataa gttattcgta    11760
ttagttatac gtttactttt atccaaataa aattagtgca tttaaactaa aagaatgatt    11820
ttatcggagt tgatagcatt ggattaacct aaagatgttt ataagctata tctgataagt    11880
atttaaggtt attttgttat tctgtttatt gacattatca gaataaaaga atagaatata    11940
attgttgaga gataagaggt ttaagtgatt atggttaaga agttagttgg ttatgtcagg    12000
gtcagtagtg aatcgcaaga ggataacact agcttacaga atcagataga gagaattgaa    12060
gcatattgta tggcttttgg ttatgagttg gtaaaaatat tcaaagaggt tgccactggt    12120
acaaaagcag atattgaaac ccgtcctatt tttaatgaag ctatagaata cttgaaacag    12180
gataatgcta atggaattat tgccttgaag ctagaccgaa tcgcacggaa tgctttagat    12240
gtattgcgtt tggttcgtga aaccttagaa ccacaaaata aaatgttagt gttactagat    12300
attcaggtag atacttcgac accttcagga aaaatgattt taactgtaat gagtgccgtt    12360
gctgaactcg aaagagacat gatctatgat cgcactcagg ggggtagaaa gactaaagcc    12420
caaaagggcg ggtatgccta cgggaaacct aaatttggct ataagactga agaaaaggaa    12480
ctaaaagaag attcagcaca acaggaaact attaaactaa ttaagagaca ccgtaggtca    12540
gggaaaagct accagaaaat agctgattat ctcaatgccc aaagtattcc cactaaacaa    12600
ggtaagaaat ggagttctag cgtcgtctat cgaatctgtc aggaaaaagc tggttaagtc    12660
tgtttataga tatttagaat ttattgaata aaaatagtat gaacaataaa tatttatgga    12720
ctaaccacgc tcggaaacgt ttaactgaac gatgggaaat aaaagaatca tgggttattg    12780
ataccatcga aaatcctgaa cgttcagaat ttattgttga tgagtcaggg gaaaaatatc    12840
attactataa aagaatagct aagtttaaga atagagtgtt agaagtgata acttctgcca    12900
actcaacacc cacaagaata ataacctttt actttaaccg taacatgagg aaaaatttat    12960
gattgttact tacgataatg aagttgacgc aatttatttt aagttaacgg aaaataaaat    13020
tgatagcacc gaacctcaaa cagacaggat tatcattgat tacgatgaaa gtaataatat    13080
tgttggcatt gaggtattag atttaatta tcttgtcaag aaaggtttaa ccgttgctga    13140
tttacctttt tctgaagatg aaagattaac agcttctcaa tattttaatt ttcctgttgc    13200
tatctaatcc agaaggggca ataatcccct tctttcatcg agttagactt aatatcacaa    13260
aagtcatttt cattttaccg tttcttttcc acagcgtccg tacgcccctc gttaaatctc    13320
aaaaccgaca atttatgatg tttataaaaa gttactcact ttaataagta tttatactca    13380
ttaaagggtt attctttttt tgtagcctga taggttggga aggaatattt cagattatca    13440
gatttgttg                                                           13449
```

FIG. 11(continued)

TK295 pABICyano1-6.8 PnirAABICyano1-PDCmax-PpsbAABICyano1-synADHmax-PrbcABICyano1-Km**-oriVT

```
ID   TK295\pABICyano1-6.8_PnirAABICyano1-PDCmax-PpsbAABICyano1-synADHmax-
PrbcABICyano1-Km**-oriVT standard; circular DNA;    ; 13033 BP.
CC   This file is created by Vector NTI
CC   http://www.invitrogen.com/
CC   VNTDATE|620148482|
CC   VNTDBDATE|620148482|
CC   LSOWNER|
CC   VNTAUTHORNAME|Frank Uliczka|
FH   Key             Location/Qualifiers
FH
FT   promoter        3639..4164
FT                   /vntifkey="30"
FT                   /label=PrbcABICyano1
FT   CDS             4166..4981
FT                   /vntifkey="4"
FT                   /label=Km**
FT                   /note=" maximal codon optimized kanamycin resistance gene "
FT   CDS             12543..12791
FT                   /vntifkey="4"
FT                   /label=ORF\6
FT                   /note="orf6"
FT   CDS             12283..12546
FT                   /vntifkey="4"
FT                   /label=ORF\5
FT                   /note="orf5"
FT   CDS             11555..12241
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(10465..11229)
FT                   /vntifkey="4"
FT                   /label=ORF\3
FT                   /note="orf3"
FT   CDS             10020..10205
FT                   /vntifkey="4"
FT                   /label=ORF\2
FT                   /note="orf2"
FT   rep_origin      complement(9320..9337)
FT                   /vntifkey="33"
FT                   /label=Rep_Origin_1\(potential)
FT                   /note="potential rep origin; match pNostoc (Acc# M81381) nick
site (358-375); on reserse strand"
FT   misc_feature    9580..9613
FT                   /vntifkey="21"
FT                   /label=Rep\motif
FT                   /note="Rep protein active site motig EXXKYXVKXXD"
FT   CDS             6799..9984
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
```

FIG. 13

```
FT   rep_origin      complement(5224..6282)
FT                   /vntifkey="33"
FT                   /label=OriVT
FT   insertion_seq   6289..89
FT                   /source="pABICyano1-6HindIIIBamHI"
FT                   /type="Custom cloned insert"
FT                   /vntifkey="14"
FT                   /label=pABICyano1-6HindIIIBamHI
FT                   /note="Unknown feature type:insert"
FT   promoter        2112..2264
FT                   /vntifkey="30"
FT                   /label=PpsbAABICyano1
FT   gene            379..2088
FT                   /vntifkey="60"
FT                   /note="PDC"
FT   gene            2268..3278
FT                   /vntifkey="60"
FT                   /note="ADH"
FT   CDS             379..2085
FT                   /vntifkey="4"
FT                   /label=PDCmax
FT   CDS             2268..3275
FT                   /vntifkey="4"
FT                   /label=synADHmax
FT   promoter        96..378
FT                   /vntifkey="30"
FT                   /label=PnirAABICyano1
FT   terminator      3279..3434
FT                   /vntifkey="43"
FT                   /label=TrbcSABICyano1
SQ   Sequence 13033 BP; 4048 A; 2285 C; 2558 G; 4142 t;
     aatatttttc gtcagatacg caaaccttac aaacataatt aacaactgaa actattgata        60
     tgtctaggtt ttagctctat cacaggttgg atctgtcgac aattaataac ttcttcctgt       120
     acgggcgaat ggccatttgc tcctaactaa ctccgtactg ctttgcggaa cgagcgtagc       180
     gaactctccg aattactaag ccttcatccc tgatagatgc aaaaaacgaa ttaaaattat       240
     gtgtaaaaag aaaatgtgtc tttatttagt agtcaaagtt acaaaatatt aagaatcaaa       300
     ttaataatgt attgggcagt taagtatata agtctttaaa tatttatttg tattcaatat       360
     attaaccgag gacaaattat gaattcttat accgtgggta cttatttagc cgaacgctta       420
     gtgcaaattg gtttaaaaca tcattttgcc gtggctgggg actataattt agtgttattg       480
     gataacttat tattaaataa aaacatggaa caagtgtatt gttgtaatga attaaattgt       540
     ggtttttctg ctgaaggtta tgctagagct aaaggtgcag ctgctgctgt tgttacttat       600
     tctgtgggtg ctttatctgc ttttgatgct attggtggtg cttatgccga aaatttaccc       660
     gtgattttaa tttctggtgc ccctaataat aatgatcatg ccgctggaca tgttttacat       720
     catgccttag gtaaaaccga ttatcattat caattagaaa tggccaaaaa tattactgct       780
     gctgccgaag ctatttatac tcctgaagaa gcccctgcca aaattgatca tgtgattaaa       840
     accgccttac gcgaaaaaaa acccgtgtat ttagaaattg cctgtaatat tgcttctatg       900
     ccttgtgctg ctcctgggcc tgcttctgct ttatttaatg atgaagcctc tgatgaagct       960
     agtttaaatg ctgccgtgga agaaacctta aaatttattg ccaatcgcga taaagttgcc      1020
     gtgttagttg gttctaaatt aagagctgct ggtgctgaag aagctgctgt taaatttgct      1080
     gatgctttag gtggtgcagt tgctactatg gctgctgcca aatctttttt tcccgaagaa      1140
     aatccccatt atattggaac tagttgggga gaagtttctt atcctggtgt ggaaaaaact      1200
```

FIG. 13 (continued)

```
atgaaagaag ccgacgctgt tattgcttta gcccctgtgt ttaatgatta ttctaccact    1260
ggttggactg atattcccga tcccaaaaaa ttagttttag ccgaacctcg ttctgttgtt    1320
gttaatggtg ttcgctttcc ctctgtgcat ttaaaagatt atttaacccg cttagcccaa    1380
aaagtttcta aaaaaactgg tgccttagat ttttttaaat ctttaaatgc gggtgaatta    1440
aaaaaagctg ctcctgctga tccttctgct cctttagtta atgctgaaat tgcccgtcaa    1500
gttgaagcct tattaacccc taatactacc gttattgccg aaactggtga ttcttggttt    1560
aatgcccaac gcatgaaatt acctaatggt gcccgtgttg aatatgaaat gcaatggggt    1620
catattggtt ggtctgtacc tgctgctttt ggttatgctg ttggtgctcc tgaacgtcgt    1680
aatattttaa tggtgggtga tggttctttt caattaactg cccaagaagt tgcccaaatg    1740
gttcgcttaa aattacccgt tattattttt ttaataaata attatggtta taccattgaa    1800
gtgatgattc atgatgggcc atataataat attaaaaatt gggattatgc gggtttaatg    1860
gaagtgttta atggtaatgg tggttatgat tctggtgctg gtaaaggttt aaaagccaaa    1920
actggtggtg aattagctga agctattaaa gttgccttag ccaatactga tgggccaacc    1980
ttaattgaat gttttattgg tcgcgaagat tgtaccgaag aattagttaa atggggtaaa    2040
cgtgttgctg ctgctaattc tcgcaaaccc gtgaataaat tattgtaatt tttggggatc    2100
aattcgagct cgccttacta taaacaaaag ttatctgaga aataactata actattctga    2160
aaatatttga caaaacttta caattttgtt atattagtaa gtgaggtgag caaatcaccc    2220
aaaatatata agtacctcga aaaattcata actgaaatca taagcatatg attaaagcct    2280
atgctgcctt agaagccaat ggtaaattac aaccctttga atatgatcct ggtgctttag    2340
gtgccaatga agtggaaatt gaagtgcaat attgtggtgt gtgtcattct gatttatcta    2400
tgattaataa tgaatggggt atttctaatt atcccttagt tcctggtcat gaagttgttg    2460
gtactgttgc tgctatgggt gaaggtgtta atcatgtgga agtgggtgat ttagttggtt    2520
taggttggca ttctggttat tgtatgacct gtcattcttg tttatctggt tatcataatt    2580
tatgtgccac tgccgaatct actattgtgg gtcattatgg tggttttggt gatagagttc    2640
gtgctaaagg tgtttctgtg gtgaaattac ccaaaggtat tgatttagcc tctgctgggc    2700
ctttattttg tggtggtatt accgtttttt ctcccatggt ggaattatct ttaaaaccta    2760
ccgccaaagt tgctgttatt ggtattggtg gtttaggtca tttagccgtt caatttttaa    2820
gagcctgggg ttgtgaagtt actgctttta cctcttctgc ccgtaaacaa accgaagttt    2880
tagaattagg tgcccatcat attttagatt ctaccaatcc tgaagctatt gcttctgccg    2940
aaggtaaatt tgattatatt atttctaccg tgaatttaaa attagattgg aatttatata    3000
tcagtacctt agcccctcaa ggtcattttc attttgttgg tgtggtgtta gaacccttgg    3060
acttaaactt atttccctta ttaatgggac aacgttctgt ttctgcttct cctgttggtt    3120
ctcctgctac tattgccact atgttagatt ttgccgtgcg tcatgatatt aaacccgtgg    3180
tggaacaatt ttcttttgat caaattaatg aagccattgc ccatttagaa tctggtaaag    3240
cccattatcg cgtggtgtta tctcattcta aaaattaata agattaactt ctaaactgaa    3300
acaaatttga gggtaggctt cattgtctgc ccttattttt ttatttagga aaagtgaaca    3360
gactaaagag tgttggctct attgctttga gtatgtaaat taggcgttgc tgaattaagg    3420
tatgattttt gacccttct ctcttctgca gttacctagg atttctggcg aaagggggat    3480
gtgctgcaag gcgattaagt tgggtaacgc cagggttttc ccagtcacga cgttgtaaaa    3540
cgacggccag tgagcgcgac gtaatacgac tcactatagg gcgaattggc ggaaggccgt    3600
caaggccgca tggcgcgcct acgtagacaa ttgtcgatgt aattattaac tatcttatta    3660
tagatgaggg gagagggaga aattagttcg gagagaacgc tcgagcgctc gttccgcaaa    3720
gcggtacgga gttagttagg ggctaatggg cattctcccg tacaggaaag agttagaagt    3780
tattaattat caacaattct cctttgccta gtgcatcgtt accttttttaa ttaaaacata    3840
aggaaaacta ataatcgtaa taatttaacc tcaaagtgta aagaaatgtg aaattctgac    3900
ttttataacg ttaaagaggg aaaaattagc agtttaaaat acctagagaa tagtctgggg    3960
taagcataga gaattagatt agttaagtta atcaaattca gaaaaaataa taatcgtaaa    4020
tagttaatct gggtgtatag aaaatgatcc ccttcatgat aagatttaaa ctcgaaaagc    4080
aaaagccaaa aaactaactt ccattaaaag aagttgttac atataacgct ataaagaaaa    4140
tttatatatt tggaggatac caaccatgtc tcatattcaa cgtgaaacta gttgttctcg    4200
tcctcgttta aattctaata tggatgccga tttatatggt tataaatggg ctcgtgataa    4260
```

FIG. 13 (continued)

tgttggtcaa tctggtgcta ctatttatcg tttatatggt aaacctgatg ctcctgaatt 4320
attcttgaaa catggtaaag gttctgttgc taatgatgtt actgatgaaa tggttcgttt 4380
aaactggttg actgaattta tgcctttacc tactattaaa cattttattc gtactcccga 4440
tgatgcttgg ttattaacta ctgctattcc tggtaaaact gcttttcaag ttttagaaga 4500
atatcctgat tctggtgaaa atattgttga tgctttagct gtttttttac gtcgtttaca 4560
ttctattccc gtttgtaatt gtccttttaa ttctgatcgt gtttttcgtt tagctcaagc 4620
tcaatctcgt atgaataatg gtttagttga tgcttctgat tttgatgatg aacgtaatgg 4680
ttggcctgtt gaacaagttt ggaaagaaat gcacaaattg ttaccttttt ctcctgattc 4740
tgttgttact catggtgatt tttctttaga taatttgatc tttgatgaag gtaaattgat 4800
tggttgtatt gatgttggtc gtgttggtat tgctgatcgt tatcaagatt tagctatttt 4860
atggaattgt ttaggtgaat tttctccttc tttacagaaa cgtttatttc agaaatatgg 4920
tattgataat cctgatatga acaagttaca atttcattta atgttggacg agttctttta 4980
agaattaatt catgaccaaa atcccttaac gtgagttttc gttccactga gcgtcagacc 5040
ccgtagaaaa gatcaaagga tcttcttgag atcctttttt tctgcgcgta atctgctgct 5100
atttaaatta cgtacacgtg ttattacttt gttaacgaca attgtcttaa ttaactgggc 5160
ctcatgggcc ttccgctcac tgcccgcttt ccagtcggga aacctgtcgt gccagctctg 5220
cagatgacgg tgaaaacctc tgacacatgc agctcccgga gacggtcaca gcttgtctgt 5280
aagcggatgc cgggagcaga caagcccgtc agggcgcgtc agcgggtgtt ggcgggtgtc 5340
ggggcgcagc catgacccag tcacgtagcg atagcggagt gtatactggc ttaactatgc 5400
ggcatcagag cagattgtac tgagagtgca ccatatgcgg tgtgaaatac cgcacagatg 5460
cgtaaggaga aaataccgca tcaggcgctc ttccgcttcc tcgctcactg actcgctgcg 5520
ctcggtcgtt cggctgcggc gagcggtatc agctcactca aaggcggtaa tacggttatc 5580
cacagaatca ggggataacg caggaaagaa catgtgagca aaaggccagc aaaaggccag 5640
gaaccgtaaa aaggccgcgt tgctggcgtt tttccatagg ctccgccccc ctgacgagca 5700
tcacaaaaat cgacgctcaa gtcagaggtg gcgaaacccg acaggactat aaagatacca 5760
ggcgtttccc cctggaagct ccctcgtgcg ctctcctgtt ccgaccctgc cgcttaccgg 5820
atacctgtcc gcctttctcc cttcgggaag cgtggcgctt tctcatagct cacgctgtag 5880
gtatctcagt tcggtgtagg tcgttcgctc caagctgggc tgtgtgcacg aaccccccgt 5940
tcagcccgac cgctgcgcct tatccggtaa ctatcgtctt gagtccaacc cggtaagaca 6000
cgacttatcg ccactggcag cagccactgg taacaggatt agcagagcga ggtatgtagg 6060
cggtgctaca gagttcttga agtggtggcc taactacggc tacactagaa ggacagtatt 6120
tggtatctgc gctctgctga agccagttac cttcggaaaa agagttggta gctcttgatc 6180
cggcaaacaa accaccgctg gtagcggtgg tttttttgtt tgcaagcagc agattacgcg 6240
cagaaaaaaa ggatctcaag aagatccttt gatcttttct actgcagaag cttgttagac 6300
accctgtcat gtattttata ttatttattt caccatacgg attaagtgaa acctaatgaa 6360
aatagtactt tcggagcttt aactttaatg aaggtatgtt tttttataga catcgatgtc 6420
tggtttaaca ataggaaaaa gtagctaaaa ctcccatgaa ttaaagaaat aacaaggtgt 6480
ctaacaacct gttattaaga atgttagaaa agacttaaca tttgtgttga gtttttatag 6540
acattggtgt ctagacatac ggtagataag gtttgctcaa aaataaaata aaaaaagatt 6600
ggactaaaaa acatttaatt tagtacaatt taattagtta tttttcgtc tcaaattttg 6660
ctttgttgag cagaaattta gataaaaaaa tccccgtgat cagattacaa tgtcgttcat 6720
tgtacgatgt gtcgaaaaat ctttacgaca ctctaaactg accacacggg ggaaaaagaa 6780
aactgaacta ataacatcat gatactcgga aaacctagca attctcaacc cctaaacaaa 6840
agaaacttcc aaaaccctga ccatataaag gagtggcaac aatcagcaat cagtcaagat 6900
ttgatagcag aaaatcttgt atcggttgct aatggttttg atgtactatt tatcggcaat 6960
aaataccgaa ctaacacggg tgttctgtca cggcacatat taaactccta ttctcattta 7020
gaagatggtg gttcgtatgg tagaacattt gacccattta ccaataaaga aatgcagtgg 7080
gttcaattta aaccgaatag accaagaaaa ggttctactg gtaaggtaat caaatatgaa 7140
tcgccaaaag gtgaacctac aagagttcta atgccgtttg tgcctatgaa aatatggcaa 7200
cggattagcg ataagttcgg agtaccgatt aatccgaaaa aagatactca cttttgggaa 7260
tgggtaaaga ataatccatc gataccgatt gccattacag aaggaaataa aaaagctaat 7320
tgcctattat cctatggcta tcctgctatt gcctttgtag gcatttggaa cggattagag 7380

FIG. 13 (continued)

```
aaaataaatg atttctcgaa ggaaaagcag ttaaaagagg atttgaaatg gttgttatcc    7440
aacggcaacc gaaatattaa tatcatcttt gaccaagacc agaaacaaaa aactgtaatt    7500
aatgtaaaca aagctatttt cgctttatct tctctaataa gtagaaatgg tcataaagtt    7560
aatattgtgc aatggttgcc gtcaaaaggt aaaggaatag atgattattt ggtagcttta    7620
ccttttgaga aaagagaaaa tcatttagac aacttaatta aaattgcacc atcatttaat    7680
ttttggtcaa ctaaatactt attcaagtgt cgtaaaccag atttaaccgt aaattgccgt    7740
tatttgagcg atgcagtaaa agaattacct caagaggata tagcattaat agcacctcac    7800
ggcacgggta aaacttcatt agtagctact cacgttaaga atcggagtta tcacggaagg    7860
aaaactattt cattggtgca tcttgaaagt ttagccaaag ctaatggcaa cgcacttgga    7920
ttatattacc gaaccgaaaa taatattgaa aagcaatatc ttggatttag cttatgtgta    7980
gatagttgcc gtgataagat taacggcatt acaactgata ttatttcagg tcaagattat    8040
tgccttttca ttgatgaaat tgaccaagta attccacaca tccttaacag tgaaactgaa    8100
gtaagtaagt atagatgcac catcattgac actttttctg aactggtgag aaatgctgaa    8160
caggtcatta ttgctgatgc tgatttatcc gatgtgacga ttgacctaat agaaaacatc    8220
agaggtaaaa aactatatgt aatcaagaat gaatatcagt atcagggaat gacttttaac    8280
gccgttggtt caccattaga aatgatggca atgatgggaa aatcggtgtc agaaggcaag    8340
aaattattta ttaacaccac atcccaaaag gcaaaaagta agtacggcac aatcgctctt    8400
gagtcttata tttttggtct aaataaagaa gcaaagatat taagaataga ctctgaaacc    8460
actaaaaacc ctgaacatcc agcctataaa atcattgacc aagacttaaa taatatcctc    8520
aaagattatg attatgtcat tgcctcacct tgccttcaaa caggtgtcag tattacctta    8580
aaagggcatt ttgaccagca atttaacttt tccagtggaa acattacacc tcattgcttt    8640
ttacagcaaa tgtggcggtt gagggatgca gaaattgaaa gattctatta tgtgccgaac    8700
tcatctaacc tcaatctcat tgggaataag tcaagttcac catcagacct tctaaagagc    8760
aataacaaga tggcaacggc aacggttaac cttttgggta gaatcgactc cgaatattcc    8820
ctagagtatg aatcgcacgg catttggctt gagacgtggg caaaattatc agcacggcat    8880
aacagttcaa tgcgttgtta ctctgaaatt cttacctatc taattacgtc tcaagggcat    8940
aaattaaata tcaacattcc ctcacctctt gcagatatta agaagctaaa tgatgaggta    9000
agtagtaaca gggaaaaggt aaaaaatgag agatactctc agaggttaaa ctcaccagat    9060
attaacgatg cagaagctac catactcgaa tctaaagagc aaaaaatcgg attgactctc    9120
aatgagagat gcaccctaga aaagcataaa gttaagaagc ggtatgggaa tgtaaagatg    9180
gatattctca cctttgatga tgatggacta taccccaaac tcagactatt ttattacctc    9240
accatcggta aacctcatct caaggctaat gacagaaaag ctattgccaa aatgggcaat    9300
gacaataaag gcaagattct atcaaaagac ttagttaata aaacttactc cgctcgtgtg    9360
aaggtcttag agattcttaa actaactgac tttatcgaca atcttagaga tgaactctta    9420
ataactccca ataatccagc tatcaccgat tttaataatc ttctgctaag agctaagaag    9480
gatttaagag tattaggagt caacatcgga aaatatccaa tggccaacat taatgccgta    9540
cttactctca ttggtcacaa actttctgta atgagagatg agttcggaaa agagaaaagg    9600
ataaaagtag atggtaaatc ataccgatgt tatcaacttg aaacattacc agattttacc    9660
aatgatactc ttgactactg gttagaaaat gatagccaaa aagaagtaac agcaacagaa    9720
aattactccg aaaattttaa cccttcaaat agctacaatc cagacagtaa gacactttca    9780
gagggtgcaa atttcctata tataaataaa gaagaattgc atccaaataa attgcaccta    9840
gaaataaaag aaggtgctga actttttta ttcggggtaa aggtgattgt gaaaggaatc    9900
ttggacgggg cagtaactat attctctatg ggtcaagaat acgatttatc cctcaatgaa    9960
ctagaggga tgttaacatc atgaacttta caagaatctt tttaaagggc gatcgcacca   10020
tgttaaatga tggtacattt gttcagatat ttgatattta ccatgaccac gcattgggag   10080
tgacccttga ccttaagaca gaaaaaatta tttccgatga tgttagggta attactgtca   10140
aagacttatt gttcgatggc acttataaag gggtaaaatc ttttatgccc gataatgccc   10200
gataatgccc gattgatgct acaaaatccc ataatcataa gcgataatcc cctaatagct   10260
tgtaattctt gaaccgtagc gattttagag tattccaaaa agaagaaata aacaccgcaa   10320
aatgtcgtat ttcacatata taaaccaagg ttttttgccc taaaatcttt atgtttgtag   10380
tgtgatgttg ggtcaaaatg gtcagaaaag ttgcaaggtt tttatggatg cttacgcgcg   10440
```

FIG. 13 (continued)

```
cgaggggtaa gcatccccaa atagttactt tatcctagtc catgcccatt tattgccgtc    10500
ccgttcggct ttaaaaaagt gccaaaactc acaaggtgca ataaaaagtt ctgtaccttt    10560
cgcaacccta gataatcttt caacagttac tttttttcct attatctcgg tacaaagttt    10620
ggctagtttc tcttttccct ctttttcaat caagccttct tgtatgccca actcattgat    10680
taatctctct atttttacca ttatttcccg ttcaggtagt ttatccccta aatcttcatc    10740
ggggggcaat gtagggcatt ctgaaggggc tttttcttct gtctggacat tatctaatat    10800
tgaagtaacc aaactatctt cagtttttc tattcctatt aattcatatt cggttactgt     10860
atccgtatca atatccgaat aactatcttt atccgtatta gctattcggt taagtttatc    10920
cgttaactca gaaacaagac tatatagcgg ttttagcttt tcttctatcc tgttatctaa    10980
tacggataag tttatacggt tatcattatc cgtattagta tcattgggct tttttggtag    11040
ttctaccccc tcataaaccg cttttattcc caattccaac agactgataa cagtatcctt    11100
tataatgggt tttttgctga tatggtgaac ttttgcccct tccatcattg cgatactttc    11160
tatctcactc atcaacttat cgcttaagtg aatctcgtat ctgtttaatc ccttactggt    11220
tttattcata tccgtttact ttattcggtt aacaattcta ttttatacga ataaaatatt    11280
atacggttaa ctttatacgt ttaactattt tatctatacg gataacagta ataagttatt    11340
cgtattagtt atacgtttac ttttatccaa ataaaattag tgcatttaaa ctaaaagaat    11400
gattttatcg gagttgatag cattggatta acctaaagat gtttataagc tatatctgat    11460
aagtatttaa ggttattttg ttattctgtt tattgacatt atcagaataa aagaatagaa    11520
tataattgtt gagagataag aggtttaagt gattatggtt aagaagttag ttggttatgt    11580
cagggtcagt agtgaatcgc aagaggataa cactagctta cagaatcaga tagagagaat    11640
tgaagcatat tgtatggctt ttggttatga gttggtaaaa atattcaaag aggttgccac    11700
tggtacaaaa gcagatattg aaacccgtcc tatttttaat gaagctatag aatacttgaa    11760
acaggataat gctaatggaa ttattgcctt gaagctagac cgaatcgcac ggaatgcttt    11820
agatgtattg cgtttggttc gtgaaacctt agaaccacaa aataaaatgt tagtgttact    11880
agatattcag gtagatactt cgacaccttc aggaaaaatg attttaactg taatgagtgc    11940
cgttgctgaa ctcgaaagag acatgatcta tgatcgcact caggggggta gaaagactaa    12000
agcccaaaag ggcgggtatg cctacgggaa acctaaattt ggctataaga ctgaagaaaa    12060
ggaactaaaa gaagattcag cacaacagga aactattaaa ctaattaaga gacaccgtag    12120
gtcagggaaa agctaccaga aaatagctga ttatctcaat gcccaaagta ttcccactaa    12180
acaaggtaag aaatggagtt ctagcgtcgt ctatcgaatc tgtcaggaaa aagctggtta    12240
agtctgttta tagatattta gaatttattg aataaaaata gtatgaacaa taaatattta    12300
tggactaacc acgctcggaa acgtttaact gaacgatggg aaataaaaga atcatgggtt    12360
attgatacca tcgaaaatcc tgaacgttca gaatttattg ttgatgagtc aggggaaaaa    12420
tatcattact ataaaagaat agctaagttt aagaatagag tgttagaagt gataacttct    12480
gccaactcaa cacccacaag aataataacc ttttacttta accgtaacat gaggaaaaat    12540
ttatgattgt tacttacgat aatgaagttg acgcaattta ttttaagtta acggaaaata    12600
aaattgatag caccgaacct caaacagaca ggattatcat tgattacgat gaaagtaata    12660
atattgttgg cattgaggta ttagatttta attatcttgt caagaaaggt ttaaccgttg    12720
ctgatttacc tttttctgaa gatgaaagat taacagcttc tcaatatttt aattttcctg    12780
ttgctatcta atccagaagg ggcaataatc cccttctttc atcgagttag acttaatatc    12840
acaaaagtca ttttcatttt accgtttctt ttccacagcg tccgtacgcc cctcgttaaa    12900
tctcaaaacc gacaatttat gatgtttata aaaagttact cactttaata agtatttata    12960
ctcattaaag ggttattctt tttttgtagc ctgataggtt gggaaggaat atttcagatt    13020
atcagatttg ttg                                                       13033
```

FIG. 13 (continued)

TK229 pABICyano1-6.8 PpetEABICyano1-PDCmax-synADHmax-PrbcABICyano1-Km**-oriVT

```
ID   TK229\pABICyano1-6.8_PpetEABICyano1-PDCmax-synADHmax-PrbcABICyano1-Km**-oriVT
standard; circular DNA;    ; 13081 BP.
DT   25-JAN-2012
CC
CC   This file is created by Vector NTI
CC   http://www.invitrogen.com/
CC   ORIGDB|GenBank
CC   VNTDATE|621691376|
CC   VNTDBDATE|621691376|
CC   LSOWNER|
CC   VNTAUTHORNAME|Frank Uliczka|
CC   SSBMSPEC|8|NONE|GenBank|0
FH   Key             Location/Qualifiers
FH
FT   promoter        3687..4212
FT                   /vntifkey="30"
FT                   /label=PrbcLABICyano1
FT   CDS             4214..5029
FT                   /vntifkey="4"
FT                   /label=Km**
FT                   /note=" maximal codon optimized kanamycin resistance gene "
FT   CDS             12591..12839
FT                   /vntifkey="4"
FT                   /label=ORF\6
FT                   /note="orf6"
FT   CDS             12331..12594
FT                   /vntifkey="4"
FT                   /label=ORF\5
FT                   /note="orf5"
FT   CDS             11603..12289
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(10513..11277)
FT                   /vntifkey="4"
FT                   /label=ORF\3
FT                   /note="orf3"
FT   CDS             10068..10253
FT                   /vntifkey="4"
FT                   /label=ORF\2
FT                   /note="orf2"
FT   rep_origin      complement(9368..9385)
FT                   /vntifkey="33"
FT                   /label=Rep_Origin_1\(potential)
FT                   /note="potential rep origin; match pNostoc (Acc# M81381) nick
site (358-375); on reserse strand"
FT   misc_feature    9628..9661
FT                   /vntifkey="21"
FT                   /label=Rep\motif
FT                   /note="Rep protein active site motig EXXKYXVKXXD"
FT   CDS             6847..10032
```

FIG. 15

```
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   rep_origin      complement(5272..6330)
FT                   /vntifkey="33"
FT                   /label=OriVT
FT   insertion_seq   6337..89
FT                   /source="pABICyanol-6HindIIIBamHI"
FT                   /type="Custom cloned insert"
FT                   /vntifkey="14"
FT                   /label=pABICyanol-6HindIIIBamHI
FT                   /note="Unknown feature type:insert"
FT   CDS             2316..3323
FT                   /vntifkey="4"
FT                   /label=synADH
FT   CDS             494..2198
FT                   /vntifkey="4"
FT                   /label=PDC
FT   gene            2316..3326
FT                   /vntifkey="60"
FT                   /note="ADH"
FT   gene            494..2201
FT                   /vntifkey="60"
FT                   /note="PDC"
FT   promoter        101..493
FT                   /vntifkey="30"
FT                   /label=PpetEABICyanol
SQ   Sequence 13081 BP; 4061 A; 2280 C; 2573 G; 4167 t;
     aatatttttc gtcagatacg caaaccttac aaacataatt aacaactgaa actattgata        60
     tgtctaggtt ttagctctat cacaggttgg atctgtcgac gagaagggga acagggaaaa       120
     gtatttataa ttgatacaaa ctgtggttca acttatttta aagacatttt tctccattta       180
     atgattattt cggggaaaat tttgaggatt tttgattctt aaattgacga tattttgtca       240
     ctaacacaac gtgagcggta aatttatata tagacctaaa acctttacta taagtgttat       300
     atatttaaat cgctaagtat atagttaaag tgtagccaat aattaacttt taacaagtga       360
     ttaccgttaa gtcccttaat ttatcactac aagctaaaac aaatttttca attagatatg       420
     acattaggtc aaagttcata gtatgatagt aaaaaataaa atttgacgat ctgtaaaaat       480
     aaaaaaacac aatgaattct tataccgtgg gtacttattt agccgaacgc ttagtgcaaa       540
     ttggtttaaa acatcatttt gccgtggctg ggactataa tttagtgtta ttggataact        600
     tattattaaa taaaaacatg gaacaagtgt attgttgtaa tgaattaaat tgtggttttt       660
     ctgctgaagg ttatgctaga gctaaaggtg cagctgctgc tgttgttact tattctgtgg       720
     gtgctttatc tgcttttgat gctattggtg gtgcttatgc cgaaaattta cccgtgattt       780
     taatttctgg tgcccctaat aataatgatc atgccgctgg acatgtttta catcatgcct       840
     taggtaaaac cgattatcat tatcaattag aaatggccaa aaatattact gctgctgccg       900
     aagctattta tactcctgaa gaagcccctg ccaaaattga tcatgtgatt aaaaccgcct       960
     tacgcgaaaa aaaacccgtg tatttagaaa ttgcctgtaa tattgcttct atgccttgtg      1020
     ctgctcctgg gcctgcttct gctttattta atgatgaagc ctctgatgaa gctagtttaa      1080
     atgctgccgt ggaagaaacc ttaaaattta ttgccaatcg cgataaagtt gccgtgttag      1140
     ttggttctaa attaagagct gctggtgctg aagaagctgc tgttaaattt gctgatgctt      1200
     taggtggtgc agttgctact atggctgctg ccaaatcttt ttttcccgaa gaaaatcccc      1260
     attatattgg aactagttgg ggagaagttt cttatcctgg tgtggaaaaa actatgaaag      1320
```

FIG. 15 (continued)

```
aagccgacgc tgttattgct ttagcccctg tgtttaatga ttattctacc actggttgga 1380
ctgatattcc cgatcccaaa aaattagttt tagccgaacc tcgttctgtt gttgttaatg 1440
gtgttcgctt tccctctgtg catttaaaag attatttaac ccgcttagcc caaaaagttt 1500
ctaaaaaaac tggtgcctta gatttttta aatctttaaa tgcgggtgaa ttaaaaaaag 1560
ctgctcctgc tgatccttct gctcctttag ttaatgctga aattgcccgt caagttgaag 1620
ccttattaac ccctaatact accgttattg ccgaaactgg tgattcttgg tttaatgccc 1680
aacgcatgaa attacctaat ggtgcccgtg ttgaatatga aatgcaatgg ggtcatattg 1740
gttggtctgt acctgctgct tttggttatg ctgttggtgc tcctgaacgt cgtaatattt 1800
taatggtggg tgatggttct tttcaattaa ctgcccaaga agttgcccaa atggttcgct 1860
taaaattacc cgttattatt tttttaataa ataattatgg ttataccatt gaagtgatga 1920
ttcatgatgg gccatataat aatattaaaa attgggatta tgcgggttta atggaagtgt 1980
ttaatggtaa tggtggttat gattctggtg ctggtaaagg tttaaaagcc aaaactggtg 2040
gtgaattagc tgaagctatt aaagttgcct tagccaatac tgatgggcca accttaattg 2100
aatgttttat tggtcgcgaa gattgtaccg aagaattagt taaatggggt aaacgtgttg 2160
ctgctgctaa ttctcgcaaa cccgtgaata aattattgta atttttgggg atcaattcga 2220
gctcggtacc caaactagta tgtagggtga ggttatagct agcgctttta attaatccgc 2280
ggatttgtat tcaatatatt aaccgaggac aacatatgat taaagcctat gctgccttag 2340
aagccaatgg taaattacaa ccctttgaat atgatcctgg tgctttaggt gccaatgaag 2400
tggaaattga agtgcaatat tgtggtgtgt gtcattctga tttatctatg attaataatg 2460
aatggggtat ttctaattat cccttagttc ctggtcatga agttgttggt actgttgctg 2520
ctatgggtga aggtgttaat catgtggaag tgggtgattt agttggttta ggttggcatt 2580
ctggttattg tatgacctgt cattcttgtt tatctggtta tcataattta tgtgccactg 2640
ccgaatctac tattgtgggt cattatggtg gttttggtga tagagttcgt gctaaaggtg 2700
tttctgtggt gaaattaccc aaaggtattg atttagcctc tgctgggcct ttatttgtg 2760
gtggtattac cgtttttct cccatggtgg aattatcttt aaaacctacc gccaaagttg 2820
ctgttattgg tattggtggt ttaggtcatt tagccgttca atttttaaga gcctggggtt 2880
gtgaagttac tgcttttacc tcttctgccc gtaaacaaac cgaagtttta gaattaggtg 2940
cccatcatat tttagattct accaatcctg aagctattgc ttctgccgaa ggtaaatttg 3000
attatattat ttctaccgtg aatttaaaat tagattggaa tttatatatc agtaccttag 3060
cccctcaagg tcattttcat tttgttggtg tggtgttaga acccttggac ttaaacttat 3120
ttcccttatt aatgggacaa cgttctgttt ctgcttctcc tgttggttct cctgctacta 3180
ttgccactat gttagatttt gccgtgcgtc atgatattaa acccgtggtg gaacaatttt 3240
cttttgatca aattaatgaa gccattgccc atttagaatc tggtaaagcc cattatcgcg 3300
tggtgttatc tcattctaaa aattaataag attaacttct aaactgaaac aaatttgagg 3360
gtaggcttca ttgtctgccc ttattttttt atttaggaaa agtgaacaga ctaaagagtg 3420
ttggctctat tgctttgagt atgtaaatta ggcgttgctg aattaaggta tgatttttga 3480
ccccttctct cttctgcagt tacctaggat ttctggcgaa agggggatgt gctgcaaggc 3540
gattaagttg ggtaacgcca gggttttccc agtcacgacg ttgtaaaacg acggccagtg 3600
agcgcgacgt aatacgactc actatagggc gaattggcgg aaggccgtca aggccgcatg 3660
gcgcgcctac gtagacaatt gtcgatgtaa ttattaacta tcttattata gatgagggga 3720
gagggagaaa ttagttcgga gagaacgctc gagcgctcgt tccgcaaagc ggtacggagt 3780
tagttagggg ctaatgggca ttctcccgta caggaaagag ttagaagtta ttaattatca 3840
acaattctcc tttgcctagt gcatcgttac ctttttaatt aaaacataag gaaaactaat 3900
aatcgtaata atttaacctc aaagtgtaaa gaaatgtgaa attctgactt ttataacgtt 3960
aaagagggaa aaattagcag tttaaaatac ctagagaata gtctggggta agcatagaga 4020
attagattag ttaagttaat caaattcaga aaaaataata atcgtaaata gttaatctgg 4080
gtgtatagaa aatgatcccc ttcatgataa gatttaaact cgaaaagcaa aagccaaaaa 4140
actaacttcc attaaaagaa gttgttacat ataacgctat aaagaaaatt tatatatttg 4200
gaggatacca accatgtctc atattcaacg tgaaactagt tgttctcgtc ctcgtttaaa 4260
ttctaatatg gatgccgatt tatatggtta taaatgggct cgtgataatg ttggtcaatc 4320
tggtgctact atttatcgtt tatatggtaa acctgatgct cctgaattat tcttgaaaca 4380
tggtaaaggt tctgttgcta atgatgttac tgatgaaatg gttcgtttaa actggttgac 4440
```

FIG. 15 (continued)

```
tgaatttatg cctttaccta ctattaaaca ttttattcgt actcccgatg atgcttggtt     4500
attaactact gctattcctg gtaaaactgc ttttcaagtt ttagaagaat atcctgattc     4560
tggtgaaaat attgttgatg ctttagctgt ttttttacgt cgtttacatt ctattcccgt     4620
ttgtaattgt ccttttaatt ctgatcgtgt tttcgttta gctcaagctc aatctcgtat      4680
gaataatggt ttagttgatg cttctgattt tgatgatgaa cgtaatggtt ggcctgttga     4740
acaagtttgg aaagaaatgc acaaattgtt acctttttct cctgattctg ttgttactca     4800
tggtgatttt tctttagata atttgatctt tgatgaaggt aaattgattg gttgtattga     4860
tgttggtcgt gttggtattg ctgatcgtta tcaagattta gctattttat ggaattgttt     4920
aggtgaattt tctccttctt tacagaaacg tttatttcag aaatatggta ttgataatcc     4980
tgatatgaac aagttacaat ttcatttaat gttggacgag ttcttttaag aattaattca     5040
tgaccaaaat cccttaacgt gagttttcgt tccactgagc gtcagacccc gtagaaaaga     5100
tcaaaggatc ttcttgagat cctttttttc tgcgcgtaat ctgctgctat ttaaattacg     5160
tacacgtgtt attactttgt taacgacaat tgtcttaatt aactgggcct catgggcctt     5220
ccgctcactg cccgctttcc agtcgggaaa cctgtcgtgc cagctctgca gatgacggtg     5280
aaaacctctg acacatgcag ctcccggaga cggtcacagc ttgtctgtaa gcggatgccg     5340
ggagcagaca agcccgtcag ggcgcgtcag cgggtgttgg cgggtgtcgg ggcgcagcca     5400
tgacccagtc acgtagcgat agcggagtgt atactggctt aactatgcgg catcagagca     5460
gattgtactg agagtgcacc atatgcggtg tgaaataccg cacagatgcg taaggagaaa     5520
ataccgcatc aggcgctctt ccgcttcctc gctcactgac tcgctgcgct cggtcgttcg     5580
gctgcggcga gcggtatcag ctcactcaaa ggcggtaata cggttatcca cagaatcagg     5640
ggataacgca ggaaagaaca tgtgagcaaa aggccagcaa aaggccagga accgtaaaaa     5700
ggccgcgttg ctggcgtttt tccataggct ccgcccccct gacgagcatc acaaaaatcg     5760
acgctcaagt cagaggtggc gaaacccgac aggactataa agataccagg cgtttccccc     5820
tggaagctcc ctcgtgcgct ctcctgttcc gaccctgccg cttaccggat acctgtccgc     5880
ctttctccct tcgggaagcg tggcgctttc tcatagctca cgctgtaggt atctcagttc     5940
ggtgtaggtc gttcgctcca agctgggctg tgtgcacgaa ccccccgttc agcccgaccg     6000
ctgcgcctta tccggtaact atcgtcttga gtccaacccg gtaagacacg acttatcgcc     6060
actggcagca gccactggta acaggattag cagagcgagg tatgtaggcg gtgctacaga     6120
gttcttgaag tggtggccta actacggcta cactagaagg acagtatttg gtatctgcgc     6180
tctgctgaag ccagttacct tcggaaaaag agttggtagc tcttgatccg gcaaacaaac     6240
caccgctggt agcggtggtt tttttgtttg caagcagcag attacgcgca gaaaaaaagg     6300
atctcaagaa gatcctttga tcttttctac tgcagaagct tgttagacac cctgtcatgt     6360
attttatatt atttatttca ccatacggat taagtgaaac ctaatgaaaa tagtactttc     6420
ggagctttaa ctttaatgaa ggtatgtttt tttatagaca tcgatgtctg gtttaacaat     6480
aggaaaaagt agctaaaact cccatgaatt aaagaaataa caaggtgtct aacaacctgt     6540
tattaagaat gttagaaaag acttaacatt tgtgttgagt ttttatagac attggtgtct     6600
agacatacgg tagataaggt ttgctcaaaa ataaaataaa aaaagattgg actaaaaaac     6660
atttaattta gtacaattta attagttatt ttttcgtctc aaattttgct ttgttgagca     6720
gaaatttaga taaaaaaatc cccgtgatca gattacaatg tcgttcattg tacgatgtgt     6780
cgaaaaatct ttacgacact ctaaactgac cacacggggg aaaaagaaaa ctgaactaat     6840
aacatcatga tactcggaaa acctagcaat tctcaacccc taaacaaaag aaacttccaa     6900
aaccctgacc atataaagga gtggcaacaa tcagcaatca gtcaagattt gatagcagaa     6960
aatcttgtat cggttgctaa tggttttgat gtactattta tcggcaataa ataccgaact     7020
aacacgggtg ttctgtcacg gcacatatta aactcctatt ctcatttaga agatggtggt     7080
tcgtatggta gaacatttga cccatttacc aataaagaaa tgcagtgggt tcaatttaaa     7140
ccgaatagac caagaaaagg ttctactggt aaggtaatca aatatgaatc gccaaaaggt     7200
gaacctacaa gagttctaat gccgtttgtg cctatgaaaa tatggcaacg gattagcgat     7260
aagttcggag taccgattaa tccgaaaaaa gatactcact tttgggaatg ggtaaagaat     7320
aatccatcga taccgattgc cattacagaa ggaaataaaa aagctaattg cctattatcc     7380
tatggctatc ctgctattgc ctttgtaggc atttggaacg gattagagaa aataaatgat     7440
ttctcgaagg aaaagcagtt aaaagaggat ttgaaatggt tgttatccaa cggcaaccga     7500
```

FIG. 15 (continued)

```
aatattaata tcatctttga ccaagaccag aaacaaaaaa ctgtaattaa tgtaaacaaa 7560
gctattttcg ctttatcttc tctaataagt agaaatggtc ataaagttaa tattgtgcaa 7620
tggttgccgt caaaaggtaa aggaatagat gattatttgg tagctttacc ttttgagaaa 7680
agagaaaatc atttagacaa cttaattaaa attgcaccat catttaattt ttggtcaact 7740
aaatacttat tcaagtgtcg taaaccagat ttaaccgtaa attgccgtta tttgagcgat 7800
gcagtaaaag aattacctca agaggatata gcattaatag cacctcacgg cacgggtaaa 7860
acttcattag tagctactca cgttaagaat cggagttatc acggaaggaa aactatttca 7920
ttggtgcatc ttgaaagttt agccaaagct aatggcaacg cacttggatt atattaccga 7980
accgaaaata atattgaaaa gcaatatctt ggatttagct tatgtgtaga tagttgccgt 8040
gataagatta acggcattac aactgatatt atttcaggtc aagattattg ccttttcatt 8100
gatgaaattg accaagtaat tccacacatc cttaacagtg aaactgaagt aagtaagtat 8160
agatgcacca tcattgacac tttttctgaa ctggtgagaa atgctgaaca ggtcattatt 8220
gctgatgctg atttatccga tgtgacgatt gacctaatag aaaacatcag aggtaaaaaa 8280
ctatatgtaa tcaagaatga atatcagtat cagggaatga cttttaacgc cgttggttca 8340
ccattagaaa tgatggcaat gatgggaaaa tcggtgtcag aaggcaagaa attatttatt 8400
aacaccacat cccaaaaggc aaaaagtaag tacggcacaa tcgctcttga gtcttatatt 8460
tttggtctaa ataaagaagc aaagatatta agaatagact ctgaaaccac taaaaaccct 8520
gaacatccag cctataaaat cattgaccaa gacttaaata atatcctcaa agattatgat 8580
tatgtcattg cctcaccttg ccttcaaaca ggtgtcagta ttaccttaaa agggcatttt 8640
gaccagcaat ttaacttttc cagtggaaac attacacctc attgcttttt acagcaaatg 8700
tggcggttga gggatgcaga aattgaaaga ttctattatg tgccgaactc atctaacctc 8760
aatctcattg ggaataagtc aagttcacca tcagaccttc taaagagcaa taacaagatg 8820
gcaacggcaa cggttaacct tttgggtaga atcgactccg aatattccct agagtatgaa 8880
tcgcacggca tttggcttga gacgtgggca aaattatcag cacggcataa cagttcaatg 8940
cgttgttact ctgaaattct tacctatcta attacgtctc aagggcataa attaaatatc 9000
aacattccct cacctcttgc agatattaag aagctaaatg atgaggtaag tagtaacagg 9060
gaaaaggtaa aaaatgagag atactctcag aggttaaact caccagatat taacgatgca 9120
gaagctacca tactcgaatc taaagagcaa aaaatcggat tgactctcaa tgagagatgc 9180
accctagaaa agcataaagt taagaagcgg tatgggaatg taaagatgga tattctcacc 9240
tttgatgatg atggactata ccccaaactc agactatttt attacctcac catcggtaaa 9300
cctcatctca aggctaatga cagaaaagct attgccaaaa tgggcaatga caataaaggc 9360
aagattctat caaaagactt agttaataaa acttactccg ctcgtgtgaa ggtcttagag 9420
attcttaaac taactgactt tatcgacaat cttagagatg aactcttaat aactcccaat 9480
aatccagcta tcaccgattt taataatctt ctgctaagag ctaagaagga tttaagagta 9540
ttaggagtca acatcggaaa atatccaatg gccaacatta atgccgtact tactctcatt 9600
ggtcacaaac tttctgtaat gagagatgag ttcggaaaag agaaaaggat aaaagtagat 9660
ggtaaatcat accgatgtta tcaacttgaa acattaccag attttaccaa tgatactctt 9720
gactactggt tagaaaatga tagccaaaaa gaagtaacag caacagaaaa ttactccgaa 9780
aattttaacc cttcaaatag ctacaatcca gacagtaaga cactttcaga gggtgcaaat 9840
ttcctatata taaataaaga agaattgcat ccaaataaat tgcacctaga aataaaagaa 9900
ggtgctgaac ttttttttatt cggggtaaag gtgattgtga aaggaatctt ggacggggca 9960
gtaactatat tctctatggg tcaagaatac gatttatccc tcaatgaact agaggggatg 10020
ttaacatcat gaactttaca agaatctttt taaagggcga tcgcaccatg ttaaatgatg 10080
gtacatttgt tcagatattt gatatttacc atgaccacgc attgggagtg acccttgacc 10140
ttaagacaga aaaaattatt tccgatgatg ttagggtaat tactgtcaaa gacttattgt 10200
tcgatggcac ttataaaggg gtaaaatctt ttatgcccga taatgcccga taatgcccga 10260
ttgatgctac aaaatcccat aatcataagc gataatcccc taatagcttg taattcttga 10320
accgtagcga ttttagagta ttccaaaaag aagaaataaa caccgcaaaa tgtcgtattt 10380
cacatatata aaccaaggtt ttttgcccta aaatctttat gtttgtagtg tgatgttggg 10440
tcaaaatggt cagaaaagtt gcaaggtttt tatggatgct tacgcgcgcg aggggtaagc 10500
atccccaaat agttacttta tcctagtcca tgcccattta ttgccgtccc gttcggcttt 10560
```

FIG. 15 (continued)

```
aaaaaagtgc caaaactcac aaggtgcaat aaaaagttct gtacctttcg caaccctaga    10620
taatctttca acagttactt tttttcctat tatctcggta caaagtttgg ctagtttctc    10680
ttttccctct ttttcaatca agccttcttg tatgcccaac tcattgatta atctctctat    10740
ttttaccatt atttcccgtt caggtagttt atcccctaaa tcttcatcgg ggggcaatgt    10800
agggcattct gaagggggctt tttcttctgt ctggacatta tctaatattg aagtaaccaa    10860
actatcttca gttttttcta ttcctattaa ttcatattcg gttactgtat ccgtatcaat    10920
atccgaataa ctatctttat ccgtattagc tattcggtta agtttatccg ttaactcaga    10980
aacaagacta tatagcggtt ttagcttttc ttctatcctg ttatctaata cggataagtt    11040
tatacggtta tcattatccg tattagtatc attgggcttt tttggtagtt ctacccccctc    11100
ataaaccgct tttattccca attccaacag actgataaca gtatccttta taatgggttt    11160
tttgctgata tggtgaactt ttgccccttc catcattgcg atactttcta tctcactcat    11220
caacttatcg cttaagtgaa tctcgtatct gtttaatccc ttactggttt tattcatatc    11280
cgtttacttt attcggttaa caattctatt ttatacgaat aaaatattat acggttaact    11340
ttatacgttt aactatttta tctatacgga taacagtaat aagttattcg tattagttat    11400
acgtttactt ttatccaaat aaaattagtg catttaaact aaaagaatga ttttatcgga    11460
gttgatagca ttggattaac ctaaagatgt ttataagcta tatctgataa gtatttaagg    11520
ttattttgtt attctgttta ttgacattat cagaataaaa gaatagaata taattgttga    11580
gagataagag gtttaagtga ttatggttaa gaagttagtt ggttatgtca gggtcagtag    11640
tgaatcgcaa gaggataaca ctagcttaca gaatcagata gagagaattg aagcatattg    11700
tatggctttt ggttatgagt tggtaaaaat attcaaagag gttgccactg gtacaaaagc    11760
agatattgaa acccgtccta tttttaatga agctatagaa tacttgaaac aggataatgc    11820
taatggaatt attgccttga agctagaccg aatcgcacgg aatgctttag atgtattgcg    11880
tttggttcgt gaaaccttag aaccacaaaa taaaatgtta gtgttactag atattcaggt    11940
agatacttcg acaccttcag gaaaaatgat tttaactgta atgagtgccg ttgctgaact    12000
cgaaagagac atgatctatg atcgcactca ggggggtaga aagactaaag cccaaaaggg    12060
cgggtatgcc tacgggaaac ctaaatttgg ctataagact gaagaaaagg aactaaaaga    12120
agattcagca caacaggaaa ctattaaact aattaagaga caccgtaggt cagggaaaag    12180
ctaccagaaa atagctgatt atctcaatgc ccaaagtatt ccccactaaac aaggtaagaa    12240
atggagttct agcgtcgtct atcgaatctg tcaggaaaaa gctggttaag tctgtttata    12300
gatatttaga atttattgaa taaaaatagt atgaacaata aatatttatg gactaaccac    12360
gctcggaaac gtttaactga acgatgggaa ataaaagaat catgggttat tgataccatc    12420
gaaaatcctg aacgttcaga atttattgtt gatgagtcag gggaaaaata tcattactat    12480
aaaagaatag ctaagtttaa gaatagagtg ttagaagtga taacttctgc caactcaaca    12540
cccacaagaa taataacctt ttactttaac cgtaacatga ggaaaaattt atgattgtta    12600
cttacgataa tgaagttgac gcaatttatt ttaagttaac ggaaaataaa attgatagca    12660
ccgaacctca aacagacagg attatcattg attacgatga aagtaataat attgttggca    12720
ttgaggtatt agattttaat tatcttgtca agaaaggttt aaccgttgct gatttacctt    12780
tttctgaaga tgaaagatta acagcttctc aatattttaa ttttcctgtt gctatctaat    12840
ccagaagggg caataatccc cttctttcat cgagttagac ttaatatcac aaaagtcatt    12900
ttcattttac cgtttctttt ccacagcgtc cgtacgcccc tcgttaaatc tcaaaaccga    12960
caatttatga tgtttataaa aagttactca ctttaataag tatttatact cattaaaggg    13020
ttattctttt tttgtagcct gataggttgg gaaggaatat ttcagattat cagatttgtt    13080
g                                                                   13081
```

FIG. 15 (continued)

TK368 pABICyano1-6.8 PpetEABICyano1-PDCmax- PrpsLABICyano1-synADHmax-PrbcABICyano1-Km**-oriVT

```
ID   TK368\pABICyano1-6.8_PpetEABICyano1-PDCmax-PrpsLABICyano1-synADHmax-
PrbcABICyano1-Km**-oriVT standard; circular DNA;    ; 13562 BP.
CC   This file is created by Vector NTI
CC   http://www.invitrogen.com/
CC   VNTDATE|630061176|
CC   VNTDBDATE|630061267|
CC   LSOWNER|
CC   VNTAUTHORNAME|Frank Uliczka|
FH   Key             Location/Qualifiers
FH
FT   terminator      3808..3963
FT                   /vntifkey="43"
FT                   /label=TrbcSABICyano1
FT   CDS             2797..3804
FT                   /vntifkey="4"
FT                   /label=synADHmax
FT   gene            2797..3807
FT                   /vntifkey="60"
FT                   /note="ADH"
FT   promoter        2225..2793
FT                   /vntifkey="30"
FT                   /label=PrpsLABICyano1
FT   insertion_seq   6818..89
FT                   /source="pABICyano1-6HindIIIBamHI"
FT                   /type="Custom cloned insert"
FT                   /vntifkey="14"
FT                   /label=pABICyano1-6HindIIIBamHI
FT                   /note="Unknown feature type:insert"
FT   misc_difference 4137..4140
FT                   /vntifkey="85"
FT                   /label=TA\in\pMA\data
FT   rep_origin      complement(5753..6811)
FT                   /vntifkey="33"
FT                   /label=OriVT
FT   CDS             7328..10513
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   misc_feature    10109..10142
FT                   /vntifkey="21"
FT                   /label=Rep\motif
FT                   /note="Rep protein active site motig EXXKYXVKXXD"
FT   rep_origin      complement(9849..9866)
FT                   /vntifkey="33"
FT                   /label=Rep_Origin_1\(potential)
FT                   /note="potential rep origin; match pNostoc (Acc# M81381) nick
site (358-375); on reserse strand"
FT   CDS             10549..10734
FT                   /vntifkey="4"
FT                   /label=ORF\2
FT                   /note="orf2"
```

FIG. 17

```
FT   CDS             complement(10994..11758)
FT                   /vntifkey="4"
FT                   /label=ORF\3
FT                   /note="orf3"
FT   CDS             12084..12770
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             12812..13075
FT                   /vntifkey="4"
FT                   /label=ORF\5
FT                   /note="orf5"
FT   CDS             13072..13320
FT                   /vntifkey="4"
FT                   /label=ORF\6
FT                   /note="orf6"
FT   CDS             4695..5510
FT                   /vntifkey="4"
FT                   /label=Km**
FT                   /note=" maximal codon optimized kanamycin resistance gene "
FT   promoter        4168..4693
FT                   /vntifkey="30"
FT                   /label=PrbcLABICyanol
FT   promoter        96..494
FT                   /vntifkey="30"
FT                   /label=PpetEABICyanol
FT   CDS             492..2198
FT                   /vntifkey="4"
FT                   /label=PDCmax
SQ   Sequence 13562 BP; 4246 A; 2339 C; 2611 G; 4366 t;
     aatatttttc gtcagatacg caaaccttac aaacataatt aacaactgaa actattgata        60
     tgtctaggtt ttagctctat cacaggttgg atctgtcgac gagaagggga acagggaaaa       120
     gtatttataa ttgatacaaa ctgtggttca acttatttta aagacatttt tctccattta       180
     atgattattt cggggaaaat tttgaggatt tttgattctt aaattgacga tattttgtca       240
     ctaacacaac gtgagcggta aatttatata tagacctaaa acctttacta taagtgttat       300
     atatttaaat cgctaagtat atagttaaag tgtagccaat aattaacttt taacaagtga       360
     ttaccgttaa gtcccttaat ttatcactac aagctaaaac aaatttttca attagatatg       420
     acattaggtc aaagttcata gtatgatagt aaaaaataaa atttgacgat ctgtaaaaat       480
     aaaaaaacac aatgaattct tataccgtgg gtacttattt agccgaacgc ttagtgcaaa       540
     ttggtttaaa acatcatttt gccgtggctg gggactataa tttagtgtta ttggataact       600
     tattattaaa taaaaacatg gaacaagtgt attgttgtaa tgaattaaat tgtggttttt       660
     ctgctgaagg ttatgctaga gctaaaggtg cagctgctgc tgttgttact tattctgtgg       720
     gtgctttatc tgcttttgat gctattggtg gtgcttatgc cgaaaattta cccgtgattt       780
     taatttctgg tgccccctaat aataatgatc atgccgctgg acatgtttta catcatgcct       840
     taggtaaaac cgattatcat tatcaattag aaatggccaa aaatattact gctgctgccg       900
     aagctattta tactcctgaa gaagccccctg ccaaaattga tcatgtgatt aaaaccgcct       960
     tacgcgaaaa aaaacccgtg tatttagaaa ttgcctgtaa tattgcttct atgccttgtg      1020
     ctgctcctgg gcctgcttct gctttattta atgatgaagc ctctgatgaa gctagtttaa      1080
     atgctgccgt ggaagaaacc ttaaaattta ttgccaatcg cgataaagtt gccgtgttag      1140
     ttggttctaa attaagagct gctggtgctg aagaagctgc tgttaaattt gctgatgctt      1200
```

FIG. 17 (continued)

```
taggtggtgc agttgctact atggctgctg ccaaatcttt ttttcccgaa gaaaatcccc      1260
     attatattgg aactagttgg ggagaagttt cttatcctgg tgtggaaaaa actatgaaag      1320
     aagccgacgc tgttattgct ttagcccctg tgtttaatga ttattctacc actggttgga      1380
     ctgatattcc cgatcccaaa aaattagttt tagccgaacc tcgttctgtt gttgttaatg      1440
     gtgttcgctt tccctctgtg catttaaaag attatttaac ccgcttagcc caaaaagttt      1500
     ctaaaaaaac tggtgcctta gattttttta aatctttaaa tgcgggtgaa ttaaaaaaag      1560
     ctgctcctgc tgatccttct gctcctttag ttaatgctga aattgcccgt caagttgaag      1620
     ccttattaac ccctaatact accgttattg ccgaaactgg tgattcttgg tttaatgccc      1680
     aacgcatgaa attacctaat ggtgcccgtg ttgaatatga aatgcaatgg ggtcatattg      1740
     gttggtctgt acctgctgct tttggttatg ctgttggtgc tcctgaacgt cgtaatattt      1800
     taatggtggg tgatggttct tttcaattaa ctgcccaaga agttgcccaa atggttcgct      1860
     taaaattacc cgttattatt tttttaataa ataattatgg ttataccatt gaagtgatga      1920
     ttcatgatgg gccatataat aatattaaaa attgggatta tgcgggttta atggaagtgt      1980
     ttaatggtaa tggtggttat gattctggtg ctggtaaagg tttaaaagcc aaaactggtg      2040
     gtgaattagc tgaagctatt aaagttgcct tagccaatac tgatgggcca accttaattg      2100
     aatgttttat tggtcgcgaa gattgtaccg aagaattagt taaatggggt aaacgtgttg      2160
     ctgctgctaa ttctcgcaaa cccgtgaata aattattgta atttttgggg atcaattcga      2220
     gctcctccgc ttaaaaaatt tcatttttcg atcaaaaaag acaaattatt actaattagc      2280
     tcatggcaat aaataatcag tagtaatctg ttttcacatt ttattgttaa tttttattat      2340
     tgctaatatc aaccttttct acttctgctt aatattttat ttatgctcaa tgggaaaatc      2400
     tgaaataaga ttgagaacag tgttaccaat agaagtattt aaggtttaaa gcatacctta      2460
     aagataacat tttttttga aaagagtcaa attatttttg aaaggctgat atttttgata       2520
     tttactaata ttttatttat ttctttttcc cttaaaataa gagctaaatc tgtttttatt      2580
     atcatttatc aagctctatt aatacctcaa ctttttcaag aaaaaataat aataattttt      2640
     ccctctattc tcatgacctt ttaggaaaat taattttaga aaaactattg acaaacccat      2700
     aaaaaatgag ataagattat agattgtcac tggtatttta tactagaggc aaattatatt      2760
     tatatataca aaaatgctgt ataaaaaaca tctcatatga ttaaagccta tgctgcctta      2820
     gaagccaatg gtaaattaca accctttgaa tatgatcctg gtgctttagg tgccaatgaa      2880
     gtggaaattg aagtgcaata ttgtggtgtg tgtcattctg atttatctat gattaataat      2940
     gaatggggta tttctaatta tcccttagtt cctggtcatg aagttgttgg tactgttgct      3000
     gctatgggtg aaggtgttaa tcatgtggaa gtgggtgatt tagttggttt aggttggcat      3060
     tctggttatt gtatgacctg tcattcttgt ttatctggtt atcataattt atgtgccact      3120
     gccgaatcta ctattgtggg tcattatggt ggttttggtg atagagttcg tgctaaaggt      3180
     gtttctgtgg tgaaattacc caaaggtatt gatttagcct ctgctgggcc tttattttgt      3240
     ggtggtatta ccgtttttc tcccatggtg gaattatctt taaaacctac cgccaaagtt       3300
     gctgttattg gtattggtgg tttaggtcat ttagccgttc aatttttaag agcctggggt      3360
     tgtgaagtta ctgcttttac ctcttctgcc cgtaaacaaa ccgaagtttt agaattaggt      3420
     gcccatcata ttttagattc taccaatcct gaagctattg cttctgccga aggtaaattt      3480
     gattatatta tttctaccgt gaatttaaaa ttagattgga atttatatat cagtacctta      3540
     gcccctcaag gtcattttca ttttgttggt gtggtgttag aaccccttgga cttaaactta     3600
     tttcccttat taatgggaca acgttctgtt tctgcttctc ctgttggttc tcctgctact      3660
     attgccacta tgttagattt tgccgtgcgt catgatatta aacccgtggt ggaacaattt      3720
     tcttttgatc aaattaatga agccattgcc catttagaat ctggtaaagc ccattatcgc      3780
     gtggtgttat ctcattctaa aaattaataa gattaacttc taaactgaaa caaatttgag      3840
     ggtaggcttc attgtctgcc cttatttttt tatttaggaa aagtgaacag actaaagagt      3900
     gttggctcta ttgctttgag tatgtaaatt aggcgttgct gaattaaggt atgatttttg      3960
     accccttctc tcttctgcag ttacctagga tttctggcga aagggggatg tgctgcaagg      4020
     cgattaagtt gggtaacgcc agggttttcc cagtcacgac gttgtaaaac gacggccagt      4080
     gagcgcgacg taatacgact cactataggg cgaattggcg gaaggccgtc aaggccgcat      4140
     ggcgcgccta cgtagacaat tgtcgatgta attattaact atcttattat agatgagggg      4200
     agagggagaa attagttcgg agagaacgct cgagcgctcg ttccgcaaag cggtacggag      4260
```

FIG. 17 (continued)

ttagttaggg gctaatgggc attctcccgt acaggaaaga gttagaagtt attaattatc 4320
aacaattctc ctttgcctag tgcatcgtta ccttttttaat taaaacataa ggaaaactaa 4380
taatcgtaat aatttaacct caaagtgtaa agaaatgtga aattctgact tttataacgt 4440
taaagaggga aaaattagca gtttaaaata cctagagaat agtctggggt aagcatagag 4500
aattagatta gttaagttaa tcaaattcag aaaaaataat aatcgtaaat agttaatctg 4560
ggtgtataga aaatgatccc cttcatgata agatttaaac tcgaaaagca aaagccaaaa 4620
aactaacttc cattaaaaga agttgttaca tataacgcta taaagaaaat ttatatattt 4680
ggaggatacc aaccatgtct catattcaac gtgaaactag ttgttctcgt cctcgtttaa 4740
attctaatat ggatgccgat ttatatggtt ataaatgggc tcgtgataat gttggtcaat 4800
ctggtgctac tatttatcgt ttatatggta aacctgatgc tcctgaatta ttcttgaaac 4860
atggtaaagg ttctgttgct aatgatgtta ctgatgaaat ggttcgttta aactggttga 4920
ctgaatttat gcctttacct actattaaac attttattcg tactcccgat gatgcttggt 4980
tattaactac tgctattcct ggtaaaactg cttttcaagt tttagaagaa tatcctgatt 5040
ctggtgaaaa tattgttgat gctttagctg tttttttacg tcgtttacat tctattcccg 5100
tttgtaattg tccttttaat tctgatcgtg tttttcgttt agctcaagct caatctcgta 5160
tgaataatgg tttagttgat gcttctgatt ttgatgatga acgtaatggt tggcctgttg 5220
aacaagtttg gaaagaaatg cacaaattgt taccttttc tcctgattct gttgttactc 5280
atggtgattt ttctttagat aatttgatct ttgatgaagg taaattgatt ggttgtattg 5340
atgttggtcg tgttggtatt gctgatcgtt atcaagattt agctatttta tggaattgtt 5400
taggtgaatt ttctccttct ttacagaaac gtttatttca gaaatatggt attgataatc 5460
ctgatatgaa caagttacaa tttcatttaa tgttggacga gttcttttaa gaattaattc 5520
atgaccaaaa tcccttaacg tgagttttcg ttccactgag cgtcagaccc cgtagaaaag 5580
atcaaaggat cttcttgaga tcctttttt ctgcgcgtaa tctgctgcta tttaaattac 5640
gtacacgtgt tattactttg ttaacgacaa ttgtcttaat taactgggcc tcatgggcct 5700
tccgctcact gcccgctttc cagtcgggaa acctgtcgtg ccagctctgc agatgacggt 5760
gaaaacctct gacacatgca gctcccggag acggtcacag cttgtctgta agcggatgcc 5820
gggagcagac aagcccgtca gggcgcgtca gcgggtgttg gcgggtgtcg gggcgcagcc 5880
atgacccagt cacgtagcga tagcggagtg tatactggct taactatgcg gcatcagagc 5940
agattgtact gagagtgcac catatgcggt gtgaaatacc gcacagatgc gtaaggagaa 6000
aataccgcat caggcgctct tccgcttcct cgctcactga ctcgctgcgc tcggtcgttc 6060
ggctgcggcg agcggtatca gctcactcaa aggcggtaat acggttatcc acagaatcag 6120
gggataacgc aggaaagaac atgtgagcaa aaggccagca aaaggccagg aaccgtaaaa 6180
aggccgcgtt gctggcgttt ttccataggc tccgcccccc tgacgagcat cacaaaaatc 6240
gacgctcaag tcagaggtgg cgaaacccga caggactata aagataccag gcgtttcccc 6300
ctggaagctc cctcgtgcgc tctcctgttc cgaccctgcc gcttaccgga tacctgtccg 6360
cctttctccc ttcgggaagc gtggcgcttt ctcatagctc acgctgtagg tatctcagtt 6420
cggtgtaggt cgttcgctcc aagctgggct gtgtgcacga accccccgtt cagcccgacc 6480
gctgcgcctt atccggtaac tatcgtcttg agtccaaccc ggtaagacac gacttatcgc 6540
cactggcagc agccactggt aacaggatta gcagagcgag gtatgtaggc ggtgctacag 6600
agttcttgaa gtggtggcct aactacggct acactagaag gacagtattt ggtatctgcg 6660
ctctgctgaa gccagttacc ttcggaaaaa gagttggtag ctcttgatcc ggcaaacaaa 6720
ccaccgctgg tagcggtggt ttttttgttt gcaagcagca gattacgcgc agaaaaaaag 6780
gatctcaaga agatcctttg atcttttcta ctgcagaagc ttgttagaca ccctgtcatg 6840
tattttatat tatttatttc accatacgga ttaagtgaaa cctaatgaaa atagtacttt 6900
cggagcttta actttaatga aggtatgttt ttttatagac atcgatgtct ggtttaacaa 6960
taggaaaaag tagctaaaac tcccatgaat taaagaaata acaaggtgtc taacaacctg 7020
ttattaagaa tgttagaaaa gacttaacat ttgtgttgag tttttataga cattggtgtc 7080
tagacatacg gtagataagg tttgctcaaa aataaaataa aaaaagattg gactaaaaaa 7140
catttaattt agtacaattt aattagttat tttttcgtct caaattttgc tttgttgagc 7200
agaaatttag ataaaaaaat ccccgtgatc agattacaat gtcgttcatt gtacgatgtg 7260
tcgaaaaatc tttacgacac tctaaactga ccacacgggg gaaaaagaaa actgaactaa 7320
taacatcatg atactcggaa aacctagcaa ttctcaaccc ctaaacaaaa gaaacttcca 7380

FIG. 17 (continued)

```
aaaccctgac catataaagg agtggcaaca atcagcaatc agtcaagatt tgatagcaga    7440
aaatcttgta tcggttgcta atggttttga tgtactattt atcggcaata aataccgaac    7500
taacacgggt gttctgtcac ggcacatatt aaactcctat tctcatttag aagatggtgg    7560
ttcgtatggt agaacatttg acccatttac caataaagaa atgcagtggg ttcaatttaa    7620
accgaataga ccaagaaaag gttctactgg taaggtaatc aaatatgaat cgccaaaagg    7680
tgaacctaca agagttctaa tgccgtttgt gcctatgaaa atatggcaac ggattagcga    7740
taagttcgga gtaccgatta atccgaaaaa agatactcac ttttgggaat gggtaaagaa    7800
taatccatcg ataccgattg ccattacaga aggaaataaa aaagctaatt gcctattatc    7860
ctatggctat cctgctattg cctttgtagg catttggaac ggattagaga aaataaatga    7920
tttctcgaag gaaaagcagt taaaagagga tttgaaatgg ttgttatcca acggcaaccg    7980
aaatattaat atcatctttg accaagacca gaaacaaaaa actgtaatta atgtaaacaa    8040
agctattttc gctttatctt ctctaataag tagaaatggt cataaagtta atattgtgca    8100
atggttgccg tcaaaaggta aaggaataga tgattatttg gtagctttac cttttgagaa    8160
aagagaaaat catttagaca acttaattaa aattgcacca tcatttaatt tttggtcaac    8220
taaatactta ttcaagtgtc gtaaaccaga tttaaccgta aattgccgtt atttgagcga    8280
tgcagtaaaa gaattacctc aagaggatat agcattaata gcacctcacg gcacgggtaa    8340
aacttcatta gtagctactc acgttaagaa tcggagttat cacggaagga aaactatttc    8400
attggtgcat cttgaaagtt tagccaaagc taatggcaac gcacttggat tatattaccg    8460
aaccgaaaat aatattgaaa agcaatatct tggatttagc ttatgtgtag atagttgccg    8520
tgataagatt aacggcatta caactgatat tatttcaggt caagattatt gccttttcat    8580
tgatgaaatt gaccaagtaa ttccacacat ccttaacagt gaaactgaag taagtaagta    8640
tagatgcacc atcattgaca ctttttctga actggtgaga aatgctgaac aggtcattat    8700
tgctgatgct gatttatccg atgtgacgat tgacctaata gaaaacatca gaggtaaaaa    8760
actatatgta atcaagaatg aatatcagta tcagggaatg acttttaacg ccgttggttc    8820
accattagaa atgatggcaa tgatgggaaa atcggtgtca gaaggcaaga aattatttat    8880
taacaccaca tcccaaaagg caaaaagtaa gtacggcaca atcgctcttg agtcttatat    8940
ttttggtcta aataaagaag caaagatatt aagaatagac tctgaaacca ctaaaaaccc    9000
tgaacatcca gcctataaaa tcattgacca agacttaaat aatatcctca aagattatga    9060
ttatgtcatt gcctcacctt gccttcaaac aggtgtcagt attaccttaa aagggcattt    9120
tgaccagcaa tttaactttt ccagtggaaa cattacacct cattgctttt tacagcaaat    9180
gtggcggttg agggatgcag aaattgaaag attctattat gtgccgaact catctaacct    9240
caatctcatt gggaataagt caagttcacc atcagacctt ctaaagagca ataacaagat    9300
ggcaacggca acggttaacc ttttgggtag aatcgactcc gaatattccc tagagtatga    9360
atcgcacggc atttggcttg agacgtgggc aaaattatca gcacggcata acagttcaat    9420
gcgttgttac tctgaaattc ttacctatct aattacgtct caagggcata aattaaatat    9480
caacattccc tcacctcttg cagatattaa gaagctaaat gatgaggtaa gtagtaacag    9540
ggaaaaggta aaaaatgaga gatactctca gaggttaaac tcaccagata ttaacgatgc    9600
agaagctacc atactcgaat ctaaagagca aaaaatcgga ttgactctca atgagagatg    9660
caccctagaa aagcataaag ttaagaagcg gtatgggaat gtaaagatgg atattctcac    9720
ctttgatgat gatggactat accccaaact cagactattt tattacctca ccatcggtaa    9780
acctcatctc aaggctaatg acagaaaagc tattgccaaa atgggcaatg acaataaagg    9840
caagattcta tcaaaagact tagttaataa aacttactcc gctcgtgtga aggtcttaga    9900
gattcttaaa ctaactgact ttatcgacaa tcttagagat gaactcttaa taactcccaa    9960
taatccagct atcaccgatt ttaataatct tctgctaaga gctaagaagg atttaagagt   10020
attaggagtc aacatcggaa aatatccaat ggccaacatt aatgccgtac ttactctcat   10080
tggtcacaaa ctttctgtaa tgagagatga gttcggaaaa gagaaaagga taaaagtaga   10140
tggtaaatca taccgatgtt atcaacttga aacattacca gatttacca atgatactct   10200
tgactactgg ttagaaaatg atagccaaaa agaagtaaca gcaacagaaa attactccga   10260
aaattttaac ccttcaaata gctacaatcc agacagtaag acactttcag agggtgcaaa   10320
tttcctatat ataaataaag aagaattgca tccaaataaa ttgcacctag aaataaaaga   10380
aggtgctgaa cttttttat tcggggtaaa ggtgattgtg aaaggaatct tggacggggc   10440
```

FIG. 17 (continued)

```
agtaactata ttctctatgg gtcaagaata cgatttatcc ctcaatgaac tagaggggat      10500
gttaacatca tgaactttac aagaatcttt ttaaagggcg atcgcaccat gttaaatgat      10560
ggtacatttg ttcagatatt tgatatttac catgaccacg cattgggagt gacccttgac      10620
cttaagacag aaaaaattat ttccgatgat gttagggtaa ttactgtcaa agacttattg      10680
ttcgatggca cttataaagg ggtaaaatct tttatgcccg ataatgcccg ataatgcccg      10740
attgatgcta caaaatccca taatcataag cgataatccc ctaatagctt gtaattcttg      10800
aaccgtagcg attttagagt attccaaaaa gaagaaataa acaccgcaaa atgtcgtatt      10860
tcacatatat aaaccaaggt tttttgccct aaaatcttta tgtttgtagt gtgatgttgg      10920
gtcaaaatgg tcagaaaagt tgcaaggttt ttatggatgc ttacgcgcgc gaggggtaag      10980
catccccaaa tagttacttt atcctagtcc atgcccattt attgccgtcc cgttcggctt      11040
taaaaaagtg ccaaaactca caaggtgcaa taaaaagttc tgtacctttc gcaaccctag      11100
ataatctttc aacagttact ttttttccta ttatctcggt acaaagtttg gctagtttct      11160
cttttccctc tttttcaatc aagccttctt gtatgcccaa ctcattgatt aatctctcta      11220
tttttaccat tatttcccgt tcaggtagtt tatcccctaa atcttcatcg gggggcaatg      11280
tagggcattc tgaaggggct ttttcttctg tctggacatt atctaatatt gaagtaacca      11340
aactatcttc agttttttct attcctatta attcatattc ggttactgta tccgtatcaa      11400
tatccgaata actatcttta tccgtattag ctattcggtt aagtttatcc gttaactcag      11460
aaacaagact atatagcggt tttagctttt cttctatcct gttatctaat acggataagt      11520
ttatacggtt atcattatcc gtattagtat cattgggctt ttttggtagt tctacccccct      11580
cataaaccgc ttttattccc aattccaaca gactgataac agtatccttt ataatgggtt      11640
ttttgctgat atggtgaact tttgcccctt ccatcattgc gatactttct atctcactca      11700
tcaacttatc gcttaagtga atctcgtatc tgtttaatcc cttactggtt ttattcatat      11760
ccgtttactt tattcggtta acaattctat tttatacgaa taaaatatta tacggttaac      11820
tttatacgtt taactatttt atctatacgg ataacagtaa taagttattc gtattagtta      11880
tacgtttact tttatccaaa taaaattagt gcatttaaac taaaagaatg attttatcgg      11940
agttgatagc attggattaa cctaaagatg tttataagct atatctgata agtatttaag      12000
gttattttgt tattctgttt attgacatta tcagaataaa agaatagaat ataattgttg      12060
agagataaga ggtttaagtg attatggtta agaagttagt tggttatgtc agggtcagta      12120
gtgaatcgca agaggataac actagcttac agaatcagat agagagaatt gaagcatatt      12180
gtatggcttt tggttatgag ttggtaaaaa tattcaaaga ggttgccact ggtacaaaag      12240
cagatattga aacccgtcct atttttaatg aagctataga atacttgaaa caggataatg      12300
ctaatggaat tattgccttg aagctagacc gaatcgcacg gaatgcttta gatgtattgc      12360
gtttggttcg tgaaacctta gaaccacaaa ataaaatgtt agtgttacta gatattcagg      12420
tagatacttc gacaccttca ggaaaaatga ttttaactgt aatgagtgcc gttgctgaac      12480
tcgaaagaga catgatctat gatcgcactc agggggtag aaagactaaa gcccaaaagg      12540
gcgggtatgc ctacgggaaa cctaaatttg gctataagac tgaagaaaag gaactaaaag      12600
aagattcagc acaacaggaa actattaaac taattaagag acaccgtagg tcagggaaaa      12660
gctaccagaa aatagctgat tatctcaatg cccaaagtat tcccactaaa caaggtaaga      12720
aatggagttc tagcgtcgtc tatcgaatct gtcaggaaaa agctggttaa gtctgtttat      12780
agatatttag aatttattga ataaaaatag tatgaacaat aaatatttat ggactaacca      12840
cgctcggaaa cgtttaactg aacgatggga aataaaagaa tcatgggtta ttgataccat      12900
cgaaaatcct gaacgttcag aatttattgt tgatgagtca ggggaaaaat atcattacta      12960
taaaagaata gctaagttta agaatagagt gttagaagtg ataacttctg ccaactcaac      13020
acccacaaga ataataacct tttactttaa ccgtaacatg aggaaaaatt tatgattgtt      13080
acttacgata atgaagttga cgcaatttat tttaagttaa cggaaaataa aattgatagc      13140
accgaacctc aaacagacag gattatcatt gattacgatg aaagtaataa tattgttggc      13200
attgaggtat tagattttaa ttatcttgtc aagaaaggtt taaccgttgc tgatttacct      13260
ttttctgaag atgaaagatt aacagcttct caatatttta attttcctgt tgctatctaa      13320
tccagaaggg gcaataatcc ccttctttca tcgagttaga cttaatatca caaaagtcat      13380
tttcatttta ccgtttcttt tccacagcgt ccgtacgccc ctcgttaaat ctcaaaaccg      13440
acaatttatg atgtttataa aaagttactc actttaataa gtatttatac tcattaaagg      13500
gttattcttt ttttgtagcc tgataggttg ggaaggaata tttcagatta tcagatttgt      13560
tg                                                                     13562
```

FIG. 17 (continued)

#1495 pABICyano1-6.8::PnirAABICyano1-zmPDCABICyano1(opt3)-PrpsLABICyano1-ADHABICyano1(opt3) ter-PrbcABICyano1-Km**

```
ID   #1495\pABICyano1-6.8::PnirAABICyano1-zmPDCABICyano1(opt3)-PrpsLABICyano1-
ADHABICyani1(opt3)_ter-PrbcABICyano1-Km** standard; circular DNA;    ; 13119 BP.
CC   This file is created by Vector NTI
CC   http://www.invitrogen.com/
CC   VNTDATE|624110553|
CC   VNTDBDATE|626784563|
CC   LSOWNER|
FH   Key             Location/Qualifiers
FH
FT   gene            2581..3591
FT                   /vntifkey="60"
FT                   /note="SycADHopti"
FT   terminator      3604..3649
FT                   /vntifkey="43"
FT                   /label=Terminator_1
FT                   /note="Ter_B0011"
FT   CDS             2581..3588
FT                   /vntifkey="4"
FT                   /label=SynADHABICyano1(opt3)
FT   promoter        2009..2577
FT                   /vntifkey="30"
FT                   /label=PrpsLABICyano1
FT   promoter        1..283
FT                   /vntifkey="30"
FT                   /label=PnirAABICyano1
FT   insertion_seq   6280..13113
FT                   /source="pABICyano1-6HindIIIBamHI"
FT                   /type="Custom cloned insert"
FT                   /vntifkey="14"
FT                   /label=pABICyano1-6HindIIIBamHI
FT                   /note="Unknown feature type:insert"
FT   rep_origin      complement(5215..6273)
FT                   /vntifkey="33"
FT                   /label=OriVT
FT   CDS             6790..9975
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   misc_feature    9571..9604
FT                   /vntifkey="21"
FT                   /label=Rep\motif
FT                   /note="Rep protein active site motig EXXKYXVKXXD"
FT   rep_origin      complement(9311..9328)
FT                   /vntifkey="33"
FT                   /label=Rep_Origin_1\(potential)
FT                   /note="potential rep origin; match pNostoc (Acc# M81381) nick
site (358-375); on reserse strand"
FT   CDS             10011..10196
FT                   /vntifkey="4"
FT                   /label=ORF\2
FT                   /note="orf2"
```

FIG. 19

```
FT   CDS             complement(10456..11220)
FT                   /vntifkey="4"
FT                   /label=ORF\3
FT                   /note="orf3"
FT   CDS             11546..12232
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             12274..12537
FT                   /vntifkey="4"
FT                   /label=ORF\5
FT                   /note="orf5"
FT   CDS             12534..12782
FT                   /vntifkey="4"
FT                   /label=ORF\6
FT                   /note="orf6"
FT   CDS             4157..4972
FT                   /vntifkey="4"
FT                   /label=Km**
FT                   /note=" maximal codon optimized kanamycin resistance gene "
FT   CDS             284..1990
FT                   /vntifkey="4"
FT                   /label=zmPDCABICyanol(opt3)
FT   promoter        3692..4155
FT                   /vntifkey="30"
FT                   /label=PrbcLABICyanol
SQ   Sequence 13119 BP; 4182 A; 2307 C; 2512 G; 4118 t;
     tcgacaatta ataacttctt cctgtacggg cgaatggcca tttgctccta actaactccg        60
     tactgctttg cggaacgagc gtagcgaact ctccgaatta ctaagccttc atccctgata       120
     gatgcaaaaa acgaattaaa attatgtgta aaaagaaaat gtgtctttat ttagtagtca       180
     aagttacaaa atattaagaa tcaaattaat aatgtattgg gcagttaagt atataagtct       240
     ttaaatattt atttgtattc aatatattaa ccgaggacaa attatgaatt cttacactgt       300
     tggaacctat ttagcagaac gtttagttca aattggtctc aaacaccatt ttgcagtagc       360
     tggtgattat aatttagttt tattggataa cttattgtta aataagaata tggaacaagt       420
     gtattgttgt aatgaattaa actgtggttt ttctgctgag ggatatgctc gtgcaaaagg       480
     tgctgccgca gcagttgtta cttattctgt tggagcatta agtgcttttg acgctattgg       540
     aggtgcttat gcagaaaatt tacctgtaat cttaatctct ggtgcaccca ataacaacga       600
     tcacgctgct ggtcatgtat tgcatcatgc tttaggtaaa accgattatc attaccaatt       660
     agaaatggca aaaaatatta ccgctgccgc agaagctatt tatactcccg aagaagcacc       720
     tgctaagatc gatcacgtaa ttaaaaccgc tctccgtgag aaaaaacccg tatatttaga       780
     aatcgcttgc aatatcgctt ctatgccttg tgcagctcct ggacctgcta gtgctttatt       840
     taacgatgaa gcatctgatg aggctagttt aaatgccgct gttgaagaaa ctttgaaatt       900
     tattgctaat cgtgataaag tagctgtttt agttggttct aaactccgtg ccgctggtgc       960
     agaagaagcg gctgtaaaat tcgcagatgc cttaggaggt gctgttgcca caatggcagc      1020
     cgctaaaagt tttttccccg aagaaaatcc tcattacatt ggtacttctt ggggtgaggt      1080
     atcttaccct ggtgtagaaa aaaccatgaa ggaagctgat gcagtaattg cattagctcc      1140
     tgttttcaat gattactcta ccactggttg gactgatatt ccagacccca aaaaattagt      1200
     tttagcagaa cctcgctctg tagttgtgaa tggtgttaga tttcccagtg tacatctcaa      1260
     agattattta actcgtttag ctcaaaaagt gagtaaaaag actggcgcac tcgatttctt      1320
     taaatcttta aatgctggtg aattaaagaa agcagctcct gctgatccca gtgctccttt      1380
     agtgaatgcc gaaatcgcaa gacaagttga agccttgtta actcctaaca ctaccgttat      1440
```

FIG. 19 (continued)

```
tgccgagact ggtgatagtt ggttcaatgc tcaacgcatg aaattaccca atggtgctcg 1500
tgttgagtat gaaatgcaat ggggtcacat tggatggtct gttcctgctg catttggata 1560
tgcagttgga gcacctgagc gtagaaacat tttaatggta ggtgatggtt ctttccaact 1620
cactgctcaa gaagttgcac aaatggtacg tttaaaattg cctgttatta tctttctcat 1680
taacaactat ggttacacca ttgaagttat gattcatgat ggtccttata ataacattaa 1740
gaattgggat tacgcaggtt taatggaggt atttaacggt aatggtggat acgacagtgg 1800
agcaggtaaa ggattaaaag ctaaaacagg aggtgagtta gctgaagcaa ttaaagtagc 1860
tttagccaat acagatggtc ctaccttaat cgaatgtttc attggacgtg aagattgtac 1920
tgaagagtta gttaaatggg gaaagcgtgt tgccgctgca aattctcgta aacctgtaaa 1980
caaactcttg tagttaggat ccgagctcct ccgcttaaaa aatttcattt ttcgatcaaa 2040
aaagacaaat tattactaat tagctcatgg caataaataa tcagtagtaa tctgttttca 2100
cattttattg ttaattttta ttattgctaa tatcaacctt ttctacttct gcttaatatt 2160
ttatttatgc tcaatgggaa aatctgaaat aagattgaga acagtgttac caatagaagt 2220
atttaaggtt taaagcatac cttaaagata acattttttt ttgaaaagag tcaaattatt 2280
tttgaaaggc tgatattttt gatatttact aatattttat ttatttcttt ttcccttaaa 2340
ataagagcta aatctgtttt tattatcatt tatcaagctc tattaatacc tcaacttttt 2400
caagaaaaaa taataataat ttttccctct attctcatga ccttttagga aaattaattt 2460
tagaaaaact attgacaaac ccataaaaaa tgagataaga ttatagattg tcactggtat 2520
tttatactag aggcaaatta tatttatata tacaaaaatg ctgtataaaa aacatctcat 2580
atgattaagg cttatgctgc attagaagct aatggtaaat tacaaccttt tgaatacgat 2640
cccggtgctt taggtgcaaa tgaagtagaa attgaggttc agtattgtgg tgtatgtcat 2700
tctgatttat ctatgattaa caacgaatgg ggaatttcca attatccctt agttcctgga 2760
cacgaagttg ttggtactgt agcagctatg ggagaaggag ttaatcatgt tgaagtaggt 2820
gacttagtag gtttgggatg gcattctggt tactgtatga cctgtcatag ttgtttatct 2880
ggttatcaca acttatgtgc aactgctgaa agtaccattg ttggtcatta cggtggtttt 2940
ggtgatagag taagagctaa aggagttagt gttgttaaat taccaaaagg tatcgactta 3000
gcaagtgcag gtcctctctt ttgtggaggt attactgttt ttagtcctat ggttgaatta 3060
agtttaaagc caactgcaaa agtagccgtc attggtattg gaggattggg acacttagct 3120
gttcaatttc tccgtgcatg ggatgtgaa gttactgcct ttacttctag tgctcgtaaa 3180
caaaccgagg tattagaatt aggagcacac catatcttag attccaccaa ccctgaagct 3240
atcgctagtg cagagggaaa attcgattat attattagta ctgttaattt gaaattagat 3300
tggaacctct acatctctac tttagctccc caaggtcatt ttcactttgt tggagttgta 3360
ttagaacccc tcgatttaaa cttattccct ttattaatgg gacaacgttc tgttagtgca 3420
tctcctgttg gatctcccgc tactattgct accatgttag attttgcagt acgtcacgat 3480
attaaacctg tagtagaaca attctctttc gatcaaatca acgaagctat tgctcattta 3540
gaaagtggta aggctcatta ccgtgttgtt ttatctcact ctaaaaacta actagatctc 3600
tgcagagaat ataaaaagcc agattattaa tccggctttt ttattattta aatactgtgc 3660
acgatcctgc aggatcatct tgctgaaaaa ctcgagcgct cgttccgcaa agcggtacgg 3720
agttagttag gggctaatgg gcattctccc gtacaggaaa gagttagaag ttattaatta 3780
tcaacaattc tcctttgcct agtgcatcgt tacctttttta attaaaacat aaggaaaact 3840
aataatcgta ataatttaac ctcaaagtgt aaagaaatgt gaaattctga cttttataac 3900
gttaaagagg gaaaaattag cagtttaaaa tacctagaga atagtctggg gtaagcatag 3960
agaattagat tagttaagtt aatcaaattc agaaaaaata ataatcgtaa atagttaatc 4020
tgggtgtata gaaaatgatc cccttcatga taagatttaa actcgaaaag caaaagccaa 4080
aaaactaact tccattaaaa gaagttgtta catataacgc tataaagaaa atttatatat 4140
ttggaggata ccaaccatgt ctcatattca acgtgaaact agttgttctc gccctcgttt 4200
aaattctaat atggatgccg atttatatgg ttataaatgg gctcgtgata atgttggtca 4260
atctggtgct actatttatc gtttatatgg taaacctgat gctcctgaat tattcttgaa 4320
acatggtaaa ggttctgttg ctaatgatgt tactgatgaa atggttcgtt taaactggtt 4380
gactgaattt atgcctttac ctactattaa acattttatt cgtactcccg atgatgcttg 4440
gttattaact actgctattc ctggtaaaac tgcttttcaa gttttagaag aatatcctga 4500
```

FIG. 19 (continued)

```
ttctggtgaa aatattgttg atgctttagc tgttttttta cgtcgtttac attctattcc     4560
cgtttgtaat tgtcctttta attctgatcg tgtttttcgt ttagctcaag ctcaatctcg     4620
tatgaataat ggtttagttg atgcttctga ttttgatgat gaacgtaatg gttggcctgt     4680
tgaacaagtt tggaaagaaa tgcacaaatt gttacctttt tctcctgatt ctgttgttac     4740
tcatggtgat ttttctttag ataatttgat ctttgatgaa ggtaaattga ttggttgtat     4800
tgatgttggt cgtgttggta ttgctgatcg ttatcaagat ttagctattt tatggaattg     4860
tttaggtgaa ttttctcctt ctttacagaa acgtttattt cagaaatatg gtattgataa     4920
tcctgatatg aacaagttac aatttcattt aatgttggac gagttctttt aagaattaat     4980
tcatgaccaa aatcccttaa cgtgagtttt cgttccactg agcgtcagac cccgtagaaa     5040
agatcaaagg atcttcttga gatccttttt ttctgcgcgt aatctgctgc tatttaaatt     5100
acgtacacgt gttattactt tgttaacgac aattgtctta attaactggg cctcatgggc     5160
cttccgctca ctgcccgctt tccagtcggg aaacctgtcg tgccagctct gcagatgacg     5220
gtgaaaacct ctgacacatg cagctcccgg agacggtcac agcttgtctg taagcggatg     5280
ccgggagcag acaagcccgt cagggcgcgt cagcgggtgt tggcgggtgt cggggcgcag     5340
ccatgaccca gtcacgtagc gatagcggag tgtatactgg cttaactatg cggcatcaga     5400
gcagattgta ctgagagtgc accatatgcg gtgtgaaata ccgcacagat gcgtaaggag     5460
aaaataccgc atcaggcgct cttccgcttc ctcgctcact gactcgctgc gctcggtcgt     5520
tcggctgcgg cgagcggtat cagctcactc aaaggcggta atacggttat ccacagaatc     5580
aggggataac gcaggaaaga acatgtgagc aaaaggccag caaaaggcca ggaaccgtaa     5640
aaaggccgcg ttgctggcgt ttttccatag gctccgcccc cctgacgagc atcacaaaaa     5700
tcgacgctca agtcagaggt ggcgaaaccc gacaggacta taaagatacc aggcgtttcc     5760
ccctggaagc tccctcgtgc gctctcctgt tccgaccctg ccgcttaccg gatacctgtc     5820
cgcctttctc ccttcgggaa gcgtggcgct ttctcatagc tcacgctgta ggtatctcag     5880
ttcggtgtag gtcgttcgct ccaagctggg ctgtgtgcac gaaccccccg ttcagcccga     5940
ccgctgcgcc ttatccggta actatcgtct tgagtccaac ccggtaagac acgacttatc     6000
gccactggca gcagccactg gtaacaggat tagcagagcg aggtatgtag gcggtgctac     6060
agagttcttg aagtggtggc ctaactacgg ctacactaga aggacagtat ttggtatctg     6120
cgctctgctg aagccagtta ccttcggaaa aagagttggt agctcttgat ccggcaaaca     6180
aaccaccgct ggtagcggtg gtttttttgt ttgcaagcag cagattacgc gcagaaaaaa     6240
aggatctcaa gaagatcctt tgatcttttc tactgcagaa gcttgttaga caccctgtca     6300
tgtattttat attatttatt tcaccatacg gattaagtga aacctaatga aaatagtact     6360
ttcggagctt taactttaat gaaggtatgt ttttttatag acatcgatgt ctggtttaac     6420
aataggaaaa agtagctaaa actcccatga attaaagaaa taacaaggtg tctaacaacc     6480
tgttattaag aatgttagaa aagacttaac atttgtgttg agtttttata gacattggtg     6540
tctagacata cggtagataa ggtttgctca aaaataaaat aaaaaaagat tggactaaaa     6600
aacatttaat ttagtacaat ttaattagtt attttttcgt ctcaaatttt gctttgttga     6660
gcagaaattt agataaaaaa atccccgtga tcagattaca atgtcgttca ttgtacgatg     6720
tgtcgaaaaa tctttacgac actctaaact gaccacacgg gggaaaaaga aaactgaact     6780
aataacatca tgatactcgg aaaacctagc aattctcaac ccctaaacaa aagaaacttc     6840
caaaaccctg accatataaa ggagtggcaa caatcagcaa tcagtcaaga tttgatagca     6900
gaaaatcttg tatcggttgc taatggtttt gatgtactat ttatcggcaa taaataccga     6960
actaacacgg gtgttctgtc acggcacata ttaaactcct attctcattt agaagatggt     7020
ggttcgtatg gtagaacatt tgacccattt accaataaag aaatgcagtg ggttcaattt     7080
aaaccgaata gaccaagaaa aggttctact ggtaaggtaa tcaaatatga atcgccaaaa     7140
ggtgaaccta caagagttct aatgccgttt gtgcctatga aaatatggca acggattagc     7200
gataagttcg gagtaccgat taatccgaaa aaagatactc acttttggga atgggtaaag     7260
aataatccat cgataccgat tgccattaca gaaggaaata aaaaagctaa ttgcctatta     7320
tcctatggct atcctgctat tgcctttgta ggcatttgga acggattaga gaaaataaat     7380
gatttctcga aggaaaagca gttaaaagag gatttgaaat ggttgttatc caacggcaac     7440
cgaaatatta atatcatctt tgaccaagac cagaaacaaa aaactgtaat taatgtaaac     7500
aaagctattt tcgctttatc ttctctaata agtagaaatg gtcataaagt taatattgtg     7560
```

FIG. 19 (continued)

```
caatggttgc cgtcaaaagg taaaggaata gatgattatt tggtagcttt accttttgag     7620
aaaagagaaa atcatttaga caacttaatt aaaattgcac catcatttaa tttttggtca     7680
actaaatact tattcaagtg tcgtaaacca gatttaaccg taaattgccg ttatttgagc     7740
gatgcagtaa aagaattacc tcaagaggat atagcattaa tagcacctca cggcacgggt     7800
aaaacttcat tagtagctac tcacgttaag aatcggagtt atcacggaag gaaaactatt     7860
tcattggtgc atcttgaaag tttagccaaa gctaatggca acgcacttgg attatattac     7920
cgaaccgaaa ataatattga aaagcaatat cttggattta gcttatgtgt agatagttgc     7980
cgtgataaga ttaacggcat tacaactgat attatttcag gtcaagatta ttgccttttc     8040
attgatgaaa ttgaccaagt aattccacac atccttaaca gtgaaactga agtaagtaag     8100
tatagatgca ccatcattga cacttttct gaactggtga gaaatgctga acaggtcatt     8160
attgctgatg ctgatttatc cgatgtgacg attgacctaa tagaaaacat cagaggtaaa     8220
aaactatatg taatcaagaa tgaatatcag tatcagggaa tgacttttaa cgccgttggt     8280
tcaccattag aaatgatggc aatgatggga aaatcggtgt cagaaggcaa gaaattattt     8340
attaacacca catcccaaaa ggcaaaaagt aagtacggca caatcgctct tgagtcttat     8400
atttttggtc taaataaaga agcaaagata ttaagaatag actctgaaac cactaaaaac     8460
cctgaacatc cagcctataa aatcattgac caagacttaa ataatatcct caaagattat     8520
gattatgtca ttgcctcacc ttgccttcaa acaggtgtca gtattacctt aaaagggcat     8580
tttgaccagc aatttaactt ttccagtgga aacattacac ctcattgctt tttacagcaa     8640
atgtggcggt tgagggatgc agaaattgaa agattctatt atgtgccgaa ctcatctaac     8700
ctcaatctca ttgggaataa gtcaagttca ccatcagacc ttctaaagag caataacaag     8760
atggcaacgg caacggttaa ccttttgggt agaatcgact ccgaatattc cctagagtat     8820
gaatcgcacg gcatttggct tgagacgtgg gcaaaattat cagcacggca taacagttca     8880
atgcgttgtt actctgaaat tcttacctat ctaattacgt ctcaagggca taaattaaat     8940
atcaacattc cctcacctct tgcagatatt aagaagctaa atgatgaggt aagtagtaac     9000
agggaaaagg taaaaaatga gagatactct cagaggttaa actcaccaga tattaacgat     9060
gcagaagcta ccatactcga atctaaagag caaaaaatcg gattgactct caatgagaga     9120
tgcaccctag aaaagcataa agttaagaag cggtatggga atgtaaagat ggatattctc     9180
acctttgatg atgatggact atacccccaaa ctcagactat tttattacct caccatcggt     9240
aaacctcatc tcaaggctaa tgacagaaaa gctattgcca aaatgggcaa tgacaataaa     9300
ggcaagattc tatcaaaaga cttagttaat aaaacttact ccgctcgtgt gaaggtctta     9360
gagattctta aactaactga ctttatcgac aatcttagag atgaactctt aataactccc     9420
aataatccag ctatcaccga ttttaataat cttctgctaa gagctaagaa ggatttaaga     9480
gtattaggag tcaacatcgg aaaatatcca atggccaaca ttaatgccgt acttactctc     9540
attggtcaca aactttctgt aatgagagat gagttcggaa aagagaaaag gataaaagta     9600
gatggtaaat cataccgatg ttatcaactt gaaacattac cagattttac caatgatact     9660
cttgactact ggttagaaaa tgatagccaa aaagaagtaa cagcaacaga aaattactcc     9720
gaaaatttta acccttcaaa tagctacaat ccagacagta agacactttc agagggtgca     9780
aatttcctat atataaataa agaagaattg catccaaata aattgcacct agaaataaaa     9840
gaaggtgctg aacttttttt attcggggta aaggtgattg tgaaaggaat cttggacggg     9900
gcagtaacta tattctctat gggtcaagaa tacgatttat ccctcaatga actagagggg     9960
atgttaacat catgaacttt acaagaatct ttttaaaggg cgatcgcacc atgttaaatg    10020
atggtacatt tgttcagata tttgatattt accatgacca cgcattggga gtgacccttg    10080
accttaagac agaaaaaatt atttccgatg atgttagggt aattactgtc aaagacttat    10140
tgttcgatgg cacttataaa ggggtaaaat cttttatgcc cgataatgcc cgataatgcc    10200
cgattgatgc tacaaaatcc cataatcata agcgataatc ccctaatagc ttgtaattct    10260
tgaaccgtag cgattttaga gtattccaaa aagaagaaat aaacaccgca aaatgtcgta    10320
tttcacatat ataaaccaag gtttttgcc ctaaaatctt tatgtttgta gtgtgatgtt    10380
gggtcaaaat ggtcagaaaa gttgcaaggt ttttatggat gcttacgcgc gcgaggggta    10440
agcatcccca aatagttact ttatcctagt ccatgcccat ttattgccgt cccgttcggc    10500
tttaaaaaag tgccaaaact cacaaggtgc aataaaaagt tctgtacctt tcgcaaccct    10560
agataatctt tcaacagtta cttttttcc tattatctcg gtacaaagtt tggctagttt    10620
ctcttttccc tctttttcaa tcaagccttc ttgtatgccc aactcattga ttaatctctc    10680
```

FIG. 19 (continued)

```
tatttttacc attatttccc gttcaggtag tttatcccct aaatcttcat cggggggcaa 10740
tgtagggcat tctgaagggg ctttttcttc tgtctggaca ttatctaata ttgaagtaac 10800
caaactatct tcagtttttt ctattcctat taattcatat tcggttactg tatccgtatc 10860
aatatccgaa taactatctt tatccgtatt agctattcgg ttaagtttat ccgttaactc 10920
agaaacaaga ctatatagcg gttttagctt ttcttctatc ctgttatcta atacggataa 10980
gtttatacgg ttatcattat ccgtattagt atcattgggc ttttttggta gttctacccc 11040
ctcataaacc gcttttattc ccaattccaa cagactgata acagtatcct ttataatggg 11100
ttttttgctg atatggtgaa cttttgcccc ttccatcatt gcgatacttt ctatctcact 11160
catcaactta tcgcttaagt gaatctcgta tctgtttaat cccttactgg ttttattcat 11220
atccgtttac tttattcggt taacaattct attttatacg aataaaatat tatacggtta 11280
actttatacg tttaactatt ttatctatac ggataacagt aataagttat tcgtattagt 11340
tatacgttta cttttatcca aataaaatta gtgcatttaa actaaaagaa tgattttatc 11400
ggagttgata gcattggatt aacctaaaga tgtttataag ctatatctga taagtattta 11460
aggttatttt gttattctgt ttattgacat tatcagaata aaagaataga atataattgt 11520
tgagagataa gaggtttaag tgattatggt taagaagtta gttggttatg tcagggtcag 11580
tagtgaatcg caagaggata acactagctt acagaatcag atagagagaa ttgaagcata 11640
ttgtatggct tttggttatg agttggtaaa aatattcaaa gaggttgcca ctggtacaaa 11700
agcagatatt gaaacccgtc ctatttttaa tgaagctata gaatacttga aacaggataa 11760
tgctaatgga attattgcct tgaagctaga ccgaatcgca cggaatgctt tagatgtatt 11820
gcgtttggtt cgtgaaacct tagaaccaca aaataaaatg ttagtgttac tagatattca 11880
ggtagatact tcgacacctt caggaaaaat gattttaact gtaatgagtg ccgttgctga 11940
actcgaaaga gacatgatct atgatcgcac tcaggggggt agaaagacta aagcccaaaa 12000
gggcgggtat gcctacggga aacctaaatt tggctataag actgaagaaa aggaactaaa 12060
agaagattca gcacaacagg aaactattaa actaattaag agacaccgta ggtcagggaa 12120
aagctaccag aaaatagctg attatctcaa tgcccaaagt attcccacta aacaaggtaa 12180
gaaatggagt tctagcgtcg tctatcgaat ctgtcaggaa aaagctggtt aagtctgttt 12240
atagatattt agaatttatt gaataaaaat agtatgaaca ataaatattt atggactaac 12300
cacgctcgga aacgtttaac tgaacgatgg gaaataaaag aatcatgggt tattgatacc 12360
atcgaaaatc ctgaacgttc agaatttatt gttgatgagt caggggaaaa atatcattac 12420
tataaaagaa tagctaagtt taagaataga gtgttagaag tgataacttc tgccaactca 12480
acacccacaa gaataataac cttttacttt aaccgtaaca tgaggaaaaa tttatgattg 12540
ttacttacga taatgaagtt gacgcaattt attttaagtt aacggaaaat aaaattgata 12600
gcaccgaacc tcaaacagac aggattatca ttgattacga tgaaagtaat aatattgttg 12660
gcattgaggt attagatttt aattatcttg tcaagaaagg tttaaccgtt gctgatttac 12720
ctttttctga agatgaaaga ttaacagctt ctcaatattt taattttcct gttgctatct 12780
aatccagaag gggcaataat ccccttcttt catcgagtta gacttaatat cacaaaagtc 12840
attttcattt taccgtttct tttccacagc gtccgtacgc ccctcgttaa atctcaaaac 12900
cgacaattta tgatgtttat aaaaagttac tcactttaat aagtatttat actcattaaa 12960
gggttattct ttttttgtag cctgataggt tgggaaggaa tatttcagat tatcagattt 13020
gttgaatatt tttcgtcaga tacgcaaacc ttacaaacat aattaacaac tgaaactatt 13080
gatatgtcta ggttttagct ctatcacagg ttggatctg 13119
```

FIG. 19 (continued)

#1578 pABICyano1-6.8::PnirAABICyano1-zmPDCABICyano1(opt3)-dsrA-Prbc*(optRBS)-synADHoop-PrbcABICyano1-Km**

```
ID   #1578\pABICyano1-6.8::PnirAABICyano1-zmPDCABICyano1(opt3)-dsrA-Prbc*(optRBS)-
synADH\oop-PrbcABICyano1-Km** standard; circular DNA;    ; 12648 BP.
CC   This file is created by Vector NTI
CC   http://www.invitrogen.com/
CC   VNTDATE|634296508|
CC   VNTDBDATE|634296508|
CC   LSOWNER|
FH   Key             Location/Qualifiers
FH
FT   promoter        48..116
FT                   /vntifkey="30"
FT                   /label=Prbc*(optRBS)
FT   insertion_seq   2..47
FT                   /vntifkey="14"
FT                   /label=dsrA\ter
FT   CDS             117..1127
FT                   /vntifkey="4"
FT                   /label=synADH
FT   terminator      1157..1187
FT                   /vntifkey="43"
FT                   /label=oop\terminator
FT   promoter        1214..1677
FT                   /vntifkey="30"
FT                   /label=PrbcABICyano1
FT   CDS             10925..12631
FT                   /vntifkey="4"
FT                   /label=zmPDCABICyano1(opt3)
FT   CDS             1679..2494
FT                   /vntifkey="4"
FT                   /label=Km**
FT                   /note=" maximal codon optimized kanamycin resistance gene "
FT   CDS             10056..10304
FT                   /vntifkey="4"
FT                   /label=ORF\6
FT                   /note="orf6"
FT   CDS             9796..10059
FT                   /vntifkey="4"
FT                   /label=ORF\5
FT                   /note="orf5"
FT   CDS             9068..9754
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(7978..8742)
FT                   /vntifkey="4"
FT                   /label=ORF\3
FT                   /note="orf3"
FT   CDS             7533..7718
FT                   /vntifkey="4"
FT                   /label=ORF\2
FT                   /note="orf2"
```

FIG. 21

```
FT   rep_origin      complement(6833..6850)
FT                   /vntifkey="33"
FT                   /label=Rep_Origin_1\(potential)
FT                   /note="potential rep origin; match pNostoc (Acc# M81381) nick
site (358-375); on reserse strand"
FT   misc_feature    7093..7126
FT                   /vntifkey="21"
FT                   /label=Rep\motif
FT                   /note="Rep protein active site motig EXXKYXVKXXD"
FT   CDS             4312..7497
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   rep_origin      complement(2737..3795)
FT                   /vntifkey="33"
FT                   /label=OriVT
FT   insertion_seq   3802..10635
FT                   /source="pABICyano1-6HindIIIBamHI"
FT                   /type="Custom cloned insert"
FT                   /vntifkey="14"
FT                   /label=pABICyano1-6HindIIIBamHI
FT                   /note="Unknown feature type:insert"
FT   promoter        10642..10924
FT                   /vntifkey="30"
FT                   /label=PnirAABICyano1
SQ   Sequence 12648 BP; 3928 A; 2331 C; 2557 G; 3832 t;
     cagcaagttt catcccgacc ccctcagggt cgggattttt ttattgtact agttgacata       60
     agtaaaggca tcccctgcgt gatataatta ccttcagttt aaggaggtat acacatatga      120
     ttaaagccta cgctgccctg gaagccaacg gaaaactcca acctttgaa tacgaccccg       180
     gtgccctggg tgctaatgag gtggagattg aggtgcagta ttgtggggtg tgccacagtg      240
     atttgtccat gattaataac gaatggggca tttccaatta ccccctagtg ccgggtcatg      300
     aggtggtggg tactgtggcc gccatgggcg aaggggtgaa ccatgttgag gtgggggatt      360
     tagtggggct gggttggcat tcgggctact gcatgacctg ccatagttgt ttatctggct      420
     accacaacct ttgtgccacg gcggaatcga ccattgtggg ccactacggt ggctttggcg      480
     atcgggttcg ggccaaggga gtcagcgtgg tgaaattacc taaaggcatt gacctagcca      540
     gtgccgggcc ccttttctgt ggaggaatta ccgttttcag tcctatggtg gaactgagtt      600
     taaagcccac tgcaaaagtg gcagtgatcg gcattggggg cttgggccat ttagcggtgc      660
     aatttctccg ggcctggggc tgtgaagtga ctgcctttac ctccagtgcc aggaagcaaa      720
     cggaagtgtt ggaattgggc gctcaccaca tactagattc caccaatcca gaggcgatcg      780
     ccagtgcgga aggcaaattt gactatatta tctccactgt gaacctgaag cttgactgga      840
     acttatacat cagcaccctg gcgccccagg gacatttcca ctttgttggg gtggtgttgg      900
     agcctttgga tctaaatctt tttccccttt tgatgggaca acgctccgtt tctgcctccc      960
     cagtgggtag tcccgccacc attgccacca tgttggactt tgctgtgcgc catgacatta     1020
     aacccgtggt ggaacaattt agctttgatc agatcaacga ggcgatcgcc catctagaaa     1080
     gcggcaaagc ccattatcgg gtagtgctca gccatagtaa aaattagctc tgcaaaggtt     1140
     gcttctgggt ccgtggaacg ctcggttgcc gccgggcgtt ttttattcct gcaggatcat     1200
     cttgctgaaa aactcgagcg ctcgttccgc aaagcggtac ggagttagtt aggggctaat     1260
     gggcattctc ccgtacagga aagagttaga agttattaat tatcaacaat tctcctttgc     1320
     ctagtgcatc gttacctttt taattaaaac ataaggaaaa ctaataatcg taataattta     1380
     acctcaaagt gtaaagaaat gtgaaattct gacttttata acgttaaaga gggaaaaatt     1440
```

FIG. 21 (continued)

```
agcagtttaa aatacctaga gaatagtctg gggtaagcat agagaattag attagttaag      1500
ttaatcaaat tcagaaaaaa taataatcgt aaatagttaa tctgggtgta tagaaaatga      1560
tccccttcat gataagattt aaactcgaaa agcaaaagcc aaaaaactaa cttccattaa      1620
aagaagttgt tacatataac gctataaaga aaatttatat atttggagga taccaaccat      1680
gtctcatatt caacgtgaaa ctagttgttc tcgccctcgt ttaaattcta atatggatgc      1740
cgatttatat ggttataaat gggctcgtga taatgttggt caatctggtg ctactattta      1800
tcgtttatat ggtaaacctg atgctcctga attattcttg aaacatggta aaggttctgt      1860
tgctaatgat gttactgatg aaatggttcg tttaaactgg ttgactgaat ttatgccttt      1920
acctactatt aaacatttta ttcgtactcc cgatgatgct tggttattaa ctactgctat      1980
tcctggtaaa actgcttttc aagttttaga agaatatcct gattctggtg aaaatattgt      2040
tgatgcttta gctgtttttt tacgtcgttt acattctatt cccgtttgta attgtccttt      2100
taattctgat cgtgtttttc gtttagctca agctcaatct cgtatgaata atggtttagt      2160
tgatgcttct gatttgatg atgaacgtaa tggttggcct gttgaacaag tttggaaaga      2220
aatgcacaaa ttgttacctt tttctcctga ttctgttgtt actcatggtg atttttcttt      2280
agataatttg atctttgatg aaggtaaatt gattggttgt attgatgttg gtcgtgttgg      2340
tattgctgat cgttatcaag atttagctat tttatggaat tgtttaggtg aattttctcc      2400
ttctttacag aaacgtttat ttcagaaata tggtattgat aatcctgata tgaacaagtt      2460
acaatttcat ttaatgttgg acgagttctt ttaagaatta attcatgacc aaaatccctt      2520
aacgtgagtt ttcgttccac tgagcgtcag accccgtaga aaagatcaaa ggatcttctt      2580
gagatccttt ttttctgcgc gtaatctgct gctatttaaa ttacgtacac gtgttattac      2640
tttgttaacg acaattgtct taattaactg ggcctcatgg gccttccgct cactgcccgc      2700
tttccagtcg ggaaacctgt cgtgccagct ctgcagatga cggtgaaaac ctctgacaca      2760
tgcagctccc ggagacggtc acagcttgtc tgtaagcgga tgccgggagc agacaagccc      2820
gtcagggcgc gtcagcgggt gttggcgggt gtcggggcgc agccatgacc cagtcacgta      2880
gcgatagcgg agtgtatact ggcttaacta tgcggcatca gagcagattg tactgagagt      2940
gcaccatatg cggtgtgaaa taccgcacag atgcgtaagg agaaaatacc gcatcaggcg      3000
ctcttccgct tcctcgctca ctgactcgct gcgctcggtc gttcggctgc ggcgagcggt      3060
atcagctcac tcaaaggcgg taatacggtt atccacagaa tcaggggata acgcaggaaa      3120
gaacatgtga gcaaaaggcc agcaaaaggc caggaaccgt aaaaaggccg cgttgctggc      3180
gtttttccat aggctccgcc cccctgacga gcatcacaaa aatcgacgct caagtcagag      3240
gtggcgaaac ccgacaggac tataaagata ccaggcgttt ccccctggaa gctccctcgt      3300
gcgctctcct gttccgaccc tgccgcttac cggatacctg tccgcctttc tcccttcggg      3360
aagcgtggcg ctttctcata gctcacgctg taggtatctc agttcggtgt aggtcgttcg      3420
ctccaagctg ggctgtgtgc acgaaccccc cgttcagccc gaccgctgcg ccttatccgg      3480
taactatcgt cttgagtcca acccggtaag acacgactta tcgccactgg cagcagccac      3540
tggtaacagg attagcagag cgaggtatgt aggcggtgct acagagttct tgaagtggtg      3600
gcctaactac ggctacacta gaaggacagt atttggtatc tgcgctctgc tgaagccagt      3660
taccttcgga aaaagagttg gtagctcttg atccggcaaa caaaccaccg ctggtagcgg      3720
tggttttttt gtttgcaagc agcagattac gcgcagaaaa aaaggatctc aagaagatcc      3780
tttgatcttt tctactgcag aagcttgtta gacaccctgt catgtatttt atattattta      3840
tttcaccata cggattaagt gaaacctaat gaaaatagta ctttcggagc tttaacttta      3900
atgaaggtat gttttttat agacatcgat gtctggttta acaataggaa aaagtagcta      3960
aaactcccat gaattaaaga aataacaagg tgtctaacaa cctgttatta agaatgttag      4020
aaaagactta acatttgtgt tgagttttta tagacattgg tgtctagaca tacggtagat      4080
aaggtttgct caaaaataaa ataaaaaaag attggactaa aaacatttta atttagtaca      4140
atttaattag ttattttttc gtctcaaatt ttgctttgtt gagcagaaat ttagataaaa      4200
aaatccccgt gatcagatta caatgtcgtt cattgtacga tgtgtcgaaa aatctttacg      4260
acactctaaa ctgaccacac gggggaaaaa gaaaactgaa ctaataacat catgatactc      4320
ggaaaaccta gcaattctca acccctaaac aaaagaaact tccaaaaccc tgaccatata      4380
aaggagtggc aacaatcagc aatcagtcaa gatttgatag cagaaaatct tgtatcggtt      4440
gctaatggtt ttgatgtact atttatcggc aataaatacc gaactaacac gggtgttctg      4500
```

FIG. 21 (continued)

```
tcacggcaca tattaaactc ctattctcat ttagaagatg gtggttcgta tggtagaaca    4560
tttgacccat ttaccaataa agaaatgcag tgggttcaat ttaaaccgaa tagaccaaga    4620
aaaggttcta ctggtaaggt aatcaaatat gaatcgccaa aaggtgaacc tacaagagtt    4680
ctaatgccgt ttgtgcctat gaaaatatgg caacggatta gcgataagtt cggagtaccg    4740
attaatccga aaaaagatac tcacttttgg gaatgggtaa agaataatcc atcgataccg    4800
attgccatta cagaaggaaa taaaaaagct aattgcctat tatcctatgg ctatcctgct    4860
attgcctttg taggcatttg gaacggatta gagaaaataa atgatttctc gaaggaaaag    4920
cagttaaaag aggatttgaa atggttgtta tccaacggca accgaaatat taatatcatc    4980
tttgaccaag accagaaaca aaaaactgta attaatgtaa acaaagctat tttcgcttta    5040
tcttctctaa taagtagaaa tggtcataaa gttaatattg tgcaatggtt gccgtcaaaa    5100
ggtaaaggaa tagatgatta tttggtagct ttaccttttg agaaaagaga aaatcattta    5160
gacaacttaa ttaaaattgc accatcattt aatttttggt caactaaata cttattcaag    5220
tgtcgtaaac cagatttaac cgtaaattgc cgttatttga gcgatgcagt aaaagaatta    5280
cctcaagagg atatagcatt aatagcacct cacggcacgg gtaaaacttc attagtagct    5340
actcacgtta agaatcggag ttatcacgga aggaaaacta tttcattggt gcatcttgaa    5400
agtttagcca aagctaatgg caacgcactt ggattatatt accgaaccga aaataatatt    5460
gaaaagcaat atcttggatt tagcttatgt gtagatagtt gccgtgataa gattaacggc    5520
attacaactg atattatttc aggtcaagat tattgccttt tcattgatga aattgaccaa    5580
gtaattccac acatccttaa cagtgaaact gaagtaagta agtatagatg caccatcatt    5640
gacacttttt ctgaactggt gagaaatgct gaacaggtca ttattgctga tgctgattta    5700
tccgatgtga cgattgacct aatagaaaac atcagaggta aaaaactata tgtaatcaag    5760
aatgaatatc agtatcaggg aatgactttt aacgccgttg gttcaccatt agaaatgatg    5820
gcaatgatgg gaaaatcggt gtcagaaggc aagaaattat ttattaacac cacatcccaa    5880
aaggcaaaaa gtaagtacgg cacaatcgct cttgagtctt atatttttgg tctaaataaa    5940
gaagcaaaga tattaagaat agactctgaa accactaaaa accctgaaca tccagcctat    6000
aaaatcattg accaagactt aaataatatc ctcaaagatt atgattatgt cattgcctca    6060
ccttgccttc aaacaggtgt cagtattacc ttaaaagggc attttgacca gcaatttaac    6120
ttttccagtg gaaacattac acctcattgc tttttacagc aaatgtggcg gttgagggat    6180
gcagaaattg aaagattcta ttatgtgccg aactcatcta acctcaatct cattgggaat    6240
aagtcaagtt caccatcaga ccttctaaag agcaataaca agatggcaac ggcaacggtt    6300
aaccttttgg gtagaatcga ctccgaatat tccctagagt atgaatcgca cggcatttgg    6360
cttgagacgt gggcaaaatt atcagcacgg cataacagtt caatgcgttg ttactctgaa    6420
attcttacct atctaattac gtctcaaggg cataaattaa atatcaacat tccctcacct    6480
cttgcagata ttaagaagct aaatgatgag gtaagtagta acagggaaaa ggtaaaaaat    6540
gagagatact ctcagaggtt aaactcacca gatattaacg atgcagaagc taccatactc    6600
gaatctaaag agcaaaaaat cggattgact ctcaatgaga gatgcaccct agaaaagcat    6660
aaagttaaga agcggtatgg gaatgtaaag atggatattc tcacctttga tgatgatgga    6720
ctatacccca aactcagact attttattac ctcaccatcg gtaaacctca tctcaaggct    6780
aatgacagaa aagctattgc caaaatgggc aatgacaata aaggcaagat tctatcaaaa    6840
gacttagtta ataaaactta ctccgctcgt gtgaaggtct tagagattct taaactaact    6900
gactttatcg acaatcttag agatgaactc ttaataactc ccaataatcc agctatcacc    6960
gattttaata atcttctgct aagagctaag aaggatttaa gagtattagg agtcaacatc    7020
ggaaaatatc caatggccaa cattaatgcc gtacttactc tcattggtca caaactttct    7080
gtaatgagag atgagttcgg aaaagagaaa aggataaaag tagatggtaa atcataccga    7140
tgttatcaac ttgaaacatt accagatttt accaatgata ctcttgacta ctggttagaa    7200
aatgatagcc aaaaagaagt aacagcaaca gaaaattact ccgaaaattt taacccttca    7260
aatagctaca atccagacag taagacactt tcagagggtg caaatttcct atatataaat    7320
aaagaagaat tgcatccaaa taaattgcac ctagaaataa aagaaggtgc tgaacttttt    7380
ttattcgggg taaaggtgat tgtgaaagga atcttggacg gggcagtaac tatattctct    7440
atgggtcaag aatacgattt atccctcaat gaactagagg ggatgttaac atcatgaact    7500
ttacaagaat ctttttaaag ggcgatcgca ccatgttaaa tgatggtaca tttgttcaga    7560
tatttgatat ttaccatgac cacgcattgg gagtgaccct tgaccttaag acagaaaaaa    7620
```

FIG. 21 (continued)

ttatttccga tgatgttagg gtaattactg tcaaagactt attgttcgat ggcacttata 7680
aaggggtaaa atcttttatg cccgataatg cccgataatg cccgattgat gctacaaaat 7740
cccataatca taagcgataa tcccctaata gcttgtaatt cttgaaccgt agcgatttta 7800
gagtattcca aaaagaagaa ataaacaccg caaaatgtcg tatttcacat atataaacca 7860
aggtttttg ccctaaaatc tttatgtttg tagtgtgatg ttgggtcaaa atggtcagaa 7920
aagttgcaag gtttttatgg atgcttacgc gcgcgagggg taagcatccc caaatagtta 7980
ctttatccta gtccatgccc atttattgcc gtcccgttcg gctttaaaaa agtgccaaaa 8040
ctcacaaggt gcaataaaaa gttctgtacc tttcgcaacc ctagataatc tttcaacagt 8100
tactttttt cctattatct cggtacaaag tttggctagt ttctctttc cctcttttc 8160
aatcaagcct tcttgtatgc ccaactcatt gattaatctc tctattttta ccattatttc 8220
ccgttcaggt agtttatccc ctaaatcttc atcgggggc aatgtagggc attctgaagg 8280
ggctttttct tctgtctgga cattatctaa tattgaagta accaaactat cttcagtttt 8340
ttctattcct attaattcat attcggttac tgtatccgta tcaatatccg aataactatc 8400
tttatccgta ttagctattc ggttaagttt atccgttaac tcagaaacaa gactatatag 8460
cggttttagc ttttcttcta tcctgttatc taatacggat aagtttatac ggttatcatt 8520
atccgtatta gtatcattgg gcttttttgg tagttctacc ccctcataaa ccgcttttat 8580
tcccaattcc aacagactga taacagtatc ctttataatg ggtttttgc tgatatggtg 8640
aacttttgcc ccttccatca ttgcgatact ttctatctca ctcatcaact tatcgcttaa 8700
gtgaatctcg tatctgttta atcccttact ggttttattc atatccgttt actttattcg 8760
gttaacaatt ctattttata cgaataaaat attatacggt taactttata cgtttaacta 8820
ttttatctat acggataaca gtaataagtt attcgtatta gttatacgtt tacttttatc 8880
caaataaaat tagtgcattt aaactaaaag aatgatttta tcggagttga tagcattgga 8940
ttaacctaaa gatgtttata agctatatct gataagtatt taaggttatt ttgttattct 9000
gtttattgac attatcagaa taaaagaata gaatataatt gttgagagat aagaggttta 9060
agtgattatg gttaagaagt tagttggtta tgtcagggtc agtagtgaat cgcaagagga 9120
taacactagc ttacagaatc agatagagag aattgaagca tattgtatgg cttttggtta 9180
tgagttggta aaaatattca aagaggttgc cactggtaca aaagcagata ttgaaacccg 9240
tcctattttt aatgaagcta tagaatactt gaaacaggat aatgctaatg gaattattgc 9300
cttgaagcta gaccgaatcg cacggaatgc tttagatgta ttgcgtttgg ttcgtgaaac 9360
cttagaacca caaaataaaa tgttagtgtt actagatatt caggtagata cttcgacacc 9420
ttcaggaaaa atgattttaa ctgtaatgag tgccgttgct gaactcgaaa gagacatgat 9480
ctatgatcgc actcaggggg gtagaaagac taaagcccaa aagggcgggt atgcctacgg 9540
gaaacctaaa tttggctata agactgaaga aaaggaacta aaagaagatt cagcacaaca 9600
ggaaactatt aaactaatta agagacaccg taggtcaggg aaaagctacc agaaaatagc 9660
tgattatctc aatgcccaaa gtattcccac taaacaaggt aagaaatgga gttctagcgt 9720
cgtctatcga atctgtcagg aaaaagctgg ttaagtctgt ttatagatat ttagaattta 9780
ttgaataaaa atagtatgaa caataaatat ttatggacta accacgctcg gaaacgttta 9840
actgaacgat gggaaataaa agaatcatgg gttattgata ccatcgaaaa tcctgaacgt 9900
tcagaattta ttgttgatga gtcaggggaa aaatatcatt actataaaag aatagctaag 9960
tttaagaata gagtgttaga agtgataact tctgccaact caacacccac aagaataata 10020
accttttact ttaaccgtaa catgaggaaa aatttatgat tgttacttac gataatgaag 10080
ttgacgcaat ttattttaag ttaacggaaa ataaaattga tagcaccgaa cctcaaacag 10140
acaggattat cattgattac gatgaaagta ataatattgt tggcattgag gtattagatt 10200
ttaattatct tgtcaagaaa ggtttaaccg ttgctgattt accttttct gaagatgaaa 10260
gattaacagc ttctcaatat tttaattttc ctgttgctat ctaatccaga aggggcaata 10320
atccccttct ttcatcgagt tagacttaat atcacaaaag tcattttcat tttaccgttt 10380
cttttccaca gcgtccgtac gcccctcgtt aaatctcaaa accgacaatt tatgatgttt 10440
ataaaaagtt actcacttta ataagtattt atactcatta aagggttatt ctttttttgt 10500
agcctgatag gttgggaagg aatatttcag attatcagat ttgttgaata tttttcgtca 10560
gatacgcaaa ccttacaaac ataattaaca actgaaacta ttgatatgtc taggttttag 10620
ctctatcaca ggttggatct gtcgacaatt aataacttct tcctgtacgg gcgaatggcc 10680

FIG. 21 (continued)

```
atttgctcct aactaactcc gtactgcttt gcggaacgag cgtagcgaac tctccgaatt     10740
actaagcctt catccctgat agatgcaaaa aacgaattaa aattatgtgt aaaaagaaaa     10800
tgtgtcttta tttagtagtc aaagttacaa aatattaaga atcaaattaa taatgtattg     10860
ggcagttaag tatataagtc tttaaatatt tatttgtatt caatatatta accgaggaca     10920
aattatgaat tcttacactg ttggaaccta tttagcagaa cgtttagttc aaattggtct     10980
caaacaccat tttgcagtag ctggtgatta taatttagtt ttattggata acttattgtt     11040
aaataagaat atggaacaag tgtattgttg taatgaatta aactgtggtt tttctgctga     11100
gggatatgct cgtgcaaaag gtgctgccgc agcagttgtt acttattctg ttggagcatt     11160
aagtgctttt gacgctattg gaggtgctta tgcagaaaat ttacctgtaa tcttaatctc     11220
tggtgcaccc aataacaacg atcacgctgc tggtcatgta ttgcatcatg ctttaggtaa     11280
aaccgattat cattaccaat tagaaatggc aaaaaatatt accgctgccg cagaagctat     11340
ttatactccc gaagaagcac ctgctaagat cgatcacgta attaaaaccg ctctccgtga     11400
gaaaaaaccc gtatatttag aaatcgcttg caatatcgct tctatgcctt gtgcagctcc     11460
tggacctgct agtgctttat ttaacgatga agcatctgat gaggctagtt taaatgccgc     11520
tgttgaagaa actttgaaat ttattgctaa tcgtgataaa gtagctgttt tagttggttc     11580
taaactccgt gccgctggtg cagaagaagc ggctgtaaaa ttcgcagatg ccttaggagg     11640
tgctgttgcc acaatggcag ccgctaaaag tttttttccc gaagaaaatc ctcattacat     11700
tggtacttct tggggtgagg tatcttaccc tggtgtagaa aaaaccatga aggaagctga     11760
tgcagtaatt gcattagctc ctgttttcaa tgattactct accactggtt ggactgatat     11820
tccagacccc aaaaaattag ttttagcaga acctcgctct gtagttgtga atggtgttag     11880
atttcccagt gtacatctca aagattattt aactcgttta gctcaaaaag tgagtaaaaa     11940
gactggcgca ctcgatttct ttaaatcttt aaatgctggt gaattaaaga aagcagctcc     12000
tgctgatccc agtgctcctt tagtgaatgc cgaaatcgca agacaagttg aagccttgtt     12060
aactcctaac actaccgtta ttgccgagac tggtgatagt tggttcaatg ctcaacgcat     12120
gaaattaccc aatggtgctc gtgttgagta tgaaatgcaa tggggtcaca ttggatggtc     12180
tgttcctgct gcatttggat atgcagttgg agcacctgag cgtagaaaca ttttaatggt     12240
aggtgatggt tctttccaac tcactgctca agaagttgca caaatggtac gtttaaaatt     12300
gcctgttatt atctttctca ttaacaacta tggttacacc attgaagtta tgattcatga     12360
tggtccttat aataacatta agaattggga ttacgcaggt ttaatggagg tatttaacgg     12420
taatggtgga tacgacagtg gagcaggtaa aggattaaaa gctaaaacag gaggtgagtt     12480
agctgaagca attaaagtag ctttagccaa tacagatggt cctaccttaa tcgaatgttt     12540
cattggacgt gaagattgta ctgaagagtt agttaaatgg ggaaagcgtg ttgccgctgc     12600
aaattctcgt aaacctgtaa acaaactctt gtagttagga tccgagct                  12648
```

FIG. 21 (continued)

#1581 pABICyano1-6.8::PnirAABICyano1-zmPDCABICyano1(opt3)-dsrA-PrpsLABICyano1-ADHABICyano1(opt3)ter-PrbcABICyano1-Km**

```
ID   #1581\pABICyano1-6.8::PnirAABICyano1-zmPDCABICyano1(opt3)-dsrA-PrpsLABICyano1-
ADHABICyano1(opt3)_ter-PrbcABICyano1-Km** standard; circular DNA;    ; 13165 BP.
CC   This file is created by Vector NTI
CC   http://www.invitrogen.com/
CC   VNTDATE|634480119|
CC   VNTDBDATE|634484179|
CC   LSOWNER|
FH   Key             Location/Qualifiers
FH
FT   promoter        1741..2204
FT                   /vntifkey="30"
FT                   /label=PrbcLABICyano1
FT   CDS             11452..13158
FT                   /vntifkey="4"
FT                   /label=zmPDCABICyano1(opt3)
FT   CDS             2206..3021
FT                   /vntifkey="4"
FT                   /label=Km**
FT                   /note=" maximal codon optimized kanamycin resistance gene "
FT   CDS             10583..10831
FT                   /vntifkey="4"
FT                   /label=ORF\6
FT                   /note="orf6"
FT   CDS             10323..10586
FT                   /vntifkey="4"
FT                   /label=ORF\5
FT                   /note="orf5"
FT   CDS             9595..10281
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(8505..9269)
FT                   /vntifkey="4"
FT                   /label=ORF\3
FT                   /note="orf3"
FT   CDS             8060..8245
FT                   /vntifkey="4"
FT                   /label=ORF\2
FT                   /note="orf2"
FT   rep_origin      complement(7360..7377)
FT                   /vntifkey="33"
FT                   /label=Rep_Origin_1\(potential)
FT                   /note="potential rep origin; match pNostoc (Acc# M81381) nick
site (358-375); on reserse strand"
FT   misc_feature    7620..7653
FT                   /vntifkey="21"
FT                   /label=Rep\motif
FT                   /note="Rep protein active site motig EXXKYXVKXXD"
FT   CDS             4839..8024
FT                   /vntifkey="4"
FT                   /label=ORF\1
```

FIG. 23

```
FT                   /note="orf1  rep ori binding protein slr7037 homolog Similar to
hypothetical protein slr7037 of plasmid pSYSA (103 kb)  of Synechocystis sp. PCC 6803"
FT   rep_origin      complement(3264..4322)
FT                   /vntifkey="33"
FT                   /label=OriVT
FT   insertion_seq   4329..11162
FT                   /source="pABICyanol-6HindIIIBamHI"
FT                   /type="Custom cloned insert"
FT                   /vntifkey="14"
FT                   /label=pABICyanol-6HindIIIBamHI
FT                   /note="Unknown feature type:insert"
FT   promoter        11169..11451
FT                   /vntifkey="30"
FT                   /label=PnirAABICyanol
FT   promoter        58..626
FT                   /vntifkey="30"
FT                   /label=PrpsLABICyanol
FT   CDS             630..1637
FT                   /vntifkey="4"
FT                   /label=SynADH(ABICyanolopt3)
FT   terminator      1653..1698
FT                   /vntifkey="43"
FT                   /label=Terminator_1
FT                   /note="Ter_B0011"
FT   gene            630..1640
FT                   /vntifkey="60"
FT                   /note="SycADHopti"
FT   terminator      1..56
FT                   /vntifkey="43"
FT                   /label=dsrA
SQ   Sequence 13165 BP; 4190 A; 2319 C; 2522 G; 4134 t;
     gatccagcaa gtttcatccc gaccccctca gggtcgggat ttttttattg tgagctcctc        60
     cgcttaaaaa atttcatttt tcgatcaaaa aagacaaatt attactaatt agctcatggc       120
     aataaataat cagtagtaat ctgttttcac attttattgt taatttttat tattgctaat       180
     atcaaccttt tctacttctg cttaatattt tatttatgct caatgggaaa atctgaaata       240
     agattgagaa cagtgttacc aatagaagta tttaaggttt aaagcatacc ttaaagataa       300
     catttttttt tgaaaagagt caaattattt ttgaaaggct gatatttttg atatttacta       360
     atattttatt tatttctttt tcccttaaaa taagagctaa atctgttttt attatcattt       420
     atcaagctct attaatacct caactttttc aagaaaaaat aataataatt tttccctcta       480
     ttctcatgac cttttaggaa aattaatttt agaaaaacta ttgacaaacc cataaaaaat       540
     gagataagat tatagattgt cactggtatt ttatactaga ggcaaattat atttatatat       600
     acaaaaatgc tgtataaaaa acatctcata tgattaaggc ttatgctgca ttagaagcta       660
     atggtaaatt acaacctttt gaatacgatc ccggtgcttt aggtgcaaat gaagtagaaa       720
     ttgaggttca gtattgtggt gtatgtcatt ctgatttatc tatgattaac aacgaatggg       780
     gaatttccaa ttatccctta gttcctggac acgaagttgt tggtactgta gcagctatgg       840
     gagaaggagt taatcatgtt gaagtaggtg acttagtagg tttgggatgg cattctggtt       900
     actgtatgac ctgtcatagt tgtttatctg gttatcacaa cttatgtgca actgctgaaa       960
     gtaccattgt tggtcattac ggtggttttg gtgatagagt aagagctaaa ggagttagtg      1020
     ttgttaaatt accaaaaggt atcgacttag caagtgcagg tcctctcttt tgtgggggta      1080
     ttactgtttt tagtcctatg gttgaattaa gtttaaagcc aactgcaaaa gtagccgtca      1140
     ttggtattgg aggattggga cacttagctg ttcaatttct ccgtgcatgg ggatgtgaag      1200
     ttactgcctt tacttctagt gctcgtaaac aaaccgaggt attagaatta ggagcacacc      1260
```

FIG. 23 (continued)

```
atatcttaga ttccaccaac cctgaagcta tcgctagtgc agagggaaaa ttcgattata    1320
ttattagtac tgttaatttg aaattagatt ggaacctcta catctctact ttagctcccc    1380
aaggtcattt tcactttgtt ggagttgtat tagaacccct cgatttaaac ttattccctt    1440
tattaatggg acaacgttct gttagtgcat ctcctgttgg atctcccgct actattgcta    1500
ccatgttaga ttttgcagta cgtcacgata ttaaacctgt agtagaacaa ttctctttcg    1560
atcaaatcaa cgaagctatt gctcatttag aaagtggtaa ggctcattac cgtgttgttt    1620
tatctcactc taaaaactaa ctagatctct gcagagaata taaaaagcca gattattaat    1680
ccggcttttt tattatttaa atactgtgca cgatcctgca ggatcatctt gctgaaaaac    1740
tcgagcgctc gttccgcaaa gcggtacgga gttagttagg ggctaatggg cattctcccg    1800
tacaggaaag agttagaagt tattaattat caacaattct cctttgccta gtgcatcgtt    1860
acctttttaa ttaaaacata aggaaaacta ataatcgtaa taatttaacc tcaaagtgta    1920
aagaaatgtg aaattctgac ttttataacg ttaaagaggg aaaaattagc agtttaaaat    1980
acctagagaa tagtctgggg taagcataga gaattagatt agttaagtta atcaaattca    2040
gaaaaaataa taatcgtaaa tagttaatct gggtgtatag aaaatgatcc ccttcatgat    2100
aagatttaaa ctcgaaaagc aaaagccaaa aaactaactt ccattaaaag aagttgttac    2160
atataacgct ataaagaaaa tttatatatt tggaggatac caaccatgtc tcatattcaa    2220
cgtgaaacta gttgttctcg ccctcgttta aattctaata tggatgccga tttatatggt    2280
tataaatggg ctcgtgataa tgttggtcaa tctggtgcta ctatttatcg tttatatggt    2340
aaacctgatg ctcctgaatt attcttgaaa catggtaaag gttctgttgc taatgatgtt    2400
actgatgaaa tggttcgttt aaactggttg actgaattta tgcctttacc tactattaaa    2460
cattttattc gtactcccga tgatgcttgg ttattaacta ctgctattcc tggtaaaact    2520
gcttttcaag ttttagaaga atatcctgat tctggtgaaa atattgttga tgctttagct    2580
gtttttttac gtcgtttaca ttctattccc gtttgtaatt gtccttttaa ttctgatcgt    2640
gtttttcgtt tagctcaagc tcaatctcgt atgaataatg gtttagttga tgcttctgat    2700
tttgatgatg aacgtaatgg ttggcctgtt gaacaagttt ggaaagaaat gcacaaattg    2760
ttaccttttt ctcctgattc tgttgttact catggtgatt tttctttaga taatttgatc    2820
tttgatgaag gtaaattgat tggttgtatt gatgttggtc gtgttggtat tgctgatcgt    2880
tatcaagatt tagctatttt atggaattgt ttaggtgaat tttctccttc tttacagaaa    2940
cgtttatttc agaaatatgg tattgataat cctgatatga acaagttaca atttcattta    3000
atgttggacg agttctttta agaattaatt catgaccaaa atcccttaac gtgagttttc    3060
gttccactga gcgtcagacc ccgtagaaaa gatcaaagga tcttcttgag atcctttttt    3120
tctgcgcgta atctgctgct atttaaatta cgtacacgtg ttattacttt gttaacgaca    3180
attgtcttaa ttaactgggc ctcatgggcc ttccgctcac tgcccgcttt ccagtcggga    3240
aacctgtcgt gccagctctg cagatgacgg tgaaaacctc tgacacatgc agctcccgga    3300
gacggtcaca gcttgtctgt aagcggatgc cgggagcaga caagcccgtc agggcgcgtc    3360
agcgggtgtt ggcgggtgtc ggggcgcagc catgacccag tcacgtagcg atagcggagt    3420
gtatactggc ttaactatgc ggcatcagag cagattgtac tgagagtgca ccatatgcgg    3480
tgtgaaatac cgcacagatg cgtaaggaga aaataccgca tcaggcgctc ttccgcttcc    3540
tcgctcactg actcgctgcg ctcggtcgtt cggctgcggc gagcggtatc agctcactca    3600
aaggcggtaa tacggttatc cacagaatca ggggataacg caggaaagaa catgtgagca    3660
aaaggccagc aaaaggccag gaaccgtaaa aaggccgcgt tgctggcgtt tttccatagg    3720
ctccgccccc ctgacgagca tcacaaaaat cgacgctcaa gtcagaggtg gcgaaacccg    3780
acaggactat aaagatacca ggcgtttccc cctggaagct ccctcgtgcg ctctcctgtt    3840
ccgaccctgc cgcttaccgg atacctgtcc gcctttctcc cttcgggaag cgtggcgctt    3900
tctcatagct cacgctgtag gtatctcagt tcggtgtagg tcgttcgctc caagctgggc    3960
tgtgtgcacg aaccccccgt tcagcccgac cgctgcgcct tatccggtaa ctatcgtctt    4020
gagtccaacc cggtaagaca cgacttatcg ccactggcag cagccactgg taacaggatt    4080
agcagagcga ggtatgtagg cggtgctaca gagttcttga agtggtggcc taactacggc    4140
tacactagaa ggacagtatt tggtatctgc gctctgctga agccagttac cttcggaaaa    4200
agagttggta gctcttgatc cggcaaacaa accaccgctg gtagcggtgg tttttttgtt    4260
tgcaagcagc agattacgcg cagaaaaaaa ggatctcaag aagatccttt gatcttttct    4320
```

FIG. 23 (continued)

```
actgcagaag cttgttagac accctgtcat gtattttata ttatttattt caccatacgg 4380
attaagtgaa acctaatgaa aatagtactt tcggagcttt aactttaatg aaggtatgtt 4440
tttttataga catcgatgtc tggtttaaca ataggaaaaa gtagctaaaa ctcccatgaa 4500
ttaaagaaat aacaaggtgt ctaacaacct gttattaaga atgttagaaa agacttaaca 4560
tttgtgttga gtttttatag acattggtgt ctagacatac ggtagataag gtttgctcaa 4620
aaataaaata aaaaaagatt ggactaaaaa acatttaatt tagtacaatt taattagtta 4680
ttttttcgtc tcaaattttg ctttgttgag cagaaattta gataaaaaaa tccccgtgat 4740
cagattacaa tgtcgttcat tgtacgatgt gtcgaaaaat ctttacgaca ctctaaactg 4800
accacacggg ggaaaaagaa aactgaacta ataacatcat gatactcgga aaacctagca 4860
attctcaacc cctaaacaaa agaaacttcc aaaaccctga ccatataaag gagtggcaac 4920
aatcagcaat cagtcaagat ttgatagcag aaaatcttgt atcggttgct aatggttttg 4980
atgtactatt tatcggcaat aaataccgaa ctaacacggg tgttctgtca cggcacatat 5040
taaactccta ttctcattta gaagatggtg gttcgtatgg tagaacattt gacccattta 5100
ccaataaaga aatgcagtgg gttcaattta aaccgaatag accaagaaaa ggttctactg 5160
gtaaggtaat caaatatgaa tcgccaaaag gtgaacctac aagagttcta atgccgtttg 5220
tgcctatgaa aatatggcaa cggattagcg ataagttcgg agtaccgatt aatccgaaaa 5280
aagatactca cttttgggaa tgggtaaaga ataatccatc gataccgatt gccattacag 5340
aaggaaataa aaaagctaat tgcctattat cctatggcta tcctgctatt gcctttgtag 5400
gcatttggaa cggattagag aaaataaatg atttctcgaa ggaaaagcag ttaaaagagg 5460
atttgaaatg gttgttatcc aacggcaacc gaaatattaa tatcatcttt gaccaagacc 5520
agaaacaaaa aactgtaatt aatgtaaaca aagctatttt cgctttatct tctctaataa 5580
gtagaaatgg tcataaagtt aatattgtgc aatggttgcc gtcaaaaggt aaaggaatag 5640
atgattattt ggtagcttta ccttttgaga aaagagaaaa tcatttagac aacttaatta 5700
aaattgcacc atcatttaat ttttggtcaa ctaaatactt attcaagtgt cgtaaaccag 5760
atttaaccgt aaattgccgt tatttgagcg atgcagtaaa agaattacct caagaggata 5820
tagcattaat agcacctcac ggcacgggta aaacttcatt agtagctact cacgttaaga 5880
atcggagtta tcacggaagg aaaactattt cattggtgca tcttgaaagt ttagccaaag 5940
ctaatggcaa cgcacttgga ttatattacc gaaccgaaaa taatattgaa aagcaatatc 6000
ttggatttag cttatgtgta gatagttgcc gtgataagat taacggcatt acaactgata 6060
ttatttcagg tcaagattat tgccttttca ttgatgaaat tgaccaagta attccacaca 6120
tccttaacag tgaaactgaa gtaagtaagt atagatgcac catcattgac actttttctg 6180
aactggtgag aaatgctgaa caggtcatta ttgctgatgc tgatttatcc gatgtgacga 6240
ttgacctaat agaaaacatc agaggtaaaa aactatatgt aatcaagaat gaatatcagt 6300
atcagggaat gacttttaac gccgttggtt caccattaga aatgatggca atgatgggaa 6360
aatcggtgtc agaaggcaag aaattattta ttaacaccac atcccaaaag gcaaaaagta 6420
agtacggcac aatcgctctt gagtcttata tttttggtct aaataaagaa gcaaagatat 6480
taagaataga ctctgaaacc actaaaaacc ctgaacatcc agcctataaa atcattgacc 6540
aagacttaaa taatatcctc aaagattatg attatgtcat tgcctcacct tgccttcaaa 6600
caggtgtcag tattacctta aaagggcatt ttgaccagca atttaacttt tccagtggaa 6660
acattacacc tcattgcttt ttacagcaaa tgtggcggtt gagggatgca gaaattgaaa 6720
gattctatta tgtgccgaac tcatctaacc tcaatctcat tgggaataag tcaagttcac 6780
catcagacct tctaaagagc aataacaaga tggcaacggc aacggttaac cttttgggta 6840
gaatcgactc cgaatattcc ctagagtatg aatcgcacgg catttggctt gagacgtggg 6900
caaaattatc agcacggcat aacagttcaa tgcgttgtta ctctgaaatt cttacctatc 6960
taattacgtc tcaagggcat aaattaaata tcaacattcc ctcacctctt gcagatatta 7020
agaagctaaa tgatgaggta agtagtaaca gggaaaaggt aaaaaatgag agatactctc 7080
agaggttaaa ctcaccagat attaacgatg cagaagctac catactcgaa tctaaagagc 7140
aaaaaatcgg attgactctc aatgagagat gcaccctaga aaagcataaa gttaagaagc 7200
ggtatgggaa tgtaaagatg gatattctca cctttgatga tgatggacta taccccaaac 7260
tcagactatt ttattacctc accatcggta aacctcatct caaggctaat gacagaaaag 7320
ctattgccaa aatgggcaat gacaataaag gcaagattct atcaaaagac ttagttaata 7380
```

FIG. 23 (continued)

```
aaacttactc cgctcgtgtg aaggtcttag agattcttaa actaactgac tttatcgaca      7440
atcttagaga tgaactctta ataactccca ataatccagc tatcaccgat tttaataatc      7500
ttctgctaag agctaagaag gatttaagag tattaggagt caacatcgga aaatatccaa      7560
tggccaacat taatgccgta cttactctca ttggtcacaa actttctgta atgagagatg      7620
agttcggaaa agagaaaagg ataaaagtag atggtaaatc ataccgatgt tatcaacttg      7680
aaacattacc agattttacc aatgatactc ttgactactg gttagaaaat gatagccaaa      7740
aagaagtaac agcaacagaa aattactccg aaaattttaa cccttcaaat agctacaatc      7800
cagacagtaa gacactttca gagggtgcaa atttcctata tataaataaa gaagaattgc      7860
atccaaataa attgcaccta gaaataaaag aaggtgctga actttttta ttcggggtaa      7920
aggtgattgt gaaaggaatc ttggacgggg cagtaactat attctctatg ggtcaagaat      7980
acgatttatc cctcaatgaa ctagagggga tgttaacatc atgaacttta caagaatctt      8040
tttaaagggc gatcgcacca tgttaaatga tggtacattt gttcagatat ttgatattta      8100
ccatgaccac gcattgggag tgacccttga ccttaagaca gaaaaaatta tttccgatga      8160
tgttagggta attactgtca aagacttatt gttcgatggc acttataaag ggtaaaatc      8220
ttttatgccc gataatgccc gataatgccc gattgatgct acaaaatccc ataatcataa      8280
gcgataatcc cctaatagct tgtaattctt gaaccgtagc gattttagag tattccaaaa      8340
agaagaaata aacaccgcaa aatgtcgtat ttcacatata taaaccaagg tttttgccc      8400
taaaatcttt atgtttgtag tgtgatgttg ggtcaaaatg gtcagaaaag ttgcaaggtt      8460
tttatggatg cttacgcgcg cgaggggtaa gcatccccaa atagttactt tatcctagtc      8520
catgcccatt tattgccgtc ccgttcggct ttaaaaaagt gccaaaactc acaaggtgca      8580
ataaaaagtt ctgtaccttt cgcaacccta gataatcttt caacagttac ttttttcct      8640
attatctcgg tacaaagttt ggctagtttc tcttttccct ctttttcaat caagccttct      8700
tgtatgccca actcattgat taatctctct atttttacca ttatttcccg ttcaggtagt      8760
ttatccccta aatcttcatc gggggcaat gtagggcatt ctgaaggggc tttttcttct      8820
gtctggacat tatctaatat tgaagtaacc aaactatctt cagtttttc tattcctatt      8880
aattcatatt cggttactgt atccgtatca atatccgaat aactatcttt atccgtatta      8940
gctattcggt taagtttatc cgttaactca gaaacaagac tatatagcgg ttttagcttt      9000
tcttctatcc tgttatctaa tacggataag tttatacggt tatcattatc cgtattagta      9060
tcattgggct tttttggtag ttctaccccc tcataaaccg cttttattcc caattccaac      9120
agactgataa cagtatcctt tataatgggt tttttgctga tatggtgaac ttttgcccct      9180
tccatcattg cgatactttc tatctcactc atcaacttat cgcttaagtg aatctcgtat      9240
ctgtttaatc ccttactggt tttattcata tccgtttact ttattcggtt aacaattcta      9300
ttttatacga ataaaatatt atacggttaa ctttatacgt ttaactattt tatctatacg      9360
gataacagta ataagttatt cgtattagtt atacgtttac ttttatccaa ataaaattag      9420
tgcatttaaa ctaaaagaat gattttatcg gagttgatag cattggatta acctaaagat      9480
gtttataagc tatatctgat aagtatttaa ggttattttg ttattctgtt tattgacatt      9540
atcagaataa aagaatagaa tataattgtt gagagataag aggtttaagt gattatggtt      9600
aagaagttag ttggttatgt cagggtcagt agtgaatcgc aagaggataa cactagctta      9660
cagaatcaga tagagagaat tgaagcatat tgtatggctt ttggttatga gttggtaaaa      9720
atattcaaag aggttgccac tggtacaaaa gcagatattg aaacccgtcc tatttttaat      9780
gaagctatag aatacttgaa acaggataat gctaatggaa ttattgcctt gaagctagac      9840
cgaatcgcac ggaatgcttt agatgtattg cgtttggttc gtgaaacctt agaaccacaa      9900
aataaaatgt tagtgttact agatattcag gtagatactt cgacaccttc aggaaaaatg      9960
attttaactg taatgagtgc cgttgctgaa ctcgaaagag acatgatcta tgatcgcact      10020
caggggggta gaaagactaa agcccaaaag ggcgggtatg cctacgggaa acctaaattt      10080
ggctataaga ctgaagaaaa ggaactaaaa gaagattcag cacaacagga aactattaaa      10140
ctaattaaga gacaccgtag gtcagggaaa agctaccaga aaatagctga ttatctcaat      10200
gcccaaagta ttcccactaa acaaggtaag aaatggagtt ctagcgtcgt ctatcgaatc      10260
tgtcaggaaa aagctggtta agtctgttta tagatattta gaatttattg aataaaaata      10320
gtatgaacaa taaatattta tggactaacc acgctcggaa acgtttaact gaacgatggg      10380
aaataaaaga atcatgggtt attgatacca tcgaaaatcc tgaacgttca gaatttattg      10440
ttgatgagtc aggggaaaaa tatcattact ataaaagaat agctaagttt aagaatagag      10500
```

FIG. 23 (continued)

```
tgttagaagt gataacttct gccaactcaa cacccacaag aataataacc ttttacttta 10560
accgtaacat gaggaaaaat ttatgattgt tacttacgat aatgaagttg acgcaattta 10620
ttttaagtta acggaaaata aaattgatag caccgaacct caaacagaca ggattatcat 10680
tgattacgat gaaagtaata atattgttgg cattgaggta ttagatttta attatcttgt 10740
caagaaaggt ttaaccgttg ctgatttacc tttttctgaa gatgaaagat taacagcttc 10800
tcaatatttt aattttcctg ttgctatcta atccagaagg ggcaataatc cccttctttc 10860
atcgagttag acttaatatc acaaaagtca ttttcatttt accgtttctt ttccacagcg 10920
tccgtacgcc cctcgttaaa tctcaaaacc gacaatttat gatgtttata aaaagttact 10980
cactttaata agtatttata ctcattaaag ggttattctt tttttgtagc ctgataggtt 11040
gggaaggaat atttcagatt atcagatttg ttgaatattt ttcgtcagat acgcaaacct 11100
tacaaacata attaacaact gaaactattg atatgtctag gttttagctc tatcacaggt 11160
tggatctgtc gacaattaat aacttcttcc tgtacgggcg aatggccatt tgctcctaac 11220
taactccgta ctgctttgcg gaacgagcgt agcgaactct ccgaattact aagccttcat 11280
ccctgataga tgcaaaaaac gaattaaaat tatgtgtaaa aagaaaatgt gtctttattt 11340
agtagtcaaa gttacaaaat attaagaatc aaattaataa tgtattgggc agttaagtat 11400
ataagtcttt aaatatttat ttgtattcaa tatattaacc gaggacaaat tatgaattct 11460
tacactgttg gaacctattt agcagaacgt ttagttcaaa ttggtctcaa acaccatttt 11520
gcagtagctg gtgattataa tttagtttta ttggataact tattgttaaa taagaatatg 11580
gaacaagtgt attgttgtaa tgaattaaac tgtggttttt ctgctgaggg atatgctcgt 11640
gcaaaaggtg ctgccgcagc agttgttact tattctgttg gagcattaag tgcttttgac 11700
gctattggag gtgcttatgc agaaaattta cctgtaatct taatctctgg tgcacccaat 11760
aacaacgatc acgctgctgg tcatgtattg catcatgctt taggtaaaac cgattatcat 11820
taccaattag aaatggcaaa aaatattacc gctgccgcag aagctattta tactcccgaa 11880
gaagcacctg ctaagatcga tcacgtaatt aaaaccgctc tccgtgagaa aaaacccgta 11940
tatttagaaa tcgcttgcaa tatcgcttct atgccttgtg cagctcctgg acctgctagt 12000
gctttattta acgatgaagc atctgatgag gctagtttaa atgccgctgt tgaagaaact 12060
ttgaaattta ttgctaatcg tgataaagta gctgttttag ttggttctaa actccgtgcc 12120
gctggtgcag aagaagcggc tgtaaaattc gcagatgcct taggaggtgc tgttgccaca 12180
atggcagccg ctaaaagttt tttccccgaa gaaaatcctc attacattgg tacttcttgg 12240
ggtgaggtat cttaccctgg tgtagaaaaa accatgaagg aagctgatgc agtaattgca 12300
ttagctcctg ttttcaatga ttactctacc actggttgga ctgatattcc agaccccaaa 12360
aaattagttt tagcagaacc tcgctctgta gttgtgaatg gtgttagatt tcccagtgta 12420
catctcaaag attatttaac tcgtttagct caaaaagtga gtaaaaagac tggcgcactc 12480
gatttcttta aatctttaaa tgctggtgaa ttaaagaaag cagctcctgc tgatcccagt 12540
gctcctttag tgaatgccga aatcgcaaga caagttgaag ccttgttaac tcctaacact 12600
accgttattg ccgagactgg tgatagttgg ttcaatgctc aacgcatgaa attacccaat 12660
ggtgctcgtg ttgagtatga aatgcaatgg ggtcacattg gatggtctgt tcctgctgca 12720
tttggatatg cagttggagc acctgagcgt agaaacattt taatggtagg tgatggttct 12780
ttccaactca ctgctcaaga agttgcacaa atggtacgtt taaaattgcc tgttattatc 12840
tttctcatta acaactatgg ttacaccatt gaagttatga ttcatgatgg tccttataat 12900
aacattaaga attgggatta cgcaggttta atggaggtat ttaacggtaa tggtggatac 12960
gacagtggag caggtaaagg attaaaagct aaaacaggag gtgagttagc tgaagcaatt 13020
aaagtagctt tagccaatac agatggtcct accttaatcg aatgtttcat tggacgtgaa 13080
gattgtactg aagagttagt taaatgggga aagcgtgttg ccgctgcaaa ttctcgtaaa 13140
cctgtaaaca aactcttgta gttag 13165
```

FIG. 23 (continued)

#1606 pABICyano1::PnirA ABICyano1-zmPDC ABICyano1(opt1)_dsrA-Prbc*(optRBS)-synADH(opt1)_ter PrbcABICyano1-Km**

```
ID   #1606\\pABICyano1::PnirA-zmPDC(opt1)_dsrA-Prbc*(optRBS)-synADH(opt1)_ter
standard; circular DNA;    ; 12762 BP.
CC   This file is created by Vector NTI
CC   http://www.invitrogen.com/
CC   VNTDATE|645465372|
CC   VNTDBDATE|645465372|
CC   LSOWNER|
CC   VNTAUTHORNAME|Ulf Duehring|
FH   Key             Location/Qualifiers
FH
FT   promoter        2063..2131
FT                   /vntifkey="30"
FT                   /label=Prbc*(optRBS)
FT   promoter        1..283
FT                   /vntifkey="30"
FT                   /label=PnirAABICyano1
FT   rep_origin      complement(4858..5916)
FT                   /vntifkey="33"
FT                   /label=OriVT
FT   primer_bind     4903..4934
FT                   /vntifkey="28"
FT                   /label=Bom-R
FT   primer_bind     complement(5221..5252)
FT                   /vntifkey="28"
FT                   /label=Bom-F
FT   CDS             6433..9618
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   misc_feature    9214..9247
FT                   /vntifkey="21"
FT                   /label=Rep\motif
FT                   /note="Rep protein active site motig EXXKYXVKXXD"
FT   rep_origin      complement(8954..8971)
FT                   /vntifkey="33"
FT                   /label=Rep_Origin_1
FT                   /note="potential rep origin; match pNostoc (Acc# M81381) nick
site (358-375); on reserse strand"
FT   CDS             9654..9839
FT                   /vntifkey="4"
FT                   /label=ORF\2
FT                   /note="orf2"
FT   CDS             complement(10099..10863)
FT                   /vntifkey="4"
FT                   /label=ORF\3
FT                   /note="orf3"
FT   CDS             11189..11875
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             11917..12180
FT                   /vntifkey="4"
FT                   /label=ORF\5
FT                   /note="orf5"
FT   CDS             12177..12425
FT                   /vntifkey="4"
FT                   /label=ORF\6
FT                   /note="orf6"
FT   misc_marker     3800..4615
```

FIG. 25

```
FT                   /vntifkey="22"
FT                   /label=Km**
FT                   /note="Km**"
FT   promoter        3335..3798
FT                   /vntifkey="30"
FT                   /label=PrbcABICyano1
FT   terminator      3143..3298
FT                   /vntifkey="43"
FT                   /label=TrbcSABICyano1
FT   CDS             2132..3139
FT                   /vntifkey="4"
FT                   /label=synADHABICyano1(opt1)
FT   gene            2132..3142
FT                   /vntifkey="60"
FT                   /note="ADH"
FT   insertion_seq   2017..2062
FT                   /vntifkey="14"
FT                   /label=dsrA
FT                   /note="dsr terminator from E.coli"
FT   CDS             284..1990
FT                   /vntifkey="4"
FT                   /label=zmPDCABICyano1(opt1)
SQ   Sequence 12762 BP; 3950 A; 2245 C; 2488 G; 4079 t;
     tcgacaatta ataacttctt cctgtacggg cgaatggcca tttgctccta actaactccg        60
     tactgctttg cggaacgagc gtagcgaact ctccgaatta ctaagccttc atccctgata       120
     gatgcaaaaa acgaattaaa attatgtgta aaaagaaaat gtgtctttat ttagtagtca       180
     aagttacaaa atattaagaa tcaaattaat aatgtattgg gcagttaagt atataagtct       240
     ttaaatattt atttgtattc aatatattaa ccgaggacaa attatgaatt cttataccgt       300
     gggtacttat ttagccgaac gcttagtgca aattggttta aaacatcatt ttgccgtggc       360
     tggggactat aatttagtgt tattggataa cttattatta aataaaaaca tggaacaagt       420
     gtattgttgt aatgaattaa attgtggttt ttctgctgaa ggttatgcta gagctaaagg       480
     tgcagctgct gctgttgtta cttattctgt gggtgcttta tctgcttttg atgctattgg       540
     tggtgcttat gccgaaaatt tacccgtgat tttaatttct ggtgccccta ataataatga       600
     tcatgccgct ggacatgttt tacatcatgc cttaggtaaa accgattatc attatcaatt       660
     agaaatggcc aaaaatatta ctgctgctgc cgaagctatt tatactcctg aagaagcccc       720
     tgccaaaatt gatcatgtga ttaaaaccgc cttacgcgaa aaaaaacccg tgtatttaga       780
     aattgcctgt aatattgctt ctatgccttg tgctgctcct gggcctgctt ctgctttatt       840
     taatgatgaa gcctctgatg aagctagttt aaatgctgcc gtggaagaaa ccttaaaatt       900
     tattgccaat cgcgataaag ttgccgtgtt agttggttct aaattaagag ctgctggtgc       960
     tgaagaagct gctgttaaat ttgctgatgc tttaggtggt gcagttgcta ctatggctgc      1020
     tgccaaatct ttttttcccg aagaaaatcc ccattatatt ggaactagtt ggggagaagt      1080
     ttcttatcct ggtgtggaaa aaactatgaa agaagccgac gctgttattg ctttagcccc      1140
     tgtgtttaat gattattcta ccactggttg gactgatatt cccgatccca aaaaattagt      1200
     tttagccgaa cctcgttctg ttgttgttaa tggtgttcgc tttccctctg tgcatttaaa      1260
     agattattta acccgcttag cccaaaaagt ttctaaaaaa actggtgcct tagatttttt      1320
     taaatcttta aatgcgggtg aattaaaaaa agctgctcct gctgatcctt ctgctccttt      1380
     agttaatgct gaaattgccc gtcaagttga agccttatta acccctaata ctaccgttat      1440
     tgccgaaact ggtgattctt ggtttaatgc ccaacgcatg aaattaccta atggtgcccg      1500
     tgttgaatat gaaatgcaat ggggtcatat tggttggtct gtacctgctg cttttggtta      1560
     tgctgttggt gctcctgaac gtcgtaatat tttaatggtg ggtgatggtt cttttcaatt      1620
     aactgcccaa gaagttgccc aaatggttcg cttaaaatta cccgttatta tttttttaat      1680
     aaataattat ggttatacca ttgaagtgat gattcatgat gggccatata ataatattaa      1740
     aaattgggat tatgcgggtt taatggaagt gtttaatggt aatggtggtt atgattctgg      1800
     tgctggtaaa ggtttaaaag ccaaaactgg tggtgaatta gctgaagcta ttaaagttgc      1860
     cttagccaat actgatgggc caaccttaat tgaatgtttt attggtcgcg aagattgtac      1920
     cgaagaatta gttaaatggg gtaaacgtgt tgctgctgct aattctcgca aacccgtgaa      1980
     taaattattg taatttttgg ggatcaattc gagctcagca agtttcatcc cgacccccctc     2040
     agggtcggga tttttttatt gtactagttg acataagtaa aggcatcccc tgcgtgatat      2100
     aattaccttc agtttaagga ggtatacaca tatgattaaa gcctatgctg ccttagaagc      2160
     caatggtaaa ttacaaccct ttgaatatga tcctggtgct ttaggtgcca atgaagtgga      2220
```

FIG. 25 (continued)

```
aattgaagtg caatattgtg gtgtgtgtca ttctgattta tctatgatta ataatgaatg      2280
gggtatttct aattatccct tagttcctgg tcatgaagtt gttggtactg ttgctgctat      2340
gggtgaaggt gttaatcatg tggaagtggg tgatttagtt ggtttaggtt ggcattctgg      2400
ttattgtatg acctgtcatt cttgtttatc tggttatcat aatttatgtg ccactgccga      2460
atctactatt gtgggtcatt atggtggttt tggtgataga gttcgtgcta aaggtgtttc      2520
tgtggtgaaa ttacccaaag gtattgattt agcctctgct gggcctttat tttgtggtgg      2580
tattaccgtt ttttctccca tggtggaatt atctttaaaa cctaccgcca aagttgctgt      2640
tattggtatt ggtggtttag gtcatttagc cgttcaattt ttaagagcct ggggttgtga      2700
agttactgct tttacctctt ctgcccgtaa acaaaccgaa gttttagaat taggtgccca      2760
tcatatttta gattctacca atcctgaagc tattgcttct gccgaaggta aatttgatta      2820
tattatttct accgtgaatt taaaattaga ttggaattta tatatcagta ccttagcccc      2880
tcaaggtcat tttcattttg ttggtgtggt gttagaaccc ttggacttaa acttatttcc      2940
cttattaatg ggacaacgtt ctgtttctgc ttctcctgtt ggttctcctg ctactattgc      3000
cactatgtta gattttgccg tgcgtcatga tattaaaccc gtggtggaac aattttcttt      3060
tgatcaaatt aatgaagcca ttgcccattt agaatctggt aaagcccatt atcgcgtggt      3120
gttatctcat tctaaaaatt aataagatta acttctaaac tgaaacaaat ttgagggtag      3180
gcttcattgt ctgcccttat ttttttattt aggaaaagtg aacagactaa agagtgttgg      3240
ctctattgct ttgagtatgt aaattaggcg ttgctgaatt aaggtatgat ttttgacccc      3300
ttctctcttc tgcaggatca tcttgctgaa aaactcgagc gctcgttccg caaagcggta      3360
cggagttagt taggggctaa tgggcattct cccgtacagg aaagagttag aagttattaa      3420
ttatcaacaa ttctcctttg cctagtgcat cgttaccttt ttaattaaaa cataaggaaa      3480
actaataatc gtaataattt aacctcaaag tgtaaagaaa tgtgaaattc tgacttttat      3540
aacgttaaag agggaaaaat tagcagttta aaatacctag agaatagtct ggggtaagca      3600
tagagaatta gattagttaa gttaatcaaa ttcagaaaaa ataataatcg taaatagtta      3660
atctgggtgt atagaaaatg atccccttca tgataagatt taaactcgaa aagcaaaagc      3720
caaaaaacta acttccatta aaagaagttg ttacatataa cgctataaag aaaatttata      3780
tatttggagg ataccaacca tgtctcatat tcaacgtgaa actagttgtt ctcgccctcg      3840
tttaaattct aatatggatg ccgatttata tggttataaa tgggctcgtg ataatgttgg      3900
tcaatctggt gctactattt atcgtttata tggtaaacct gatgctcctg aattattctt      3960
gaaacatggt aaaggttctg ttgctaatga tgttactgat gaaatggttc gtttaaactg      4020
gttgactgaa tttatgcctt tacctactat taaacatttt attcgtactc ccgatgatgc      4080
ttggttatta actactgcta ttcctggtaa aactgctttt caagttttag aagaatatcc      4140
tgattctggt gaaaatattg ttgatgcttt agctgttttt ttacgtcgtt tacattctat      4200
tcccgtttgt aattgtcctt ttaattctga tcgtgttttt cgtttagctc aagctcaatc      4260
tcgtatgaat aatggtttag ttgatgcttc tgattttgat gatgaacgta atggttggcc      4320
tgttgaacaa gtttggaaag aaatgcacaa attgttacct ttttctcctg attctgttgt      4380
tactcatggt gatttttctt tagataattt gatctttgat gaaggtaaat tgattggttg      4440
tattgatgtt ggtcgtgttg gtattgctga tcgttatcaa gatttagcta ttttatggaa      4500
ttgtttaggt gaattttctc cttctttaca gaaacgttta tttcagaaat atggtattga      4560
taatcctgat atgaacaagt tacaatttca tttaatgttg gacgagttct tttaagaatt      4620
aattcatgac caaaatccct taacgtgagt tttcgttcca ctgagcgtca gaccccgtag      4680
aaaagatcaa aggatcttct tgagatcctt tttttctgcg cgtaatctgc tgctatttaa      4740
attacgtaca cgtgttatta ctttgttaac gacaattgtc ttaattaact gggcctcatg      4800
ggccttccgc tcactgcccg ctttccagtc gggaaacctg tcgtgccagc tctgcagatg      4860
acggtgaaaa cctctgacac atgcagctcc cggagacggt cacagcttgt ctgtaagcgg      4920
atgccgggag cagacaagcc cgtcagggcg cgtcagcggg tgttggcggg tgtcggggcg      4980
cagccatgac ccagtcacgt agcgatagcg gagtgtatac tggcttaact atgcggcatc      5040
agagcagatt gtactgagag tgcaccatat gcggtgtgaa ataccgcaca gatgcgtaag      5100
gagaaaatac cgcatcaggc gctcttccgc ttcctcgctc actgactcgc tgcgctcggt      5160
cgttcggctg cggcgagcgg tatcagctca ctcaaaggcg gtaatacggt tatccacaga      5220
atcaggggat aacgcaggaa agaacatgtg agcaaaaggc cagcaaaagg ccaggaaccg      5280
taaaaaggcc gcgttgctgg cgtttttcca taggctccgc ccccctgacg agcatcacaa      5340
aaatcgacgc tcaagtcaga ggtggcgaaa cccgacagga ctataaagat accaggcgtt      5400
tccccctgga agctccctcg tgcgctctcc tgttccgacc ctgccgctta ccggatacct      5460
gtccgccttt ctcccttcgg gaagcgtggc gctttctcat agctcacgct gtaggtatct      5520
cagttcggtg taggtcgttc gctccaagct gggctgtgtg cacgaacccc ccgttcagcc      5580
cgaccgctgc gccttatccg gtaactatcg tcttgagtcc aacccggtaa gacacgactt      5640
atcgccactg gcagcagcca ctggtaacag gattagcaga gcgaggtatg taggcggtgc      5700
```

FIG. 25 (continued)

```
tacagagttc ttgaagtggt ggcctaacta cggctacact agaaggacag tatttggtat     5760
ctgcgctctg ctgaagccag ttaccttcgg aaaaagagtt ggtagctctt gatccggcaa     5820
acaaaccacc gctggtagcg gtggtttttt tgtttgcaag cagcagatta cgcgcagaaa     5880
aaaaggatct caagaagatc ctttgatctt ttctactgca gaagcttgtt agacaccctg     5940
tcatgtattt tatattattt atttcaccat acggattaag tgaaacctaa tgaaaatagt     6000
actttcggag ctttaacttt aatgaaggta tgttttttta tagacatcga tgtctggttt     6060
aacaatagga aaaagtagct aaaactccca tgaattaaag aaataacaag gtgtctaaca     6120
acctgttatt aagaatgtta gaaaagactt aacatttgtg ttgagttttt atagacattg     6180
gtgtctagac atacggtaga taaggtttgc tcaaaaataa aataaaaaaa gattggacta     6240
aaaaacattt aatttagtac aatttaatta gttatttttt cgtctcaaat tttgctttgt     6300
tgagcagaaa tttagataaa aaaatccccg tgatcagatt acaatgtcgt tcattgtacg     6360
atgtgtcgaa aaatctttac gacactctaa actgaccaca cgggggaaaa agaaaactga     6420
actaataaca tcatgatact cggaaaacct agcaattctc aacccctaaa caaaagaaac     6480
ttccaaaacc ctgaccatat aaaggagtgg caacaatcag caatcagtca agatttgata     6540
gcagaaaatc ttgtatcggt tgctaatggt tttgatgtac tatttatcgg caataaatac     6600
cgaactaaca cgggtgttct gtcacggcac atattaaact cctattctca tttagaagat     6660
ggtggttcgt atggtagaac atttgaccca tttaccaata aagaaatgca gtgggttcaa     6720
tttaaaccga atagaccaag aaaaggttct actggtaagg taatcaaata tgaatcgcca     6780
aaaggtgaac ctacaagagt tctaatgccg tttgtgccta tgaaaatatg gcaacggatt     6840
agcgataagt tcggagtacc gattaatccg aaaaaagata ctcacttttg ggaatgggta     6900
aagaataatc catcgatacc gattgccatt acagaaggaa ataaaaaagc taattgccta     6960
ttatcctatg gctatcctgc tattgccttt gtaggcattt ggaacggatt agagaaaata     7020
aatgatttct cgaaggaaaa gcagttaaaa gaggatttga aatggttgtt atccaacggc     7080
aaccgaaata ttaatatcat ctttgaccaa gaccagaaac aaaaaactgt aattaatgta     7140
aacaaagcta ttttcgcttt atcttctcta ataagtagaa atggtcataa agttaatatt     7200
gtgcaatggt tgccgtcaaa aggtaaagga atagatgatt atttggtagc tttacctttt     7260
gagaaaagag aaaatcattt agacaactta attaaaattg caccatcatt taatttttgg     7320
tcaactaaat acttattcaa gtgtcgtaaa ccagatttaa ccgtaaattg ccgttatttg     7380
agcgatgcag taaaagaatt acctcaagag gatatagcat taatagcacc tcacggcacg     7440
ggtaaaactt cattagtagc tactcacgtt aagaatcgga gttatcacgg aaggaaaact     7500
atttcattgg tgcatcttga aagtttagcc aaagctaatg gcaacgcact tggattatat     7560
taccgaaccg aaaataatat tgaaaagcaa tatcttggat ttagcttatg tgtagatagt     7620
tgccgtgata agattaacgg cattacaact gatattattt caggtcaaga ttattgcctt     7680
ttcattgatg aaattgacca agtaattcca cacatcctta acagtgaaac tgaagtaagt     7740
aagtatagat gcaccatcat tgacactttt tctgaactgg tgagaaatgc tgaacaggtc     7800
attattgctg atgctgattt atccgatgtg acgattgacc taatagaaaa catcagaggt     7860
aaaaaactat atgtaatcaa gaatgaatat cagtatcagg gaatgacttt taacgccgtt     7920
ggttcaccat tagaaatgat ggcaatgatg ggaaaatcgg tgtcagaagg caagaaatta     7980
tttattaaca ccacatccca aaaggcaaaa agtaagtacg gcacaatcgc tcttgagtct     8040
tatatttttg gtctaaataa agaagcaaag atattaagaa tagactctga aaccactaaa     8100
aaccctgaac atccagccta taaaatcatt gaccaagact taaataatat cctcaaagat     8160
tatgattatg tcattgcctc accttgcctt caaacaggtg tcagtattac cttaaaaggg     8220
catttgacc agcaatttaa cttttccagt ggaaacatta cacctcattg ctttttacag     8280
caaatgtggc ggttgaggga tgcagaaatt gaaagattct attatgtgcc gaactcatct     8340
aacctcaatc tcattgggaa taagtcaagt tcaccatcag accttctaaa gagcaataac     8400
aagatggcaa cggcaacggt taacctttg ggtagaatcg actccgaata ttccctagag     8460
tatgaatcgc acggcatttg gcttgagacg tgggcaaaat tatcagcacg gcataacagt     8520
tcaatgcgtt gttactctga aattcttacc tatctaatta cgtctcaagg gcataaatta     8580
aatatcaaca ttccctcacc tcttgcagat attaagaagc taaatgatga ggtaagtagt     8640
aacagggaaa aggtaaaaaa tgagagatac tctcagaggt taaactcacc agatattaac     8700
gatgcagaag ctaccatact cgaatctaaa gagcaaaaaa tcggattgac tctcaatgag     8760
agatgcaccc tagaaaagca taaagttaag aagcggtatg ggaatgtaaa gatggatatt     8820
ctcacctttg atgatgatgg actataccce aaactcagac tattttatta cctcaccatc     8880
ggtaaacctc atctcaaggc taatgacaga aaagctattg ccaaaatggg caatgacaat     8940
aaaggcaaga ttctatcaaa agacttagtt aataaaactt actccgctcg tgtgaaggtc     9000
ttagagattc ttaaactaac tgactttatc gacaatctta gagatgaact cttaataact     9060
cccaataatc cagctatcac cgattttaat aatcttctgc taagagctaa gaaggattta     9120
agagtattag gagtcaacat cggaaaatat ccaatggcca acattaatgc cgtacttact     9180
ctcattggtc acaaactttc tgtaatgaga gatgagttcg gaaaagagaa aaggataaaa     9240
gtagatggta aatcataccg atgttatcaa cttgaaacat taccagattt taccaatgat     9300
```

FIG. 25 (continued)

actcttgact actggttaga aaatgatagc caaaaagaag taacagcaac agaaaattac 9360
tccgaaaatt ttaacccttc aaatagctac aatccagaca gtaagacact ttcagagggt 9420
gcaaatttcc tatatataaa taaagaagaa ttgcatccaa ataaattgca cctagaaata 9480
aaagaaggtg ctgaactttt tttattcggg gtaaaggtga ttgtgaaagg aatcttggac 9540
ggggcagtaa ctatattctc tatgggtcaa gaatacgatt tatccctcaa tgaactagag 9600
gggatgttaa catcatgaac tttacaagaa tctttttaaa gggcgatcgc accatgttaa 9660
atgatggtac atttgttcag atatttgata tttaccatga ccacgcattg ggagtgaccc 9720
ttgaccttaa gacagaaaaa attatttccg atgatgttag ggtaattact gtcaaagact 9780
tattgttcga tggcacttat aaaggggtaa aatcttttat gcccgataat gcccgataat 9840
gcccgattga tgctacaaaa tcccataatc ataagcgata atcccctaat agcttgtaat 9900
tcttgaaccg tagcgatttt agagtattcc aaaaagaaga aataaacacc gcaaaatgtc 9960
gtatttcaca tatataaacc aaggtttttt gccctaaaat ctttatgttt gtagtgtgat 10020
gttgggtcaa aatggtcaga aaagttgcaa ggtttttatg gatgcttacg cgcgcgaggg 10080
gtaagcatcc ccaaatagtt actttatcct agtccatgcc catttattgc cgtcccgttc 10140
ggctttaaaa aagtgccaaa actcacaagg tgcaataaaa agttctgtac ctttcgcaac 10200
cctagataat ctttcaacag ttactttttt tcctattatc tcggtacaaa gtttggctag 10260
tttctctttt ccctcttttt caatcaagcc ttcttgtatg cccaactcat tgattaatct 10320
ctctattttt accattattt cccgttcagg tagtttatcc cctaaatctt catcgggggg 10380
caatgtaggg cattctgaag gggctttttc ttctgtctgg acattatcta atattgaagt 10440
aaccaaacta tcttcagttt tttctattcc tattaattca tattcggtta ctgtatccgt 10500
atcaatatcc gaataactat ctttatccgt attagctatt cggttaagtt tatccgttaa 10560
ctcagaaaca agactatata gcggttttag cttttcttct atcctgttat ctaatacgga 10620
taagtttata cggttatcat tatccgtatt agtatcattg ggcttttttg gtagttctac 10680
cccctcataa accgctttta ttcccaattc caacagactg ataacagtat cctttataat 10740
gggttttttg ctgatatggt gaacttttgc cccttccatc attgcgatac tttctatctc 10800
actcatcaac ttatcgctta agtgaatctc gtatctgttt aatcccttac tggttttatt 10860
catatccgtt tactttattc ggttaacaat tctattttat acgaataaaa tattatacgg 10920
ttaactttat acgtttaact attttatcta tacggataac agtaataagt tattcgtatt 10980
agttatacgt ttacttttat ccaaataaaa ttagtgcatt taaactaaaa gaatgatttt 11040
atcggagttg atagcattgg attaacctaa agatgtttat aagctatatc tgataagtat 11100
ttaaggttat tttgttattc tgtttattga cattatcaga ataaaagaat agaatataat 11160
tgttgagaga taagaggttt aagtgattat ggttaagaag ttagttggtt atgtcagggt 11220
cagtagtgaa tcgcaagagg ataacactag cttacagaat cagatagaga gaattgaagc 11280
atattgtatg gcttttggtt atgagttggt aaaaatattc aaagaggttg ccactggtac 11340
aaaagcagat attgaaaccc gtcctatttt taatgaagct atagaatact tgaaacagga 11400
taatgctaat ggaattattg ccttgaagct agaccgaatc gcacggaatg ctttagatgt 11460
attgcgtttg gttcgtgaaa ccttagaacc acaaaataaa atgttagtgt tactagatat 11520
tcaggtagat acttcgacac cttcaggaaa aatgatttta actgtaatga gtgccgttgc 11580
tgaactcgaa agagacatga tctatgatcg cactcagggg ggtagaaaga ctaaagccca 11640
aaagggcggg tatgcctacg ggaaacctaa atttggctat aagactgaag aaaaggaact 11700
aaaagaagat tcagcacaac aggaaactat taaactaatt aagagacacc gtaggtcagg 11760
gaaaagctac cagaaaatag ctgattatct caatgcccaa agtattccca ctaaacaagg 11820
taagaaatgg agttctagcg tcgtctatcg aatctgtcag gaaaaagctg gttaagtctg 11880
tttatagata tttagaattt attgaataaa aatagtatga acaataaata tttatggact 11940
aaccacgctc ggaaacgttt aactgaacga tgggaaataa aagaatcatg ggttattgat 12000
accatcgaaa atcctgaacg ttcagaattt attgttgatg agtcagggga aaaatatcat 12060
tactataaaa gaatagctaa gtttaagaat agagtgttag aagtgataac ttctgccaac 12120
tcaacaccca caagaataat aacctttac tttaaccgta acatgaggaa aaatttatga 12180
ttgttactta cgataatgaa gttgacgcaa tttattttaa gttaacggaa aataaaattg 12240
atagcaccga acctcaaaca gacaggatta tcattgatta cgatgaaagt aataatattg 12300
ttggcattga ggtattagat tttaattatc ttgtcaagaa aggtttaacc gttgctgatt 12360
tacctttttc tgaagatgaa agattaacag cttctcaata ttttaatttt cctgttgcta 12420
tctaatccag aaggggcaat aatccccttc tttcatcgag ttagacttaa tatcacaaaa 12480
gtcattttca ttttaccgtt tcttttccac agcgtccgta cgcccctcgt taaatctcaa 12540
aaccgacaat ttatgatgtt tataaaaagt tactcacttt aataagtatt tatactcatt 12600
aaagggttat tctttttttg tagcctgata ggttgggaag gaatatttca gattatcaga 12660
tttgttgaat atttttcgtc agatacgcaa accttacaaa cataattaac aactgaaact 12720
attgatatgt ctaggtttta gctctatcac aggttggatc tg 12762

FIG. 25 (continued)

TK471 pABICyano1::pilT-PrbcLABICyano1_Km**pilC-sacB-oriVT

```
ID   TK471\ pABICyano1::pilT-PrbcLABICyano1_Km**pilC-sacB-oriVT standard; circular
DNA;   ; 13354 BP.
CC   This file is created by Vector NTI
CC   http://www.invitrogen.com/
CC   VNTDATE|641221300|
CC   VNTDBDATE|645294711|
CC   LSOWNER|
CC   VNTAUTHORNAME|Irina Piven|
FH   Key             Location/Qualifiers
FH
FT   insertion_seq   6610..89
FT                   /source="pABICyano-6HindIIIBamHI"
FT                   /type="Custom cloned insert"
FT                   /vntifkey="14"
FT                   /label=pABICyano1-6.8
FT                   /note="Unknown feature type:insert"
FT   rep_origin      complement(5545..6603)
FT                   /vntifkey="33"
FT                   /label=OriVT
FT   CDS             7120..10305
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   CDS             10341..10526
FT                   /vntifkey="4"
FT                   /label=ORF\2
FT                   /note="orf2"
FT   CDS             complement(10786..11550)
FT                   /vntifkey="4"
FT                   /label=ORF\3
FT                   /note="orf3"
FT   CDS             11876..12562
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             12604..12867
FT                   /vntifkey="4"
FT                   /label=ORF\5
FT                   /note="orf5"
FT   CDS             12864..13112
FT                   /vntifkey="4"
FT                   /label=ORF\6
FT                   /note="orf6"
FT   3'UTR           4649..5422
FT                   /vntifkey="50"
FT                   /label=pilT-flank
FT   3'UTR           2105..2972
FT                   /vntifkey="50"
FT                   /label=pilC-flank
FT   promoter        complement(3924..4383)
```

FIG. 27

```
FT                   /vntifkey="30"
FT                   /label=PrbcLABICyano
FT   CDS             complement(3108..3923)
FT                   /vntifkey="4"
FT                   /label=Km**
FT   promoter        101..563
FT                   /vntifkey="30"
FT                   /label=PsacB
FT   CDS             564..1985
FT                   /vntifkey="4"
FT                   /label=sacB
SQ   Sequence 13354 BP; 4435 A; 2630 C; 2459 G; 3830 t;
     aatatttttc gtcagatacg caaaccttac aaacataatt aacaactgaa actattgata        60
     tgtctaggtt ttagctctat cacaggttgg atctgtcgac gatccttttt aacccatcac       120
     atatacctgc cgttcactat tatttagtga aatgagatat tatgatattt tctgaattgt       180
     gattaaaaag gcaactttat gcccatgcaa cagaaactat aaaaaataca gagaatgaaa       240
     agaaacagat agatttttta gttctttagg cccgtagtct gcaaatcctt ttatgatttt       300
     ctatcaaaca aaagaggaaa atagaccagt tgcaatccaa acgagagtct aatagaatga       360
     ggtcgaaaag taaatcgcgc gggtttgtta ctgataaagc aggcaagacc taaaatgtgt       420
     aaagggcaaa gtgtatactt tggcgtcacc ccttacatat tttaggtctt tttttattgt       480
     gcgtaactaa cttgccatct tcaaacagga gggctggaag aagcagaccg ctaacacagt       540
     acataaaaaa ggagacatga acgatgaaca tcaaaaagtt tgcaaaacaa gcaacagtat       600
     taacctttac taccgcactg ctggcaggag gcgcaactca agcgtttgcg aaagaaacga       660
     accaaaagcc atataaggaa acatacggca tttcccatat tacacgccat gatatgctgc       720
     aaatccctga acagcaaaaa aatgaaaaat atcaagttcc tgaattcgat tcgtccacaa       780
     ttaaaaatat ctcttctgca aaaggcctgg aggtttggga cagctggcca ttacaaaacg       840
     ctgacggcac tgtcgcaaac tatcacggct accacatcgt ctttgcatta gccggagatc       900
     ctaaaaatgc ggatgacaca tcgatttaca tgttctatca aaaagtcggc gaaacttcta       960
     ttgacagctg gaaaaacgct ggccgcgtct ttaaagacag cgacaaattc gatgcaaatg      1020
     attctatcct aaaagaccaa acacaagaat ggtcaggttc agccacattt acatctgacg      1080
     gaaaaatccg tttattctac actgatttct ccggtaaaca ttacggcaaa caaacactga      1140
     caactgcaca agttaacgta tcagcatcag acagctcttt gaacatcaac ggtgtagagg      1200
     attataaatc aatctttgac ggtgacggaa aaacgtatca aaatgtacag cagttcatcg      1260
     atgaaggcaa ctacagctca ggcgacaacc atacgctgag agatcctcac tacgtagaag      1320
     ataaaggcca caaatactta gtatttgaag caaacactgg aactgaagat ggctaccaag      1380
     gcgaagaatc tttatttaac aaagcatact atggcaaaag cacatcattc ttccgtcaag      1440
     aaagtcaaaa acttctgcaa agcgataaaa aacgcacggc tgagttagca aacggcgctc      1500
     tcggtatgat tgagctaaac gatgattaca cactgaaaaa agtgatgaaa ccgctgattg      1560
     catctaacac agtaacagat gaaattgaac gcgcgaacgt ctttaaaatg aacggcaaat      1620
     ggtacctgtt cactgactcc cgcggatcaa aaatgacgat tgacggcatt acgtctaacg      1680
     atatttacat gcttggttat gtttctaatt ctttaactgg cccatacaag ccgctgaaca      1740
     aaactggcct tgtgttaaaa atggatcttg atcctaacga tgtaaccttt acttactcac      1800
     acttcgctgt acctcaagcg aaaggaaaca atgtcgtgat tacaagctat atgacaaaca      1860
     gaggattcta cgcagacaaa caatcaacgt ttgcgccaag cttcctgctg aacatcaaag      1920
     gcaagaaaac atctgttgtc aaagacagca tccttgaaca aggacaatta acagttaaca      1980
     aataaaaacg caaaagaaaa tgccgatatc ctattggcat ttcttttat ttcttatcaa       2040
     cataaaggtg aatcccatat gaactatgga tcggcgcagc atgctcccgg ccgccatcac      2100
     tagtgctcga tgacgctggt taatgcctta actgcttgtt ctacttcatc ttcataaaaa      2160
     tctgcaactt tcatcatcat tgcatctaat tcccccgttt cttcaccaat catcatcatt      2220
     tgaattgcca tagagggaaa aacctttctt tccgagatcg caacacttaa catacctcct      2280
     tctaaaatag aatcttttgc ggcgccaatg gcattagaaa ttactttatt agggatagtc      2340
```

FIG. 27 (continued)

```
tcttgagata tttctaaaca ttgtaagata ggcacaccag aacgggttaa agtaccaaaa 2400
atacgacaaa aacgagcaac agcacttttt tcatttaagt ccccaaaaat gggagcttta 2460
agtgcgatcg tatctatttg taaacgtcca gcaggagttt tataatattg acggaaggca 2520
aaaacaaccc caataatcac acccacggga ataattgctt tccagctacg caaaaaatca 2580
ctaagagtaa ccataaattg agtcaaagcc ggcaattctg cacccaattg gtcgaaaata 2640
ccagcaaata caggaatcaa gaaaatggtc atacccaaaa aagcaatgac cgcaaaaata 2700
ccaacagtga caggataagc cattgctgat ttaatttggt tttgcaaacg agcaacatct 2760
tcgagaagtt tagcaagacg attcatgact tcgtctaaaa ccccccctgt ttctcccgct 2820
tctaccatac tcacatatag cctatcaaaa cagtcgggat gctttgccat tgcttcagat 2880
aaattaaccc cctgttgaac atcctctcca atagtagtta gagccttctt aaatttagga 2940
tttcctgatt gctctgccaa tactgacaaa gagcggccgc atttaaatag cagcagatta 3000
cgcgcagaaa aaaaggatct caagaagatc ctttgatctt ttctacgggg tctgacgctc 3060
agtggaacga aaactcacgt taagggattt tggtcatgaa ttaattctta aaagaactcg 3120
tccaacatta aatgaaattg taacttgttc atatcaggat tatcaatacc atatttctga 3180
aataaacgtt tctgtaaaga aggagaaaat tcacctaaac aattccataa aatagctaaa 3240
tcttgataac gatcagcaat accaacacga ccaacatcaa tacaaccaat caatttacct 3300
tcatcaaaga tcaaattatc taaagaaaaa tcaccatgag taacaacaga atcaggagaa 3360
aaaggtaaca atttgtgcat ttctttccaa acttgttcaa caggccaacc attacgttca 3420
tcatcaaaat cagaagcatc aactaaacca ttattcatac gagattgagc ttgagctaaa 3480
cgaaaaacac gatcagaatt aaaaggacaa ttacaaacgg gaatagaatg taaacgacgt 3540
aaaaaaacag ctaaagcatc aacaatattt tcaccagaat caggatattc ttctaaaact 3600
tgaaaagcag ttttaccagg aatagcagta gttaataacc aagcatcatc gggagtacga 3660
ataaaatgtt taatagtagg taaaggcata aattcagtca accagtttaa acgaaccatt 3720
tcatcagtaa catcattagc aacagaacct ttaccatgtt tcaagaataa ttcaggagca 3780
tcaggtttac catataaacg ataaatagta gcaccagatt gaccaacatt atcacgagcc 3840
catttataac catataaatc ggcatccata ttagaattta aacgaggacg agaacaacta 3900
gtttcacgtt gaatatgaga catggttggt atcctccaaa tatataaatt ttctttatag 3960
cgttatatgt aacaacttct tttaatggaa gttagttttt tggcttttgc ttttcgagtt 4020
taaatcttat catgaagggg atcattttct atacacccag attaactatt tacgattatt 4080
atttttctg aatttgatta acttaactaa tctaattctc tatgcttacc ccagactatt 4140
ctctaggtat tttaaactgc taatttttcc ctctttaacg ttataaaagt cagaatttca 4200
catttcttta cactttgagg ttaaattatt acgattatta gtttcctta tgttttaatt 4260
aaaaaggtaa cgatgcacta ggcaaaggag aattgttgat aattaataac ttctaactct 4320
ttcctgtacg ggagaatgcc cattagcccc taactaactc cgtaccgctt tgcggaacga 4380
gcgctcgagc gttctctccg aactaatttc tccctctccc ctcatctata ataagatagt 4440
taataattac atcgacaatt gtctacgtag gcgcgccatg cggccttgac ggccttccgc 4500
caattcgccc tatagtgagt cgtattacgt cgcgctcact ggccgtcgtt ttacaacgtc 4560
gtgactggga aaaccctggc gttacccaac ttaatcgcct tgcagcacat ccccctttcg 4620
ccagctgcgc cggatccctg caggtcgacg atcgcaggtg tcacaatcat gatttcttga 4680
gccattgccc taccaaattc gcccggtttg ggatttttct ttttagccaa agtttgagca 4740
aatactgcca ataaagagtt agataacatt gctctaattt gggcttgttc tgccgaagga 4800
aatacatcaa taatacgatc aattgttccc gccgcagagc tagtatgtaa agtaccaaag 4860
acaaggtgtc cagtttccgc cgccgtaatc gccaaagaaa tggtttctaa gtcgcgcatc 4920
tcacccacta gaataatatc tggatcttcc cttaacgccg cttttaaggc attggcaaaa 4980
cttttagtat cttctccttt ttgacgttgg tgaaatagac tgttaatatt gggaaaaaca 5040
tactcgatcg gatcttctac tgttaagatg tgttctgcac gagtgcggtt aattaagtcc 5100
aacattgccg ctaaagtagt agtttttcca gaacctgtct gccctgtcac taaaatcata 5160
cccctagggc gttcggacat ctccttgaca atatctggta agcctaattg atcaaaattg 5220
ggaattttgg aagataaagc ccttaaacaa gcggcataac aaccccttc cttataaaca 5280
tttacacgaa atcgagccaa gcctttttacc ccgtaggaac agtctaactc ccattcttgc 5340
tctaatgttt tacgttgagt attattgagc atactaaaaa ttaatttttg gcactcttga 5400
```

FIG. 27 (continued)

gcattaaggg gttcatctcc aatgcaaaat tacgtacacg tgttattact ttgttaacga 5460
caattgtctt aattaactgg cctcatgggc cttccgctca ctgcccgctt tccagtcggg 5520
aaacctgtcg tgccagctct gcagatgacg gtgaaaacct ctgacacatg cagctcccgg 5580
agacggtcac agcttgtctg taagcggatg ccgggagcag acaagcccgt cagggcgcgt 5640
cagcgggtgt tggcgggtgt cggggcgcag ccatgaccca gtcacgtagc gatagcggag 5700
tgtatactgg cttaactatg cggcatcaga gcagattgta ctgagagtgc accatatgcg 5760
gtgtgaaata ccgcacagat gcgtaaggag aaaataccgc atcaggcgct cttccgcttc 5820
ctcgctcact gactcgctgc gctcggtcgt tcggctgcgg cgagcggtat cagctcactc 5880
aaaggcggta atacggttat ccacagaatc aggggataac gcaggaaaga acatgtgagc 5940
aaaaggccag caaaaggcca ggaaccgtaa aaaggccgcg ttgctggcgt ttttccatag 6000
gctccgcccc cctgacgagc atcacaaaaa tcgacgctca agtcagaggt ggcgaaaccc 6060
gacaggacta taaagatacc aggcgtttcc ccctggaagc tccctcgtgc gctctcctgt 6120
tccgaccctg ccgcttaccg gatacctgtc cgcctttctc ccttcgggaa gcgtggcgct 6180
ttctcaatgc tcacgctgta ggtatctcag ttcggtgtag gtcgttcgct ccaagctggg 6240
ctgtgtgcac gaaccccccg ttcagcccga ccgctgcgcc ttatccggta actatcgtct 6300
tgagtccaac ccggtaagac acgacttatc gccactggca gcagccactg gtaacaggat 6360
tagcagagcg aggtatgtag gcggtgctac agagttcttg aagtggtggc ctaactacgg 6420
ctacactaga aggacagtat ttggtatctg cgctctgctg aagccagtta ccttcggaaa 6480
aagagttggt agctcttgat ccggcaaaca aaccaccgct ggtagcggtg gtttttttgt 6540
ttgcaagcag cagattacgc gcagaaaaaa aggatctcaa gaagatcctt tgatcttttc 6600
tactgcagaa gcttgttaga caccctgtca tgtattttat attatttatt tcaccatacg 6660
gattaagtga aacctaatga aaatagtact ttcggagctt taactttaat gaaggtatgt 6720
ttttttatag acatcgatgt ctggtttaac aataggaaaa agtagctaaa actcccatga 6780
attaaagaaa taacaaggtg tctaacaacc tgttattaag aatgttagaa aagacttaac 6840
atttgtgttg agtttttata gacattggtg tctagacata cggtagataa ggtttgctca 6900
aaaataaaat aaaaaaagat tggactaaaa aacatttaat ttagtacaat ttaattagtt 6960
attttttcgt ctcaaatttt gctttgttga gcagaaattt agataaaaaa atccccgtga 7020
tcagattaca atgtcgttca ttgtacgatg tgtcgaaaaa tctttacgac actctaaact 7080
gaccacacgg gggaaaaaga aaactgaact aataacatca tgatactcgg aaaacctagc 7140
aattctcaac ccctaaacaa aagaaacttc caaaaccctg accatataaa ggagtggcaa 7200
caatcagcaa tcagtcaaga tttgatagca gaaaatcttg tatcggttgc taatggtttt 7260
gatgtactat ttatcggcaa taaataccga actaacacgg gtgttctgtc acggcacata 7320
ttaaactcct attctcattt agaagatggt ggttcgtatg gtagaacatt tgacccattt 7380
accaataaag aaatgcagtg ggttcaattt aaaccgaata gaccaagaaa aggttctact 7440
ggtaaggtaa tcaaatatga atcgccaaaa ggtgaaccta caagagttct aatgccgttt 7500
gtgcctatga aaatatggca acggattagc gataagttcg gagtaccgat taatccgaaa 7560
aaagatactc acttttggga atgggtaaag aataatccat cgataccgat tgccattaca 7620
gaaggaaata aaaaagctaa ttgcctatta tcctatggct atcctgctat tgcctttgta 7680
ggcatttgga acggattaga gaaaataaat gatttctcga aggaaaagca gttaaaagag 7740
gatttgaaat ggttgttatc caacggcaac cgaaatatta atatcatctt tgaccaagac 7800
cagaaacaaa aaactgtaat taatgtaaac aaagctattt tcgctttatc ttctctaata 7860
agtagaaatg gtcataaagt taatattgtg caatggttgc cgtcaaaagg taaaggaata 7920
gatgattatt tggtagcttt accttttgag aaaagagaaa atcatttaga caacttaatt 7980
aaaattgcac catcatttaa tttttggtca actaaatact tattcaagtg tcgtaaacca 8040
gatttaaccg taaattgccg ttatttgagc gatgcagtaa aagaattacc tcaagaggat 8100
atagcattaa tagcacctca cggcacgggt aaaacttcat tagtagctac tcacgttaag 8160
aatcggagtt atcacggaag gaaaactatt tcattggtgc atcttgaaag tttagccaaa 8220
gctaatggca acgcacttgg attatattac cgaaccgaaa ataatattga aaagcaatat 8280
cttggattta gcttatgtgt agatagttgc cgtgataaga ttaacggcat tacaactgat 8340
attatttcag gtcaagatta ttgccttttc attgatgaaa ttgaccaagt aattccacac 8400
atccttaaca gtgaaactga agtaagtaag tatagatgca ccatcattga cactttttct 8460
gaactggtga gaaatgctga acaggtcatt attgctgatg ctgatttatc cgatgtgacg 8520

FIG. 27 (continued)

```
attgacctaa tagaaaacat cagaggtaaa aaactatatg taatcaagaa tgaatatcag     8580
tatcagggaa tgacttttaa cgccgttggt tcaccattag aaatgatggc aatgatggga     8640
aaatcggtgt cagaaggcaa gaaattattt attaacacca catcccaaaa ggcaaaaagt     8700
aagtacggca caatcgctct tgagtcttat atttttggtc taaataaaga agcaaagata     8760
ttaagaatag actctgaaac cactaaaaac cctgaacatc cagcctataa aatcattgac     8820
caagacttaa ataatatcct caaagattat gattatgtca ttgcctcacc ttgccttcaa     8880
acaggtgtca gtattacctt aaaagggcat tttgaccagc aatttaactt ttccagtgga     8940
aacattacac ctcattgctt tttacagcaa atgtggcggt tgagggatgc agaaattgaa     9000
agattctatt atgtgccgaa ctcatctaac ctcaatctca ttgggaataa gtcaagttca     9060
ccatcagacc ttctaaagag caataacaag atggcaacgg caacggttaa ccttttgggt     9120
agaatcgact ccgaatattc cctagagtat gaatcgcacg gcatttggct tgagacgtgg     9180
gcaaaattat cagcacggca taacagttca atgcgttgtt actctgaaat tcttacctat     9240
ctaattacgt ctcaaggcca taaattaaat atcaacattc cctcacctct tgcagatatt     9300
aagaagctaa atgatgaggt aagtagtaac agggaaaagg taaaaaatga gagatactct     9360
cagaggttaa actcaccaga tattaacgat gcagaagcta ccatactcga atctaaagag     9420
caaaaaatcg gattgactct caatgagaga tgcaccctag aaaagcataa agttaagaag     9480
cggtatggga atgtaaagat ggatattctc acctttgatg atgatggact ataccccaaa     9540
ctcagactat tttattacct caccatcggt aaacctcatc tcaaggctaa tgacagaaaa     9600
gctattgcca aaatgggcaa tgacaataaa ggcaagattc tatcaaaaga cttagttaat     9660
aaaacttact ccgctcgtgt gaaggtctta gagattctta aactaactga ctttatcgac     9720
aatcttagag atgaactctt aataactccc aataatccag ctatcaccga ttttaataat     9780
cttctgctaa gagctaagaa ggatttaaga gtattaggag tcaacatcgg aaaatatcca     9840
atggccaaca ttaatgccgt acttactctc attggtcaca aactttctgt aatgagagat     9900
gagttcggaa aagagaaaag gataaaagta gatggtaaat cataccgatg ttatcaactt     9960
gaaacattac cagattttac caatgatact cttgactact ggttagaaaa tgatagccaa    10020
aaagaagtaa cagcaacaga aaattactcc gaaaatttta acccttcaaa tagctacaat    10080
ccagacagta agacactttc agagggtgca aatttcctat atataaataa agaagaattg    10140
catccaaata aattgcacct agaaataaaa gaaggtgctg aacttttttt attcggggta    10200
aaggtgattg tgaaaggaat cttggacggg gcagtaacta tattctctat gggtcaagaa    10260
tacgatttat ccctcaatga actagagggg atgttaacat catgaacttt acaagaatct    10320
ttttaaaggg cgatcgcacc atgttaaatg atggtacatt tgttcagata tttgatattt    10380
accatgacca cgcattggga gtgacccttg accttaagac agaaaaaatt atttccgatg    10440
atgttagggt aattactgtc aaagacttat tgttcgatgg cacttataaa ggggtaaaat    10500
cttttatgcc cgataatgcc cgataatgcc cgattgatgc tacaaaatcc cataatcata    10560
agcgataatc ccctaatagc ttgtaattct tgaaccgtag cgatttaga gtattccaaa     10620
aagaagaaat aaacaccgca aaatgtcgta tttcacatat ataaaccaag gtttttgcc     10680
ctaaaatctt tatgtttgta gtgtgatgtt gggtcaaaat ggtcagaaaa gttgcaaggt    10740
ttttatggat gcttacgcgc gcgagggta agcatcccca aatagttact ttatcctagt     10800
ccatgcccat ttattgccgt cccgttcggc tttaaaaaag tgccaaaact cacaaggtgc    10860
aataaaaagt tctgtacctt tcgcaaccct agataatctt tcaacagtta cttttttcc     10920
tattatctcg gtacaaagtt tggctagttt ctcttttccc tcttttcaa tcaagccttc      10980
ttgtatgccc aactcattga ttaatctctc tatttttacc attatttccc gttcaggtag    11040
tttatcccct aaatcttcat cgggggcaa tgtagggcat tctgaagggg cttttcttc       11100
tgtctggaca ttatctaata ttgaagtaac caaactatct tcagtttttt ctattcctat    11160
taattcatat tcggttactg tatccgtatc aatatccgaa taactatctt tatccgtatt    11220
agctattcgg ttaagtttat ccgttaactc agaaacaaga ctatatagcg gttttagctt    11280
ttcttctatc ctgttatcta atacggataa gtttatacgg ttatcattat ccgtattagt    11340
atcattgggc ttttttggta gttctacccc ctcataaacc gcttttattc ccaattccaa    11400
cagactgata acagtatcct ttataatggg tttttgctg atatggtgaa cttttgcccc      11460
ttccatcatt gcgatacttt ctatctcact catcaactta tcgcttaagt gaatctcgta    11520
tctgtttaat cccttactgg ttttattcat atccgtttac tttattcggt taacaattct    11580
```

FIG. 27 (continued)

```
attttatacg aataaaatat tatacggtta actttatacg tttaactatt ttatctatac   11640
ggataacagt aataagttat tcgtattagt tatacgttta cttttatcca aataaaatta   11700
gtgcatttaa actaaaagaa tgattttatc ggagttgata gcattggatt aacctaaaga   11760
tgtttataag ctatatctga taagtattta aggttatttt gttattctgt ttattgacat   11820
tatcagaata aaagaataga atataattgt tgagagataa gaggtttaag tgattatggt   11880
taagaagtta gttggttatg tcagggtcag tagtgaatcg caagaggata acactagctt   11940
acagaatcag atagagagaa ttgaagcata ttgtatggct tttggttatg agttggtaaa   12000
aatattcaaa gaggttgcca ctggtacaaa agcagatatt gaaacccgtc ctatttttaa   12060
tgaagctata gaatacttga aacaggataa tgctaatgga attattgcct tgaagctaga   12120
ccgaatcgca cggaatgctt tagatgtatt gcgtttggtt cgtgaaacct tagaaccaca   12180
aaataaaatg ttagtgttac tagatattca ggtagatact tcgacacctt caggaaaaat   12240
gattttaact gtaatgagtg ccgttgctga actcgaaaga gacatgatct atgatcgcac   12300
tcaggggggt agaaagacta aagcccaaaa gggcgggtat gcctacggga aacctaaatt   12360
tggctataag actgaagaaa aggaactaaa agaagattca gcacaacagg aaactattaa   12420
actaattaag agacaccgta ggtcagggaa aagctaccag aaaatagctg attatctcaa   12480
tgcccaaagt attcccacta aacaaggtaa gaaatggagt tctagcgtcg tctatcgaat   12540
ctgtcaggaa aaagctggtt aagtctgttt atagatattt agaatttatt gaataaaaat   12600
agtatgaaca ataaatattt atggactaac cacgctcgga aacgtttaac tgaacgatgg   12660
gaaataaaag aatcatgggt tattgatacc atcgaaaatc ctgaacgttc agaatttatt   12720
gttgatgagt caggggaaaa atatcattac tataaaagaa tagctaagtt taagaataga   12780
gtgttagaag tgataacttc tgccaactca acacccacaa gaataataac cttttacttt   12840
aaccgtaaca tgaggaaaaa tttatgattg ttacttacga taatgaagtt gacgcaattt   12900
attttaagtt aacggaaaat aaaattgata gcaccgaacc tcaaacagac aggattatca   12960
ttgattacga tgaaagtaat aatattgttg gcattgaggt attagatttt aattatcttg   13020
tcaagaaagg tttaaccgtt gctgatttac ctttttctga agatgaaaga ttaacagctt   13080
ctcaatattt taattttcct gttgctatct aatccagaag gggcaataat ccccttcttt   13140
catcgagtta gacttaatat cacaaaagtc attttcattt taccgtttct tttccacagc   13200
gtccgtacgc ccctcgttaa atctcaaaac cgacaattta tgatgtttat aaaaagttac   13260
tcactttaat aagtatttat actcattaaa gggttattct ttttttgtag cctgataggt   13320
tgggaaggaa tatttcagat tatcagattt gttg                               13354
```

FIG. 27 (continued)

```
ID    #1629\\pABICyano1::PnirA(opt2)-zmPDC(opt1)_dsrA-Prbc*(optRBS)-synADH(opt1)_ter
standard; circular DNA;    ; 12763 BP.
CC    This file is created by Vector NTI
CC    http://www.invitrogen.com/
CC    VNTDATE|645468924|
CC    VNTDBDATE|645468924|
CC    LSOWNER|
CC    VNTAUTHORNAME|Ulf Duehring|
FH    Key             Location/Qualifiers
FH
FT    insertion_seq   2018..2063
FT                    /vntifkey="14"
FT                    /label=dsrA
FT                    /note="dsr terminator from E.coli"
FT    gene            2133..3143
FT                    /vntifkey="60"
FT                    /note="ADH"
FT    CDS             2133..3140
FT                    /vntifkey="4"
FT                    /label=synADH(opt1)
FT    terminator      3144..3299
FT                    /vntifkey="43"
FT                    /label=TrbcSABICyano1
FT    promoter        3336..3799
FT                    /vntifkey="30"
FT                    /label=PrbcABICyano1
FT    CDS             3801..4616
FT                    /vntifkey="4"
FT                    /label=Km**
FT                    /note="Km**"
FT    CDS             12178..12426
FT                    /vntifkey="4"
FT                    /label=ORF\6
FT                    /note="orf6"
FT    CDS             11918..12181
FT                    /vntifkey="4"
FT                    /label=ORF\5
FT                    /note="orf5"
FT    CDS             11190..11876
FT                    /vntifkey="4"
FT                    /label=ORF\4
FT                    /note="orf4 Integrase/Recombinase Similar to Site-specific
recombinase of Bacillus thuringiensis serovar israelensis ATCC 35646"
FT    CDS             complement(10100..10864)
FT                    /vntifkey="4"
FT                    /label=ORF\3
FT                    /note="orf3"
FT    CDS             9655..9840
FT                    /vntifkey="4"
FT                    /label=ORF\2
FT                    /note="orf2"
FT    rep_origin      complement(8955..8972)
FT                    /vntifkey="33"
FT                    /label=Rep_Origin_1
FT                    /note="potential rep origin; match pNostoc (Acc# M81381) nick
site (358-375); on reserse strand"
FT    misc_feature    9215..9248
FT                    /vntifkey="21"
FT                    /label=Rep\motif
FT                    /note="Rep protein active site motig EXXKYXVKXXD"
```

FIG. 29

```
FT   CDS             6434..9619
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   primer_bind     complement(5222..5253)
FT                   /vntifkey="28"
FT                   /label=Bom-F
FT   primer_bind     4904..4935
FT                   /vntifkey="28"
FT                   /label=Bom-R
FT   rep_origin      complement(4859..5917)
FT                   /vntifkey="33"
FT                   /label=OriVT
FT   promoter        2064..2132
FT                   /vntifkey="30"
FT                   /label=Prbc*(optRBS)
FT                   /note="improved version of the rbcL promoter from PCC6803"
FT   promoter        1..287
FT                   /vntifkey="30"
FT                   /label=PnirA*2
FT                   /note="improved version of nirA promoter"
FT   CDS             285..1991
FT                   /vntifkey="4"
FT                   /label=zmPDC(opt1)
SQ   Sequence 12763 BP; 3948 A; 2245 C; 2490 G; 4080 t;
     tcgacaatta ataacttctt cctgtacggg cgaatggcca tttgctccta actaactccg        60
     tactgctttg cggaacgagc gtagcgaact ctccgaatta ctaagccttc atccctgata       120
     gatgcaaaaa acgaattaaa attatgtgta aaaagaaaat gtgtctttat ttagtagtca       180
     aagttacaaa atattaagaa tcaaattaat aatgtattgg gcagttaagt atataagtct       240
     ttaaatattt atttgtattc aatatattaa ggaggatcag ccttatgaat tcttataccg       300
     tgggtactta tttagccgaa cgcttagtgc aaattggttt aaaacatcat tttgccgtgg       360
     ctggggacta taatttagtg ttattggata acttattatt aaataaaaac atggaacaag       420
     tgtattgttg taatgaatta aattgtggtt tttctgctga aggttatgct agagctaaag       480
     gtgcagctgc tgctgttgtt acttattctg tgggtgcttt atctgctttt gatgctattg       540
     gtggtgctta tgccgaaaat ttacccgtga ttttaatttc tggtgcccct aataataatg       600
     atcatgccgc tggacatgtt ttacatcatg ccttaggtaa aaccgattat cattatcaat       660
     tagaaatggc caaaaatatt actgctgctg ccgaagctat ttatactcct gaagaagccc       720
     ctgccaaaat tgatcatgtg attaaaaccg ccttacgcga aaaaaaaccc gtgtatttag       780
     aaattgcctg taatattgct tctatgcctt gtgctgctcc tgggcctgct tctgctttat       840
     ttaatgatga agcctctgat gaagctagtt taaatgctgc cgtggaagaa accttaaaat       900
     ttattgccaa tcgcgataaa gttgccgtgt tagttggttc taaattaaga gctgctggtg       960
     ctgaagaagc tgctgttaaa tttgctgatg ctttaggtgg tgcagttgct actatggctg      1020
     ctgccaaatc tttttttccc gaagaaaatc cccattatat tggaactagt tggggagaag      1080
     tttcttatcc tggtgtggaa aaaactatga aagaagccga cgctgttatt gctttagccc      1140
     ctgtgtttaa tgattattct accactggtt ggactgatat tcccgatccc aaaaaattag      1200
     ttttagccga acctcgttct gttgttgtta atggtgttcg ctttccctct gtgcatttaa      1260
     aagattattt aacccgctta gcccaaaaag tttctaaaaa aactggtgcc ttagattttt      1320
     ttaaatcttt aaatgcgggt gaattaaaaa aagctgctcc tgctgatcct tctgctcctt      1380
     tagttaatgc tgaaattgcc cgtcaagttg aagccttatt aacccctaat actaccgtta      1440
     ttgccgaaac tggtgattct tggtttaatg cccaacgcat gaaattacct aatggtgccc      1500
     gtgttgaata tgaaatgcaa tggggtcata ttggttggtc tgtacctgct gcttttggtt      1560
     atgctgttgg tgctcctgaa cgtcgtaata ttttaatggt gggtgatggt tcttttcaat      1620
     taactgccca agaagttgcc caaatggttc gcttaaaatt acccgttatt attttttaa       1680
     taaataatta tggttatacc attgaagtga tgattcatga tgggccatat aataatatta      1740
     aaaattggga ttatgcgggt ttaatggaag tgtttaatgg taatggtggt tatgattctg      1800
     gtgctggtaa aggtttaaaa gccaaaactg gtggtgaatt agctgaagct attaaagttg      1860
     ccttagccaa tactgatggg ccaaccttaa ttgaatgttt tattggtcgc gaagattgta      1920
     ccgaagaatt agttaaatgg ggtaaacgtg ttgctgctgc taattctcgc aaacccgtga      1980
     ataaattatt gtaatttttg ggatcaatt cgagctcagc aagtttcatc ccgacccccct      2040
     cagggtcggg attttttat tgtactagtt gacataagta aaggcatccc ctgcgtgata       2100
```

FIG. 29 (continued)

```
taattacctt cagtttaagg aggtatacac atatgattaa agcctatgct gccttagaag   2160
ccaatggtaa attacaaccc tttgaatatg atcctggtgc tttaggtgcc aatgaagtgg   2220
aaattgaagt gcaatattgt ggtgtgtgtc attctgattt atctatgatt aataatgaat   2280
ggggtatttc taattatccc ttagttcctg gtcatgaagt tgttggtact gttgctgcta   2340
tgggtgaagg tgttaatcat gtggaagtgg gtgatttagt tggtttaggt tggcattctg   2400
gttattgtat gacctgtcat tcttgtttat ctggttatca taatttatgt gccactgccg   2460
aatctactat tgtgggtcat tatggtggtt ttggtgatag agttcgtgct aaaggtgttt   2520
ctgtggtgaa attacccaaa ggtattgatt tagcctctgc tgggccttta ttttgtggtg   2580
gtattaccgt tttttctccc atggtggaat tatctttaaa acctaccgcc aaagttgctg   2640
ttattggtat tggtggttta ggtcatttag ccgttcaatt tttaagagcc tggggttgtg   2700
aagttactgc ttttacctct tctgcccgta aacaaaccga agttttagaa ttaggtgccc   2760
atcatatttt agattctacc aatcctgaag ctattgcttc tgccgaaggt aaatttgatt   2820
atattatttc taccgtgaat ttaaaattag attggaattt atatatcagt accttagccc   2880
ctcaaggtca ttttcatttt gttggtgtgg tgttagaacc cttggactta aacttatttc   2940
ccttattaat gggacaacgt tctgtttctg cttctcctgt tggttctcct gctactattg   3000
ccactatgtt agattttgcc gtgcgtcatg atattaaacc cgtggtggaa caatttctct   3060
ttgatcaaat taatgaagcc attgcccatt tagaatctgg taaagcccat tatcgcgtgg   3120
tgttatctca ttctaaaaat taataagatt aacttctaaa ctgaaacaaa tttgagggta   3180
ggcttcattg tctgccctta ttttttttatt taggaaaagt gaacagacta aagagtgttg   3240
gctctattgc tttgagtatg taaattaggc gttgctgaat taaggtatga tttttgaccc   3300
cttctctctt ctgcaggatc atcttgctga aaaactcgag cgctcgttcc gcaaagcggt   3360
acggagttag ttaggggcta atgggcattc tcccgtacag gaaagagtta gaagttatta   3420
attatcaaca attctccttt gcctagtgca tcgttacctt tttaattaaa acataaggaa   3480
aactaataat cgtaataatt taacctcaaa gtgtaaagaa atgtgaaatt ctgactttta   3540
taacgttaaa gagggaaaaa ttagcagttt aaaataccta gagaatagtc tggggtaagc   3600
atagagaatt agattagtta agttaatcaa attcagaaaa aataataatc gtaaatagtt   3660
aatctgggtg tatagaaaat gatccccttc atgataagat ttaaactcga aagcaaaag    3720
ccaaaaaact aacttccatt aaaagaagtt gttacatata acgctataaa gaaaatttat   3780
atatttggag gataccaacc atgtctcata ttcaacgtga aactagttgt tctcgccctc   3840
gtttaaattc taatatggat gccgatttat atggttataa atgggctcgt gataatgttg   3900
gtcaatctgg tgctactatt tatcgtttat atggtaaacc tgatgctcct gaattattct   3960
tgaaacatgg taaaggttct gttgctaatg atgttactga tgaaatggtt cgtttaaact   4020
ggttgactga atttatgcct ttacctacta ttaaacattt tattcgtact cccgatgatg   4080
cttggttatt aactactgct attcctggta aaactgcttt tcaagtttta gaagaatatc   4140
ctgattctgg tgaaaatatt gttgatgctt tagctgtttt tttacgtcgt ttacattcta   4200
ttcccgtttg taattgtcct tttaattctg atcgtgtttt tcgtttagct caagctcaat   4260
ctcgtatgaa taatggttta gttgatgctt ctgattttga tgatgaacgt aatggttggc   4320
ctgttgaaca agtttggaaa gaaatgcaca aattgttacc tttttctcct gattctgttg   4380
ttactcatgg tgattttttct ttagataatt tgatctttga tgaaggtaaa ttgattggtt   4440
gtattgatgt tggtcgtgtt ggtattgctg atcgttatca agatttagct attttatgga   4500
attgtttagg tgaatttttct ccttctttac agaaacgttt atttcagaaa tatggtattg   4560
ataatcctga tatgaacaag ttacaatttc atttaatgtt ggacgagttc ttttaagaat   4620
taattcatga ccaaaatccc ttaacgtgag ttttcgttcc actgagcgtc agaccccgta   4680
gaaaagatca aaggatcttc ttgagatcct ttttttctgc gcgtaatctg ctgctattta   4740
aattacgtac acgtgttatt actttgttaa cgacaattgt cttaattaac tgggcctcat   4800
gggccttccg ctcactgccc gctttccagt cgggaaacct gtcgtgccag ctctgcagat   4860
gacggtgaaa acctctgaca catgcagctc ccggagacgg tcacagcttg tctgtaagcg   4920
gatgccggga gcagacaagc ccgtcagggc gcgtcagcgg gtgttggcgg gtgtcggggc   4980
gcagccatga cccagtcacg tagcgatagc ggagtgtata ctggcttaac tatgcggcat   5040
cagagcagat tgtactgaga gtgcaccata tgcggtgtga aataccgcac agatgcgtaa   5100
ggagaaaata ccgcatcagg cgctcttccg cttcctcgct cactgactcg ctgcgctcgg   5160
tcgttcggct gcggcgagcg gtatcagctc actcaaaggc ggtaatacgg ttatccacag   5220
aatcagggga taacgcagga aagaacatgt gagcaaaagg ccagcaaaag gccaggaacc   5280
gtaaaaaggc cgcgttgctg gcgtttttcc ataggctccg cccccctgac gagcatcaca   5340
aaaatcgacg ctcaagtcag aggtggcgaa acccgacagg actataaaga taccaggcgt   5400
ttccccctgg aagctccctc gtgcgctctc ctgttccgac cctgccgctt accggatacc   5460
tgtccgcctt tctcccttcg ggaagcgtgg cgctttctca tagctcacgc tgtaggtatc   5520
tcagttcggt gtaggtcgtt cgctccaagc tgggctgtgt gcacgaaccc cccgttcagc   5580
ccgaccgctg cgccttatcc ggtaactatc gtcttgagtc caacccggta agacacgact   5640
tatcgccact ggcagcagcc actggtaaca ggattagcag agcgaggtat gtaggcggtg   5700
```

FIG. 29 (continued)

```
ctacagagtt cttgaagtgg tggcctaact acggctacac tagaaggaca gtatttggta 5760
tctgcgctct gctgaagcca gttaccttcg gaaaaagagt tggtagctct tgatccggca 5820
aacaaaccac cgctggtagc ggtggttttt ttgtttgcaa gcagcagatt acgcgcagaa 5880
aaaaaggatc tcaagaagat cctttgatct tttctactgc agaagcttgt tagacaccct 5940
gtcatgtatt ttatattatt tatttcacca tacggattaa gtgaaaccta atgaaaatag 6000
tactttcgga gctttaactt taatgaaggt atgttttttt atagacatcg atgtctggtt 6060
taacaatagg aaaaagtagc taaaactccc atgaattaaa gaaataacaa ggtgtctaac 6120
aacctgttat taagaatgtt agaaaagact taacatttgt gttgagtttt tatagacatt 6180
ggtgtctaga catacggtag ataaggtttg ctcaaaaata aaataaaaaa agattggact 6240
aaaaaacatt taatttagta caatttaatt agttattttt tcgtctcaaa ttttgctttg 6300
ttgagcagaa atttagataa aaaaatcccc gtgatcagat tacaatgtcg ttcattgtac 6360
gatgtgtcga aaaatcttta cgacactcta aactgaccac acgggggaaa aagaaaactg 6420
aactaataac atcatgatac tcggaaaacc tagcaattct caacccctaa acaaaagaaa 6480
cttccaaaac cctgaccata taaaggagtg gcaacaatca gcaatcagtc aagatttgat 6540
agcagaaaat cttgtatcgg ttgctaatgg ttttgatgta ctatttatcg gcaataaata 6600
ccgaactaac acgggtgttc tgtcacggca catattaaac tcctattctc atttagaaga 6660
tggtggttcg tatggtagaa catttgaccc atttaccaat aaagaaatgc agtgggttca 6720
atttaaaccg aatagaccaa gaaaaggttc tactggtaag gtaatcaaat atgaatcgcc 6780
aaaaggtgaa cctacaagag ttctaatgcc gtttgtgcct atgaaaatat ggcaacggat 6840
tagcgataag ttcggagtac cgattaatcc gaaaaaagat actcactttt gggaatgggt 6900
aaagaataat ccatcgatac cgattgccat tacagaagga aataaaaaag ctaattgcct 6960
attatcctat ggctatcctg ctattgcctt tgtaggcatt tggaacggat tagagaaaat 7020
aaatgatttc tcgaaggaaa agcagttaaa agaggatttg aaatggttgt tatccaacgg 7080
caaccgaaat attaatatca tctttgacca agaccagaaa caaaaaactg taattaatgt 7140
aaacaaagct attttcgctt tatcttctct aataagtaga aatggtcata aagttaatat 7200
tgtgcaatgg ttgccgtcaa aaggtaaagg aatagatgat tatttggtag ctttaccttt 7260
tgagaaaaga gaaaatcatt tagacaactt aattaaaatt gcaccatcat ttaatttttg 7320
gtcaactaaa tacttattca agtgtcgtaa accagattta accgtaaatt gccgttattt 7380
gagcgatgca gtaaaagaat tacctcaaga ggatatagca ttaatagcac ctcacggcac 7440
gggtaaaact tcattagtag ctactcacgt taagaatcgg agttatcacg gaaggaaaac 7500
tatttcattg gtgcatcttg aaagtttagc caaagctaat ggcaacgcac ttggattata 7560
ttaccgaacc gaaaataata ttgaaaagca atatcttgga tttagcttat gtgtagatag 7620
ttgccgtgat aagattaacg gcattacaac tgatattatt tcaggtcaag attattgcct 7680
tttcattgat gaaattgacc aagtaattcc acacatcctt aacagtgaaa ctgaagtaag 7740
taagtataga tgcaccatca ttgacacttt ttctgaactg gtgagaaatg ctgaacaggt 7800
cattattgct gatgctgatt tatccgatgt gacgattgac ctaatagaaa acatcagagg 7860
taaaaaacta tatgtaatca agaatgaata tcagtatcag ggaatgactt ttaacgccgt 7920
tggttcacca ttagaaatga tggcaatgat gggaaaatcg gtgtcagaag gcaagaaatt 7980
atttattaac accacatccc aaaaggcaaa aagtaagtac ggcacaatcg ctcttgagtc 8040
ttatattttt ggtctaaata aagaagcaaa gatattaaga atagactctg aaaccactaa 8100
aaaccctgaa catccagcct ataaaatcat tgaccaagac ttaaataata tcctcaaaga 8160
ttatgattat gtcattgcct caccttgcct tcaaacaggt gtcagtatta ccttaaaagg 8220
gcattttgac cagcaattta acttttccag tggaaacatt acacctcatt gctttttaca 8280
gcaaatgtgg cggttgaggg atgcagaaat tgaaagattc tattatgtgc cgaactcatc 8340
taacctcaat ctcattggga ataagtcaag ttcaccatca gaccttctaa agagcaataa 8400
caagatggca acggcaacgg ttaacctttt gggtagaatc gactccgaat attccctaga 8460
gtatgaatcg cacggcattt ggcttgagac gtgggcaaaa ttatcagcac ggcataacag 8520
ttcaatgcgt tgttactctg aaattcttac ctatctaatt acgtctcaag ggcataaatt 8580
aaatatcaac attccctcac ctcttgcaga tattaagaag ctaaatgatg aggtaagtag 8640
taacagggaa aaggtaaaaa atgagagata ctctcagagg ttaaactcac cagatattaa 8700
cgatgcagaa gctaccatac tcgaatctaa agagcaaaaa atcggattga ctctcaatga 8760
gagatgcacc ctagaaaagc ataaagttaa gaagcggtat gggaatgtaa agatggatat 8820
tctcaccttt gatgatgatg gactataccc caaactcaga ctattttatt acctcaccat 8880
cggtaaacct catctcaagg ctaatgacag aaaagctatt gccaaaatgg gcaatgacaa 8940
taaaggcaag attctatcaa aagacttagt taataaaact tactccgctc gtgtgaaggt 9000
cttagagatt cttaaactaa ctgactttat cgacaatctt agagatgaac tcttaataac 9060
tcccaataat ccagctatca ccgattttaa taatcttctg ctaagagcta agaaggattt 9120
aagagtatta ggagtcaaca tcggaaaata tccaatggcc aacattaatg ccgtacttac 9180
tctcattggt cacaaacttt ctgtaatgag agatgagttc ggaaaagaga aaaggataaa 9240
```

FIG. 29 (continued)

```
agtagatggt aaatcatacc gatgttatca acttgaaaca ttaccagatt ttaccaatga   9300
tactcttgac tactggttag aaaatgatag ccaaaaagaa gtaacagcaa cagaaaatta   9360
ctccgaaaat tttaaccctt caaatagcta caatccagac agtaagacac tttcagaggg   9420
tgcaaatttc ctatatataa ataaagaaga attgcatcca aataaattgc acctagaaat   9480
aaaagaaggt gctgaacttt ttttattcgg ggtaaaggtg attgtgaaag gaatcttgga   9540
cggggcagta actatattct ctatgggtca agaatacgat ttatccctca atgaactaga   9600
ggggatgtta acatcatgaa ctttacaaga atctttttaa agggcgatcg caccatgtta   9660
aatgatggta catttgttca gatatttgat atttaccatg accacgcatt gggagtgacc   9720
cttgacctta agacagaaaa aattatttcc gatgatgtta gggtaattac tgtcaaagac   9780
ttattgttcg atggcactta taaaggggta aaatctttta tgcccgataa tgcccgataa   9840
tgcccgattg atgctacaaa atcccataat cataagcgat aatcccctaa tagcttgtaa   9900
ttcttgaacc gtagcgattt tagagtattc caaaaagaag aaataaacac cgcaaaatgt   9960
cgtatttcac atatataaac caaggttttt tgccctaaaa tctttatgtt tgtagtgtga   10020
tgttgggtca aaatggtcag aaaagttgca aggtttttat ggatgcttac gcgcgcgagg   10080
ggtaagcatc cccaaatagt tactttatcc tagtccatgc ccatttattg ccgtcccgtt   10140
cggctttaaa aaagtgccaa aactcacaag gtgcaataaa aagttctgta cctttcgcaa   10200
ccctagataa tctttcaaca gttacttttt ttcctattat ctcggtacaa agtttggcta   10260
gtttctcttt tccctctttt tcaatcaagc cttcttgtat gcccaactca ttgattaatc   10320
tctctatttt taccattatt tcccgttcag gtagtttatc ccctaaatct tcatcggggg   10380
gcaatgtagg gcattctgaa ggggcttttt cttctgtctg gacattatct aatattgaag   10440
taaccaaact atcttcagtt ttttctattc ctattaattc atattcggtt actgtatccg   10500
tatcaatatc cgaataacta tctttatccg tattagctat tcggttaagt ttatccgtta   10560
actcagaaac aagactatat agcggtttta gcttttcttc tatcctgtta tctaatacgg   10620
ataagtttat acggttatca ttatccgtat tagtatcatt gggctttttt ggtagttcta   10680
ccccctcata aaccgctttt attcccaatt ccaacagact gataacagta tcctttataa   10740
tgggtttttt gctgatatgg tgaacttttg ccccttccat cattgcgata ctttctatct   10800
cactcatcaa cttatcgctt aagtgaatct cgtatctgtt taatccctta ctggttttat   10860
tcatatccgt ttactttatt cggttaacaa ttctatttta tacgaataaa atattatacg   10920
gttaacttta tacgtttaac tattttatct atacggataa cagtaataag ttattcgtat   10980
tagttatacg tttactttta tccaaataaa attagtgcat ttaaactaaa agaatgattt   11040
tatcggagtt gatagcattg gattaaccta aagatgttta taagctatat ctgataagta   11100
tttaaggtta ttttgttatt ctgtttattg acattatcag aataaaagaa tagaatataa   11160
ttgttgagag ataagaggtt taagtgatta tggttaagaa gttagttggt tatgtcaggg   11220
tcagtagtga atcgcaagag gataacacta gcttacagaa tcagatagag agaattgaag   11280
catattgtat ggcttttggt tatgagttgg taaaaatatt caaagaggtt gccactggta   11340
caaaagcaga tattgaaacc cgtcctattt ttaatgaagc tatagaatac ttgaaacagg   11400
ataatgctaa tggaattatt gccttgaagc tagaccgaat cgcacggaat gctttagatg   11460
tattgcgttt ggttcgtgaa accttagaac cacaaaataa aatgttagtg ttactagata   11520
ttcaggtaga tacttcgaca ccttcaggaa aaatgatttt aactgtaatg agtgccgttg   11580
ctgaactcga aagagacatg atctatgatc gcactcaggg gggtagaaag actaaagccc   11640
aaaagggcgg gtatgcctac gggaaaccta aatttggcta taagactgaa gaaaaggaac   11700
taaaagaaga ttcagcacaa caggaaacta ttaaactaat taagagacac cgtaggtcag   11760
ggaaaagcta ccagaaaata gctgattatc tcaatgccca aagtattccc actaaacaag   11820
gtaagaaatg gagttctagc gtcgtctatc gaatctgtca ggaaaaagct ggttaagtct   11880
gtttatagat atttagaatt tattgaataa aaatagtatg aacaataaat atttatggac   11940
taaccacgct cggaaacgtt taactgaacg atgggaaata aaagaatcat gggttattga   12000
taccatcgaa aatcctgaac gttcagaatt tattgttgat gagtcagggg aaaaatatca   12060
ttactataaa agaatagcta agtttaagaa tagagtgtta gaagtgataa cttctgccaa   12120
ctcaacaccc acaagaataa taacctttta ctttaaccgt aacatgagga aaaatttatg   12180
attgttactt acgataatga agttgacgca atttatttta agttaacgga aaataaaatt   12240
gatagcaccg aacctcaaac agacaggatt atcattgatt acgatgaaag taataatatt   12300
gttggcattg aggtattaga ttttaattat cttgtcaaga aaggtttaac cgttgctgat   12360
ttaccttttt ctgaagatga aagattaaca gcttctcaat attttaattt tcctgttgct   12420
atctaatcca gaaggggcaa taatcccctt ctttcatcga gttagactta atatcacaaa   12480
agtcatttc attttaccgt ttcttttcca cagcgtccgt acgcccctcg ttaaatctca   12540
aaaccgacaa tttatgatgt ttataaaaag ttactcactt taataagtat ttatactcat   12600
taaagggtta ttcttttttt gtagcctgat aggttgggaa ggaatatttc agattatcag   12660
atttgttgaa tatttttcgt cagatacgca aaccttacaa acataattaa caactgaaac   12720
tattgatatg tctaggtttt agctctatca caggttggat ctg                     12763
```

FIG. 29 (continued)

```
ID    #1636\\pABICyano1::PnirA(opt3)-zmPDC(opt1)_dsrA-Prbc*(optRBS)-synADH(opt1)_ter
standard; circular DNA;    ; 12762 BP.
CC    This file is created by Vector NTI
CC    http://www.invitrogen.com/
CC    VNTDATE|645469353|
CC    VNTDBDATE|645469353|
CC    LSOWNER|
CC    VNTAUTHORNAME|Ulf Duehring|
FH    Key             Location/Qualifiers
FH
FT    CDS             284..1990
FT                    /vntifkey="4"
FT                    /label=zmPDC(opt1)
FT    promoter        6..283
FT                    /vntifkey="30"
FT                    /label=PnirA*3
FT                    /note="improved version of nirA promoter"
FT    insertion_seq   2017..2062
FT                    /vntifkey="14"
FT                    /label=dsrA
FT                    /note="dsrA terminator from E.coli"
FT    gene            2132..3142
FT                    /vntifkey="60"
FT                    /note="ADH"
FT    CDS             2132..3139
FT                    /vntifkey="4"
FT                    /label=synADH(opt1)
FT    terminator      3143..3298
FT                    /vntifkey="43"
FT                    /label=TrbcSABICyano1
FT    promoter        3335..3798
FT                    /vntifkey="30"
FT                    /label=PrbcABICyano1
FT    CDS             3800..4615
FT                    /vntifkey="4"
FT                    /label=Km**
FT                    /note="Km**"
FT    CDS             12177..12425
FT                    /vntifkey="4"
FT                    /label=ORF\6
FT                    /note="orf6"
FT    CDS             11917..12180
FT                    /vntifkey="4"
FT                    /label=ORF\5
FT                    /note="orf5"
FT    CDS             11189..11875
FT                    /vntifkey="4"
FT                    /label=ORF\4
FT                    /note="orf4 Integrase/Recombinase Similar to Site-specific
recombinase of Bacillus thuringiensis serovar israelensis ATCC 35646"
FT    CDS             complement(10099..10863)
FT                    /vntifkey="4"
FT                    /label=ORF\3
FT                    /note="orf3"
FT    CDS             9654..9839
FT                    /vntifkey="4"
FT                    /label=ORF\2
FT                    /note="orf2"
FT    rep_origin      complement(8954..8971)
FT                    /vntifkey="33"
```

FIG. 31

```
FT                   /label=Rep_Origin_1
FT                   /note="potential rep origin; match pNostoc (Acc# M81381) nick
site (358-375); on reserse strand"
FT   misc_feature    9214..9247
FT                   /vntifkey="21"
FT                   /label=Rep\motif
FT                   /note="Rep protein active site motig EXXKYXVKXXD"
FT   CDS             6433..9618
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   primer_bind     complement(5221..5252)
FT                   /vntifkey="28"
FT                   /label=Bom-F
FT   primer_bind     4903..4934
FT                   /vntifkey="28"
FT                   /label=Bom-R
FT   rep_origin      complement(4858..5916)
FT                   /vntifkey="33"
FT                   /label=OriVT
FT   promoter        2063..2131
FT                   /vntifkey="30"
FT                   /label=Prbc*(optRBS)
FT                   /note="improved version of rbcL promoter from PCC6803"
SQ   Sequence 12762 BP; 3948 A; 2248 C; 2485 G; 4081 t;
     tcgacaatta ataacttctt cctgtacggg cgaatggcca tttgctccta actaactccg        60
     tactgctttg cggaacgagc gtagcgaact ctccgaatta ctaagccttc atccctgata       120
     gatgcaaaaa acgcattaaa attatgcgta aaaagcatat ttgtctttat ttagtaatca       180
     aagttacaaa ttattaagaa tcaaattaat aatatattgg gcagttaagt atataagtct       240
     ttaaatattt atttgtattc aatatattaa ccgaggacaa attatgaatt cttataccgt       300
     gggtacttat ttagccgaac gcttagtgca aattggttta aaacatcatt ttgccgtggc       360
     tggggactat aatttagtgt tattggataa cttattatta aataaaaaca tggaacaagt       420
     gtattgttgt aatgaattaa attgtggttt ttctgctgaa ggttatgcta gagctaaagg       480
     tgcagctgct gctgttgtta cttattctgt gggtgcttta tctgcttttg atgctattgg       540
     tggtgcttat gccgaaaatt tacccgtgat tttaatttct ggtgccccta ataataatga       600
     tcatgccgct ggacatgttt tacatcatgc cttaggtaaa accgattatc attatcaatt       660
     agaaatggcc aaaaatatta ctgctgctgc cgaagctatt tatactcctg aagaagcccc       720
     tgccaaaatt gatcatgtga ttaaaaccgc cttacgcgaa aaaaaacccg tgtatttaga       780
     aattgcctgt aatattgctt ctatgccttg tgctgctcct gggcctgctt ctgctttatt       840
     taatgatgaa gcctctgatg aagctagttt aaatgctgcc gtggaagaaa ccttaaaatt       900
     tattgccaat cgcgataaag ttgccgtgtt agttggttct aaattaagag ctgctggtgc       960
     tgaagaagct gctgttaaat ttgctgatgc tttaggtggt gcagttgcta ctatggctgc      1020
     tgccaaatct ttttttcccg aagaaaatcc ccattatatt ggaactagtt ggggagaagt      1080
     ttcttatcct ggtgtggaaa aaactatgaa agaagccgac gctgttattg ctttagcccc      1140
     tgtgtttaat gattattcta ccactggttg gactgatatt cccgatccca aaaaattagt      1200
     tttagccgaa cctcgttctg ttgttgttaa tggtgttcgc tttccctctg tgcatttaaa      1260
     agattattta acccgcttag cccaaaaagt ttctaaaaaa actggtgcct tagatttttt      1320
     taaatcttta aatgcgggtg aattaaaaaa agctgctcct gctgatcctt ctgctccttt      1380
     agttaatgct gaaattgccc gtcaagttga agccttatta acccctaata ctaccgttat      1440
     tgccgaaact ggtgattctt ggtttaatgc ccaacgcatg aaattaccta atggtgcccg      1500
     tgttgaatat gaaatgcaat ggggtcatat tggttggtct gtacctgctg cttttggtta      1560
     tgctgttggt gctcctgaac gtcgtaatat tttaatggtg ggtgatggtt cttttcaatt      1620
     aactgcccaa gaagttgccc aaatggttcg cttaaaatta cccgttatta ttttttttaat      1680
     aaataattat ggttatacca ttgaagtgat gattcatgat gggccatata ataatattaa      1740
     aaattgggat tatgcgggtt taatggaagt gtttaatggt aatggtggtt atgattctgg      1800
     tgctggtaaa ggtttaaaag ccaaaactgg tggtgaatta gctgaagcta ttaaagttgc      1860
     cttagccaat actgatgggc caaccttaat tgaatgtttt attggtcgcg aagattgtac      1920
     cgaagaatta gttaaatggg gtaaacgtgt tgctgctgct aattctcgca aacccgtgaa      1980
```

FIG. 31 (continued)

```
taaattattg taatttttgg ggatcaattc gagctcagca agtttcatcc cgaccccctc 2040
agggtcggga tttttttatt gtactagttg acataagtaa aggcatcccc tgcgtgatat 2100
aattaccttc agtttaagga ggtatacaca tatgattaaa gcctatgctg ccttagaagc 2160
caatggtaaa ttacaaccct ttgaatatga tcctggtgct ttaggtgcca atgaagtgga 2220
aattgaagtg caatattgtg gtgtgtgtca ttctgattta tctatgatta ataatgaatg 2280
gggtatttct aattatccct tagttcctgg tcatgaagtt gttggtactg ttgctgctat 2340
gggtgaaggt gttaatcatg tggaagtggg tgatttagtt ggtttaggtt ggcattctgg 2400
ttattgtatg acctgtcatt cttgtttatc tggttatcat aatttatgtg ccactgccga 2460
atctactatt gtgggtcatt atggtggttt tggtgataga gttcgtgcta aaggtgtttc 2520
tgtggtgaaa ttacccaaag gtattgattt agcctctgct gggcctttat tttgtggtgg 2580
tattaccgtt ttttctccca tggtggaatt atctttaaaa cctaccgcca aagttgctgt 2640
tattggtatt ggtggtttag gtcatttagc cgttcaattt ttaagagcct ggggttgtga 2700
agttactgct tttacctctt ctgcccgtaa acaaaccgaa gttttagaat taggtgccca 2760
tcatatttta gattctacca atcctgaagc tattgcttct gccgaaggta aatttgatta 2820
tattatttct accgtgaatt taaaattaga ttggaattta tatatcagta ccttagcccc 2880
tcaaggtcat tttcattttg ttggtgtggt gttagaaccc ttggacttaa acttatttcc 2940
cttattaatg ggacaacgtt ctgtttctgc ttctcctgtt ggttctcctg ctactattgc 3000
cactatgtta gattttgccg tgcgtcatga tattaaaccc gtggtggaac aatttctttt 3060
tgatcaaatt aatgaagcca ttgcccattt agaatctggt aaagcccatt atcgcgtggt 3120
gttatctcat tctaaaaatt aataagatta acttctaaac tgaaacaaat ttgagggtag 3180
gcttcattgt ctgcccttat ttttttattt aggaaaagtg aacagactaa agagtgttgg 3240
ctctattgct ttgagtatgt aaattaggcg ttgctgaatt aaggtatgat ttttgacccc 3300
ttctctcttc tgcaggatca tcttgctgaa aaactcgagc gctcgttccg caaagcggta 3360
cggagttagt taggggctaa tgggcattct cccgtacagg aaagagttag aagttattaa 3420
ttatcaacaa ttctcctttg cctagtgcat cgttaccttt ttaattaaaa cataaggaaa 3480
actaataatc gtaataattt aacctcaaag tgtaaagaaa tgtgaaattc tgacttttat 3540
aacgttaaag agggaaaaat tagcagttta aaatacctag agaatagtct ggggtaagca 3600
tagagaatta gattagttaa gttaatcaaa ttcagaaaaa ataataatcg taaatagtta 3660
atctgggtgt atagaaaatg atccccttca tgataagatt taaactcgaa aagcaaaagc 3720
caaaaaacta acttccatta aaagaagttg ttacatataa cgctataaag aaaatttata 3780
tatttggagg ataccaacca tgtctcatat tcaacgtgaa actagttgtt ctcgccctcg 3840
tttaaattct aatatggatg ccgatttata tggttataaa tgggctcgtg ataatgttgg 3900
tcaatctggt gctactattt atcgtttata tggtaaacct gatgctcctg aattattctt 3960
gaaacatggt aaaggttctg ttgctaatga tgttactgat gaaatggttc gtttaaactg 4020
gttgactgaa tttatgcctt tacctactat taaacatttt attcgtactc ccgatgatgc 4080
ttggttatta actactgcta ttcctggtaa aactgctttt caagttttag aagaatatcc 4140
tgattctggt gaaaatattg ttgatgcttt agctgttttt ttacgtcgtt tacattctat 4200
tcccgtttgt aattgtcctt ttaattctga tcgtgttttt cgtttagctc aagctcaatc 4260
tcgtatgaat aatggtttag ttgatgcttc tgattttgat gatgaacgta atggttggcc 4320
tgttgaacaa gtttggaaag aaatgcacaa attgttacct ttttctcctg attctgttgt 4380
tactcatggt gattttctt tagataattt gatctttgat gaaggtaaat tgattggttg 4440
tattgatgtt ggtcgtgttg gtattgctga tcgttatcaa gatttagcta ttttatggaa 4500
ttgtttaggt gaattttctc cttctttaca gaaacgttta tttcagaaat atggtattga 4560
taatcctgat atgaacaagt tacaatttca tttaatgttg gacgagttct tttaagaatt 4620
aattcatgac caaaatccct taacgtgagt tttcgttcca ctgagcgtca gaccccgtag 4680
aaaagatcaa aggatcttct tgagatcctt tttttctgcg cgtaatctgc tgctatttaa 4740
attacgtaca cgtgttatta ctttgttaac gacaattgtc ttaattaact gggcctcatg 4800
ggccttccgc tcactgcccg ctttccagtc gggaaacctg tcgtgccagc tctgcagatg 4860
acggtgaaaa cctctgacac atgcagctcc cggagacggt cacagcttgt ctgtaagcgg 4920
atgccgggag cagacaagcc cgtcagggcg cgtcagcggg tgttggcggg tgtcggggcg 4980
cagccatgac ccagtcacgt agcgatagcg gagtgtatac tggcttaact atgcggcatc 5040
agagcagatt gtactgagag tgcaccatat gcggtgtgaa ataccgcaca gatgcgtaag 5100
gagaaaatac cgcatcaggc gctcttccgc ttcctcgctc actgactcgc tgcgctcggt 5160
cgttcggctg cggcgagcgg tatcagctca ctcaaaggcg gtaatacggt tatccacaga 5220
atcaggggat aacgcaggaa agaacatgtg agcaaaaggc cagcaaaagg ccaggaaccg 5280
taaaaaggcc gcgttgctgg cgtttttcca taggctccgc cccccctgacg agcatcacaa 5340
aaatcgacgc tcaagtcaga ggtggcgaaa cccgacagga ctataaagat accaggcgtt 5400
tccccctgga agctccctcg tgcgctctcc tgttccgacc ctgccgctta ccggatacct 5460
gtccgccttt ctcccttcgg gaagcgtggc gctttctcat agctcacgct gtaggtatct 5520
cagttcggtg taggtcgttc gctccaagct gggctgtgtg cacgaacccc ccgttcagcc 5580
cgaccgctgc gccttatccg gtaactatcg tcttgagtcc aacccggtaa gacacgactt 5640
```

FIG. 31 (continued)

```
atcgccactg gcagcagcca ctggtaacag gattagcaga gcgaggtatg taggcggtgc 5700
tacagagttc ttgaagtggt ggcctaacta cggctacact agaaggacag tatttggtat 5760
ctgcgctctg ctgaagccag ttaccttcgg aaaaagagtt ggtagctctt gatccggcaa 5820
acaaaccacc gctggtagcg gtggtttttt tgtttgcaag cagcagatta cgcgcagaaa 5880
aaaaggatct caagaagatc ctttgatctt ttctactgca gaagcttgtt agacaccctg 5940
tcatgtattt tatattattt atttcaccat acggattaag tgaaacctaa tgaaaatagt 6000
actttcggag ctttaacttt aatgaaggta tgttttttta tagacatcga tgtctggttt 6060
aacaatagga aaaagtagct aaaactccca tgaattaaag aaataacaag gtgtctaaca 6120
acctgttatt aagaatgtta gaaaagactt aacatttgtg ttgagttttt atagacattg 6180
gtgtctagac atacggtaga taaggtttgc tcaaaaataa aataaaaaaa gattggacta 6240
aaaaacattt aatttagtac aatttaatta gttatttttt cgtctcaaat tttgctttgt 6300
tgagcagaaa tttagataaa aaaatccccg tgatcagatt acaatgtcgt tcattgtacg 6360
atgtgtcgaa aaatctttac gacactctaa actgaccaca cggggggaaaa agaaaactga 6420
actaataaca tcatgatact cggaaaacct agcaattctc aacccctaaa caaaagaaac 6480
ttccaaaacc ctgaccatat aaaggagtgg caacaatcag caatcagtca agatttgata 6540
gcagaaaatc ttgtatcggt tgctaatggt tttgatgtac tatttatcgg caataaatac 6600
cgaactaaca cgggtgttct gtcacggcac atattaaact cctattctca tttagaagat 6660
ggtggttcgt atggtagaac atttgaccca tttaccaata aagaaatgca gtgggttcaa 6720
tttaaaccga atagaccaag aaaaggttct actggtaagg taatcaaata tgaatcgcca 6780
aaaggtgaac ctacaagagt tctaatgccg tttgtgccta tgaaaatatg gcaacggatt 6840
agcgataagt tcggagtacc gattaatccg aaaaaagata ctcacttttg ggaatgggta 6900
aagaataatc catcgatacc gattgccatt acagaaggaa ataaaaaagc taattgccta 6960
ttatcctatg gctatcctgc tattgccttt gtaggcattt ggaacggatt agagaaaata 7020
aatgatttct cgaaggaaaa gcagttaaaa gaggatttga aatggttgtt atccaacggc 7080
aaccgaaata ttaatatcat ctttgaccaa gaccagaaac aaaaaactgt aattaatgta 7140
aacaaagcta ttttcgcttt atcttctcta ataagtagaa atggtcataa agttaatatt 7200
gtgcaatggt tgccgtcaaa aggtaaagga atagatgatt atttggtagc tttacctttt 7260
gagaaaagag aaaatcattt agacaactta attaaaattg caccatcatt taatttttgg 7320
tcaactaaat acttattcaa gtgtcgtaaa ccagatttaa ccgtaaattg ccgttatttg 7380
agcgatgcag taaaagaatt acctcaagag gatatagcat taatagcacc tcacggcacg 7440
ggtaaaactt cattagtagc tactcacgtt aagaatcgga gttatcacgg aaggaaaact 7500
atttcattgg tgcatcttga aagtttagcc aaagctaatg gcaacgcact tggattatat 7560
taccgaaccg aaaataatat tgaaaagcaa tatcttggat ttagcttatg tgtagatagt 7620
tgccgtgata agattaacgg cattacaact gatattattt caggtcaaga ttattgcctt 7680
ttcattgatg aaattgacca agtaattcca cacatcctta acagtgaaac tgaagtaagt 7740
aagtatagat gcaccatcat tgacactttt tctgaactgg tgagaaatgc tgaacaggtc 7800
attattgctg atgctgattt atccgatgtg acgattgacc taatagaaaa catcagaggt 7860
aaaaaactat atgtaatcaa gaatgaatat cagtatcagg gaatgacttt taacgccgtt 7920
ggttcaccat tagaaatgat ggcaatgatg ggaaaatcgg tgtcagaagg caagaaatta 7980
tttattaaca ccacatccca aaaggcaaaa agtaagtacg gcacaatcgc tcttgagtct 8040
tatatttttg gtctaaataa agaagcaaag atattaagaa tagactctga aaccactaaa 8100
aaccctgaac atccagccta taaaatcatt gaccaagact taaataatat cctcaaagat 8160
tatgattatg tcattgcctc accttgcctt caaacaggtg tcagtattac cttaaaaggg 8220
cattttgacc agcaatttaa cttttccagt ggaaacatta cacctcattg ctttttacag 8280
caaatgtggc ggttgaggga tgcagaaatt gaaagattct attatgtgcc gaactcatct 8340
aacctcaatc tcattgggaa taagtcaagt tcaccatcag accttctaaa gagcaataac 8400
aagatggcaa cggcaacggt taacctttttg ggtagaatcg actccgaata ttccctagag 8460
tatgaatcgc acggcatttg gcttgagacg tgggcaaaat tatcagcacg gcataacagt 8520
tcaatgcgtt gttactctga aattcttacc tatctaatta cgtctcaagg gcataaatta 8580
aatatcaaca ttccctcacc tcttgcagat attaagaagc taaatgatga ggtaagtagt 8640
aacagggaaa aggtaaaaaa tgagagatac tctcagaggt taaactcacc agatattaac 8700
gatgcagaag ctaccatact cgaatctaaa gagcaaaaaa tcggattgac tctcaatgag 8760
agatgcaccc tagaaaagca taaagttaag aagcggtatg ggaatgtaaa gatggatatt 8820
ctcacctttg atgatgatgg actataccc aaactcagac tattttatta cctcaccatc 8880
ggtaaacctc atctcaaggc taatgacaga aaagctattg ccaaaatggg caatgacaat 8940
aaaggcaaga ttctatcaaa agacttagtt aataaaactt actccgctcg tgtgaaggtc 9000
ttagagattc ttaaactaac tgactttatc gacaatctta gagatgaact cttaataact 9060
cccaataatc cagctatcac cgattttaat aatcttctgc taagagctaa gaaggattta 9120
agagtattag gagtcaacat cggaaaatat ccaatggcca acattaatgc cgtacttact 9180
ctcattggtc acaaactttc tgtaatgaga gatgagttcg gaaaagagaa aaggataaaa 9240
gtagatggta aatcataccg atgttatcaa cttgaaacat taccagattt taccaatgat 9300
```

<u>FIG. 31 (continued)</u>

```
actcttgact actggttaga aaatgatagc caaaaagaag taacagcaac agaaaattac      9360
tccgaaaatt ttaacccttc aaatagctac aatccagaca gtaagacact ttcagaggt       9420
gcaaatttcc tatatataaa taaagaagaa ttgcatccaa ataaattgca cctagaaata      9480
aaagaaggtg ctgaactttt tttattcggg gtaaaggtga ttgtgaaagg aatcttggac      9540
ggggcagtaa ctatattctc tatgggtcaa gaatacgatt tatccctcaa tgaactagag      9600
gggatgttaa catcatgaac tttacaagaa tctttttaaa gggcgatcgc accatgttaa      9660
atgatggtac atttgttcag atatttgata tttaccatga ccacgcattg ggagtgaccc      9720
ttgaccttaa gacagaaaaa attatttccg atgatgttag ggtaattact gtcaaagact      9780
tattgttcga tggcacttat aaagggggtaa aatcttttat gcccgataat gcccgataat     9840
gcccgattga tgctacaaaa tcccataatc ataagcgata atcccctaat agcttgtaat      9900
tcttgaaccg tagcgatttt agagtattcc aaaaagaaga aataaacacc gcaaaatgtc      9960
gtatttcaca tatataaacc aaggtttttt gccctaaaat ctttatgttt gtagtgtgat     10020
gttgggtcaa aatggtcaga aaagttgcaa ggtttttatg gatgcttacg cgcgcgaggg     10080
gtaagcatcc ccaaatagtt actttatcct agtccatgcc catttattgc cgtcccgttc     10140
ggctttaaaa aagtgccaaa actcacaagg tgcaataaaa agttctgtac ctttcgcaac     10200
cctagataat ctttcaacag ttactttttt tcctattatc tcggtacaaa gtttggctag     10260
tttctctttt ccctcttttt caatcaagcc ttcttgtatg cccaactcat tgattaatct     10320
ctctattttt accattattt cccgttcagg tagtttatcc cctaaatctt catcgggggg     10380
caatgtaggg cattctgaag gggctttttc ttctgtctgg acattatcta atattgaagt     10440
aaccaaacta tcttcagttt tttctattcc tattaattca tattcggtta ctgtatccgt     10500
atcaatatcc gaataactat ctttatccgt attagctatt cggttaagtt tatccgttaa     10560
ctcagaaaca agactatata gcggttttag cttttcttct atcctgttat ctaatacgga     10620
taagtttata cggttatcat tatccgtatt agtatcattg ggcttttttg gtagttctac     10680
cccctcataa accgctttta ttcccaattc caacagactg ataacagtat cctttataat     10740
gggtttttttg ctgatatggt gaactttttgc cccttccatc attgcgatac tttctatctc   10800
actcatcaac ttatcgctta agtgaatctc gtatctgttt aatcccttac tggttttatt     10860
catatccgtt tactttattc ggttaacaat tctattttat acgaataaaa tattatacgg     10920
ttaactttat acgtttaact attttatcta tacggataac agtaataagt tattcgtatt     10980
agttatacgt ttactttttat ccaaataaaa ttagtgcatt taaactaaaa gaatgatttt    11040
atcggagttg atagcattgg attaacctaa agatgtttat aagctatatc tgataagtat     11100
ttaaggttat tttgttattc tgtttattga cattatcaga ataaaagaat agaatataat     11160
tgttgagaga taagaggttt aagtgattat ggttaagaag ttagttggtt atgtcagggt     11220
cagtagtgaa tcgcaagagg ataacactag cttacagaat cagatagaga gaattgaagc     11280
atattgtatg gcttttggtt atgagttggt aaaaatattc aaagaggttg ccactggtac     11340
aaaagcagat attgaaaccc gtcctatttt taatgaagct atagaatact tgaaacagga     11400
taatgctaat ggaattattg ccttgaagct agaccgaatc gcacggaatg ctttagatgt     11460
attgcgtttg gttcgtgaaa ccttagaacc acaaaataaa atgttagtgt tactagatat     11520
tcaggtagat acttcgacac cttcaggaaa aatgatttta actgtaatga gtgccgttgc     11580
tgaactcgaa agagacatga tctatgatcg cactcagggg ggtagaaaga ctaaagccca     11640
aaagggcggg tatgcctacg ggaaacctaa atttggctat aagactgaag aaaaggaact     11700
aaaagaagat tcagcacaac aggaaactat taaactaatt aagagacacc gtaggtcagg     11760
gaaaagctac cagaaaatag ctgattatct caatgcccaa agtattccca ctaaacaagg     11820
taagaaatgg agttctagcg tcgtctatcg aatctgtcag gaaaaagctg gttaagtctg     11880
tttatagata tttagaattt attgaataaa aatagtatga acaataaata tttatggact     11940
aaccacgctc ggaaacgttt aactgaacga tgggaaataa aagaatcatg ggttattgat     12000
accatcgaaa atcctgaacg ttcagaattt attgttgatg agtcagggga aaaatatcat     12060
tactataaaa gaatagctaa gtttaagaat agagtgttag aagtgataac ttctgccaac     12120
tcaacaccca caagaataat aacctttttac tttaaccgta acatgaggaa aaatttatga    12180
ttgttactta cgataatgaa gttgacgcaa tttattttaa gttaacggaa aataaaattg     12240
atagcaccga acctcaaaca gacaggatta tcattgatta cgatgaaagt aataatattg     12300
ttggcattga ggtattagat tttaattatc ttgtcaagaa aggtttaacc gttgctgatt     12360
tacctttttc tgaagatgaa agattaacag cttctcaata ttttaatttt cctgttgcta     12420
tctaatccag aaggggcaat aatccccttc tttcatcgag ttagacttaa tatcacaaaa     12480
gtcattttca ttttaccgtt tcttttccac agcgtccgta cgcccctcgt taaatctcaa     12540
aaccgacaat tttatgatgtt tataaaaagt tactcacttt aataagtatt tatactcatt    12600
aaagggttat tctttttttg tagcctgata ggttgggaag gaatatttca gattatcaga     12660
tttgttgaat atttttcgtc agatacgcaa accttacaaa cataattaac aactgaaact     12720
attgatatgt ctaggtttta gctctatcac aggttggatc tg                         12762
```

FIG. 31 (continued)

```
ID   #1630\\pABICyano1::corR-PcorT*1-zmPDC(opt1)_dsrA-Prbc*(optRBS)-synADH(opt1)_ter
standard; circular DNA;    ; 13726 BP.
CC   This file is created by Vector NTI
CC   http://www.invitrogen.com/
CC   VNTDATE|645469723|
CC   VNTDBDATE|645469723|
CC   LSOWNER|
CC   VNTAUTHORNAME|Ulf Duehring|
FH   Key             Location/Qualifiers
FH
FT   insertion_seq   2981..3026
FT                   /vntifkey="14"
FT                   /label=dsrA
FT                   /note="dsr terminator from E.coli"
FT   gene            3096..4106
FT                   /vntifkey="60"
FT                   /note="ADH"
FT   CDS             3096..4103
FT                   /vntifkey="4"
FT                   /label=synADH(opt1)
FT   terminator      4107..4262
FT                   /vntifkey="43"
FT                   /label=TrbcSABICyano1
FT   promoter        4299..4762
FT                   /vntifkey="30"
FT                   /label=PrbcABICyano1
FT   CDS             4764..5579
FT                   /vntifkey="4"
FT                   /label=Km**
FT                   /note="Km**"
FT   CDS             13141..13389
FT                   /vntifkey="4"
FT                   /label=ORF\6
FT                   /note="orf6"
FT   CDS             12881..13144
FT                   /vntifkey="4"
FT                   /label=ORF\5
FT                   /note="orf5"
FT   CDS             12153..12839
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(11063..11827)
FT                   /vntifkey="4"
FT                   /label=ORF\3
FT                   /note="orf3"
FT   CDS             10618..10803
FT                   /vntifkey="4"
FT                   /label=ORF\2
FT                   /note="orf2"
FT   rep_origin      complement(9918..9935)
FT                   /vntifkey="33"
FT                   /label=Rep_Origin_1
FT                   /note="potential rep origin; match pNostoc (Acc# M81381) nick
site (358-375); on reserse strand"
FT   misc_feature    10178..10211
FT                   /vntifkey="21"
FT                   /label=Rep\motif
FT                   /note="Rep protein active site motig EXXKYXVKXXD"
FT   CDS             7397..10582
```

FIG. 33

```
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   primer_bind     complement(6185..6216)
FT                   /vntifkey="28"
FT                   /label=Bom-F
FT   primer_bind     5867..5898
FT                   /vntifkey="28"
FT                   /label=Bom-R
FT   rep_origin      complement(5822..6880)
FT                   /vntifkey="33"
FT                   /label=OriVT
FT   promoter        3027..3095
FT                   /vntifkey="30"
FT                   /label=Prbc*(optRBS)
FT                   /note="improved version of rbcL promoter from PCC6803"
FT   CDS             complement(54..1166)
FT                   /vntifkey="4"
FT                   /label=corR
FT   promoter        1168..1247
FT                   /vntifkey="30"
FT                   /label=PcorT*1
FT                   /note="improved version of corT promoter from PCC6803"
FT   CDS             1248..2954
FT                   /vntifkey="4"
FT                   /label=zmPDC(opt1)
SQ   Sequence 13726 BP; 4160 A; 2504 C; 2756 G; 4306 t;
     tcgaccatgc gtccaaaact ttcaccatcc tttccctatc aacctttact gcactaaaga        60
     caagtgagat agcagtggca atctggcttt gcaatcaatg tttccactaa agcgtttagc       120
     gttactgcgg ctagaagtcc tccaccgagg ctcccctgaa tggtgatatg gggaatggga       180
     ctggtcatca gtcgtcgttt tgcccccgga gcatgactaa aaccgatcgg cattccgatc       240
     acaagagccg gctgaatatg ttgttgctct atcagcttac aggcagtgag taaaacagaa       300
     ggggcatagc cgatcgccag cacacatcct tggggaatct gttgtaaccg ctgttgccaa       360
     tggtcatggt gccaaaaagc ttgctcggct tccctaagcc ctgtgatgtg agggtcgtca       420
     atcagcgttt taaccgtaca tcctaaatga gctaaccgag tttgatcaag agccgcagcc       480
     acaaccggaa catcggtgac gactggacac cctgctttca gtgcatctcg tgccgaggcg       540
     atcgctccct gactcaatcg aacggcgttt accaagctaa catcaccaca ggccagcact       600
     aattgatgta gtaagtgaat ggtaatttca gagtaagccg ataaatccgg tagcaggtgt       660
     ttgagggatt cctgaaaggc ttctggatga gttgttgtct ccgcatctag gttcgtccac       720
     aactgatcga gttttcctaa cccctcctgg acatccacat caagctgttt cagttgggcc       780
     agagcttccg cttgggtaat ctggcaactc tggtcgcgtc ccagtaatcc ttctaaagca       840
     gatgcggttt ggcggagtcg agtaatctgc tgaatcacag cctgatattg ctgttgcaac       900
     tgcaccatta gggtgggatc aaggctctct tcagaatggc tatccagcag ttgccgaata       960
     tgagacaact gaaagccctg ctgtttgagg gcaatgactc gttggagccg ttgtacgtcc      1020
     tgctgagtat aaaggcggta gttgccctct gagcgttgaa cggggggaag caatcccagg      1080
     gtgtggtaat ggcgcaccat gcgaggcgta acgccacctc ccactgcatc tgtgagttct      1140
     ttaatcgtta agtgattagt cttcatgact ttagtttact caaaaccttg acattgacac      1200
     taatgttaag gtttaggctg agaaggtaaa aatcgaggat aaaaagcatg aattcttata      1260
     ccgtgggtac ttatttagcc gaacgcttag tgcaaattgg tttaaaacat cattttgccg      1320
     tggctgggga ctataattta gtgttattgg ataacttatt attaaataaa aacatggaac      1380
     aagtgtattg ttgtaatgaa ttaaattgtg gtttttctgc tgaaggttat gctagagcta      1440
     aaggtgcagc tgctgctgtt gttacttatt ctgtgggtgc tttatctgct tttgatgcta      1500
     ttggtggtgc ttatgccgaa aatttacccg tgattttaat ttctggtgcc cctaataata      1560
     atgatcatgc cgctggacat gttttacatc atgccttagg taaaaccgat tatcattatc      1620
     aattagaaat ggccaaaaat attactgctg ctgccgaagc tatttatact cctgaagaag      1680
     cccctgccaa aattgatcat gtgattaaaa ccgccttacg cgaaaaaaaa cccgtgtatt      1740
     tagaaattgc ctgtaatatt gcttctatgc cttgtgctgc tcctgggcct gcttctgctt      1800
     tatttaatga tgaagcctct gatgaagcta gtttaaatgc tgccgtggaa gaaaccttaa      1860
     aatttattgc caatcgcgat aaagttgccg tgttagttgg ttctaaatta agagctgctg      1920
```

FIG. 33 (continued)

```
gtgctgaaga agctgctgtt aaatttgctg atgctttagg tggtgcagtt gctactatgg 1980
ctgctgccaa atcttttttt cccgaagaaa atccccatta tattggaact agttggggag 2040
aagtttctta tcctggtgtg gaaaaaacta tgaaagaagc cgacgctgtt attgctttag 2100
cccctgtgtt taatgattat tctaccactg gttggactga tattcccgat cccaaaaaat 2160
tagttttagc cgaacctcgt tctgttgttg ttaatggtgt tcgctttccc tctgtgcatt 2220
taaaagatta tttaacccgc ttagcccaaa aagtttctaa aaaaactggt gccttagatt 2280
tttttaaatc tttaaatgcg ggtgaattaa aaaaagctgc tcctgctgat ccttctgctc 2340
ctttagttaa tgctgaaatt gcccgtcaag ttgaagcctt attaacccct aatactaccg 2400
ttattgccga aactggtgat tcttggttta atgcccaacg catgaaatta cctaatggtg 2460
cccgtgttga atatgaaatg caatggggtc atattggttg gtctgtacct gctgctttg 2520
gttatgctgt tggtgctcct gaacgtcgta atattttaat ggtgggtgat ggttcttttc 2580
aattaactgc ccaagaagtt gcccaaatgg ttcgcttaaa attacccgtt attatttttt 2640
taataaataa ttatggttat accattgaag tgatgattca tgatgggcca tataataata 2700
ttaaaaattg ggattatgcg ggtttaatgg aagtgtttaa tggtaatggt ggttatgatt 2760
ctggtgctgg taaaggttta aaagccaaaa ctggtggtga attagctgaa gctattaaag 2820
ttgccttagc caatactgat gggccaacct taattgaatg ttttattggt cgcgaagatt 2880
gtaccgaaga attagttaaa tggggtaaac gtgttgctgc tgctaattct cgcaaacccg 2940
tgaataaatt attgtaattt ttggggatca attcgagctc agcaagtttc atcccgaccc 3000
cctcagggtc gggatttttt tattgtacta gttgacataa gtaaaggcat cccctgcgtg 3060
atataattac cttcagttta aggaggtata cacatatgat taaagcctat gctgccttag 3120
aagccaatgg taaattacaa ccctttgaat atgatcctgg tgctttaggt gccaatgaag 3180
tggaaattga agtgcaatat tgtggtgtgt gtcattctga tttatctatg attaataatg 3240
aatggggtat ttctaattat cccttagttc ctggtcatga agttgttggt actgttgctg 3300
ctatgggtga aggtgttaat catgtggaag tgggtgattt agttggttta ggttggcatt 3360
ctggttattg tatgacctgt cattcttgtt tatctggtta tcataattta tgtgccactg 3420
ccgaatctac tattgtgggt cattatggtg gttttggtga tagagttcgt gctaaaggtg 3480
tttctgtggt gaaattaccc aaaggtattg atttagcctc tgctgggcct ttattttgtg 3540
gtggtattac cgtttttttct cccatggtgg aattatcttt aaaacctacc gccaaagttg 3600
ctgttattgg tattggtggt ttaggtcatt tagccgttca atttttaaga gcctggggtt 3660
gtgaagttac tgcttttacc tcttctgccc gtaaacaaac cgaagtttta gaattaggtg 3720
cccatcatat tttagattct accaatcctg aagctattgc ttctgccgaa ggtaaatttg 3780
attatattat ttctaccgtg aatttaaaat tagattggaa tttatatatc agtaccttag 3840
cccctcaagg tcattttcat tttgttggtg tggtgttaga acccttggac ttaaacttat 3900
ttcccttatt aatgggacaa cgttctgttt ctgcttctcc tgttggttct cctgctacta 3960
ttgccactat gttagatttt gccgtgcgtc atgatattaa acccgtggtg gaacaatttt 4020
cttttgatca aattaatgaa gccattgccc atttagaatc tggtaaagcc cattatcgcg 4080
tggtgttatc tcattctaaa aattaataag attaacttct aaactgaaac aaatttgagg 4140
gtaggcttca ttgtctgccc ttattttttt atttaggaaa agtgaacaga ctaaagagtg 4200
ttggctctat tgctttgagt atgtaaatta ggcgttgctg aattaaggta tgatttttga 4260
ccccttctct cttctgcagg atcatcttgc tgaaaaactc gagcgctcgt tccgcaaagc 4320
ggtacggagt tagttagggg ctaatgggca ttctcccgta caggaaagag ttagaagtta 4380
ttaattatca acaattctcc tttgcctagt gcatcgttac ctttttaatt aaaacataag 4440
gaaaactaat aatcgtaata atttaacctc aaagtgtaaa gaaatgtgaa attctgactt 4500
ttataacgtt aaagagggaa aaattagcag tttaaaatac ctagagaata gtctggggta 4560
agcatagaga attagattag ttaagttaat caaattcaga aaaaataata atcgtaaata 4620
gttaatctgg gtgtatagaa aatgatcccc ttcatgataa gatttaaact cgaaaagcaa 4680
aagccaaaaa actaacttcc attaaaagaa gttgttacat ataacgctat aaagaaaatt 4740
tatatatttg gaggatacca accatgtctc atattcaacg tgaaactagt tgttctcgcc 4800
ctcgtttaaa ttctaatatg gatgccgatt tatatggtta taaatgggct cgtgataatg 4860
ttggtcaatc tggtgctact atttatcgtt tatatggtaa acctgatgct cctgaattat 4920
tcttgaaaca tggtaaaggt tctgttgcta atgatgttac tgatgaaatg gttcgtttaa 4980
actggttgac tgaatttatg ccttttaccta ctattaaaca ttttattcgt actcccgatg 5040
atgcttggtt attaactact gctattcctg gtaaaactgc ttttcaagtt ttagaagaat 5100
atcctgattc tggtgaaaat attgttgatg ctttagctgt ttttttacgt cgtttacatt 5160
ctattcccgt ttgtaattgt ccttttaatt ctgatcgtgt ttttcgttta gctcaagctc 5220
aatctcgtat gaataatggt ttagttgatg cttctgattt tgatgatgaa cgtaatggtt 5280
ggcctgttga acaagtttgg aaagaaatgc acaaattgtt acctttttct cctgattctg 5340
ttgttactca tggtgatttt tctcttagata atttgatctt tgatgaaggt aaattgattg 5400
gttgtattga tgttggtcgt gttggtattg ctgatcgtta tcaagattta gctattttat 5460
ggaattgttt aggtgaattt tctccttctt tacagaaacg tttatttcag aaatatggta 5520
```

FIG. 33 (continued)

```
ttgataatcc tgatatgaac aagttacaat ttcatttaat gttggacgag ttcttttaag      5580
aattaattca tgaccaaaat cccttaacgt gagttttcgt tccactgagc gtcagacccc      5640
gtagaaaaga tcaaaggatc ttcttgagat cctttttttc tgcgcgtaat ctgctgctat      5700
ttaaattacg tacacgtgtt attactttgt taacgacaat tgtcttaatt aactgggcct      5760
catgggcctt ccgctcactg cccgctttcc agtcgggaaa cctgtcgtgc cagctctgca      5820
gatgacggtg aaaacctctg acacatgcag ctcccggaga cggtcacagc ttgtctgtaa      5880
gcggatgccg ggagcagaca agcccgtcag ggcgcgtcag cgggtgttgg cgggtgtcgg      5940
ggcgcagcca tgacccagtc acgtagcgat agcggagtgt atactggctt aactatgcgg      6000
catcagagca gattgtactg agagtgcacc atatgcggtg tgaaataccg cacagatgcg      6060
taaggagaaa ataccgcatc aggcgctctt ccgcttcctc gctcactgac tcgctgcgct      6120
cggtcgttcg gctgcggcga gcggtatcag ctcactcaaa ggcggtaata cggttatcca      6180
cagaatcagg ggataacgca ggaaagaaca tgtgagcaaa aggccagcaa aaggccagga      6240
accgtaaaaa ggccgcgttg ctggcgtttt tccataggct ccgcccccct gacgagcatc      6300
acaaaaatcg acgctcaagt cagaggtggc gaaacccgac aggactataa agataccagg      6360
cgtttccccc tggaagctcc ctcgtgcgct ctcctgttcc gaccctgccg cttaccggat      6420
acctgtccgc ctttctccct tcgggaagcg tggcgctttc tcatagctca cgctgtaggt      6480
atctcagttc ggtgtaggtc gttcgctcca agctgggctg tgtgcacgaa ccccccgttc      6540
agcccgaccg ctgcgcctta tccggtaact atcgtcttga gtccaacccg gtaagacacg      6600
acttatcgcc actggcagca gccactggta acaggattag cagagcgagg tatgtaggcg      6660
gtgctacaga gttcttgaag tggtggccta actacggcta cactagaagg acagtatttg      6720
gtatctgcgc tctgctgaag ccagttacct tcggaaaaag agttggtagc tcttgatccg      6780
gcaaacaaac caccgctggt agcggtggtt tttttgtttg caagcagcag attacgcgca      6840
gaaaaaaagg atctcaagaa gatcctttga tcttttctac tgcagaagct tgttagacac      6900
cctgtcatgt attttatatt atttatttca ccatacggat taagtgaaac ctaatgaaaa      6960
tagtactttc ggagctttaa ctttaatgaa ggtatgtttt tttatagaca tcgatgtctg      7020
gtttaacaat aggaaaaagt agctaaaact cccatgaatt aaagaaataa caaggtgtct      7080
aacaacctgt tattaagaat gttagaaaag acttaacatt tgtgttgagt ttttatagac      7140
attggtgtct agacatacgg tagataaggt ttgctcaaaa ataaaataaa aaaagattgg      7200
actaaaaaac atttaattta gtacaattta attagttatt ttttcgtctc aaattttgct      7260
ttgttgagca gaaatttaga taaaaaaatc cccgtgatca gattacaatg tcgttcattg      7320
tacgatgtgt cgaaaaatct ttacgacact ctaaactgac cacacggggg aaaaagaaaa      7380
ctgaactaat aacatcatga tactcggaaa acctagcaat tctcaacccc taaacaaaag      7440
aaacttccaa aaccctgacc atataaagga gtggcaacaa tcagcaatca gtcaagattt      7500
gatagcagaa aatcttgtat cggttgctaa tggttttgat gtactattta tcggcaataa      7560
ataccgaact aacacgggtg ttctgtcacg gcacatatta aactcctatt ctcatttaga      7620
agatggtggt tcgtatggta gaacatttga cccatttacc aataaagaaa tgcagtgggt      7680
tcaatttaaa ccgaatagac caagaaaagg ttctactggt aaggtaatca aatatgaatc      7740
gccaaaaggt gaacctacaa gagttctaat gccgtttgtg cctatgaaaa tatggcaacg      7800
gattagcgat aagttcggag taccgattaa tccgaaaaaa gatactcact tttgggaatg      7860
ggtaaagaat aatccatcga taccgattgc cattacagaa ggaaataaaa aagctaattg      7920
cctattatcc tatggctatc ctgctattgc ctttgtaggc atttggaacg gattagagaa      7980
aataaatgat ttctcgaagg aaaagcagtt aaaagaggat ttgaaatggt tgttatccaa      8040
cggcaaccga aatattaata tcatctttga ccaagaccag aaacaaaaaa ctgtaattaa      8100
tgtaaacaaa gctattttcg ctttatcttc tctaataagt agaaatggtc ataaagttaa      8160
tattgtgcaa tggttgccgt caaaaggtaa aggaatagat gattatttgg tagctttacc      8220
ttttgagaaa agagaaaatc atttagacaa cttaattaaa attgcaccat catttaattt      8280
ttggtcaact aaatacttat tcaagtgtcg taaaccagat ttaaccgtaa attgccgtta      8340
tttgagcgat gcagtaaaag aattacctca agaggatata gcattaatag cacctcacgg      8400
cacgggtaaa acttcattag tagctactca cgttaagaat cggagttatc acggaaggaa      8460
aactatttca ttggtgcatc ttgaaagttt agccaaagct aatggcaacg cacttggatt      8520
atattaccga accgaaaata atattgaaaa gcaatatctt ggatttagct tatgtgtaga      8580
tagttgccgt gataagatta acggcattac aactgatatt atttcaggtc aagattattg      8640
ccttttcatt gatgaaattg accaagtaat tccacacatc cttaacagtg aaactgaagt      8700
aagtaagtat agatgcacca tcattgacac tttttctgaa ctggtgagaa atgctgaaca      8760
ggtcattatt gctgatgctg atttatccga tgtgacgatt gacctaatag aaaacatcag      8820
aggtaaaaaa ctatatgtaa tcaagaatga atatcagtat cagggaatga cttttaacgc      8880
cgttggttca ccattagaaa tgatggcaat gatgggaaaa tcggtgtcag aaggcaagaa      8940
attatttatt aacaccacat cccaaaaggc aaaaagtaag tacggcacaa tcgctcttga      9000
gtcttatatt tttggtctaa ataaagaagc aaagatatta agaatagact ctgaaaccac      9060
```

FIG. 33 (continued)

```
taaaaaccct gaacatccag cctataaaat cattgaccaa gacttaaata atatcctcaa     9120
agattatgat tatgtcattg cctcaccttg ccttcaaaca ggtgtcagta ttaccttaaa     9180
agggcatttt gaccagcaat ttaacttttc cagtggaaac attacacctc attgcttttt     9240
acagcaaatg tggcggttga gggatgcaga aattgaaaga ttctattatg tgccgaactc     9300
atctaacctc aatctcattg ggaataagtc aagttcacca tcagaccttc taaagagcaa     9360
taacaagatg gcaacggcaa cggttaacct tttgggtaga atcgactccg aatattccct     9420
agagtatgaa tcgcacggca tttggcttga gacgtgggca aaattatcag cacggcataa     9480
cagttcaatg cgttgttact ctgaaattct tacctatcta attacgtctc aagggcataa     9540
attaaatatc aacattccct cacctcttgc agatattaag aagctaaatg atgaggtaag     9600
tagtaacagg gaaaaggtaa aaaatgagag atactctcag aggttaaact caccagatat     9660
taacgatgca gaagctacca tactcgaatc taaagagcaa aaaatcggat tgactctcaa     9720
tgagagatgc accctagaaa agcataaagt taagaagcgg tatgggaatg taaagatgga     9780
tattctcacc tttgatgatg atggactata ccccaaactc agactatttt attacctcac     9840
catcggtaaa cctcatctca aggctaatga cagaaaagct attgccaaaa tgggcaatga     9900
caataaaggc aagattctat caaaagactt agttaataaa acttactccg ctcgtgtgaa     9960
ggtcttagag attcttaaac taactgactt tatcgacaat cttagagatg aactcttaat    10020
aactcccaat aatccagcta tcaccgattt taataatctt ctgctaagag ctaagaagga    10080
tttaagagta ttaggagtca acatcggaaa atatccaatg gccaacatta atgccgtact    10140
tactctcatt ggtcacaaac tttctgtaat gagagatgag ttcggaaaag agaaaaggat    10200
aaaagtagat ggtaaatcat accgatgtta tcaacttgaa acattaccag atttaccaa    10260
tgatactctt gactactggt tagaaaatga tagccaaaaa gaagtaacag caacagaaaa    10320
ttactccgaa aattttaacc cttcaaatag ctacaatcca gacagtaaga cactttcaga    10380
gggtgcaaat ttcctatata taaataaaga agaattgcat ccaaataaat tgcacctaga    10440
aataaaagaa ggtgctgaac ttttttttatt cggggtaaag gtgattgtga aaggaatctt    10500
ggacggggca gtaactatat tctctatggg tcaagaatac gatttatccc tcaatgaact    10560
agaggggatg ttaacatcat gaactttaca agaatctttt taaagggcga tcgcaccatg    10620
ttaaatgatg gtacatttgt tcagatattt gatatttacc atgaccacgc attgggagtg    10680
acccttgacc ttaagacaga aaaaattatt tccgatgatg ttagggtaat tactgtcaaa    10740
gacttattgt tcgatggcac ttataaaggg gtaaaatctt ttatgcccga taatgcccga    10800
taatgcccga ttgatgctac aaaatcccat aatcataagc gataatcccc taatagcttg    10860
taattcttga accgtagcga ttttagagta ttccaaaaag aagaaataaa caccgcaaaa    10920
tgtcgtattt cacatatata aaccaaggtt ttttgcccta aaatctttat gtttgtagtg    10980
tgatgttggg tcaaaatggt cagaaaagtt gcaaggtttt tatggatgct tacgcgcgcg    11040
aggggtaagc atccccaaat agttacttta tcctagtcca tgcccattta ttgccgtccc    11100
gttcggcttt aaaaaagtgc caaaactcac aaggtgcaat aaaaagttct gtacctttcg    11160
caaccctaga taatctttca acagttactt tttttcctat tatctcggta caaagtttgg    11220
ctagtttctc ttttccctct ttttcaatca agccttcttg tatgcccaac tcattgatta    11280
atctctctat ttttaccatt atttcccgtt caggtagttt atcccctaaa tcttcatcgg    11340
ggggcaatgt agggcattct gaaggggctt tttcttctgt ctggacatta tctaatattg    11400
aagtaaccaa actatcttca gttttttcta ttcctattaa ttcatattcg gttactgtat    11460
ccgtatcaat atccgaataa ctatctttat ccgtattagc tattcggtta agtttatccg    11520
ttaactcaga aacaagacta tatagcggtt ttagcttttc ttctatcctg ttatctaata    11580
cggataagtt tatacggtta tcattatccg tattagtatc attgggcttt tttggtagtt    11640
ctacccccctc ataaaccgct tttattccca attccaacag actgataaca gtatccttta    11700
taatgggttt tttgctgata tggtgaactt ttgccccttc catcattgcg atactttcta    11760
tctcactcat caacttatcg cttaagtgaa tctcgtatct gtttaatccc ttactggttt    11820
tattcatatc cgtttacttt attcggttaa caattctatt ttatacgaat aaaatattat    11880
acggttaact ttatacgttt aactatttta tctatacgga taacagtaat aagttattcg    11940
tattagttat acgtttactt ttatccaaat aaaattagtg catttaaact aaaagaatga    12000
ttttatcgga gttgatagca ttggattaac ctaaagatgt ttataagcta tatctgataa    12060
gtatttaagg ttattttgtt attctgttta ttgacattat cagaataaaa gaatagaata    12120
taattgttga gagataagag gtttaagtga ttatggttaa gaagttagtt ggttatgtca    12180
gggtcagtag tgaatcgcaa gaggataaca ctagcttaca gaatcagata gagagaattg    12240
aagcatattg tatggctttt ggttatgagt tggtaaaaat attcaaagag gttgccactg    12300
gtacaaaagc agatattgaa acccgtccta tttttaatga agctatagaa tacttgaaac    12360
aggataatgc taatggaatt attgccttga agctagaccg aatcgcacgg aatgctttag    12420
atgtattgcg tttggttcgt gaaaccttag aaccacaaaa taaaatgtta gtgttactag    12480
atattcaggt agatacttcg acaccttcag gaaaaatgat tttaactgta atgagtgccg    12540
ttgctgaact cgaaagagac atgatctatg atcgcactca gggggggtaga aagactaaag    12600
cccaaaaggg cgggtatgcc tacgggaaac ctaaatttgg ctataagact gaagaaaagg    12660
aactaaaaga agattcagca caacaggaaa ctattaaact aattaagaga caccgtaggt    12720
```

FIG. 33 (continued)

```
caggggaaaag ctaccagaaa atagctgatt atctcaatgc ccaaagtatt cccactaaac     12780
aaggtaagaa atggagttct agcgtcgtct atcgaatctg tcaggaaaaa gctggttaag     12840
tctgtttata gatatttaga atttattgaa taaaaatagt atgaacaata aatatttatg     12900
gactaaccac gctcggaaac gtttaactga acgatgggaa ataaaagaat catgggttat     12960
tgataccatc gaaaatcctg aacgttcaga atttattgtt gatgagtcag gggaaaaata     13020
tcattactat aaaagaatag ctaagtttaa gaatagagtg ttagaagtga taacttctgc     13080
caactcaaca cccacaagaa taataacctt ttactttaac cgtaacatga ggaaaaattt     13140
atgattgtta cttacgataa tgaagttgac gcaatttatt ttaagttaac ggaaaataaa     13200
attgatagca ccgaacctca aacagacagg attatcattg attacgatga aagtaataat     13260
attgttggca ttgaggtatt agattttaat tatcttgtca agaaaggttt aaccgttgct     13320
gatttacctt tttctgaaga tgaaagatta acagcttctc aatattttaa ttttcctgtt     13380
gctatctaat ccagaagggg caataatccc cttctttcat cgagttagac ttaatatcac     13440
aaaagtcatt ttcattttac cgtttctttt ccacagcgtc cgtacgcccc tcgttaaatc     13500
tcaaaaccga caatttatga tgtttataaa aagttactca ctttaataag tatttatact     13560
cattaaaggg ttattctttt tttgtagcct gataggttgg gaaggaatat ttcagattat     13620
cagatttgtt gaatattttt cgtcagatac gcaaacctta caaacataat taacaactga     13680
aactattgat atgtctaggt tttagctcta tcacaggttg gatctg                    13726
```

FIG. 33 (continued)

```
ID   #1631\\pABICyanol::corR-PcorT*2-zmPDC(opt1)_dsrA-Prbc*(optRBS)-synADH(opt1)_ter
standard; circular DNA;    ; 13726 BP.
CC   This file is created by Vector NTI
CC   http://www.invitrogen.com/
CC   VNTDATE|645470012|
CC   VNTDBDATE|645470012|
CC   LSOWNER|
CC   VNTAUTHORNAME|Ulf Duehring|
FH   Key             Location/Qualifiers
FH
FT   insertion_seq   2981..3026
FT                   /vntifkey="14"
FT                   /label=dsrA
FT                   /note="dsrA terminator from E.coli"
FT   gene            3096..4106
FT                   /vntifkey="60"
FT                   /note="ADH"
FT   CDS             3096..4103
FT                   /vntifkey="4"
FT                   /label=synADH(opt1)
FT   terminator      4107..4262
FT                   /vntifkey="43"
FT                   /label=TrbcSABICyanol
FT   promoter        4299..4762
FT                   /vntifkey="30"
FT                   /label=PrbcABICyanol
FT   CDS             4764..5579
FT                   /vntifkey="4"
FT                   /label=Km**
FT                   /note="Km**"
FT   CDS             13141..13389
FT                   /vntifkey="4"
FT                   /label=ORF\6
FT                   /note="orf6"
FT   CDS             12881..13144
FT                   /vntifkey="4"
FT                   /label=ORF\5
FT                   /note="orf5"
FT   CDS             12153..12839
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(11063..11827)
FT                   /vntifkey="4"
FT                   /label=ORF\3
FT                   /note="orf3"
FT   CDS             10618..10803
FT                   /vntifkey="4"
FT                   /label=ORF\2
FT                   /note="orf2"
FT   rep_origin      complement(9918..9935)
FT                   /vntifkey="33"
FT                   /label=Rep_Origin_1
FT                   /note="potential rep origin; match pNostoc (Acc# M81381) nick
site (358-375); on reserse strand"
FT   misc_feature    10178..10211
FT                   /vntifkey="21"
FT                   /label=Rep\motif
FT                   /note="Rep protein active site motig EXXKYXVKXXD"
FT   CDS             7397..10582
```

FIG. 35

```
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   primer_bind     complement(6185..6216)
FT                   /vntifkey="28"
FT                   /label=Bom-F
FT   primer_bind     5867..5898
FT                   /vntifkey="28"
FT                   /label=Bom-R
FT   rep_origin      complement(5822..6880)
FT                   /vntifkey="33"
FT                   /label=OriVT
FT   promoter        3027..3095
FT                   /vntifkey="30"
FT                   /label=Prbc*(optRBS)
FT                   /note="improved version of rbcL promoter from PCC6803"
FT   CDS             complement(54..1166)
FT                   /vntifkey="4"
FT                   /label=corR
FT   promoter        1169..1247
FT                   /vntifkey="30"
FT                   /label=PcorT*2
FT                   /note="improved version of corT promoter from PCC6803"
FT   CDS             1248..2954
FT                   /vntifkey="4"
FT                   /label=zmPDC(opt1)
SQ   Sequence 13726 BP; 4162 A; 2504 C; 2753 G; 4307 t;
     tcgaccatgc gtccaaaact ttcaccatcc tttccctatc aacctttact gcactaaaga        60
     caagtgagat agcagtggca atctggcttt gcaatcaatg tttccactaa agcgtttagc       120
     gttactgcgg ctagaagtcc tccaccgagg ctcccctgaa tggtgatatg gggaatggga       180
     ctggtcatca gtcgtcgttt tgcccccgga gcatgactaa aaccgatcgg cattccgatc       240
     acaagagccg gctgaatatg ttgttgctct atcagcttac aggcagtgag taaaacagaa       300
     ggggcatagc cgatcgccag cacacatcct tggggaatct gttgtaaccg ctgttgccaa       360
     tggtcatggt gccaaaaagc ttgctcggct tccctaagcc ctgtgatgtg agggtcgtca       420
     atcagcgttt taaccgtaca tcctaaatga gctaaccgag tttgatcaag agccgcagcc       480
     acaaccggaa catcggtgac gactggacac cctgctttca gtgcatctcg tgccgaggcg       540
     atcgctccct gactcaatcg aacggcgttt accaagctaa catcaccaca ggccagcact       600
     aattgatgta gtaagtgaat ggtaatttca gagtaagccg ataaatccgg tagcaggtgt       660
     ttgagggatt cctgaaaggc ttctggatga gttgttgtct ccgcatctag gttcgtccac       720
     aactgatcga gttttcctaa cccctcctgg acatccacat caagctgttt cagttgggcc       780
     agagcttccg cttgggtaat ctggcaactc tggtcgcgtc ccagtaatcc ttctaaagca       840
     gatgcggttt ggcggagtcg agtaatctgc tgaatcacag cctgatattg ctgttgcaac       900
     tgcaccatta gggtgggatc aaggctctct tcagaatggc tatccagcag ttgccgaata       960
     tgagacaact gaaagccctg ctgtttgagg gcaatgactc gttggagccg ttgtacgtcc      1020
     tgctgagtat aaaggcggta gttgccctct gagcgttgaa cgggggggaag caatcccagg      1080
     gtgtggtaat ggcgcaccat gcgaggcgta acgccacctc ccactgcatc tgtgagttct      1140
     ttaatcgtta agtgattagt cttcatgact ttagtttact caaaaccttg acattgacac      1200
     taatgttaag gtttagaatg agaaggtaaa aatccaagtt aaaaagcatg aattcttata      1260
     ccgtgggtac ttatttagcc gaacgcttag tgcaaattgg tttaaaacat cattttgccg      1320
     tggctgggga ctataattta gtgttattgg ataacttatt attaaataaa aacatggaac      1380
     aagtgtattg ttgtaatgaa ttaaattgtg gtttttctgc tgaaggttat gctagagcta      1440
     aaggtgcagc tgctgctgtt gttacttatt ctgtgggtgc tttatctgct tttgatgcta      1500
     ttggtggtgc ttatgccgaa aatttacccg tgattttaat ttctggtgcc cctaataata      1560
     atgatcatgc cgctggacat gttttacatc atgccttagg taaaaccgat tatcattatc      1620
     aattagaaat ggccaaaaat attactgctg ctgccgaagc tatttatact cctgaagaag      1680
     cccctgccaa aattgatcat gtgattaaaa ccgccttacg cgaaaaaaaa cccgtgtatt      1740
     tagaaattgc ctgtaatatt gcttctatgc cttgtgctgc tcctgggcct gcttctgctt      1800
     tatttaatga tgaagcctct gatgaagcta gtttaaatgc tgccgtggaa gaaaccttaa      1860
     aatttattgc caatcgcgat aaagttgccg tgttagttgg ttctaaatta agagctgctg      1920
```

FIG. 35 (continued)

```
gtgctgaaga agctgctgtt aaatttgctg atgctttagg tggtgcagtt gctactatgg   1980
ctgctgccaa atcttttttt cccgaagaaa atccccatta tattggaact agttggggag   2040
aagtttctta tcctggtgtg gaaaaaacta tgaaagaagc cgacgctgtt attgctttag   2100
cccctgtgtt taatgattat tctaccactg gttggactga tattcccgat cccaaaaaat   2160
tagttttagc cgaacctcgt tctgttgttg ttaatggtgt tcgctttccc tctgtgcatt   2220
taaaagatta tttaacccgc ttagcccaaa aagtttctaa aaaaactggt gccttagatt   2280
tttttaaatc tttaaatgcg ggtgaattaa aaaaagctgc tcctgctgat ccttctgctc   2340
ctttagttaa tgctgaaatt gcccgtcaag ttgaagcctt attaaccccct aatactaccg   2400
ttattgccga aactggtgat tcttggttta atgcccaacg catgaaatta cctaatggtg   2460
cccgtgttga atatgaaatg caatggggtc atattggttg gtctgtacct gctgcttttg   2520
gttatgctgt tggtgctcct gaacgtcgta atattttaat ggtgggtgat ggttcttttc   2580
aattaactgc ccaagaagtt gcccaaatgg ttcgcttaaa attacccgtt attatttttt   2640
taataaataa ttatggttat accattgaag tgatgattca tgatggccca tataataata   2700
ttaaaaattg ggattatgcg ggtttaatgg aagtgtttaa tggtaatggt ggttatgatt   2760
ctggtgctgg taaaggttta aaagccaaaa ctggtggtga attagctgaa gctattaaag   2820
ttgccttagc caatactgat gggccaacct taattgaatg ttttattggt cgcgaagatt   2880
gtaccgaaga attagttaaa tggggtaaac gtgttgctgc tgctaattct cgcaaacccg   2940
tgaataaatt attgtaattt ttggggatca attcgagctc agcaagtttc atcccgaccc   3000
cctcagggtc gggatttttt tattgtacta gttgacataa gtaaaggcat cccctgcgtg   3060
atataattac cttcagttta aggaggtata cacatatgat taaagcctat gctgccttag   3120
aagccaatgg taaattacaa ccctttgaat atgatcctgg tgctttaggt gccaatgaag   3180
tggaaattga agtgcaatat tgtggtgtgt gtcattctga tttatctatg attaataatg   3240
aatggggtat ttctaattat cccttagttc ctggtcatga agttgttggt actgttgctg   3300
ctatgggtga aggtgttaat catgtggaag tgggtgattt agttggttta ggttggcatt   3360
ctggttattg tatgacctgt cattcttgtt tatctggtta tcataattta tgtgccactg   3420
ccgaatctac tattgtgggt cattatggtg gttttggtga tagagttcgt gctaaaggtg   3480
tttctgtggt gaaattaccc aaaggtattg atttagcctc tgctgggcct ttattttgtg   3540
gtggtattac cgtttttct cccatggtgg aattatcttt aaaacctacc gccaaagttg   3600
ctgttattgg tattggtggt ttaggtcatt tagccgttca atttttaaga gcctggggtt   3660
gtgaagttac tgcttttacc tcttctgccc gtaaacaaac cgaagtttta gaattaggtg   3720
cccatcatat tttagattct accaatcctg aagctattgc ttctgccgaa ggtaaatttg   3780
attatattat ttctaccgtg aatttaaaat tagattggaa tttatatatc agtaccttag   3840
cccctcaagg tcattttcat tttgttggtg tggtgttaga acccttggac ttaaacttat   3900
ttcccttatt aatgggacaa cgttctgttt ctgcttctcc tgttggttct cctgctacta   3960
ttgccactat gttagatttt gccgtgcgtc atgatattaa acccgtggtg gaacaatttt   4020
cttttgatca aattaatgaa gccattgccc atttagaatc tggtaaagcc cattatcgcg   4080
tggtgttatc tcattctaaa aattaataag attaacttct aaactgaaac aaatttgagg   4140
gtaggcttca ttgtctgccc ttattttttt atttaggaaa agtgaacaga ctaaagagtg   4200
ttggctctat tgctttgagt atgtaaatta ggcgttgctg aattaaggta tgatttttga   4260
ccccttctct cttctgcagg atcatcttgc tgaaaaactc gagcgctcgt tccgcaaagc   4320
ggtacggagt tagttagggg ctaatgggca ttctcccgta caggaaagag ttagaagtta   4380
ttaattatca acaattctcc tttgcctagt gcatcgttac ctttttaatt aaaacataag   4440
gaaaactaat aatcgtaata atttaacctc aaagtgtaaa gaaatgtgaa attctgactt   4500
ttataacgtt aaagagggaa aaattagcag tttaaaatac ctagagaata gtctggggta   4560
agcatagaga attagattag ttaagttaat caaattcaga aaaaataata atcgtaaata   4620
gttaatctgg gtgtatagaa aatgatcccc ttcatgataa gatttaaact cgaaaagcaa   4680
aagccaaaaa actaacttcc attaaaagaa gttgttacat ataacgctat aaagaaaatt   4740
tatatatttg gaggatacca accatgtctc atattcaacg tgaaactagt tgttctcgcc   4800
ctcgtttaaa ttctaatatg gatgccgatt tatatggtta taaatgggct cgtgataatg   4860
ttggtcaatc tggtgctact atttatcgtt tatatggtaa acctgatgct cctgaattat   4920
tcttgaaaca tggtaaaggt tctgttgcta atgatgttac tgatgaaatg gttcgtttaa   4980
actggttgac tgaatttatg cctttaccta ctattaaaca ttttattcgt actcccgatg   5040
atgcttggtt attaactact gctattcctg gtaaaactgc ttttcaagtt ttagaagaat   5100
atcctgattc tggtgaaaat attgttgatg ctttagctgt ttttttacgt cgtttacatt   5160
ctattcccgt ttgtaattgt ccttttaatt ctgatcgtgt ttttcgttta gctcaagctc   5220
aatctcgtat gaataatggt ttagttgatg cttctgattt tgatgatgaa cgtaatggtt   5280
ggcctgttga acaagtttgg aaagaaatgc acaaattgtt acctttttct cctgattctg   5340
ttgttactca tggtgatttt tctttagata atttgatctt tgatgaaggt aaattgattg   5400
gttgtattga tgttggtcgt gttggtattg ctgatcgtta tcaagattta gctatttttat  5460
```

FIG. 35 (continued)

```
ggaattgttt aggtgaattt tctccttctt tacagaaacg tttatttcag aaatatggta 5520
ttgataatcc tgatatgaac aagttacaat ttcatttaat gttggacgag ttcttttaag 5580
aattaattca tgaccaaaat cccttaacgt gagttttcgt tccactgagc gtcagacccc 5640
gtagaaaaga tcaaaggatc ttcttgagat cctttttttc tgcgcgtaat ctgctgctat 5700
ttaaattacg tacacgtgtt attactttgt taacgacaat tgtcttaatt aactgggcct 5760
catgggcctt ccgctcactg cccgctttcc agtcgggaaa cctgtcgtgc cagctctgca 5820
gatgacggtg aaaacctctg acacatgcag ctcccggaga cggtcacagc ttgtctgtaa 5880
gcggatgccg ggagcagaca agcccgtcag ggcgcgtcag cgggtgttgg cgggtgtcgg 5940
ggcgcagcca tgacccagtc acgtagcgat agcggagtgt atactggctt aactatgcgg 6000
catcagagca gattgtactg agagtgcacc atatgcggtg tgaaataccg cacagatgcg 6060
taaggagaaa ataccgcatc aggcgctctt ccgcttcctc gctcactgac tcgctgcgct 6120
cggtcgttcg gctgcggcga gcggtatcag ctcactcaaa ggcggtaata cggttatcca 6180
cagaatcagg ggataacgca ggaaagaaca tgtgagcaaa aggccagcaa aaggccagga 6240
accgtaaaaa ggccgcgttg ctggcgtttt tccataggct ccgcccccct gacgagcatc 6300
acaaaaatcg acgctcaagt cagaggtggc gaaacccgac aggactataa agataccagg 6360
cgtttccccc tggaagctcc ctcgtgcgct ctcctgttcc gaccctgccg cttaccggat 6420
acctgtccgc ctttctccct tcgggaagcg tggcgctttc tcatagctca cgctgtaggt 6480
atctcagttc ggtgtaggtc gttcgctcca agctgggctg tgtgcacgaa ccccccgttc 6540
agcccgaccg ctgcgcctta tccggtaact atcgtcttga gtccaacccg gtaagacacg 6600
acttatcgcc actggcagca gccactggta acaggattag cagagcgagg tatgtaggcg 6660
gtgctacaga gttcttgaag tggtggccta actacggcta cactagaagg acagtatttg 6720
gtatctgcgc tctgctgaag ccagttacct tcggaaaaag agttggtagc tcttgatccg 6780
gcaaacaaac caccgctggt agcggtggtt tttttgtttg caagcagcag attacgcgca 6840
gaaaaaaagg atctcaagaa gatcctttga tcttttctac tgcagaagct tgttagacac 6900
cctgtcatgt attttatatt atttatttca ccatacggat taagtgaaac ctaatgaaaa 6960
tagtactttc ggagctttaa ctttaatgaa ggtatgtttt tttatagaca tcgatgtctg 7020
gtttaacaat aggaaaaagt agctaaaact cccatgaatt aaagaaataa caaggtgtct 7080
aacaacctgt tattaagaat gttagaaaag acttaacatt tgtgttgagt ttttatagac 7140
attggtgtct agacatacgg tagataaggt ttgctcaaaa ataaaataaa aaaagattgg 7200
actaaaaaac atttaattta gtacaattta attagttatt ttttcgtctc aaattttgct 7260
ttgttgagca gaaatttaga taaaaaaatc cccgtgatca gattacaatg tcgttcattg 7320
tacgatgtgt cgaaaaatct ttacgacact ctaaactgac cacacggggg aaaaagaaaa 7380
ctgaactaat aacatcatga tactcggaaa acctagcaat tctcaacccc taaacaaaag 7440
aaacttccaa aaccctgacc atataaagga gtggcaacaa tcagcaatca gtcaagattt 7500
gatagcagaa aatcttgtat cggttgctaa tggttttgat gtactattta tcggcaataa 7560
ataccgaact aacacgggtg ttctgtcacg gcacatatta aactcctatt ctcatttaga 7620
agatggtggt tcgtatggta gaacatttga cccatttacc aataaagaaa tgcagtgggt 7680
tcaatttaaa ccgaatagac caagaaaagg ttctactggt aaggtaatca aatatgaatc 7740
gccaaaaggt gaacctacaa gagttctaat gccgtttgtg cctatgaaaa tatggcaacg 7800
gattagcgat aagttcggag taccgattaa tccgaaaaaa gatactcact tttgggaatg 7860
ggtaaagaat aatccatcga taccgattgc cattacagaa ggaaataaaa aagctaattg 7920
cctattatcc tatggctatc ctgctattgc ctttgtaggc atttggaacg gattagagaa 7980
aataaatgat ttctcgaagg aaaagcagtt aaaagaggat ttgaaatggt tgttatccaa 8040
cggcaaccga aatattaata tcatctttga ccaagaccag aaacaaaaaa ctgtaattaa 8100
tgtaaacaaa gctattttcg ctttatcttc tctaataagt agaaatggtc ataaagttaa 8160
tattgtgcaa tggttgccgt caaaaggtaa aggaatagat gattatttgg tagctttacc 8220
ttttgagaaa agagaaaatc atttagacaa cttaattaaa attgcaccat catttaattt 8280
ttggtcaact aaatacttat tcaagtgtcg taaaccagat ttaaccgtaa attgccgtta 8340
tttgagcgat gcagtaaaag aattacctca agaggatata gcattaatag cacctcacgg 8400
cacgggtaaa acttcattag tagctactca cgttaagaat cggagttatc acggaaggaa 8460
aactatttca ttggtgcatc ttgaaagttt agccaaagct aatggcaacg cacttggatt 8520
atattaccga accgaaaata atattgaaaa gcaatatctt ggatttagct tatgtgtaga 8580
tagttgccgt gataagatta acggcattac aactgatatt atttcaggtc aagattattg 8640
ccttttcatt gatgaaattg accaagtaat tccacacatc cttaacagtg aaactgaagt 8700
aagtaagtat agatgcacca tcattgacac tttttctgaa ctggtgagaa atgctgaaca 8760
ggtcattatt gctgatgctg atttatccga tgtgacgatt gacctaatag aaaacatcag 8820
aggtaaaaaa ctatatgtaa tcaagaatga atatcagtat cagggaatga cttttaacgc 8880
cgttggttca ccattagaaa tgatggcaat gatgggaaaa tcggtgtcag aaggcaagaa 8940
attatttatt aacaccacat cccaaaaggc aaaaagtaag tacggcacaa tcgctcttga 9000
gtcttatatt tttggtctaa ataaagaagc aaagatatta agaatagact ctgaaaccac 9060
taaaaaccct gaacatccag cctataaaat cattgaccaa gacttaaata atatcctcaa 9120
```

FIG. 35 (continued)

```
agattatgat tatgtcattg cctcaccttg ccttcaaaca ggtgtcagta ttaccttaaa 9180
agggcatttt gaccagcaat ttaactttc cagtggaaac attacacctc attgcttttt 9240
acagcaaatg tggcggttga gggatgcaga aattgaaaga ttctattatg tgccgaactc 9300
atctaacctc aatctcattg ggaataagtc aagttcacca tcagaccttc taaagagcaa 9360
taacaagatg gcaacggcaa cggttaacct tttgggtaga atcgactccg aatattccct 9420
agagtatgaa tcgcacggca tttggcttga gacgtgggca aaattatcag cacggcataa 9480
cagttcaatg cgttgttact ctgaaattct tacctatcta attacgtctc aagggcataa 9540
attaaatatc aacattccct cacctcttgc agatattaag aagctaaatg atgaggtaag 9600
tagtaacagg gaaaaggtaa aaaatgagag atactctcag aggttaaact caccagatat 9660
taacgatgca gaagctacca tactcgaatc taaagagcaa aaaatcggat tgactctcaa 9720
tgagagatgc accctagaaa agcataaagt taagaagcgg tatgggaatg taaagatgga 9780
tattctcacc tttgatgatg atggactata ccccaaactc agactatttt attacctcac 9840
catcggtaaa cctcatctca aggctaatga cagaaaagct attgccaaaa tgggcaatga 9900
caataaaggc aagattctat caaaagactt agttaataaa acttactccg ctcgtgtgaa 9960
ggtcttagag attcttaaac taactgactt tatcgacaat cttagagatg aactcttaat 10020
aactcccaat aatccagcta tcaccgattt taataatctt ctgctaagag ctaagaagga 10080
tttaagagta ttaggagtca acatcggaaa atatccaatg gccaacatta atgccgtact 10140
tactctcatt ggtcacaaac tttctgtaat gagagatgag ttcggaaaag agaaaaggat 10200
aaaagtagat ggtaaatcat accgatgtta tcaacttgaa acattaccag attttaccaa 10260
tgatactctt gactactggt tagaaaatga tagccaaaaa gaagtaacag caacagaaaa 10320
ttactccgaa aattttaacc cttcaaatag ctacaatcca gacagtaaga cactttcaga 10380
gggtgcaaat ttcctatata taaataaaga agaattgcat ccaaataaat tgcacctaga 10440
aataaaagaa ggtgctgaac ttttttttatt cggggtaaag gtgattgtga aaggaatctt 10500
ggacggggca gtaactatat tctctatggg tcaagaatac gatttatccc tcaatgaact 10560
agaggggatg ttaacatcat gaactttaca agaatctttt taaagggcga tcgcaccatg 10620
ttaaatgatg gtacatttgt tcagatattt gatatttacc atgaccacgc attgggagtg 10680
acccttgacc ttaagacaga aaaaattatt tccgatgatg ttagggtaat tactgtcaaa 10740
gacttattgt tcgatggcac ttataaaggg gtaaaatctt ttatgcccga taatgcccga 10800
taatgcccga ttgatgctac aaaatcccat aatcataagc gataatcccc taatagcttg 10860
taattcttga accgtagcga ttttagagta ttccaaaaag aagaaataaa caccgcaaaa 10920
tgtcgtattt cacatatata aaccaaggtt ttttgcccta aaatctttat gtttgtagtg 10980
tgatgttggg tcaaaatggt cagaaaagtt gcaaggtttt tatggatgct tacgcgcgcg 11040
aggggtaagc atccccaaat agttacttta tcctagtcca tgcccattta ttgccgtccc 11100
gttcggcttt aaaaaagtgc caaaactcac aaggtgcaat aaaaagttct gtacctttcg 11160
caaccctaga taatctttca acagttactt tttttcctat tatctcggta caaagtttgg 11220
ctagtttctc ttttccctct ttttcaatca agccttcttg tatgcccaac tcattgatta 11280
atctctctat ttttaccatt atttcccgtt caggtagttt atcccctaaa tcttcatcgg 11340
ggggcaatgt agggcattct gaaggggctt tttcttctgt ctggacatta tctaatattg 11400
aagtaaccaa actatcttca gtttttttcta ttcctattaa ttcatattcg gttactgtat 11460
ccgtatcaat atccgaataa ctatctttat ccgtattagc tattcggtta agtttatccg 11520
ttaactcaga aacaagacta tatagcggtt ttagcttttc ttctatcctg ttatctaata 11580
cggataagtt tatacggtta tcattatccg tattagtatc attgggcttt tttggtagtt 11640
ctaccccctc ataaaccgct tttattccca attccaacag actgataaca gtatccttta 11700
taatgggttt tttgctgata tggtgaactt ttgccccttc catcattgcg atactttcta 11760
tctcactcat caacttatcg cttaagtgaa tctcgtatct gtttaatccc ttactggttt 11820
tattcatatc cgtttacttt attcggttaa caattctatt tttatacgaat aaaatattat 11880
acggttaact ttatacgttt aactatttta tctatacgga taacagtaat aagttattcg 11940
tattagttat acgtttactt ttatccaaat aaaattagtg catttaaact aaaagaatga 12000
ttttatcgga gttgatagca ttggattaac ctaaagatgt ttataagcta tatctgataa 12060
gtatttaagg ttattttgtt attctgttta ttgacattat cagaataaaa gaatagaata 12120
taattgttga gagataagag gtttaagtga ttatggttaa gaagttagtt ggttatgtca 12180
gggtcagtag tgaatcgcaa gaggataaca ctagcttaca gaatcagata gagagaattg 12240
aagcatattg tatggctttt ggttatgagt tggtaaaaat attcaaagag gttgccactg 12300
gtacaaaagc agatattgaa acccgtccta tttttaatga agctatagaa tacttgaaac 12360
aggataatgc taatggaatt attgccttga agctagaccg aatcgcacgg aatgctttag 12420
atgtattgcg tttggttcgt gaaaccttag aaccacaaaa taaaatgtta gtgttactag 12480
atattcaggt agatacttcg acaccttcag gaaaaatgat tttaactgta atgagtgccg 12540
ttgctgaact cgaaagagac atgatctatg atcgcactca ggggggtaga aagactaaag 12600
```

FIG. 35 (continued)

```
cccaaaaggg cgggtatgcc tacgggaaac ctaaatttgg ctataagact gaagaaaagg      12660
aactaaaaga agattcagca caacaggaaa ctattaaact aattaagaga caccgtaggt      12720
cagggaaaag ctaccagaaa atagctgatt atctcaatgc ccaaagtatt cccactaaac      12780
aaggtaagaa atggagttct agcgtcgtct atcgaatctg tcaggaaaaa gctggttaag      12840
tctgtttata gatatttaga atttattgaa taaaaatagt atgaacaata aatatttatg      12900
gactaaccac gctcggaaac gtttaactga acgatgggaa ataaaagaat catgggttat      12960
tgataccatc gaaaatcctg aacgttcaga atttattgtt gatgagtcag gggaaaaata      13020
tcattactat aaaagaatag ctaagtttaa gaatagagtg ttagaagtga taacttctgc      13080
caactcaaca cccacaagaa taataacctt ttactttaac cgtaacatga ggaaaaattt      13140
atgattgtta cttacgataa tgaagttgac gcaatttatt ttaagttaac ggaaaataaa      13200
attgatagca ccgaacctca aacagacagg attatcattg attacgatga aagtaataat      13260
attgttggca ttgaggtatt agattttaat tatcttgtca agaaaggttt aaccgttgct      13320
gatttacctt tttctgaaga tgaaagatta acagcttctc aatattttaa ttttcctgtt      13380
gctatctaat ccagaagggg caataatccc cttctttcat cgagttagac ttaatatcac      13440
aaaagtcatt ttcattttac cgtttctttt ccacagcgtc cgtacgcccc tcgttaaatc      13500
tcaaaaccga caatttatga tgtttataaa aagttactca ctttaataag tatttatact      13560
cattaaaggg ttattctttt tttgtagcct gataggttgg gaaggaatat ttcagattat      13620
cagatttgtt gaatattttt cgtcagatac gcaaacctta caaacataat taacaactga      13680
aactattgat atgtctaggt tttagctcta tcacaggttg gatctg                     13726
```

FIG. 35 (continued)

```
ID   #1632\\pABICyanol::corR-PcorT*3-zmPDCABICyanol(opt1)_dsrA-Prbc*(optRBS)-
synADH(opt1)_ter standard; circular DNA;    ; 13726 BP.
CC   This file is created by Vector NTI
CC   http://www.invitrogen.com/
CC   VNTDATE|645696278|
CC   VNTDBDATE|645696292|
CC   LSOWNER|
CC   VNTAUTHORNAME|Ulf Duehring|
FH   Key             Location/Qualifiers
FH
FT   insertion_seq   2981..3026
FT                   /vntifkey="14"
FT                   /label=dsrA
FT                   /note="dsrA terminator from E.coli"
FT   gene            3096..4106
FT                   /vntifkey="60"
FT                   /note="ADH"
FT   CDS             3096..4103
FT                   /vntifkey="4"
FT                   /label=synADH(opt1)
FT   terminator      4107..4262
FT                   /vntifkey="43"
FT                   /label=TrbcSABICyanol
FT   promoter        4299..4762
FT                   /vntifkey="30"
FT                   /label=PrbcABICyanol
FT   CDS             4764..5579
FT                   /vntifkey="4"
FT                   /label=Km**
FT                   /note="Km**"
FT   CDS             13141..13389
FT                   /vntifkey="4"
FT                   /label=ORF\6
FT                   /note="orf6"
FT   CDS             12881..13144
FT                   /vntifkey="4"
FT                   /label=ORF\5
FT                   /note="orf5"
FT   CDS             12153..12839
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(11063..11827)
FT                   /vntifkey="4"
FT                   /label=ORF\3
FT                   /note="orf3"
FT   CDS             10618..10803
FT                   /vntifkey="4"
FT                   /label=ORF\2
FT                   /note="orf2"
FT   rep_origin      complement(9918..9935)
FT                   /vntifkey="33"
FT                   /label=Rep_Origin_1
FT                   /note="potential rep origin; match pNostoc (Acc# M81381) nick
site (358-375); on reserse strand"
FT   misc_feature    10178..10211
FT                   /vntifkey="21"
FT                   /label=Rep\motif
FT                   /note="Rep protein active site motig EXXKYXVKXXD"
FT   CDS             7397..10582
```

FIG. 37

```
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   primer_bind     complement(6185..6216)
FT                   /vntifkey="28"
FT                   /label=Bom-F
FT   primer_bind     5867..5898
FT                   /vntifkey="28"
FT                   /label=Bom-R
FT   rep_origin      complement(5822..6880)
FT                   /vntifkey="33"
FT                   /label=OriVT
FT   promoter        3027..3095
FT                   /vntifkey="30"
FT                   /label=Prbc*(optRBS)
FT                   /note="improved version of rbcL promoter from PCC6803"
FT   promoter        1169..1247
FT                   /vntifkey="30"
FT                   /label=PcorT*3
FT                   /note="improved version of corT promoter from PCC6803"
FT   CDS             complement(54..1166)
FT                   /vntifkey="4"
FT                   /label=corR
FT   CDS             1248..2954
FT                   /vntifkey="4"
FT                   /label=zmPDC(opt1)
SQ   Sequence 13726 BP; 4162 A; 2503 C; 2755 G; 4306 t;
     tcgaccatgc gtccaaaact ttcaccatcc tttccctatc aacctttact gcactaaaga        60
     caagtgagat agcagtggca atctggcttt gcaatcaatg tttccactaa agcgtttagc       120
     gttactgcgg ctagaagtcc tccaccgagg ctcccctgaa tggtgatatg gggaatggga       180
     ctggtcatca gtcgtcgttt tgcccccgga gcatgactaa aaccgatcgg cattccgatc       240
     acaagagccg gctgaatatg ttgttgctct atcagcttac aggcagtgag taaaacagaa       300
     ggggcatagc cgatcgccag cacacatcct tggggaatct gttgtaaccg ctgttgccaa       360
     tggtcatggt gccaaaaagc ttgctcggct tccctaagcc ctgtgatgtg agggtcgtca       420
     atcagcgttt taaccgtaca tcctaaatga gctaaccgag tttgatcaag agccgcagcc       480
     acaaccggaa catcggtgac gactggacac cctgctttca gtgcatctcg tgccgaggcg       540
     atcgctccct gactcaatcg aacggcgttt accaagctaa catcaccaca ggccagcact       600
     aattgatgta gtaagtgaat ggtaatttca gagtaagccg ataaatccgg tagcaggtgt       660
     ttgagggatt cctgaaaggc ttctggatga gttgttgtct ccgcatctag gttcgtccac       720
     aactgatcga gttttcctaa cccctcctgg acatccacat caagctgttt cagttgggcc       780
     agagcttccg cttgggtaat ctggcaactc tggtcgcgtc ccagtaatcc ttctaaagca       840
     gatgcggttt ggcggagtcg agtaatctgc tgaatcacag cctgatattg ctgttgcaac       900
     tgcaccatta gggtgggatc aaggctctct tcagaatggc tatccagcag ttgccgaata       960
     tgagacaact gaaagccctg ctgtttgagg gcaatgactc gttggagccg ttgtacgtcc      1020
     tgctgagtat aaaggcggta gttgccctct gagcgttgaa cggggggaag caatcccagg      1080
     gtgtggtaat ggcgcaccat gcgaggcgta acgccacctc ccactgcatc tgtgagttct      1140
     ttaatcgtta agtgattagt cttcatgact ttagtttact caaaaccttg acattgacac      1200
     taatgttaag gtttagaatg agaaggtaaa aatcgaggat aaaaagcatg aattcttata      1260
     ccgtgggtac ttatttagcc gaacgcttag tgcaaattgg tttaaaacat cattttgccg      1320
     tggctgggga ctataattta gtgttattgg ataacttatt attaaataaa aacatggaac      1380
     aagtgtattg ttgtaatgaa ttaaattgtg gtttttctgc tgaaggttat gctagagcta      1440
     aaggtgcagc tgctgctgtt gttacttatt ctgtgggtgc tttatctgct tttgatgcta      1500
     ttggtggtgc ttatgccgaa aatttacccg tgattttaat ttctggtgcc cctaataata      1560
     atgatcatgc cgctggacat gttttacatc atgccttagg taaaaccgat tatcattatc      1620
     aattagaaat ggccaaaaat attactgctg ctgccgaagc tatttatact cctgaagaag      1680
     cccctgccaa aattgatcat gtgattaaaa ccgccttacg cgaaaaaaaa cccgtgtatt      1740
     tagaaattgc ctgtaatatt gcttctatgc cttgtgctgc tcctgggcct gcttctgctt      1800
     tatttaatga tgaagcctct gatgaagcta gtttaaatgc tgccgtggaa gaaaccttaa      1860
```

```
aatttattgc caatcgcgat aaagttgccg tgttagttgg ttctaaatta agagctgctg     1920
gtgctgaaga agctgctgtt aaatttgctg atgctttagg tggtgcagtt gctactatgg     1980
ctgctgccaa atcttttttt cccgaagaaa atccccatta tattggaact agttggggag     2040
aagtttctta tcctggtgtg gaaaaaacta tgaaagaagc cgacgctgtt attgctttag     2100
cccctgtgtt taatgattat tctaccactg gttggactga tattcccgat cccaaaaaat     2160
tagttttagc cgaacctcgt tctgttgttg ttaatggtgt tcgctttccc tctgtgcatt     2220
taaaagatta tttaacccgc ttagcccaaa aagtttctaa aaaaactggt gccttagatt     2280
tttttaaatc tttaaatgcg ggtgaattaa aaaaagctgc tcctgctgat ccttctgctc     2340
ctttagttaa tgctgaaatt gcccgtcaag ttgaagcctt attaacccct aatactaccg     2400
ttattgccga aactggtgat tcttggttta atgcccaacg catgaaatta cctaatggtg     2460
cccgtgttga atatgaaatg caatggggtc atattggttg gtctgtacct gctgcttttg     2520
gttatgctgt tggtgctcct gaacgtcgta atattttaat ggtgggtgat ggttcttttc     2580
aattaactgc ccaagaagtt gcccaaatgg ttcgcttaaa attacccgtt attatttttt     2640
taataaataa ttatggttat accattgaag tgatgattca tgatgggcca tataataata     2700
ttaaaaattg ggattatgcg ggtttaatgg aagtgtttaa tggtaatggt ggttatgatt     2760
ctggtgctgg taaaggttta aaagccaaaa ctggtggtga attagctgaa gctattaaag     2820
ttgccttagc caatactgat gggccaacct taattgaatg ttttattggt cgcgaagatt     2880
gtaccgaaga attagttaaa tggggtaaac gtgttgctgc tgctaattct cgcaaacccg     2940
tgaataaatt attgtaattt ttggggatca attcgagctc agcaagtttc atcccgaccc     3000
cctcagggtc gggatttttt tattgtacta gttgacataa gtaaaggcat cccctgcgtg     3060
atataattac cttcagttta aggaggtata cacatatgat taaagcctat gctgccttag     3120
aagccaatgg taaattacaa ccctttgaat atgatcctgg tgctttaggt gccaatgaag     3180
tggaaattga agtgcaatat tgtggtgtgt gtcattctga tttatctatg attaataatg     3240
aatggggtat ttctaattat cccttagttc ctggtcatga agttgttggt actgttgctg     3300
ctatgggtga aggtgttaat catgtggaag tgggtgattt agttggttta ggttggcatt     3360
ctggttattg tatgacctgt cattcttgtt tatctggtta tcataattta tgtgccactg     3420
ccgaatctac tattgtgggt cattatggtg gttttggtga tagagttcgt gctaaaggtg     3480
tttctgtggt gaaattaccc aaaggtattg atttagcctc tgctgggcct ttattttgtg     3540
gtggtattac cgtttttttct cccatggtgg aattatcttt aaaacctacc gccaaagttg     3600
ctgttattgg tattggtggt ttaggtcatt tagccgttca atttttaaga gcctggggtt     3660
gtgaagttac tgcttttacc tcttctgccc gtaaacaaac cgaagtttta gaattaggtg     3720
cccatcatat tttagattct accaatcctg aagctattgc ttctgccgaa ggtaaatttg     3780
attatattat ttctaccgtg aatttaaaat tagattggaa tttatatatc agtaccttag     3840
cccctcaagg tcattttcat tttgttggtg tggtgttaga acccttggac ttaaacttat     3900
ttcccttatt aatgggacaa cgttctgttt ctgcttctcc tgttggttct cctgctacta     3960
ttgccactat gttagatttt gccgtgcgtc atgatattaa acccgtggtg gaacaatttt     4020
cttttgatca aattaatgaa gccattgccc atttagaatc tggtaaagcc cattatcgcg     4080
tggtgttatc tcattctaaa aattaataag attaacttct aaactgaaac aaatttgagg     4140
gtaggcttca ttgtctgccc ttattttttt atttaggaaa agtgaacaga ctaaagagtg     4200
ttggctctat tgctttgagt atgtaaatta ggcgttgctg aattaaggta tgatttttga     4260
ccccttctct cttctgcagg atcatcttgc tgaaaaactc gagcgctcgt tccgcaaagc     4320
ggtacggagt tagttagggg ctaatgggca ttctccccgta caggaaagag ttagaagtta     4380
ttaattatca acaattctcc tttgcctagt gcatcgttac ctttttaatt aaaacataag     4440
gaaaactaat aatcgtaata atttaacctc aaagtgtaaa gaaatgtgaa attctgactt     4500
ttataacgtt aaagagggaa aaattagcag tttaaaatac ctagagaata gtctggggta     4560
agcatagaga attagattag ttaagttaat caaattcaga aaaaataata atcgtaaata     4620
gttaatctgg gtgtatagaa aatgatcccc ttcatgataa gatttaaact cgaaaagcaa     4680
aagccaaaaa actaacttcc attaaaagaa gttgttacat ataacgctat aaagaaaatt     4740
tatatatttg gaggatacca accatgtctc atattcaacg tgaaactagt tgttctcgcc     4800
ctcgtttaaa ttctaatatg gatgccgatt tatatggtta taaatgggct cgtgataatg     4860
ttggtcaatc tggtgctact atttatcgtt tatatggtaa acctgatgct cctgaattat     4920
tcttgaaaca tggtaaaggt tctgttgcta atgatgttac tgatgaaatg gttcgtttaa     4980
actggttgac tgaatttatg cctttaccta ctattaaaca ttttattcgt actcccgatg     5040
atgcttggtt attaactact gctattcctg gtaaaactgc ttttcaagtt ttagaagaat     5100
atcctgattc tggtgaaaat attgttgatg ctttagctgt ttttttacgt cgtttacatt     5160
ctattcccgt ttgtaattgt ccttttaatt ctgatcgtgt ttttcgttta gctcaagctc     5220
aatctcgtat gaataatggt ttagttgatg cttctgattt tgatgatgaa cgtaatggtt     5280
ggcctgttga acaagtttgg aaagaaatgc acaaattgtt accttttttct cctgattctg     5340
ttgttactca tggtgatttt tctttagata atttgatctt tgatgaaggt aaattgattg     5400
gttgtattga tgttggtcgt gttggtattg ctgatcgtta tcaagattta gctattttat     5460
ggaattgttt aggtgaattt tctccttctt tacagaaacg tttatttcag aaatatggta     5520
```

FIG. 37 (continued)

```
ttgataatcc tgatatgaac aagttacaat ttcatttaat gttggacgag ttcttttaag 5580
aattaattca tgaccaaaat cccttaacgt gagttttcgt tccactgagc gtcagacccc 5640
gtagaaaaga tcaaaggatc ttcttgagat cctttttttc tgcgcgtaat ctgctgctat 5700
ttaaattacg tacacgtgtt attactttgt taacgacaat tgtcttaatt aactgggcct 5760
catgggcctt ccgctcactg cccgctttcc agtcgggaaa cctgtcgtgc cagctctgca 5820
gatgacggtg aaaacctctg acacatgcag ctcccggaga cggtcacagc ttgtctgtaa 5880
gcggatgccg ggagcagaca agcccgtcag ggcgcgtcag cgggtgttgg cgggtgtcgg 5940
ggcgcagcca tgacccagtc acgtagcgat agcggagtgt atactggctt aactatgcgg 6000
catcagagca gattgtactg agagtgcacc atatgcggtg tgaaataccg cacagatgcg 6060
taaggagaaa ataccgcatc aggcgctctt ccgcttcctc gctcactgac tcgctgcgct 6120
cggtcgttcg gctgcggcga gcggtatcag ctcactcaaa ggcggtaata cggttatcca 6180
cagaatcagg ggataacgca ggaaagaaca tgtgagcaaa aggccagcaa aaggccagga 6240
accgtaaaaa ggccgcgttg ctggcgtttt tccataggct ccgcccccct gacgagcatc 6300
acaaaaatcg acgctcaagt cagaggtggc gaaacccgac aggactataa agataccagg 6360
cgtttccccc tggaagctcc ctcgtgcgct ctcctgttcc gaccctgccg cttaccggat 6420
acctgtccgc ctttctccct tcgggaagcg tggcgctttc tcatagctca cgctgtaggt 6480
atctcagttc ggtgtaggtc gttcgctcca agctgggctg tgtgcacgaa ccccccgttc 6540
agcccgaccg ctgcgcctta tccggtaact atcgtcttga gtccaacccg gtaagacacg 6600
acttatcgcc actggcagca gccactggta acaggattag cagagcgagg tatgtaggcg 6660
gtgctacaga gttcttgaag tggtggccta actacggcta cactagaagg acagtatttg 6720
gtatctgcgc tctgctgaag ccagttacct tcggaaaaag agttggtagc tcttgatccg 6780
gcaaacaaac caccgctggt agcggtggtt tttttgtttg caagcagcag attacgcgca 6840
gaaaaaaagg atctcaagaa gatcctttga tcttttctac tgcagaagct tgttagacac 6900
cctgtcatgt attttatatt atttatttca ccatacggat taagtgaaac ctaatgaaaa 6960
tagtactttc ggagctttaa ctttaatgaa ggtatgtttt tttatagaca tcgatgtctg 7020
gtttaacaat aggaaaaagt agctaaaact cccatgaatt aaagaaataa caaggtgtct 7080
aacaacctgt tattaagaat gttagaaaag acttaacatt tgtgttgagt ttttatagac 7140
attggtgtct agacatacgg tagataaggt ttgctcaaaa ataaaataaa aaaagattgg 7200
actaaaaaac atttaattta gtacaattta attagttatt ttttcgtctc aaattttgct 7260
ttgttgagca gaaatttaga taaaaaaatc cccgtgatca gattacaatg tcgttcattg 7320
tacgatgtgt cgaaaaatct ttacgacact ctaaactgac cacacggggg aaaaagaaaa 7380
ctgaactaat aacatcatga tactcggaaa acctagcaat tctcaacccc taaacaaaag 7440
aaacttccaa aaccctgacc atataaagga gtggcaacaa tcagcaatca gtcaagattt 7500
gatagcagaa aatcttgtat cggttgctaa tggttttgat gtactattta tcggcaataa 7560
ataccgaact aacacgggtg ttctgtcacg gcacatatta aactcctatt ctcatttaga 7620
agatggtggt tcgtatggta gaacatttga cccatttacc aataaagaaa tgcagtgggt 7680
tcaatttaaa ccgaatagac caagaaaagg ttctactggt aaggtaatca aatatgaatc 7740
gccaaaaggt gaacctacaa gagttctaat gccgtttgtg cctatgaaaa tatggcaacg 7800
gattagcgat aagttcggag taccgattaa tccgaaaaaa gatactcact tttgggaatg 7860
ggtaaagaat aatccatcga taccgattgc cattacagaa ggaaataaaa aagctaattg 7920
cctattatcc tatggctatc ctgctattgc ctttgtaggc atttggaacg gattagagaa 7980
aataaatgat ttctcgaagg aaaagcagtt aaaagaggat ttgaaatggt tgttatccaa 8040
cggcaaccga aatattaata tcatctttga ccaagaccag aaacaaaaaa ctgtaattaa 8100
tgtaaacaaa gctattttcg ctttatcttc tctaataagt agaaatggtc ataaagttaa 8160
tattgtgcaa tggttgccgt caaaaggtaa aggaatagat gattatttgg tagctttacc 8220
ttttgagaaa agagaaaatc atttagacaa cttaattaaa attgcaccat catttaattt 8280
ttggtcaact aaatacttat tcaagtgtcg taaaccagat ttaaccgtaa attgccgtta 8340
tttgagcgat gcagtaaaag aattacctca agaggatata gcattaatag cacctcacgg 8400
cacgggtaaa acttcattag tagctactca cgttaagaat cggagttatc acggaaggaa 8460
aactatttca ttggtgcatc ttgaaagttt agccaaagct aatggcaacg cacttggatt 8520
atattaccga accgaaaata atattgaaaa gcaatatctt ggatttagct tatgtgtaga 8580
tagttgccgt gataagatta acggcattac aactgatatt atttcaggtc aagattattg 8640
ccttttcatt gatgaaattg accaagtaat tccacacatc cttaacagtg aaactgaagt 8700
aagtaagtat agatgcacca tcattgacac tttttctgaa ctggtgagaa atgctgaaca 8760
ggtcattatt gctgatgctg atttatccga tgtgacgatt gacctaatag aaaacatcag 8820
aggtaaaaaa ctatatgtaa tcaagaatga atatcagtat cagggaatga cttttaacgc 8880
cgttggttca ccattagaaa tgatggcaat gatgggaaaa tcggtgtcag aaggcaagaa 8940
attatttatt aacaccacat cccaaaaggc aaaaagtaag tacggcacaa tcgctcttga 9000
gtcttatatt tttggtctaa ataaagaagc aaagatatta agaatagact ctgaaaccac 9060
```

FIG. 37 (continued)

```
taaaaaccct gaacatccag cctataaaat cattgaccaa gacttaaata atatcctcaa     9120
agattatgat tatgtcattg cctcaccttg ccttcaaaca ggtgtcagta ttaccttaaa     9180
agggcatttt gaccagcaat ttaacttttc cagtggaaac attacacctc attgcttttt     9240
acagcaaatg tggcggttga gggatgcaga aattgaaaga ttctattatg tgccgaactc     9300
atctaacctc aatctcattg ggaataagtc aagttcacca tcagaccttc taaagagcaa     9360
taacaagatg gcaacggcaa cggttaacct tttgggtaga atcgactccg aatattccct     9420
agagtatgaa tcgcacggca tttggcttga gacgtgggca aaattatcag cacggcataa     9480
cagttcaatg cgttgttact ctgaaattct tacctatcta attacgtctc aagggcataa     9540
attaaatatc aacattccct cacctcttgc agatattaag aagctaaatg atgaggtaag     9600
tagtaacagg gaaaaggtaa aaaatgagag atactctcag aggttaaact caccagatat     9660
taacgatgca gaagctacca tactcgaatc taaagagcaa aaaatcggat tgactctcaa     9720
tgagagatgc accctagaaa agcataaagt taagaagcgg tatgggaatg taaagatgga     9780
tattctcacc tttgatgatg atggactata ccccaaactc agactatttt attacctcac     9840
catcggtaaa cctcatctca aggctaatga cagaaaagct attgccaaaa tgggcaatga     9900
caataaaggc aagattctat caaaagactt agttaataaa acttactccg ctcgtgtgaa     9960
ggtcttagag attcttaaac taactgactt tatcgacaat cttagagatg aactcttaat    10020
aactcccaat aatccagcta tcaccgattt taataatctt ctgctaagag ctaagaagga    10080
tttaagagta ttaggagtca acatcggaaa atatccaatg gccaacatta atgccgtact    10140
tactctcatt ggtcacaaac tttctgtaat gagagatgag ttcggaaaag agaaaaggat    10200
aaaagtagat ggtaaatcat accgatgtta tcaacttgaa acattaccag attttaccaa    10260
tgatactctt gactactggt tagaaaatga tagccaaaaa gaagtaacag caacagaaaa    10320
ttactccgaa aattttaacc cttcaaatag ctacaatcca gacagtaaga cactttcaga    10380
gggtgcaaat ttcctatata taaataaaga agaattgcat ccaaataaat tgcacctaga    10440
aataaaagaa ggtgctgaac tttttttatt cggggtaaag gtgattgtga aaggaatctt    10500
ggacggggca gtaactatat tctctatggg tcaagaatac gatttatccc tcaatgaact    10560
agaggggatg ttaacatcat gaactttaca agaatctttt taaagggcga tcgcaccatg    10620
ttaaatgatg gtacatttgt tcagatattt gatatttacc atgaccacgc attgggagtg    10680
acccttgacc ttaagacaga aaaaattatt tccgatgatg ttagggtaat tactgtcaaa    10740
gacttattgt tcgatggcac ttataaaggg gtaaaatctt ttatgcccga taatgcccga    10800
taatgcccga ttgatgctac aaaatcccat aatcataagc gataatcccc taatagcttg    10860
taattcttga accgtagcga ttttagagta ttccaaaaag aagaaataaa caccgcaaaa    10920
tgtcgtattt cacatatata aaccaaggtt ttttgcccta aaatctttat gtttgtagtg    10980
tgatgttggg tcaaaatggt cagaaaagtt gcaaggtttt tatggatgct tacgcgcgcg    11040
aggggtaagc atccccaaat agttacttta tcctagtcca tgcccattta ttgccgtccc    11100
gttcggcttt aaaaaagtgc caaaactcac aaggtgcaat aaaaagttct gtacctttcg    11160
caaccctaga taatctttca acagttactt tttttcctat tatctcggta caaagtttgg    11220
ctagtttctc ttttccctct ttttcaatca agccttcttg tatgcccaac tcattgatta    11280
atctctctat ttttaccatt atttcccgtt caggtagttt atcccctaaa tcttcatcgg    11340
ggggcaatgt agggcattct gaaggggctt tttcttctgt ctggacatta tctaatattg    11400
aagtaaccaa actatcttca gtttttttcta ttcctattaa ttcatattcg gttactgtat    11460
ccgtatcaat atccgaataa ctatctttat ccgtattagc tattcggtta agtttatccg    11520
ttaactcaga aacaagacta tatagcggtt ttagcttttc ttctatcctg ttatctaata    11580
cggataagtt tatacggtta tcattatccg tattagtatc attgggcttt tttggtagtt    11640
ctacccccctc ataaaccgct tttattccca attccaacag actgataaca gtatccttta    11700
taatgggttt tttgctgata tggtgaactt ttgccccttc catcattgcg atactttcta    11760
tctcactcat caacttatcg cttaagtgaa tctcgtatct gtttaatccc ttactggttt    11820
tattcatatc cgtttacttt attcggttaa caattctatt ttatacgaat aaaatattat    11880
acggttaact ttatacgttt aactatttta tctatacgga taacagtaat aagttattcg    11940
tattagttat acgtttactt ttatccaaat aaaattagtg catttaaact aaaagaatga    12000
ttttatcgga gttgatagca ttggattaac ctaaagatgt ttataagcta tatctgataa    12060
gtatttaagg ttattttgtt attctgttta ttgacattat cagaataaaa gaatagaata    12120
taattgttga gagataagag gtttaagtga ttatggttaa gaagttagtt ggttatgtca    12180
gggtcagtag tgaatcgcaa gaggataaca ctagcttaca gaatcagata gagagaattg    12240
aagcatattg tatggctttt ggttatgagt tggtaaaaat attcaaagag gttgccactg    12300
gtacaaaagc agatattgaa acccgtccta tttttaatga agctatagaa tacttgaaac    12360
aggataatgc taatggaatt attgccttga agctagaccg aatcgcacgg aatgctttag    12420
atgtattgcg tttggttcgt gaaaccttag aaccacaaaa taaaatgtta gtgttactag    12480
atattcaggt agatacttcg acaccttcag gaaaaatgat tttaactgta atgagtgccg    12540
ttgctgaact cgaaagagac atgatctatg atcgcactca ggggggtaga aagactaaag    12600
cccaaaaggg cgggtatgcc tacgggaaac ctaaatttgg ctataagact gaagaaaagg    12660
aactaaaaga agattcagca caacaggaaa ctattaaact aattaagaga caccgtaggt    12720
```

FIG. 37 (continued)

```
cagggaaaag ctaccagaaa atagctgatt atctcaatgc ccaaagtatt cccactaaac     12780
aaggtaagaa atggagttct agcgtcgtct atcgaatctg tcaggaaaaa gctggttaag     12840
tctgtttata gatatttaga atttattgaa taaaaatagt atgaacaata aatatttatg     12900
gactaaccac gctcggaaac gtttaactga acgatgggaa ataaaagaat catgggttat     12960
tgataccatc gaaaatcctg aacgttcaga atttattgtt gatgagtcag gggaaaaata     13020
tcattactat aaaagaatag ctaagtttaa gaatagagtg ttagaagtga taacttctgc     13080
caactcaaca cccacaagaa taataacctt ttactttaac cgtaacatga ggaaaaattt     13140
atgattgtta cttacgataa tgaagttgac gcaatttatt ttaagttaac ggaaaataaa     13200
attgatagca ccgaacctca aacagacagg attatcattg attacgatga aagtaataat     13260
attgttggca ttgaggtatt agattttaat tatcttgtca agaaaggttt aaccgttgct     13320
gatttacctt tttctgaaga tgaaagatta acagcttctc aatattttaa ttttcctgtt     13380
gctatctaat ccagaagggg caataatccc cttctttcat cgagttagac ttaatatcac     13440
aaaagtcatt ttcattttac cgtttctttt ccacagcgtc cgtacgcccc tcgttaaatc     13500
tcaaaaccga caatttatga tgtttataaa aagttactca ctttaataag tatttatact     13560
cattaaaggg ttattctttt tttgtagcct gataggttgg gaaggaatat ttcagattat     13620
cagatttgtt gaatattttt cgtcagatac gcaaacctta caaacataat taacaactga     13680
aactattgat atgtctaggt tttagctcta tcacaggttg gatctg                    13726
```

FIG. 37 (continued)

```
ID   #1635\pABICyano1::smtB-PsmtA-zmPDC(opt1)_dsrA-Prbc*(optRBS)-synADH(opt1)_ter
standard; circular DNA;    ; 12973 BP.
CC   This file is created by Vector NTI
CC   http://www.invitrogen.com/
CC   VNTDATE|645699239|
CC   VNTDBDATE|645699239|
CC   LSOWNER|
CC   VNTAUTHORNAME|Ulf Duehring|
FH   Key             Location/Qualifiers
FH
FT   CDS             582..2288
FT                   /vntifkey="4"
FT                   /label=zmPDC(opt1)
FT   CDS             complement(153..479)
FT                   /vntifkey="4"
FT                   /label=smtB
FT                   /note="smtB gene from Synechococcus PCC7002"
FT   promoter        480..581
FT                   /vntifkey="30"
FT                   /label=PsmtA
FT                   /note="smtA promoter from Synechococcus PCC7002"
FT   insertion_seq   2315..2360
FT                   /vntifkey="14"
FT                   /label=dsrA
FT                   /note="dsrA terminator from E.coli"
FT   gene            2430..3440
FT                   /vntifkey="60"
FT                   /note="ADH"
FT   CDS             2430..3437
FT                   /vntifkey="4"
FT                   /label=synADH(opt1)
FT   terminator      3441..3596
FT                   /vntifkey="43"
FT                   /label=TrbcSABICyano1
FT   promoter        3633..4096
FT                   /vntifkey="30"
FT                   /label=PrbcABICyano1
FT   CDS             4098..4913
FT                   /vntifkey="4"
FT                   /label=Km**
FT                   /note="Km**"
FT   CDS             12475..12723
FT                   /vntifkey="4"
FT                   /label=ORF\6
FT                   /note="orf6"
FT   CDS             12215..12478
FT                   /vntifkey="4"
FT                   /label=ORF\5
FT                   /note="orf5"
FT   CDS             11487..12173
FT                   /vntifkey="4"
FT                   /label=ORF\4
FT                   /note="orf4 Integrase/Recombinase Similar to Site-specific
FT   recombinase of Bacillus thuringiensis serovar israelensis ATCC 35646"
FT   CDS             complement(10397..11161)
FT                   /vntifkey="4"
FT                   /label=ORF\3
FT                   /note="orf3"
FT   CDS             9952..10137
FT                   /vntifkey="4"
FT                   /label=ORF\2
```

FIG. 39

```
FT                   /note="orf2"
FT   rep_origin      complement(9252..9269)
FT                   /vntifkey="33"
FT                   /label=Rep_Origin_1
FT                   /note="potential rep origin; match pNostoc (Acc# M81381) nick
site (358-375); on reserse strand"
FT   misc_feature    9512..9545
FT                   /vntifkey="21"
FT                   /label=Rep\motif
FT                   /note="Rep protein active site motig EXXKYXVKXXD"
FT   CDS             6731..9916
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   primer_bind     complement(5519..5550)
FT                   /vntifkey="28"
FT                   /label=Bom-F
FT   primer_bind     5201..5232
FT                   /vntifkey="28"
FT                   /label=Bom-R
FT   rep_origin      complement(5156..6214)
FT                   /vntifkey="33"
FT                   /label=OriVT
FT   promoter        2361..2429
FT                   /vntifkey="30"
FT                   /label=Prbc*(optRBS)
FT                   /note="improver version of rbcL promoter from PCC6803"
SQ   Sequence 12973 BP; 3972 A; 2324 C; 2561 G; 4116 t;
     tcgtcagata cgcaaacctt acaaacataa ttaacaactg aaactattga tatgtctagg        60
     ttttagctct atcacaggtt ggatctgtcg acgggcaaac tttatgaagc agatcaagcc       120
     tatatccgcc aagcaaccgg cagccgcgtt gattagtggg tgtgtccatc ctctggttcg       180
     tctaggtgct ccgaagcgtc acgatagaga ttaagaatgt ggtgatcctt gaggcgataa       240
     atcacattcc gcccttcctt gcgatagctc actaaacgtg ctgtgcgcag ggttcttagt       300
     tggtgagaga cagccgattc actcatttca acggcggcgg cgagttcccc caccccgcatc       360
     tctccagtgg ccagggccga aagaatacgc cagcggttgg catcccccaa gacaccaaaa       420
     aattcggcca tccgttgggc cttggcttgg ttcaagattt tgccactgtg gtctgtcatt       480
     gttcgctgat ctaaacaata cctgaataat tgttcatgtg ttaatctaaa aatgtgaaca       540
     atcgttcaac tatttaagac aataccttgg aggtttaaac catgaattct tataccgtgg       600
     gtacttattt agccgaacgc ttagtgcaaa ttggtttaaa acatcatttt gccgtggctg       660
     gggactataa tttagtgtta ttggataact tattattaaa taaaaacatg gaacaagtgt       720
     attgttgtaa tgaattaaat tgtggttttt ctgctgaagg ttatgctaga gctaaaggtg       780
     cagctgctgc tgttgttact tattctgtgg gtgctttatc tgcttttgat gctattggtg       840
     gtgcttatgc cgaaaattta cccgtgattt taatttctgg tgcccctaat aataatgatc       900
     atgccgctgg acatgtttta catcatgcct taggtaaaac cgattatcat tatcaattag       960
     aaatggccaa aaatattact gctgctgccg aagctattta tactcctgaa gaagcccctg      1020
     ccaaaattga tcatgtgatt aaaaccgcct tacgcgaaaa aaaacccgtg tatttagaaa      1080
     ttgcctgtaa tattgcttct atgccttgtg ctgctcctgg gcctgcttct gctttattta      1140
     atgatgaagc ctctgatgaa gctagtttaa atgctgccgt ggaagaaacc ttaaaattta      1200
     ttgccaatcg cgataaagtt gccgtgttag ttggttctaa attaagagct gctggtgctg      1260
     aagaagctgc tgttaaattt gctgatgctt taggtggtgc agttgctact atggctgctg      1320
     ccaaatcttt ttttcccgaa gaaaatcccc attatattgg aactagttgg ggagaagttt      1380
     cttatcctgg tgtggaaaaa actatgaaag aagccgacgc tgttattgct ttagcccctg      1440
     tgtttaatga ttattctacc actggttgga ctgatattcc cgatcccaaa aaattagttt      1500
     tagccgaacc tcgttctgtt gttgttaatg gtgttcgctt tccctctgtg catttaaaag      1560
     attatttaac ccgcttagcc caaaaagttt ctaaaaaaac tggtgcctta gattttttta      1620
     aatctttaaa tgcgggtgaa ttaaaaaaag ctgctcctgc tgatccttct gctcctttag      1680
     ttaatgctga aattgcccgt caagttgaag ccttattaac ccctaatact accgttattg      1740
     ccgaaactgg tgattcttgg tttaatgccc aacgcatgaa attacctaat ggtgcccgtg      1800
     ttgaatatga aatgcaatgg ggtcatattg gttggtctgt acctgctgct tttggttatg      1860
     ctgttggtgc tcctgaacgt cgtaatattt taatggtggg tgatggttct tttcaattaa      1920
```

FIG. 39 (continued)

```
ctgcccaaga agttgcccaa atggttcgct taaaattacc cgttattatt tttttaataa 1980
ataattatgg ttataccatt gaagtgatga ttcatgatgg gccatataat aatattaaaa 2040
attgggatta tgcgggttta atggaagtgt ttaatggtaa tggtggttat gattctggtg 2100
ctggtaaagg tttaaaagcc aaaactggtg gtgaattagc tgaagctatt aaagttgcct 2160
tagccaatac tgatgggcca accttaattg aatgttttat tggtcgcgaa gattgtaccg 2220
aagaattagt taaatggggt aaacgtgttg ctgctgctaa ttctcgcaaa cccgtgaata 2280
aattattgta atttttgggg atcaattcga gctcagcaag tttcatcccg accccctcag 2340
ggtcgggatt tttttattgt actagttgac ataagtaaag gcatcccctg cgtgatataa 2400
ttaccttcag tttaaggagg tatacacata tgattaaagc ctatgctgcc ttagaagcca 2460
atggtaaatt acaacccttt gaatatgatc ctggtgcttt aggtgccaat gaagtggaaa 2520
ttgaagtgca atattgtggt gtgtgtcatt ctgatttatc tatgattaat aatgaatggg 2580
gtatttctaa ttatccctta gttcctggtc atgaagttgt tggtactgtt gctgctatgg 2640
gtgaaggtgt taatcatgtg gaagtgggtg atttagttgg tttaggttgg cattctggtt 2700
attgtatgac ctgtcattct tgtttatctg gttatcataa tttatgtgcc actgccgaat 2760
ctactattgt gggtcattat ggtggttttg gtgatagagt tcgtgctaaa ggtgtttctg 2820
tggtgaaatt acccaaaggt attgatttag cctctgctgg gcctttattt tgtggtggta 2880
ttaccgtttt ttctcccatg gtggaattat ctttaaaacc taccgccaaa gttgctgtta 2940
ttggtattgg tggtttaggt catttagccg ttcaattttt aagagcctgg ggttgtgaag 3000
ttactgcttt tacctcttct gcccgtaaac aaaccgaagt tttagaatta ggtgcccatc 3060
atattttaga ttctaccaat cctgaagcta ttgcttctgc cgaaggtaaa tttgattata 3120
ttatttctac cgtgaattta aaattagatt ggaatttata tatcagtacc ttagcccctc 3180
aaggtcattt tcattttgtt ggtgtggtgt tagaaccctt ggacttaaac ttatttccct 3240
tattaatggg acaacgttct gtttctgctt ctcctgttgg ttctcctgct actattgcca 3300
ctatgttaga ttttgccgtg cgtcatgata ttaaacccgt ggtggaacaa ttttcttttg 3360
atcaaattaa tgaagccatt gcccatttag aatctggtaa agcccattat cgcgtggtgt 3420
tatctcattc taaaaattaa taagattaac ttctaaactg aaacaaattt gagggtaggc 3480
ttcattgtct gcccttattt ttttatttag gaaaagtgaa cagactaaag agtgttggct 3540
ctattgcttt gagtatgtaa attaggcgtt gctgaattaa ggtatgattt ttgacccctt 3600
ctctcttctg caggatcatc ttgctgaaaa actcgagcgc tcgttccgca aagcggtacg 3660
gagttagtta ggggctaatg ggcattctcc cgtacaggaa agagttagaa gttattaatt 3720
atcaacaatt ctcctttgcc tagtgcatcg ttaccttttt aattaaaaca taaggaaaac 3780
taataatcgt aataatttaa cctcaaagtg taaagaaatg tgaaattctg acttttataa 3840
cgttaaagag ggaaaaatta gcagtttaaa atacctagag aatagtctgg ggtaagcata 3900
gagaattaga ttagttaagt taatcaaatt cagaaaaaat aataatcgta aatagttaat 3960
ctgggtgtat agaaaatgat ccccttcatg ataagattta aactcgaaaa gcaaaagcca 4020
aaaaactaac ttccattaaa agaagttgtt acatataacg ctataaagaa aatttatata 4080
tttggaggat accaaccatg tctcatattc aacgtgaaac tagttgttct cgccctcgtt 4140
taaattctaa tatggatgcc gatttatatg gttataaatg ggctcgtgat aatgttggtc 4200
aatctggtgc tactatttat cgtttatatg gtaaacctga tgctcctgaa ttattcttga 4260
aacatggtaa aggttctgtt gctaatgatg ttactgatga aatggttcgt ttaaactggt 4320
tgactgaatt tatgccttta cctactatta aacattttat tcgtactccc gatgatgctt 4380
ggttattaac tactgctatt cctggtaaaa ctgcttttca agttttagaa gaatatcctg 4440
attctggtga aaatattgtt gatgctttag ctgttttttt acgtcgttta cattctattc 4500
ccgtttgtaa ttgtcctttt aattctgatc gtgtttttcg tttagctcaa gctcaatctc 4560
gtatgaataa tggtttagtt gatgcttctg attttgatga tgaacgtaat ggttggcctg 4620
ttgaacaagt ttggaaagaa atgcacaaat tgttaccttt ttctcctgat tctgttgtta 4680
ctcatggtga tttttcttta gataatttga tctttgatga aggtaaattg attggttgta 4740
ttgatgttgg tcgtgttggt attgctgatc gttatcaaga tttagctatt ttatggaatt 4800
gtttaggtga attttctcct tctttacaga aacgtttatt tcagaaatat ggtattgata 4860
atcctgatat gaacaagtta caatttcatt taatgttgga cgagttcttt taagaattaa 4920
ttcatgacca aaatccctta acgtgagttt tcgttccact gagcgtcaga ccccgtagaa 4980
aagatcaaag gatcttcttg agatcctttt tttctgcgcg taatctgctg ctatttaaat 5040
tacgtacacg tgttattact ttgttaacga caattgtctt aattaactgg gcctcatggg 5100
ccttccgctc actgcccgct ttccagtcgg gaaacctgtc gtgccagctc tgcagatgac 5160
ggtgaaaacc tctgacacat gcagctcccg gagacggtca cagcttgtct gtaagcggat 5220
gccgggagca gacaagcccg tcagggcgcg tcagcgggtg ttggcgggtg tcggggcgca 5280
gccatgaccc agtcacgtag cgatagcgga gtgtatactg gcttaactat gcggcatcag 5340
agcagattgt actgagagtg caccatatgc ggtgtgaaat accgcacaga tgcgtaagga 5400
gaaaataccg catcaggcgc tcttccgctt cctcgctcac tgactcgctg cgctcggtcg 5460
ttcggctgcg gcgagcggta tcagctcact caaaggcggt aatacggtta tccacagaat 5520
caggggataa cgcaggaaag aacatgtgag caaaaggcca gcaaaaggcc aggaaccgta 5580
```

FIG. 39 (continued)

```
aaaaggccgc gttgctggcg tttttccata ggctccgccc ccctgacgag catcacaaaa 5640
atcgacgctc aagtcagagg tggcgaaacc cgacaggact ataaagatac caggcgtttc 5700
cccctggaag ctccctcgtg cgctctcctg ttccgaccct gccgcttacc ggatacctgt 5760
ccgcctttct cccttcggga agcgtggcgc tttctcatag ctcacgctgt aggtatctca 5820
gttcggtgta ggtcgttcgc tccaagctgg gctgtgtgca cgaacccccc gttcagcccg 5880
accgctgcgc cttatccggt aactatcgtc ttgagtccaa cccggtaaga cacgacttat 5940
cgccactggc agcagccact ggtaacagga ttagcagagc gaggtatgta ggcggtgcta 6000
cagagttctt gaagtggtgg cctaactacg gctacactag aaggacagta tttggtatct 6060
gcgctctgct gaagccagtt accttcggaa aaagagttgg tagctcttga tccggcaaac 6120
aaaccaccgc tggtagcggt ggtttttttg tttgcaagca gcagattacg cgcagaaaaa 6180
aaggatctca agaagatcct ttgatctttt ctactgcaga agcttgttag acaccctgtc 6240
atgtatttta tattatttat ttcaccatac ggattaagtg aaacctaatg aaaatagtac 6300
tttcggagct ttaactttaa tgaaggtatg tttttttata gacatcgatg tctggtttaa 6360
caataggaaa aagtagctaa aactcccatg aattaaagaa ataacaaggt gtctaacaac 6420
ctgttattaa gaatgttaga aaagacttaa catttgtgtt gagtttttat agacattggt 6480
gtctagacat acggtagata aggtttgctc aaaaataaaa taaaaaaaga ttggactaaa 6540
aaacatttaa tttagtacaa tttaattagt tatttttttcg tctcaaattt tgctttgttg 6600
agcagaaatt tagataaaaa aatccccgtg atcagattac aatgtcgttc attgtacgat 6660
gtgtcgaaaa atctttacga cactctaaac tgaccacacg gggaaaaag aaaactgaac 6720
taataacatc atgatactcg gaaaacctag caattctcaa cccctaaaca aaagaaactt 6780
ccaaaaccct gaccatataa aggagtggca acaatcagca atcagtcaag atttgatagc 6840
agaaaatctt gtatcggttg ctaatggttt tgatgtacta tttatcggca ataaataccg 6900
aactaacacg ggtgttctgt cacggcacat attaaactcc tattctcatt tagaagatgg 6960
tggttcgtat ggtagaacat ttgacccatt taccaataaa gaaatgcagt gggttcaatt 7020
taaaccgaat agaccaagaa aaggttctac tggtaaggta atcaaatatg aatcgccaaa 7080
aggtgaacct acaagagttc taatgccgtt tgtgcctatg aaaatatggc aacggattag 7140
cgataagttc ggagtaccga ttaatccgaa aaaagatact cacttttggg aatgggtaaa 7200
gaataatcca tcgataccga ttgccattac agaaggaaat aaaaaagcta attgcctatt 7260
atcctatggc tatcctgcta ttgcctttgt aggcatttgg aacggattag agaaaataaa 7320
tgatttctcg aaggaaaagc agttaaaaga ggatttgaaa tggttgttat ccaacggcaa 7380
ccgaaatatt aatatcatct ttgaccaaga ccagaaacaa aaaactgtaa ttaatgtaaa 7440
caaagctatt ttcgctttat cttctctaat aagtagaaat ggtcataaag ttaatattgt 7500
gcaatggttg ccgtcaaaag gtaaaggaat agatgattat ttggtagctt taccttttga 7560
gaaaagagaa aatcatttag acaacttaat taaaattgca ccatcattta atttttggtc 7620
aactaaatac ttattcaagt gtcgtaaacc agatttaacc gtaaattgcc gttatttgag 7680
cgatgcagta aaagaattac ctcaagagga tatagcatta atagcacctc acggcacggg 7740
taaaacttca ttagtagcta ctcacgttaa gaatcggagt tatcacggaa ggaaaactat 7800
ttcattggtg catcttgaaa gtttagccaa agctaatggc aacgcacttg gattatatta 7860
ccgaaccgaa aataatattg aaaagcaata tcttggattt agcttatgtg tagatagttg 7920
ccgtgataag attaacggca ttacaactga tattatttca ggtcaagatt attgcctttt 7980
cattgatgaa attgaccaag taattccaca catccttaac agtgaaactg aagtaagtaa 8040
gtatagatgc accatcattg acacttttc tgaactggtg agaaatgctg aacaggtcat 8100
tattgctgat gctgatttat ccgatgtgac gattgaccta atagaaaaca tcagaggtaa 8160
aaaactatat gtaatcaaga atgaatatca gtatcaggga atgactttta acgccgttgg 8220
ttcaccatta gaaatgatgg caatgatggg aaaatcggtg tcagaaggca agaaattatt 8280
tattaacacc acatcccaaa aggcaaaaag taagtacggc acaatcgctc ttgagtctta 8340
tatttttggt ctaaataaag aagcaaagat attaagaata gactctgaaa ccactaaaaa 8400
ccctgaacat ccagcctata aaatcattga ccaagactta aataatatcc tcaaagatta 8460
tgattatgtc attgcctcac cttgccttca aacaggtgtc agtattacct taaaagggca 8520
ttttgaccag caatttaact tttccagtgg aaacattaca cctcattgct ttttacagca 8580
aatgtggcgg ttgagggatg cagaaattga aagattctat tatgtgccga actcatctaa 8640
cctcaatctc attgggaata agtcaagttc accatcagac cttctaaaga gcaataacaa 8700
gatggcaacg gcaacggtta acctttttggg tagaatcgac tccgaatatt ccctagagta 8760
tgaatcgcac ggcatttggc ttgagacgtg ggcaaaatta tcagcacggc ataacagttc 8820
aatgcgttgt tactctgaaa ttcttaccta tctaattacg tctcaagggc ataaattaaa 8880
tatcaacatt ccctcacctc ttgcagatat taagaagcta aatgatgagg taagtagtaa 8940
cagggaaaag gtaaaaaatg agagatactc tcagaggtta aactcaccag atattaacga 9000
tgcagaagct accatactcg aatctaaaga gcaaaaaatc ggattgactc tcaatgagag 9060
atgcacccta gaaaagcata aagttaagaa gcggtatggg aatgtaaaga tggatattct 9120
cacctttgat gatgatggac tataccccaa actcagacta ttttattacc tcaccatcgg 9180
taaacctcat ctcaaggcta atgacagaaa agctattgcc aaaatgggca atgacaataa 9240
```

FIG. 39 (continued)

aggcaagatt ctatcaaaag acttagttaa taaaacttac tccgctcgtg tgaaggtctt 9300
agagattctt aaactaactg actttatcga caatcttaga gatgaactct taataactcc 9360
caataatcca gctatcaccg atttaataa tcttctgcta agagctaaga aggatttaag 9420
agtattagga gtcaacatcg gaaaatatcc aatggccaac attaatgccg tacttactct 9480
cattggtcac aaactttctg taatgagaga tgagttcgga aaagagaaaa ggataaaagt 9540
agatggtaaa tcataccgat gttatcaact tgaaacatta ccagatttta ccaatgatac 9600
tcttgactac tggttagaaa atgatagcca aaaagaagta acagcaacag aaaattactc 9660
cgaaaatttt aacccttcaa atagctacaa tccagacagt aagacacttt cagagggtgc 9720
aaatttccta tatataaata aagaagaatt gcatccaaat aaattgcacc tagaaataaa 9780
agaaggtgct gaactttttt tattcggggt aaaggtgatt gtgaaaggaa tcttggacgg 9840
ggcagtaact atattctcta tgggtcaaga atacgattta tccctcaatg aactagaggg 9900
gatgttaaca tcatgaactt tacaagaatc tttttaaagg gcgatcgcac catgttaaat 9960
gatggtacat ttgttcagat atttgatatt taccatgacc acgcattggg agtgaccctt 10020
gaccttaaga cagaaaaaat tatttccgat gatgttaggg taattactgt caaagactta 10080
ttgttcgatg gcacttataa aggggtaaaa tcttttatgc ccgataatgc ccgataatgc 10140
ccgattgatg ctacaaaatc ccataatcat aagcgataat cccctaatag cttgtaattc 10200
ttgaaccgta gcgattttag agtattccaa aaagaagaaa taaacaccgc aaaatgtcgt 10260
atttcacata tataaaccaa ggttttttgc cctaaaatct ttatgtttgt agtgtgatgt 10320
tgggtcaaaa tggtcagaaa agttgcaagg tttttatgga tgcttacgcg cgcgaggggt 10380
aagcatcccc aaatagttac tttatcctag tccatgccca tttattgccg tcccgttcgg 10440
ctttaaaaaa gtgccaaaac tcacaaggtg caataaaaag ttctgtacct ttcgcaaccc 10500
tagataatct ttcaacagtt actttttttc ctattatctc ggtacaaagt ttggctagtt 10560
tctcttttcc ctctttttca atcaagcctt cttgtatgcc caactcattg attaatctct 10620
ctatttttac cattatttcc cgttcaggta gtttatcccc taaatcttca tcggggggca 10680
atgtagggca ttctgaaggg gctttttctt ctgtctggac attatctaat attgaagtaa 10740
ccaaactatc ttcagttttt tctattccta ttaattcata ttcggttact gtatccgtat 10800
caatatccga ataactatct ttatccgtat tagctattcg gttaagttta tccgttaact 10860
cagaaacaag actatatagc ggttttagct tttcttctat cctgttatct aatacggata 10920
agtttatacg gttatcatta tccgtattag tatcattggg ctttttttggt agttctaccc 10980
cctcataaac cgcttttatt cccaattcca acagactgat aacagtatcc tttataatgg 11040
gtttttttgct gatatggtga acttttgccc cttccatcat tgcgatactt tctatctcac 11100
tcatcaactt atcgcttaag tgaatctcgt atctgtttaa tcccttactg gttttattca 11160
tatccgttta ctttattcgg ttaacaattc tattttatac gaataaaata ttatacggtt 11220
aactttatac gtttaactat tttatctata cggataacag taataagtta ttcgtattag 11280
ttatacgttt acttttatcc aaataaaatt agtgcattta aactaaaaga atgattttat 11340
cggagttgat agcattggat taacctaaag atgtttataa gctatatctg ataagtattt 11400
aaggttattt tgttattctg tttattgaca ttatcagaat aaaagaatag aatataattg 11460
ttgagagata agaggtttaa gtgattatgg ttaagaagtt agttggttat gtcagggtca 11520
gtagtgaatc gcaagaggat aacactagct tacagaatca gatagagaga attgaagcat 11580
attgtatggc ttttggttat gagttggtaa aaatattcaa agaggttgcc actggtacaa 11640
aagcagatat tgaaacccgt cctattttta atgaagctat agaatacttg aaacaggata 11700
atgctaatgg aattattgcc ttgaagctag accgaatcgc acggaatgct ttagatgtat 11760
tgcgtttggt tcgtgaaacc ttagaaccac aaaataaaat gttagtgtta ctagatattc 11820
aggtagatac ttcgacacct tcaggaaaaa tgattttaac tgtaatgagt gccgttgctg 11880
aactcgaaag agacatgatc tatgatcgca ctcagggggg tagaaagact aaagcccaaa 11940
agggcgggta tgcctacggg aaacctaaat ttggctataa gactgaagaa aaggaactaa 12000
aagaagattc agcacaacag gaaactatta aactaattaa gagacaccgt aggtcaggga 12060
aaagctacca gaaaatagct gattatctca atgcccaaag tattcccact aaacaaggta 12120
agaaatggag ttctagcgtc gtctatcgaa tctgtcagga aaaagctggt taagtctgtt 12180
tatagatatt tagaatttat tgaataaaaa tagtatgaac aataaatatt tatggactaa 12240
ccacgctcgg aaacgtttaa ctgaacgatg ggaaataaaa gaatcatggg ttattgatac 12300
catcgaaaat cctgaacgtt cagaatttat tgttgatgag tcaggggaaa aatatcatta 12360
ctataaaaga atagctaagt ttaagaatag agtgttagaa gtgataactt ctgccaactc 12420
aacacccaca agaataataa ccttttactt taaccgtaac atgaggaaaa atttatgatt 12480
gttacttacg ataatgaagt tgacgcaatt tattttaagt taacggaaaa taaaattgat 12540
agcaccgaac ctcaaacaga caggattatc attgattacg atgaaagtaa taatattgtt 12600
ggcattgagg tattagattt taattatctt gtcaagaaag gtttaaccgt tgctgattta 12660
cctttttctg aagatgaaag attaacagct tctcaatatt ttaattttcc tgttgctatc 12720
taatccagaa ggggcaataa tccccttctt tcatcgagtt agacttaata tcacaaaagt 12780

FIG. 39 (continued)

```
cattttcatt ttaccgtttc ttttccacag cgtccgtacg cccctcgtta aatctcaaaa     12840
ccgacaattt atgatgttta taaaaagtta ctcactttaa taagtattta tactcattaa     12900
agggttattc tttttttgta gcctgatagg ttgggaagga atatttcaga ttatcagatt     12960
tgttgaatat ttt                                                         12973
```

FIG. 39 (continued)

```
ID   #1639\\pABICyano1::smtB-PsmtA*1-zmPDC(opt1)_dsrA-Prbc*(optRBS)-synADH(opt1)_ter
standard; circular DNA;    ; 12973 BP.
CC   This file is created by Vector NTI
CC   http://www.invitrogen.com/
CC   VNTDATE|645696825|
CC   VNTDBDATE|645697025|
CC   LSOWNER|
CC   VNTAUTHORNAME|Ulf Duehring|
FH   Key             Location/Qualifiers
FH
FT   insertion_seq   2228..2273
FT                   /vntifkey="14"
FT                   /label=dsrA
FT                   /note="dsrA terminator from E.coli"
FT   gene            2343..3353
FT                   /vntifkey="60"
FT                   /note="ADH"
FT   CDS             2343..3350
FT                   /vntifkey="4"
FT                   /label=synADH(opt1)
FT   terminator      3354..3509
FT                   /vntifkey="43"
FT                   /label=TrbcSABICyano1
FT   promoter        3546..4009
FT                   /vntifkey="30"
FT                   /label=PrbcABICyano1
FT   CDS             4011..4826
FT                   /vntifkey="4"
FT                   /label=Km**
FT                   /note="Km**"
FT   CDS             12388..12636
FT                   /vntifkey="4"
FT                   /label=ORF\6
FT                   /note="orf6"
FT   CDS             12128..12391
FT                   /vntifkey="4"
FT                   /label=ORF\5
FT                   /note="orf5"
FT   CDS             11400..12086
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(10310..11074)
FT                   /vntifkey="4"
FT                   /label=ORF\3
FT                   /note="orf3"
FT   CDS             9865..10050
FT                   /vntifkey="4"
FT                   /label=ORF\2
FT                   /note="orf2"
FT   rep_origin      complement(9165..9182)
FT                   /vntifkey="33"
FT                   /label=Rep_Origin_1
FT                   /note="potential rep origin; match pNostoc (Acc# M81381) nick
site (358-375); on reserse strand"
FT   misc_feature    9425..9458
FT                   /vntifkey="21"
FT                   /label=Rep\motif
FT                   /note="Rep protein active site motig EXXKYXVKXXD"
FT   CDS             6644..9829
```

FIG. 41

```
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   primer_bind     complement(5432..5463)
FT                   /vntifkey="28"
FT                   /label=Bom-F
FT   primer_bind     5114..5145
FT                   /vntifkey="28"
FT                   /label=Bom-R
FT   rep_origin      complement(5069..6127)
FT                   /vntifkey="33"
FT                   /label=OriVT
FT   promoter        2274..2342
FT                   /vntifkey="30"
FT                   /label=Prbc*(optRBS)
FT                   /note="improved version of rbcL promoter from PCC6803"
FT   CDS             503..2201
FT                   /vntifkey="4"
FT                   /label=zmPDC(opt1)
FT   CDS             complement(69..392)
FT                   /vntifkey="4"
FT                   /label=smtB
FT                   /note="smtB gene drom Synechococcus PCC7002"
FT   promoter        394..494
FT                   /vntifkey="30"
FT                   /label=PsmtA*1
FT                   /note="improved version of smtA promoter from PCC7002"
SQ   Sequence 12973 BP; 3974 A; 2324 C; 2562 G; 4113 t;
     tcgacgggca aactttatga agcagatcaa gcctatatcc gccaagcaac cggcagccgc        60
     gttgattagt gggtgtgtcc atcctctggt tcgtctaggt gctccgaagc gtcacgatag       120
     agattaagaa tgtggtgatc cttgaggcga taaatcacat tccgcccttc cttgcgatag       180
     ctcactaaac gtgctgtgcg cagggttctt agttggtgag agacagccga ttcactcatt       240
     tcaacggcgg cggcgagttc ccccacccgc atctctccag tggccagggc cgaaagaata       300
     cgccagcggt tggcatcccc caagacacca aaaaattcgg ccatccgttg ggccttggct       360
     tggttcaaga ttttgccact gtggtctgtc attgttcgct gatctaaaca atacctgaat       420
     aattgttcat gtgttaatct aaaaatgtga acaatcgttc aactatttaa gacaatacca       480
     aggaggtgat aaccatgaat tcttataccg tgggtactta tttagccgaa cgcttagtgc       540
     aaattggttt aaaacatcat tttgccgtgg ctggggacta taatttagtg ttattggata       600
     acttattatt aaataaaaac atggaacaag tgtattgttg taatgaatta aattgtggtt       660
     tttctgctga aggttatgct agagctaaag gtgcagctgc tgctgttgtt acttattctg       720
     tgggtgcttt atctgctttt gatgctattg gtggtgctta tgccgaaaat ttacccgtga       780
     ttttaatttc tggtgcccct aataataatg atcatgccgc tggacatgtt ttacatcatg       840
     ccttaggtaa aaccgattat cattatcaat tagaaatggc caaaaatatt actgctgctg       900
     ccgaagctat ttatactcct gaagaagccc ctgccaaaat tgatcatgtg attaaaaccg       960
     ccttacgcga aaaaaaaccc gtgtatttag aaattgcctg taatattgct tctatgcctt      1020
     gtgctgctcc tgggcctgct tctgctttat ttaatgatga agcctctgat gaagctagtt      1080
     taaatgctgc cgtggaagaa accttaaaat ttattgccaa tcgcgataaa gttgccgtgt      1140
     tagttggttc taaattaaga gctgctggtg ctgaagaagc tgctgttaaa tttgctgatg      1200
     ctttaggtgg tgcagttgct actatggctg ctgccaaatc ttttttttccc gaagaaaatc      1260
     cccattatat tggaactagt tggggagaag tttcttatcc tggtgtggaa aaaactatga      1320
     aagaagccga cgctgttatt gctttagccc ctgtgtttaa tgattattct accactggtt      1380
     ggactgatat tcccgatccc aaaaaattag ttttagccga acctcgttct gttgttgtta      1440
     atggtgttcg ctttccctct gtgcatttaa aagattattt aacccgctta gcccaaaaag      1500
     tttctaaaaa aactggtgcc ttagattttt ttaaatcttt aaatgcgggt gaattaaaaa      1560
     aagctgctcc tgctgatcct tctgctcctt tagttaatgc tgaaattgcc cgtcaagttg      1620
     aagccttatt aacccctaat actaccgtta ttgccgaaac tggtgattct tggtttaatg      1680
     cccaacgcat gaaattacct aatggtgccc gtgttgaata tgaaatgcaa tggggtcata      1740
```

FIG. 41 (continued)

```
ttggttggtc tgtacctgct gcttttggtt atgctgttgg tgctcctgaa cgtcgtaata 1800
ttttaatggt gggtgatggt tcttttcaat taactgccca agaagttgcc caaatggttc 1860
gcttaaaatt acccgttatt attttttaa taaataatta tggttatacc attgaagtga 1920
tgattcatga tgggccatat aataatatta aaaattggga ttatgcgggt ttaatggaag 1980
tgtttaatgg taatggtggt tatgattctg gtgctggtaa aggtttaaaa gccaaaactg 2040
gtggtgaatt agctgaagct attaaagttg ccttagccaa tactgatggg ccaaccttaa 2100
ttgaatgttt tattggtcgc gaagattgta ccgaagaatt agttaaatgg ggtaaacgtg 2160
ttgctgctgc taattctcgc aaacccgtga ataaattatt gtaatttttg gggatcaatt 2220
cgagctcagc aagtttcatc ccgacccccct cagggtcggg attttttat tgtactagtt 2280
gacataagta aaggcatccc ctgcgtgata taattacctt cagtttaagg aggtatacac 2340
atatgattaa agcctatgct gccttagaag ccaatggtaa attacaaccc tttgaatatg 2400
atcctggtgc tttaggtgcc aatgaagtgg aaattgaagt gcaatattgt ggtgtgtgtc 2460
attctgattt atctatgatt aataatgaat ggggtatttc taattatccc ttagttcctg 2520
gtcatgaagt tgttggtact gttgctgcta tgggtgaagg tgttaatcat gtggaagtgg 2580
gtgatttagt tggtttaggt tggcattctg gttattgtat gacctgtcat tcttgtttat 2640
ctggttatca taatttatgt gccactgccg aatctactat tgtgggtcat tatggtggtt 2700
ttggtgatag agttcgtgct aaaggtgttt ctgtggtgaa attacccaaa ggtattgatt 2760
tagcctctgc tgggcctttta ttttgtggtg gtattaccgt tttttctccc atggtggaat 2820
tatctttaaa acctaccgcc aaagttgctg ttattggtat tggtggttta ggtcatttag 2880
ccgttcaatt tttaagagcc tggggttgtg aagttactgc ttttacctct tctgcccgta 2940
aacaaaccga agttttagaa ttaggtgccc atcatatttt agattctacc aatcctgaag 3000
ctattgcttc tgccgaaggt aaatttgatt atattatttc taccgtgaat ttaaaattag 3060
attggaattt atatatcagt accttagccc ctcaaggtca ttttcatttt gttggtgtgg 3120
tgttagaacc cttggactta aacttatttc ccttattaat gggacaacgt tctgtttctg 3180
cttctcctgt tggttctcct gctactattg ccactatgtt agattttgcc gtgcgtcatg 3240
atattaaacc cgtggtggaa caattttctt ttgatcaaat taatgaagcc attgcccatt 3300
tagaatctgg taaagcccat tatcgcgtgg tgttatctca ttctaaaaat taataagatt 3360
aacttctaaa ctgaaacaaa tttgagggta ggcttcattg tctgccctta ttttttatt 3420
taggaaaagt gaacagacta aagagtgttg gctctattgc tttgagtatg taaattaggc 3480
gttgctgaat taaggtatga tttttgaccc cttctctctt ctgcaggatc atcttgctga 3540
aaaactcgag cgctcgttcc gcaaagcggt acggagttag ttaggggcta atgggcattc 3600
tcccgtacag gaaagagtta gaagttatta attatcaaca attctccttt gcctagtgca 3660
tcgttacctt tttaattaaa acataaggaa aactaataat cgtaataatt taacctcaaa 3720
gtgtaaagaa atgtgaaatt ctgactttta taacgttaaa gagggaaaaa ttagcagttt 3780
aaaataccta gagaatagtc tggggtaagc atagagaatt agattagtta agttaatcaa 3840
attcagaaaa aataataatc gtaaatagtt aatctgggtg tatagaaaat gatccccttc 3900
atgataagat ttaaactcga aaagcaaaag ccaaaaaact aacttccatt aaaagaagtt 3960
gttacatata acgctataaa gaaaatttat atatttggag gataccaacc atgtctcata 4020
ttcaacgtga aactagttgt tctcgccctc gtttaaattc taatatggat gccgatttat 4080
atggttataa atgggctcgt gataatgttg gtcaatctgg tgctactatt tatcgtttat 4140
atggtaaacc tgatgctcct gaattattct tgaaacatgg taaaggttct gttgctaatg 4200
atgttactga tgaaatggtt cgtttaaact ggttgactga atttatgcct ttacctacta 4260
ttaaacattt tattcgtact cccgatgatg cttggttatt aactactgct attcctggta 4320
aaactgcttt tcaagtttta gaagaatatc ctgattctgg tgaaaatatt gttgatgctt 4380
tagctgtttt tttacgtcgt ttacattcta ttcccgtttg taattgtcct tttaattctg 4440
atcgtgtttt tcgtttagct caagctcaat ctcgtatgaa taatggttta gttgatgctt 4500
ctgattttga tgatgaacgt aatggttggc ctgttgaaca agtttggaaa gaaatgcaca 4560
aattgttacc tttttctcct gattctgttg ttactcatgg tgatttttct ttagataatt 4620
tgatctttga tgaaggtaaa ttgattggtt gtattgatgt tggtcgtgtt ggtattgctg 4680
atcgttatca agatttagct attttatgga attgtttagg tgaattttct ccttctttac 4740
agaaacgttt atttcagaaa tatggtattg ataatcctga tatgaacaag ttacaatttc 4800
atttaatgtt ggacgagttc ttttaagaat taattcatga ccaaaatccc ttaacgtgag 4860
ttttcgttcc actgagcgtc agaccccgta gaaaagatca aaggatcttc ttgagatcct 4920
tttttctgc gcgtaatctg ctgctattta aattacgtac acgtgttatt actttgttaa 4980
cgacaattgt cttaattaac tgggcctcat gggccttccg ctcactgccc gctttccagt 5040
cgggaaacct gtcgtgccag ctctgcagat gacggtgaaa acctctgaca catgcagctc 5100
ccggagacgg tcacagcttg tctgtaagcg gatgccggga gcagacaagc ccgtcagggc 5160
gcgtcagcgg gtgttggcgg gtgtcggggc gcagccatga cccagtcacg tagcgatagc 5220
ggagtgtata ctggcttaac tatgcggcat cagagcagat tgtactgaga gtgcaccata 5280
tgcggtgtga aataccgcac agatgcgtaa ggagaaaata ccgcatcagg cgctcttccg 5340
cttcctcgct cactgactcg ctgcgctcgg tcgttcggct gcggcgagcg gtatcagctc 5400
```

FIG. 41 (continued)

```
actcaaaggc ggtaatacgg ttatccacag aatcagggga taacgcagga aagaacatgt 5460
gagcaaaagg ccagcaaaag gccaggaacc gtaaaaaggc cgcgttgctg gcgtttttcc 5520
ataggctccg cccccctgac gagcatcaca aaaatcgacg ctcaagtcag aggtggcgaa 5580
acccgacagg actataaaga taccaggcgt ttccccctgg aagctccctc gtgcgctctc 5640
ctgttccgac cctgccgctt accggatacc tgtccgcctt tctcccttcg ggaagcgtgg 5700
cgctttctca tagctcacgc tgtaggtatc tcagttcggt gtaggtcgtt cgctccaagc 5760
tgggctgtgt gcacgaaccc cccgttcagc ccgaccgctg cgccttatcc ggtaactatc 5820
gtcttgagtc caacccggta agacacgact tatcgccact ggcagcagcc actggtaaca 5880
ggattagcag agcgaggtat gtaggcggtg ctacagagtt cttgaagtgg tggcctaact 5940
acggctacac tagaaggaca gtatttggta tctgcgctct gctgaagcca gttaccttcg 6000
gaaaaagagt tggtagctct tgatccggca aacaaaccac cgctggtagc ggtggttttt 6060
ttgtttgcaa gcagcagatt acgcgcagaa aaaaaggatc tcaagaagat cctttgatct 6120
tttctactgc agaagcttgt tagacaccct gtcatgtatt ttatattatt tatttcacca 6180
tacggattaa gtgaaaccta atgaaaatag tactttcgga gctttaactt taatgaaggt 6240
atgttttttt atagacatcg atgtctggtt taacaatagg aaaaagtagc taaaactccc 6300
atgaattaaa gaaataacaa ggtgtctaac aacctgttat taagaatgtt agaaaagact 6360
taacatttgt gttgagtttt tatagacatt ggtgtctaga catacggtag ataaggtttg 6420
ctcaaaaata aaataaaaaa agattggact aaaaaacatt taatttagta caatttaatt 6480
agttattttt tcgtctcaaa ttttgctttg ttgagcagaa atttagataa aaaaatcccc 6540
gtgatcagat tacaatgtcg ttcattgtac gatgtgtcga aaaatcttta cgacactcta 6600
aactgaccac acgggggaaa aagaaaactg aactaataac atcatgatac tcggaaaacc 6660
tagcaattct caacccctaa acaaaagaaa cttccaaaac cctgaccata taaaggagtg 6720
gcaacaatca gcaatcagtc aagatttgat agcagaaaat cttgtatcgg ttgctaatgg 6780
ttttgatgta ctatttatcg gcaataaata ccgaactaac acgggtgttc tgtcacggca 6840
catattaaac tcctattctc atttagaaga tggtggttcg tatggtagaa catttgaccc 6900
atttaccaat aaagaaatgc agtgggttca atttaaaccg aatagaccaa gaaaaggttc 6960
tactggtaag gtaatcaaat atgaatcgcc aaaaggtgaa cctacaagag ttctaatgcc 7020
gtttgtgcct atgaaaatat ggcaacggat tagcgataag ttcggagtac cgattaatcc 7080
gaaaaaagat actcactttt gggaatgggt aaagaataat ccatcgatac cgattgccat 7140
tacagaagga aataaaaaag ctaattgcct attatcctat ggctatcctg ctattgcctt 7200
tgtaggcatt tggaacggat tagagaaaat aaatgatttc tcgaaggaaa agcagttaaa 7260
agaggatttg aaatggttgt tatccaacgg caaccgaaat attaatatca tctttgacca 7320
agaccagaaa caaaaaactg taattaatgt aaacaaagct attttcgctt tatcttctct 7380
aataagtaga aatggtcata aagttaatat tgtgcaatgg ttgccgtcaa aaggtaaagg 7440
aatagatgat tatttggtag ctttaccttt tgagaaaaga gaaaatcatt tagacaactt 7500
aattaaaatt gcaccatcat ttaatttttg gtcaactaaa tacttattca agtgtcgtaa 7560
accagattta accgtaaatt gccgttattt gagcgatgca gtaaaagaat tacctcaaga 7620
ggatatagca ttaatagcac ctcacggcac gggtaaaact tcattagtag ctactcacgt 7680
taagaatcgg agttatcacg gaaggaaaac tatttcattg gtgcatcttg aaagtttagc 7740
caaagctaat ggcaacgcac ttggattata ttaccgaacc gaaaataata ttgaaaagca 7800
atatcttgga tttagcttat gtgtagatag ttgccgtgat aagattaacg gcattacaac 7860
tgatattatt tcaggtcaag attattgcct tttcattgat gaaattgacc aagtaattcc 7920
acacatcctt aacagtgaaa ctgaagtaag taagtataga tgcaccatca ttgacacttt 7980
ttctgaactg gtgagaaatg ctgaacaggt cattattgct gatgctgatt tatccgatgt 8040
gacgattgac ctaatagaaa acatcagagg taaaaaacta tatgtaatca agaatgaata 8100
tcagtatcag ggaatgactt ttaacgccgt tggttcacca ttagaaatga tggcaatgat 8160
gggaaaatcg gtgtcagaag gcaagaaatt atttattaac accacatccc aaaaggcaaa 8220
aagtaagtac ggcacaatcg ctcttgagtc ttatattttt ggtctaaata aagaagcaaa 8280
gatattaaga atagactctg aaaccactaa aaaccctgaa catccagcct ataaaatcat 8340
tgaccaagac ttaaataata tcctcaaaga ttatgattat gtcattgcct caccttgcct 8400
tcaaacaggt gtcagtatta ccttaaaagg gcattttgac cagcaattta acttttccag 8460
tggaaacatt acacctcatt gcttttttaca gcaaatgtgg cggttgaggg atgcagaaat 8520
tgaaagattc tattatgtgc cgaactcatc taacctcaat ctcattggga ataagtcaag 8580
ttcaccatca gaccttctaa agagcaataa caagatggca acggcaacgg ttaacctttt 8640
gggtagaatc gactccgaat attccctaga gtatgaatcg cacggcattt ggcttgagac 8700
gtgggcaaaa ttatcagcac ggcataacag ttcaatgcgt tgttactctg aaattcttac 8760
ctatctaatt acgtctcaag ggcataaatt aaatatcaac attccctcac ctcttgcaga 8820
tattaagaag ctaaatgatg aggtaagtag taacagggaa aaggtaaaaa atgagagata 8880
```

FIG. 41 (continued)

```
ctctcagagg ttaaactcac cagatattaa cgatgcagaa gctaccatac tcgaatctaa     8940
agagcaaaaa atcggattga ctctcaatga gagatgcacc ctagaaaagc ataaagttaa     9000
gaagcggtat gggaatgtaa agatggatat tctcaccttt gatgatgatg gactataccc     9060
caaactcaga ctattttatt acctcaccat cggtaaacct catctcaagg ctaatgacag     9120
aaaagctatt gccaaaatgg gcaatgacaa taaaggcaag attctatcaa aagacttagt     9180
taataaaact tactccgctc gtgtgaaggt cttagagatt cttaaactaa ctgactttat     9240
cgacaatctt agagatgaac tcttaataac tcccaataat ccagctatca ccgattttaa     9300
taatcttctg ctaagagcta agaaggattt aagagtatta ggagtcaaca tcggaaaata     9360
tccaatggcc aacattaatg ccgtacttac tctcattggt cacaaacttt ctgtaatgag     9420
agatgagttc ggaaaagaga aaaggataaa agtagatggt aaatcatacc gatgttatca     9480
acttgaaaca ttaccagatt ttaccaatga tactcttgac tactggttag aaaatgatag     9540
ccaaaaagaa gtaacagcaa cagaaaatta ctccgaaaat tttaaccctt caaatagcta     9600
caatccagac agtaagacac tttcagaggg tgcaaatttc ctatatataa ataaagaaga     9660
attgcatcca aataaattgc acctagaaat aaaagaaggt gctgaacttt ttttattcgg     9720
ggtaaaggtg attgtgaaag gaatcttgga cggggcagta actatattct ctatgggtca     9780
agaatacgat ttatccctca atgaactaga ggggatgtta acatcatgaa ctttacaaga     9840
atctttttaa agggcgatcg caccatgtta aatgatggta catttgttca gatatttgat     9900
atttaccatg accacgcatt gggagtgacc cttgacctta agacagaaaa aattatttcc     9960
gatgatgtta gggtaattac tgtcaaagac ttattgttcg atggcactta taaaggggta    10020
aaatctttta tgcccgataa tgcccgataa tgcccgattg atgctacaaa atcccataat    10080
cataagcgat aatcccctaa tagcttgtaa ttcttgaacc gtagcgattt tagagtattc    10140
caaaaagaag aaataaacac cgcaaaatgt cgtatttcac atatataaac caaggttttt    10200
tgccctaaaa tctttatgtt tgtagtgtga tgttgggtca aaatggtcag aaaagttgca    10260
aggtttttat ggatgcttac gcgcgcgagg ggtaagcatc cccaaatagt tactttatcc    10320
tagtccatgc ccatttattg ccgtcccgtt cggctttaaa aaagtgccaa aactcacaag    10380
gtgcaataaa aagttctgta cctttcgcaa ccctagataa tctttcaaca gttacttttt    10440
ttcctattat ctcggtacaa agtttggcta gtttctcttt tccctctttt tcaatcaagc    10500
cttcttgtat gcccaactca ttgattaatc tctctatttt taccattatt tcccgttcag    10560
gtagtttatc ccctaaatct tcatcggggg gcaatgtagg gcattctgaa ggggcttttt    10620
cttctgtctg gacattatct aatattgaag taaccaaact atcttcagtt ttttctattc    10680
ctattaattc atattcggtt actgtatccg tatcaatatc cgaataacta tctttatccg    10740
tattagctat tcggttaagt ttatccgtta actcagaaac aagactatat agcggtttta    10800
gcttttcttc tatcctgtta tctaatacgg ataagtttat acggttatca ttatccgtat    10860
tagtatcatt gggctttttt ggtagttcta ccccctcata aaccgctttt attcccaatt    10920
ccaacagact gataacagta tcctttataa tgggtttttt gctgatatgg tgaacttttg    10980
ccccttccat cattgcgata ctttctatct cactcatcaa cttatcgctt aagtgaatct    11040
cgtatctgtt taatccctta ctggttttat tcatatccgt ttactttatt cggttaacaa    11100
ttctatttta tacgaataaa atattatacg gttaacttta tacgtttaac tattttatct    11160
atacggataa cagtaataag ttattcgtat tagttatacg tttactttta tccaaataaa    11220
attagtgcat ttaaactaaa agaatgattt tatcggagtt gatagcattg gattaaccta    11280
aagatgttta taagctatat ctgataagta tttaaggtta ttttgttatt ctgtttattg    11340
acattatcag aataaaagaa tagaatataa ttgttgagag ataagaggtt taagtgatta    11400
tggttaagaa gttagttggt tatgtcaggg tcagtagtga atcgcaagag gataacacta    11460
gcttacagaa tcagatagag agaattgaag catattgtat ggcttttggt tatgagttgg    11520
taaaaatatt caaagaggtt gccactggta caaaagcaga tattgaaacc cgtcctattt    11580
ttaatgaagc tatagaatac ttgaaacagg ataatgctaa tggaattatt gccttgaagc    11640
tagaccgaat cgcacggaat gctttagatg tattgcgttt ggttcgtgaa accttagaac    11700
cacaaaataa aatgttagtg ttactagata ttcaggtaga tacttcgaca ccttcaggaa    11760
aaatgatttt aactgtaatg agtgccgttg ctgaactcga aagagacatg atctatgatc    11820
gcactcaggg gggtagaaag actaaagccc aaaagggcgg gtatgcctac gggaaaccta    11880
aatttggcta taagactgaa gaaaaggaac taaaagaaga ttcagcacaa caggaaacta    11940
ttaaactaat taagagacac cgtaggtcag ggaaaagcta ccagaaaata gctgattatc    12000
tcaatgccca aagtattccc actaaacaag gtaagaaatg gagttctagc gtcgtctatc    12060
gaatctgtca ggaaaaagct ggttaagtct gtttatagat atttagaatt tattgaataa    12120
aaatagtatg aacaataaat atttatggac taaccacgct cggaaacgtt taactgaacg    12180
atgggaaata aaagaatcat gggttattga taccatcgaa aatcctgaac gttcagaatt    12240
tattgttgat gagtcagggg aaaaatatca ttactataaa agaatagcta agtttaagaa    12300
tagagtgtta gaagtgataa cttctgccaa ctcaacaccc acaagaataa taacctttta    12360
ctttaaccgt aacatgagga aaaatttatg attgttactt acgataatga agttgacgca    12420
atttatttta agttaacgga aaataaaatt gatagcaccg aacctcaaac agacaggatt    12480
```

FIG. 41 (continued)

```
atcattgatt acgatgaaag taataatatt gttggcattg aggtattaga ttttaattat     12540
cttgtcaaga aaggtttaac cgttgctgat ttaccttttt ctgaagatga aagattaaca     12600
gcttctcaat attttaattt tcctgttgct atctaatcca gaaggggcaa taatcccctt     12660
ctttcatcga gttagactta atatcacaaa agtcattttc attttaccgt ttcttttcca     12720
cagcgtccgt acgcccctcg ttaaatctca aaaccgacaa tttatgatgt ttataaaaag     12780
ttactcactt taataagtat ttatactcat taaagggtta ttcttttttt gtagcctgat     12840
aggttgggaa ggaatatttc agattatcag atttgttgaa tatttttcgt cagatacgca     12900
aaccttacaa acataattaa caactgaaac tattgatatg tctaggtttt agctctatca     12960
caggttggat ctg                                                        12973
```

FIG. 41 (continued)

```
ID   #1640\pABICyano1::smtB-PsmtA*2-zmPDC(opt1)_dsrA-Prbc*(optRBS)-synADH(opt1)_ter
standard; circular DNA;    ; 12973 BP.

CC   This file is created by Vector NTI
CC   http://www.invitrogen.com/
CC   VNTDATE|645697411|
CC   VNTDBDATE|645697411|
CC   LSOWNER|
CC   VNTAUTHORNAME|Ulf Duehring|
FH   Key             Location/Qualifiers
FH
FT   insertion_seq   2228..2273
FT                   /vntifkey="14"
FT                   /label=dsrA
FT                   /note="dsrA terminator from E.coli"
FT   gene            2343..3353
FT                   /vntifkey="60"
FT                   /note="ADH"
FT   CDS             2343..3350
FT                   /vntifkey="4"
FT                   /label=synADH(opt1)
FT   terminator      3354..3509
FT                   /vntifkey="43"
FT                   /label=TrbcSABICyano1
FT   promoter        3546..4009
FT                   /vntifkey="30"
FT                   /label=PrbcABICyano1
FT   CDS             4011..4826
FT                   /vntifkey="4"
FT                   /label=Km**
FT                   /note="Km**"
FT   CDS             12388..12636
FT                   /vntifkey="4"
FT                   /label=ORF\6
FT                   /note="orf6"
FT   CDS             12128..12391
FT                   /vntifkey="4"
FT                   /label=ORF\5
FT                   /note="orf5"
FT   CDS             11400..12086
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(10310..11074)
FT                   /vntifkey="4"
FT                   /label=ORF\3
FT                   /note="orf3"
FT   CDS             9865..10050
FT                   /vntifkey="4"
FT                   /label=ORF\2
FT                   /note="orf2"
FT   rep_origin      complement(9165..9182)
FT                   /vntifkey="33"
FT                   /label=Rep_Origin_1
FT                   /note="potential rep origin; match pNostoc (Acc# M81381) nick
site (358-375); on reserse strand"
FT   misc_feature    9425..9458
FT                   /vntifkey="21"
FT                   /label=Rep\motif
FT                   /note="Rep protein active site motig EXXKYXVKXXD"
```

FIG. 43

```
FT   CDS             6644..9829
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   primer_bind     complement(5432..5463)
FT                   /vntifkey="28"
FT                   /label=Bom-F
FT   primer_bind     5114..5145
FT                   /vntifkey="28"
FT                   /label=Bom-R
FT   rep_origin      complement(5069..6127)
FT                   /vntifkey="33"
FT                   /label=OriVT
FT   promoter        2274..2342
FT                   /vntifkey="30"
FT                   /label=Prbc*(optRBS)
FT                   /note="improved version of rbcL promoter from PCC6803"
FT   CDS             503..2201
FT                   /vntifkey="4"
FT                   /label=zmPDC(opt1)
FT   CDS             complement(69..392)
FT                   /vntifkey="4"
FT                   /label=smtB
FT                   /note="smtB gene from Synechococcus PCC7002"
FT   promoter        393..494
FT                   /vntifkey="30"
FT                   /label=PsmtB*2
FT                   /note="improvers version of the smtB promoter from PCC7002"
SQ   Sequence 12973 BP; 3975 A; 2324 C; 2561 G; 4113 t;
     tcgacgggca aactttatga agcagatcaa gcctatatcc gccaagcaac cggcagccgc        60
     gttgattagt gggtgtgtcc atcctctggt tcgtctaggt gctccgaagc gtcacgatag       120
     agattaagaa tgtggtgatc cttgaggcga taaatcacat tccgcccttc cttgcgatag       180
     ctcactaaac gtgctgtgcg cagggttctt agttggtgag agacagccga ttcactcatt       240
     tcaacggcgg cggcgagttc ccccacccgc atctctccag tggccagggc cgaaagaata       300
     cgccagcggt tggcatcccc caagacacca aaaaattcgg ccatccgttg ggccttggct       360
     tggttcaaga ttttgccact gtggtctgtc attgttcgct gatctaaaca atacctgaat       420
     aattgttcat gtgttaatct aaaaatgtga acaatcgttc aactatttaa gacaatacca       480
     aggaggtata aaccatgaat tcttataccg tgggtactta tttagccgaa cgcttagtgc       540
     aaattggttt aaaacatcat tttgccgtgg ctggggacta taatttagtg ttattggata       600
     acttattatt aaataaaaac atggaacaag tgtattgttg taatgaatta aattgtggtt       660
     tttctgctga aggttatgct agagctaaag gtgcagctgc tgctgttgtt acttattctg       720
     tgggtgcttt atctgctttt gatgctattg gtggtgctta tgccgaaaat ttacccgtga       780
     ttttaatttc tggtgcccct aataataatg atcatgccgc tggacatgtt ttacatcatg       840
     ccttaggtaa aaccgattat cattatcaat tagaaatggc caaaaatatt actgctgctg       900
     ccgaagctat ttatactcct gaagaagccc ctgccaaaat tgatcatgtg attaaaaccg       960
     ccttacgcga aaaaaaaccc gtgtatttag aaattgcctg taatattgct tctatgcctt      1020
     gtgctgctcc tgggcctgct tctgctttat ttaatgatga agcctctgat gaagctagtt      1080
     taaatgctgc cgtggaagaa accttaaaat ttattgccaa tcgcgataaa gttgccgtgt      1140
     tagttggttc taaattaaga gctgctggtg ctgaagaagc tgctgttaaa tttgctgatg      1200
     ctttaggtgg tgcagttgct actatggctg ctgccaaatc tttttttccc gaagaaaatc      1260
     cccattatat tggaactagt tggggagaag tttcttatcc tggtgtggaa aaaactatga      1320
     aagaagccga cgctgttatt gctttagccc ctgtgtttaa tgattattct accactggtt      1380
     ggactgatat tcccgatccc aaaaaattag ttttagccga acctcgttct gttgttgtta      1440
     atggtgttcg ctttccctct gtgcatttaa aagattattt aacccgctta gcccaaaaag      1500
     tttctaaaaa aactggtgcc ttagattttt ttaaatcttt aaatgcgggt gaattaaaaa      1560
     aagctgctcc tgctgatcct tctgctcctt tagttaatgc tgaaattgcc cgtcaagttg      1620
     aagccttatt aacccctaat actaccgtta ttgccgaaac tggtgattct tggtttaatg      1680
     cccaacgcat gaaattacct aatggtgccc gtgttgaata tgaaatgcaa tggggtcata      1740
     ttggttggtc tgtacctgct gcttttggtt atgctgttgg tgctcctgaa cgtcgtaata      1800
     ttttaatggt gggtgatggt tcttttcaat taactgccca agaagttgcc caaatggttc      1860
```

FIG. 43 (continued)

```
gcttaaaatt acccgttatt attttttaa taaataatta tggttatacc attgaagtga 1920
tgattcatga tgggccatat aataatatta aaaattggga ttatgcgggt ttaatggaag 1980
tgtttaatgg taatggtggt tatgattctg gtgctggtaa aggtttaaaa gccaaaactg 2040
gtggtgaatt agctgaagct attaaagttg ccttagccaa tactgatggg ccaaccttaa 2100
ttgaatgttt tattggtcgc gaagattgta ccgaagaatt agttaaatgg ggtaaacgtg 2160
ttgctgctgc taattctcgc aaacccgtga ataaattatt gtaatttttg gggatcaatt 2220
cgagctcagc aagtttcatc ccgacccccct cagggtcggg atttttttat tgtactagtt 2280
gacataagta aaggcatccc ctgcgtgata taattacctt cagtttaagg aggtatacac 2340
atatgattaa agcctatgct gccttagaag ccaatggtaa attacaaccc tttgaatatg 2400
atcctggtgc tttaggtgcc aatgaagtgg aaattgaagt gcaatattgt ggtgtgtgtc 2460
attctgattt atctatgatt aataatgaat ggggtatttc taattatccc ttagttcctg 2520
gtcatgaagt tgttggtact gttgctgcta tgggtgaagg tgttaatcat gtggaagtgg 2580
gtgatttagt tggtttaggt tggcattctg gttattgtat gacctgtcat tcttgtttat 2640
ctggttatca taatttatgt gccactgccg aatctactat tgtgggtcat tatggtggtt 2700
ttggtgatag agttcgtgct aaaggtgttt ctgtggtgaa attacccaaa ggtattgatt 2760
tagcctctgc tgggccttta ttttgtggtg gtattaccgt tttttctccc atggtggaat 2820
tatctttaaa acctaccgcc aaagttgctg ttattggtat tggtggttta ggtcatttag 2880
ccgttcaatt tttaagagcc tggggttgtg aagttactgc ttttacctct tctgcccgta 2940
aacaaaccga agttttagaa ttaggtgccc atcatatttt agattctacc aatcctgaag 3000
ctattgcttc tgccgaaggt aaatttgatt atattatttc taccgtgaat ttaaaattag 3060
attggaattt atatatcagt accttagccc ctcaaggtca ttttcatttt gttggtgtgg 3120
tgttagaacc cttggactta aacttatttc ccttattaat gggacaacgt tctgtttctg 3180
cttctcctgt tggttctcct gctactattg ccactatgtt agattttgcc gtgcgtcatg 3240
atattaaacc cgtggtggaa caattttctt ttgatcaaat taatgaagcc attgcccatt 3300
tagaatctgg taaagcccat tatcgcgtgg tgttatctca ttctaaaaat taataagatt 3360
aacttctaaa ctgaaacaaa tttgagggta ggcttcattg tctgccctta tttttttatt 3420
taggaaaagt gaacagacta aagagtgttg gctctattgc tttgagtatg taaattaggc 3480
gttgctgaat taaggtatga tttttgaccc cttctctctt ctgcaggatc atcttgctga 3540
aaaactcgag cgctcgttcc gcaaagcggt acggagttag ttaggggcta atgggcattc 3600
tcccgtacag gaaagagtta gaagttatta attatcaaca attctccttt gcctagtgca 3660
tcgttacctt tttaattaaa acataaggaa aactaataat cgtaataatt taacctcaaa 3720
gtgtaaagaa atgtgaaatt ctgactttta taacgttaaa gagggaaaaa ttagcagttt 3780
aaaataccta gagaatagtc tggggtaagc atagagaatt agattagtta agttaatcaa 3840
attcagaaaa aataataatc gtaaatagtt aatctgggtg tatagaaaat gatccccttc 3900
atgataagat ttaaactcga aaagcaaaag ccaaaaaact aacttccatt aaaagaagtt 3960
gttacatata acgctataaa gaaaatttat atatttggag gataccaacc atgtctcata 4020
ttcaacgtga aactagttgt tctcgccctc gtttaaattc taatatggat gccgatttat 4080
atggttataa atgggctcgt gataatgttg gtcaatctgg tgctactatt tatcgtttat 4140
atggtaaacc tgatgctcct gaattattct tgaaacatgg taaaggttct gttgctaatg 4200
atgttactga tgaaatggtt cgtttaaact ggttgactga atttatgcct ttacctacta 4260
ttaaacattt tattcgtact cccgatgatg cttggttatt aactactgct attcctggta 4320
aaactgcttt tcaagtttta gaagaatatc ctgattctgg tgaaaatatt gttgatgctt 4380
tagctgtttt tttacgtcgt ttacattcta ttcccgtttg taattgtcct tttaattctg 4440
atcgtgtttt tcgtttagct caagctcaat ctcgtatgaa taatggttta gttgatgctt 4500
ctgattttga tgatgaacgt aatggttggc ctgttgaaca agtttggaaa gaaatgcaca 4560
aattgttacc tttttctcct gattctgttg ttactcatgg tgatttttct ttagataatt 4620
tgatctttga tgaaggtaaa ttgattggtt gtattgatgt tggtcgtgtt ggtattgctg 4680
atcgttatca agatttagct attttatgga attgtttagg tgaattttct ccttctttac 4740
agaaacgttt atttcagaaa tatggtattg ataatcctga tatgaacaag ttacaatttc 4800
atttaatgtt ggacgagttc ttttaagaat taattcatga ccaaaatccc ttaacgtgag 4860
ttttcgttcc actgagcgtc agaccccgta gaaaagatca aaggatcttc ttgagatcct 4920
tttttctgc gcgtaatctg ctgctattta aattacgtac acgtgttatt actttgttaa 4980
cgacaattgt cttaattaac tgggcctcat gggccttccg ctcactgccc gctttccagt 5040
cgggaaacct gtcgtgccag ctctgcagat gacggtgaaa acctctgaca catgcagctc 5100
ccggagacgg tcacagcttg tctgtaagcg gatgccggga gcagacaagc ccgtcagggc 5160
gcgtcagcgg gtgttggcgg gtgtcggggc gcagccatga cccagtcacg tagcgatagc 5220
ggagtgtata ctggcttaac tatgcggcat cagagcagat tgtactgaga gtgcaccata 5280
tgcggtgtga aataccgcac agatgcgtaa ggagaaaata ccgcatcagg cgctcttccg 5340
cttcctcgct cactgactcg ctgcgctcgg tcgttcggct gcggcgagcg gtatcagctc 5400
```

FIG. 43 (continued)

```
actcaaaggc ggtaatacgg ttatccacag aatcagggga taacgcagga aagaacatgt   5460
gagcaaaagg ccagcaaaag gccaggaacc gtaaaaaggc cgcgttgctg gcgtttttcc   5520
ataggctccg cccccctgac gagcatcaca aaaatcgacg ctcaagtcag aggtggcgaa   5580
acccgacagg actataaaga taccaggcgt ttccccctgg aagctccctc gtgcgctctc   5640
ctgttccgac cctgccgctt accggatacc tgtccgcctt tctcccttcg ggaagcgtgg   5700
cgctttctca tagctcacgc tgtaggtatc tcagttcggt gtaggtcgtt cgctccaagc   5760
tgggctgtgt gcacgaaccc cccgttcagc ccgaccgctg cgccttatcc ggtaactatc   5820
gtcttgagtc caacccggta agacacgact tatcgccact ggcagcagcc actggtaaca   5880
ggattagcag agcgaggtat gtaggcggtg ctacagagtt cttgaagtgg tggcctaact   5940
acggctacac tagaaggaca gtatttggta tctgcgctct gctgaagcca gttaccttcg   6000
gaaaaagagt tggtagctct tgatccggca aacaaaccac cgctggtagc ggtggttttt   6060
ttgtttgcaa gcagcagatt acgcgcagaa aaaaaggatc tcaagaagat cctttgatct   6120
tttctactgc agaagcttgt tagacaccct gtcatgtatt ttatattatt tatttcacca   6180
tacggattaa gtgaaaccta atgaaaatag tactttcgga gctttaactt taatgaaggt   6240
atgttttttt atagacatcg atgtctggtt taacaatagg aaaaagtagc taaaactccc   6300
atgaattaaa gaaataacaa ggtgtctaac aacctgttat taagaatgtt agaaaagact   6360
taacatttgt gttgagtttt tatagacatt ggtgtctaga catacggtag ataaggtttg   6420
ctcaaaaata aaataaaaaa agattggact aaaaaacatt taatttagta caatttaatt   6480
agttattttt tcgtctcaaa ttttgctttg ttgagcagaa atttagataa aaaaatcccc   6540
gtgatcagat tacaatgtcg ttcattgtac gatgtgtcga aaaatcttta cgacactcta   6600
aactgaccac acgggggaaa aagaaaactg aactaataac atcatgatac tcggaaaacc   6660
tagcaattct caacccctaa acaaaagaaa cttccaaaac cctgaccata taaaggagtg   6720
gcaacaatca gcaatcagtc aagatttgat agcagaaaat cttgtatcgg ttgctaatgg   6780
ttttgatgta ctatttatcg gcaataaata ccgaactaac acgggtgttc tgtcacggca   6840
catattaaac tcctattctc atttagaaga tggtggttcg tatggtagaa catttgaccc   6900
atttaccaat aaagaaatgc agtgggttca atttaaaccg aatagaccaa gaaaaggttc   6960
tactggtaag gtaatcaaat atgaatcgcc aaaaggtgaa cctacaagag ttctaatgcc   7020
gtttgtgcct atgaaaatat ggcaacggat tagcgataag ttcggagtac cgattaatcc   7080
gaaaaaagat actcactttt gggaatgggt aaagaataat ccatcgatac cgattgccat   7140
tacagaagga aataaaaaag ctaattgcct attatcctat ggctatcctg ctattgcctt   7200
tgtaggcatt tggaacggat tagagaaaat aaatgatttc tcgaaggaaa agcagttaaa   7260
agaggatttg aaatggttgt tatccaacgg caaccgaaat attaatatca tctttgacca   7320
agaccagaaa caaaaaactg taattaatgt aaacaaagct attttcgctt tatcttctct   7380
aataagtaga aatggtcata aagttaatat tgtgcaatgg ttgccgtcaa aaggtaaagg   7440
aatagatgat tatttggtag ctttaccttt tgagaaaaga gaaaatcatt tagacaactt   7500
aattaaaatt gcaccatcat ttaatttttg gtcaactaaa tacttattca agtgtcgtaa   7560
accagattta accgtaaatt gccgttattt gagcgatgca gtaaaagaat tacctcaaga   7620
ggatatagca ttaatagcac ctcacggcac gggtaaaact tcattagtag ctactcacgt   7680
taagaatcgg agttatcacg gaaggaaaac tatttcattg gtgcatcttg aaagtttagc   7740
caaagctaat ggcaacgcac ttggattata ttaccgaacc gaaaataata ttgaaaagca   7800
atatcttgga tttagcttat gtgtagatag ttgccgtgat aagattaacg gcattacaac   7860
tgatattatt tcaggtcaag attattgcct ttcattgat gaaattgacc aagtaattcc   7920
acacatcctt aacagtgaaa ctgaagtaag taagtataga tgcaccatca ttgacacttt   7980
ttctgaactg gtgagaaatg ctgaacaggt cattattgct gatgctgatt tatccgatgt   8040
gacgattgac ctaatagaaa acatcagagg taaaaaacta tatgtaatca agaatgaata   8100
tcagtatcag ggaatgactt ttaacgccgt tggttcacca ttagaaatga tggcaatgat   8160
gggaaaatcg gtgtcagaag gcaagaaatt atttattaac accacatccc aaaaggcaaa   8220
aagtaagtac ggcacaatcg ctcttgagtc ttatattttt ggtctaaata aagaagcaaa   8280
gatattaaga atagactctg aaaccactaa aaaccctgaa catccagcct ataaaatcat   8340
tgaccaagac ttaaataata tcctcaaaga ttatgattat gtcattgcct caccttgcct   8400
tcaaacaggt gtcagtatta ccttaaaagg gcattttgac cagcaattta acttttccag   8460
tggaaacatt acacctcatt gctttttaca gcaaatgtgg cggttgaggg atgcagaaat   8520
tgaaagattc tattatgtgc cgaactcatc taacctcaat ctcattggga ataagtcaag   8580
ttcaccatca gaccttctaa agagcaataa caagatggca acggcaacgg ttaacctttt   8640
gggtagaatc gactccgaat attccctaga gtatgaatcg cacggcattt ggcttgagac   8700
gtgggcaaaa ttatcagcac ggcataacag ttcaatgcgt tgttactctg aaattcttac   8760
ctatctaatt acgtctcaag ggcataaatt aaatatcaac attccctcac ctcttgcaga   8820
tattaagaag ctaaatgatg aggtaagtag taacagggaa aaggtaaaaa atgagagata   8880
ctctcagagg ttaaactcac cagatattaa cgatgcagaa gctaccatac tcgaatctaa   8940
agagcaaaaa atcggattga ctctcaatga gagatgcacc ctagaaaagc ataaagttaa   9000
gaagcggtat gggaatgtaa agatggatat tctcaccttt gatgatgatg gactataccc   9060
```

FIG. 43 (continued)

```
caaactcaga ctattttatt acctcaccat cggtaaacct catctcaagg ctaatgacag     9120
aaaagctatt gccaaaatgg gcaatgacaa taaaggcaag attctatcaa aagacttagt     9180
taataaaact tactccgctc gtgtgaaggt cttagagatt cttaaactaa ctgactttat     9240
cgacaatctt agagatgaac tcttaataac tcccaataat ccagctatca ccgattttaa     9300
taatcttctg ctaagagcta agaaggattt aagagtatta ggagtcaaca tcggaaaata     9360
tccaatggcc aacattaatg ccgtacttac tctcattggt cacaaacttt ctgtaatgag     9420
agatgagttc ggaaaagaga aaaggataaa agtagatggt aaatcatacc gatgttatca     9480
acttgaaaca ttaccagatt ttaccaatga tactcttgac tactggttag aaaatgatag     9540
ccaaaaagaa gtaacagcaa cagaaaatta ctccgaaaat tttaaccctt caaatagcta     9600
caatccagac agtaagacac tttcagaggg tgcaaatttc ctatatataa ataaagaaga     9660
attgcatcca aataaattgc acctagaaat aaaagaaggt gctgaacttt ttttattcgg     9720
ggtaaaggtg attgtgaaag gaatcttgga cggggcagta actatattct ctatgggtca     9780
agaatacgat ttatccctca atgaactaga ggggatgtta acatcatgaa ctttacaaga     9840
atctttttaa agggcgatcg caccatgtta aatgatggta catttgttca gatatttgat     9900
atttaccatg accacgcatt gggagtgacc cttgacctta agacagaaaa aattatttcc     9960
gatgatgtta gggtaattac tgtcaaagac ttattgttcg atggcactta taaaggggta    10020
aaatctttta tgcccgataa tgcccgataa tgcccgattg atgctacaaa atcccataat    10080
cataagcgat aatcccctaa tagcttgtaa ttcttgaacc gtagcgattt tagagtattc    10140
caaaaagaag aaataaacac cgcaaaatgt cgtatttcac atatataaac caaggttttt    10200
tgccctaaaa tctttatgtt tgtagtgtga tgttgggtca aaatggtcag aaaagttgca    10260
aggtttttat ggatgcttac gcgcgcgagg ggtaagcatc cccaaatagt tactttatcc    10320
tagtccatgc ccatttattg ccgtcccgtt cggctttaaa aaagtgccaa aactcacaag    10380
gtgcaataaa aagttctgta cctttcgcaa ccctagataa tctttcaaca gttacttttt    10440
ttcctattat ctcggtacaa agtttggcta gtttctcttt tccctctttt tcaatcaagc    10500
cttcttgtat gcccaactca ttgattaatc tctctatttt taccattatt tcccgttcag    10560
gtagtttatc ccctaaatct tcatcggggg gcaatgtagg gcattctgaa ggggcttttt    10620
cttctgtctg gacattatct aatattgaag taaccaaact atcttcagtt ttttctattc    10680
ctattaattc atattcggtt actgtatccg tatcaatatc cgaataacta tctttatccg    10740
tattagctat tcggttaagt ttatccgtta actcagaaac aagactatat agcggtttta    10800
gcttttcttc tatcctgtta tctaatacgg ataagtttat acggttatca ttatccgtat    10860
tagtatcatt gggctttttt ggtagttcta ccccctcata aaccgctttt attcccaatt    10920
ccaacagact gataacagta tcctttataa tgggtttttt gctgatatgg tgaacttttg    10980
ccccttccat cattgcgata ctttctatct cactcatcaa cttatcgctt aagtgaatct    11040
cgtatctgtt taatccctta ctggttttat tcatatccgt ttactttatt cggttaacaa    11100
ttctatttta tacgaataaa atattatacg gttaacttta tacgtttaac tattttatct    11160
atacggataa cagtaataag ttattcgtat tagttatacg tttactttta tccaaataaa    11220
attagtgcat ttaaactaaa agaatgattt tatcggagtt gatagcattg gattaaccta    11280
aagatgttta taagctatat ctgataagta tttaaggtta ttttgttatt ctgtttattg    11340
acattatcag aataaaagaa tagaatataa ttgttgagag ataagaggtt taagtgatta    11400
tggttaagaa gttagttggt tatgtcaggg tcagtagtga atcgcaagag gataacacta    11460
gcttacagaa tcagatagag agaattgaag catattgtat ggcttttggt tatgagttgg    11520
taaaaatatt caaagaggtt gccactggta caaaagcaga tattgaaacc cgtcctattt    11580
ttaatgaagc tatagaatac ttgaaacagg ataatgctaa tggaattatt gccttgaagc    11640
tagaccgaat cgcacggaat gctttagatg tattgcgttt ggttcgtgaa accttagaac    11700
cacaaaataa aatgttagtg ttactagata ttcaggtaga tacttcgaca ccttcaggaa    11760
aaatgatttt aactgtaatg agtgccgttg ctgaactcga aagagacatg atctatgatc    11820
gcactcaggg ggtagaaag actaaagccc aaaagggcgg gtatgcctac gggaaaccta    11880
aatttggcta taagactgaa gaaaaggaac taaaagaaga ttcagcacaa caggaaacta    11940
ttaaactaat taagagacac cgtaggtcag ggaaaagcta ccagaaaata gctgattatc    12000
tcaatgccca aagtattccc actaaacaag gtaagaaatg gagttctagc gtcgtctatc    12060
gaatctgtca ggaaaaagct ggttaagtct gtttatagat atttagaatt tattgaataa    12120
aaatagtatg aacaataaat atttatggac taaccacgct cggaaacgtt taactgaacg    12180
atgggaaata aaagaatcat gggttattga taccatcgaa aatcctgaac gttcagaatt    12240
tattgttgat gagtcagggg aaaaatatca ttactataaa agaatagcta agtttaagaa    12300
tagagtgtta gaagtgataa cttctgccaa ctcaacaccc acaagaataa taacctttta    12360
ctttaaccgt aacatgagga aaaatttatg attgttactt acgataatga agttgacgca    12420
atttatttta agttaacgga aaataaaatt gatagcaccg aacctcaaac agacaggatt    12480
atcattgatt acgatgaaag taataatatt gttggcattg aggtattaga ttttaattat    12540
cttgtcaaga aaggtttaac cgttgctgat ttaccttttt ctgaagatga aagattaaca    12600
```

FIG. 43 (continued)

```
gcttctcaat attttaattt tcctgttgct atctaatcca gaaggggcaa taatcccctt     12660
ctttcatcga gttagactta atatcacaaa agtcattttc attttaccgt ttcttttcca     12720
cagcgtccgt acgcccctcg ttaaatctca aaaccgacaa tttatgatgt ttataaaaag     12780
ttactcactt taataagtat ttatactcat taaagggtta ttcttttttt gtagcctgat     12840
aggttgggaa ggaatatttc agattatcag atttgttgaa tatttttcgt cagatacgca     12900
aaccttacaa acataattaa caactgaaac tattgatatg tctaggtttt agctctatca     12960
caggttggat ctg                                                        12973
```

FIG. 43 (continued)

ABICyano1 P*nirA** variants :

PnirA (native)
gtcgacaattaataacttcttcctgtacgggcgaatggccatttgctcctaactaactccgtactgctttgcggaacgagcgtagcgaactctccgaat
tactaagccttcatccctgatagATGCAAAAAACGAATtaaaattATGTGTAAAAAGAAAatgtgtctttatttaGTAGTCAAAGTTACaaaatattaa
gaatcaaattaa[redacted]attgggcagttaagtatataagtctttaaatatttatttgtattcaatatattaaCC[redacted]CAAAtt[redacted]aattc

**PnirA*2 (optimized ribosomal binding site)**
gtcgacaattaataacttcttcctgtacgggcgaatggccatttgctcctaactaactccgtactgctttgcggaacgagcgtagcgaactctccgaat
tactaagccttcatccctgatagATGCAAAAAACGAATtaaaattATGTGTAAAAAGAAAatgtgtctttatttaGTAGTCAAAGTTACaaaatattaa
gaatcaaattaa[redacted]attgggcagttaagtatataagtctttaaatatttatttgtattcaatatattaaG[redacted]TCAGCCtt[redacted]aattc

**PnirA*3 (optimized NtcA and NtcB binding sites and TATA box)**
GTCGactaagccttcatccctgatagATGCAAAAAACGCATtaaaattATGCGTAAAAAGCATatgtgtctttatttaGTAATCAAAGTTACaaattat
taagaatcaaattaa[redacted]attgggcagttaagtatataagtctttaaatatttatttgtattcaatatattaaCC[redacted]CAAAtt[redacted]aattc

**PnirA*4 (optimized NtcA and NtcB binding sites, TATA box and ribosomal binding site)**
GTCGactaagccttcatccctgatagATGCAAAAAACGCATtaaaattATGCGTAAAAAGCATatgtgtctttatttaGTAATCAAAGTTACaaattat
taagaatcaaattaa[redacted]attgggcagttaagtatataagtctttaaatatttatttgtattcaatatattaaG[redacted]TCAGCCtt[redacted]aattc

FIG. 44

Synechococcus PCC7002 PsmtA* variants for ABICyano1:

PsmtA native
ATCTAAAC...T...C...T...AT...G...T...G...AATC...A...TG...AATC...AC...A...AGACAATACCTTGGAGGTTTAAACC...aattc PsmtA*1
ATCTAAAC...T...C...T...AT...G...T...G...AATC...A...TG...AATC...AC...A...AGACAATACCAAGGAGGTGATAACC...aattc PsmtA*2
ATCTAAAC...T...C...T...AT...G...T...G...AATC...A...TG...AATC...AC...A...AGACAATACCAAGGAGGTATAAACC...aattc SmtB binding site 1     SmtB bindig site 2     RBS     EcoRI

Porf0128
cctcaactacaagttcttttatatattactttaacctgagttttggataagctgaaagcattattttctcgtagtcagaaaacctt
atagcttcttagaaataacgataaaattaccttaatccgaactgacgttaaatatattcacccctatcaccccaaaaccctaagcc
cctacttccccctttcccttcatcacctcatccccccatcccctaacacttaaccttattctttattcttaaaccgaactgaggtg
aagttgcagaatacccatggggggttacagcattgtagaaaaataaatattctttcattattaaggttgtttggtaaaaatatGTG
aaaaccctaataatt

FIG. 51A

Porf1486
ggggacagacatatttttatcataatggtaaattcataataattttagactttttttgcaaaaattaatctcactctcttctttc
cctatctcccattgtttcttatatcccaatgccccaatacccaaagctcagaaaataggtattagcgaagaggtgttgatcccctc
ccctagcaaaatatactcctatatagtaaagtgagaaagtgaagaaataagatcaagttcgcaattt

FIG. 51B

Porf3164
caaatcacgagaatttatgtagggactattttgggttgacggtggagagtatgtcgcccttgaattatgacccgaagatgaagatg
tcggggaggtggaaggacggtctttaagaggtttaacatcaaagttggtcataatctctgtccctgtttgataactactatttaat
tttgagttgttttaggtacatcaaaatacccaaatccttactctcccctcaatatacaacaaaaaaaactttttgattcactttag
tcataaaaattagaatttatctaccgaaatattacataaatgtaatgtatatattttctgatttattccgtgtgagccatgattca
taatttataattcataatttctaaatatgcccctacaatggatatagaatgtcattttaattataggtatcataatcgtggtagtt
actccggaaaaaactattgaatcaaattcagtctcacctgctacagatagagtagccgttattctt

FIG. 51C

Porf3293
ttgacgattgtattgacttacgccaaatggcttaccctcatagtgaatagttgataattaagaattaaaaatcccgttcacgacag
aagggagtgtaagagccttcggtgcgaactctcatcttccctgaaacctgacacctgaaacctgacacctgaaacctgacacctca
tctccctaatcccctaattttaatgaaaaaataccctgagtgggcattgaaaaaaaagaaaagttgttcgactatgaaataagaat
tctgcacttcgtgagaaaaaaggaaatgaaat

FIG. 51D

Porf3621 ctatttaactaggaaaaggtaaagttaaaaggacaagggtaaataattaaaaattaagaattaagaacttctaactctcattactc
attacttatttcctcctctcaccccttctcctgatcacctcttctcctcaatactcggaactcatttccccatggtgtgacactca
aatcaaaagtctgttattgactttcagatgaaatattactatgataacaatatccccccctatgggtatataaaaatatgagcgata
ttagttaaaaatcaaatttggatttttttttctgaaaatattttaagattaagtaaagataagtaaagaaattataagcaattttgt
taaatcatacc

FIG. 51E

Porf3635 ctcacactgaaaatattgccacaagaaataaagatcaagcaataatcctgactaaaaaggaataaagtaattatccttttcctgat
atgttatctgacttgttgtttcttagtcatgttccttccattttttattttttgtttttatcatttttattacaaaaatttcttaata
gggctaaagcatttagttagtttttttagctctcaacaagttgactaatcaatataatgccctaagttaatttgcccttggtttgac
ggaggatattggaaaaaagaaacttctcgttgtatttcacagggaaaaggggggaaattttattaataactaaacaatagaaaataa
ttatttatttatattattttgtgaacaaatgttcaagaattaaagtgtaataagaaaatttatttttttatatttatttaaaactt
agatataagcctaaaggtctgaaattattattagacaatcaattgattcagaggtaatagtttttttacttaaaaatatttttttcaa
aattatcccctatttgggtattgaaaaataaataaattcaagtaataatatacagaataaaggaaaatctaatcttaaaaatttttg
tgtgtgaggaattgaaa

FIG. 51F

Porf3858

TATCACCATTGTAGAAAAGCCAGAAAATCAATTAACACAAATTTCCTGTAAATTATTATGTATGATTTTC
CCCTTCTCCCCTTAAAAGGAGAAATAAAAAACTATATCCCCCAACCACCGATAAGCATTGTGAGAGAAAA
ATCATTTAGGTAGGATCAATGCTGTAACCGATAAAGATAAATAAATAATT

FIG. 51G

Porf1071 attctgtgaattgattagatttgaggtttttttaagaggttgattaccttgcctccaaaaaaaatcataacacactaatgctctatat
gaaagggctttagacccataggtttttgagaaaaaaaacttgctaactctcggacaatgtcagcataactaaagtcaattcttttcg
tactttataattgtctataatttaatatacaactgttctgaaactagtttttctctacattccttagttttatctgagtaaggttg
cttgtaacttaacttcggttgggcctaaaaatatccgattaggagcaggtgtcagactttaattaattattaattattaattgctt
attgccaaccctcggcgacaccactttttcatcagccccagataaagattgatgttttagttttgtttctttttatcccctaattc
aactaatacaagtaaaactaaggttgtttatcaaaaatgatggttgatgtttgggtaaattttaagatattatgaaaagaaaatga
ataaaaaatgaaaaatcttt

FIG. 51H

Porf1072 ctacaggggcaagatttggcggaaatctatatgtggattctctttcaagtgaagaaggtgcagtgccgacttatctggacttatta
gaatacgatattcgcactattactaatggtttgttagcaggagtgaacaattaaaaatttttcctaattgacgaataaaaaatca
atgtcaactaatagttaacaatactctctgaaaaccaaaaattgtcaaccaaaacataacataattttacccaaaaacctcattt
ataaactttaaggataaaatcaatg

FIG. 51I

Porf1074
gggattagagagttcaaagttaggaatgaggtgtcaggttttaggtttcaggtttaggggagcaatgagaaagaggtttcaggttt
caggtgtcaggttgcaggtgtcacaggtgatgaggggatgggggatgaggggaaacaagtaagtaataagtgttcggagttttta
attcttaattcttaatttttcctttgcctcttgccttttgccttgtcttaattactaatttctaattaaaatgattgtgttttcta
gtttagtctcatggttacttgaacccttacagcatagtttt

FIG. 51J

Porf1075
ttacaaacggcgggaattattatggtagtagcgatgttagtaaccccgggtgcgatcgcatatttacttacagatcgttttgatca
aatgttaatcttatcaatagttagtagtgttctatcttgtgttttaggcacttatttaagttatcattttgatgtttctacggggg
gaagtattgtcgttttaatgaccataatttttattttagcgatgatttttgctcctaaatatggcatcatcaatcaaaataccaaa
atatattctgcttaacttgtttactgatacttcaaataatcatataacctatcttccgagttaaaaataatggatattatccaact
gaggtcgagaatagagtttctttttttgatagaatttttttacaccagttattcattactatcatgggata

FIG. 51K

Porf1542
taatatagtgattattataaatgcaatgtgaatcaaacctatattttaccgtacattgaccatggaacttaatttgaggtgattag
tagagggtgcgatcgccctatttgtcaaataataaagataacatttgacattgctgattgaagacataaaacacagaaaaaatcag
gtaaaaatataaagctaaagtctaaatatggtttacttttgccttcgacttacaacaaaaaatcatagctagaatcaccaacgcct
aatattttatttagctgaaattttgggatgaacttttttgtaaaaatcgggggtctaaaaatatagcaaccacgatattaaataact
gagtgattattttaatctattggggggcttattaactaaatacttgcatttttatggagggttttaatt

FIG. 51L

Porf1823
aaagattattttctacagaagcaaccctttcatcttccgaattttcaggaatttcctgcttttgtttctgaatattagcataggcg
gcttttgcccactctaaagaaggttgagactgaatttctgaggtttcagaaggagcattagattgtttatcttcaacaacaggagg
tttttgttcaatattttccttattctctttttttacggcgaaaccaattaaacataatgattgtgcataaatattcgttaatatatt
gtaaccctagaaaggaatcggtttcaggtttatccccagagaatgtgaacctttacagaaagtaaaaagtctaaaatcgtagcaac
aataaatcacagaaattgag

FIG. 51M

Porf1824
ATCTAGTAATAATCATCAAGAGTTGTTAAAACTTCACTATCAAGAATTGGTAGCAAGAGGATTACAACAT
CTGAGTTTAGATCATCGAGCAGTTATTGTTCTTCATGATTTGGAAGATTTACCACAACAGGAAATAGCGG
AAATATTATCTATTCCCCTTGGTACGGTCAAATCTCGTTTATTCAAAGCCAGAAAAAATTTGCGTCAATT
TTTAGAACTTGAAGGTATTAGCTT

FIG. 51N

Porf3126
ccaatatcttgtcatacatacttatttgcctcactattagccctatatgtctctattgtatttttctttttctcctattcctagat
cttgtaatgaatcattactctctgaaatatagctactaattttatggttgtttgtaaaatatattaacaaatgaacaataaatcat
attttgtgttaatctaattattagacaactactgaatttatattcagatattcacagataggagaattttgatt

FIG. 51O

Porf3389
Attctattaccctccgagggtggctatctccttttatttggtggctgataaaaccctattctattaaagtagccaatgagttagtt
aatgcggcggctaaatgtcactaaaatttcatcttaggttcacatcaaagtcatatcggttgtttatagtattaagtgtcagggag
aaagataggttttcctctttagctccttcgcacctttaatccctgactttttttatttttttgttcgtgtgattaatctatttgtg
tagcaattatttttatcttattttcttttcagtctagtaattaattatttttatatttgtattatttttagagaggtttgagctg
tt

FIG. 51P

Porf0221
gaatatctcatccttagcttctacttataccttcagcatagttaaaaatcatccctttattgatggtaataaaagaacaggtttta
ttagtggagtaacctttttaatgctcaatggttctcactttactgcttctgaagtggaagtagtacatatcatccaaaccttagct
agtggcagaattaccgaggaagaattacaacaatggttcgtaaggaaaagtaagcagatgaataattaaagcatcatttcatcctc
atttcatattctcctgtcaccatggtatggaagattaggtaaaaatgaggaaaaagtttatt

FIG. 51Q

Porf0222
gcgattatcaaccacgaaaacatacaattattatcaaacctgctgagaaattatccacagaaatagatgtttctgcgaagggaaaa
tgggcttttcattgccatttaatgtatcacatggatgtgggaatgtttcggactattaatgttatttcctaaaaaataatagtatt
aaagcctaaaatttttataaaaaaattcatgtcttttattagggtgagcattcttcctttatgtctccttattttacctctttaga
ggtaactacaaacttaatcaaaaaatttagataattaattatatca

FIG. 51R

Porf0223 atacatggttggttcactgacttttaccccagttttctctttgaacaattggcataactctgaaaaaatcagatcgggcttttgtt
gaattatttgttcaatcaaagcaaaaccgtgattgtctattttcttttttttcccaccactcatagataaaaatttatcccgaact
caggttatattaagttcggatgatcacttaagataattgatcagattggttaagatagagaaaaattctttttcatagtgatttca
taattgatagttacaataacgattattatttagtaaaaagattttcaaatc

FIG. 51S

Porf0316 tggtcaagttactatatgtttagaaacaacaaaaaaagaagtcattataaaaataattgatacaggaattggcattaataaagaag
aacaaaaattaattttaatcgtttttatcgaatcaataaagcaagaaatagagagaaaggcagttgcggattaggtttagctatt
gcaaatgcgatcgcgcttaatcatggtggtagaataattttagaaagtcaagaaaatcaaggcagtatttttaccgtttatttacc
gaaaatcatttcatcctaatttcatattcttttgacagaatcaaaggtaaagataaaaagagagaaacagtc

FIG. 51T

Porf3232 catctttacttttgactaacatttcataggtatcatgacgaaaatttttagtctgttatatttgttcatgtagagagattttaat
ttgtgattattttatttctctctatttttctttttgtcttgtccttcctcatttttctctacatttagtctaaactacagctct
ttaatcttcagtttctctttcctcctcttcctcatcaaggtaatcatcccaattaatatcttcttcttgttctaatttgggttgag
attgttgtttatcaatcatatttcatactcctaaaactttcttacttatttatcagttacttttttacccatttatgcaatagtgta
gaaatttttttcgatcgagttaattaatttttatttcaaccatatctaaataattcttgatggacattctagttaactagaaggtt
taagctaaaaataattattgatattgccttcggtataactaactatatccagagaaaaag

FIG. 51U

Porf3461 (petJ)

tttatatataaactcgaataaaattatcaatataaagtcaaactatatctatcctattttaactgctattggtaagtcccttaatt
agtgttggggtgaatagattttaaaagggcaaacccccctttatcctccctcgagagggggagggcaaaaggcaaggggcaaggg
aaaaattaagaattaagaattaaaaactccgaacacctgtaggggcgaatagccattcgcttcccctcatccccccatctccccaa
caccctaagcccctactcgttactcatttatttacatcatttatttacatcattaagaaaagtaacaaattttgacaagtagtctt
ttgacaggaaaaagcaaattctcgaagatgaaaacaatagaaaaaaattcaatcttacagtaacgatgaaaaaacttttaggctta
att

FIG. 51V

Porf3749 ctcaagagatagttaaaaaacaaatagctttagtctatcaattaatcgaattatttttacaaacaaattttcataaacccatagaa
ctagaggaggaagttatttatgtttaaaaatctaaaagagttttatattcccctaaaaccccccttagtaagagtgactttttcat
catttgcctgtaaattctcctcttttaataagagagctagggtgttttaaaagaggattttattgctttccaattctaactacttc
aaaaacttattttatactcaataatttattaatcaagaggaaattacc

FIG. 51W

TK441 pABICyano:PpetJABICyano1-PDCmax-PrpsLABICyano-synADHmax-PrbcABICyano-Km**

```
ID   TK441\pABICyano:PpetJABICyano1-PDCmax-PrpsLABICyano-synADHmax-PrbcABICyano-Km**-
oriVT standard; circular DNA;    ; 13604 BP.
CC   This file is created by Vector NTI
CC   http://www.invitrogen.com/
CC   VNTDATE|639135285|
CC   VNTDBDATE|639135515|
CC   LSOWNER|
CC   VNTAUTHORNAME|Irina Piven|
FH   Key             Location/Qualifiers
FH
FT   promoter        4210..4735
FT                   /vntifkey="30"
FT                   /label=PrbcABICyano
FT   CDS             4737..5552
FT                   /vntifkey="4"
FT                   /label=Km**
FT                   /note="Km**"
FT   CDS             13114..13362
FT                   /vntifkey="4"
FT                   /label=ORF\6
FT                   /note="orf6"
FT   CDS             12854..13117
FT                   /vntifkey="4"
FT                   /label=ORF\5
FT                   /note="orf5"
FT   CDS             12126..12812
FT                   /vntifkey="4"
FT                   /label=ORF\4
FT                   /note="orf4 Integrase/Recombinase Similar to Site-specific
recombinase of Bacillus thuringiensis serovar israelensis ATCC 35646"
FT   CDS             complement(11036..11800)
FT                   /vntifkey="4"
FT                   /label=ORF\3
FT                   /note="orf3"
FT   CDS             10591..10776
FT                   /vntifkey="4"
FT                   /label=ORF\2
FT                   /note="orf2"
FT   rep_origin      complement(9891..9908)
FT                   /vntifkey="33"
FT                   /label=Rep_Origin_1\(potential)
FT                   /note="potential rep origin; match pNostoc (Acc# M81381) nick
site (358-375); on reserse strand"
FT   misc_feature    10151..10184
FT                   /vntifkey="21"
FT                   /label=Rep\motif
FT                   /note="Rep protein active site motig EXXKYXVKXXD"
FT   CDS             7370..10555
```

FIG. 54

```
FT                   /vntifkey="4"
FT                   /label=ORF\1
FT                   /note="orf1  rep ori binding protein slr7037 homolog Similar to
hypothetical protein slr7037 of plasmid pSYSA (103 kb)  of Synechocystis sp. PCC 6803"
FT   rep_origin      complement(5795..6853)
FT                   /vntifkey="33"
FT                   /label=OriVT
FT   insertion_seq   6860..89
FT                   /source="pABICyano1-6HindIIIBamHI"
FT                   /type="Custom cloned insert"
FT                   /vntifkey="14"
FT                   /label=pABICyano1-6HindIIIBamHI
FT                   /note="Unknown feature type:insert"
FT   promoter        2267..2835
FT                   /vntifkey="30"
FT                   /label=PrpsLABICyano
FT   gene            534..2243
FT                   /vntifkey="60"
FT                   /note="PDC"
FT   gene            2839..3849
FT                   /vntifkey="60"
FT                   /note="ADH"
FT   CDS             534..2240
FT                   /vntifkey="4"
FT                   /label=PDCmax
FT   CDS             2839..3846
FT                   /vntifkey="4"
FT                   /label=synADHmax
FT   terminator      3850..4005
FT                   /vntifkey="43"
FT                   /label=TrbcSABICyano1
FT   promoter        101..509
FT                   /vntifkey="30"
FT                   /label=PpetJABICyano
FT   CDS             510..533
FT                   /vntifkey="4"
FT                   /label=petJABICYano
SQ   Sequence 13604 BP; 4252 A; 2378 C; 2622 G; 4352 t;
     aatatttttc gtcagatacg caaaccttac aaacataatt aacaactgaa actattgata        60
     tgtctaggtt ttagctctat cacaggttgg atctgtcgac tttatatata aactcgaata       120
     aaattatcaa tataaagtca aactatatct atcctatttt aactgctatt ggtaagtccc       180
     ttaattagtg ttggggtgaa tagattttaa aagggcaaac ccccctttat cctccctcga       240
     gaggggggag ggcaaaaggc aaggggcaag ggaaaaatta agaattaaga attaaaaact       300
     ccgaacacct gtaggggcga atagccattc gcttcccctc atccccccat ctccccaaca       360
     ccctaagccc ctactcgtta ctcatttatt tacatcattt atttacatca ttaagaaaag       420
     taacaaattt tgacaagtag tcttttgaca ggaaaaagca aattctcgaa gatgaaaaca       480
     atagaaaaaa attcaatctt acagtaacga tgaaaaaact tttaggctta attatgaatt       540
     cttataccgt gggtacttat ttagccgaac gcttagtgca aattggttta aaacatcatt       600
     ttgccgtggc tggggactat aatttagtgt tattggataa cttattatta aataaaaaca       660
     tggaacaagt gtattgttgt aatgaattaa attgtggttt ttctgctgaa ggttatgcta       720
     gagctaaagg tgcagctgct gctgttgtta cttattctgt gggtgcttta tctgcttttg       780
     atgctattgg tggtgcttat gccgaaaatt tacccgtgat tttaatttct ggtgccccta       840
     ataataatga tcatgccgct ggacatgttt tacatcatgc cttaggtaaa accgattatc       900
```

FIG. 54 (continued)

```
attatcaatt agaaatggcc aaaaatatta ctgctgctgc cgaagctatt tatactcctg    960
aagaagcccc tgccaaaatt gatcatgtga ttaaaaccgc cttacgcgaa aaaaaacccg   1020
tgtatttaga aattgcctgt aatattgctt ctatgccttg tgctgctcct gggcctgctt   1080
ctgctttatt taatgatgaa gcctctgatg aagctagttt aaatgctgcc gtggaagaaa   1140
ccttaaaatt tattgccaat cgcgataaag ttgccgtgtt agttggttct aaattaagag   1200
ctgctggtgc tgaagaagct gctgttaaat ttgctgatgc tttaggtggt gcagttgcta   1260
ctatggctgc tgccaaatct ttttttcccg aagaaaatcc ccattatatt ggaactagtt   1320
ggggagaagt ttcttatcct ggtgtggaaa aaactatgaa agaagccgac gctgttattg   1380
ctttagcccc tgtgtttaat gattattcta ccactggttg gactgatatt cccgatccca   1440
aaaaattagt tttagccgaa cctcgttctg ttgttgttaa tggtgttcgc tttccctctg   1500
tgcatttaaa agattattta acccgcttag cccaaaaagt ttctaaaaaa actggtgcct   1560
tagatttttt taaatcttta aatgcgggtg aattaaaaaa agctgctcct gctgatcctt   1620
ctgctccttt agttaatgct gaaattgccc gtcaagttga agccttatta acccctaata   1680
ctaccgttat tgccgaaact ggtgattctt ggtttaatgc ccaacgcatg aaattaccta   1740
atggtgcccg tgttgaatat gaaatgcaat ggggtcatat tggttggtct gtacctgctg   1800
cttttggtta tgctgttggt gctcctgaac gtcgtaatat tttaatggtg ggtgatggtt   1860
cttttcaatt aactgcccaa gaagttgccc aaatggttcg cttaaaatta cccgttatta   1920
tttttttaat aaataattat ggttatacca ttgaagtgat gattcatgat gggccatata   1980
ataatattaa aaattgggat tatgcgggtt taatggaagt gtttaatggt aatggtggtt   2040
atgattctgg tgctggtaaa ggtttaaaag ccaaaactgg tggtgaatta gctgaagcta   2100
ttaaagttgc cttagccaat actgatgggc caaccttaat tgaatgtttt attggtcgcg   2160
aagattgtac cgaagaatta gttaaatggg gtaaacgtgt tgctgctgct aattctcgca   2220
aacccgtgaa taaattattg taatttttgg ggatcaattc gagctcctcc gcttaaaaaa   2280
tttcattttt cgatcaaaaa agacaaatta ttactaatta gctcatggca ataaataatc   2340
agtagtaatc tgttttcaca ttttattgtt aatttttatt attgctaata tcaacctttt   2400
ctacttctgc ttaatatttt atttatgctc aatgggaaaa tctgaaataa gattgagaac   2460
agtgttacca atagaagtat ttaaggttta aagcatacct taaagataac attttttttt   2520
gaaaagagtc aaattatttt tgaaaggctg atatttttga tatttactaa tattttattt   2580
atttcttttt cccttaaaat aagagctaaa tctgttttta ttatcattta tcaagctcta   2640
ttaatacctc aactttttca agaaaaaata ataataattt ttccctctat tctcatgacc   2700
ttttaggaaa attaatttta gaaaaactat tgacaaaccc ataaaaaatg agataagatt   2760
atagattgtc actggtattt tatactagag gcaaattata tttatatata caaaaatgct   2820
gtataaaaaa catctcatat gattaaagcc tatgctgcct tagaagccaa tggtaaatta   2880
caaccctttg aatatgatcc tggtgcttta ggtgccaatg aagtggaaat tgaagtgcaa   2940
tattgtggtg tgtgtcattc tgatttatct atgattaata atgaatgggg tatttctaat   3000
tatcccttag ttcctggtca tgaagttgtt ggtactgttg ctgctatggg tgaaggtgtt   3060
aatcatgtgg aagtgggtga tttagttggt ttaggttggc attctggtta ttgtatgacc   3120
tgtcattctt gtttatctgg ttatcataat ttatgtgcca ctgccgaatc tactattgtg   3180
ggtcattatg gtggttttgg tgatagagtt cgtgctaaag gtgtttctgt ggtgaaatta   3240
cccaaaggta ttgatttagc ctctgctggg cctttatttt gtggtggtat taccgttttt   3300
tctcccatgg tggaattatc tttaaaacct accgccaaag ttgctgttat tggtattggt   3360
ggtttaggtc atttagccgt tcaattttta agagcctggg gttgtgaagt tactgctttt   3420
acctcttctg cccgtaaaca aaccgaagtt ttagaattag gtgcccatca tattttagat   3480
tctaccaatc ctgaagctat tgcttctgcc gaaggtaaat ttgattatat tatttctacc   3540
gtgaatttaa aattagattg gaatttatat atcagtacct tagcccctca aggtcatttt   3600
cattttgttg gtgtggtgtt agaacccttg gacttaaact tatttccctt attaatggga   3660
caacgttctg tttctgcttc tcctgttggt tctcctgcta ctattgccac tatgttagat   3720
tttgccgtgc gtcatgatat taaacccgtg gtggaacaat ttcttttgga tcaaattaat   3780
gaagccattg cccatttaga atctggtaaa gcccattatc gcgtggtgtt atctcattct   3840
aaaaattaat aagattaact tctaaactga aacaaatttg agggtaggct tcattgtctg   3900
cccttatttt tttatttagg aaaagtgaac agactaaaga gtgttggctc tattgctttg   3960
agtatgtaaa ttaggcgttg ctgaattaag gtatgatttt tgacccccttc tctcttctgc   4020
agttacctag gatttctggc gaaaggggga tgtgctgcaa ggcgattaag ttgggtaacg   4080
```

FIG. 54 (continued)

```
ccagggtttt cccagtcacg acgttgtaaa acgacggcca gtgagcgcga cgtaatacga 4140
ctcactatag ggcgaattgg cggaaggccg tcaaggccgc atggcgcgcc tacgtagaca 4200
attgtcgatg taattattaa ctatcttatt atagatgagg ggagagggag aaattagttc 4260
ggagagaacg ctcgagcgct cgttccgcaa agcggtacgg agttagttag ggctaatgg 4320
gcattctccc gtacaggaaa gagttagaag ttattaatta tcaacaattc tcctttgcct 4380
agtgcatcgt taccttttta attaaaacat aaggaaaact aataatcgta ataatttaac 4440
ctcaaagtgt aaagaaatgt gaaattctga cttttataac gttaaagagg gaaaaattag 4500
cagtttaaaa tacctagaga atagtctggg gtaagcatag agaattagat tagttaagtt 4560
aatcaaattc agaaaaaata ataatcgtaa atagttaatc tgggtgtata gaaaatgatc 4620
cccttcatga taagatttaa actcgaaaag caaaagccaa aaaactaact tccattaaaa 4680
gaagttgtta catataacgc tataaagaaa atttatatat ttggaggata ccaaccatgt 4740
ctcatattca acgtgaaact agttgttctc gtcctcgttt aaattctaat atggatgccg 4800
atttatatgg ttataaatgg gctcgtgata atgttggtca atctggtgct actatttatc 4860
gtttatatgg taaacctgat gctcctgaat tattcttgaa acatggtaaa ggttctgttg 4920
ctaatgatgt tactgatgaa atggttcgtt taaactggtt gactgaattt atgcctttac 4980
ctactattaa acatttttatt cgtactcccg atgatgcttg gttattaact actgctattc 5040
ctggtaaaac tgcttttcaa gttttagaag aatatcctga ttctggtgaa aatattgttg 5100
atgctttagc tgttttttta cgtcgtttac attctattcc cgtttgtaat tgtcctttta 5160
attctgatcg tgtttttcgt ttagctcaag ctcaatctcg tatgaataat ggtttagttg 5220
atgcttctga ttttgatgat gaacgtaatg gttggcctgt tgaacaagtt tggaaagaaa 5280
tgcacaaatt gttacctttt tctcctgatt ctgttgttac tcatggtgat ttttctttag 5340
ataatttgat ctttgatgaa ggtaaattga ttggttgtat tgatgttggt cgtgttggta 5400
ttgctgatcg ttatcaagat ttagctattt tatggaattg tttaggtgaa ttttctcctt 5460
ctttacagaa acgtttattt cagaaatatg gtattgataa tcctgatatg aacaagttac 5520
aatttcattt aatgttggac gagttctttt aagaattaat tcatgaccaa aatcccttaa 5580
cgtgagtttt cgttccactg agcgtcagac cccgtagaaa agatcaaagg atcttcttga 5640
gatccttttt ttctgcgcgt aatctgctgc tatttaaatt acgtacacgt gttattactt 5700
tgttaacgac aattgtctta attaactggg cctcatgggc cttccgctca ctgcccgctt 5760
tccagtcggg aaacctgtcg tgccagctct gcagatgacg gtgaaaacct ctgacacatg 5820
cagctcccgg agacggtcac agcttgtctg taagcggatg ccgggagcag acaagcccgt 5880
cagggcgcgt cagcgggtgt tggcgggtgt cggggcgcag ccatgaccca gtcacgtagc 5940
gatagcggag tgtatactgg cttaactatg cggcatcaga gcagattgta ctgagagtgc 6000
accatatgcg gtgtgaaata ccgcacagat gcgtaaggag aaaataccgc atcaggcgct 6060
cttccgcttc ctcgctcact gactcgctgc gctcggtcgt tcggctgcgg cgagcggtat 6120
cagctcactc aaaggcggta atacggttat ccacagaatc aggggataac gcaggaaaga 6180
acatgtgagc aaaaggccag caaaaggcca ggaaccgtaa aaaggccgcg ttgctggcgt 6240
ttttccatag gctccgcccc cctgacgagc atcacaaaaa tcgacgctca agtcagaggt 6300
ggcgaaaccc gacaggacta taaagatacc aggcgtttcc ccctggaagc tccctcgtgc 6360
gctctcctgt tccgaccctg ccgcttaccg gatacctgtc cgcctttctc ccttcgggaa 6420
gcgtggcgct ttctcatagc tcacgctgta ggtatctcag ttcggtgtag gtcgttcgct 6480
ccaagctggg ctgtgtgcac gaaccccccg ttcagcccga ccgctgcgcc ttatccggta 6540
actatcgtct tgagtccaac ccggtaagac acgacttatc gccactggca gcagccactg 6600
gtaacaggat tagcagagcg aggtatgtag gcggtgctac agagttcttg aagtggtggc 6660
ctaactacgg ctacactaga aggacagtat ttggtatctg cgctctgctg aagccagtta 6720
ccttcggaaa aagagttggt agctcttgat ccggcaaaca aaccaccgct ggtagcggtg 6780
gtttttttgt ttgcaagcag cagattacgc gcagaaaaaa aggatctcaa gaagatcctt 6840
tgatcttttc tactgcagaa gcttgttaga caccctgtca tgtattttat attatttatt 6900
tcaccatacg gattaagtga aacctaatga aaatagtact ttcggagctt taactttaat 6960
gaaggtatgt ttttttatag acatcgatgt ctggtttaac aataggaaaa agtagctaaa 7020
actcccatga attaaagaaa taacaaggtg tctaacaacc tgttattaag aatgttagaa 7080
aagacttaac atttgtgttg agtttttata gacattggtg tctagacata cggtagataa 7140
```

FIG. 54 (continued)

```
ggtttgctca aaaataaaat aaaaaaagat tggactaaaa aacatttaat ttagtacaat    7200
ttaattagtt attttttcgt ctcaaatttt gctttgttga gcagaaattt agataaaaaa    7260
atccccgtga tcagattaca atgtcgttca ttgtacgatg tgtcgaaaaa tctttacgac    7320
actctaaact gaccacacgg gggaaaaaga aaactgaact aataacatca tgatactcgg    7380
aaaacctagc aattctcaac ccctaaacaa aagaaacttc caaaaccctg accatataaa    7440
ggagtggcaa caatcagcaa tcagtcaaga tttgatagca gaaaatcttg tatcggttgc    7500
taatggtttt gatgtactat ttatcggcaa taaataccga actaacacgg gtgttctgtc    7560
acggcacata ttaaactcct attctcattt agaagatggt ggttcgtatg gtagaacatt    7620
tgacccattt accaataaag aaatgcagtg ggttcaattt aaaccgaata gaccaagaaa    7680
aggttctact ggtaaggtaa tcaaatatga atcgccaaaa ggtgaaccta caagagttct    7740
aatgccgttt gtgcctatga aaatatggca acggattagc gataagttcg gagtaccgat    7800
taatccgaaa aaagatactc acttttggga atgggtaaag aataatccat cgataccgat    7860
tgccattaca gaaggaaata aaaaagctaa ttgcctatta tcctatggct atcctgctat    7920
tgcctttgta ggcatttgga acggattaga gaaaataaat gatttctcga aggaaaagca    7980
gttaaaagag gatttgaaat ggttgttatc caacggcaac cgaaatatta atatcatctt    8040
tgaccaagac cagaaacaaa aaactgtaat taatgtaaac aaagctattt tcgctttatc    8100
ttctctaata agtagaaatg gtcataaagt taatattgtg caatggttgc cgtcaaaagg    8160
taaaggaata gatgattatt tggtagcttt acctttgag aaaagagaaa atcatttaga    8220
caacttaatt aaaattgcac catcatttaa tttttggtca actaaatact tattcaagtg    8280
tcgtaaacca gatttaaccg taaattgccg ttatttgagc gatgcagtaa aagaattacc    8340
tcaagaggat atagcattaa tagcacctca cggcacgggt aaaacttcat tagtagctac    8400
tcacgttaag aatcggagtt atcacggaag gaaaactatt tcattggtgc atcttgaaag    8460
tttagccaaa gctaatggca acgcacttgg attatattac cgaaccgaaa ataatattga    8520
aaagcaatat cttggattta gcttatgtgt agatagttgc cgtgataaga ttaacggcat    8580
tacaactgat attatttcag gtcaagatta ttgccttttc attgatgaaa ttgaccaagt    8640
aattccacac atccttaaca gtgaaactga agtaagtaag tatagatgca ccatcattga    8700
cactttttct gaactggtga gaaatgctga acaggtcatt attgctgatg ctgatttatc    8760
cgatgtgacg attgacctaa tagaaaacat cagaggtaaa aaactatatg taatcaagaa    8820
tgaatatcag tatcagggaa tgacttttaa cgccgttggt tcaccattag aaatgatggc    8880
aatgatggga aaatcggtgt cagaaggcaa gaaattattt attaacacca catcccaaaa    8940
ggcaaaaagt aagtacggca caatcgctct tgagtcttat atttttggtc taaataaaga    9000
agcaaagata ttaagaatag actctgaaac cactaaaaac cctgaacatc cagcctataa    9060
aatcattgac caagacttaa ataatatcct caaagattat gattatgtca ttgcctcacc    9120
ttgccttcaa acaggtgtca gtattacctt aaaagggcat tttgaccagc aatttaactt    9180
ttccagtgga aacattacac ctcattgctt tttacagcaa atgtggcggt tgagggatgc    9240
agaaattgaa agattctatt atgtgccgaa ctcatctaac ctcaatctca ttgggaataa    9300
gtcaagttca ccatcagacc ttctaaagag caataacaag atggcaacgg caacggttaa    9360
cctttgggt agaatcgact ccgaatattc cctagagtat gaatcgcacg gcatttggct    9420
tgagacgtgg gcaaaattat cagcacggca taacagttca atgcgttgtt actctgaaat    9480
tcttacctat ctaattacgt ctcaagggca taaattaaat atcaacattc cctcacctct    9540
tgcagatatt aagaagctaa atgatgaggt aagtagtaac agggaaaagg taaaaaatga    9600
gagatactct cagaggttaa actcaccaga tattaacgat gcagaagcta ccatactcga    9660
atctaaagag caaaaaatcg gattgactct caatgagaga tgcaccctag aaaagcataa    9720
agttaagaag cggtatggga atgtaaagat ggatattctc acctttgatg atgatggact    9780
ataccccaaa ctcagactat tttattacct caccatcggt aaacctcatc tcaaggctaa    9840
tgacagaaaa gctattgcca aaatgggcaa tgacaataaa ggcaagattc tatcaaaaga    9900
cttagttaat aaaacttact ccgctcgtgt gaaggtctta gagattctta aactaactga    9960
ctttatcgac aatcttagag atgaactctt aataactccc aataatccag ctatcaccga   10020
ttttaataat cttctgctaa gagctaagaa ggatttaaga gtattaggag tcaacatcgg   10080
aaaatatcca atggccaaca ttaatgccgt acttactctc attggtcaca aactttctgt   10140
aatgagagat gagttcggaa aagagaaaag gataaaagta gatggtaaat cataccgatg   10200
ttatcaactt gaaacattac cagattttac caatgatact cttgactact ggttagaaaa   10260
tgatagccaa aaagaagtaa cagcaacaga aaattactcc gaaaatttta acccttcaaa   10320
```

FIG. 54 (continued)

tagctacaat ccagacagta agacactttc agagggtgca aatttcctat atataaataa 10380
agaagaattg catccaaata aattgcacct agaaataaaa gaaggtgctg aacttttttt 10440
attcggggta aaggtgattg tgaaaggaat cttggacggg gcagtaacta tattctctat 10500
gggtcaagaa tacgatttat ccctcaatga actagagggg atgttaacat catgaacttt 10560
acaagaatct ttttaaaggg cgatcgcacc atgttaaatg atggtacatt tgttcagata 10620
tttgatattt accatgacca cgcattggga gtgacccttg accttaagac agaaaaaatt 10680
atttccgatg atgttagggt aattactgtc aaagacttat tgttcgatgg cacttataaa 10740
ggggtaaaat cttttatgcc cgataatgcc cgataatgcc cgattgatgc tacaaaatcc 10800
cataatcata agcgataatc ccctaatagc ttgtaattct tgaaccgtag cgattttaga 10860
gtattccaaa aagaagaaat aaacaccgca aaatgtcgta tttcacatat ataaaccaag 10920
gtttttgcc ctaaaatctt tatgtttgta gtgtgatgtt gggtcaaaat ggtcagaaaa 10980
gttgcaaggt ttttatggat gcttacgcgc gcgaggggta agcatcccca aatagttact 11040
ttatcctagt ccatgcccat ttattgccgt cccgttcggc tttaaaaaag tgccaaaact 11100
cacaaggtgc aataaaaagt tctgtacctt tcgcaaccct agataatctt tcaacagtta 11160
cttttttcc tattatctcg gtacaaagtt tggctagttt ctcttttccc tctttttcaa 11220
tcaagccttc ttgtatgccc aactcattga ttaatctctc tatttttacc attatttccc 11280
gttcaggtag tttatcccct aaatcttcat cggggggcaa tgtagggcat tctgaagggg 11340
ctttttcttc tgtctggaca ttatctaata ttgaagtaac caaactatct tcagtttttt 11400
ctattcctat taattcatat tcggttactg tatccgtatc aatatccgaa taactatctt 11460
tatccgtatt agctattcgg ttaagtttat ccgttaactc agaaacaaga ctatatagcg 11520
gttttagctt ttcttctatc ctgttatcta atacggataa gtttatacgg ttatcattat 11580
ccgtattagt atcattgggc tttttggta gttctacccc ctcataaacc gcttttattc 11640
ccaattccaa cagactgata acagtatcct ttataatggg tttttgctg atatggtgaa 11700
cttttgcccc ttccatcatt gcgatacttt ctatctcact catcaactta tcgcttaagt 11760
gaatctcgta tctgtttaat cccttactgg ttttattcat atccgtttac tttattcggt 11820
taacaattct attttatacg aataaaatat tatacggtta actttatacg tttaactatt 11880
ttatctatac ggataacagt aataagttat tcgtattagt tatacgttta cttttatcca 11940
aataaaatta gtgcatttaa actaaaagaa tgattttatc ggagttgata gcattggatt 12000
aacctaaaga tgtttataag ctatatctga taagtattta aggttatttt gttattctgt 12060
ttattgacat tatcagaata aaagaataga atataattgt tgagagataa gaggtttaag 12120
tgattatggt taagaagtta gttggttatg tcagggtcag tagtgaatcg caagaggata 12180
acactagctt acagaatcag atagagagaa ttgaagcata ttgtatggct tttggttatg 12240
agttggtaaa aatattcaaa gaggttgcca ctggtacaaa agcagatatt gaaacccgtc 12300
ctatttttaa tgaagctata gaatacttga aacaggataa tgctaatgga attattgcct 12360
tgaagctaga ccgaatcgca cggaatgctt tagatgtatt gcgtttggtt cgtgaaacct 12420
tagaaccaca aaataaaatg ttagtgttac tagatattca ggtagatact tcgacacctt 12480
caggaaaaat gattttaact gtaatgagtg ccgttgctga actcgaaaga gacatgatct 12540
atgatcgcac tcaggggggt agaaagacta aagcccaaaa gggcgggtat gcctacggga 12600
aacctaaatt tggctataag actgaagaaa aggaactaaa agaagattca gcacaacagg 12660
aaactattaa actaattaag agacaccgta ggtcagggaa aagctaccag aaaatagctg 12720
attatctcaa tgcccaaagt attcccacta aacaaggtaa gaaatggagt tctagcgtcg 12780
tctatcgaat ctgtcaggaa aaagctggtt aagtctgttt atagatattt agaatttatt 12840
gaataaaaat agtatgaaca ataaatattt atggactaac cacgctcgga aacgtttaac 12900
tgaacgatgg gaaataaaag aatcatgggt tattgatacc atcgaaaatc ctgaacgttc 12960
agaatttatt gttgatgagt caggggaaaa atatcattac tataaaagaa tagctaagtt 13020
taagaataga gtgttagaag tgataacttc tgccaactca acacccacaa gaataataac 13080
cttttacttt aaccgtaaca tgaggaaaaa tttatgattg ttacttacga taatgaagtt 13140
gacgcaattt attttaagtt aacggaaaat aaaattgata gcaccgaacc tcaaacagac 13200
aggattatca ttgattacga tgaaagtaat aatattgttg gcattgaggt attagatttt 13260
aattatcttg tcaagaaagg tttaaccgtt gctgatttac ctttttctga agatgaaaga 13320
ttaacagctt ctcaatattt taatttcct gttgctatct aatccagaag ggcaataat 13380
ccccttcttt catcgagtta gacttaatat cacaaaagtc attttcattt taccgtttct 13440
tttccacagc gtccgtacgc ccctcgttaa atctcaaaac cgacaattta tgatgtttat 13500

FIG. 54 (continued)

```
aaaaagttac tcactttaat aagtatttat actcattaaa gggttattct ttttttgtag     13560
cctgataggt tgggaaggaa tatttcagat tatcagattt gttg                     13604
//
```

FIG. 54 (continued)

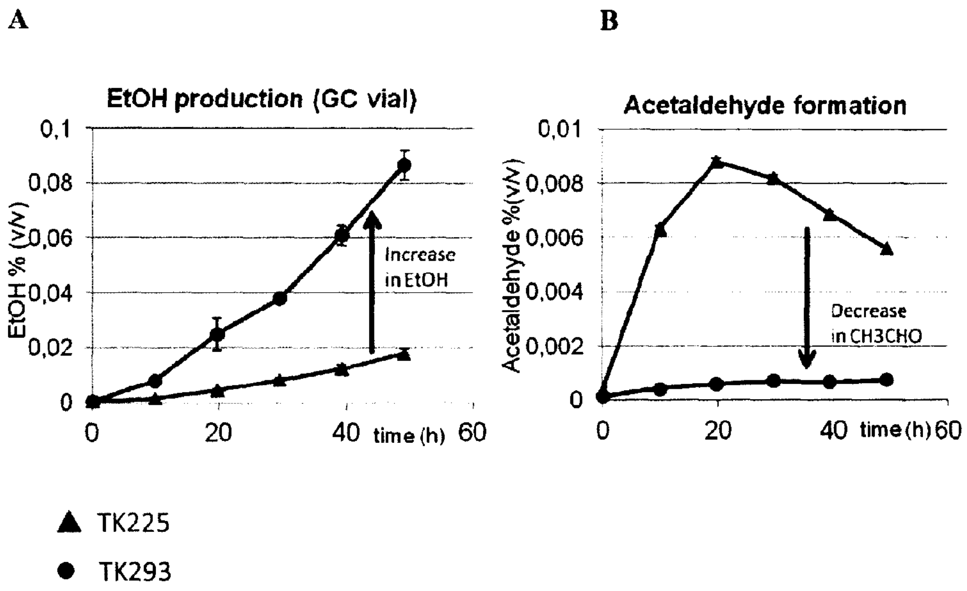
FIG. 56 A and 56B

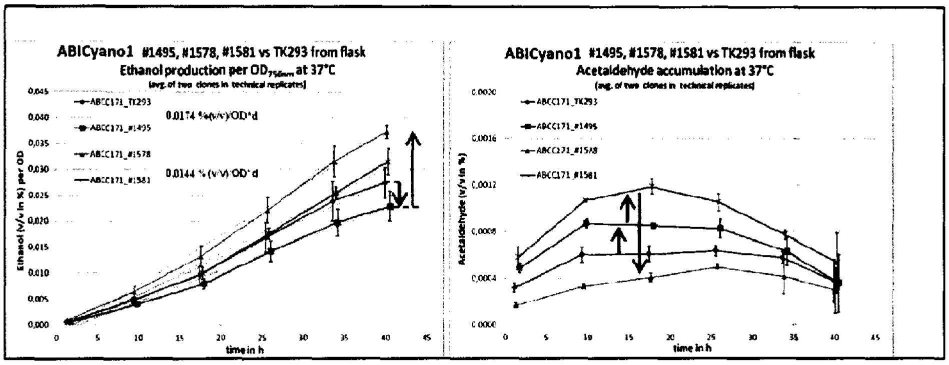
FIG. 59 A and 59B

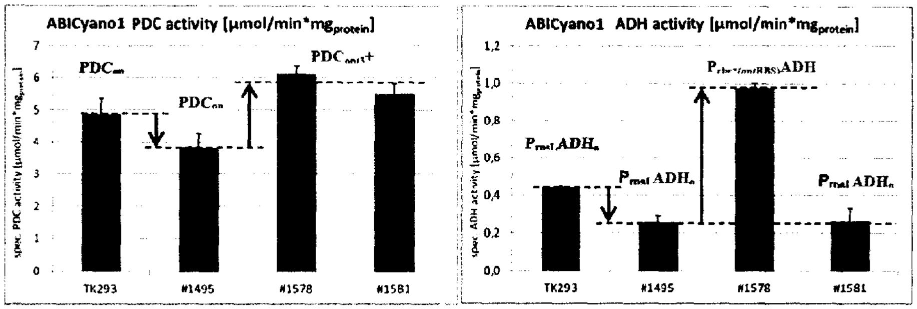
FIG. 60 A and 60 B

**<18_*lrtA* gene promoter;DNA;Cyanobacterium ABICyano1>**

TAGAGTATGATAAAATGACAAGGAAAGGATTATTTTCTCTTGTTTAAATTCTCAAGATTCTTATGCTTATT
TATTTTATGTAAGTGTCTCTTTTCCTTGAAATAGAAAGAAAAAAGTGGCTAATTTTGAGAAAAGCTAACA
ACGCTTTGGTTAACTAAAAATCAAAAGTGAGATTACTGATCGCTTAAGAAATGGAGTATTGATT

FIG. 61 A

**<19_*mrgA* gene promoter;DNA;Cyanobacterium ABICyano1>**

AGAGTTATATTTACATAGTGTGTGCGAGTAAGGGCAACTTTTGTAGGTAGATGAATAAACCTCAAATTAC
TCATCTTAAAAGACGATATTTTTAATCTATTCTTCTGTAATAAAATACTTCTTTCGATAGAGATATTTAATA
CTTTTGAGAGATGAAAATAATTTCAATAATTGTCATGATAGAGAGTAAGTGCAAATAAGAAAAAATTGAT
TT

FIG. 61 B

**<20_*nblA* gene promoter;DNA;Cyanobacterium ABICyano1>**

GCAGTTAGATAAATAAGTAATGAGCGGGAGAAATAGGGGCAAATGGCCATTCGCCCCTACAGGGAGGTG
GCAGGTGTTAGGGTGTTTAGGGGATGAGGTGATGAGGGTAGAGGGAGATAAGGTGTCGGGTTTCAGAT
TTCAGGTTTTAGAAGAAAGTAACGAGTAATTATCAACTATTCACTATTCACTATTGCCTGTTGCCCTTCTC
TCCTTGAAATATAAAAAAATGTAAAAATATCATTAAGAAAAGTAACAAAATAAACAGAAAGGTTGACAAA
GTTGACGCTTTAATATCCGTATGTTAGCTTTATAACAACGAAATCAACGGAGGAGTGAAA

FIG. 61 C

**<21_*ggpS* (glucosylglycerol-phosphate synthase) gene promoter;DNA;Cyanobacterium ABICyano1>**

CTTGAAAAAGTTGAGGTATTAATAGAGCTTGATAAATGATAATAAAAACAGATTTAGCTCTTATTTTAAG
GGAAAAAGAAATAAATAAAATATTAGTAAATATCAAAAATATCAGCCTTTCAAAAATAATTTGACTCTTTT
CAAAAAAAAAATGTTATCTTTAAGGTATGCTTTAAACCTTAAATACTTCTATTGGTAACACTGTTCTCAATC
TTATTTCAGATTTTCCCATTGAGCATAAATAAAATATTAAGCAGAAGTAGAAAAGGTTGATATTAGCAAT
AATAAAAATTAACAATAAAATGTGAAAACAGATTACTACTGATTATTTATTGCCATGAGCTAATTAGTAAT
AATTTGTCTTTTTTGATCGAAAAATGAAATTTTTTAAGCGGAGGAACTGAAAATT

FIG. 61 D

**<22_*petJ* gene promoter;DNA;Cyanobacterium ABICyano1>**

TATTTATATATAAACTCGAATAAAATTATCAATATAAAGTCAAACTATATCTATCCTATTTTAACTGCTATT
GGTAAGTCCCTTAATTAGTGTTGGGGTGAATAGATTTTAAAAGGGCAAACCCCCCTTTATCCTCCCTCGA
GAGGGGGGAGGGCAAAAGGCAAGGGGCAAGGGAAAAATTAAGAATTAAGAATTAAAAACTCCGAACAC
CTGTAGGGGCGAATAGCCATTCGCTTCCCCTCATCCCCCCATCTCCCCAACACCCTAAGCCCCTACTCGTT
ACTCATTTATTTACATCATTTATTTACATCATTAAGAAAAGTAACAAATTTTGACAAGTAGTCTTTTGACA
GGAAAAAGCAAATTCTCGAAGATGAAAACAATAGAAAAAAATTCAATCTTACAGTAACG

FIG. 61 E

**<23_*ppsA* promoter;DNA;Cyanobacterium ABICyano1>**

GTGATATTTGGTTTATTCTATATTTTCCTTAAGTAAAAATTCAGTCATGAGGGAAACTTTTGTTAAAATTT
GCTTTAAATTAATAGGAAGATCATTAAGAAAATCTTAAAAAGATTGAGTTTTTAGATCGAAATTATTGAA
GAAAAATTAACAGGGGTTCTGCTCAAAATTTTATTAAATTACTCTACTGTAGTAAAGGAGAAATTTTATT

FIG. 61 F

**<24_*rnpA* gene promoter;DNA;Cyanobacterium ABICyano1>**

GAATAGTTGATAATTACTCGTTACTCATTACTCACTTAAACCTGCCACCTGATACCTGCCACCTCTCCCCC
CATCACCTCATCCCCTCAACATTCCGAACCCCTTGACACTTTGAACTAAAATTGTATTAAAGTGCAAATCT
GGACGGGGTTAACCAGTGTGACTTATAATAGTAAACGCTGTTTTTTATAATAAATAAGCTAAATATTTAA
AAACTATGAGTAAATATACACTAAATGGTACTAGACGTAAGCAGAAAAGAACCTCCGGTTTCCGCGCCCG
TATGAGAACCAAAAATGGTAGAAAAGTAATTCAAGCTCGTCGTAATAAGGGTAGAAAAAGATTAGCAGT
ATAAAATTACTGTTAAATAAGGAAGCTAAGTTTAGCATTTTAAGTTTGATATTACTAATCATTAAATTTAC
TGTGAAATATAGGTGGGACTACCATCAAAGCATCGACTGAAACGGCGTTTAAATTTCCAATCTGTTTATC
AACAGGGTATTCGCCGCTCTAGTCGTTATTTTATTGTCCGAGGGTTACGG

FIG. 61 G

**<25_*pstS* gene promoter;DNA;Cyanobacterium ABICyano1>**

ATAACCAATGGGACTTGAATTTTAGATCCATTTATTTAATTCTATTTTTGTTACATTTCTTTATATTAATCA
GAATTATGTTACTTTGTTTTGTTTTATGTCGTTACCTTATTGAAGAAAGAGTGGATGAGAAGGTAAATGA
CGGGGCATAAATATCGATTCGTTGTCAGAATAAGCTGTTTTATTCACTTAACTGGTTGTTTGCCAATTTCT
CCCTAATTCCCATAACTTGTATAACTAAATTTAATAATCAATTTTAGTAAATTAAGAATAGGTTAAAAGTA
GTATTTAGAATTAAGTTAACTTTAATAAATTTCCTGTATTTTTTTATAGAAAAAAGTATAAAATAAAAACA
TATCAAAAAAGTTTGAAATGACAAT

FIG. 61 H

<69_ cpcBA promoter;DNA;Cynobacterium ABICyano1>

TGAGAAAAAGTGTAAACAAATATTAAGAAAAAGATCAGAAAAATTTAACAACACGTAATAAAAAAATGCG
TCACTACGGGTTATAAATTTACATGAAAGGTTAAAACACTTTTCTGAGACGATTTTGATAAAAAAGTTGTC
AAAAAATTAAGTTTCTTTACAAATGCTTAACAAAAACTTGGTTTTAAGCACAAAATAAGAGAGACTAATTT
GCAGAAGTTTTACAAGGAAATCTTGAAGAAAAAGATCTAAGTAAAACGACTCTGTTTAACCAAAATTTAA
CAAATTTAACAAAACAAACTAAATCTATTAGGAGATTAACTAAGC

FIG. 61 I

*CYANOBACTERIUM* SP. HOST CELL AND VECTOR FOR PRODUCTION OF CHEMICAL COMPOUNDS IN CYANOBACTERIAL CULTURES

CROSS-REFERENCE TO RELATED APPLICATION

This application claims priority to U.S. Provisional Application No. 61/741,000 filed on Dec. 21, 2012 which is incorporated herein by reference.

STATEMENT REGARDING FEDERALLY SPONSORED RESEARCH

This invention was made in part with United States government support under the Department of Energy grant number DE-EE0002867. The government has certain rights associated with this invention.

REFERENCE TO SEQUENCE LISTING

This application contains a sequence listing submitted by EFS-Web, thereby satisfying the requirements of 37 C.F.R. §1.821-1.825.

FIELD OF THE INVENTION

The present invention relates to the genetic enhancement of Cyanobacteria to produce compounds of interest. In particular, the genus Cyanobacterium includes hardy organisms that can be useful for genetic engineering.

BACKGROUND OF THE INVENTION

Cyanobacteria are small, prokaryotic, generally aquatic organisms that can be genetically manipulated to be capable of utilizing light and $CO_2$ to produce compounds of interest, such as biofuels, industrial chemicals, pharmaceuticals, nutrients, carotenoids, food supplements, etc. Because cyanobacterial cells are capable of fixing carbon dioxide as a carbon source for autotrophic growth, they do not require the costly input of organic carbon as a starting material. Further, the $CO_2$ that is utilized by the cyanobacterial culture can be derived from any source, such as a waste byproduct of industrial production. In this way, Cyanobacteria can be used to recycle $CO_2$ to desired products, such as biofuel.

Various cyanobacterial species have been genetically enhanced to produce compounds of interest. The transformation of the cyanobacterial germs *Synechococcus* with genes that encode enzymes that can produce ethanol for biofuel production has been described (U.S. Pat. Nos. 6,699,696 and 6,306,639, both to Woods et al.). The transformation of the cyanobacterial genus *Synechocystis* has been described, for example, in PCT/EP2009/000892 and in PCT/EP2009/060526.

The cyanobacteria as a whole are a very divergent group of organisms. Due to this diversity, it is often difficult to find a method to effectively and efficiently transform a given host cyanobacterial species. Further, it is also often difficult for the inserted DNA vehicle to replicate adequately once it is present in the host cyanobacterial cell.

Certain strains of cyanobacteria can be naturally and relatively easily transformed. Other cyanobacterial strains can be transformed, for example, by the use of conjugation or electroporation. Some cyanobacterial strains are difficult to transform by any known means. For many of these types of difficult to transform strains, specific methods of preparing the cells for transformation, as well as specific methods of allowing entry of the foreign DNA into the cells, need to be designed.

The transfer of foreign genes into cyanobacteria often involves the construction of vectors having a backbone from a broad-host range bacterial plasmid, such as RSF1010. The RSF1010-based vector has been widely used as a conjugation vector for transforming bacteria, including cyanobacteria (Mermet-Bouvier et al. (1993) "Transfer and replication of RSF1010-derived plasmids in several cyanobacteria of the genera *Synechocystis* and *Synechococcus*" Current Microbiology 27:323-327). This plasmid has an *E. coli* origin of replication, but does not have a cyanobacterial origin of replication.

Several endogenous plasmids from *Synechococcus* sp. PCC 7002 have been utilized as a backbone plasmid to prepare vectors for heterologous gene expression (Xu et al., Photosynthesis Research Protocols 684:273-293 (2011). Other vectors for transformation of cyanobacteria include the pDUI-based vectors. The pDUI origin of replication is best suited for filamentous cyanobacteria, however. Attempts to transform certain species of cyanobacteria, such as *Cyanobacterium* sp. ABICyano1, with either RSF1010 or pDUI -based shuttle vectors were previously unsuccessful.

The cyanobacterial genus *Cyanobacterium* was first established in 1983 (see Rippka et al. (2001), Bergey's Manual of Systematic Bacteriology, Vol. 1, p. 497-498). In general, the genus differs from the genus *Synechococcus* by differences in DNA base composition and by differences in sensitivity to cyanophages (Moro, et al., 2007, Algological Studies, 123:1-15), Members of the *Cyanobacterium* genus are often found in thermal mats.

The species *Cyanobacterium* ABICyano1 is a coccoid, unicellular cell somewhat similar to *Synechococcus* when viewed under the microscope. Cells of *Cyanobacterium* ABICyano1 appear to have a substantial layer of mucilaginous sheath covering each individual cell. This mucilage can participate in the formation of cellular aggregates or "clumps". The species differs from other species in the *Cyanobacterium* genus, as well as from other cyanobacteria such as *Synechococcus* and *Synechocystis*, by differences in the carotenoid and chlorophyll composition. The species also appears to differ from other cyanobacteria, such as the above two species, by differences in its 16S rDNA and its internal transcribed spacer rDNA (ITS) composition, What is needed in the art is a new cyanobacterial strain that grows relatively quickly, is tolerant to various environmental stresses, and can successfully harbor foreign genes for the production of compounds of interest, such as biofuels.

SUMMARY

An object of this invention is a new cyanobacterial strain, *Cyanobacterium* sp. ABICyano1, that is capable of tolerating exposure to elevated temperatures and is capable of being transformed.

A further object of this invention is a new cyanobacterial strain, *Cyanobacterium* sp. ABICyano1, that is capable of tolerating exposure to elevated oxygen concentrations and is capable of being transformed.

A further object of this invention is a new cyanobacterial strain, *Cyanobacterium* sp. ABICyano1, that is capable of tolerating exposure to ethanol and is capable of being transformed.

A further object of this invention is a new cyanobacterial strain, *Cyanobacterium* sp. ABICyano1, that is capable of tolerating exposure to elevated salinity and is capable of being transformed.

A further object of this invention is a new cyanobacterial strain, *Cyanobacterium* sp. ABICyano1, that is capable of being transformed and exhibits native biocidal properties with respect to potential contaminants.

A genetically enhanced *Cyanobacterium* sp. host cell of the present invention comprises at least one recombinant gene, wherein said recombinant gene encodes one protein selected from a group consisting of a protein that is involved in a biosynthetic pathway for the production of chemical compound or a marker protein.

A method of the present invention for producing a chemical compound comprises the method steps of culturing the genetically enhanced *Cyanobacterium* sp. host cells in a culture medium, the host cells thereby producing the chemical compound, and retrieving the chemical compound from either one of: the host cells, the medium or the headspace above the medium.

A plasmid vector of the present invention suitable for transformation of *Cyanobacterium* sp. ABICyano1 comprises a recombinant gene, wherein said recombinant gene encodes at least one protein selected from a group consisting of a protein that is involved in a biosynthetic pathway for the production of a chemical compound or a marker protein and an origin of replication suitable for replication in the *Cyanobacterium* ABICyano1.

An isolated nucleic acid sequence of the present invention has at least 95% identity to the sequence of the 6.8 kb plasmid shown in FIG. 4A.

An isolated *Cyanobacterium* sp. ABICyano1 of the present invention has the deposition number ATCC No. PTA-13311.

A method of the present invention for introducing a recombinant nucleic acid sequence into a cyanobacterial cell with an extracellular polymeric layer (EPS) comprises the method steps of subjecting the cyanobacterial cell to compounds increasing the permeability of the extracellular polymeric layer (EPS) and cell wall, respectively of the cyanobacterial cell, and introducing said recombinant nucleic acid sequence into the cyanobacterial cell.

BRIEF DESCRIPTION OF THE DRAWINGS

FIG. 2 is a panel of graphs comparing the growth of *Synechococcus* PCC 7002 (panel B) and *Cyanobacterium* ABICyano1 (panel A) under simulated high daylight temperatures that often occur in outdoor photobioreactor environments, particularly in hotter climates. The graph shows that *Cyanobacterium* ABICyano1 grows well even when daytime temperatures get up to about 45° C. to 50° C. for about 2 hours. Growth was measured by chlorophyll content (diamonds; μg/ml) and absorbance at $OD_{750}$ (squares).

FIG. 7 is the nucleotide sequence (SEQ ID NO: 8) of this helper plasmid.

FIG. 44 shows a sequence comparison between the native promoter nirA (SEQ ID NO: 66) from ABICyano1 and different variants of the promoter harboring nucleotide changes in the ribosomal binding site (PnirA*2 SEQ ID NO: 67), the binding sites for the regulators NtcA and NtcB (PnirA*3 SEQ ID NO: 68), and the TATA box (PnirA*4 SEQ ID NO: 69). These promoters are included in the plasmids # 1606, # 1629 and # 1636.

Figure 45:
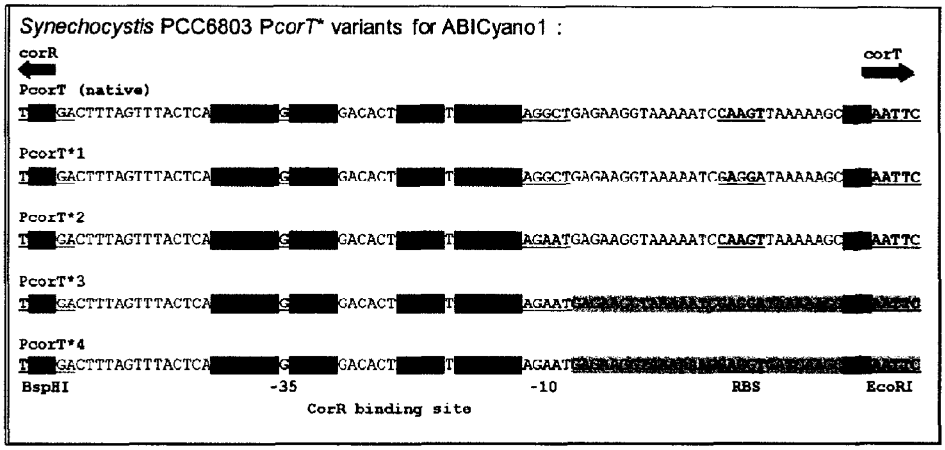

A nucleotide sequence comparison between different corT promoters including the native promoter from Synechocystis PCC68O3 (SEQ ID NO: 70) and variants containing nucleotide changes in the TATA box, ribosomal binding site and the binding sites for the regulator corR including promoter corT*1 (SEQ ID NO: 71), promoter corT*2 (SEQ ID NO: 72), promoter corT*3 (SEQ ID NO: 73), and promoter corT*4 (SE Q ID NO: 74) is shown in FIG. 45. These promoters are included in the above described plasmids # 1630, # 1631 and # 1632.

Figure 46:
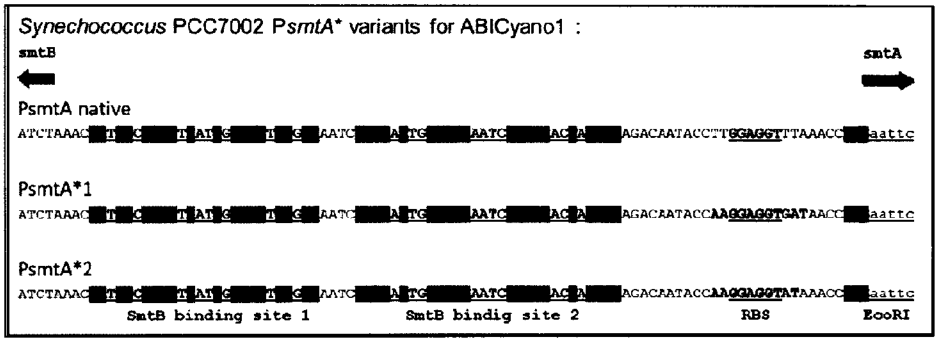

FIG. 46 presents a sequence comparison between the native smtA promoter from Synechococcus PCC 7002 (SEQ ID NO: 75) and two different variants of the promoter harboring mutations in the ribosomal binding site, smtA*1 (SEQ ID NO: 76) and smtA*2 (SEQ ID NO: 77). These promoters are included in the above described plasmids 1635, # 1639 and # 1640.

Figure 47:
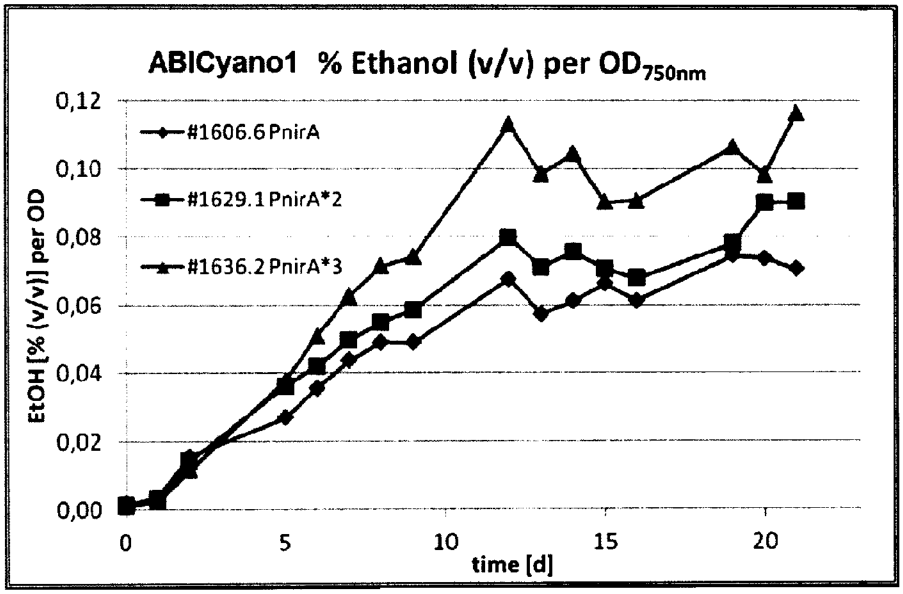

FIG. 47 shows the ethanol production normalized to the growth ($OD_{750nm}$) determined by the CG vial method for ABICyano1 strains transformed with the plasmids # 1606, plasmid 1629 and plasmid # 1636 for a period of time of at least 20 days.

FIGS. 48 A and 48B show the specific activity of PDC enzyme and ADH enzyme during the course of the above mentioned cultivation.

Figure 49:
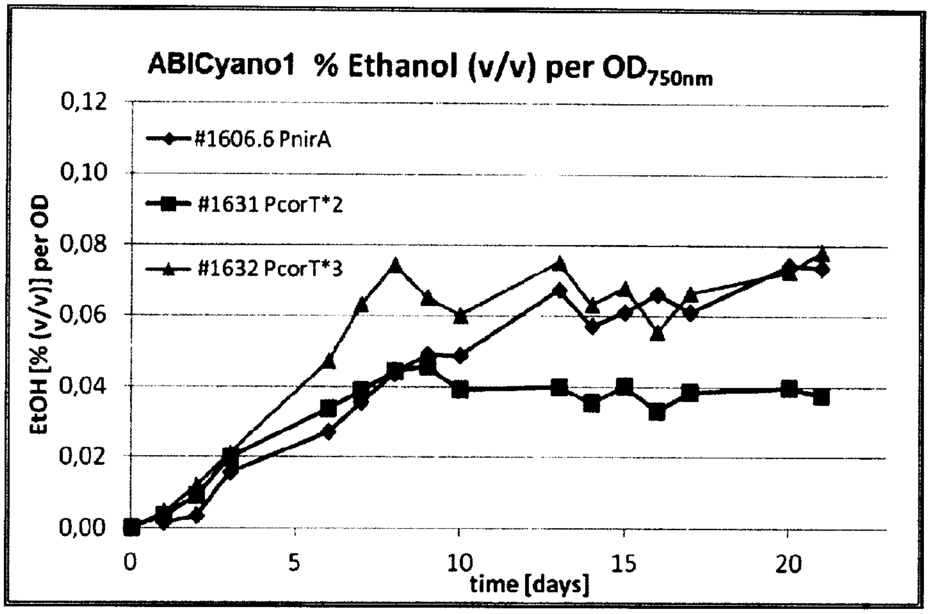

FIG. 49 shows the ethanol production normalized to the growth ($OD_{750nm}$) determined by the GC vial method for ABICyano1 strains transformed with the plasmids # 1606, plasmid 1631 and plasmid # 1632 for a period of time of at least 20 days.

Figure 50A:
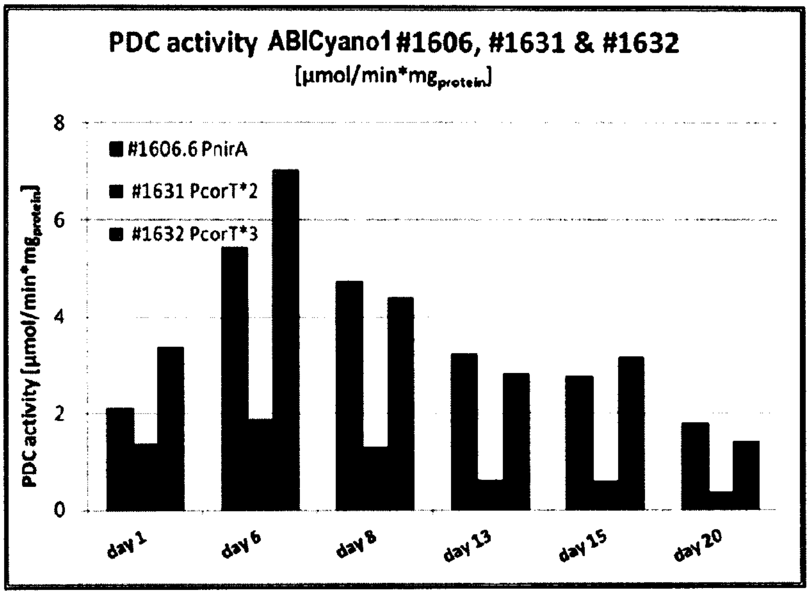
Figure 50B:
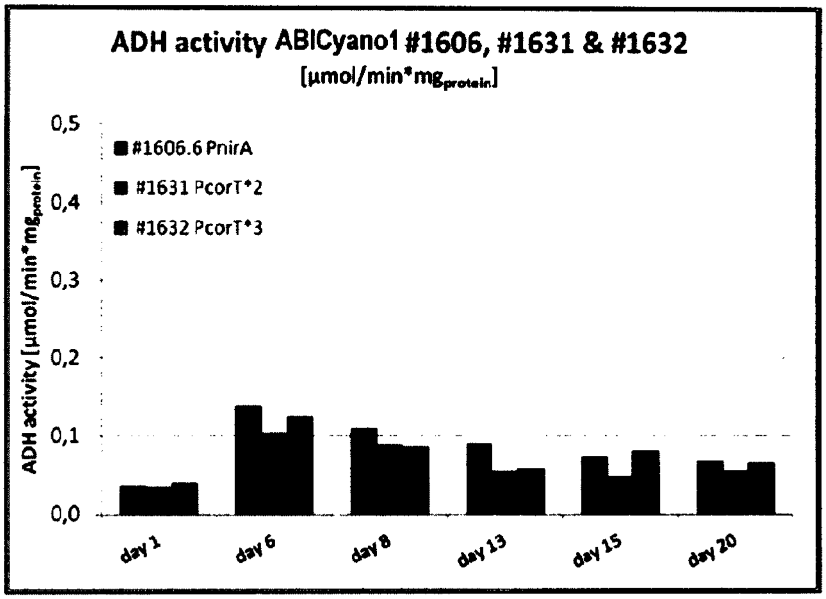
Figure 50C:
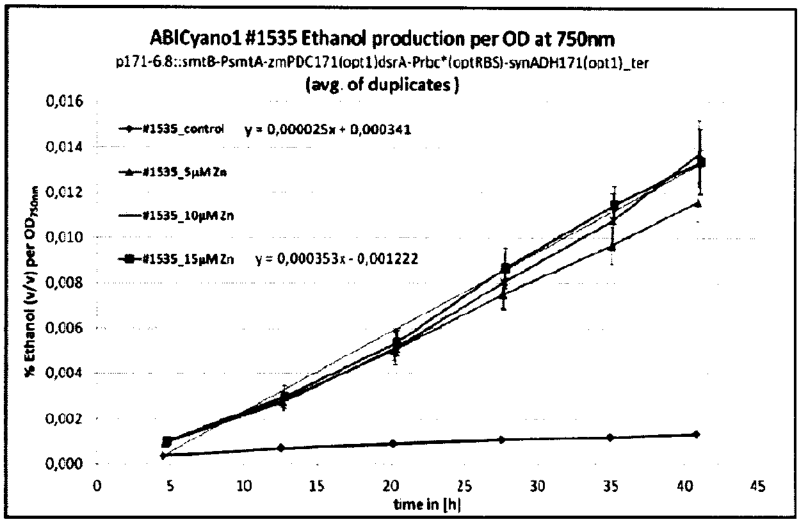
Figure 50D:
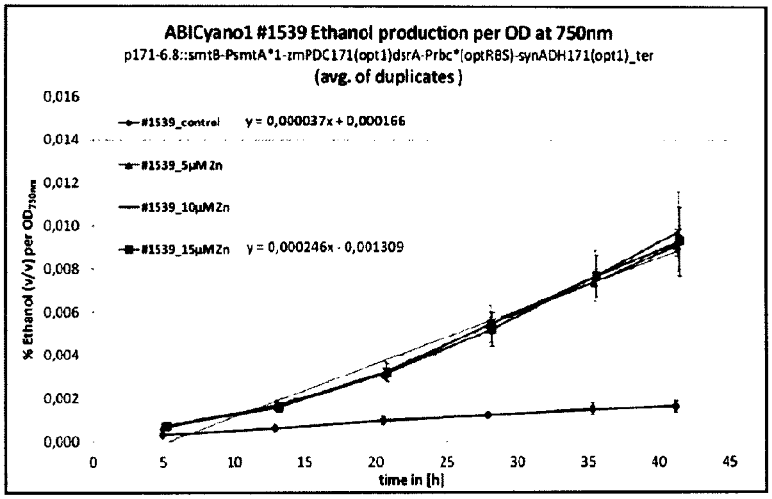
Figure 50E:
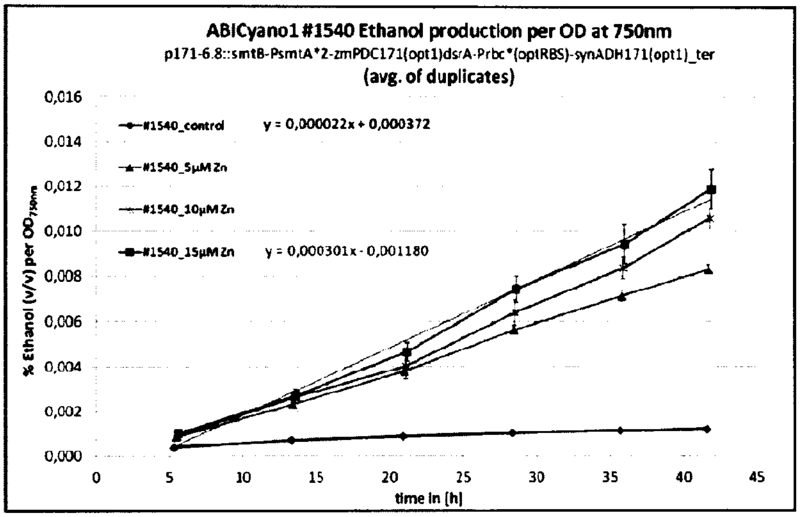

FIGS. 50A and 50B show the specific activity of PDC enzyme and ADH enzyme during the course of the above mentioned cultivation. FIGS. 50C to 50E show the ethanol production rates of the ABICyano1 strains transformed with the plasmids # 1535, # 1539 and # 1540, respectively, including the native PsmtA promoter from Synechococcus PCC 7002 as well as modified versions of PsmtA. It can clearly be seen that all promoters are repressed in the absence of Zn2+ and can be induced upon addition of Zn2+.

FIGS 51A to 51W (SEQ ID NOs: 27-49, respectively) denote the nucleic acid sequences of various putative metal inducible promoters found in ABICyano1.

Figure 52A:
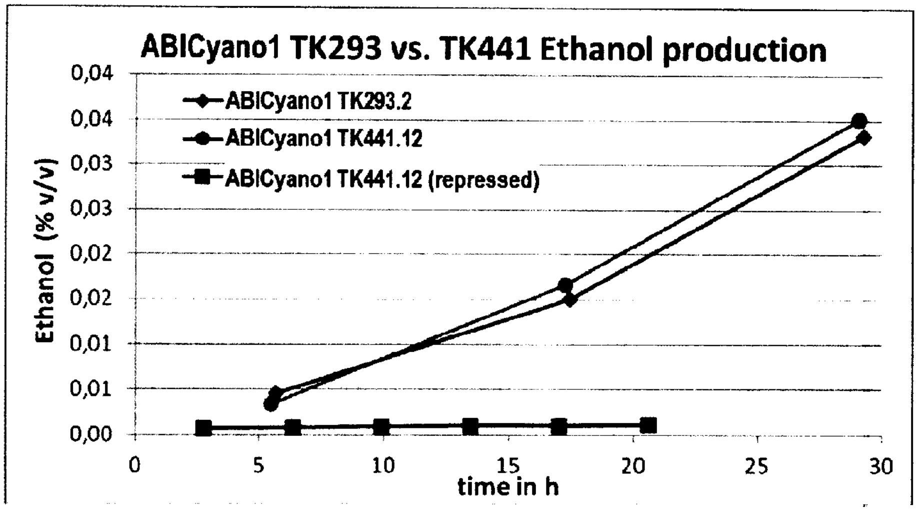
Figure 52B:
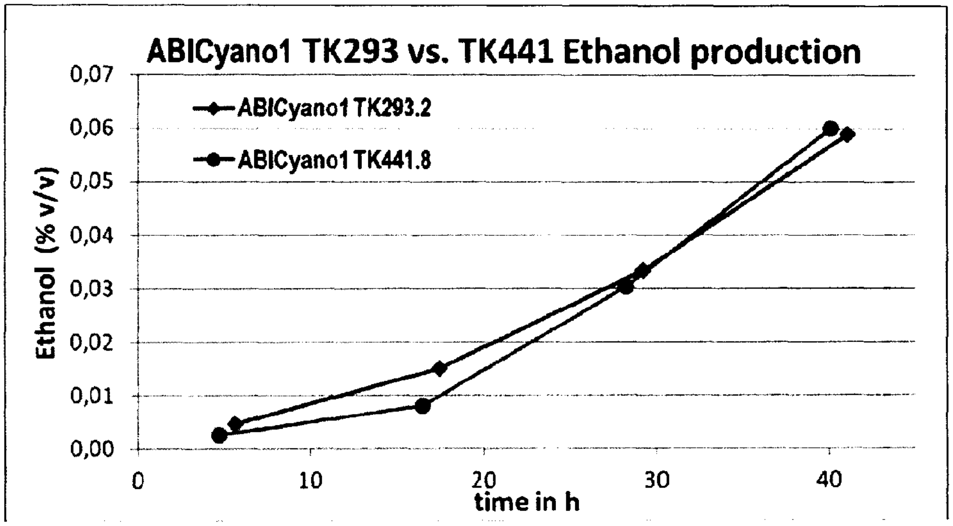

FIG. 52A to 52B depict a graph showing the ethanol production determined by the GC vial method of a new ABICyano1 strain with PpetJ from ABICyano1 as promoter.

Figure 53:
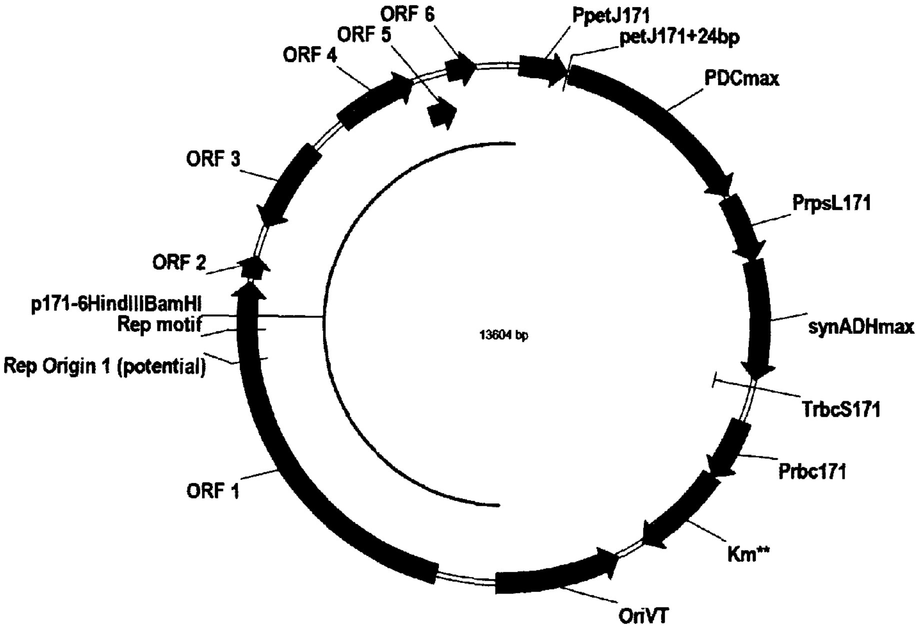

The plasmid map of plasmid TK441 is shown in FIG. 53 and its nucleic acid sequence is depicted in FIG. 54 (SEQ ID NO: 50).

Figure 55:
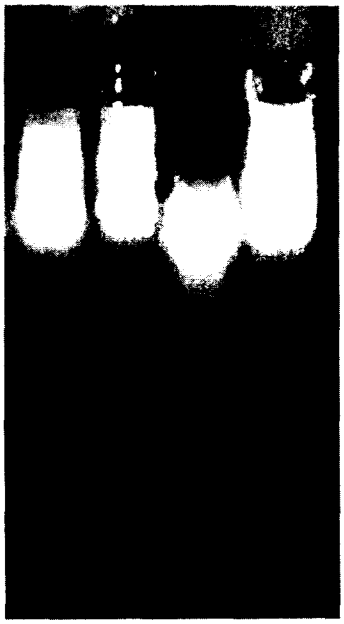
Figure 57A:
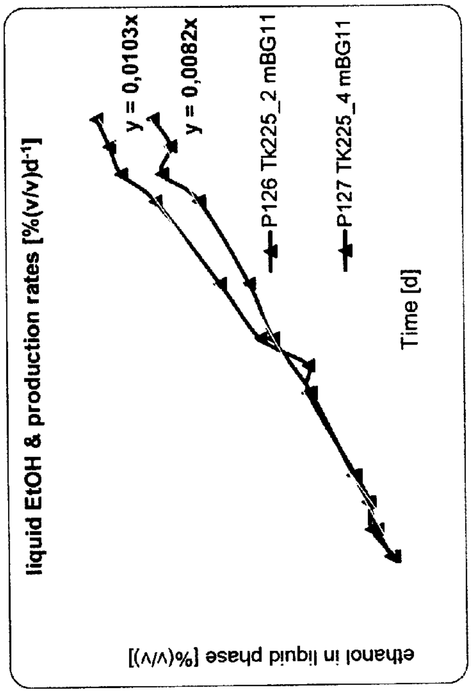
Figure 57C:
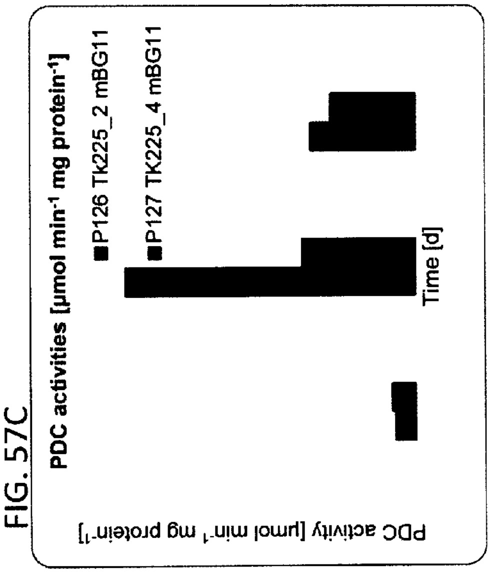
Figure 57B:
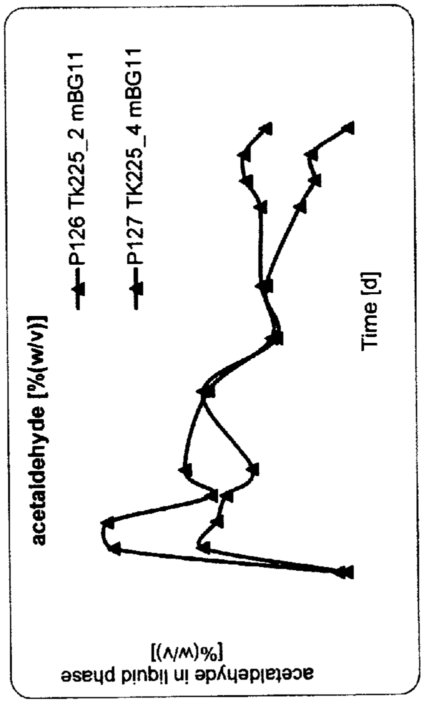
Figure 57D:
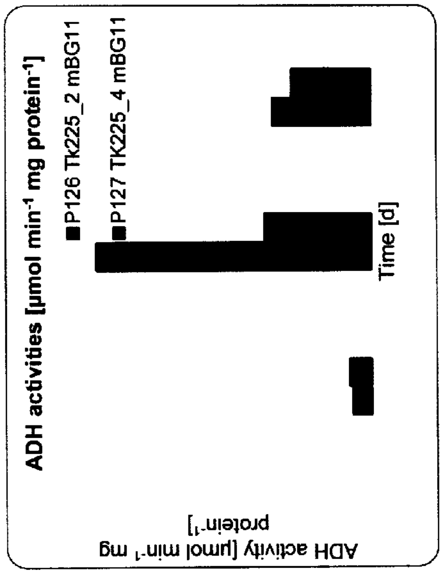

FIG. 55 is a photograph of a gel separation showing how methylation of a plasmid only containing antibiotic resistance genes may at least partially protect it from digestion by a crude extract of ABICyano1. A plasmid including AvaI and AcyI (BsaHI) restriction sites, was incubated with ABICyano1 crude extract, either with or without methylation to protect the plasmid (first plasmid: AvaI: 2x, AcyI: 2x), Lane 1: plasmid without crude extract, lane 2: methylated plasmid without crude extract, lane 3: plasmid with crude extract (digestion), lane 4: methylated plasmid with crude extract. The plasmid was fully protected from digestion by the methylation procedure.

FIGS. 56A and 56B are line graphs showing the production of ethanol and acetaldehyde determined by the GC vial method from *Cyanobacterium ABICyano*1 harboring the ethanologenic plasmids TK293 and TK225.

FIG. 57A to 57D show the results of a 15 day cultivation of *Cyanobacterium ABICyano*1 harboring the ethanologenic plasmid TK225, including the ethanol production rate, acetaldehyde accumulation and enzyme activities. Panel A: ethanol production (% ethanol per volume per day); Panel B: Acetaldehyde (% w/v) Panel C: PDC enzyme activity over time; Panel D: ADH enzyme activity over time.

Figure 58A:
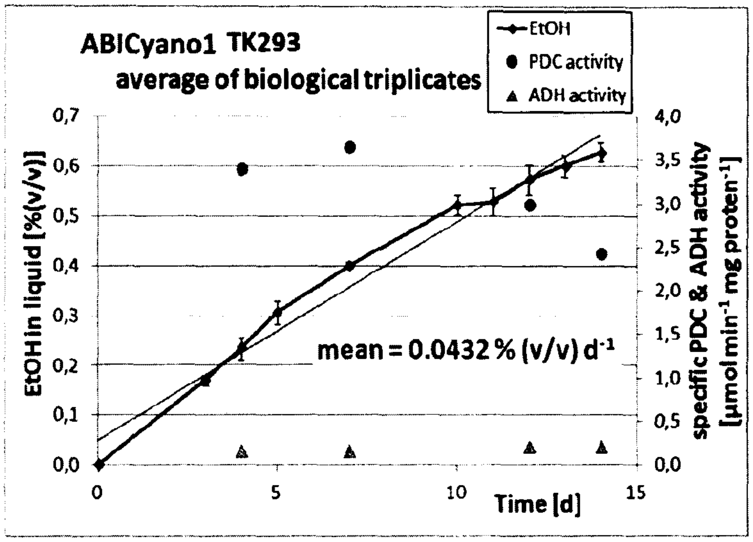
Figure 58B:
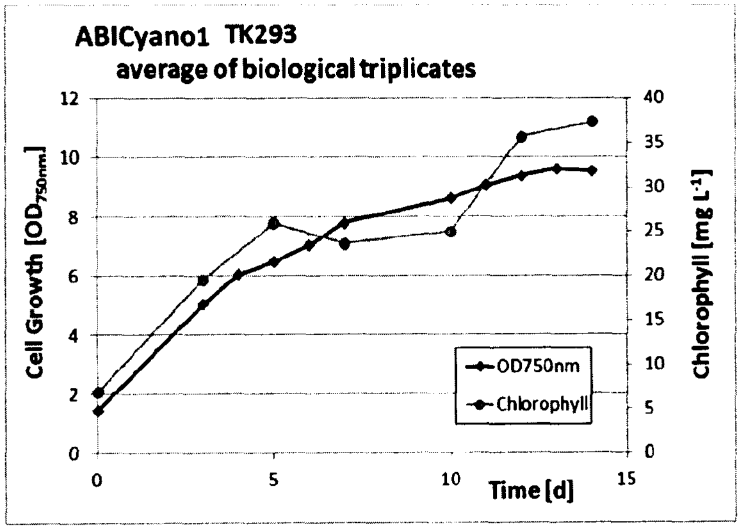
Figure 58C:
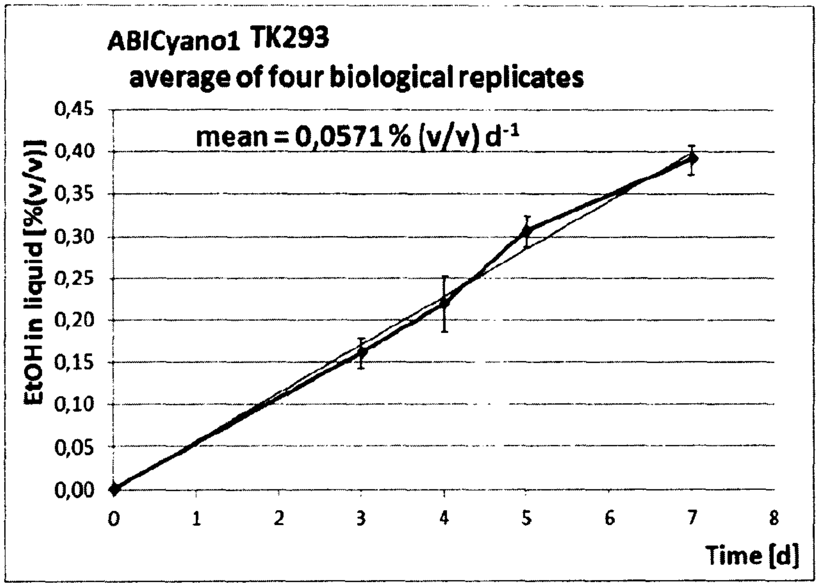

FIG. 58A to 58C show the results of a 14 day cultivation of *Cyanobacterium ABICyano*1 harboring the ethanologenic plasmid TK293, including the ethanol production rate, the cell growth and the maximum ethanol production rate for 7 days.

FIGS. 59A and 59B show the ethanol production rates and the acetaldehyde accumulation determined by the GC vial method for *Cyanobacterium* ABICyano1 harboring the different ethanologenic plasmids TK293, # 1495, # 1578 and # 1581, cultured for 40 hours.

FIGS. 60A and 60B depict the PDC enzyme and ADH enzyme activity of the culturing experiments already presented in the FIGS. 59A and 59B.

Figure 6:
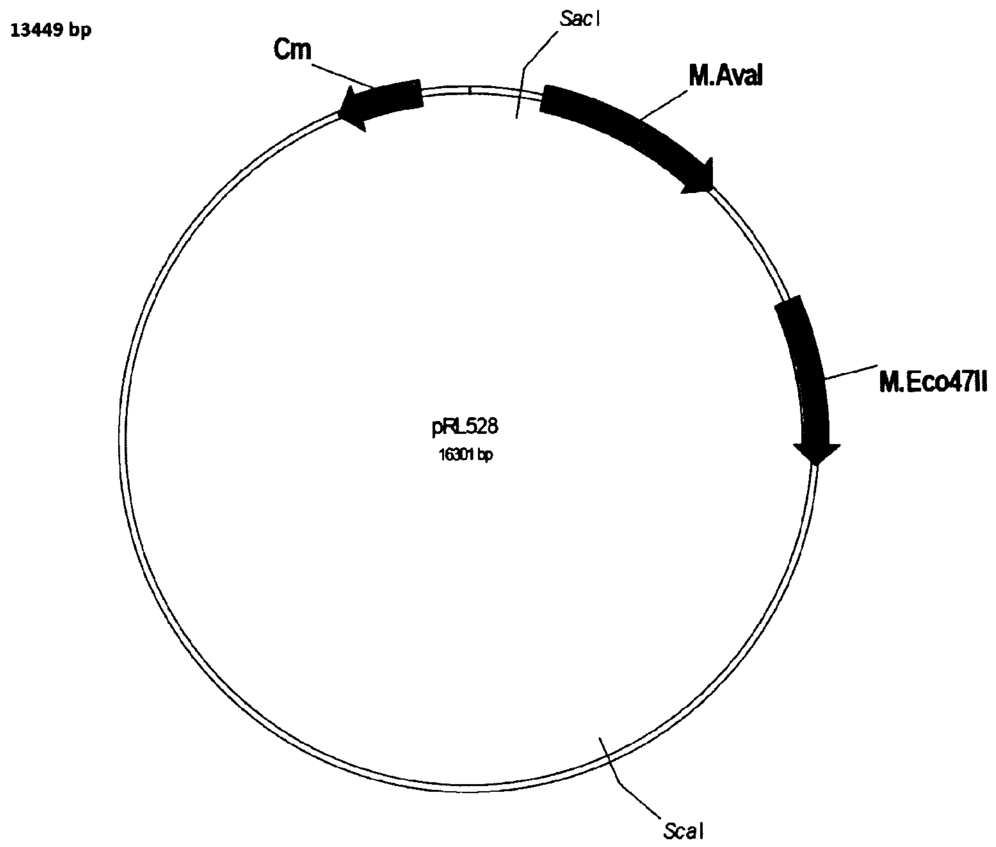
FIG. 6 is a plasmid map of pRL528, a helper plasmid for conjugal transfer, as described in Elhai and Wolk, 1988. The indicated genes are M. AvaI coding for the methyltransferase protecting against the restriction endonuclease AvaI and the respective gene coding for M. AvaII. The latter is not required for transformation of ABICyano1, as it lacks any endonuclease activity of AvaII.

FIGS. 61A-61I depict nucleotide sequences of exemplary promoters from ABICyano1, including cpcB from *Cyanobacterium* ABICyano1 (see FIG. 61I (SEQ ID NO: 52)), mrgA gene promoter (214bp) from *Cyanobacterium* ABICyano1 (see FIG. 6IB (SEQ ID NO: 53)), nblA gene promoter (338 bp) from *Cyanobacterium* ABICyano1 (see FIG. 61C (SEQ ID NO: 54)), ggpS (glucosylglycerol-phosphate synthase) gene promoter (408 bp) from *Cyanobacterium* ABICyano1 (see FIG. 61D (SEQ ID NO: 55)), petJ gene promoter (411 bp) from *Cyanobacterium* ABICyano1 (see FIG. 61E (SEQ ID NO: 56)), ppsA (phosphoenolpyruvate synthase gene) promoter (211 bp) from *Cyanobacterium* ABICyano1 (see FIG. 61F (SEQ ID NO: 57)), rnpA (Ribonuclease P) gene promoter (542 bp) from *Cyanobacterium* ABICyano1 (see FIG. 61G (SEQ ID NO: 58)), the pstS gene promoter (380 bp) from *Cyanobacterium* ABICyano1 (see FIG. 61H (SEQ ID NO: 59)), and the lrtA gene promoter (see FIG. 61A (SEQ ID NO: 51)).

FIG. 61B depicts the sequence of promoter mrgA (SEQ ID NO: 53) from *Cyanobacterium ABICyano*1.

FIG. 61C depicts the sequence of promoter nblA (SEQ ID NO: 54) from *Cyanobacterium* ABICyano1.

FIG. 61D depicts the sequence of promoter ggpS (SEQ ID NO: 55) from *Cyanobacterium ABICyano*1.

FIG. 61E depicts the sequence of promoter petJ (SEQ ID NO: 56) from *Cyanobacterium ABICyano*1.

FIG. 61F depicts the sequence of promoter ppsA (SEQ ID NO: 57) from *Cyanobacterium ABICyano*1.

FIG. 61G depicts the sequence of promoter rnpA (SEQ ID NO: 58) from *Cyanobacterium ABICyano*1.

FIG. 61H depicts the sequence of promoter pstS (SEQ ID NO: 59) from *Cyanobacterium ABICyano*1.

FIG. 61I depicts the sequence of promoter cpcB (SEQ ID NO: 52) from *Cyanobacterium ABICyano*1.

DETAILED DESCRIPTION

One strain of *Cyanobacterium* sp. named *Cyanobacterium* sp. ABICyano1, has been isolated and examined for its hardiness in various environmental conditions that would he likely to be present in a large-scale algae culture system, such as temperature extremes, oxygen level extremes, extremes in light levels, pH variation, as well as the presence of contaminants. Further, an endogenous plasmid (p6.8) derived from this strain can be modified, either in vivo or in vitro, to be a useful plasmid vector capable of carrying production genes of interest in a wide range of host cyanobacterial cells (either *Cyanobacterium*, or other cyanobacterial genera such as *Synechocystis* and *Synechococcus*).

Figure 1:
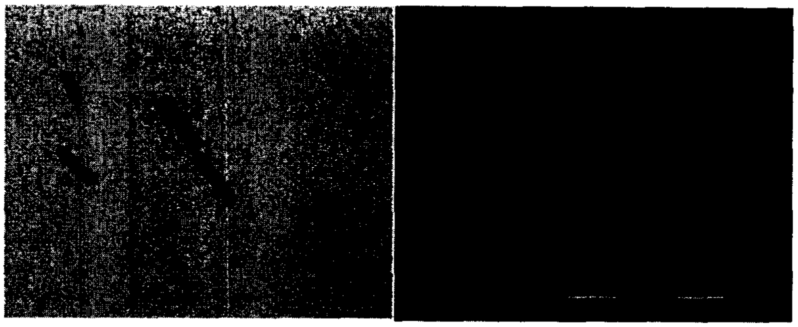
FIG. 1 is a panel of microscopic images that demonstrate the presence of the extracellular polymer (EPS) layer that is present in a sheath surrounding the *Cyanobacterium ABICyano*1 cell. Panel A: unstained cells. Panel B: the cells are stained with scribtol black, which cannot penetrate the EPS layer. The thick EPS layer can be seen. Bar=50 μm.

The cyanobacterial genus *Cyanobacterium* includes several species. As mentioned above, a new isolate of this genus, *Cyanobacterium ABICyano*1, has been found. The new isolate is hardy, grows quickly, is high temperature tolerant, and can tolerate a range of salinities. The new strain can also tolerate high temperatures, in comparison to other cyanobacterial species. This new strain has been analyzed by DNA sequencing, and appears to be a member of the species *Cyanobacterium*, which has been found in thermal mats in Italy (Moro, et al., 2007, Algological Studies, 123:1-15). The new isolate appears to be sheathed with copious amounts of mucilaginous extracellular material, as shown in FIG. 1B. This material may help the cell survive in adverse environmental conditions.

Although this new *Cyanobacterium* isolate has shown a hardy and fast growing phenotype, it has been very difficult to transform the cells with foreign DNA. The mucilaginous sheath may play a role in the transformation difficulties, as may the presence of certain restriction enzyme systems in the host cell. Nevertheless, it has recently been found to be transformable when using certain plasmids, certain cell pretreatments, and growth conditions. An embodiment of the invention thus relates to the transformation of this species with heterologous DNA.

General explanations and definitions:

Aspects of the invention utilize techniques and methods common to the fields of molecular biology, microbiology and cell culture. Useful laboratory references for these types of methodologies are readily available to those skilled in the art. See, for example, Molecular Cloning: A Laboratory Manual (Third Edition), Sambrook, J., et al. (2001) Cold Spring Harbor Laboratory Press; Current Protocols in Microbiology (2007) Edited by Coico, R. et al., John Wiley and Sons, Inc.; The Molecular Biology of Cyanobacteria (1994) Donald Bryant (Ed.). Springer Netherlands; Handbook Of Microalgal Culture Biotechnology And Applied Phycology (2003) Richmond, A.; (ed.), Blackwell Publishing; and "The cyanobacteria, molecular Biology, Genomics and Evolution", Edited by Antonia Herrero and Enrique Flores, Caister Academic. Press, Norfolk, UK, 2008.

It is well known to a person of ordinary skill in the art that large plasmids can be produced using techniques such as the ones described in the U.S. Pat. No. 6,472,184 B1 titled "method for producing nucleic acid polymers" and U.S. Pat. No. 5,750,380 titled "DNA polymerase mediated synthesis of double stranded nucleic acid molecules", which are hereby incorporated in their entirety.

Denominations of genes are in the following presented in a three letter lower case name followed by a capitalized letter if more than one related gene exists, for example nirA. The respective protein encoded by that gene is denominated by the same name with the first letter capitalized, such as NirA.

Denominations for promoter sequences, which control the transcription of a certain gene in their natural environment are given by a capitalized letter "P" followed by the gene name according, to the above described nomenclature, for example "PnirA" for the promoter controlling the transcription of the nirA gene, Denominations for enzyme names can be given in a two or three letter code indicating the origin of the enzyme, followed by the above mentioned three letter code for the enzyme itself, such as SynAdh ($Zn^{2+}$dependent Alcohol dehydrogenase from Synechocystis PCC6803), ZmPdc (pyruvate decarboxylase from Zymomonas mobilis).

All publications and patent applications mentioned in this specification are herein incorporated by reference to the same extent as if each individual publication or patent application was specifically and individually indicated to be incorporated by reference.

Unless defined otherwise, all technical and scientific terms used herein have the meaning commonly understood by a person skilled in the art to which this invention belongs. As used herein, the following terms have the meanings ascribed to them unless specified otherwise.

The term "about" is used herein to mean approximately, in the region of, roughly, or around. When the term "about" is used in conjunction with a numerical value/range, it modifies that value /range by extending the boundaries above and below the numerical value(s) set forth. In general, the term "about" is used herein to modify a numerical value(s) above and below the stated value(s) by a variance of 20%.

The term "Cyanobacteria" refers to a member from the group of photoautotrophic prokaryotic microorganisms which can utilize solar energy and fix carbon dioxide. Cyanobacteria are also referred to as blue-green algae.

The term "terminator" refers to a nucleic acid sequence, which is able to terminate the transcription of a mRNA. The terminators can exert their function in various ways including, but not limited to forming a hairpin structure in the mRNA transcript, which disrupts the mRNA-DNA RNA polymerase complex during transcription or via forming a recognition site for a transcription termination factor. Non-limiting examples are dsrA from *E. coli*, the oop terminator or the rho terminator.

The term "*Cyanobacterium* sp." refers to a cyanobacterial member of the genus *Cyanobacterium*, which was among other characterized by Rippka et Cohen-Bazire, 1983. Ann. Microbiol. (Inst. Pasteur) 134B:32.

The terms "host cell" and "recombinant host cell" are intended to include a cell suitable for metabolic manipulation, e.g., which can incorporate heterologous polynucleotide sequences, e.g., which can be transformed. The term is intended to include progeny of the cell originally transformed. In particular embodiments, the cell is a prokaryotic cell , e.g., a cyanobacterial cell. The term recombinant host cell is intended to include a cell that has already been selected or engineered to have certain desirable properties and suitable for further enhancement using the compositions and methods of the invention. The term "shuttle vector" refers to vector, such as a plasmid, which can propagate in different host species. For example a shuttle vector can be propagated in different cyanobacterial species such as *Cyanobacterium* sp., *Synechococcus* sp., and *Synechocystis* sp. because the cyanobacterial origin of replication of the vector allows for a separate replication in different species. Alternatively or in addition a shuttle vector also can contain an origin of replication for different families of bacteria such as Enterobacteriaceae and for cyanobacterial genera, so that cloning/genetic enhancements can be easily done in *E. coli* and the recombinant plasmid can be expressed /maintained in cyanobacterial hosts. In the latter case, the shuttle vector is either a broad host range vector whose origin of replication is recognized by *E. coli* and cyanobacteria, or a plasmid, which contains at least two different origins of replication for the species The term "genome" refers to the chromosomal genome as well as to extrachromosomal plasmids which are normally present in the wild type cyanobacterium without having performed recombinant DNA technology. For example, cyanobacteria such as Synechococcus PCC7002 can include at least up to 6 extrachromosomal plasmids in their wild type form.

"Competent to express" refers to a host cell that provides a sufficient cellular environment for expression of endogenous and/or exogenous polynucleotides.

As used herein, the term "genetically enhanced" refers to any change in the endogenous genome of a wild type cell or to the addition of non-endogenous genetic code to a wild type cell, e.g., the introduction of a heterologous gene. More specifically, such changes are made by the hand of man through the use of recombinant DNA technology or mutagenesis. The changes can involve protein coding sequences or non-protein co ding sequences, including regulatory sequences such as promoters or enhancers.

As used herein, the term "recombinant" refers to nucleic acid sequences and in particular to genes, which are changed by laboratory methods thereby creating combinations of nucleic acid sequences in a host cell which are not found in the respective wild type host cell. This term can apply nucleic acid sequences which are both endogenous as well as heterologous with respect to the host cell.

The terms "Polynucleotide" and "nucleic acid" also refer to as polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs. It will be understood that, where required by context, when a nucleotide sequence is represented by a DNA sequence (i.e., A, T, G, C), this also includes an RNA sequence (i.e., A, U, G, C) in which "U" replaces "T."

The nucleic acids of this present invention may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages, charged linkages, alkylators, intercalators, pendent moieties, modified linkages. and chelators. Also included are synthetic molecules that mimic polynucleotides in their ability to bind to a designated sequence via hydrogen bonding and other chemical interactions.

The term "nucleic acid" (also referred to as polynucleotide) is also intended to include nucleic acid molecules having an open reading frame encoding a polypeptide, and can further include non-coding regulatory sequences and introns. In addition, the terms are intended to include one or more genes that map to a functional locus. In addition, the terms are intended to include a specific gene for a selected purpose. The gene can be endogenous to the host cell or can be recombinantly introduced into the host cell.

The term "homology" refers to the percentage of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, "substantially similar" refers to nucleic acid fragments wherein changes in one or more nucleotide bases results in substitution of one or more amino acids, but do not affect the functional properties of the protein encoded by the DNA sequence.

The term "substantially similar" also refers to modifications of the nucleic acid fragments of the instant invention such as deletion or insertion of one or more nucleotide bases that do not substantially affect the functional properties of the resulting transcript.

In one aspect the invention also provides nucleic acids which are at least 60%, 70%, 80% 90%, 95%, 99%, or 99.5% identical to the nucleic acids disclosed herein.

The percentage of identity of two nucleic acid sequences or two amino acid sequences can be determined using the algorithm of Thompson et al. (CLUSTALW, 1994 Nucleic Acid Research 22: 4673-4, 680). A nucleotide sequence or an amino acid sequence can also be used as a so-called "query sequence" to perform a search against public nucleic acid or protein sequence databases in order, for example, to identify further unknown homologous sequences, which can also be used in embodiments of this invention. Such searches can be performed using the algorithm of Karlin and Altschul (1999 Proceedings of the National Academy of Sciences U.S.A. 87: 2,264 to 2,268), modified as in Karlin and Altschul (1993 Proceedings of the National Academy of Sciences U.S.A. 90: 5,873 to 5,877). Such an algorithm is incorporated in the NBLAST and XBLAST programs of Altschul et al. (1999 Journal of Molecular Biology 215: 403 to 410). Where gaps exist between two sequences, gapped BLAST can be utilized as described in Altschul et al. (1997 Nucleic Acid Research, 25: 3,389 to 3,402).

"Recombinant" refers to polynucleotides synthesized or otherwise manipulated in vitro ("recombinant polynucleotides") and to methods of using recombinant polynucleotides to produce gene products encoded by those polynucleotides in cells or other biological systems. For example, a cloned polynucleotide may be inserted into a suitable expression vector, such as a bacterial plasmid, and the plasmid can be used to transform a suitable host cell. A host cell that comprises the recombinant polynucleotide is referred to as a "recombinant host cell" or a "recombinant bacterium" or a "recombinant cyanobacteria." The gene is then expressed in the recombinant host cell to produce, e.g., a "recombinant protein ," A recombinant polynucleotide may serve a non-coding function (e.g., promoter, origin of replication, ribosome-binding site, etc.) as well.

The term "recombinant nucleic acid molecule" includes a nucleic acid molecule (e.g., a DNA molecule) that has been altered, modified or engineered such that it differs in nucleotide sequence from the native or natural nucleic, acid molecule from which the recombinant nucleic acid molecule was derived (e.g. by addition, deletion or substitution of one or more nucleotides), The term "transformation" is used herein to mean the insertion of heterologous genetic material into the host cell. Typically, the genetic material is DNA on a plasmid vector, but other means can also be employed. General transformation methods and selectable markers for bacteria and cyanobacteria are known in the art (Wirth, Mol Gen Genet. 216:175-177 (1989); Koksharova, Appl Microbiol Biotechnol 58:123-137 (2002). Additionally, transformation methods and selectable markers for use in bacteria are well known (see, e.g., Sambrook et al, supra).

The term "homologous recombination" refers to the process of recombination between two nucleic acid molecules based on nucleic acid sequence similarity. The term embraces both reciprocal and nonreciprocal recombination (also referred to as gene conversion). In addition, the recombination can be the result of equivalent or non- equivalent cross-over events. Equivalent crossing over occurs between two equivalent sequences or chromosome regions, whereas non-equivalent crossing over occurs between identical (or substantially identical) segments of nonequivalent sequences or chromosome regions. Unequal crossing over typically results in gene duplications and deletions. For a description of the enzymes and mechanisms involved in homologous recombination see Court et. al., "Genetic engineering using homologous recombination," Annual Review of Genetics 36:361-388; 2002.

The term "non-homologous or random integration" refers to any process by which DNA is integrated into the genome that does not involve homologous recombination. It appears to be a random process in which incorporation can occur at any of a large number of genomic locations.

The term "vector" as used herein is intended to refer to a nucleic acid molecule capable of transporting, another nucleic acid to which it has been linked. One type of vector is a "plasmid," which generally refers to a circular double stranded DNA molecule into which additional DNA segments may be ligated, but also includes linear double-stranded molecules such as those resulting from amplification by the polymerase chain reaction (PCR) or from treatment of a circular plasmid with a restriction enzyme.

Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors").

The term "promoter" is intended to include a polynucleotide segment that can transcriptionally control a gene of interest, e.g., a pyruvate decarboxylase gene that it does or does not transcriptionally control in nature. In one embodiment, the transcriptional control of a promoter results in an increase in expression of the gene of interest. In an embodiment, a promoter is placed 5' to the gene-of-interest. A heterologous promoter can be used to replace the natural promoter, or can be used in addition to the natural promoter. A promoter can be endogenous with regard to the host cell in which it is used or it can be a heterologous polynucleotide sequence introduced into the host cell, e.g., exogenous with regard to the host cell in which it is used. Promoters of the invention may also be inducible, meaning that certain exogenous stimuli (e.g., nutrient starvation, heat shock, mechanical stress, light exposure, etc.) will induce the promoter leading to the transcription of the gene.

The phrase "operably linked" means that the nucleotide sequence of the nucleic acid molecule or gene of interest is linked to the regulatory sequence(s) in a manner which allows for regulation of expression (e.g., enhanced, increased, constitutive, basal, attenuated, decreased or repressed expression) of the nucleotide sequence and expression of a gene product encoded by the nucleotide sequence (e.g., when the recombinant nucleic acid molecule is included in a recombinant vector, as defined herein, and is introduced into a microorganism).

The term "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding, sequences) and following (3' non-coding sequences) the coding sequence.

The term "endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "fragment" refers to a nucleotide sequence of reduced length relative to the reference nucleic acid and comprising, over the common portion, a nucleotide sequence substantially identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least about 6 to about 1500 or more consecutive nucleotides of a polynucleotide according to the invention.

The term "open reading frame" abbreviated as "ORF," refers to a length of nucleic acid sequence, either DNA, cDNA or RNA, that comprises a translation start signal or initiation codon, such as an ATG or AUG, and a termination codon and can be potentially translated into a polypeptide sequence.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The terms "restriction endonuclease" and "restriction enzyme" refer to an enzyme that binds and cuts within a specific nucleotide sequence within double stranded DNA.

The term "expression" as used herein, refers to the transcription and stable accumulation mRNA derived from a nucleic acid or polynucleotide. Expression may also refer to translation of mRNA into a protein or polypeptide, An "expression cassette" or "construct" refers to a series of polynucleotide elements that permit transcription of a gene in a host cell. Typically, the expression cassette includes a promoter and a heterologous or native polynucleotide sequence that is transcribed. Expression cassettes or constructs may also include, e.g. transcription termination signals, polyadenylation signals, and enhancer elements.

The term "codon" refers to a triplet of nucleotides coding for a single amino acid.

The term "codon-anticodon recognition" refers to the interaction between a codon on an mRNA molecule and the corresponding anticodon on a tRNA molecule.

The term "codon bias" refers to the fact that different organisms use different codon frequencies.

The term "codon improvement" refers to the modification of at least some of the codons present in a heterologous gene sequence from a triplet code that is not generally used in the host organism to a triplet code that is more common in the particular host organism. This can result in a higher expression level of the gene of interest.

The term "reporter gene" means a nucleic acid encoding an identifying factor that can be identified based upon the reporter gene's effect, in order to determine or confirm that a cell or organism contains the nucleic acid of interest, and/or to measure gene expression induction or transcription. Examples of reporter genes known and used in the art include but are not limited to luciferase (Luc), green fluorescent protein (GFP), chloramphenicol acetyltransferase (CAT), βgalactosidase (LacZ ), β-glucuronidase (GUS), and the like. Selectable marker genes may also be considered reporter genes.

The term "selectable marker" means an identifying factor, usually an antibiotic or chemical resistance gene, that is able to be selected for based upon the marker gene's effect, such as resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, spectinomycin, kanamycin, hygromycin, and the like.

A "polypeptide" is a polymeric compound comprised of covalently linked amino acid residues. A "protein" is a polypeptide that performs a structural or functional role in a living cell.

A "heterologous protein" refers to a protein not naturally produced in the cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids).

The term "fragment" of a polypeptide refers to a polypeptide whose amino acid sequence is shorter than that of the reference polypeptide. Such fragments of a polypeptide according to the invention may have a length of at least about 2 to about 300 or more amino acids.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements.

As used herein, the phrase "increased activity" refers to any genetic modification resulting in increased levels of enzyme function in a host cell. As known to one of ordinary skill in the art, enzyme activity may be increased by increasing the level of transcription, either by modifying promoter function or by increasing gene copy number, increasing translational efficiency of an enzyme messenger RNA, e.g., by modifying ribosomal binding, or by increasing the stability of an enzyme, which increases the half -life of the protein, leading to the presence of more enzyme molecules in the cell. All of these represent non-limiting examples of increasing the activity of an enzyme. (mRNA Processing and Metabolism: Methods and Protocols, Edited by Daniel R. Schoenberg, Humana Press Inc., Totowa, N.J.; 2004; ISBN 1-59259-750-5; Prokaryotic Gene Expression (1999) Baumberg S., Oxford University Press, ISBN 0199636036; The Biomedical Engineering Handbook (2000) Bronzino, J. D., Springer, ISBN 354066808X).

The terms "pyruvate decarboxylase" and "PDC" refer to an enzyme that catalyzes the decarboxylation of pyruvic acid to acetaldehyde and carbon dioxide. A "pdc gene" refers to the gene encoding an enzyme that catalyzes the decarboxylation of pyruvic acid to acetaldehyde and carbon dioxide. The terms "Alcohol dehydrogenase" and "ADH" refer to an enzyme that facilitates the interconversion between alcohols and aldehydes or ketones. An "adh gene" refers to the gene encoding an enzyme that facilitates the interconversion between alcohols and aldehydes or ketones, "pdc/adh" refers to the pdc and adh genes collectively. A "pdc/adh cassette" refers to a nucleic acid sequence encoding a PDC enzyme and an ADH enzyme.

The term "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

The term "polymerase chain reaction," also termed "PCR," refers to an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

Database entry numbers given in the following are from the NCBI database (National Center for Biotechnology Information) or from the CyanoBase, the genome database for cyanobacteria (Yazukazu et al. "CyanoBase, the genome database for *Synechocystis* sp. Strain PCC6803: status for the year 2000", Nucleic Acid Research, 2000, Vol. 18, page 72).

The EC numbers cited throughout this patent application are enzyme commission numbers which is a numerical classification scheme for enzymes based on the chemical reactions which are catalyzed by the enzymes.

Description of Embodiments of the Invention:

One species of *Cyanobacterium* sp., has been found to be particularly hardy under extreme conditions that often occur in production-scale algal cultures. The cells are heat tolerant, and appear to be more tolerant to many other environmental stress conditions than are more commonly used cyanobacterial species. After several unsuccessful attempts, the inventors were able to transform these cells with desired recombinant genes, so that they can be used to harbor recombinant biosynthetic pathway genes to produce various chemical compounds of interest.

A deposit of the Algenol Biofuels Inc. proprietary strain of *Cyanobacterium* sp., strain ABICyano1 , disclosed above and recited in the appended claims has been made with the American Type Culture Collection (ATCC), 10801 University Boulevard, Manassas, Va. 20110. The date of receipt of the deposit was Nov. 9, 2012, as confirmed by ATCC on Nov. 14, 2012. The ATCC Accession Number is ATCC No. PTA-13311. The deposit includes 25 2-ml vials, each containing about 1.5 ml of cryopreserved cyanobacterial cells at a concentration of about $2.39\times10^7$ cells per mL. All restrictions will be removed upon granting of a patent, and the deposit is intended to meet all of the requirements of 37 C.F.R. §§ 1.801-1.809. The deposit will be maintained in the depository for a period of thirty years, or five years after the last request, or for the enforceable life of the patent, whichever is longer, and will be replaced as necessary during that period.

The 16S rDNA of *Cyanobacterium* sp. ABICyano1 show a high sequence identity of around 99% to the 16S rDNA sequences of different cyanobacterial species of the genus Cyanobacterium, including Cyanobacterium IHB-410, Cyanobacterium aponinum ETS-03, and Cyanobacterium sp. MBIC10216. The 16S ribosomal RNA (rRNA) gene sequences (16S rDNA) of ABICyano1 was predicted from the genuine sequence with RNAmmer program (Lagesen K, et al. (2007) RNAmmer: consistent and rapid annotation of ribosomal RNA genes. *Nucleic Acids Research* 35(9):3100-3108.). These sequences were then used as a query to search against the NCBI database and 16S rDNA sequences from 4 species belonging to the genus *Cyanobacterium* were retrieved as the top BLAST (Altschul SF, et al. (1997) Gapped BLAST and PSI-BLAST: a new generation of protein database search programs. *Nucl. Acids. Res.* 25(17):3389-3402) hits. Comparison of 16S rDNA shows that ABICyano1 (SEQ ID NO. 63) and ABICyano2 (SEQ ID NO. 62) are 99% identical to *Cyanobacterium* spp. A sequence comparison of the 16S rDNA sequences of some cyanobacterial species is shown in FIG. 5B. In this sequence comparison "Cyano10216" denotes the 16S rDNA sequence of Cyanobacterium sp. MBIC10216 (SEQ ID NO. 60) (available at the NCBI with the accession number AB058249.1). "Cyano-ETS-03" denotes the 16S rDNA of Cyanobacterium aponinum ETS-03 (SEQ ID NO. 61) (available at the NCBI with the accession number AM238427.1), the denomination "CyanoLLi5" is for *Cyanobacterium* sp. LLi5 (SEQ ID NO. 64) (available at the NCBI with the accession number DQ786164.1) and "Cyano7202" stands for Cyanobacterium stanieri PCC 7202, (SEQ ID NO. 65) which is available at the NCBI with the accession number AM258981.1.

*Cyanobacteriym* sp. ABICyano1 was examined for its hardiness in various environmental conditions that would be likely to be present in a large-scale algae culture system, such as temperature extremes, oxygen level extremes, extremes in light levels, pH variation, and the presence of contaminants, as described in Examples 7 to 9. In particular, *Cyanobacterium* for example *Cyanobacteriym* ABICyano1 was shown to withstand at least 1% (v/v) ethanol in the medium, for example marine medium, which can for example have a salinity of between 30 to 38, in particular 35 psu (practical salinity units). This culturing was done for at least 6 weeks, preferably at least 12 weeks, most preferred at least 16 weeks. The test for ethanol tolerance was as done by adding 1% ethanol to the medium of *Cyanobacterium ABICyano*1. Cyanobacterial cultures were examined, for example under the microscope after a predetermined period of time, for example 6, 12 or 16 weeks and cyanobacterial cultures were deemed to have passed the ethanol tolerance test if at least or more than 50% of the cyanobacterial cells were found to be intact, i. e. viable according to microscopic analysis meaning that the cell morphology did not change significantly, the cells were still green, and the cells were not lysed.

Another test for temperature tolerance was conducted wherein *Cyanobacterium* sp., for example Cyanobacterium ABICyano1 was cultured in a medium, for example a marine medium under conditions of light illumination and omitting light illumination (day /night cycle) at maximum temperatures between 45 to 55° C. for a certain period of time, for example 1 to 2 hours during illumination. Cyanobacterial cells were deemed to have passed the test, if the cultures were still growing after having been subjected to 7 days of day night/cycles as described above. Growth could be detected for example by an increase in the chlorophyll content of the cyanobacterial cultures. *Cyanobacterium* sp., for example *Cyanobacterium* ABICyano1 was found to withstand at 48° C., preferably 50° C. most preferred at least 53 to 55° C. for at least 2 hours per day over a time period of at least 7 days.

In addition, an oxygen tolerance test was carried out, which showed that *Cyanobacterium* sp. , for example *Cyanobacterium* ABICyano1 can tolerate purging with 60% (v/v) to 80% oxygen resulting in oxygen levels of up to. 1000 μmol/L in the culture during the day) when cultured at temperatures between 28° C. to 37° C. and when being illuminated with a light intensity of between 200 μE $m^{-2}$ $s^{-1}$ to 400 μE $m^{-2}$ $s^{-1}$ in a medium such as marine medium.

*Cyanobacterium* sp., in particular *Cyanobacterium ABICyano*1 was also shown to tolerate a wide range of pH values and can be cultured at a pH between 5.5 to 10, preferably at a pH between 6 to 7.5, most preferred at neutral or slightly alkaline pH of pH 7.5.

In addition, it could be shown that contaminating strains in *Cyanobacterium* ABICyano1 cultures do not grow to such a high density as in other cultures of known cyanobacterial strains. For comparison ~$10^5$—$10^6$ cfu/mL of contaminating strains were found in *Cyanobacterium* ABICyano1 cultures and ~$10^9$—$10^{15}$ cfu/mL of contaminating strains in *Synechococcus* sp. PCC 7002 cultures.

Subject matter of one embodiment of the invention are *Cyanobacterium* host cells, for example *Cyanobacterium* ABICyano1 host cells, which can withstand at least one of the following culturing conditions:

- 1% (v/v) ethanol in the medium for at least 6, 12 or 16 weeks,
- 48° C. preferably 50° C. most preferred at least 53 to 55° C. for at least 2 hours per day over a time period of at least 7 days, and
- Purging with 60% (v/v) to 80% oxygen, (resulting in oxygen concentrations of up to 1000 μmol/L in the culture during the day).

Preferably the *Cyanobacterium* sp., in particular *Cyanobacterium* ABICyano1 host cells can tolerate at least two or all of the above mentioned culturing conditions.

The hardiness, tolerance to a wide range of growth temperatures, and tolerance to environmental conditions in general, make *Cyanobacterium*, in particular Cyanobacterium ABICyano1 a good choice for genetic enhancements to produce chemical compounds of interest on an industrial scale.

Subject matter of another embodiment of the invention are therefore genetically enhanced *Cyanobacterium* sp. host cells, in particular *Cyanobacterium* ARICyano1 host cells, including at least one recombinant gene encoding at least one protein selected from a group consisting of a protein that is involved in a biosynthetic pathway for the production of a chemical compound or a marker protein. Owing to the recombinant gene, the genetically enhanced Cyanobacterium host cells can be used for the production of various chemical compounds of interest by culturing the host cells under harsh conditions of high temperature, high oxygen levels and in the case of the chemical compound being ethanol, under high levels of ethanol in the medium. The marker protein or reporter protein, which for example can be a fluorescent protein such as a red or green fluorescent protein or a marker gene conferring resistance to a biocide such as an antibiotic can be used in order to successfully select for and maintain cultures of the *Cyanobacterium* sp. host cells in the presence of other bacterial contaminating strains.

In a further embodiment of the invention, the recombinant gene is present on an extrachromosomal plasmid. This extrachromosomal plasmid can replicate independently from the chromosomes of the *Cyanobacterium* sp. host cells and can for example be present in a high number of copies in these cells so that the chemical compound can be produced in a high yield.

Apart from this recombinant gene, the genetically enhanced *Cyanobacterium* sp. or cyanobacterium ABICyano1 host cells can include further genetic enhancements such as partial deletions of endogenous genes of *Cyanobacterium* or further recombinant genes, which can increase the overall yield of the chemical compound being produced by the host cells. For example, if the chemical compound to be produced is ethanol, the genetic enhancements can relate to either knock out enhancements of endogenous genes coding for enzymes converting pyruvate or acetyl-CoA into a reserve or storage compound or the genetic enhancements can relate to the overexpression of enzymes of the glycolysis pathway, Calvin-cycle, intermediate steps of metabolism, amino acid metabolism, the fermentation pathway and the citric acid cycle in order to increase the production of ethanol by the *Cyanobacterium* host cells. These genetic enhancements are described in the PCT patent application WO 2009/098089 A2 starting from page 70 and following, which is hereby incorporated for this purpose. In addition, genetic enhancements further increasing the production of the chemical compound of interest can be done for example genetic enhancement of the enzymes of the carbon fixation and the subsequent carbohydrate metabolism (esp. pathways which compete with the EtOH production pathway) further genetic enhancements increasing the production of the chemical compound of interest include but are not limited to, components of the photosystems (antennas and pigment modification), components of the photosynthetic and respiratory electron transport systems and manipulations of local and global regulatory factors incl. 2-component system, sigma factors, small regulating RNAs and antisense RNAs. Further embodiments of the invention are therefore also directed to *Cyanobacterium* sp. host cells, in particular *Cyanobacterium* ABICyano1 host cells, which in comparison to the wild type cyanobacterium contain knock out mutations of endogenous genes, as long as these knock out mutations do not affect at least one of the above mentioned advantageous properties of Cyanobacterium with regard to culturing, which are as follows:

Tolerance to:

- 1%(v/v) ethanol in the medium for at least 6, 12 or 16 weeks,

48° C. preferably 50° C. most preferred at least 53 to 55° C. for at least 2 hours per day over a time period of at least 7 days, and Purging with 60% (v/v) to 80% oxygen, (resulting in oxygen concentrations of up to 1000 μmol/L in the culture during the day).

Further, an endogenous plasmid derived from this strain can be modified, either in vivo or in vitro, to be a useful plasmid vector capable of carrying production genes of interest in a wide range of host cyanobacterial cells (either *Cyanobacterium* sp., or other cyanobacterial genera such as *Synechocystis* and *Synechococcus*).

Cyanobacteria can be genetically enhanced to add enzymatic pathways of interest as shown herein in order to produce compounds of interest. The recombinant DNA sequences encoding the genes can he amplified by polymerase chain reaction (PCR) using specific primers. The amplified PCR fragments can then he digested with the appropriate restriction enzymes and cloned into either a self-replicating plasmid or an integrative plasmid. An antibiotic resistance cassette for selection of positive clones can be present on the appropriate plasmid.

In an embodiment, the recombinant nucleic acids of interest can be amplified from nucleic acid samples using known amplification techniques. PCR can be used to amplify the sequences of the genes directly from mRNA, from eDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, and for nucleic acid sequencing.

To use isolated sequences in the above techniques, recombinant DNA vectors suitable for transformation of cyanobacteria can be prepared. Techniques for transformation are well known and described in the technical and scientific literature. For example, a DNA sequence encoding one or more of the genes described herein can be combined with transcriptional and other regulatory sequences which will direct the transcription of the sequence from the gene in the transformed cyanobacteria.

In an embodiment, the recombinant genes of interest are inserted into the cyanobacterial chromosome. When the cell is polyploid, the gene insertions can be present in all of the copies of the chromosome, or in some of the copies of the chromosome.

In another embodiment, the inserted recombinant genes are present on an extrachromosomal plasmid. The extrachromosomal plasmid can be derived from an outside source, such as, for example. RSF10-based plasmid vectors, or it can be derived from an endogenous plasmid from the cyanobacterial cell or from another species of cyanobacteria.

In an embodiment, the inserted genes are present on an extrachromosomal plasmid, wherein the plasmid has multiple copies per cell. The plasmid can be present, for example, at about 1, 3, 5, 8, 10, 15, 20, 30, 40, 50, 60, 70, 80, 90, or more copies per host cyanobacterial cell. In an embodiment, the plasmids are fully segregated.

In another embodiment, the inserted genes are present on one cassette driven by one promoter. In another embodiment, the inserted genes are present on separate plasmids, or on different cassettes.

In yet another embodiment, the inserted genes are modified for optimal expression by modifying the nucleic acid sequence to accommodate the cyanobacterial cell's protein translation system. Modifying the nucleic acid sequences in this manner can result in an increased expression of the genes, Vector Suitable for Transformation of *Cyanobacterium* ABICyano1 and Its use as a Novel Shuttle Vector System for Transformation and Expression in Cyanobacteria In an embodiment, a novel vector system based on the endogenous vector from Cyanobacterium ABICyano1 has been developed. The modified vector can be used to transform cyanobacteria from a broad range of genera, including Cyanobacterium ABICyano1 itself. The new vector or extrachromosomal plasmid comprises the following minimal features:

a recombinant gene, wherein said recombinant gene encodes at least one protein selected front a group consisting of a protein that is involved in a biosynthetic pathway for the production of a chemical compound or a marker protein and an origin of replication suitable for replication in the *Cyanobacterium* ABICyano1.

One gene coding for a replication initiation factor binding to said origin of replication can either be present on the new vector itself or can be present in the chromosomes or other extrachromosomal plasmids of *Cyanobacterium* ABICyano1. The origin of replication suitable for replication in ABICyano1 and the gene coding for the replication initiation factor binding to that origin of replication ensure that the vector can be replicated in *Cyanobacterium* ABICyano1.

The nucleotide sequence of this origin of replication of this plasmid vector can have at least 80%, 90%, preferably 95% identity or can be identical to the nucleotides 3375 to 3408 of the sequence of the endogenous 68 kb plasmid shown in FIG. 4A. This putative origin of replication was found on the endogenous 6.8 kb plasmid identified and isolated from *Cyanobacterium* ABICyano1.

The sequence of the gene coding for the replication initiation factor has at least 80%. 90%, preferably 95% identity or is identical to nucleotides 594 to 3779 of the sequence of the endogenous 6.8 kb plasmid shown in FIG. 4A. Furthermore the gene coding for the replication initiation factor codes for a protein having at least 80%, 90%. preferably 95% sequence identity or is identical to the protein coded by nucleotides 594 to 3779 of the sequence of the endogenous 6.8 kb plasmid. This putative initiation replication factor is believed to bind to the putative origin of replication thereby ensuring the replication of this plasmid in *Cyanobacterium* ABICyano1.

The plasmid vector further can comprise a sequence having at least 95% identity to the sequence of the endogenous 6.8 kb plasmid shown in FIG. 4A. In a further variant of the invention, the backbone of the new vector is an endogenous plasmid originally isolated from *Cyanobacterium* strain ABICyano1.

The ABICyano1 endogenous plasmid, shown in FIG. 4A was captured by in vitro transposition reaction with EZ-Tn5 R6K γ Ori/Kan-2 transposition kit from the company Epicentre®, following the manufacturer's protocol. The cyanobacterial plasmid was rescued in surrogate *E. coli* host cells. The sequence and size of the captured plasmid was confirmed and validated by PCR, as well as by comparison with available genome sequence data. A replication protein (ORF1) was predicted to be present on the plasmid, as well as a recombinase protein (ORF4) and an origin of replication suitable for replication in *Cyanobacteriun* ABICyano1. The amino acid sequences of the putative proteins coded by ORF1, ORF2, ORF3, ORF4, ORF5 and ORF6 are depicted in FIGS. 4B, 4C, 4D, 4E, 4F and 4G, respectively.

In an embodiment, gene delivery vehicles that are developed using this plasmid (or a substantial portion of the plasmid) as a backbone may be able to be efficiently transformed to a wide range of cyanobacteria. Such vectors may also be able to efficiently produce heterologous proteins and other compounds of interest in cyanobacterial cultures.

In an embodiment of the invention, this ABICyano1-based plasmid sequence can be used to carry recombinant, for example heterologous genes of interest in a cyanobacterial host cell. This plasmid sequence was chosen to be the backbone for the construction of new modified vectors that can be utilized as a gene delivery vehicle to transform various cyanobacterial host cells.

Figure 3:
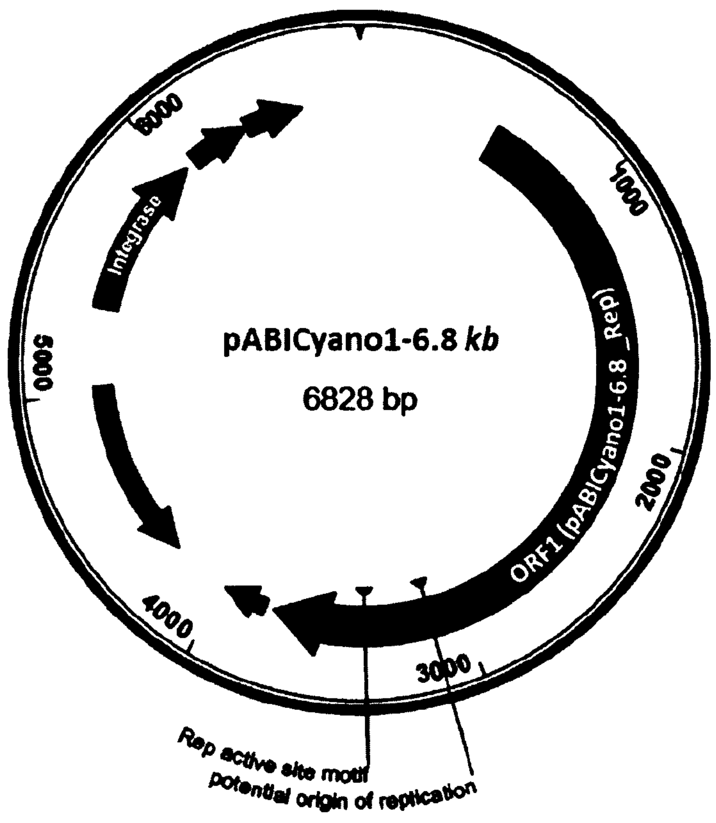
FIG. 3 is a plasmid map of the 6828 by endogenous plasmid that was identified in the *Cyanobacterium ABICyano*1 cell. The DNA sequence (SEQ ID NO: 1) is shown in FIG. 4A including the annotation of the genes and promoters done with the program vector NTI. The location of 5 putative open reading frames is shown, including the Replication Binding Protein (SEQ ID NO: 2) (ORF1) whose amino acid sequence is depicted in FIG. 4B) (CDS=complementary DNA sequence from nucleotides 594 to 3779 of the DNA sequence), which is similar to the hypothetical protein slr7037 of plasmid pSYSA (103kb) of *Synechocystis* sp. PCC 6803 and a recombinase whose amino acid sequence is depicted in FIG. 4E (SEQ ID NO: 3) (ORF4) (CDS=complementary DNA sequence from nucleotides 5350 to 6036 of the DNA sequence), which is similar to a site-specific recombinase of Bacillus thuringiensis serovar israclensis ATCC 35646. ORF2 whose amino acid sequence is depicted in FIG. 4C (SEQ ID NO: 4) runs from nucleotides 3815 to 4000, ORF3 whose amino acid sequence is depicted in FIG. 4D (SEQ ID NO: 5) from nucleotides 4260 to 5024 in antisense direction, ORF5 whose amino acid sequence is depicted in FIG. 4F (SEQ ID NO: 6) from nucleotides 6078 to 6341 and ORF6whose amino acid sequence is depicted in FIG. 4G (SEQ ID NO: 7) from nucleotides 6338 to 6586 the DNA sequence.

In an embodiment, the above-described vector was used as a starting point for producing the modified vector of the invention. FIG. 3 shows a generalized plasmid map based on the endogenous 6.8 kb plasmid from *Cyanobacterium* ABICyano1.

In an embodiment, starting with the backbone of the 6.8 plasmid from ABICyano1, modifications as described herein can be performed individually or together to increase transformation efficiency, increase the replication rate within the cell, and to increase the production of a desired product from the cyanobacterial cell. Suitable modifications include, for example, insertion of selection markers (such as antibiotic resistance genes), recombinant genes or cassettes for the production of a desired compound, and other modifications to increase the expression or stability of the plasmid in the cyanobacterial cell.

In another embodiment of the invention, codon improvement of the inserted at least one recombinant gene, to allow for improved expression in the cyanobacterial host cell, can also he performed by adapting the codon usage of the at least one recombinant gene to the codon usage of *Cyanobacterium* sp., in particular *Cyanobacterium* ABICyano1. In particular, the G and/or C wobble bases in the codons for the amino acids in the at least one recombinant gene can be replaced by A and/or T, because the GC content of the genome of *Cyanobacterium* ABICyano1 is rather low (36%). For example in variants of the recombinant genes, which are only marginally codon improved, between 1% to 10%, preferably only 2% to 6% of the codons have been changed. In highly codon improved variants of the recombinant genes at least 25%, preferably at least 50% to 65% or even at least 70% of the codons have been changed. In a further embodiment of the invention, recombinant genes can be used, which are not codon improved, such as SynAdh (see for example the extrachromosomal plasmid # 1578).

In some embodiments, the plasmid construct preparation is performed in *E. coli* to allow for ease of genetic manipulation. In order to be propagated in *E. coli*, an origin of replication suitable for Enterobacteriaceae, in particular *E. coli*, is incorporated into the plasmid vector. Once the construct is prepared and changed in *E. coli*, the plasmid can then be transferred to the cyanobacterial cell, where it can replicate as an independent plasmid. Methods of genetic engineering of plasmids using *E. coli* are generally known in the art. Alternatively the plasmid vector can also be synthesized via solid phase synthesis so that an origin of replication for Enterobacteriaceae does not need to be present in the plasmid vector.

Figure 8:
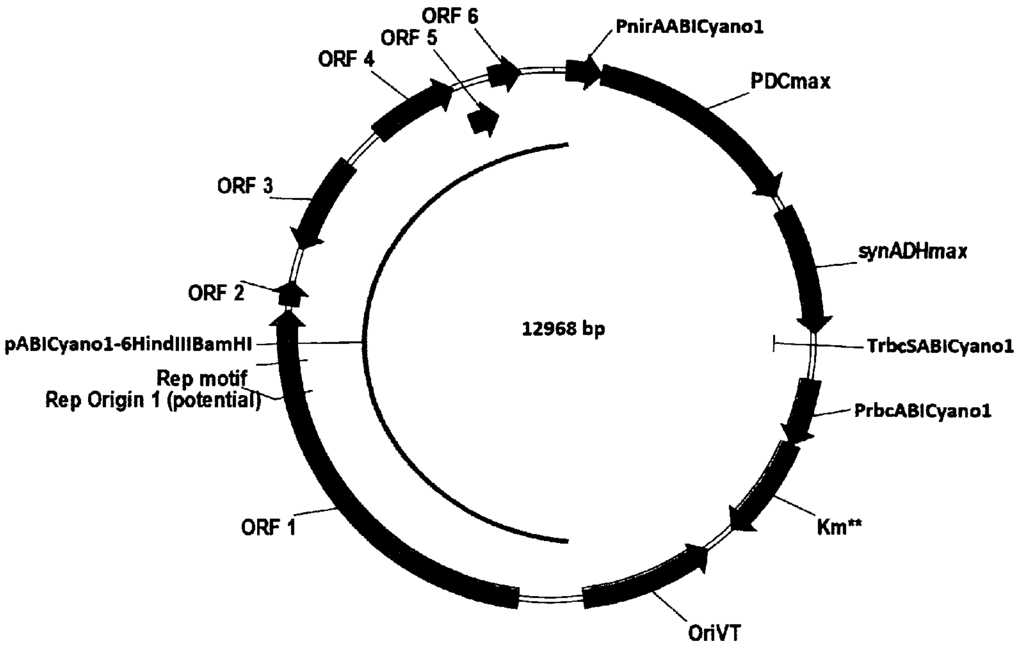
FIG. 8 is a map of the plasmid construct TK225, Its nucleotide sequence (SEQ ID NO: 9) is shown in FIG. 9. PrbcL from *Cyanobacterium ABICyano*1 runs from nucleotides 3574 to 4099, the codon improved kanamycin resistance cassette Km** is located from nucleotides 4101 to 4916, the origin of replication and transfer oriVT is located from nucleotides 5159 to 6217 in antisense direction, PnirA runs from nucleotides 96 to 378, the codon improved variant of SynAdh denoted "SynADH max" is located from nucleotides 2203 to 3210, the codon improved variant from Pyruvate decarboxylase "PDC" runs from nucleotides 379 to 2085.
Figure 10:
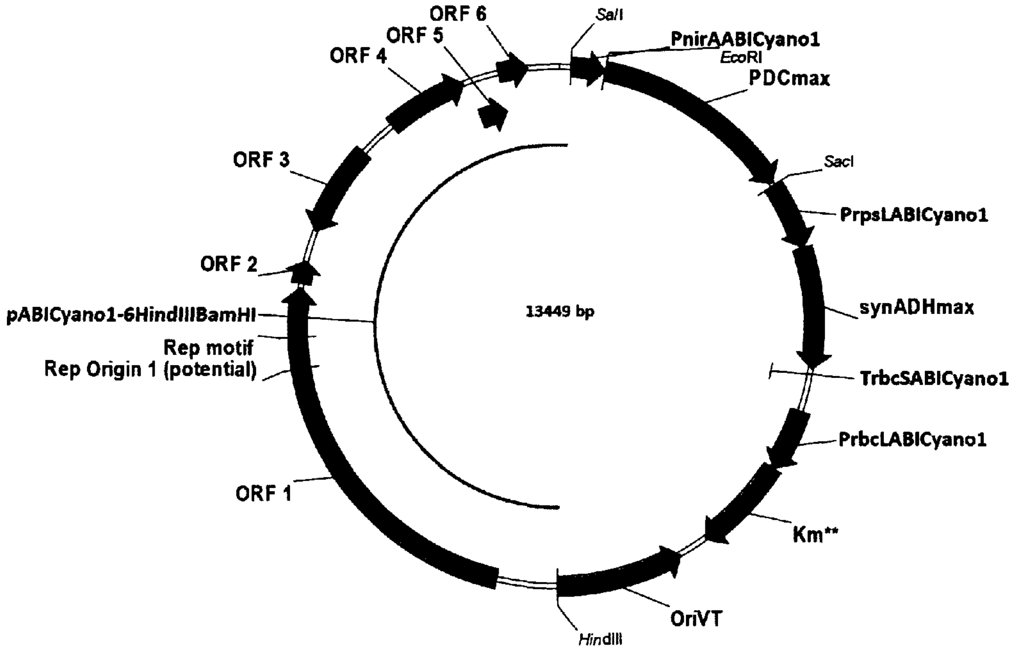
FIG. 10 is a map of the plasmid construct TK293. Its nucleotide sequence (SEQ ID NO: 10) is depicted in FIG. 11 including the annotation of the genes and promoters done with the program vector NT1.
Figure 12:
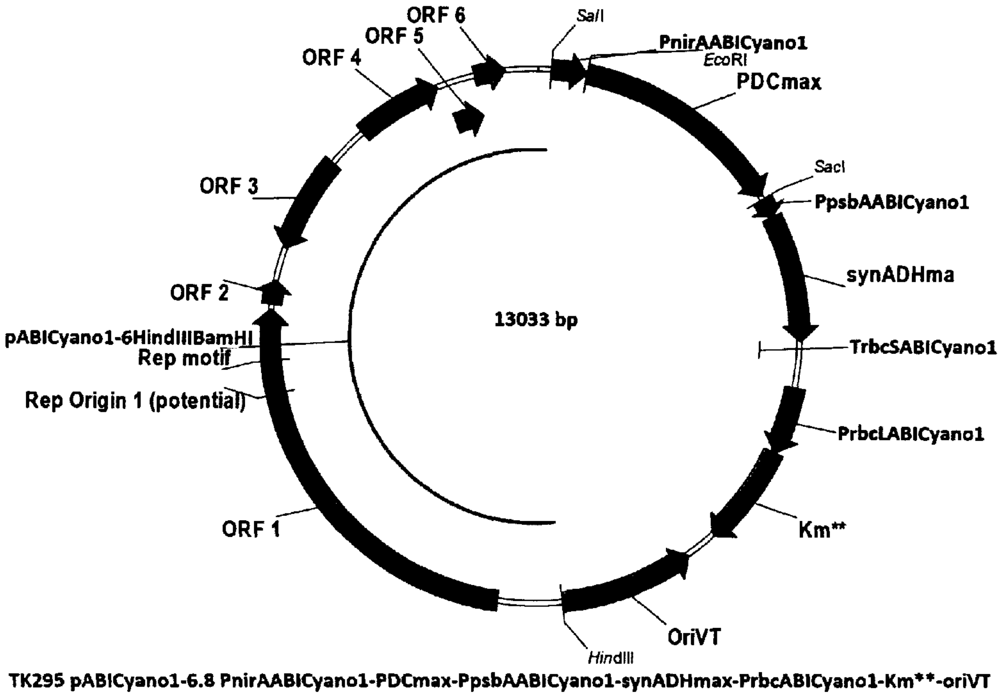
FIG. 12 is a map of the plasmid construct TK295. Its nucleotide sequence (SEQ ID NO: 11) is depicted in FIG. 13 including the annotation of the genes and promoters done with the program vector NTI.
Figure 14:
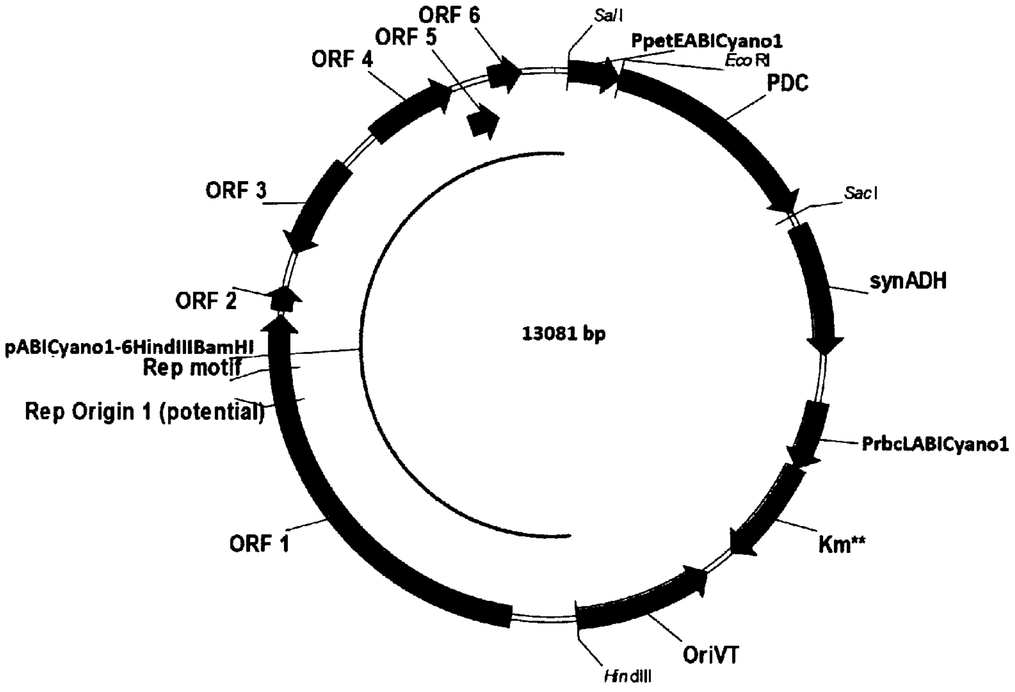
FIG. 14 is a map of the plasmid construct TK229. Its nucleotide sequence (SEQ ID NO: 12) is depicted in FIG. 15 including the annotation of the genes and promoters done with the program vector NTI.
Figure 16:
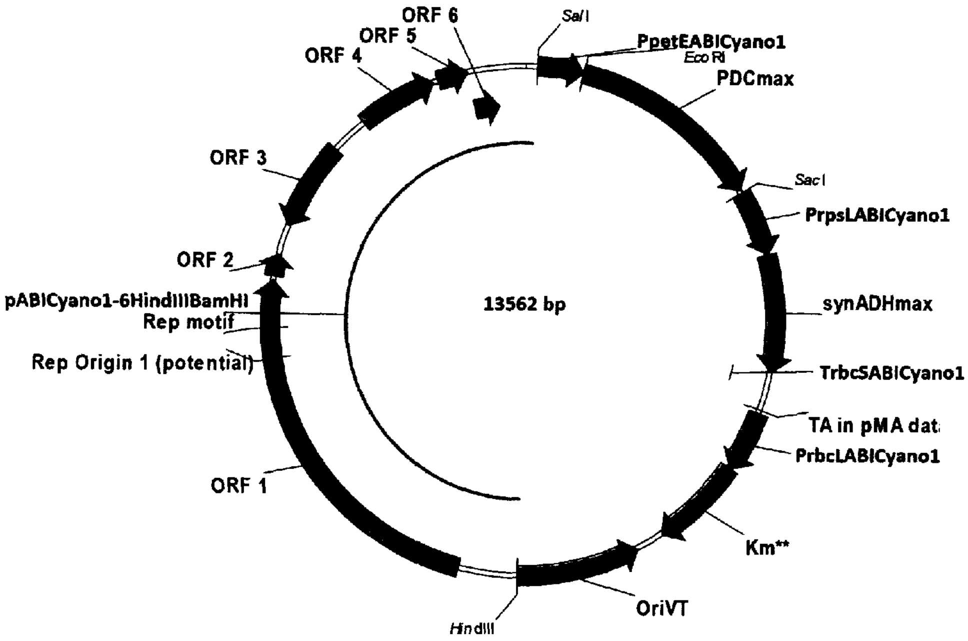
FIG. 16 is a map of the plasmid construct TK 368. Its nucleotide sequence (SEQ ID NO: 13) is depicted in FIG. 17 including the annotation of the genes and promoters done with the program vector NTI.
Figure 18:
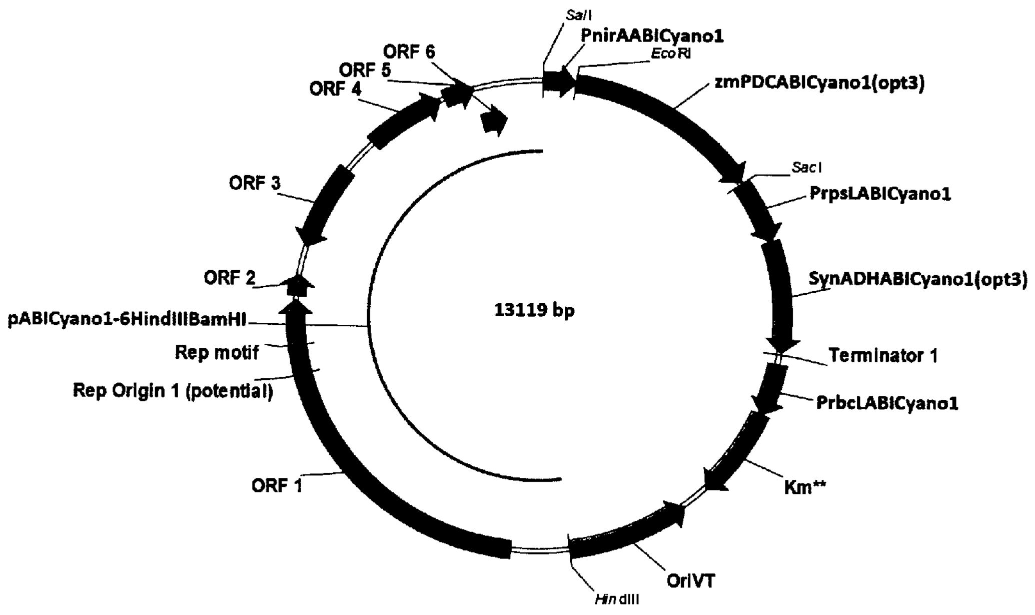
FIG. 18 is a map of the plasmid construct # 1495.Its nucleotide sequence (SEQ ID NO: 14) is depicted in FIG. 19 including the annotation of the genes and promoters done with the program vector NTI
Figure 20:
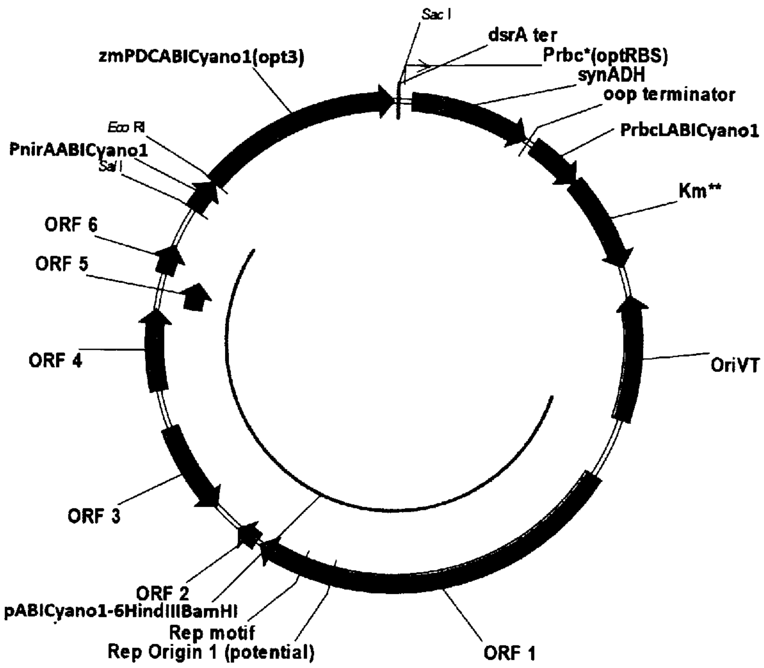
FIG. 20 is a map of the plasmid construct # 1578. Its nucleotide sequence (SEQ ID NO: 15) is depicted in FIG. 21 including the annotation of the genes and promoters done with the program vector NTI.
Figure 22:
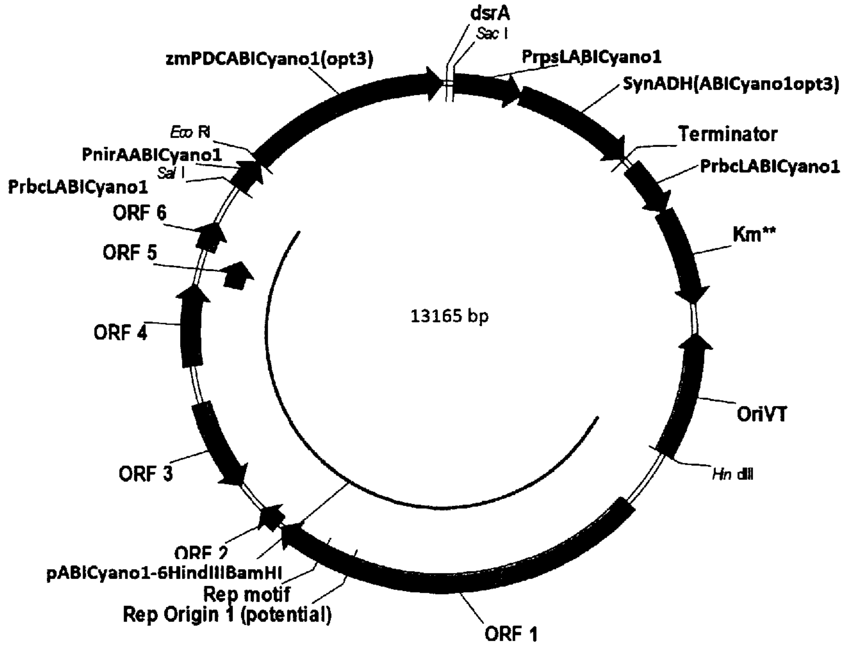
FIG. 22 is a map of the plasmid construct # 1581. Its nucleotide sequence (SEQ ID NO: 16) is depicted in FIG. 23 including the annotation of the genes and promoters done with the program vector NTI.
Figure 24:
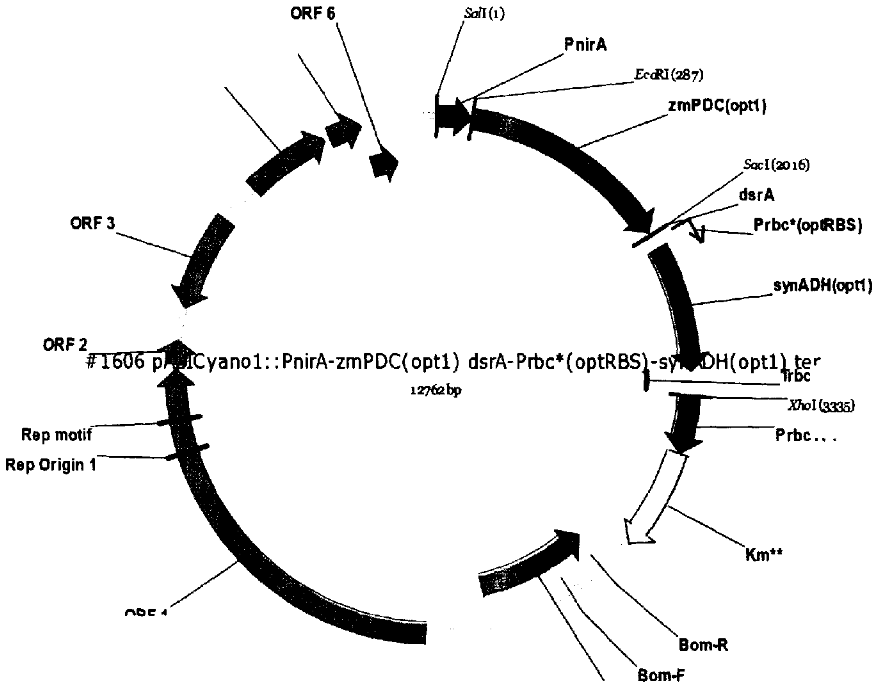
FIG. 24 is a map of the plasmid construct # 1606. Its nucleotide sequence (SEQ ID NO: 17) is depicted in FIG. 25 including the annotation of the genes and promoters done with the program vector NTI.

In an embodiment, the ABICyano1 6.8 kb endogenous plasmid (FIG. 3) was used as a backbone for the initial plasmid vector for transformation of *Cyanobacterium* sp. Since this is the endogenous vector from the species, it may be more stable when transformed to the cell than plasmids derived from completely different organisms. In an embodiment, the entire endogenous plasmid is inserted into the vector. Extrachromosomal plasmids containing the entire nucleic acid sequence of the 6.8 kb endogenous plasmid are for example shown in FIG. 8, 10 or 12. In another embodiment, a sequence of about 50%, 70%, 75%, 80% 85%, 90%, 95%, 98%, 99%, or 99.5% of the entire endogenous plasmid sequence is inserted into the vector, the extrachromosomal plasmid.

In an embodiment, the modified vector of the invention is designed to have several modular units that can be easily swapped out using specific restriction enzymes. Promoters, genes of interest, selectable markers, and other desired sequences can be moved in and out of the vector as desired. This modular design makes genetic experiments faster and more efficient.

The new vector according to certain embodiments of the invention can replicate in both cyanobacteria and in *E. coli*. The vector contains a replication unit that can function in a broad range of cyanobacterial genera. The vector also contains a replicon for propagation in *E. coli* for ease of cloning and genetic manipulation using *E. coli*.

In an embodiment, a plasmid shuttle vector is provided which is characterized by being replicable in both Escherichia coli and in a cyanobacterial species. The plasmid comprises a promoter capable of functioning in cyanobacteria and *E. coli* and a DNA sequence encoding a sequence capable of functioning as a selective marker for both Escherichia coli and cyanobacteria. Alternatively, the shuttle vector includes two different promoter systems, one functioning in cyanobacteria and the other one functional in *E. coli*. The plasmid shuttle vector enables the efficient transformation of cyanobacteria and the expression of recombinant genes of interest.

According to a further embodiment of the invention, the plasmid vector also contains an origin of transfer (oriT) which is suitable for conjugation. In particular, the plasmid vector can contain a combined origin of replication and an origin of transfer (oriVT), which enables replication in Enterobacteriaceae, in particular *E. coli* and which also enables conjugation with for example an *E. coli* donor strain and *Cyanobacterium* sp. in particular *Cyanobacterium* ABICyano1 as a recipient strain. Such an plasmid vector can be used for triparental mating wherein a conjugative plasmid present in one bacterial strain assists the transfer of a mobilizable plasmid, the plasmid vector of the present invention present in a second bacterial strain into a third recipient bacterial strain, which can be *Cyanobacterium* ABICyano1.

Also disclosed is a recombinant vector in which a gene of interest, the recombinant gene is operably linked to the shuttle vector, and cyanobacterial cells transformed with the recombinant shuttle vector. The shuttle vector is relatively small in size, relatively stable in a cyanobacterial host cell, and can replicate in a variety cyanobacterial species. This new vector is useful for expressing a variety of heterologous genes in cyanobacteria.

In an embodiment, the shuttle vector efficiently expresses a codon-optimized antibiotic resistance gene for selection of transformants, such as codon improved kanamycin or gentamycin resistance genes. The shuffle vector was constructed based on a modular basis, so that all of the key elements (replication ori, AbR gene and reporter gene) are exchangeable via unique restriction sites, providing versatile cloning options and facilitating the delivery of genes of interest to the target organisms.

Other antibiotic resistance genes can be used if desired. For example, genes conferring resistance to ampicillin, chloramphenicol, spectinomycin or other antibiotics can be inserted into the vector, under the control of a suitable promoter. In some embodiments, the vector contains more than one antibiotic resistance gene.

The vector of the invention has been modified by several factors so that it is capable of efficient replication in multiple types of cyanobacterial species. It has also been organized so that various sequences can be easily replaced with other desired sequences as needed. Thus, a construct having a different gene (or genes) of interest, a different antibiotic, a different promoter, etc. can be made with relative ease. The modified vector allows for rapid testing of various heterologous constructs in a cyanobacterial cell.

Any suitable promoter can be used to regulate the expression of the genes present in the vector. Exemplary promoter types include, for example, constitutive promoters, inducible promoters, endogenous promoters, heterologous promoters, and the like.

In an embodiment, the modular design of the modified plasmid vector allows complex sequence manipulation in cyanobacteria.

Transformation of *Cyanobacterium* sp., in particular *Cyanobacterium* ABICyano1 Cells A method for producing a genetically enhanced *Cyanobacterium* sp. host cell as described above generally comprises introducing a recombinant nucleic acid sequence including any of the recombinant genes, which were already disclosed above, into the cyanobacterial host cell. In particular, the at least one recombinant gene can be introduced into the host cells via an extrachromosomal plasmid, which can separately replicate in the host cell or the at least one recombinant gene can be introduced into the genome of the host cell, for example via homologus recombination.

In a further embodiment of the method of the invention, the method of producing a genetically enhanced *Cyanobacterium* sp. host cell comprises the method steps of:

A) Subjecting the host cell to compounds increasing the permeability of the extracellular polymer layer (EPS) and cell wall, respectively of the host cell, and B) Introducing said recombinant nucleic acid sequence into the host cell.

The inventors found out that in order to introduce the at least one recombinant gene into the *Cyanobacterium* host cell, the permeability of the extracellular polymer layer (EPS) has to be increased beforehand so that the recombinant nucleic acid sequence can pass the EPS and reach the interior of the cyanobacterial cell.

The recombinant nucleic acid sequence can be provided as part of an extrachromosomal plasmid containing cyanobacterial nucleic acid sequences in order to increase the likelihood of success for the transformation.

The method further comprises a variant, wherein during method step A) an extrachromosomal plasmid derived from an endogenous plasmid of said host cell is provided. This endogenous plasmid can for example be an extrachromosomal plasmid derived from the 6.8 kb endogenous plasmid of *Cyanobacterium* sp. ABICyano1.

Another method of the current invention further comprises protecting said recombinant nucleic acid sequence, in particular the plasmid, against endogenous restriction endonucleases of the host cell by, for example methylating at least a part of said recombinant nucleic acid sequence or modifying and/or eliminating the recognition sequences of the endogenous restriction endonucleases. By changing the nucleic acid sequence of potential recognition sites of restriction endonucleases, a digest of the recombinant nucleic acid sequence can be avoided. It was discovered that endogenous restriction endonucleases of *Cyanobacterium ABICyano*1 can cut the extrachromosomal plasmid, thereby preventing a genetic transformation of this host cell. In particular, methyltransferases, for example AvaI and AcyI can be used to protect the extrachromosomal plasmid. This plasmid can either be incubated with the methylatransferases in vitro or a helper plasmid can be present during the transformation of *Cyanobacterium ABICyano*1 in a helper *E. coli* strain in order to methylate the extrachromosomal plasmids in vivo before conjugation takes place. In addition recognition sequences for the restriction enzymes can be modified or even be deleted.

The above described method can include a further embodiment, wherein in method step A) compounds selected from a group consisting of: N-acetylcysteine, lysozyme, and β-galactosidase and combinations thereof, are used in order to increase the permeability of the EPS layer. Preferably a combination of N-acetylcysteine and lysozyme is used.

In method step B) the host cell can preferably be first subjected to N-Acetylcysteine followed by a treatment of lysozyme. The inventors found out that such a pre-treatment drastically increased the number of transformants.

The host cell can be subjected to N-acetylcysteine for 0.5 to 3 days, preferably to 1 to 2 days and can further be treated with lysozyme for 3 min. to 1 hour, preferably for 10 to 30 min, most preferred for 10 to 15 min.

The N-acetylcysteine treatment can be carried out at a temperature of 12 to 37° C., preferably 16° C., and the lysozyme treatment can be conducted in a temperature range from 20° C. to 37° C., preferably at a temperature from 20° C. to 30° C.

During method step B) the concentration of N-acetylcysteine can be kept between 0.05 mg/ml and 1 mg/ml and the concentration of lysozyme can be between 10 to 60 μg/ml.

The transformation of the plasmid vector to the host *Cyanobactrium* sp. in particular *Cyanobacterium ABICyano*1 cell can utilize any of several methods, such as natural transformation, conjugation (bi- or tri-parental mating), biolistic methods, electroporation, or other methods. In an embodiment, the transformation method is conjugation, as described in Example 19. Electroporation methods can also be used. In addition, the vector can be modified to allow for integration into the cyanobacterial chromosome by adding an appropriate DNA sequence homologous to the target region of the host genome, or through in vivo transposition by introducing the mosaic ends (ME) to the vector. Once the plasmid is established in the host cell, it can be present, for example, at a range of from 1 to many copies per cell.

Exemplary methods suitable for transformation of Cyanobacteria, include, as nonlimiting examples, natural DNA uptake (Chung, et al. (1998) FEMS Microbial. Lett. 164:353-361; Frigaard, et al. (2004) Methods Mol. Biol. 274: 325-40; Zang, et al. (2007) J. Microbial. 45:241-245), conjugation, transduction, glass bead transformation (Kindle, et al. (1989) J. Cell Biol, 109: 2589-601; Feng, et al. (2009) Mol. Biol. Rep. 36: 1433-9; U.S. Pat. No. 5,661,017), silicon carbide whisker transformation (Dunahay, et al. (1997) Methods Mol. Biol. (1997) 62: 503-9), biolistics (Dawson, et al. (1997) Curr. Microbiol. 35: 356-62; Hallmann, et al. (1997) Proc. Natl. Acad. USA 94: 7469-7474; Jakobiak, et al. (2004) Protist 155:381-93; Tan, et al. (2005) J. Microbiol. 43: 361-365; Steinbrenner, et al, (2006) Appl. Environ , Microbiol, 72: 7477-7484; Kroth (2007) Methods Mol. Biol. 390: 257-267; U.S. Pat. No. 5,661,017) electroporation (Kjaerulff, et al. (1994) Photosynth. Res. 41: 277-283; Iwai, et al. (2004) Plant Cell Physiol. 45: 171-5; Ravindran, et al. (2006) J. Microbiol. Methods 66: 174-6: Sun, et al, (2006) Gene 377: 140-149; Wang, et al. (2007) Appl. Microbiol. Biotechnol. 76: 651-657; Chaurasia, et al. (2008) J. Microbial. Methods 73: 133-141; Ludwig, et al. (2008) Appl. Microbiol, Biotechnol. 78: 729-35), laser-mediated transformation, or incubation incubation with DNA in the presence of or after pre-treatment with any of poly(amidoamine) dendrimers (Pasupathy, et al (2008) Biotechnol. J. 3: 1078-82), polyethylene glycol (Ohnuma, et al. (2008) Plant Cell Physiol. 49: 117-120), cationic lipids (Muradawa, et al. (2008) J. Biosci. Bioeng. 105: 77-80), dextran, calcium phosphate, or calcium chloride (Mendez-Alvarez, et al. (1994) J. Bacteriol. 176: 7395-7397), optionally after treatment of the cells with cell wall-degrading enzymes (Perrone, et at (1998) Mol. Biol. Cell 9: 3351-3365). Biolistic methods (see, for example, Ramesh, et al. (2004) Methods Mol. Biol. 274: 355-307; Doestch, et al. (2001) Curr. Genet. 39: 49-60; all incorporated herein by reference in their entireties).

The above described pre-treatment for the transformation of *Cyanobacterium* ABICyano1 can also be used for introducing recombinant nucleic acid sequences such as plasmids into other cyanobacterial cells harboring an extracellular polymer layer (EPS), which are different from *Cyanobacterium* ABICyano1. Non-limiting examples for cyanobacteria with an EPS include several Nostoc and Anabaena strains, such as Nostoc commune, and Anabanena cylindrica and several *Cyanothece* sp. strains, such as *Cyanothece* PCC9224, *Cyanothece* CA 3, *Cyanothece* CE 4. *Cyanothece* ET 5, *Cyanothece* ET 2. and *Cyanospira capsulata* ATCC 43193. Further non-limiting examples of cyanobacteria with an EPS are *Aphaanocapse, Anacystis, Chroococcus Gloeothece, Microcystis Synechocystis Lyngbya Microcolens Oscillatoria Phormidium Spirulina Anabaena Cyanospira Nostoc Scytonema Tolypothrix Chlorogloeopsis Fischerella Mastigocladus* (see for example: “Exopolysaccharide-producing cyanobacteria and their possible exploitation: A review” Roberto De Philippis el al., *Journal of Applied Phycology* 13: 293-299, 2001, and “Exocellular polysaccharides from cyanobacteria and their possible applications” Roberto De Philippis et al., FEMS Microbiology Reviews 22 (1998) 151-175).

Transformation to other Cyanobacterial Species using the plasmid vectors of the invention In an embodiment of the invention, the modified vector based on the endogenous 6.8 kb plasmid from *Cyanobacterium ABICyano*1 is transformed to a *Cyanobacterium ABICyano*1 host cell. In another embodiment, a vector including the endogenous 6.8 kb plasmid from *Cyanobacterium ABICyano*1 is transformed to another species in the *Cyanobacterium* genus. In yet another embodiment, the endogenous 6.8 kb plasmid from *Cyanobacterium ABICyano*1 is transformed to another species of cyanobacteria, such as, for example, *Synechocystis* or *Synechococcus*, as described in Example 36.

The novel *Cyanobacterium ABICyano*1 -based vector of the invention is capable of transforming and replicating in several different types of cyanobacteria. Exemplary cyanobacterial genera that can be transformed with the nucleic acids described herein include, but are not limited to, *Synechocystis, Synechococcus, Acaryochloris, Anabaena, ThermoSynechococcus, Chamaesiphon, Chroococcus, Cyanobacterium, Cyanobium, Dactylococcopsis, Gloeobacter, Gloeocapsa, Gloeothece, Microcystis. Prochlorococcus, Prochloron, Chroococcidiopsis, Cyanocystis, Dermocarpella, Myxosarcioa, Pleurocapsa, Stanieria, Xenococcus. Arthrospira, Borzia, Crinalinum, Geitlerinema, Halospirulina, Leptolyngbya, Limnothrix, Lyngbya, Microcoleus, Cyanodictyon, Aphanocapsa, Oscillatoria, Planktothrix, Prochlorothtix, Pseudanabuena, Spirulina, Starria, Symploca, Trichodesmium, Tychonema, Anabaenopsis, Aphanizomenon, Calothrix, Cyanospira, Cylindrospermopsis, Cylindrospermum, Nodularia, Nostoc, Chlorogloeopsis, Fischerella, Geitleria, Nostochopsis. lyengariella, Stigonema, Rivularia, Scytonema, Tolypothrix, Cyanothece, Phormidium, Adrianemo*, and the like.

Promoters

Any desired promoter can be used to regulate the expression of the genes for the production of a desired compound in *Cyanobacterium ABICyano*1. Exemplary promoter types include but are not limited to, for example, constitutive promoters, inducible promoters (e.g., by nutrient starvation, heat shock, mechanical stress, environmental stress, metal concentration, light exposure, etc.), endogenous promoters, heterologous promoters, and the like.

In an embodiment, the inserted genes are placed under the transcriptional control of promoters selected from a group consisting of: rbcLS, ntcA, nblA, isiA, petJ, petE, PcorT, PsmtA, PziaA, sigB, lrtA (see FIG. 61A (SEQ 1D NO: 51)), htpG, hspA, clpBl, hliB, ggpS, psbA2, psaA, nirA, PnarB, PnrtA and crhC. The inserted genes can be regulated by one promoter, or they can be regulated by individual promoters. The promoters can be constitutive or inducible. The promoter sequences can be derived, for example, from the host cell, from another organism, or can be synthetically derived.

Exemplary promoters for expression in Cyanobacteria include but are not limited to PpetJ, PpsbD, PnblA, PrpoA, PisiB, PrbcLS, PntcA, pnblA, PisiA, PpetJ, PpetE, PcorT, PsmtA, PziaA, PsigB, PlrtA, PhtpG, PhspA, PclpB1, PhliB, PggpS, PpsbA2, PpsaA, PnirA, PnarB, PnrtA, PcrhC, and further metal ion inducible promoters and the like. Examples of constitutive promoters that can be used include but are not limited to PrbcL, PrnpA, PrpsL, PrpoA, PpsaA, PpsbA2, PpsbD, PcpcB.

The promoters hspA, clpBl, and hliB can be induced by heat shock (raising the growth temperature of the host cell culture from 300° C. to 400° C.), cold shock (reducing the growth temperature of the cell culture from 300° C. to 20 ° C.), oxidative stress (for example by adding oxidants such as hydrogen peroxide to the culture), or osmotic stress (for example by increasing the salinity). The promoter sigB can be induced by stationary growth, heat shock, and osmotic stress. The promoters ntcA and nblA can be induced by decreasing the concentration of nitrogen in the growth medium and the promoters psaA and psbA2 can be induced by low light or high light conditions. The promoter htpG can be induced by osmotic stress and heat shock. The promoter crhC can be induced by cold shock. An increase in copper concentration can be used in order to induce the promoter petE, whereas the promoter petJ is induced by decreasing the copper concentration. Additional details of these promoters can be found, for example, in PCT/EP2009/060526, which is incorporated by reference herein in its entirety.

In certain other preferred embodiments, truncated or partially truncated versions of these promoters including only a small portion of the native promoters upstream of the transcription start point, such as the region ranging from −35 to the transcription start can often be used. Furthermore, introducing nucleotide changes into the promoter sequence, e.g. into the TATA box, the operator sequence and/or the ribosomal binding site (RBS) can be used to tailor or improve the promoter strength and/or its induction condition, e.g. the concentration of inductor required for induction. For example the inducible promoter can be PnirA from Cyanobacterium ABICyano1, which is repressed by ammonium and induced by nitrite. This promoter may harbor nucleotide changes in either one of the ribosomal binding site, the TATA box, the operator the 5'-UTR (untranslated region).

In particular, PnirA can have the following generalized nucleotide sequence (SEQ ID NO: 78):

5'(N)$_{116}$ATGCAAAAAACGAAT(N)$_{7}$ATGTGTAAAAAGAAA(N)$_{15}$GTA

GTCAAAGTTAC(N)$_{22}$TAATGT(N)$_{55}$CCGAGGACAAA(N)$_{2}$ATG-3' wherein each of the nucleotides N is independently selected from a group consisting of A, T, C and G and wherein the two ATGs in the 5'-region of the promoter are the start for NtcB binding sites the capital letter GTA is the start for the NtcA binding site, the capital letter CCG denotes the start of the RBS, and the 3'-ATG is the start codon for the first recombinant gene transcriptionally controlled by this promoter.

Another generalized DNA sequence of the nirA promoter includes nucleotide changes in the ribosomal binding site leading to the following general DNA sequence (SEQ ID NO: 79):

5'(N)$_{116}$ATGCAAAAAACGAAT(N)$_{7}$ATGTGTAAAAAGAAA(N)$_{15}$GTA

GTCAAAGTTAC(N)$_{22}$TAATGT(N)$_{55}$GGAGGATCAGCC(N)$_{2}$ATG-3' wherein the capitalized underlined nucleotides denote nucleotide changes in comparison to the native promoter.

In another embodiment the modified nirA promoter can include changes in the operator region (binding, site for NtcB and NtcA) and the TATA box leading to the following general nucleotide sequence (SEQ ID NO: 80):

5'(N)$_{116}$ATGCAAAAAACGCAT(N)$_{7}$ATGCGTAAAAAGCAT(N)$_{15}$GTA

ATCAAAGTTAC(N)$_{22}$TAATAT(N)$_{55}$CCGAGGACAAA(N)$_{2}$ATG-3' wherein the capitalized underlined nucleotides denote nucleotide changes in comparison to the native promoter.

Another variant of PnirA combines the above changes thereby having the following DNA sequence (SEQ ID NO: 81):

5'(N)$_{116}$ATGCAAAAAACGCAT(N)$_{7}$ATGCGTAAAAAGCAT(N)$_{15}$GTA

ATCAAAGTTAC(N)$_{22}$TAATAT(N)$_{55}$GGAGGATCAGCC(N)$_{2}$ATG-3'

Another embodiment of the invention provides the $Co^{2+}$-inducible promoter corT, which has the general nucleotide sequence (SEQ ID NO: 82) of:

CAT(N)$_{7}$GTTTACTCAAAACCTTGACATTGACACTAATGTTAAGGTTTAG

GCT(N)$_{15}$CAAGTTAAAAAGCATG, wherein each of the nucleotides N is independently selected from a group consisting of: A, T, C and G and wherein the 5'-CAT is the start codon of corR (antisense orientation) the 3'-ATG is the start codon for the first recombinant gene transcriptionally controlled by this promoter.

A modified variant of PcorT includes changes in the RBS having the following nucleotide sequence (SEQ ID NO: 83):

CAT(N)$_{7}$GTTTACTCAAAACCTTGACATTGACACTAATGTTAAGGTTTAG

GCT(N)$_{15}$GAGGATAAAAAGCATG, wherein the capitalized underlined nucleotides denote nucleotide changes in comparison to the native promoter.

Yet another variant of PcorT includes changes in the TATA box having the general DNA sequence (SEQ ID NO: 84) of:

CAT(N)$_{7}$GTTTACTCAAAACCTTGACATTGACACTAATGTTAAGGTTTAG

AAT(N)$_{15}$CAAGTTAAAAAGCATG wherein the capitalized underlined nucleotides denote nucleotide changes in comparison to the native promoter.

A third modified corT promoter combines the above mentioned two modifications having the following DNA sequence (SEQ ID NO: 85):

CAT(N)$_{7}$GTTTACTCAAAACCTTGACATTGACACTAATGTTAAGGTTTAG

AAT(N)$_{15}$GAGGATAAAAAGCATG

Furthermore the Zn2+-inducible promoter smtA from Synechococcus PCC 7002 can be used having the following general nucleotide sequence (SEQ ID NO: 86):

(N)$_{8}$AATACCTGAATAATTGTTCATGTGTT(N)$_{4}$TAAAAATGTGAACAAT

CGTTCAACTATTTA(N)$_{12}$GGAGGT(N)$_{7}$ATG

Changes in the ribosomal binding site can lead to the following generalized nucleotide sequences of PsmtA (SEQ ID NO: 87):

(N)$_{8}$AATACCTGAATAATTGTTCATGTGTT(N)$_{4}$TAAAAATGTGAACAAT

CGTTCAACTATTTA(N)$_{10}$AAGGAGGTGAT(N)$_{4}$ATG, or (SEQ ID NO: 88)

(N)$_{8}$AATACCTGAATAATTGTTCATGTGTT(N)$_{4}$TAAAAATGTGAACAAT

CGTTCAACTATTTA(N)$_{10}$AAGGAGGTAT(N)$_{5}$ATG wherein the capitalized underlined nucleotides denote nucleotide changes in comparison to the native promoter.

In an embodiment of the invention, the recombinant genes to be inserted into the shuttle vector can have an inducible promoter or a constitutive promoter. The promoter can be upstream of one gene to regulate that gene, or the promoter can be upstream of several genes, so that one promoter regulates the expression of more than one gene. Alternatively, in some embodiments, each inserted gene can be regulated by a separate promoter. In an embodiment, the promoter can be derived from the cyanobacterial host cell, or can be obtained from another cyanobacterial species, or can be obtained from another organism.

Exemplary promoters include, but are not limited to the psbA2 promoter from *Synechocystis* PCC6803, cpcBA promoter from *Synechocystis* PCC6803, cpcB from Cyanobacterium ABICyano1 (see FIG. 61I (SEQ ID NO: 52)), nirA gene promoter (278 bp) from Cyanobacterium ABICyano1 lrtA (light-repressed protein, ribosomal subunit interface protein) gene promoter from *Cyanobacterium ABICyano*1, mrgA gene promoter (214 bp) from *Cyanobacterium ABICyano*1 (see FIG. 61B (SEQ ID NO: 53)), nblA gene promoter (338 bp) from *Cyanobacterium ABICyano*1 (see FIG. 61C (SEQ ID NO: 54)), ggpS (glucosylglycerol-phosphate synthase) gene promoter (408 bp) from *Cyanobacterium ABICyano*1 (see FIG. 61D (SEQ ID NO: 55)), petJ gene promoter (411 bp) from *Cyanobacterium ABICyano*1 (see FIG. 61E (SEQ ID NO: 56)), ppsA (phosphoenolpyruvate synthase gene) promoter (211 bp) from *Cyanobacterium ABICyano*1 (see FIG. 61F (SEQ ID NO: 57)), rnpA (Ribonuclease P) gene promoter (542 bp) from *Cyanobacterium ABICyano*1 (see FIG. 61G (SEQ ID NO: 58)), the pstS gene promoter (380 bp) from *Cyanobacterium ABICyano*1 (see FIG. 61H (SEQ ID NO: 59)), and the like.

Examples of other suitable promoters include, for instance, the PrpsL promoter, The PnblA7120 promoter from Nostoc sp. PCC7120, The PrbcL6803 promoter from *Synechocystis* sp. PCC6803 and the PsmtA1535 promoter from *Synechococcus* sp. PCC7002.

Many types of inducible promoters can be used. Exemplary inducible promoters include but are not limited to PpetJ, PnirA, PnblA, and PisiB, further metal-inducible promoters e.g. PsmtA, PziaA, PcorT, PnrsB, and the like. Differentially expressed promoters like PlrtA, PmrgA, PpstS, as well as synthetic promoters can also be used.

The promoters hspA, clpB1, and hliB, for example, can be induced by heat shock (raising the growth temperature of the host cell culture from 30° C. to 40° C.), cold shock (reducing the growth temperature of the cell culture from 30° C. to 20° C.), oxidative stress (for example by adding oxidants such as hydrogen peroxide to the culture), or osmotic stress (for example by increasing the salinity). The promoter sigB can be induced by stationary growth, heat shock, and osmotic stress. The promoters ntcA and nblA can be induced by decreasing the concentration of nitrogen in the growth medium.

The promoters PpsaA and PpsbA2 can be induced by low light or high light conditions. The promoter htpG can be induced by osmotic stress and heat shock. The promoter PcrhC can be induced by cold shock.

The promoter petE can be induced by an increase in copper concentration. Alternatively, the promoter petJ can be induced by decreasing the copper concentration.

Furthermore the promoter controlling the transcription of the at least one recombinant gene can be as cyanobacterial promoter. The promoter can be endogenous to the genetically enhanced *Cyanobacterium* sp. or can be a promoter, which was modified in order to increase its efficiency. The promoter can also be a heterologous promoter from a different cyanobacterial or bacterial species. For example the promoter and transcription regulator gene combinations of ziaR-PziaA from *Synechocystis* sp. PCC6803, smtB-PsmtA from *Synechoccocus* sp. PCC7002, corR-PcoT from *Synchocyctis* sp. PCC6803, nrsRS-PnrsB from *Synechoccocus* sp. PCC6803, and aztR-PaztA from *Anabaena (Nostoc)* sp. strain PCC7120 can be used to control the transcription of the at least one recombinant gene in *Cyanobacterium* sp. in particular in *Cyanobacterium* ABICyano1. The promoter/regulator pair aztR-PaztA can be activated by adding $Zn^{2+}$. In *Synechococcus* PCC7002 smtB-PsmtA is induced by $Zn^{2+}$and corR-PcorT by adding $Co^{2+}$, The regulator/promoter combination nrsRS-PnrsB can be induced by the addition of $Ni^{2+}$. The combination of ziaR-PziaA with the ziaA promoter and the ziaR repressor can be induced by the addition of $Zn^{2+}$.

Another possibility is to use the promoter PsmtA which is endogenous to *Synechococcus* PCC7942 and *Synechococcus* PCC7002. The gene smtA (SYNPCC7002_A2563) which is transcriptionally controlled by this promoter codes for a metallothionein (YP_001735795.1) involved in resistance to inter alia zinc. A repressor protein (YP_001735796.1) binds to the PsmtA in the uninduced state which is encoded by the gene smtB (SYNPCC7002_A2564).

In Anabaena PCC7120 the gene aztA (a1r7622) codes for a Zn2+, Cd2+ and Pb2+ transporting ATPase (NP__478269.1) which is transcriptionally controlled by the promoter PaztA. The promoter is blocked in the uninduced state by a repressor protein (NP__478268.1) coded by the gene aztR (all7621).

In Synechocystis PCC 6803 the gene corT (s1r0797 ) can be found coding for a cobalt transporting ATPase (NP__442633.1). This gene is transcriptionally controlled by the promoter PcorT, which is transcriptionally controlled by a regulator protein (NP__442632.1) coded by the gene corR (sll0794), which binds to the corT promoter. The promoter PcorT is one example for a cobalt inducible promoter, whereas the other already mentioned promoters PziaA, PsmtA, and PsmtA are examples for zinc inducible promoters.

It is also possible to improve the tightness and the level of expression of the protein involved in the biosynthetic pathway for the production of a chemical compound or the marker protein if mutations are introduced in the TATA-box, the operator sequence and/or the ribosomal binding site of the promoter controlling the recombinant gene so that the promoter can have at least 90% sequence identity to an endogenous promoter of the genetically enhanced *Cyanobacterium* sp. or to another cyanobacterial promoter.

The promoter also can be another inducible promoter selected from a group consisting of PnirA for example from *Cyanobacterium* sp. ABICyano1, PnrtA, and PnarB. The nirA promoter is repressed by ammonium and induced by nitrite.

The promoter can furthermore be a constitutive promoter selected from a group consisting of: PrpsL, Prbc, PcpcB and Ppeth which for example all can be endogenous promoters of *Cyanobacterium* sp. ABICyano1.

In the case that more than one recombinant gene is present, the for example first and second recombinant gene can be controlled by one promoter thereby forming a transcriptional operon. Alternatively the first and second recombinant genes can be controlled by different first and second promoters. In the case that the first recombinant gene codes for a protein catalyzing a reaction not present in the wild-type *Cyanobacterium* sp. directing the carbon flux away from the metabolic pathways of the wild-type cyanobacterium, such as Pyruvate decarboxylase enzyme, this gene can be controlled by an inducible promoter such as PnirA from *Cyanobacterium* sp. ABICyano1. Such a configuration ensures that this gene is only turned on upon induction if a sufficiently high culture density of *Cyanobacterium* sp. is reached. In the case that the second recombinant gene codes for a protein catalyzing a chemical reaction present in the wild-type *Cyanobacterium* sp., such as alcohol dehydrogenase, this gene can be under the control of either an inducible or a constitutive promoter, because it does not disturb the carbon flux to the same extend as the protein coded by the first recombinant gene. The second recombinant gene then may be under the control of constitutive promoters such as PrbcL. PpetE, or PrpsL all from *Cyanobacterium* sp. ABICyano1.

The chosen promoter elements can be combined with any of the genes encoding any of the enzymes of the invention by using standard molecular cloning techniques. Further description and characterization of constitutive or inducible promoters that can be useful in combination with the genes inserted onto the shuttle vector of the invention can include, for example: Samartzidou et al., "Transcriptional and Post-transcriptional Control of mRNA from IrtA, a Light-repressed Transcript in *Synechococcus* sp. PCC 7002," Plant Physiol. 117:225-234(1998); Duran et al., "The Efficient Functioning of Photosynthesis and Respiration in *Synechocystis* sp. PCC 6803 Strictly Requires the Presence of either Cytochrome c6 or Plastocyanin," Journal of Biological Chemistry 279:7229-7233 (2004); Singh et al., "The Heat Shock Response in the Cyanobacterium *Synechocystis* sp. Strain PCC 6803 and Regulation of Gene Expression by HrcA and SigB," Arch Microbiol. 186:273-286 (2006); Imamura et al., "Antagonistic Dark/light-induced SigB/SigD, Group 2 Sigma Factors, Expression Through Redox Potential and their Roles in Cyanobacteria," FEBS Lett. 554:357-362 (2003); Imamura et al., "Growth Phase-dependent Activation of Nitrogen-related Genes by a Control Network of Group 1 and Group 2 Sigma Factors in a Cyanobacterium," Jour. Biol. Chem. 281:2668-2675 (2006); Agrawal et al., "Light-dependent and Rhythmic psbA Transcripts in Homologous/heterologous Cyanobacterial Cells," Biochem. Biophys. Res. Commun. 255:47-53(1999); Mohamed et al., "Influence of Light on Accumulation of Photosynthesis-specific Transcripts in the Cyanobacterium *Synechocystis* 6803," Plant Mol. Biol. 13:693-700 (1989); Muramatsu et al., "Characterization of High-light-responsive Promoters of the psaAB Genes in *Synechocystis* sp. PCC 6803," Plant Cell Physiol. 47:878-89 0 (2006); Marin et al., "Gene Expression Profiling Reflects Physiological Processes in Salt Acclimation of *Synechocystis sp. strain PCC* 6803," Plant Physiol, 136:3290-3300 (2004). Marin et al. , "Salt-dependent Expression of Glucosylglycerol-phosphate Synthase, Involved in Osmolyte Synthesis in the Cyanobacterium *Synechocystis* sp. Strain PCC 6803," Jour. Bacteriol. 184:2870-2877 (2002). Qi et al., "Application of the *Synechocystis* nirA Promoter to Establish an Inducible Expression System for Engineering the *Synechocystis* Tocopherol Pathway," Appl. Environ. Microbiol. 71:5678-5684 (2005); Maeda et al., "cis-acting Sequences Required for NtcB-dependent, Nitrite-responsive Positive Regulation of the Nitrate Assimilation Operon in the Cyanobacterium *Synechococcus* sp. Strain PCC 7942," Jour. Bacteriol. 180:4080-4088 (1998); and Herranen et al., "Regulation of Photosystem I Reaction Center Genes in *Synechocystis* sp. Strain PCC 6803 During Light Acclimation," Plant Cell Physiol. 46:1484-1493 (2005; Buikema et al., "Expression of the Anabaena hetR gene from a Copper-regulated Promoter Leads to Heterocyst Differentiation under Repressing Conditions," Proc. Natl. Acad. Sci. U S A. 98:2729-2734(2001). Mary et al ., "Effects of High Light on Transcripts of Stress-associated Genes for the Cyanobacteria *Synechocystis* sp. PCC 6803 and Prochlorococcus MED4 and MIT9313," Microbiology 150:1271-1281 (2004); He et al., "The High Light-inducible Polypeptides in *Synechocystis* PCC 6803. Expression and Function in High Light," Jour, Biol, Chem.276:306-314 (2001); Fang et al., "Expression of the Heat Shock Gene hsp16.6 and Promoter Analysis in the Cyanobacterium, *Synechocystis* sp. PCC 6803," Curr Microbiol. 49:192-198 (2004); Kappell et al., "The Response Regulator RpaB Binds the High Light Regulatory 1 Sequence Upstream of the High-light-inducible hliB Gene from the Cyanobacterium *Synechocystis* PCC 6803," Arch. Microbiol. 187:337-342 (2007).

Codon Improvement of the Inserted Sequences

At least some of the nucleic acid sequences to be expressed in the cyanobacterial cell can be codon optimized for optimal expression in the target cyanobacterial strain. The underlying rationale is that the codon usage frequency of highly expressed genes is generally correlated to the host cognate tRNA abundance, (Bulmer, Nature 325:728-730; 1987). In an embodiment, the codon optimization is based on the cyanobacterium ABICyano1 (as well as its close relative species) codon usage frequency (host codon bias), in order to achieve desirable heterologous gene expression (Sharp et al., Nucleic Acids Res. 15:1281-1295).

The codon optimization can be performed with the assistance of publicly available software, such as Gene Designer (DNA 2.o). Additional modifications to minimize unwanted restriction sites, internal Shine-Dalgarno sequences, and other sequences such as internal termination sequences and repeat sequences can also be performed. These general codon-optimization methods have been shown to result in up to approximately 1000 fold higher expression of heterologous genes in target organisms (Welch et al., PLoS One 4, e7002;2009; and Welch et al., Journal of the Royal Society; Interface 6 (Suppl 4), S467-S476; 2009).

Accordingly, in an embodiment of the invention, the nucleic acid sequences of the inserted genes are modified so that they will have improved expression in cyanobacteria. For example, the selectable marker gene that confers spectinomycin resistance was codon optimized for higher expression in cyanobacteria. Additionally, the selectable marker gene that confers kanamycin resistance was codon optimized for higher expression in cyanobacteria, The gene that encodes the GFP marker was also codon optimized for higher expression in cyanobacteria using this method.

Further, the gene that encodes ADH was codon optimized for higher expression in cyanobacteria. The gene that encodes PDC was codon optimized for higher expression in cyanobacteria.

Restriction Systems in Cyanobacterium

Restriction systems are important barriers for the introduction of DNA in cyanobacteria. Foreign DNA is restricted and degraded by restriction enzymes and other non-specific nucleases during its entry into a cell. An understanding of the restriction systems is therefore critical in developing new transformation systems and protocols, especially in uncharacterized bacteria.

In a cyanobacterial cell, restriction systems occur in pairs comprising a restriction enzyme and a specific DNA methyltransferase. Specific methylation of the restriction enzyme recognition sequence protects DNA in the cell from degradation by the corresponding restriction enzyme. In natural systems, this is one mechanism of protecting the cell from foreign invasion.

Different cyanobacterial cells have different restriction systems. Knowledge of the specific system that is naturally present in a cell can assist in making necessary modifications to foreign plasmid DNA to make the transformation process proceed more readily. For example, knowing which restriction systems exist in a given host cell can allow one to protect foreign plasmid DNA prior to entry into the cell by treating it with either a specific methylase, or a general methylase, that allows for protection of the DNA from degradation by the host cell's restriction enzyme(s). This type of DNA methylation can provide an effective protection against restriction barriers during the transformation or conjugation process. The selection of suitable DNA methyltransferases relies on the thorough understanding of the restriction enzyme repertoire of the organism. Since restriction enzymes and DNA methyltransferases occur in pairs, identification of the restriction enzymes implies the existence and specificity of the corresponding DNA methyltransferases.

As described in Examples 13 and 14, *Cyanobacterium ABICyano*1 was found to have an endogenous restriction enzyme system. This was initially observed using sequence analysis, which predicted the presence of AvaI and HgiD1 (AcyI) in ABICyano1. Subsequent detection of restriction activity in ABICyano1 crude extracts confirmed this finding. Because of this finding, the appropriate methylating agent can be added to protect foreign genes from being degraded soon after entry into the cell, as described in Example 18 and demonstrated in FIG. 26. In an embodiment, this is performed in vivo during conjugation using, a "helper plasmid" having genes encoding specific methylases that are capable of protecting the identified restriction sites from degradation. Another possibility would be to first incubate the nucleic acid constructs to be transferred to ABICyano1 with the methylases and then introduced these methylated nucleic acid constructs into ABICyano1.

Selecting for Successful Transformation

The presence of a foreign gene encoding antibiotic resistance can be selected, for example, by placing the putative transformed cells into an amount of the corresponding antibiotic, and picking the cells that survive. The selected cells are then scaled-up in the appropriate culture medium, to allow for further testing.

Production of Compounds of Interest in Cyanobacteria

The 6.8 endogenous plasmid vector from *Cyanobacterium* sp. ABICyano1 cell can be genetically enhanced to carry genes of interest into a new host *Cyanobacterium* sp. ABICyano1 cell. In an embodiment, the added genes are part of a biochemical pathway to produce a chemical compound of interest in the cyanobacterial host cell. One, two, three, four, five, six, or seven or more recombinant genes can be added to the vector. In an embodiment, the compound of interest is a biofuel. In another embodiment, the compound of interest is ethanol.

The introduction of the first as well as, if necessary, second recombinant gene or even further recombinant genes, directs the metabolic flux of the genetically enhanced *Cyanobacterium* sp. towards the production of the chemical compound. During the course of the synthesis of the chemical compound, $CO_2$ is consumed and oxygen and carbon based compounds, like sugars are produced. Owing to the at least one recombinant gene the carbon based compounds are further converted into the chemical compound of interest.

In particular, the chemical compound can be a biofuel or an organic compound which, for example, can be selected from the group of: alkanols, alkanes, polyhydroxyalkanoates, e.g. PHB, fatty acids, fatty acid esters, carboxylic acids, such as amino acids, hydrogen, terpenes and terpenoids, peptides, polyketides, alkaloids, lactams, such as pyrrolidone, alkenes and ethers, such as THF and combinations thereof.

In a further variant of the genetically enhanced *Cyanobacterium* of the invention, the chemical compound is selected from various alkanols, such as ethanol, propanol or butanol, alkanes and alkenes, such as ethylene or propylene, biopolymers such as polyhdyroxyalkanoates like polyhydroxybutyrate, fatty acids, fatty acid esters, carboxylic acids such a amino acids, terpenes and terpenoids. Furthermore, the valuable chemical compound can be selected from peptides, polyketides, alkaloids, lactams and ethers such as tetrahydrofuran or any combinations of the above-mentioned chemical compounds.

Depending on the valuable chemical compound to be produced, the respective recombinant genes encoding the proteins for the production of these chemical compounds have to be introduced into the *Cyanobacterium* sp. For example, if the first chemical compound is ethanol, the recombinant genes encoding enzymes for ethanol production can be Pdcenzyme (pyruvate decarboxylase) catalyzing the reaction from pyruvate to acetaldehyde. Adh enzyme (alcohol dehydrogenase), catalyzing the reaction from acetaldehyde to ethanol, or a AdhE enzyme (alcohol dehydrogenase E) which directly converts acetyl-coenzyme A to ethanol. The Adh enzyme can, for example, be a $Zn^{2+}$-dependent alcohol dehydrogenase such as AdhI from Zymomonas mobilis (ZmAdh) or the Adh enzyme from Synechocystis PCC6803 (SynAdh). Alternatively or in addition, the enzyme can also be an iron-dependent alcohol dehydrogenase (e.g. AdhII from Zymomonas mobilis). The $Zn^{2+}$-dependent alcohol dehydrogenase can, for example, be an alcohol dehydrogenase enzyme having at least 60%, 70%, preferably 80% and most preferred 90% or even more than 90% sequence identity to the amino acid sequence of Zn2+ dependent Synechocystis Adh. Experiments have shown that in particular Synechocystis alcohol dehydrogenase SynAdh (slrll92) is able to ensure a high ethanol production in genetically enhanced cyanobacteria due to the fact that the forward reaction, the reduction of acetaldehyde to ethanol is much more preferred for Synechocystis alcohol dehydmgenase enzyme than the unwanted back reaction from ethanol to acetaldehyde. For these reasons the use of a SynAdh encoding recombinant gene for production of ethanol as a first chemical compound is preferred.

The AdhE is an iron-dependent, bifunctional enzyme containing a CoA-depending aldehyde dehydrogenase and an alcohol dehydrogenase activity. One characteristic of iron-dependent alcohol dehydrogenases (e.g. AdhE and AdhII) is the sensitivity to oxygen. In the case of the AdhE from *E. coli* a mutant was described that shows in contrast to the wild type also Adh activity under aerobic conditions. The site of the mutation was determined in the coding region at the codon position 568. The G to A nucleotide transition in this codon results in an amino acid exchange from glutamate to lysine (E568K). The E568K derivate of the *E. coli* AdhE is active both aerobically and anaerobically. [Holland-Staley et al., Aerobic activity of Escherichia coli alcohol dehydrogenase is determined by a single amino acid, J Bacteriol. 2000 Nov; 182(21):6049-54].

AdhE enzymes directly converting acetyl coenzyme A to ethanol can preferably be from a thermophilic source thereby conferring an enhanced degree of stability. The AdhE can be from Thermosynechococcus elongatus BP-1 or also can be a non-thermophilic AdhE enzyme from *E. coli.*

The pyruvate decarboxylase can for example be from Zymomonas mobilis, Zymobacter palmae or the yeast Saccharomyces cerevisiae. Regarding the nucleic acid sequences, protein sequences and properties of these above mentioned ethanologenic enzymes, reference is made to the PCT patent application WO 2009/098089 A2, which is hereby incorporated for this purpose.

Two other alcohols which are relatively widespread are propanol and butanol. Similar to ethanol, they can be produced by fermentation processes. The following enzymes are involved in isopropanol fermentation and can be encoded first and/or second recombinant genes: acetyl-CoA acetyltransferase (EC:2.3.1.9), acetyl-CoA:acetoacetyl-CoA transferase (EC:2.8.3.8), acetoacetate decarboxylase (EC:4.1.1.4) and isopropanol dehydrogenase (EC:1.1.1.80).

The following enzymes are involved in isobutanol fermentation: acetolactate synthase (EC:2.2.1.6), acetolactate reductoisonierase(EC:1.1.1.86), 2,3-dihydroxy-3-methyl butanoate dehydratase (EC:4.2.1.9), α-ketoisovalerate decarboxylase (EC:4,1.1.74), and alcohol dehydrogenase (EC: 1.1.1.1).

In the case that ethylene is to be produced as a chemical compound, the at least one recombinant gene encodes an enzyme for ethylene formation, in particular the ethylene-forming enzyme 1-aminocyclopropane-1-carboxylate oxidase (EC 1.14.17.4), which catalyzes the last step of ethylene formation, the oxidation of 1-aminocyclopropane-l-carboxylic acid to ethylene. The substrate for the ethylene-forming enzyme is synthesized by the enzyme 1-aminocyclopropane-l-carboxylic acid synthase (EC 4.4.1.14) from the amino acid methionine.

If the chemical compound is an isoprenoid such as isoprene, the at least one recombinant gene encodes an enzyme such as isoprene synthase. Isoprene synthase (EC 4.2.3.27) catalyzes the chemical reaction from dimethylallyldiphosphate to isoprene and diphosphate.

Terpenes are a large and very diverse class of organic compounds, produced primarily by a wide variety of plants, particularly conifers. Terpenes are derived biosynthetically from units of isoprene and are major biosynthetic building blocks in nearly every living organism. For example, steroids are derivatives of the triterpene squalene. When terpenes are modified chemically, such as by oxidation or rearrangement of the carbon skeleton, the resulting compounds are generally referred to as terpenoids. Terpenes and terpenoids are the primary constituents of the essential oils for many types of plants and flowers. Examples of biosynthetic enzymes are farnesyl pyrophosphate synthase (EC 2.5.1.1), which catalyzes the reaction of dimethylallylpyrophosphate and isopentenyl pryrophosphate yielding farnesyl pyrophosphate. Another example is geranylgeranyl pyrophosphate synthase (EC 2.5.1.29), which catalyzes the reaction between transfarnesyl diphosphate and isopentenyl diphosphate yielding diphosphate and geranylgeranyl diphosphate.

In the case that the chemical compound is hydrogen, the first and/or second recombinant genes can for example code for hydrogenase an enzyme catalyzing the following reaction:

$$12H^{+}+12X_{reduced}\rightarrow 6H_{2}+12X_{oxidized},$$

wherein X is an electron carrier such as ferredoxin.

Further examples of valuable chemical compounds are the so-called non-ribosomal peptides (NRP) and the polyketides (PK). These compounds are synthesized by plants, fungi and only a few bacteria such as actinomycetes, myxobacteria and cyanobacteria. They are a group of structurally diverse secondary metabolites and often possess bioactivities of high pharmacological relevance. Hybrids of non-ribosomal peptides and polyketides also exist, exhibiting both a peptide and a polyketide part. Recombinant genes for the production of non-ribosomal peptides as the first chemical compounds are for example gene clusters encoding for non-ribosomal peptide synthetases (NRPS). NRPS are characteristic modular multidomain enzyme complexes encoded by modular non-ribosomal peptide synthetase gene clusters. Examples for non-ribosomal peptide synthetases are actinomycin synthetase and gramicidin synthetase.

In general there are two distinct groups of polyketides (PK), the reduced polyketides of type I, the so-called macrolides and the aromatic polyketides of type II. Type I polyketides are synthesized by modular polyketide synthases (PKS), which are characteristic modular multidomain enzyme complexes encoded by modular PKS gene clusters. Examples for recombinant genes for the production of type I polyketides are the rapamycin synthase gene cluster and the oleandomycin synthase gene duster. One example for a recombinant gene for type II polyketides is the actinorhodin polyketide synthase gene cluster.

Examples for recombinant genes for the production of hybrids of polyketides and non-ribosomal peptides are the microcystin synthetase gene cluster, microginin synthetase gene cluster, and myxothiazole synthetase gene cluster.

Further examples of valuable chemical compounds are the alkaloids. Alkaloids are a compound group which is synthesized by plants. Alkaloids have highly complex chemical structures and pronounced pharmacological activities. Examples for biosynthetic enzymes for alkaloids which can be encoded by recombinant genes f or the production of the chemical compound are strictosidine synthase, which catalyzes the stereoselective Pictet-Spengler reaction of tryptamine and secologanin to form 3a(S)-strictosidine. The primary importance of strictosidine is not only its precursor role for the biosynthetic pathway of ajmaline but also because it initiates all pathways leading to the entire monoterpene indol alkaloid family. Another example of an enzyme encoded by a first recombinant gene is strictosidine glucosidase from the ajmaline biosynthetic pathway. This enzyme is able to activate strictosidine by deglycosylation thus generating an aglycon. This aglycon of strictosidine is the precursor for more than 2,000 monoterpenoid indol alkaloids.

Further examples of enzymes encoded by at least one recombinant gene are:

(R,S)-3 '-hydroxy-N-methylcoclaurine 4'-O-methyltransferase (4'OMT) central to the biosynthesis of most tetrahydrobenzyl isoquinolin-derived alkaloids;

Berberine bridge enzyme (BBE) specific to the sanguinarine pathway;

(R,S)-reticuline 7-O-methyltransferase (7OMT) specific to laudanosine formation;

Salutaridinol 7-O-acetyltransferase (SalAT) and codeinone reductase that lead to morphine.

Vitamins, as further examples of chemical compounds, are organic compounds that are essential nutrients for certain organisms and act mainly as cofactors in enzymatic reactions but can also have further importance, e.g. as antioxidants in case of vitamin C. Vitamin C can be synthesized via the L-Ascorbic acid (L-AA) biosynthetic pathway from D-glucose in plants. The following enzymes are involved in vitamin C synthesis and can be encoded by first and/or second recombinant genes:

Hexokinase, Glucose-6-phosphate isomerase, Mannose-6-phosphate isomerase. Phosphomannomutase . Mannose-1-phosphate guanylyltransferase, GDP-mannose-3,5-epimerase, GDP-L-galactose phosphorylase, L-Galactose 1-phosphate phosphatase, L-galactose dehydrogenase, L-galactono-1,4-lactone dehydrogenase.

Lactams are cyclic amides whereas the prefixes indicate how many carbon atoms (apart from the carbonyl moiety) are present in the ring: β-lactam (2 carbon atoms outside the carbonyl, 4 ring atoms in total), γ-lactam (3 and 5), δ-lactam (4 and 6). One example for a γ-lactam is Pyrrolidone, a colorless liquid which is used in industrial settings as a high-boiling, non-corrosive, polar solvent for a wide variety of applications. It is also an intermediate in the manufacture of polymers such as polyvinylpyrrolidone and polypyrrolidone.

Ethers are a class of organic compounds that contain an ether group—an oxygen atom connected to two alkyl or aryl groups—of general formula R-O-R. A well-known example is tetrahydrofuran (THF), a colorless, water-miscible organic liquid. This heterocyclic compound is one of the most polar ethers with a wide liquid range, it is a useful solvent. Its main use, however, is as a precursor to polymers.

One example for the natural occurring ethers are the divinyl ether oxylipins. The main enzymes involved in their biosynthesis are the lipoxygenase and especially the divinyl ether synthase.

Alkanes (also known as saturated hydrocarbons) are chemical compounds that consist only of the elements carbon (C) and hydrogen (H) (i.e., hydrocarbons), wherein these atoms are linked together exclusively by single bonds (i.e., they are saturated compounds). Each carbon atom must have 4 bonds (either C-H or C-C bonds), and each hydrogen atom must be joined to a carbon atom (H-C bonds). The simplest possible alkane is methane, CH4. There is no limit to the number of carbon atoms that can he linked together. Alkanes, observed throughout nature, are produced directly from fatty acid metabolites. A two-gene pathway widespread in cyanobacteria is responsible for alkane biosynthesis and can be included in the first recombinant genes. An acyl-ACP reductase (EC: 1.3.1.9) converts a fatty acyl-ACP into a fatty aldehyde that is subsequently converted into an alkane/alkene by an aldehyde decarbonylase (EC:4.1.99.5.).

Biopolymers such as polyhydroxyalkanoates or PHAs are linear polyesters produced in nature by bacterial fermentation of sugar or lipids. They are produced by the bacteria to store carbon and energy. The simplest and most commonly occurring form of PHA is the fermentative production of poly-3-hydroxybutyrate (P3HB) but many other polymers of this class are produced by a variety of organisms: these include poly-4-hydroxybutyrate (P4HB), polyhydroxyvalerate (PHV), polyhydroxyhexanoate (PHH), polyhydroxyoctanoate (PHO) and their copolymers. The main enzymes involved in PHA synthesis are as follows: For P3HB synthesis two molecules of acetyl-CoA were condensed by a β-ketothiolase (EC:2.3.1.9) to synthesize acetoacetyl-CoA, which is converted to (R)-3-hydroxybutyryl-CoA (3HBCoA) by NADPH-dependent acetoacetyl-CoA reductase (EC: 1.1.1.36). The 3HBCoA is subsequently polymerized by poly (3-hydroxyalkanoate) synthase (EC:2.3.1.-) and converted to (P3HB).

About 100,000 metric tons of the natural fatty acids are consumed in the preparation of various fatty acid esters. The simple esters with lower chain alcohols (methyl-, ethyl-, n-propyl-, isopropyl- and butyl esters) are used as emollients in cosmetics and other personal care products and as lubricants. Esters of fatty acids with more complex alcohols, such as sorbitol, ethylene glycol, diethylene glycol and polyethylene glycol are consumed in foods, personal care, paper, water treatment, metal working fluids, rolling oils and synthetic lubricants. Fatty acids are typically present in the raw materials used for the production of biodiesel. A fatty acid ester (FAE) can be created by a transesterification reaction between fats or fatty acids and alcohols. The molecules in biodiesel are primarily fatty acid methyl esters FAMEs, usually obtained from vegetable oils by transesterification with methanol. The esterification of the ethanol with the acyl moieties of coenzyme A thioesters of fatty acids can he realized enzymatically by an unspecific long-chain-alcohol O-fatty-acyltransferase (EC 2.3.1.75) from Acinetobacter baylyi strain ADP1.

*Cyanobacterium* host cells according to certain embodiments of the invention can comprise a whole sequence of recombinant genes coding for proteins for the production of the chemical compound in the case that a cascade, for example of different enzymes, is necessary to produce the chemical compound.

In particular, the first protein encoded by the first recombinant gene can produce a first intermediate which is further converted by the second protein encoded by the second recombinant gene into another second intermediate, which then in turn is further converted by a third protein encoded by a third recombinant gene into a third intermediate, so that a sequence of consecutive recombinant biocatalysts, which provide intermediates for the next recombinant enzyme for the production of the chemical compound can be introduced into the *Cyanobacterium* host cells.

According to a further preferred embodiment of the invention, the compound can be alkanols, particularly ethanol. In the case of ethanol production as a chemical compound, the at least one recombinant gene preferably encodes a pyruvate decarboxylase as a first protein, which catalyzes the chemical reaction leading from pyruvate to acetaldehyde. According to a further embodiment of the invention, the *Cyanobacterium* of the invention further comprise at least a second recombinant gene encoding a second protein for the production of the chemical compound.

In the case that the chemical compound of interest is ethanol, the second recombinant gene preferably encodes alcohol dehydrogenase, which is able to convert the acetaldehyde provided by the pyruvate decarboxylase, the first protein, into the final chemical compound, ethanol.

The alcohol dehydrogenases can be $Zn^{2+}$or iron dependent alcohol dehydrogenases, for example AdhI, AdhII from Zymomonas mobilis, SynAdh from Synechocystis PCC6803or even AdhE, which is able to directly convert acetyl coenzyme A into ethanol. Especially with regard to AdhE only one biocatalyst can be sufficient in order to produce the first chemical compound ethanol.

In an embodiment, a Pdc protein and an Adh protein are produced, which in turn produce ethanol in the cell, as shown herein in Examples 20 and 21. In an embodiment, genes that are involved in a biosynthetic pathway are inserted.

The plasmid vector of the invention can be used to carry a gene or genes involved in other biosynthetic pathways to produce a compound of interest in the *Cyanobacterium* sp. ABICyano1 cell. Exemplary compounds include but are not limited to organic carbon compounds, alcohols, fatty acids, oils, carotenoids, proteins, enzymes, biofuels, nutraceuticals, pharmaceuticals, and the like. Additional information on the compounds that can be produced from cyanobacteria can be found, for example, in PCT/EP2009/000892, filed Feb. 9, 2009, and in PCT/EP2009/1060526, filed Aug. 13, 2009, both of which are incorporated by reference herein in their entirety. Genes involved in the biosynthetic pathway for the production of other compounds can be inserted into the vector.

In an embodiment, the compounds of interest that are produced from the recombinant *Cyanobacterium* sp. ABICyano1 can be removed intermittently as desired from the growing culture as the culture grows, or the compounds can be separated at the end of a batch growth period. The cultures can be grown indoors, or can be grown outdoors in enclosed containers such as plastic bioreactors, or in another suitable type of container.

In an embodiment of the invention, genes that encode enzymes involved in the production of ethanol can be inserted into the vector. The genes can be codon optimized for optimal expression in *Cyanobacterium* sp. ABICyano1,and can utilize any suitable promoter and regulatory sequences.

In an embodiment, the enzyme involved in the biosynthetic pathway for ethanol production is a pyruvate decarboxylase (Pdc). Pyruvate decarboxylase converts pyruvate to acetaldehyde. In a further embodiment, the enzyme involved in the biosynthetic pathway for ethanol production is an alcohol dehydrogenase (Adh). Alcohol dehydrogenase converts acetaldehyde to ethanol.

In another embodiment, the Adh and/or Pdc genes are originally derived from *Zymomoaoas mobilis, Zymobacter palmae*, or another cyanobacteria such as *Synechocystis* sp. PCC6803, *Synechococeus* sp. PCC7002, and the like. In an embodiment, the gene encoding the Pdc enzyme is from *Zymomonas* or *Zymobacter*, while the gene encoding Adh is from *Synechocystis* sp PCC6803.

Production of a Chemical Compound of Interest: Demonstration using Ethanol Production The chemical compound of interest that is produced can be chosen from a number of compounds, wherein a biosynthetic pathway for the production of the compound in known. In an embodiment, the inserted genes are derived from the genes present in a biochemical pathway in a prokaryote or a eukaryote. In an embodiment, the pathway genes are derived from a prokaryote such as *E. coli*. In another embodiment, the pathway genes are derived from a eukaryotic cell, such as yeast. The genes can be derived from one organism, or can be derived from multiple organisms. Some of the genes can be derived, for example, from a cyanobacterial cell.

In an embodiment, the vector can harbor genes for ethanol production. For example, a gene encoding a PDC enzyme, along with a gene encoding an ADH enzyme can be inserted into the vector. Each of the genes can be regulated by a separate promoter, or one upstream promoter can regulate several or all of the inserted genes. The transformed cells are cultured, and ethanol can then he produced.

The ethanol that is produced can be quantitated by several methods. In one method, gas chromatography is used, following methods derived from blood alcohol quantitation methods, as described in Example 35. In another method, ethanol is measured by a commercially available ethanol determination kit.

Cyanobacterial Growth Medium

A number of known recipes for cyanobacterial growth medium can be used. In an embodiment, BG11 medium, shown below in Tables 1 and 2, is used for growing *Cyanobacterium* sp. ABICyano1. In an embodiment, the cyanobacterial strain is a fresh water strain, and the general medium recipe below (BG-11) is used). In another embodiment of the invention, the culture grows best in a marine (salt water) medium, by adding an amount of salt to the BG11 medium.

TABLE 1

Composition of BG-11 medium

| Compound | Amount (per liter) | Final Concentration |
|---|---|---|
| $NaNO_3$ | 1.5 g | 17.6 mM |
| $K_2HPO_4$ | 0.04 g | 0.23 mM |
| $MgSO4 \cdot 7H_2O$ | 0.075 g | 0.3 mM |
| $CaCl_2 \cdot 2H_2O$ | 0.036 g | 0.24 mM |
| Citric acid | 0.006 g | 0.031 mM |
| Ferric ammonium citrate | 0.006 g | — |
| EDTA (disodium salt) | 0.001 g | 0.0030 mM |
| $NaCO_3$ | 0.02 g | 0.19 mM |
| Trace metal mix A5 | 1.0 ml | — |

TABLE 2

Trace Metal Composition of BG-11 medium

| Trace Metal mix A5 | Amount | Final Concentration in Working Medium |
|---|---|---|
| $H_3BO_3$ | 2.86 g | 46.26 μm |
| $MnCl_2 \cdot 4H_2O$ | 1.81 g | 9.15 μm |
| $ZnSO_4 \cdot 7H_2O$ | 0.222 g | 0.772 μm |
| $NaMoO_4 \cdot 2H_2O$ | 0.39 g | 1.61 μm |
| $CuSO_4 \cdot 5H_2O$ | 0.079 g | 0.32 μm |
| $Co(NO_3)_2 \cdot 6H_2O$ | 49.4 mg | 0.170 μm |
| Distilled water | 1.0 L | — |

Distilled water or seawater (35 practical salinity units=psu; see Unesco (1981a). The Practical Salinity Scale 1978 and the International Equation of State of Seawater 1980. Tech. Pap. Mar. Sci., 36: 25 pp.) is added to the final volume of 1.0 L.

In an embodiment, the cells are grown autotrophically, and the only carbon source is $CO_2$. In another embodiment, the cells are grown mixotrophically, for example with the addition of a carbon source such as glycerol, The cultures can be grown indoors or outdoors. The light cycle can be set as desired, for example: continuous light, or 16 hours on and 8 hours off, or 14 hours on and 10 hours off, or 12 hours on and 2 hours off.

The cultures can be axenic, or the cultures can also contain other contaminating species.

In an embodiment, the cyanobacteria are grown in enclosed bioreactors in quantities of at least about 100 liters, 500 liters, 1,000 liters, 2,000 liters, 5,000 liters, or more. In an embodiment, the cyanobacterial cell cultures are grown in disposable, flexible, tubular photobioreactors made of a clear plastic material.

In another embodiment, the cultures are grown indoors, with continuous light, in a sterile environment. In another embodiment, the cultures are grown outdoors in an open pond type of photobioreactor, The present invention is further described by the following non-limiting examples. However, it will be appreciated that those skilled in the art, on consideration of this disclosure, may make modifications and improvements within the spirit and scope of the present invention,

EXAMPLES

Example 1

Bacterial Strains, Growth Conditions, and Selection of Transformants

*Escherichia coli* (*E. coli*) strains HB101 (Promega), XL10-Gold (Stratagene), αselect (Bioline) were grown in Luria-Bertani (LB) medium at 37° C. Ampicillin (50 μg/m 1), kanamycin (50 μg/ml), and chloramphenicol (34 μg/ml ) were used when appropriate. Cultures were continuously shaken overnight at 200 rpm and at 100 rpm, respectively, when used for conjugation. ABICyano1 was cultured at 28° C.-37° C. in liquid BG11 fresh water medium on a reciprocal shaker at 150 rpm under continuous illumination of approximately 30-40 μmol photons* $m^{-2}$*$sec^{-1}$ Unless otherwise noted, the *Cyanobacterium* sp. ABICyano1 transformants were selected on solid BG11 medium containing 10-20 μg/ml kanamycin and were maintained on BG11 plates containing 40 μg/ml kanamycin. For growth in liquid freshwater BG11 medium, 30-40 μg/ml of kanamycin was applied.

Example 2

DNA isolation

Plasmid DNA from *E. coli* strains was isolated using a GeneJetTM Plasmid Miniprep Kit (Fermentas) according to the manufacture's protocol. For plasmid isolation from putative ABICyano1 transformants, total DNA was prepared according to Saha et al. (2005), World Jour. Microbiol Biotechnol 21:877-881. Briefly, 25 ml of *Cyanobacterium* sp. ABICyano1 culture was harvested, washed with TE buffer and frozen at −80° C for 30 minutes. The cyanobacterial cells were then lysed by a lysozyme treatment at 37° C for 60 minutes. The suspension was then incubated with 10% (v/v) SDS and proteinase K until the suspension became clear. The DNA was extracted using phenol and chloroform/isoamylalcohol (24:1 v/v) and then precipitated with isopropanol.

Example 3

Plasmid rescue

For plasmid rescue from putative *Cyanobacterium* ABICyano1 transformants, total DNA was isolated and transformed in both α-select and XL10-Gold. *E. coli* colonies were selected for kanamycin resistance; DNA was isolated from single colonies and analyzed by PCR and restriction analysis, respectively, for the presence of the correct plasmid. In particular, the endogenous plasmid of ABICyano1 was captured with the EZ-Tn5™ (R6Kγori/KAN-2) Tnp Transposome™ kit (Epicentre, Madison, WI) by following the protocol provided by the manufacture. The rescued clones were amplified in TransforMax™ EC100 D™ pir-116 electro-competent *E. coli* host cells (Epicentre, Madison, WI). Plasmid DNA was prepared with Qiagen plasmid Maxi kit (Qiagen Inc., Valencis, CA). Approximately 8 to 16 rescued clones were selected for sequencing via the conventional Sanger sequencing protocol. Protein-coding genes from each of the plasmids were predicted with the gene finder Glimmer (Delcher AL, Bratke KA, Powers EC, & Salzberg SL (2007) identifying bacterial genes and endosymbiont DNA with Glimmer. Bioinformatics 23(6):673-679) version 3.02, followed by BLAST against the NCBI NR database.

Example 4

Preparation of Cyanobacterial Culture Medium

BG-11 stock solution was purchased from Sigma Aldrich (Sigma Aldrich, St. Louis, MO). Stock solutions of the antibiotics spectinomycin (100 mg/m1) and kanamycin (50 mg/ml) were purchased from Teknova (Teknova, Hollister, CA). Stock solution of the antibiotic gentamycin (10 mg/ml) was purchased from MP Biomedicals (MP Biomedicals, Solon, OH). Marine BG-11 (mBG-11) was prepared by dissolving 35 g Crystal Sea Marinemix (Marine Enterprises International, Inc., MD) in 1 L water and supplementing with BG-11 stock solution. Vitamin B12 (Sigma Aldrich) was supplemented to mBG-11 to achieve a final concentration of 1 μg/L , as needed.

Example 5

Isolation and Initial Characterization of *Cyanobacterium* ABICyano1 strain

*Cyanobacterium* ABICyano1 is a unicellular cyanobacterium which has been found to be very hardy and tolerant to mans common environmental stresses, such as high light intensity, and high temperature. This strain also tolerates a wide range of salinities.

Figure 5A:
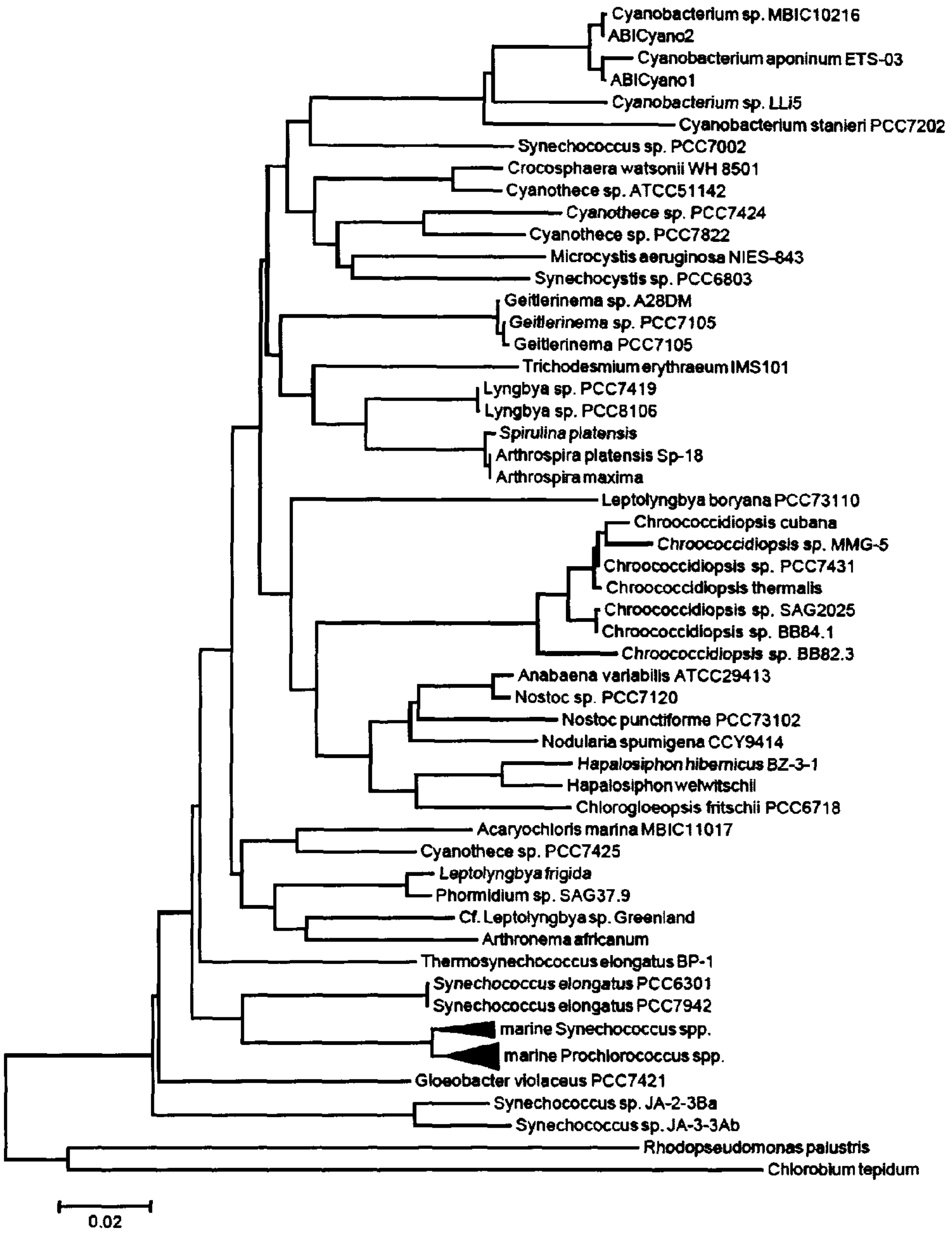
FIG. 5A is a phylogenetic tree showing the relationship between the new *Cyanobacterium* isolate (ABICyano1) and other cyanobacterial species. The tree was built with the 16S rRNA gene sequences with the Neighbor-Joining method using the Tamura-Nei nucleotide substitution model assuming uniform heterogeneity among sites. The scale bar indicates number of substitutions per site. A sequence comparison of 16S rDNA of ABICyano1 (SEQ ID NO: 63) with 16S rDNA from *Cyanobacterium* spp *Cyanobacterium* sp. MBIC10216, *Cyanobacterium* aponinum ETS-03, ABICyano2, *Cyanobacterium* sp. LLi5. and *Cyanobacterium* stanieri PCC 7202 (SEQ ID NOs: 60-62 and 64-65, respectively) which shows that ABICyano1 is 99% identical to *Cyanobacterium* spp. is presented in FIG. 5B.

A phylogenetic tree showing the relationship between the new *Cyanobacterium* isolate (ABICyano1) and other cyanobacterial species is shown in FIG. 5A. This tree utilized the 16S rRNA gene sequences with the Neighbor-Joining method using the Tamura-Nei nucleotide substitution model assuming uniform heterogeneity among sites. The scale bar indicates number of substitutions per site. In particular, the 16S ribosomal RNA (rRNA) gene sequences (16S rDNA) of ABICyano1 was predicted from the genome sequence with RNAmmer program ( Lagesen K, et al. (2007) RNAmmer: consistent and rapid annotation of ribosomal RNA genes. Nucleic Acids Research 35(9):3100-3108). These sequences were then used as a query to search against the NCBI database and 16S rDNA sequences from 4 species belonging to the genus *Cyanobacierium* were retrieved as the top BLAST hits (Altschul SF, et al. (1997) Gapped BLAST and PSI-BLAST: a new generation of protein database search programs. Nucl. Acids. Res. 25(17):3389-3402). Comparison of 16S rDNA shows that ABICyano1 is 99% identical to *Cyanobacterium* spp. (See FIG. 5B). The phylogenetic tree constructed with 16S rDNA from known cyanobacteria reveals that ABICyano1 is clustered together with *Cyanobacterium* spp. in a monophyletic clade, with ABICyano1 and *Cyanobacteerium aponimum* ETS-03 in a single sub-clade, and *Cyanobacterium* sp. MBIC10216 in another Example 6

Characterization of the *Cyanobacterium ABICyano*1 Strain: Ethanol Tolerance

The new *Cyanobacterium ABICyano*1 strain was tested to determine its tolerance to the presence of ethanol in the culture medium, in comparison to two publicly available strains, Synechocystis PCC6803 and Synechococcus PCC7002. The cells were cultured in 100 mL Erlenmeyer flasks with 50 mL culture volume in marine BG11 media [35 psu]. The cultures were spiked with 1% (v/v) ethanol. The cultures were examined weekly for cell viability and remaining ethanol concentration. At each of the weekly samplings, the ethanol level was replenished as needed in order to maintain the 1% (v/v) ethanol concentration. The cells were also examined using a microscope (light microscope, phase contrast, auto-fluorescence). If more than 50% of cells were intact the test was continued. Cyanobacterial cells were deemed to be intact if cell morphology did not change significantly upon addition of ethanol, the cells were still green, and cells were not lysed after addition of ethanol. The table below shows the number of weeks that each of the strains remained at least 50% viable in the cultures spiked with 1% ethanol. Growth for at least 8 weeks is considered to be a positive screening result. The below data therefore show that *Cyanobacterium*, in particular *Cyanobacterium* sp. ABICyano1 (ATCC No. PTA-13311 can withstand at least 1% ethanol in the medium for at least eight weeks, preferably at least 12 weeks, most preferred at least 16 weeks.

TABLE

| Cyanobacterial Strain | 1% EtOH tolerance test [weeks] |
|---|---|
| *Synechocystis* sp. PCC 6803 | 3 |
| *Synechococcus* sp. PCC 7002 | 13 |
| *Cyanobacterium* sp. ABICyano1 | >16 |

Example 7

Characterization of the New *Cyanobacterium* ABICyano1 Strain: cell survival at high temperatures The new *Cyanobacterium* ABICyano1 wild type strain was tested to determine its ability to grow at various temperatures. The initial starting cultures (50 mL its Erlenmeyer) were grown under standard growth conditions (continuous 28° C. and light). The cultures were diluted to a chlorophyll content of ~5 μg/mL . The temperature changes during the assay were made without any prior temperature adaptation of the cultures. All tests were performed in marine media in day/night cycle (14/ 10h) for temperature (test depending) and light intensity (40 μmol*m2*sec-1 / darkness). The temperature tolerance tests were performed with increasing temperature profiles: maximum peak of 2*h* at 45° C., 48° C., 50° C., 53° C., 55° C. )and a day/ night difference of 18° C. Each temperature profile (45° C., 48° C., 50° C., 53° C. and 55° C.) was run for 7 days. Cultures were sampled on days 0, 2, 5 and 7 with determination of OD750 (if possible) and chlorophyll. If a strain was grown under one temperature profile, the culture was diluted to same starting chlorophyll content and directly tested in the next higher temperature profile. An increase in chlorophyll content was used as the growth indicator. *Cyanobacterium* ABICyano1 can therefore tolerate culturing conditions of at least 48° C., preferably 50° C., most preferred at least 53 to 55° C. for at least two hours over a period of time of at least 7 days.

TABLE X

Thermotolerance Test

| Genera, strain # | 2 hours 45° C. for 1 week | 2 hours 48° C. for 1 week | 2 hours 50° C. for 1 week | 2 hours 53° C. for 1 week | 2 hours 55° C. for 1 week |
|---|---|---|---|---|---|
| *Synechocystis* sp. PCC 6803 | pos. | pos. | neg. | | |
| *Synechococcus* sp. PCC 7002 | pos. | pos. | pos. | neg. | |
| *Cyanobacterium* sp. ABICyano1 | pos. | pos. | pos. | pos. | pos. |

Example 8

Characterization of the New *Cyanobacterium* ABICyano1 Strain: Tolerance to Large Temperature Changes in 0.5 l Photobioreactors The growth of the new *Cyanobacterium* ABICyano1 wild type strain was then compared with the publicly available strain *Synechococcus* PCC 7002 to further elucidate its ability to grow in a photobioreactor environment while under extreme temperature fluxuations. Cultivation ABICyano1 was performed in 0.5 L round photobioreactor glass vessels (Schott) with implemented ports for sampling, in and out-gas tubings, and pH as well as oxygen sensors. These glass vessels are in the following called photobioreactors (PBR). Mixing is assured via magnetic stir bar (cross magnet). pH is controlled via CO2 inflow. The oxygen and pH sensors are connected to an oxygen and pH measurement box (Crison Instruments, SA), and the gas flow is controlled by mass flow controller system (Vögtlin Instruments). All parameters (oxygen, temperature, gas flow, pH) are controlled and monitored using a computer software programmed by HTK Hamburg. The system temperatures of the PBRs were set to be comparable to the temperature profiles used in the temperature tolerance test in the above example, with maximum temperatures of 45° C., 50° C and 55° C. compared to the standard PBR growth temperature of 37° C. Each temperature profile experimental culture was run for 7 days. Culture sampling was performed 3 times per week: $OD_{750}$, chlorophyll and protein content were measured. At the beginning and at the end of each week, the dry weight was determined. If a strain passed a given temperature profile, the culture was diluted to the same starting, condition (chlorophyll content ~10 μg/mL) and the next higher temperature profile was tested.

The resulting graphs (FIG. 2) show that the new wild type strain *Cyanobacterium ABICyano*1is able to grow well at high temperatures, as compared to other species, such as *Synechococcus* PCC 7002.

Example 9

Characterization of the oxygen tolerance of *Cyanobacterium* ABICyano1

Cells of *Cyanobacterium* ABICyano1 including a recombinant pdc gene under the transcriptional control of PnirA and a further recombinant synadh gene under the control of PrpsL were grown in mBG11 medium (PrpsL is the promoter of the 30S ribosomal protein S12). Cells were diluted to a starting OD of approximately OD750=1. Cells were cultivated in 500 mL photobioreactors (PBR, round vessels with 9.5 cm diameter). PBRs were illuminated with day/night cycle of 12*h*/12*h* from two sides with fluorescent tubes. The light intensity was approximately 400 μE m¯2s¯1 from each side. Temperature followed the day/night cycle with 37° C. during the illumination phase and 28° C. during the night. Cultures were constantly mixed with a magnetic stirrer with 450 rpm. CO2 was supplied pH-regulated (on/off modus); pH was maintained at 7.3±0.05 by computer-controlled supply of $CO_2$ (as 5% (v/v) $CO_2$ in air) into the medium. Growth medium was mBG11. 3 PBRs were run in parallel, the pBRs were purged with three different oxygen/nitrogen mixtures with a flow rate of 100 ml. * min¯1 during the illumination period. During the night phase gas was not supplied to the PBR. The mixtures of oxygen and nitrogen (here given in % oxygen (v/v)) were obtained with computer controlled mass flow meters. The actual oxygen concentration in the medium was measured online with an optical oxygen sensors and a multi-channel fiber optic oxygen transmitter (OXY-4 mini; PreSens). In contrast to Clark-type oxygen electrodes this setup allows the measurement of very high oxygen concentrations.

At different time points samples were taken and analyzed for (i) ethanol and acetaldehyde in the medium, (ii) $A_{750}$, (iii) chlorophyll and (iv) total protein. Chlorophyll and total protein were measured as in Tandeau De Marsac, N. and Houmard, J. in: Methods in Enzymology, Vol. 169, 318-328. L. Packer, ed., Academic Press, 1988. In order to characterize the energy metabolism of the cells the oxygen production rates in the light and the oxygen consumption rate in the dark were also measured. A Clark-type electrode (Rank brothers, diameter 1 cm) was used. Cells were diluted with mBG11 to 5 to 10 μg chlorophyll/mL, $NaHCO_3$ was added to 5 mM. Temperature was adjusted to 37° C., Illumination was with a slide projector H50 (Pentacon). For the measurement of P/I curves light intensities were adjusted by varying the distance between projector and electrode.

The cultures of the above mentioned strain were purged with gas mixtures containing 21%, 70% and 80% (v/v) oxygen in nitrogen. 21% oxygen in nitrogen corresponds to air. Purging with 21% oxygen resulted in oxygen concentration of approximately 200 μmol/L. Purging with 70% oxygen resulted in oxygen concentration of >650 μmol/L during the day period and >300 μmol/L during the "night". Purging with 80% oxygen resulted in a reading during the day of >900 μmol/L (in some cases >1000 μmol/L) and >600 μmol/L during the "night". The extremely high oxygen concentrations are caused by a high photosynthetic oxygen production.

The growth rates for the parameters $A_{750}$, ethanol production rates and chlorophyll contet were calculated. The results are summarized in table CCC. For these calculations the measured data were fitted to a regression line, and the slope was used to calculate the increase per 24 h. The quantitative analysis shows that even for the extremely high oxygen concentrations the measurable effect on ethanol production and growth was rather small.

TABLE CCC

| | 21% oxygen | 70% oxygen | 80% oxygen |
|---|---|---|---|
| Ethanol | 0.0236%/d | 0.0202%/d | 0.0213%/d |
| | 100% | 85% | 90% |
| Growth | 0.614 OD750/d | 0.583 OD750/d | 0.581 OD750/d |
| | 100% | 95% | 95% |
| Chlorophyll | 3.446 Chl/d | 2.878 Chl/d | 2.791 Chl/d |
| | 100% | 84% | 81% |

In order to ensure comparability to ABICyano1 growth and ethanol production measurements were repeated in the same way with Synechococcus PCC 7002 also including the ethanologenic genes pyruvate decarboxylase and SynADH. Significant effects were found for this strain when purged with the different oxygen concentrations similar to ABICyano1. A quantitative analysis (table XXX) shows that purging with 80% oxygen decreased the ethanol production rate by 28%, decreased the cell growth by 36% (A'), and decreased chlorophyll by 51%, respectively during the course of the experiment. The inhibitory effect of high oxygen concentrations especially on growth is therefore significantly higher for Synechococcus PCC 7002 than for Cyanobacterium ABICyano1.

TABLE XXX

| | 21% oxygen | 70% oxygen | 80% oxygen |
|---|---|---|---|
| Ethanol | 0.00646%/d | 0.00499%/d | 0.00466%/d |
| | 100% | 77% | 72% |
| Growth | 0.959 OD750/d | 0.797 OD750/d | 0.612 OD750/d |
| | 100% | 83% | 64% |
| Chlorophyll | 3.710 Chl/d | 2.455 Chl/d | 1.800 Chl/d |
| | 100% | 66% | 49% |

The above results show that ABICyano1 is much less sensitive to oxygen, than the ethanol producing Synechococcus PCC 7002, which was tested in parallel under comparable conditions. For the latter strain 70% (v/v) oxygen in nitrogen was sufficient to significantly inhibit growth and ethanol production.

Example 10

Isolation and Characterization of the Endogenous Vector(s) from *Cyanobacterium ABICyano*1

One endogenous plasmid having a size of about 6.8 kb was found to be present in *Cyanobacterium* strain ABICyano1. To isolate, characterize, and identify this plasmid, the following method was used. Genomic DNA was prepared from exponentially growing ABICyano1 cells, using QIAGEN Genomic-tip DNA extraction kit. The cyanobacterial plasmid DNA was prepared either using plasmid-safe ATP-dependent DNase (Epicentre) according to the manufacturer's instructions, or extracted from bands excised from agarose gel-electrophoresis, The ABICyano1 endogenous plasmid was captured by in vitro transposition reaction with EZ-Tn5 R6K γOri/Kan-2 transposition kit, following the manufacturer's protocol. The cyanobacterial plasmid was rescued in *surrogate E. coli host* cells.

The sequence and size of the captured plasmid was confirmed and validated by PCR, as well as by comparison with available genome sequence data. Preliminary sequence analysis and annotation was performed using DNAStar and NCB1 Blast tools. A map of the entire 6.8 kb endogenous plasmid is shown in FIG. 3.

The plasmid was found to have five putative open reading frames. ORF1 encodes a replication protein necessary for replicating the plasmid in the host cyanobacterial cell. This sequence was found to be similar to the hypothetical protein slr7037 of plasmid pSYSA (103 kb) from Synechocystis sp. PCC 6803.

ORF 4 from the 6.8 kb plasmid is a putative recombinase. Sequence analysis shows that the sequence appears to be similar to a site-specific recombinase of *Bacillus thuringiensis* serovar israelensis ATCC 35646.

Three other putative protein regions (ORF2, ORF3, ORF5) were found in the new plasmid, although their function has not yet been determined by blast searches and comparative sequence analysis.

Example 11

Construction of a Shuttle Vector Based on ABICyano1 for the Transformation of *Cyanobacterium* ABICyano1

The *Cyanobacterium endogenous* 6.8 kb plasmid can be used as a means of shuttling foreign DNA to cyanobacterial host cells. By inserting an origin of replication that is effective in *E. coli* (such as R6KOri), the plasmid DNA can be easily manipulated in bacteria such as *E. coli* to add genes and sequences of interest to the plasmid. For example, modifications to lessen the effect of endogenous restriction systems that present in *Cyanobacterium* sp. such as methylation, can be performed. The presence of the origin of replication that is already on *Cyanobacterium* sp., can assist with replication of the modified plasmid once it is transferred to a *Cyanobacterium* sp. host cell. Multiple cloning sites can be added to allow for several different antibiotic resistance genes to be added, if desired. Multiple cloning sites can also be inserted to allow for ease of insertion of various expression cassettes, such as the pdc/adh gene cassette for ethanol production. In this way, various sequence segments of the plasmid can be easily replaced with other sequence segments as needed.

Example 12

Detection of Endogenous Restriction Endonucleases

Restriction endonucleases (REN) expressed by cyanobacteria can be a major barrier for successful transformation. Accordingly, the presence of REN in *Cyanobacterium ABICyano*1 has been analyzed. Bioinformatics approaches predicted the following REN for ABICyano1: HgiDI (Acyl), AvaI, AvaII, BstEII, and HpaII (Table 5, below). In particular, automatic prediction of Restriction Endonucleases (REs) was conducted by comparing a query set of all the encoded amino acid (AA) sequences in the ABICyano1 draft genome against the REBASE, the world's largest restriction enzyme database maintained by the New England Biolabs (NEB) using the basic local alignment search tool (BLAST). Significant hits were pooled and manually examined for the presence of the Restriction-Modification motifs, based on the previous result of BLAST against NR, and SMART, which can be found on the worldwide web. These bioinformatically predicted REs were further verified through biochemical assay of crude cellular extract.

In FIG. 55 lane 3, it is shown that plasmids intended for transformation were cleaved by a crude extract of ABICyano1. In order to improve transformation efficiency, protection against the damaging effects of RENs is needed. This can be achieved by methylation using the commercial CpG methylase M.SssI (FIG. 55, lane 4).

TABLE 5

| REN Analysis | | |
|---|---|---|
| Strain | Predicted RENs (bioinformatics) | Detected RENs (by biochemical methods) |
| *Cyanobacterium* Sp. ABICyano1 | HgiDI (AcyI), AvaI, AvaIII, BstEII, HpaII | HgiDI (AcyI), AvaI |

The preparation of crude extract and the subsequent analysis for REN activity is described below. Restriction analysis on plasmids followed by sequencing was used.

Preparation of crude extract. From a liquid pre-culture 50 ml were inoculated to an $OD_{750mm}$ 0.5-1. After 10 days, 30 ml of that culture of *Cyanobacterium* strains were pelleted (5 minutes at 3000xxg at room temperature), washed once with lysis buffer (40 mM sodium hydrogenphosphate pH 7.4, 1 mM EDTA, 5% (v/v) glycerol) and resuspended in 1 ml lysis buffer. Cells were disrupted by glass beads using a tissue lysis apparatus at full speed for 4 minutes. The supernatant was then withdrawn and centrifuged twice at 14000×g at room temperature. One 1 U of RNase per ml volume was added to the final supernatant.

ABICyano1

Example 13

Protection from Restriction Endonucleases by Methylation

Enzymes whose recognition sites contain a CG stretch might be impaired or blocked in cleavage by use of the CG-methylase M.Sssl, which methylates cytosine at the C5 position. AcyI and AvaI, which were detected in the ABICyano1 crude extract recognize GRCGYC and CYCGRG, respectively. For example, pRL528, a helper plasmid for conjugal transfer, as described in Elhai and Wolk, 1988, can be used for in vivo methylation of the vectors to be transferred to *Cyanobacterium* sp. in particular Cyanobacterium sp. ABICyano1. This plasmid includes the M. AvaI gene coding for the methyltransferase protecting against the restriction endonuclease AvaI and the respective gene coding for M. AvaII. The latter is not required for transformation of ABICyana1, as it lacks any endonuclease activity of AvaII.

Example 14

Codon Optimization of the Foreign Genes

Codon optimization can be performed to increase the expression level of the foreign genes, such as the antibiotic resistance genes, the ethanologenic (or other product) cassette, and any other expressed genes on the plasmid. Codon optimization of the heterologously-derived genes (such as the genes encoding antibiotic resistance genes, and the recombinant production genes, such as genes in the ethanologenic cassette) was conducted using the software Gene Designer (DNA 2.0, Menlo Park, Calif.), guided by the *Cyanobacterium* ABICyano1 codon usage table derived from ribosomal proteins and highly expressed genes (such as photosynthesis genes). In particular; to improve heterologous gene expression, original sequences of interest (such as ZmPdc and SynAdh) were assessed with the online software OPTIMIZER (Puigbò P. Guzmán E, Romeu A, & Garcia-Vallvé S (2007) OPTIMIZER: a web server for optimizing the codon usage of DNA sequences. Nucleic Acids Research 35(suppl 2):W126-W131) based on the codon-usage table derived from ABICyano1 genome. The pre-optimized sequences were further modified with Gene Designer 2.0 to ensure that their codon adaptation index (CAI) (Sharp PM & Li W-H (1987) The codon adaptation index-a measure of directional synonymous codon usage bias, and its potential applications. *Nucleic Acids Research* 15(3): 1281-1295) and effective number of codons (ENc) (Wright F (1990) The effective number of codons used in a gene. Gene 87(1):23-29) match those of highly expressed genes (such as ribosomal proteins) in the ABICyano1 genome, and that there is no site of restriction endonucleases bioinformatically and biochemically identified from the ABICyano1 strain. The resulting improved sequences were further modified and optimized to avoid the presence of the following: 1) any known or predicted putative *Cyanobacterium ABICyano*1 endonuclease restriction sites (AvaI, BsaHI. KasI, XhoI etc.); 2) internal Shine-Dalgarno sequence and RNA destabilizing sequences; 3) internal terminator sequence ; 4) repeat sequence (<10 bp) (Welch et al., PLoS One 4, e7002; 2009; and Welch et al., Journal of the Royal Society; Interface 6 (Suppl 4), S467-S47 6; 2009).

The GC % of the optimized antibiotic resistance genes decreased from 40-53% to 33-40%, which is similar to that of the cyanobacterial strain *Cyanobacterium ABICyano*1 coding genes (about 36% on average). The codon adaptation index (CAI) of the codon-optimized antibiotic resistance genes is significantly improved from less than 0.4 to greater than 0.7, which is similar to that of ABICyano1 native genes.

Example 15

Construction of Ethanologenic Cassette

As the GC content of the ABICyano1 genome is rather low (ca. 36%), the ethanologenic gene cassette was codon-optimized for ABICyano1. Basically, two different versions were used i) a maximal codon-optimized gene cassette hereinafter referred as to pdcopt1-synadhopt1 iii) another maximal codon-optimized gene cassette, hereinafter referred as to pdcopt3-synadhopt3. The pdc genes were derived from the Zymomonas mobilis pdc and the adh genes from the Synechocystis adh. Optimization of the opt1 version was "manually codon optimized by replacing all rare codons for one amino acid were by the most frequently occurring codon for that as —based on the ABICyano1 codon usage The ethanologenic gene cassette opt3 was optimized using a two-step process which involved two programs (Optimizer and GENE designer DNA 2.0), which led to "less drastic codon-optimization"—which rather reflects the codon-usage of ABICyano1

Example 16

Construction of Ethanologenic Plasmid Vectors for Transformation of ABICyano1

The table below lists several plasmids that were prepared based on the endogenous 6.8 kb plasmid from *Cyanobacterium* ABICyano1. These plasmids contain various configurations of ethanologenic cassettes, having a gene encoding PDC and a gene encoding ADH. Various promoters, as listed below, were used. Also, the genes were optimized for expression in ABICyano1 by modifying the DNA content without modifying the protein sequence. Different origins of the genes are also noted. The ethanol production for cultures harboring the plasmids is indicated in the third column.

TABLE 7

Plasmids for Transformation of ABICyano1 with the Ethanologenic Cassette and Demonstration of Ethanol Production in ABICyano1 (in GC vials) and plasmids used for transformation of ABICyano1

| Plasmid No. | Construct | % EtOH/OD*d (GC Vial) |
|---|---|---|
| pRL528 | Helper plasmid for conjugal transfer, M.AvaI, M. AvaII (Elhai & Wolk, 1988) | Used for conjugation |
| TK225 | pABICyano1-6.8::PnirA$_{ABICyano1}$-PDC(opt1)-synADH(opt1)-Prbc$_{ABICyano}$]-Km** | ~0.007 |
| TK293 | pABICyano1-6.8::PnirA$_{ABCICyano1}$-PDC(opt1)-PrpsL$_{ABICyano1}$-synADH(opt1)-Prbc$_{ABCICyano1}$1-Km** | 0.024 |
| TK295 | pABICyano1-6.8::PnirA$_{ABCyano1}$-PDC(opt1)-PpsbA$_{ABICyano1}$-Km** synADH(opt1)-Prbc$_{ABICyano1}$-Km** | 0.005-0.01 |
| TK229 | pABCICyano1-6.8::PpetE$_{ABCICyano1}$-PDC(opt1)-synADH(opt1)-Prbc$_{ABICyano1}$-Km** | 0.002 |
| TK368 | pABICyano1-6.8::PpetE$_{ABICyano1}$-PDC(opt1)-PrpsL$_{ABICyano1}$-synADH(opt1)-Prbc$_{ABICyano1}$-Km** | >>0.02 (not inducible but constitutive) |
| #1536 | pABICyano1-6.8::smtB-PsmtA(ABCC1535)-PDC(opt1)-PrpsL$_{ABICyano1}$-synADH(opt1)-Prbc$_{ABICyano1}$-Km** | ~0.006 ($Zn^{2+}$ inducible) |
| #1495 | p$_{ABICyano1}$-6.8::PnirA$_{ABICyano1}$-zmPDC$_{ABICyano1}$ (opt3)-PrpsL$_{ABICyano1}$-ADH ABICyano1 (opt 3)_ter-Prbc ABICyano1-Km** | 0.023 |
| #1578 | pABICyano1-6.8::PnirA ABICyano1-zmPDC ABICyano1 (opt3)-dsrA-Prbc* (optRBS)-synADH\oop-Prbc ABICyano1-Km** | 0.031 |
| #1581 | pABICyano1-6.8:PnirA ABICyano1-zmPDC ABICyano1 (opt3)-dsrA-PrpsL ABICyano1-ADH ABICyano1 (opt3)_ter-Prbc ABICyano1-Km** | 0.030 |
| TK441 | pABICyano1-6.8::PpetJ ABICyano1-PDCopt1-PrpsL ABICyano1-synADHopt1-Prbc ABICyano1-Km**-oriVT | 0.017 |

Example 17

Pre-treatment of *Cyanobacterium* ABICyano1 Cells for Transformation

Many cyanobacteria produce extracellular polymeric substances (EPS), however, the appearance and composition of the EPS layer are strain-specific and dependent on environmental condition. EPS can be associated to the cell surface or released to the surrounding medium (Pereira et al., 2009, FEMS Microbiol. Rev. 33:917-941). While the released substances can in some cases easy to remove, it can be seen from LM-micrographs that the EPS attached to the cell might can represent a major barrier for transformation (FIG. 1B).

The *Cyanobacterium* sp. ABICyano1 strain was stained for EPS using scribtol black (drawing ink for calligraphy, Pelican). This stain cannot penetrate EPS. The cells stained with the dye have a wide white/yellowish layer around the cells. (FIG. 1B).

The *Cyanobacterium* sp. ABICyano1 has a significant layer of EPS outside the cell. This layer may decrease or hamper the ability for the cell to accept foreign DNA during the conjugation process for transformation. The following method was used to decrease the excess extracellular (EPS) layer prior to conjugation. The method involves several steps: treatment of cells with N-acetylcysteine (NAC); washing steps that utilize NaCl; a treatment with lysozyme and subsequent washing; followed by the conjugation procedure.

200 ml of an exponentially growing culture ($OD_{750}$mm>0.5<1) was incubated with N-acetylcysteine (NAC) for 2 days at 16° C. (end concentration: 0.1 mg/ml) without shaking. This pre-treatment was followed by several steps to degrade the EPS and to weaken the cell wall: the pretreated culture was pelleted at 4400 rpm and washed with 0.9% NaCl containing 8 mM EDTA.

For further treatment with lysozyme the cell pellet was resuspended in 0.5 M sucrose and incubated 60 minutes at room temperature (RT) with slow shaking (85 rpm). Then, cells were centrifuged and resuspended in 40 ml of a solution containing 50 mM Tris )pH 8.0), 10 mM EDTA (pH 8.0), 4% sucrose and 20-40 μg/ml lysozyme. After incubation at RT for 10-15 minutes, cells were centrifuged and washed 3 times using different washing solutions. i) with 30 mM Tris containing 4% sucrose and 1 mM EDTA, ii) with 100 mM Tris containing 2% sucrose and iii) with BG11 medium All centrifugation steps before lysozyme treatment were performed at 4400 rpm for 10 min at 10° C., all centrifugations after the lysozyme treatment were performed at 2400 rpm for 5 minutes at 4° C. Resuspended cells were used for conjugation.

Example 18

Transformation of Pre-treated *Cyanobacterium* strain ABICyano1 using Conjugation Gene transfer to ABICyano1 was performed using conjugation. The generated plasmids with oriVT were used for conjugation. The shuttle vectors could be successfully transformed into ABICyano1 following a modified conjugation protocol which includes, as critical step, the pre-treatment of ABICyano1 to reduce its EPS layer as described in Example 27, above. Briefly, pretreatment of ABICyano1 with N-Acetylcysteine for at least 2 days, followed by treatment with lysozyme, respectively, led to the generation of ABICyano1 transformants.

Triparental mating was performed as follows. *E. coli* strain J53 bearing a conjugative RP4 plasmid and *E. coli* strain HB101 bearing the cargo to be introduced into ABICyano1 and the pRL528 helper plasmid (for in vivo methylation) were used. *E. coli* strains were grown in LB broth supplemented with the appropriate antibiotics overnight at 37° C. with shaking at 100 rpm. An aliquot of 3-5 ml of each culture was centrifuged, washed twice with LB medium and resuspended in 200 μl LB medium. Subsequently, the *E. coli* strains were mixed, centrifuged and resuspended in 100 ρl BG11 medium. 200 ml of exponentially growing cyanobacterial culture ($OD_{750}$mm>0.5<1) was centrifuged (3000 rpm, 10 minutes), pretreated to degrade the EPS layer as described above, and subsequently washed and resuspended in 400 μl BG11 culture medium containing Tris/sucrose buffer (described above). A 100 μl aliquot of resuspended cyanobacterial and *E. coli* cultures was mixed and applied onto a membrane filter (Millipore GVWP, 0.22 μm pore size) placed on the surface of solid BG11 medium supplemented with 5% LB. Petri dishes were incubated under dim light (5 μmol photons/m2/s1) for 2 days. Cells were then resuspended in fresh BG11 medium and plated onto selective medium containing 10 and 15 μg/ml kanamycin, respectively. The following selection conditions were used: light intensity approximately 20-40 μmol photons/m2/sec at a temperature of approximately 28° C. Transformants were visible after approximately 10-14 days. The transformant colonies were then plated on BG11 medium containing 15 μg/ml kanamycin and then stepwise transferred to higher kanamycin concentrations (up to kanamycin 60 μg/ml ) to aid in the selection process.

Example 19

Electro-Tansformation of *Cyanobacterium* strain ABICyano1

Although the transformation of Cyanobacterium strain ABICyano1 has been performed using conjugation, for the most part, electroporation can also be used for successful transformation using e.g. the same plasmids as for the conjugation, however, so far, with lower efficiency, As for the conjugation protocol, strain-specific adaptations of standard electroporation procotols need to be made, in particular to avoid DNA digestion by endogenous restriction enzymes and to allow DNA entry through the EPS layer. To achieve successful electroporation, DNA is protected against endogenous restriction enzymes by methylation and cells are pretreated prior to electroporation with positively charged polyaminoacids such as Poly-L-lysine hydrobromide or Poly-L-ornithine hydrochloride or combinations thereof, in particular Poly-L-lysine hydrobromide in order to increase the DNA uptake efficiency.

In particular, 100 ml of exponential growing ABICyano1 cultures (corresponding to a cell density of approx $2\times10^7$ cells/mL), were harvested, washed and resuspended in 0.9% NaCl containing 25 mM Tris-HCl (pH 8.0). Poly-L-lysine hydrobromide was added at a final concentration of 50 μg/ml to the cells. Cells were incubated for several hours or overnight before electroporation.]

In a typical procedure, 50 mL of Poly-L-lysine hydrobromide treated ABICyano1 cells, are harvested and treated with 30 ml ice-cold BG11 containing 6% DMSO. After incubation on ice for 20 min, cells are harvested and frozen in liquid nitrogen for 15 min. These pre-frozen cells are thawed by adding 15 mL ice-cold buffer containing 1 mM HEPES (pH7.5), 0.2 mM K2HPO4 and 0.2 mM MgCl2.The cells are washed sequentially once more with 1 mM HEPES and ETMT buffer containing 0.1 mM HEPES, 0.2 mM K2HPO4 and 0.2 mM Mg Cl2. The cells are harvested by centrifugation at 15000 g for 5 minutes. All of the washes and centrifugations are carried out on ice or in a pre-chilled centrifuge (4° C). For each electroporation procedure 3 μg methylated DNA is added to 100 μl concentrated cells. Cells are electroporated in a cuvette with a 2-mm gap between the electrodes and pulsed once in a Gene Pulse X-cell (Bio-Rad) using exponential decay protocol (electric field strength 8 kV/cm, capacitance 25 μF; resistance of 400 ohms, time of approximately 8-9 ms). After electroporation, 1-2 ml BG11 medium were immediately added to the cyanobacterial suspension, which was subsequently transferred to a 50 ml flask containing 15 ml fresh BG11 medium. After incubation for 1- 2 days under normal light (30-40 μmol photons/m2/s1) with gentle shaking at 30° C., recovered cultures were centrifuged, resuspended in 500 μl BG11 medium and placed onto selective media (BG11 containing 20 μg/ml Km or Spectinomycin of 40-60 μg/ml).

Example 20

Confirmation of Transformants Using Colony PCR and Plasmid Rescue

Colony PCR methods were used to confirm transformants. For this procedure, three primer sets were used, which were directed against parts of the p $_{ABICyano1}$-6.8 shuttle vectors to detect specific fragments of the shuttle vector. Transformants which were proven to be correct by colony PCR were analyzed further by plasmid rescue. For plasmid rescue a 25 ml liquid culture was subjected to DNA isolation, 500 ng-1 μg of isolated DNA from transformants ABICyano1 containing the transformed plasmids were re-transformed into *E. coli* resulting usually in approx. 10-20 transformants per transformation. Plasmid DNA of 10 *E. coli* colonies was isolated and analyzed by PCR using specific primers for the transformed plasmids. The plasmid DNA was further analyzed with specific restriction enzymes and sequenced. respectively.

Example 21

Identification of Potential Metal Inducible Promoters Endogenous to *Cyanobacterium* ABICyano1

RNA-Seq experiments were conducted in order to identify potential metal-ion inducible promoters in ABICyano1. The upstream regions of metal ion responding/inducible genes in ABICyano1, listed in the below, were selected to drive/control expression of the ethanologenic gene cassette in ABICyano1. The nucleic acid sequences are given in the Figures as listed in this table. All of the below potential inducible promoters are prime candidates for the transcriptional control of the at least one recombinant gene. Especially, petJ was characterized in more detail. Expression of petJ is tightly repressed under high copper (1-3 μM) conditions and induced under copper depletion (FIG. 52A). ABICyano1:TK441 hybrids carrying the endogenous petJ promoter upstream of an ethanologenic gene cassette, produce the same amount of ethanol (%v/v) under copper depletion conditions compared to an ABICyano1:TK293 hybrid strain grown in marine BG11 (FIGS. 52A and 52B).

The plasmid map of plasmid TK441 is shown in FIG. 53 and its nucleic acid sequence is depicted in FIG. 54.

| gene id | DNA Sequence | homology | Inducible by |
|---|---|---|---|
| ABICyano1_orf0128 | FIG. 51A | hypothetical protein | nickel |
| ABICyano1_orf1486 | FIG. 51B | putative nickel-containing superoxide dismutase | nickel |
| ABICyano1_orf3161 | FIG. 51C | ferrochelatase | nickel |
| ABICyano1_orf3293 | FIG. 51D | hypothetical protein L8106_16134 | nickel |
| ABICyano1_orf3621 | FIG. 51E | hypothetical protein Cyan7822_1798 | nickel |
| ABICyano1_orf3635 | FIG. 51F | carbohydrate-selective porin | nickel |
| ABICyano1_orf3858 | FIG. 51G | manganese/iron superoxide dismutase-like protein | nickel |
| ABICyano1_orf1071 | FIG. 51H | Mn transporter | zinc |
| ABICyano1_orf1072 | FIG. 51I | ABC transporter family protein | zinc |
| ABICyano1_orf1074 | FIG. 51J | ABC 3 transport family | zinc |
| ABICyano1_orf1075 | FIG. 51K | No hits found -\|- KEGG:-\|- CyanoBase | zinc |
| ABICyano1_orf1542 | FIG. 51L | hypothetical protein PCC8801_4423 | zinc |

-continued

| gene id | DNA Sequence | homology | Inducible by |
|---|---|---|---|
| ARICyano1_orf1823 | FIG. 51M | RNA polymerase sigma factor | zinc |
| ABICyano1_orf1824 | FIG. 51N | No hits found -\|- KEGG:-\|- CyanoBase | zinc |
| ABICyano1_orf3126 | FIG. 51O | Metallothionein | zinc |
| ABICyano1_orf3389 | FIG. 51P | HtrA2 peptidase | zinc |
| ABICyano1_orf0221 | FIG. 51Q | CopA family copper-resistance protein | copper |
| ARICyano1_orf0222 | FIG. 51R | copper resistance B | copper |
| ABICyano1_orf0223 | FIG. 51S | No hits found -\|- KEGG:-\|- CyanoBase | copper |
| ABICyano1_orf0316 | FIG. 51T | hypothetical protein CY0110_11047 | copper |
| ABICyano1_orf3232 | FIG. 51U | cation-transporting ATPase | copper |
| ABICyano1_orf3461 | FIG. 51V | petJ | copper |
| ABICyano1_orf3749 | FIG. 51W | conserved hypothetical protein | cobalt |

Example 22

Construction and Transformation for Integration into the Chromosomal DNA of *Cyanobacterium* ABICyano1

Integration of target genes into the genome of ABICyano1 will be conducted with the help of plasmid TK471, which was generated to integrate a kanamycin resistance gene in the pilT/pilC region, resulting in a pilT/pilC minus strain. The TK180 based plasmid contains a pilT flanking region of ABI-Cyano1 upstream as well as a pilC flanking region of ABI-Cyano1 downstream of the kanamycin resistance gene to generate a double crossover event in ABICyano1. Moreover, sacB from *Bacillus subtilis* is encoded on TK471. Expression of sacB in gram negative bacteria grown on media supplemented with sucrose is toxic for the bacteria. Hence, only the bacteria which lose the sacB gene are able to grow on sucrose plates. ABICyano1:TX471 hybrids grown on sucrose/kanamycin plates are therefore forced to induce homologous recombination to flip the kanamycin resistance gene into the genome and to lose the plasmid TK471 due to the presence of the sacB gene. In order to integrate the EtOH cassette into the genome, plasmid TK471 will be modified carrying the EtOH cassette adjacent to the Km gene (also within the pilT and pilC flanking region).

Figure 26:
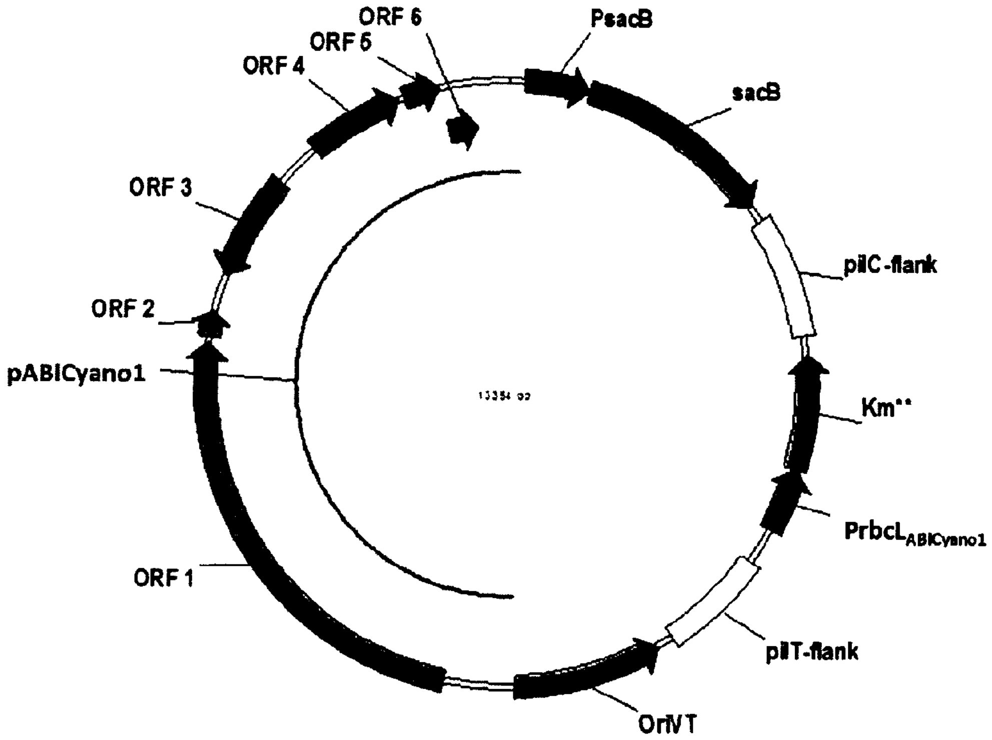
FIG. 26 is a map of the plasmid construct TK 471. Its nucleotide sequence (SEQ ID NO: 18) is depicted in FIG. 27 including the annotation of the genes and promoters done with the program vector NTI.
Figure 28:
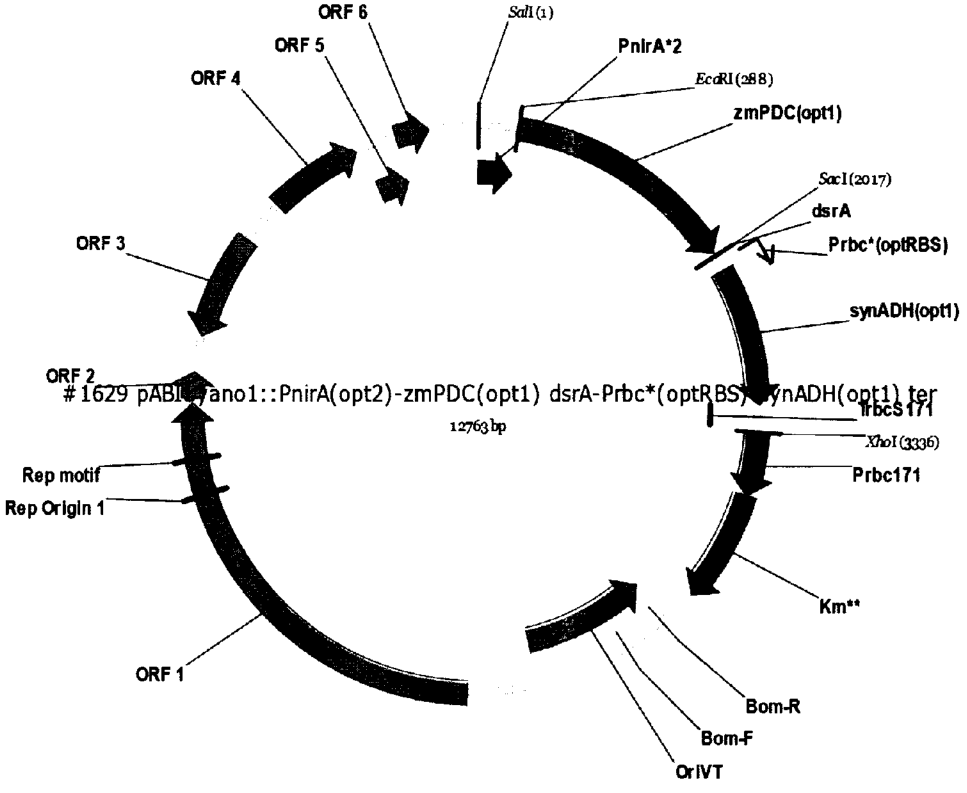
FIG. 28 is a map of the plasmid construct # 1629including the endogenous nirA promoter from ABICyano1 with an improved ribosomal binding site in comparison to the respective native promoter. This modified promoter controls the transcription of a pdc gene, which can be codon improved. The nucleotide sequence (SEQ ID NO: 19) of the plasmid is depicted in FIG. 29 including the annotation of the genes and promoters done with the program vector NTI.
Figure 30:
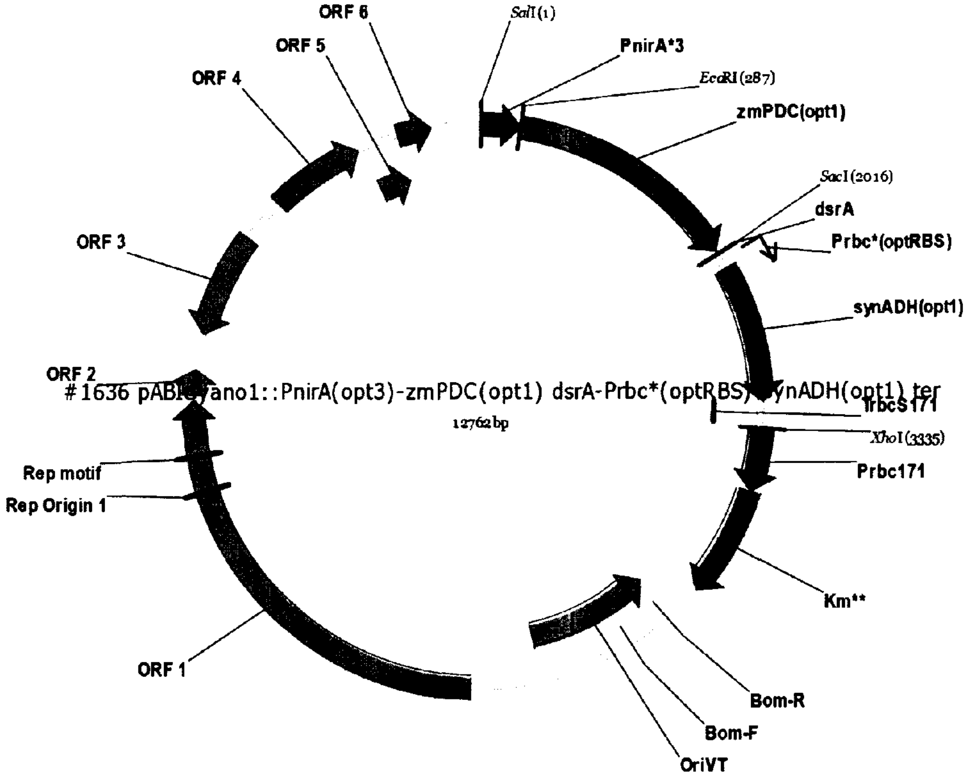
FIG. 30 is a map of the plasmid construct # 1636 including the endogenous nirA promoter from ABICyano1 with an improved binding site for the regulators NtcA and NtcB and an improved TATA box in comparison to the respective native promoter. This modified promoter controls the transcription of a pdc gene, which can be codon improved. The nucleotide sequence (SEQ ID NO: 20) of the plasmid is depicted in FIG. 31 including the annotation of the genes and promoters done with the program vector NTI.
Figure 32:
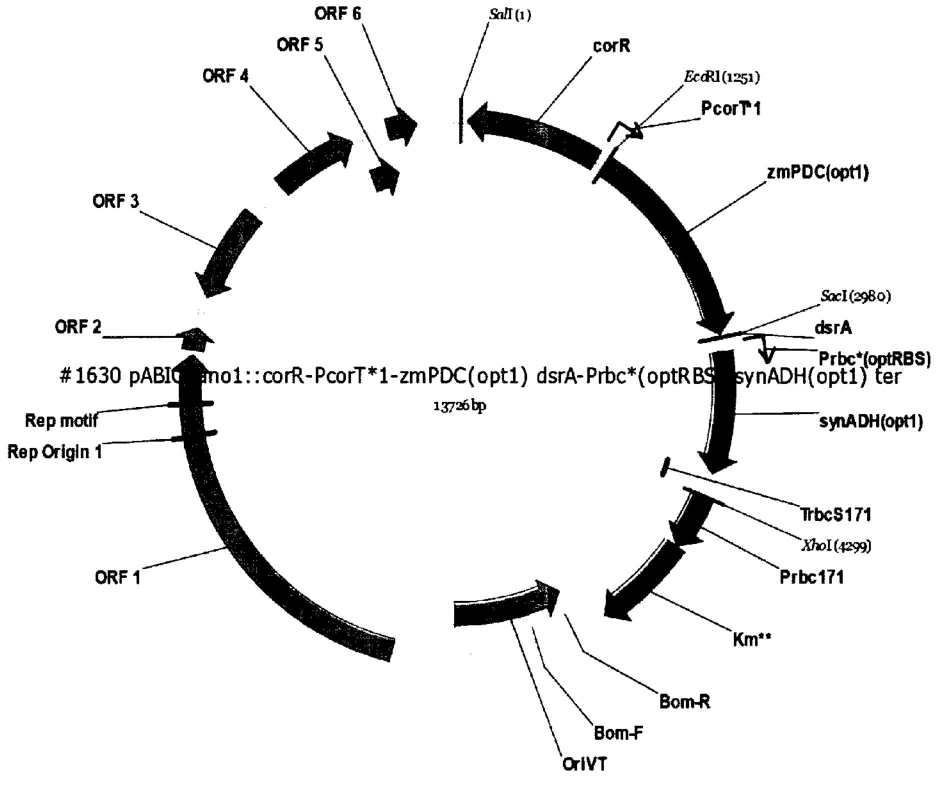
FIG. 32 is a map of the plasmid construct # 1630 including the endogenous corT promoter from Synechocystis PCC6803 with an improved ribosomal binding site in comparison to the respective native promoter. This modified promoter controls the transcription of a pdc gene, which can be codon improved. The nucleotide sequence (SEQ ID NO: 21) of the plasmid is depicted in FIG. 33 including the annotation of the genes and promoters done with the program vector NTI.
Figure 34:
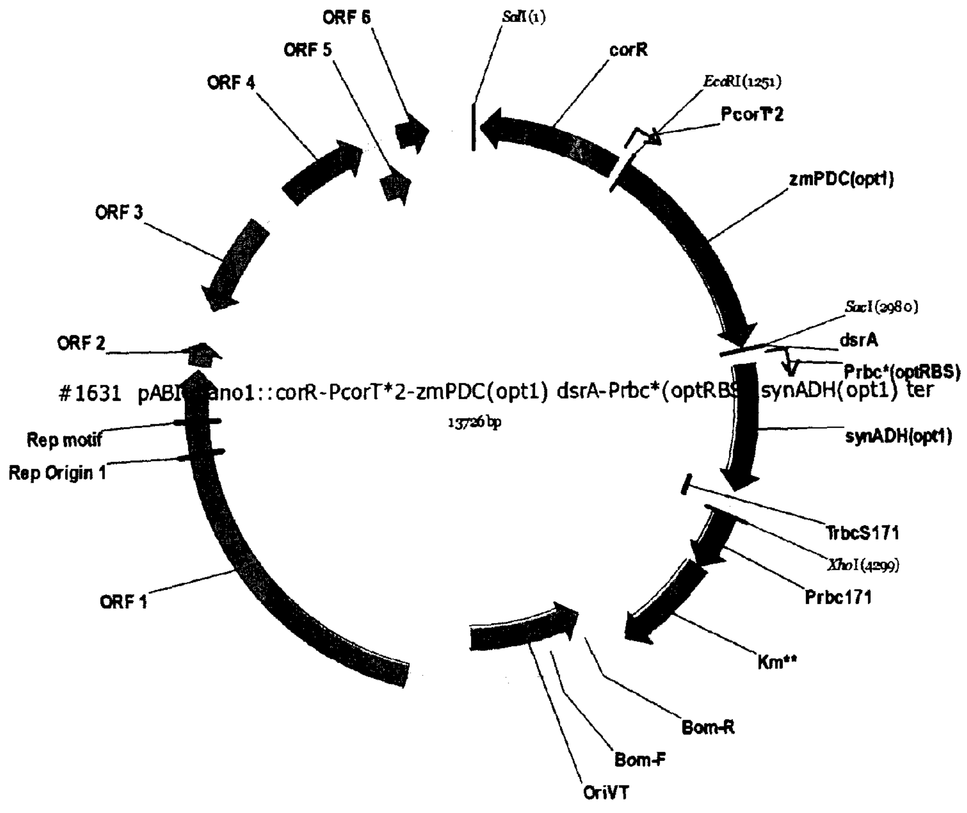
FIG. 34 is a map of the plasmid construct # 1631 including the endogenous corT promoter from Synechocystis PCC6803 with an improved TATA box in comparison to the respective native promoter. This modified promoter controls the transcription of a pdc gene, which can be codon improved. The nucleotide sequence (SEQ ID NO: 22) of the plasmid is depicted in FIG. 35 including the annotation of the genes and promoters done with the program vector NTI.
Figure 36:
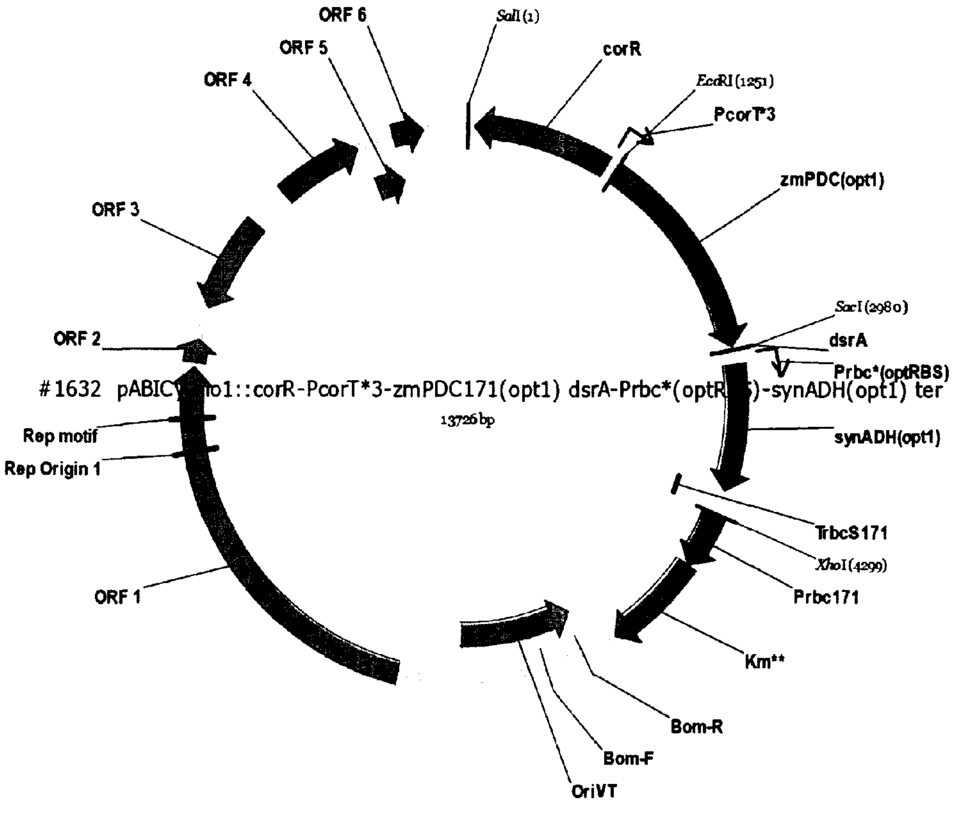
FIG. 36 is a map of the plasmid construct # 1632 including the endogenous corT promoter from Synechocystis PCC6803 with an improved TATA box and ribosomal binding site in comparison to the respective native promoter. This modified promoter controls the transcription of a pdc gene, which can be codon improved. The nucleotide sequence (SEQ ID NO: 23) of the plasmid is depicted in FIG. 37 including the annotation of the genes and promoters done with the program vector NTI.
Figure 38:
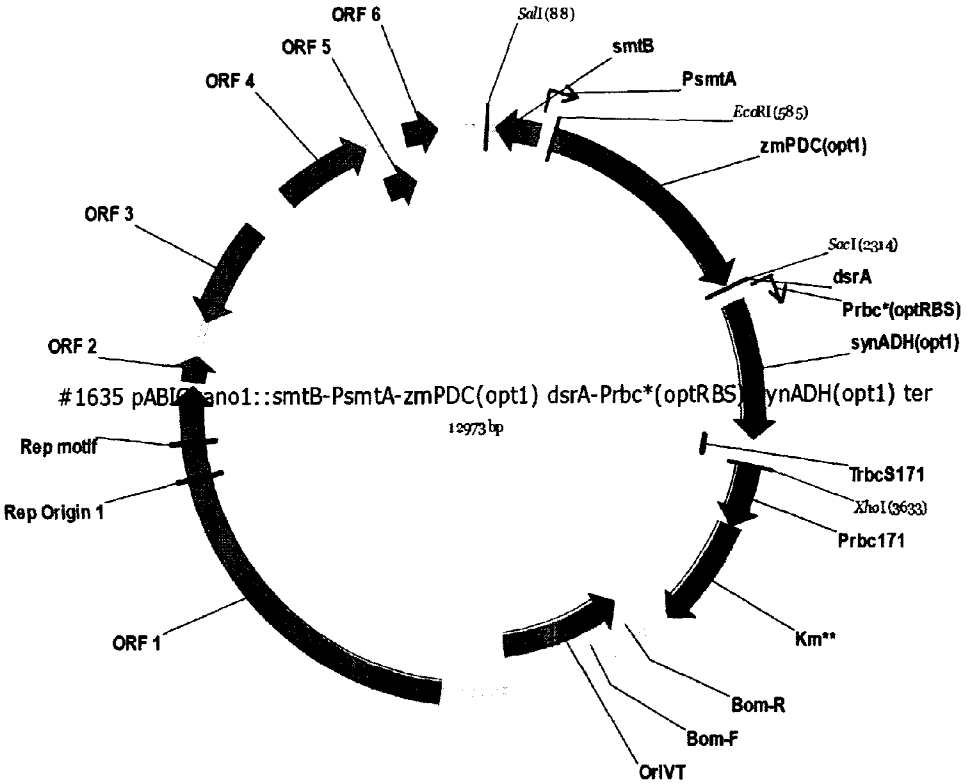
FIG. 38 is a map of the plasmid construct # 1635 including the native smtA promoter from Synechococcus PCC7002.This modified promoter controls the transcription of a pdc gene, which can be codon improved. The nucleotide sequence (SEQ ID NO: 24) of the plasmid is depicted in FIG. 39 including the annotation of the genes and promoters done with the program vector NTL.
Figure 40:
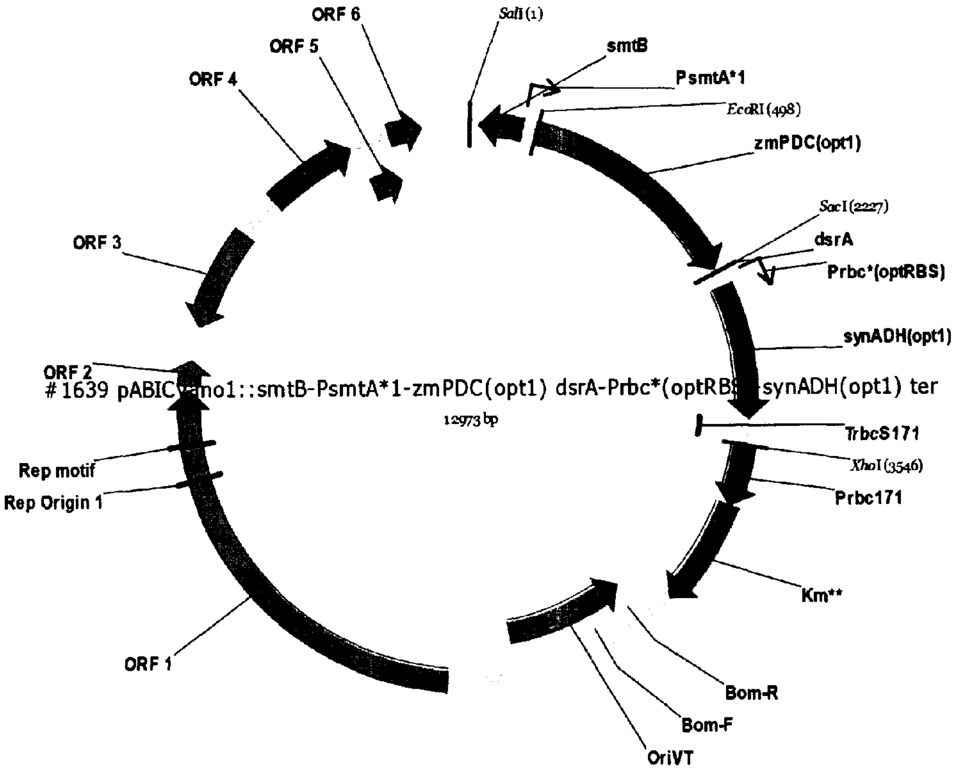
FIG. 40 is a map of the plasmid construct # 1639 including a modified smtA promoter from Synechococcus PCC7002 which includes a modified RBS in comparison to the native promoter. This modified promoter controls the transcription of a pdc gene, which can be codon improved. The nucleotide sequence (SEQ ID NO: 25) of the plasmid is depicted in FIG. 41 including the annotation of the genes and promoters done with the program vector NTI.
Figure 42:
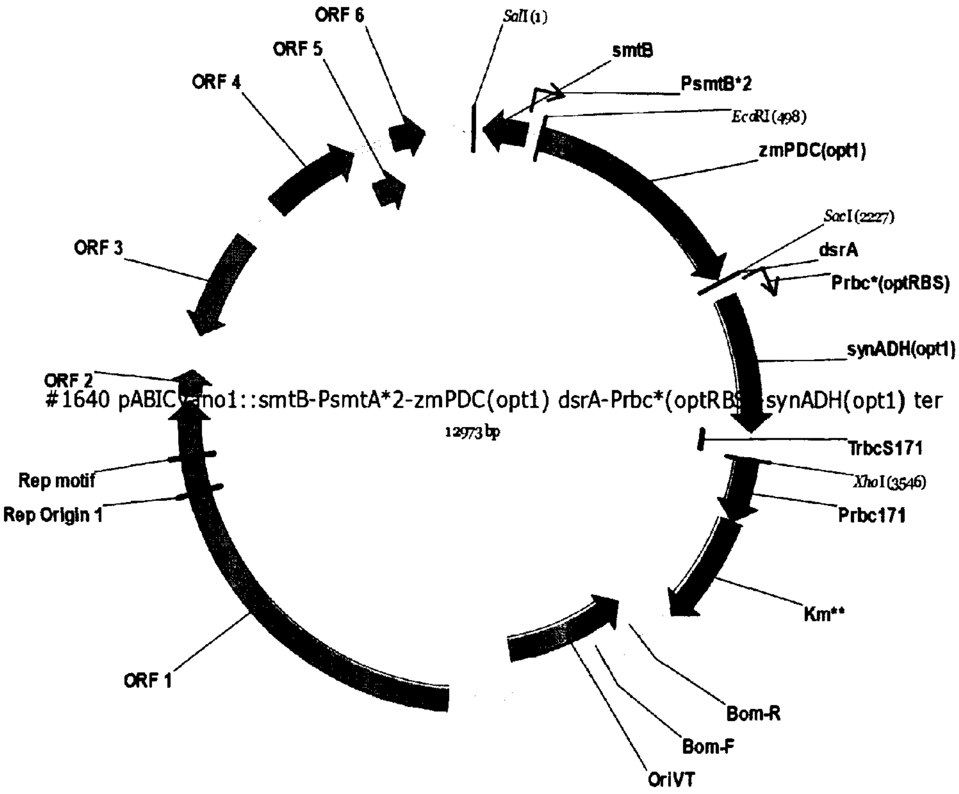
FIG. 42 is a map of the plasmid construct # 1640 including a modified smtA promoter from Synechococcus PCC7002 which includes another modified RBS in comparison to the native promoter. This modified promoter controls the transcription of a pdc gene, which can be codon improved. The nucleotide sequence (SEQ ID NO: 26) of the plasmid is depicted in FIG. 43 including the annotation of the genes and promoters done with the program vector NTI.

The plasmid map of plasmid TK471 is shown in FIG. 26 and its nucleotide sequence including the annotations of the genes and regulatory elements in shown in FIG. 27.

Example 23

Production of Ethanol from Genetically Enhanced *Cyanobacterium* ABICyano1

The transformed cells containing the ethanologenic cassettes were then grown under inducing conditions, (in marine BG11 medium), and tested for ethanol production ABICyano1 harboring the plasmids TK293 and TK225 were found to produce 0.086% (v/v) and 0.019% (v/v) ethanol, respectively, over a 50 hour period in an online GC vial system (FIG. 56A). Cultivation of ethanologenic ABICyano1 cells was performed in 0.5 L round PBR glass vessels containing marine BG11 culture medium. pH is controlled via CO2 flux. In such an experiment ethanologenic ABICyano1, harboring the ethanologenic plasmid TK225, was characterized. Cell growths and ethanol production is shown in FIG. 57. Similarly, ABICyano1 harboring TK293 was characterized with respect to EtOH productivity (FIG. 58).

Example 24

Figure 48A:
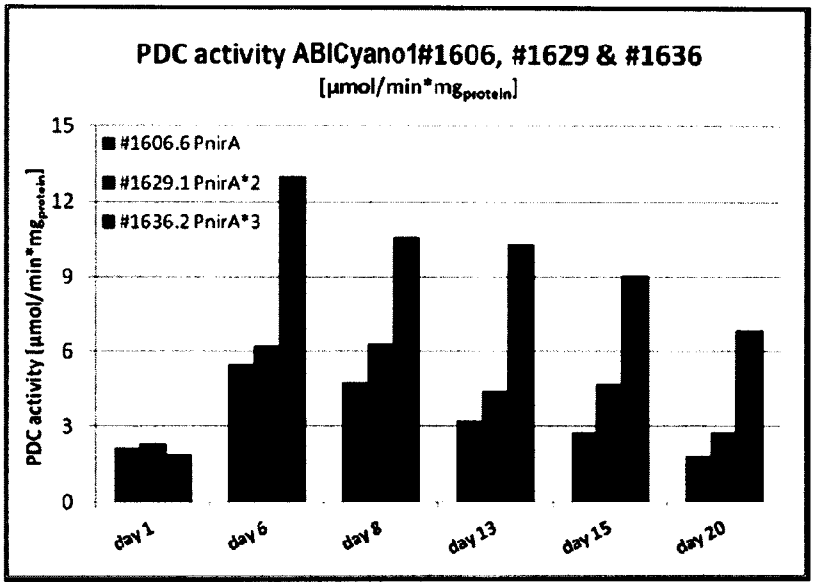
Figure 48B:
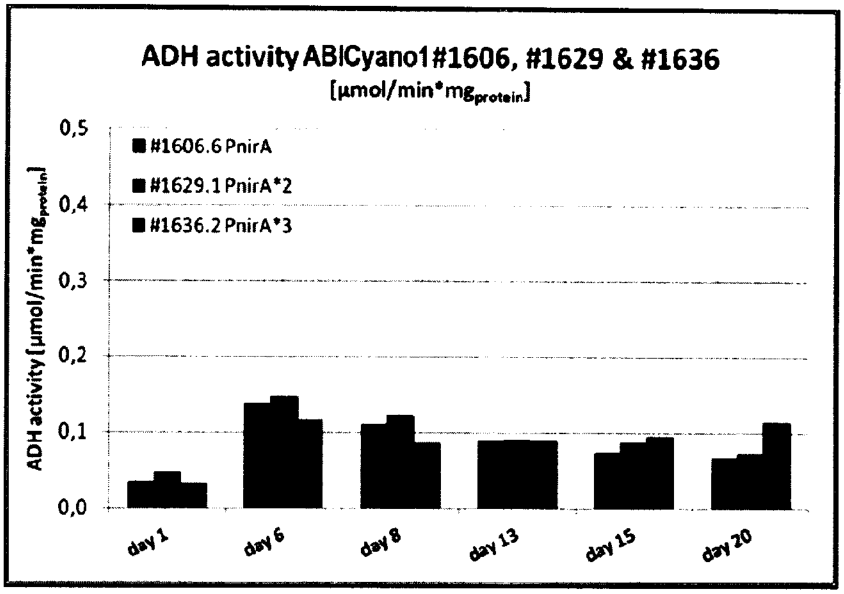

Characterization of Different Ethanologenic Strains of ABICyano1 Harboring an Ethanologenic Cassette Under the Control of Different Inducible Native and Modified Promoters Genetically enhanced Cyanobacterium ABICyano1 strains including extrachromosomal plasmids all harboring a pdc gene under the transcriptional control of either the native nirA promoter or modified variants thereof, were cultured in 0.51 photobioreactors. These strains included the plasmids # 1606, # 1629 and # 1636, which were already described earlier. FIG. 47 shows the ethanol production normalized to the growth ($OD_{750mm}$) determined by the CG vial method for ABICyano1 strains transformed with the plasmids # 1606 (pdc gene under the control of the native PnirA), plasmid # 1629 (pdc gene under the control of a modified variant of PnirA with changes in the RBS) and plasmid # 1636 (pdc gene under the control of a modified variant of PnirA with changes in the operator sequence and the TATA box) for a period of time of at least 20 days after induction was realized by transition of the pre-culture to usual mBG11 medium (containing nitrate for induction) at the beginning of the cultivation experiment. The graph clearly shows that the normalized ethanol production is higher for the strains including the plasmids with the modified promoters. FIGS. 48A and 48B show the specific activity of PDC enzyme and ADH enzyme during the course of the above mentioned cultivation. It is evident that the inducible modified nirA promoter variants PnirA*2 (#1629) and PnirA*3 (#1636) result in a higher activity of PDC enzyme compared to the native promoter (#1606).

FIG. 49 shows the ethanol production normalized to the growth ($OD_{750mm}$) determined by the CG vial method for ABICyano1 strains transformed with the plasmids #1606 (pdc gene under the control of the native PnirA), plasmid #1631 (pdc gene under the control of a modified PcorT with modifications in the TATA box) and plasmid #1632 (pdc gene under the control of a modified PcorT with modifications in the TATA box and the RBS) for a period of time of at least 20 days cultured in 0.51 photobioreactors. The ethanol production of the strain transformed with the plasmid containing the native PnirA with pdc gene is comparable to the ethanol production of the strain containing the plasmid with the pdc gene controlled by the modified corT promoter variants PcoT*3 (#1632) with modifications in the TATA box and RBS, whereas the ethanol production of the strain containing the plasmid with PcorT with modifications only in the TATA box PcorT*2 (#1631) exhibits a lower ethanol production rate, especially in the time period starting from the $10^{th}$ day of cultivation on.

FIGS. 50A and 50B show the specific activity of PDC enzyme and ADH enzyme during the course of the above mentioned cultivation. The strains with the native PnirA as well as the PcorT with modifications in the TATA box and the RBS show higher reactivity of PDC enzyme than the other strain.

FIG. 50C to 50D show the ethanol production rates of the ABICyano1 strains transformed with the plasmids '1535, # 1539 and # 1540 including the native PsmtA promoter from Synechococcus PCC 7002 as well as modified versions of PsmtA. It can clearly be seen that all promoters are repressed in the absence of Zn2+ and can be induced upon addition of Zn2 +.

Example 25

Determination of Ethanol Production using Headspace Gas Chromatography with Flame Ionization Detection Experimental setup GC headspace measurements are performed on a Shimadzu GC-2010 gas chromatograph with Flame Ionization Detector. The instrument is connected in-line with a Shimadzu PAL LHS2-SHIM/AOC-5000 autosampler, comprising a gas-tight syringe for transfer of headspace aliquots from the culture samples to the analytical unit. Culture amples in the autosampler are illuminated with NARVA fluorescence lamps (BIO vital LT24WT5/958HQ) of 24 Watt. Mixing of the samples in the autosampler is accomplished with the IKA RO5 power magnetic stirrer. A heating mat KM-SM3 of Mohr & Co in combination with the JUMO dTRON 316 temperature regulator is used for thermostatisation of the culture samples in the autosampler. The gas chromatograph is connected to helium carrier gas as well as hydrogen and artificial air as fuel gas and oxidizer gas, respectively, for the flame ionization detector. Oxidizer air is generated with the generator WGAZA50 from Science Support. The gas chromatograph is equipped with a FS-CS-624 medium bore capillary with a length of 30 m, internal diameter of 0.32 mm and film thickness of 1.8 μm from the GC supplier Chromatographic Service GmbH.

Sample preparation:

Hybrid clones are raised on BG11 plates containing inducing agent or without supplementation of the inducing agent. A sample is prepared by scratching an individual clone from the BB11 plate and resuspending the corresponding clone in marine BG11 liquid medium (mBG11). Addition of inducing agent triggers ethanol production in the sample by induction of the inducible promoter driving over-expression of the recombinant pyruvate decarboxylase and alcohol dehydrogenase gene. The cell density in the sample is then adjusted to an optical density at 750 nm of approximately 1.0. Two millilitres of sample are then filled into a gas-tight GC vial for headspace autosampling with a nominal volume of 20 millilitres. The sample headspace is supplemented with 3 millilitres $CO_2$. The vial is tightly closed with a cap with self-sealing silicone septum and placed into the autosampler rack which is temperature controlled at a given temperature for example 37° C., If necessary, reference samples can be prepared as 2 millilitre aliquots with 0.005, 0.01, 0.02, 0.05, 0.1, 0.2, 0.5, 1, 2, 5 and 10 mg /ml ethanol in 35 psu sodium cloride. Reference samples are placed into the same 20 ml sample containers with self-sealing silicon septum caps for headspace autosampling. For each reference sample at least six measurements are applied. After the measurements, the resulting peak areas of the reference samples are used for generating two calibration curves, the first in the concentration range from 0.005 to 0.5 mg/ml ethanol and the second one for the concentration range from 0.5 to 10 mg/ml ethanol. The calibration curves have to fulfil linearity.

General procedure:

The sample incubation temperature in the autosampler is adjusted to a given temperature for example 37° C. The illumination is set at 90 μE to 150 μE, preferably 100 μE. The magnetic stirrer is configured for interval mixing of the samples, with cycles of 2 minutes mixing at 400 rpm, followed by 90 minutes without mixing. An automated process follows, wherein after given periods aliquots of 500 μl of the headspace of the samples are automatically drawn with the gas-tight headspace syringe and injected via the injection port into the gas chromatograph for analysis. Before each headspace autosampling, the mixing is changed for 10 min to continuous mixing with 750 rpm at 37° C. incubation temperature. The syringe temperature is set at 70° C. The fill speed is 250 μl per second, following an initial lag time of 1 second after the septum of the samples has been pierced b the syringe needle. The injection of the aliquot into the gas chromatograph happens with an injection speed of 500 μl per second. Afterwards, the syringe flushes for 3 minutes with air to prevent sample carryover between two injections. The gas chromatograph runtime is 4 minutes and 30 seconds. The injection temperature on the gas chromatograph is 230° C. The column temperature is 60° C. Detection is accomplished with the flame ionization detector at 250 ° process temperature. The makeup gas is nitrogen at 30 ml per minute, the fuel gas is hydrogen at 35 ml per minute and the oxidizer gas is artificial air at 400 ml per minute.

After the final measurement, the final optical density at 750 nm of the samples is measured and an average cell density for each sample is determined by calculating the arithmetic mean of the optical density at the starting point and the optical density at the end point of the process divided by two. Afterwards, the average ethanol production rate per cell density is calculated.

Concrete Examples:

Two kinds of measurements were performed. a) GC online measurements (applied for clone testing and short-term characterizations, single GC measurements (applied for measurements of EtOH production for PBR cultivations)

In a typical experiment for the quantitative determination of acetaldehyde and/or ethanol content in growth media by headspace gas chromatography (GC), the ethanol production of the respective cyanobacterial culture has to be induced 1-3 days prior to the GC measurement to trigger the overexpression of the pdc and Synadh production genes. For instance, to repress the PnirA promoter (e.g. in TK225, TK293) hybrids were grown in mBG11 (artificial seawater) depleted of $NO3^-$, with 2 mM Urea and 2 mM NH4Cl. To induce the nirA promoter, cells were transferred prior to the GC measurement into mBG11 (artificial seawater salts) with nitrate. For GC measurements cells were harvested from liquid cultures by centrifugation and then resuspended in the appropriate fresh marine medium ensuring that the induction conditions were maintained. The medium was further supplemented with 50 mM TES, pH 7.3 and 20 mM $NaHCO_3$. The sample was adjusted to an $OD_{750}$mm1.2 mL samples were then aliquoted per 20 mL GC vial loaded with 3 ml pure CO2. The tightly closed GC vials were placed onto an illuminated (150 μE $m^{-}2s^{-1}$) headspace auto sampler and were analyzed on the same day on a Shimadzu GC-2010 gas chromatograph equipped with a medium-bore capillary column (FS-CS-624, length 30 m; 1.D. 0.32 mm : film 1.8 μm) and a flame ionisation detector.

The culture was stirred once in an hour under constant light (approximately 100 μE) in GC vials (temperature 35° C.) on the GC sampling tray. Acetaldehyde and ethanol content were measured online at four different time points during 18-24 hours. Measurements could be extended to 72 hours.

After completion of the GC measurements, the final $OD_{750}$mm was determined to normalise the ethanol production rate according to the average $OD_{750}$mm of the bacterial sample. The average $OD_{750}$mm was calculated as the arithmetic mean of the $OD_{750}$nm at the time of sample preparation and the $OD_{750}$mm after completion of the GC measurement.

The results of the ethanol quantitation are shown in FIG. 56. Briefly, ABICyano1 with TK293 produced a high amount of ethanol (~0.02% (v/v)/OD*d), which is 2-4 fold higher than with plasmids TK225/TK295.

Example 26

Transformation of a Modified Vector Based on the Endogenous 6.8 kb Plasmid from

*Cyanobacterium* to Other Cyanobacterial Cells

The modified plasmid vector based on the endogenous 6.8 kb plasmid backbone from *Cyonobacterium ABICyano*1, in addition to being useful for transformation to other *Cyanobacterium* host cells, can also be used to transform other cyanobacterial species. In particular, it was shown that a shuttle vector containing the 6.8 kb endogenous plasmid from *Cyanobacterium* sp. ABICyano1 including a kanamycin resistance cassette (KmR) and the oriVT for replication *in E. coli* could be transformed into Synechococcus PCC7002 by natural uptake.

In a prophetic example, the modified vectors such as TK293, and #1536 as described herein, each containing an ethanologenic cassette and an antibiotic resistance gene under the transcriptional control of an ABICyano1 and/or an endogenous promoter of Synechococcus PCC7002, respectively, are transformed to *Synechococcus* PCC7002 using electroporation, conjugation or natural uptake. The transformants are selected for on an agar plate using the appropriate antibiotic. The putative transformants are then confirmed by PCR analysis. Positive cells are streaked and scaled up to grow as a culture. Ethanol production is measured. By use of this method, ethanol is produced in the transformed cells.

Although the present invention has been described in considerable detail with reference to certain embodiments thereof, other embodiments are possible. Therefore, the spirit and scope of the appended claims should not be limited to the description of the embodiments contained therein.

What is claimed is:

1. A genetically enhanced ethanologenic *Cyanobacterium* sp. ABICyano1 host cell derived from wild type organism deposited in the American Type Culture Collection (ATCC) under ATCC accession number PTA-13311.

2. The host cell of claim 1 wherein said *Cyanobacterium* sp. ABICyano1 can tolerate salinities ranging up to about 35 practical salinity units, and can tolerate temperatures ranging up to about 55 degrees Celsius, and can tolerate dissolved oxygen concentrations ranging up to about 1000 μmol/L, and can tolerate ethanol concentrations ranging up to about one percent for 16 weeks.

3. The host cell of claim 1, wherein said host cell comprises a genetically enhanced plasmid derived from a plasmid that is endogenous to *Cyanobacterium* sp. ABICyano1.

4. The host cell of claim 3, wherein said genetically enhanced plasmid comprises an origin of replication and an origin of transfer (oriVT) that has a sequence of nucleotides 5640 to 6698 of SEQ ID NO: 10.

5. The host cell of claim 3, wherein said genetically enhanced plasmid comprises a gene encoding a replication initiation factor having an amino acid sequence identity of at least 90% to the sequence of a protein encoded by nucleotides 594 to 3779 of SEQ ID NO: 1.

6. The host cell of claim 3, wherein said genetically enhanced plasmid comprises a heterologous alcohol dehydrogenase gene and a heterologous pyruvate decarboxylase gene, and wherein said alcohol dehydrogenase gene is derived from *Synechocystis* and is operably linked to a promoter, and wherein said pyruvate decarboxylase gene is derived from *Zymomonas* and is operably linked to a promoter.

7. The host cell of claim 6, wherein said heterologous alcohol dehydrogenase gene encodes for an alcohol dehydrogenase that has an amino acid sequence identity of at least 90% to the amino acid sequence of the enzyme encoded for by nucleotides 117 to 1127 of SEQ ID NO: 15.

8. The host cell of claim 6 wherein said heterologous pyruvate decarboxylase gene encodes for a pyruvate decarboxylase having the amino acid sequence encoded by nucleotides 379 to 2085 of SEQ ID NO: 10.

9. The host cell of claim 6 wherein said promoter operably linked to an alcohol dehydrogenase gene and said promoter operably linked to a pyruvate decarboxylase gene are selected from the group consisting of PnirA, Prbc, PrpsL, PpsbA. PpetJ, PcorT, PsmtA and PpetE.

10. The host cell of claim 6 wherein said plasmid comprises # 1578 (SEQ ID NO: 15).

* * * * *

SEQUENCE LISTING

```
<160> NUMBER OF SEQ ID NOS: 88

<210> SEQ ID NO 1
<211> LENGTH: 6828
<212> TYPE: DNA
<213> ORGANISM: Cyanobacterium sp. ABICyano1

<400> SEQUENCE: 1

aatatttttc gtcagatacg caaaccttac aaacataatt aacaactgaa actattgata     60

tgtctaggtt ttagctctat cacaggttgt tagacaccct gtcatgtatt ttatattatt    120

tatttcacca tacggattaa gtgaaaccta atgaaaatag tactttcgga gctttaactt    180

taatgaaggt atgttttttt atagacatcg atgtctggtt taacaatagg aaaaagtagc    240

taaaactccc atgaattaaa gaaataacaa ggtgtctaac aacctgttat taagaatgtt    300

agaaaagact taacatttgt gttgagtttt tatagacatt ggtgtctaga catacggtag    360

ataaggtttg ctcaaaaata aaataaaaaa agattggact aaaaaacatt taatttagta    420

caatttaatt agttattttt tcgtctcaaa ttttgctttg ttgagcagaa atttagataa    480

aaaaatcccc gtgatcagat tacaatgtcg ttcattgtac gatgtgtcga aaaatcttta    540

cgacactcta aactgaccac acgggggaaa aagaaaactg aactaataac atcatgatac    600

tcggaaaacc tagcaattct caacccctaa acaaaagaaa cttccaaaac cctgaccata    660

taaaggagtg gcaacaatca gcaatcagtc aagatttgat agcagaaaat cttgtatcgg    720

ttgctaatgg ttttgatgta ctatttatcg gcaataaata ccgaactaac acgggtgttc    780

tgtcacggca catattaaac tcctattctc atttagaaga tggtggttcg tatggtagaa    840

catttgaccc atttaccaat aaagaaatgc agtgggttca atttaaaccg aatagaccaa    900

gaaaaggttc tactggtaag gtaatcaaat atgaatcgcc aaaaggtgaa cctacaagag    960

ttctaatgcc gtttgtgcct atgaaaatat ggcaacggat tagcgataag ttcggagtac   1020

cgattaatcc gaaaaaagat actcactttt gggaatgggt aaagaataat ccatcgatac   1080

cgattgccat tacagaagga aataaaaaag ctaattgcct attatcctat ggctatcctg   1140

ctattgcctt tgtaggcatt tggaacggat tagagaaaat aaatgatttc tcgaaggaaa   1200

agcagttaaa agaggatttg aaatggttgt tatccaacgg caaccgaaat attaatatca   1260
```

-continued

```
tctttgacca agaccagaaa caaaaaactg taattaatgt aaacaaagct attttcgctt   1320
tatcttctct aataagtaga aatggtcata aagttaatat tgtgcaatgg ttgccgtcaa   1380
aaggtaaagg aatagatgat tatttggtag ctttaccttt tgagaaaaga gaaaatcatt   1440
tagacaactt aattaaaatt gcaccatcat ttaatttttg gtcaactaaa tacttattca   1500
agtgtcgtaa accagattta accgtaaatt gccgttattt gagcgatgca gtaaaagaat   1560
tacctcaaga ggatatagca ttaatagcac ctcacggcac gggtaaaact tcattagtag   1620
ctactcacgt taagaatcgg agttatcacg gaaggaaaac tatttcattg gtgcatcttg   1680
aaagtttagc caaagctaat ggcaacgcac ttggattata ttaccgaacc gaaaataata   1740
ttgaaaagca atatcttgga tttagcttat gtgtagatag ttgccgtgat aagattaacg   1800
gcattacaac tgatattatt tcaggtcaag attattgcct tttcattgat gaaattgacc   1860
aagtaattcc acacatcctt aacagtgaaa ctgaagtaag taagtataga tgcaccatca   1920
ttgacacttt ttctgaactg gtgagaaatg ctgaacaggt cattattgct gatgctgatt   1980
tatccgatgt gacgattgac ctaatagaaa acatcagagg taaaaaacta tatgtaatca   2040
agaatgaata tcagtatcag ggaatgactt ttaacgccgt tggttcacca ttagaaatga   2100
tggcaatgat gggaaaatcg gtgtcagaag gcaagaaatt atttattaac accacatccc   2160
aaaaggcaaa aagtaagtac ggcacaatcg ctcttgagtc ttatattttt ggtctaaata   2220
aagaagcaaa gatattaaga atagactctg aaaccactaa aaaccctgaa catccagcct   2280
ataaaatcat tgaccaagac ttaaataata tcctcaaaga ttatgattat gtcattgcct   2340
caccttgcct tcaaacaggt gtcagtatta ccttaaaagg gcattttgac cagcaattta   2400
acttttccag tggaaacatt acacctcatt gctttttaca gcaaatgtgg cggttgaggg   2460
atgcagaaat tgaaagattc tattatgtgc cgaactcatc taacctcaat ctcattggga   2520
ataagtcaag ttcaccatca gaccttctaa agagcaataa caagatggca acggcaacgg   2580
ttaacctttt gggtagaatc gactccgaat attccctaga gtatgaatcg cacggcattt   2640
ggcttgagac gtgggcaaaa ttatcagcac ggcataacag ttcaatgcgt tgttactctg   2700
aaattcttac ctatctaatt acgtctcaag ggcataaatt aaatatcaac attccctcac   2760
ctcttgcaga tattaagaag ctaaatgatg aggtaagtag taacagggaa aaggtaaaaa   2820
atgagagata ctctcagagg ttaaactcac cagatattaa cgatgcagaa gctaccatac   2880
tcgaatctaa agagcaaaaa atcggattga ctctcaatga gagatgcacc ctagaaaagc   2940
ataaagttaa gaagcggtat gggaatgtaa agatggatat tctcaccttt gatgatgatg   3000
gactataccc caaactcaga ctattttatt acctcaccat cggtaaacct catctcaagg   3060
ctaatgacag aaaagctatt gccaaaatgg gcaatgacaa taaaggcaag attctatcaa   3120
aagacttagt taataaaact tactccgctc gtgtgaaggt cttagagatt cttaaactaa   3180
ctgactttat cgacaatctt agagatgaac tcttaataac tcccaataat ccagctatca   3240
ccgattttaa taatcttctg ctaagagcta agaaggattt aagagtatta ggagtcaaca   3300
tcggaaaata tccaatggcc aacattaatg ccgtacttac tctcattggt cacaaacttt   3360
ctgtaatgag agatgagttc ggaaaagaga aaaggataaa agtagatggt aaatcatacc   3420
gatgttatca acttgaaaca ttaccagatt ttaccaatga tactcttgac tactggttag   3480
aaaatgatag ccaaaaagaa gtaacagcaa cagaaaatta ctccgaaaat tttaaccctt   3540
caaatagcta caatccagac agtaagacac tttcagaggg tgcaaatttc ctatatataa   3600
ataaagaaga attgcatcca aataaattgc acctagaaat aaaagaaggt gctgaacttt   3660
```

```
ttttattcgg ggtaaaggtg attgtgaaag gaatcttgga cggggcagta actatattct   3720
ctatgggtca agaatacgat ttatccctca atgaactaga ggggatgtta acatcatgaa   3780
ctttacaaga atctttttaa agggcgatcg caccatgtta aatgatggta catttgttca   3840
gatatttgat atttaccatg accacgcatt gggagtgacc cttgacctta agacagaaaa   3900
aattatttcc gatgatgtta gggtaattac tgtcaaagac ttattgttcg atggcactta   3960
taaaggggta aaatctttta tgcccgataa tgcccgataa tgcccgattg atgctacaaa   4020
atcccataat cataagcgat aatcccctaa tagcttgtaa ttcttgaacc gtagcgattt   4080
tagagtattc caaaaagaag aaataaacac cgcaaaatgt cgtatttcac atatataaac   4140
caaggttttt tgccctaaaa tctttatgtt tgtagtgtga tgttgggtca aaatggtcag   4200
aaaagttgca aggtttttat ggatgcttac gcgcgcgagg ggtaagcatc cccaaatagt   4260
tactttatcc tagtccatgc ccatttattg ccgtcccgtt cggctttaaa aaagtgccaa   4320
aactcacaag gtgcaataaa aagttctgta cctttcgcaa ccctagataa tctttcaaca   4380
gttacttttt ttcctattat ctcggtacaa agtttggcta gtttctcttt tccctctttt   4440
tcaatcaagc cttcttgtat gcccaactca ttgattaatc tctctatttt taccattatt   4500
tcccgttcag gtagtttatc ccctaaatct tcatcggggg gcaatgtagg gcattctgaa   4560
ggggcttttt cttctgtctg gacattatct aatattgaag taaccaaact atcttcagtt   4620
ttttctattc ctattaattc atattcggtt actgtatccg tatcaatatc cgaataacta   4680
tctttatccg tattagctat tcggttaagt ttatccgtta actcagaaac aagactatat   4740
agcggtttta gctttcttc tatcctgtta tctaatacgg ataagtttat acggttatca   4800
ttatccgtat tagtatcatt gggctttttt ggtagttcta ccccctcata aaccgctttt   4860
attcccaatt ccaacagact gataacagta tcctttataa tgggtttttt gctgatatgg   4920
tgaacttttg ccccttccat cattgcgata ctttctatct cactcatcaa cttatcgctt   4980
aagtgaatct cgtatctgtt taatccctta ctggttttat tcatatccgt ttactttatt   5040
cggttaacaa ttctatttta tacgaataaa atattatacg gttaacttta tacgtttaac   5100
tattttatct atacggataa cagtaataag ttattcgtat tagttatacg tttactttta   5160
tccaaataaa attagtgcat ttaaactaaa agaatgattt tatcggagtt gatagcattg   5220
gattaaccta aagatgttta taagctatat ctgataagta tttaaggtta ttttgttatt   5280
ctgtttattg acattatcag aataaaagaa tagaatataa ttgttgagag ataagaggtt   5340
taagtgatta tggttaagaa gttagttggt tatgtcaggg tcagtagtga atcgcaagag   5400
gataacacta gcttacagaa tcagatagag agaattgaag catattgtat ggcttttggt   5460
tatgagttgg taaaaatatt caaagaggtt gccactggta caaaagcaga tattgaaacc   5520
cgtcctattt ttaatgaagc tatagaatac ttgaaacagg ataatgctaa tggaattatt   5580
gccttgaagc tagaccgaat cgcacggaat gctttagatg tattgcgttt ggttcgtgaa   5640
accttagaac cacaaaataa aatgttagtg ttactagata ttcaggtaga tacttcgaca   5700
ccttcaggaa aaatgatttt aactgtaatg agtgccgttg ctgaactcga aagagacatg   5760
atctatgatc gcactcaggg gggtagaaag actaaagccc aaaagggcgg gtatgcctac   5820
gggaaaccta aatttggcta taagactgaa gaaaaggaac taaaagaaga ttcagcacaa   5880
caggaaacta ttaaactaat taagagacac cgtaggtcag ggaaaagcta ccagaaaata   5940
gctgattatc tcaatgccca aagtattccc actaaacaag gtaagaaatg gagttctagc   6000
```

-continued

```
gtcgtctatc gaatctgtca ggaaaaagct ggttaagtct gtttatagat atttagaatt   6060

tattgaataa aaatagtatg aacaataaat atttatggac taaccacgct cggaaacgtt   6120

taactgaacg atgggaaata aaagaatcat gggttattga taccatcgaa aatcctgaac   6180

gttcagaatt tattgttgat gagtcagggg aaaaatatca ttactataaa agaatagcta   6240

agtttaagaa tagagtgtta gaagtgataa cttctgccaa ctcaacaccc acaagaataa   6300

taacctttta ctttaaccgt aacatgagga aaaatttatg attgttactt acgataatga   6360

agttgacgca atttatttta agttaacgga aaataaaatt gatagcaccg aacctcaaac   6420

agacaggatt atcattgatt acgatgaaag taataatatt gttggcattg aggtattaga   6480

ttttaattat cttgtcaaga aaggtttaac cgttgctgat ttaccttttt ctgaagatga   6540

aagattaaca gcttctcaat attttaattt tcctgttgct atctaatcca gaaggggcaa   6600

taatcccctt ctttcatcga gttagactta atatcacaaa agtcattttc attttaccgt   6660

ttcttttcca cagcgtccgt acgcccctcg ttaaatctca aaaccgacaa tttatgatgt   6720

ttataaaaag ttactcactt taataagtat ttatactcat taaagggtta ttcttttttt   6780

gtagcctgat aggttgggaa ggaatatttc agattatcag atttgttg               6828
```

```
<210> SEQ ID NO 2
<211> LENGTH: 1061
<212> TYPE: PRT
<213> ORGANISM: Cyanobacterium sp. ABICyano1

<400> SEQUENCE: 2

Met Ile Leu Gly Lys Pro Ser Asn Ser Gln Pro Leu Asn Lys Arg Asn
1               5                   10                  15

Phe Gln Asn Pro Asp His Ile Lys Glu Trp Gln Gln Ser Ala Ile Ser
            20                  25                  30

Gln Asp Leu Ile Ala Glu Asn Leu Val Ser Val Ala Asn Gly Phe Asp
        35                  40                  45

Val Leu Phe Ile Gly Asn Lys Tyr Arg Thr Asn Thr Gly Val Leu Ser
    50                  55                  60

Arg His Ile Leu Asn Ser Tyr Ser His Leu Glu Asp Gly Gly Ser Tyr
65                  70                  75                  80

Gly Arg Thr Phe Asp Pro Phe Thr Asn Lys Glu Met Gln Trp Val Gln
                85                  90                  95

Phe Lys Pro Asn Arg Pro Arg Lys Gly Ser Thr Gly Lys Val Ile Lys
            100                 105                 110

Tyr Glu Ser Pro Lys Gly Glu Pro Thr Arg Val Leu Met Pro Phe Val
        115                 120                 125

Pro Met Lys Ile Trp Gln Arg Ile Ser Asp Lys Phe Gly Val Pro Ile
    130                 135                 140

Asn Pro Lys Lys Asp Thr His Phe Trp Glu Trp Val Lys Asn Asn Pro
145                 150                 155                 160

Ser Ile Pro Ile Ala Ile Thr Glu Gly Asn Lys Lys Ala Asn Cys Leu
                165                 170                 175

Leu Ser Tyr Gly Tyr Pro Ala Ile Ala Phe Val Gly Ile Trp Asn Gly
            180                 185                 190

Leu Glu Lys Ile Asn Asp Phe Ser Lys Glu Lys Gln Leu Lys Glu Asp
        195                 200                 205

Leu Lys Trp Leu Leu Ser Asn Gly Asn Arg Asn Ile Asn Ile Ile Phe
    210                 215                 220

Asp Gln Asp Gln Lys Gln Lys Thr Val Ile Asn Val Asn Lys Ala Ile
```

-continued

```
225                 230                 235                 240

Phe Ala Leu Ser Ser Leu Ile Ser Arg Asn Gly His Lys Val Asn Ile
                245                 250                 255

Val Gln Trp Leu Pro Ser Lys Gly Lys Gly Ile Asp Asp Tyr Leu Val
            260                 265                 270

Ala Leu Pro Phe Glu Lys Arg Glu Asn His Leu Asp Asn Leu Ile Lys
        275                 280                 285

Ile Ala Pro Ser Phe Asn Phe Trp Ser Thr Lys Tyr Leu Phe Lys Cys
    290                 295                 300

Arg Lys Pro Asp Leu Thr Val Asn Cys Arg Tyr Leu Ser Asp Ala Val
305                 310                 315                 320

Lys Glu Leu Pro Gln Glu Asp Ile Ala Leu Ile Ala Pro His Gly Thr
                325                 330                 335

Gly Lys Thr Ser Leu Val Ala Thr His Val Lys Asn Arg Ser Tyr His
            340                 345                 350

Gly Arg Lys Thr Ile Ser Leu Val His Leu Glu Ser Leu Ala Lys Ala
        355                 360                 365

Asn Gly Asn Ala Leu Gly Leu Tyr Tyr Arg Thr Glu Asn Asn Ile Glu
    370                 375                 380

Lys Gln Tyr Leu Gly Phe Ser Leu Cys Val Asp Ser Cys Arg Asp Lys
385                 390                 395                 400

Ile Asn Gly Ile Thr Thr Asp Ile Ile Ser Gly Gln Asp Tyr Cys Leu
                405                 410                 415

Phe Ile Asp Glu Ile Asp Gln Val Ile Pro His Ile Leu Asn Ser Glu
            420                 425                 430

Thr Glu Val Ser Lys Tyr Arg Cys Thr Ile Ile Asp Thr Phe Ser Glu
        435                 440                 445

Leu Val Arg Asn Ala Glu Gln Val Ile Ile Ala Asp Ala Asp Leu Ser
    450                 455                 460

Asp Val Thr Ile Asp Leu Ile Glu Asn Ile Arg Gly Lys Lys Leu Tyr
465                 470                 475                 480

Val Ile Lys Asn Glu Tyr Gln Tyr Gln Gly Met Thr Phe Asn Ala Val
                485                 490                 495

Gly Ser Pro Leu Glu Met Met Ala Met Met Gly Lys Ser Val Ser Glu
            500                 505                 510

Gly Lys Lys Leu Phe Ile Asn Thr Thr Ser Gln Lys Ala Lys Ser Lys
        515                 520                 525

Tyr Gly Thr Ile Ala Leu Glu Ser Tyr Ile Phe Gly Leu Asn Lys Glu
    530                 535                 540

Ala Lys Ile Leu Arg Ile Asp Ser Glu Thr Thr Lys Asn Pro Glu His
545                 550                 555                 560

Pro Ala Tyr Lys Ile Ile Asp Gln Asp Leu Asn Asn Ile Leu Lys Asp
                565                 570                 575

Tyr Asp Tyr Val Ile Ala Ser Pro Cys Leu Gln Thr Gly Val Ser Ile
            580                 585                 590

Thr Leu Lys Gly His Phe Asp Gln Gln Phe Asn Phe Ser Ser Gly Asn
        595                 600                 605

Ile Thr Pro His Cys Phe Leu Gln Gln Met Trp Arg Leu Arg Asp Ala
    610                 615                 620

Glu Ile Glu Arg Phe Tyr Tyr Val Pro Asn Ser Ser Asn Leu Asn Leu
625                 630                 635                 640

Ile Gly Asn Lys Ser Ser Ser Pro Ser Asp Leu Leu Lys Ser Asn Asn
                645                 650                 655
```

-continued

```
Lys Met Ala Thr Ala Thr Val Asn Leu Leu Gly Arg Ile Asp Ser Glu
            660                 665                 670

Tyr Ser Leu Glu Tyr Glu Ser His Gly Ile Trp Leu Glu Thr Trp Ala
        675                 680                 685

Lys Leu Ser Ala Arg His Asn Ser Ser Met Arg Cys Tyr Ser Glu Ile
    690                 695                 700

Leu Thr Tyr Leu Ile Thr Ser Gln Gly His Lys Leu Asn Ile Asn Ile
705                 710                 715                 720

Pro Ser Pro Leu Ala Asp Ile Lys Lys Leu Asn Asp Glu Val Ser Ser
                725                 730                 735

Asn Arg Glu Lys Val Lys Asn Glu Arg Tyr Ser Gln Arg Leu Asn Ser
            740                 745                 750

Pro Asp Ile Asn Asp Ala Glu Ala Thr Ile Leu Glu Ser Lys Glu Gln
        755                 760                 765

Lys Ile Gly Leu Thr Leu Asn Glu Arg Cys Thr Leu Glu Lys His Lys
    770                 775                 780

Val Lys Lys Arg Tyr Gly Asn Val Lys Met Asp Ile Leu Thr Phe Asp
785                 790                 795                 800

Asp Asp Gly Leu Tyr Pro Lys Leu Arg Leu Phe Tyr Tyr Leu Thr Ile
                805                 810                 815

Gly Lys Pro His Leu Lys Ala Asn Asp Arg Lys Ala Ile Ala Lys Met
            820                 825                 830

Gly Asn Asp Asn Lys Gly Lys Ile Leu Ser Lys Asp Leu Val Asn Lys
        835                 840                 845

Thr Tyr Ser Ala Arg Val Lys Val Leu Glu Ile Leu Lys Leu Thr Asp
    850                 855                 860

Phe Ile Asp Asn Leu Arg Asp Glu Leu Leu Ile Thr Pro Asn Asn Pro
865                 870                 875                 880

Ala Ile Thr Asp Phe Asn Asn Leu Leu Leu Arg Ala Lys Lys Asp Leu
                885                 890                 895

Arg Val Leu Gly Val Asn Ile Gly Lys Tyr Pro Met Ala Asn Ile Asn
            900                 905                 910

Ala Val Leu Thr Leu Ile Gly His Lys Leu Ser Val Met Arg Asp Glu
        915                 920                 925

Phe Gly Lys Glu Lys Arg Ile Lys Val Asp Gly Lys Ser Tyr Arg Cys
    930                 935                 940

Tyr Gln Leu Glu Thr Leu Pro Asp Phe Thr Asn Asp Thr Leu Asp Tyr
945                 950                 955                 960

Trp Leu Glu Asn Asp Ser Gln Lys Glu Val Thr Ala Thr Glu Asn Tyr
                965                 970                 975

Ser Glu Asn Phe Asn Pro Ser Asn Ser Tyr Asn Pro Asp Ser Lys Thr
            980                 985                 990

Leu Ser Glu Gly Ala Asn Phe Leu  Tyr Ile Asn Lys Glu  Glu Leu His
        995                 1000                1005

Pro Asn  Lys Leu His Leu Glu  Ile Lys Glu Gly Ala  Glu Leu Phe
    1010                 1015                 1020

Leu Phe  Gly Val Lys Val Ile  Val Lys Gly Ile Leu  Asp Gly Ala
    1025                 1030                 1035

Val Thr  Ile Phe Ser Met Gly  Gln Glu Tyr Asp Leu  Ser Leu Asn
    1040                 1045                 1050

Glu Leu  Glu Gly Met Leu Thr  Ser
    1055                 1060
```

<210> SEQ ID NO 3
<211> LENGTH: 228
<212> TYPE: PRT
<213> ORGANISM: Cyanobacterium sp. ABICyano1

<400> SEQUENCE: 3

```
Met Val Lys Lys Leu Val Gly Tyr Val Arg Val Ser Ser Glu Ser Gln
1               5                   10                  15

Glu Asp Asn Thr Ser Leu Gln Asn Gln Ile Glu Arg Ile Glu Ala Tyr
            20                  25                  30

Cys Met Ala Phe Gly Tyr Glu Leu Val Lys Ile Phe Lys Glu Val Ala
        35                  40                  45

Thr Gly Thr Lys Ala Asp Ile Glu Thr Arg Pro Ile Phe Asn Glu Ala
    50                  55                  60

Ile Glu Tyr Leu Lys Gln Asp Asn Ala Asn Gly Ile Ile Ala Leu Lys
65                  70                  75                  80

Leu Asp Arg Ile Ala Arg Asn Ala Leu Asp Val Leu Arg Leu Val Arg
            85                  90                  95

Glu Thr Leu Glu Pro Gln Asn Lys Met Leu Val Leu Leu Asp Ile Gln
            100                 105                 110

Val Asp Thr Ser Thr Pro Ser Gly Lys Met Ile Leu Thr Val Met Ser
        115                 120                 125

Ala Val Ala Glu Leu Glu Arg Asp Met Ile Tyr Asp Arg Thr Gln Gly
    130                 135                 140

Gly Arg Lys Thr Lys Ala Gln Lys Gly Gly Tyr Ala Tyr Gly Lys Pro
145                 150                 155                 160

Lys Phe Gly Tyr Lys Thr Glu Glu Lys Glu Leu Lys Glu Asp Ser Ala
            165                 170                 175

Gln Gln Glu Thr Ile Lys Leu Ile Lys Arg His Arg Arg Ser Gly Lys
            180                 185                 190

Ser Tyr Gln Lys Ile Ala Asp Tyr Leu Asn Ala Gln Ser Ile Pro Thr
        195                 200                 205

Lys Gln Gly Lys Lys Trp Ser Ser Ser Val Val Tyr Arg Ile Cys Gln
    210                 215                 220

Glu Lys Ala Gly
225
```

<210> SEQ ID NO 4
<211> LENGTH: 61
<212> TYPE: PRT
<213> ORGANISM: Cyanobacterium sp. ABICyano1

<400> SEQUENCE: 4

```
Met Leu Asn Asp Gly Thr Phe Val Gln Ile Phe Asp Ile Tyr His Asp
1               5                   10                  15

His Ala Leu Gly Val Thr Leu Asp Leu Lys Thr Glu Lys Ile Ile Ser
            20                  25                  30

Asp Asp Val Arg Val Ile Thr Val Lys Asp Leu Leu Phe Asp Gly Thr
        35                  40                  45

Tyr Lys Gly Val Lys Ser Phe Met Pro Asp Asn Ala Arg
    50                  55                  60
```

<210> SEQ ID NO 5
<211> LENGTH: 254
<212> TYPE: PRT
<213> ORGANISM: Cyanobacterium sp. ABICyano1

<400> SEQUENCE: 5

```
Met Asn Lys Thr Ser Lys Gly Leu Asn Arg Tyr Glu Ile His Leu Ser
1               5                   10                  15

Asp Lys Leu Met Ser Glu Ile Glu Ser Ile Ala Met Met Glu Gly Ala
            20                  25                  30

Lys Val His His Ile Ser Lys Lys Pro Ile Ile Lys Asp Thr Val Ile
        35                  40                  45

Ser Leu Leu Glu Leu Gly Ile Lys Ala Val Tyr Glu Gly Val Glu Leu
    50                  55                  60

Pro Lys Lys Pro Asn Asp Thr Asn Thr Asp Asn Asp Asn Arg Ile Asn
65                  70                  75                  80

Leu Ser Val Leu Asp Asn Arg Ile Glu Glu Lys Leu Lys Pro Leu Tyr
                85                  90                  95

Ser Leu Val Ser Glu Leu Thr Asp Lys Leu Asn Arg Ile Ala Asn Thr
            100                 105                 110

Asp Lys Asp Ser Tyr Ser Asp Ile Asp Thr Asp Thr Val Thr Glu Tyr
        115                 120                 125

Glu Leu Ile Gly Ile Glu Lys Thr Glu Asp Ser Leu Val Thr Ser Ile
    130                 135                 140

Leu Asp Asn Val Gln Thr Glu Glu Lys Ala Pro Ser Glu Cys Pro Thr
145                 150                 155                 160

Leu Pro Pro Asp Glu Asp Leu Gly Asp Lys Leu Pro Glu Arg Glu Ile
                165                 170                 175

Met Val Lys Ile Glu Arg Leu Ile Asn Glu Leu Gly Ile Gln Glu Gly
            180                 185                 190

Leu Ile Glu Lys Glu Gly Lys Glu Lys Leu Ala Lys Leu Cys Thr Glu
        195                 200                 205

Ile Ile Gly Lys Lys Val Thr Val Glu Arg Leu Ser Arg Val Ala Lys
    210                 215                 220

Gly Thr Glu Leu Phe Ile Ala Pro Cys Glu Phe Trp His Phe Phe Lys
225                 230                 235                 240

Ala Glu Arg Asp Gly Asn Lys Trp Ala Trp Thr Arg Ile Lys
                245                 250
```

<210> SEQ ID NO 6
<211> LENGTH: 87
<212> TYPE: PRT
<213> ORGANISM: Cyanobacterium sp. ABICyano1

<400> SEQUENCE: 6

```
Met Asn Asn Lys Tyr Leu Trp Thr Asn His Ala Arg Lys Arg Leu Thr
1               5                   10                  15

Glu Arg Trp Glu Ile Lys Glu Ser Trp Val Ile Asp Thr Ile Glu Asn
            20                  25                  30

Pro Glu Arg Ser Glu Phe Ile Val Asp Glu Ser Gly Glu Lys Tyr His
        35                  40                  45

Tyr Tyr Lys Arg Ile Ala Lys Phe Lys Asn Arg Val Leu Glu Val Ile
    50                  55                  60

Thr Ser Ala Asn Ser Thr Pro Thr Arg Ile Ile Thr Phe Tyr Phe Asn
65                  70                  75                  80

Arg Asn Met Arg Lys Asn Leu
                85
```

<210> SEQ ID NO 7
<211> LENGTH: 82

```
<212> TYPE: PRT
<213> ORGANISM: Cyanobacterium sp. ABICyano1

<400> SEQUENCE: 7

Met Ile Val Thr Tyr Asp Asn Glu Val Asp Ala Ile Tyr Phe Lys Leu
1               5                   10                  15

Thr Glu Asn Lys Ile Asp Ser Thr Glu Pro Gln Thr Asp Arg Ile Ile
            20                  25                  30

Ile Asp Tyr Asp Glu Ser Asn Asn Ile Val Gly Ile Glu Val Leu Asp
        35                  40                  45

Phe Asn Tyr Leu Val Lys Lys Gly Leu Thr Val Ala Asp Leu Pro Phe
    50                  55                  60

Ser Glu Asp Glu Arg Leu Thr Ala Ser Gln Tyr Phe Asn Phe Pro Val
65                  70                  75                  80

Ala Ile


<210> SEQ ID NO 8
<211> LENGTH: 16301
<212> TYPE: DNA
<213> ORGANISM: Artificial Sequence
<220> FEATURE:
<223> OTHER INFORMATION: pRL528 helper plasmid

<400> SEQUENCE: 8

aagtcacggt actctccgga ggcctttttc atatccggcg ggcctgacac ttccggatgc      60

agcacacgaa aacagaagtc accggaacac gccattctga gaaaactgtc actaatctgt     120

tttattccgc aaacagaaaa ccaccggata accggggtat aggaagtata aaccaccttt     180

ttgggtatag gaagtataaa ccaccttttt gctcctcatc cgaagtatct tacctgaaat     240

tccctcactc gtttaccgct caagccccaa ttttaactgc cggtccagcc taaaccgctc     300

taataaggtt cgatttggcg gtaaaatctc tagcctgata gctcgagatc tagatatcga     360

tgaattcgag ctcggtaccc tattcaatat ttaacttgat tactgtagaa gtataacaaa     420

gtataatcag gttctaactg ttgtcaatta gtctataaaa aatagggttc aaatcttaag     480

tgatagacga tagtgctttg tcctgataga atcttaagtt acctctttgt tacaagaaaa     540

atataaaatg acttcatttg agcttgagag tccaatagaa ataaagactg acccgactga     600

tcttgatcaa gagagtgatt cctttgtaca agaaatttct cgattcaata aagcacttga     660

gcaacgtttt agagataaga tgcgattgca tgaaagttta agtcgaaaaa tagttagttt     720

tcaagctaat aagtcaaaac ctcagtatcg ctggtttaaa tataaagaag ctttttcagt     780

tgatttggta aatcagttaa tattcgagta cgagaaaaaa tcatttgaga ggattcttga     840

ccccttcgca ggagcaggaa caatgctatt tgcctgtagt gatgccggta ttcaagcaga     900

tggtatagaa gtgttaccta ttggtcaaga gattattgaa gtaaggaaaa taatccagcg     960

acaattccgt cgagaagatt ttttgagatt gattgaatgg tacaaacaaa aaccttggaa    1020

tcagcataat aatagaaaat atcttaatcg tttaagaatt actgacggag cttatcctcc    1080

tgaaacagaa gcatcaatag agagattttt attttctata gaaaaagaga atattcttgt    1140

gaaacaagtt ctccgttttg ctctattgtg tattcttgaa tctatcagct atacccgtaa    1200

agatggacag tatctacgtt gggataaaag agcatttagg aaaagtggat cagataaatt    1260

tgataaaggt aaaattctgg atttcgatga agcaattact gagcaaataa aattaatttt    1320

gaatgattcc tttgacttaa taagtaatac attattttgt tatgggactc aaagaagtgg    1380

aattaattta tttaatgctt catgtcttaa aattctgcct gaatttgagc aagattttta    1440
```

-continued

```
cgactgtatc attacctctc caccctattg taatcgttat gactatacac gtacatacgc   1500
tctagaatta gctctattag gtgtgggaga aagagatata gtacaactta ggcaagatat   1560
gctgagttgt actgttgaaa acaaagaaaa gtctcttatt cacaattggc aggaagcatt   1620
acgcatactt gataaacaag aattgttaca aagtatcttg cgctttcttg agcgagagct   1680
tgaaagaaaa aaacttaata ataacggtat tcctcgtatg ataaaaggat atttctatga   1740
aatggcttgc gttattatag aatgctttag agttttaaaa aatggctcac ctttatttat   1800
ggtaaatgat aatgttcgct atgcaggtat tgatatttcg gttgatttaa ttctttctaa   1860
tattgcagaa gaaattggtt ttaatgtgga gaaaattctt gtcttaccta ctggcaaagg   1920
taacagtagc caacaaatgg ggacacatgg aagaaagaca cttcgcaaat gtgtgtatgt   1980
ttggagaaaa ccctagtgcc atatcaatat catattcaaa gcaatgatga tcttgtgact   2040
ccatatcaag aagtccgagc aggatttgtt gctttagctt tagaaagaaa tcgaaaagca   2100
acaccatttg ttgagcaggc aagagcatta aagatccgag taagccaaat tgaaaggggg   2160
gatcctctag aagctttaat gcggtagttt atcacagtta aattgctaac gcagtcaggc   2220
accgtgtatg aaatctaaca atgcgctcat cgtcatcctc ggcaccgtca ccctggatgc   2280
tgtaggcata ggcttggtta tgccggtact gccgggcctc ttgcgggata tcgtccattc   2340
cgacagcatc gccagtcact atggcgtgct gctagcgcta tatgcgttga tgcaatttct   2400
atgcgcaccc gttctcggag cactgtccga ccgctttggc cgccgcccag tcctgctcgc   2460
ttcgctactt ggagccacta tcgactacgc gatcatggcg accacacccg tcctgtggat   2520
cttctcaacg aagaaagaag aatcatcgct gaggtgaaaa ataaatactc aacggttact   2580
ggcggggatt tagcagataa atataaaggc ttagatgagt tggtatcacc gaaacatagc   2640
cgatttaagg attactgtgc gtactttgtt aatataatcc ctcgtaaacc tatcagatat   2700
aacagcccct ttactccttc caataaaggt agtggtactc tgtgtccttc gaaccctaac   2760
attagaatca ttgatggtgc gagtttctat gagcttgtca ctggcagacc agatgctctg   2820
caagaactcc atagtgctct ccctcacgca attgagtata ttttgagcga acgtcttggg   2880
cagcaaggtt tttccatccc tgataaagat agttttatta agtattttgg gctcgcttac   2940
ggctgataac catgatcaat gtttgacaaa gcacatgtaa acccatacag tagtaaccat   3000
gactaatgtt ggcatggtta ctaaatatgt taaaggaaga gttttcactt tcagaagttg   3060
cagacatttt gggcgtttca aaagaaactt taaggcgttg ggatactgct ggaaaattag   3120
tttctcaaag aaatgacgaa aacaactatc gattttataa aaaagagcaa cttaaaaatt   3180
ttgaacaagc tcagttttta tttaaaagcc agtggcctga tgagactaaa ataagcaata   3240
atgtttatac tgtattagag ttatttgctg gcgcaggggg gatggcttta ggtttagaaa   3300
aagccggttt aaaatctgtt ttactaaatg aaattgactc ccatgcttgt aagacgttac   3360
gaaaaaatag gcctgaatgg aatgtggttg aaggtgatgt gagccaagta gacttcaccc   3420
cttataggaa taccgttgat gtgctggctg gtggctttcc ttgccaggca ttctcttatg   3480
caggcaaaaa acttggtttt gaagatacac ggggcaccct tttctttgaa ttcgcccgag   3540
ccgctaaaga aatcaatccg aaagttcttt tagcagagaa tgttcgaggg ttgctaaatc   3600
atgatgctgg acgaacttta gaaacaataa aaaatattat cacagacttg ggctacactt   3660
tatttgagcc aagagtgctt aaggctattt tctacaaagt gccgcaaaaa cgcgagcgtt   3720
tgatcattgt agctgtaaga aatgatcttg ctgatggcat cgattatgag tggccttctt   3780
```

-continued

```
cttacaataa aatattaacc cttaaagatg cattaaaaaa gggagagctg tatgatagcg   3840
acgtgccaga atctgaagga caaaaatatc ccaaaagaaa agcagagatc ctaagtatgg   3900
ttcctcccgg tggctactgg agagatcttc ctgaagatat tcaaaaagaa tacatgctca   3960
agagttttta cttaggtggg ggcaaaactg gtatggctcg tcgtttgtca tgggatgaac   4020
caagcctaac attaacatgc gccccagcac agaaacaaac agagcgttgc cacccagaag   4080
aaacaagacc attaactgtg cgtgagtatg caagaataca gaccttcccc gatgaatggg   4140
tatttgaagg cccaatgtca gcgaaatata agcaaatagg aaacgctgtt cctgttaatc   4200
tgtcatttgc tgttggcaaa tctgtggtac atcttttaga taagataaat aaaagataga   4260
ccctgtaaat aattctgtgt aattgctgcc atattaaagg tgatcgctca ggcggtcacc   4320
gaactcgata ataaagcgac tcatcgccag ccgccagctc tggattggca tattccattt   4380
ttttgatgca tccttgatcg ccagagaaat gaccttccgc agcgagtcgt cagtcgggaa   4440
cactttacgc ttcttaatgg ccgcacggat cacgctgttc agcgattcga tagcgttcgt   4500
ggtgtagatg gccttgcgga tatcgggcga atagccgaag aacgtgttga tatttttccca   4560
gtgcgcacgc cagcttttgc tgatttgcgg gtatttatcg tcccagacat tcgggaactg   4620
ctccggtgcc actagcgccg cctcttctgt tggcgcctga tacaccgttt ttaacccgcc   4680
agtgacggct ttgtagtcct tccacgatac gtatttcagg ctgttgcgca ccatatgaat   4740
gatgcacaac tggatgtgcg tctacggata cacgctgttt atcgcatccg gaaagccttt   4800
cagaccgtcc atgcaggcaa taaggatatc ctgaagcccc cgattcttaa gctctgtcag   4860
cccccccagc cagaacttcg ccccttcgtt ctcggccagc cacatgccca gcaactcttt   4920
ctggcctcca gtattaatac cgagtgcaag gaacaccgct ttgttaatta cggtgccacc   4980
ttgacgaact ttcaccacga tacagtcaag gtaaacaatg ggatacagtg catccagagg   5040
tcgattttgc cattctgcaa cctgctcttt gaccgcatca gtgactttac atatcagcgt   5100
gggtgacaca tctgcgtcgt acatctcttt gaaggtggcg acaatttcgc gggtagtcat   5160
atctttggcg tagagggata aaatctggct gtccatctgc gtaatgcgcg tctggtgctt   5220
cttaatcaac tgcggttcga aggtgttttc acggtcacgc gacgtgttca gttcgatcct   5280
ctacgccgga cgcatcgtgg ccggcatcac cggcgccaca ggtgcggttg ctggcgccta   5340
tatcgccgac atcaccgatg gggaagatcg ggctcgccac ttcgggctca tgagcgcttg   5400
tttcggcgtg ggtatggtgg caggccccgt ggccggggga ctgttgggcg ccatctcctt   5460
gcatgcacca ttccttgcgg cggcggtgct caacggcctc aacctactac tgggctgctt   5520
cctaatgcag gagtcgcata agggagagcg tcgactctag agtcgacctg cagcaatggc   5580
aacaacgttg cgcaaactat taactggcga actacttact ctagcttccc ggcaacaatt   5640
aatagactgg atggaggcgg ataaagttgc aggaccactt ctgcgctcgg cccttccggc   5700
tggctggttt attgctgata aatctggagc cggtgagcgt ggatctcgcg gtatcattgc   5760
agcactgggg ccagatggta agccctcccg tatcgtagtt atctacacga cggggagtca   5820
ggcaactatg gatgaacgaa atagacagat cgctgagata ggtgcctcac tgattaagca   5880
ttggtaactg tcagaccaag tttactcata tatactttag attgatttaa aacttcattt   5940
ttaatttaaa aggatctagg tgaagatcct ttttgataat ctcatgacca aaatccctta   6000
acgtgagttt tcgttccact gagcgtcaga ccccgtacat cacgaatata gtttgcttga   6060
catcctgaca agaataatat tgtaattaga aaaattatta ttttcatatt tctttccaac   6120
aaaagtaaaa atacttatgc atttaaaata ctacctacat aatttacctg aatcacttat   6180
```

accatggatt cttattttaa tatttaacga caatgataac actcctttgt tatttatatt 6240
tatatcatca atacatgtat tgctatatcc atactctaaa ttaaccatat ctagatatat 6300
caaagaaaat acaaagttaa aaaaagaacc ctggtactta tgcaagttat ctgcattgtt 6360
ttatttatta atggcaatcc cagtaggatt gccaagtttc atatattaca ctctaaagag 6420
aaattaaatc cctaacaact cattaagttt gctcaactca tcatccccta tgtaagaaga 6480
aacaatacct gtgacaattg caatccccca gaaaccaaga ggcacaccaa caataaaact 6540
aaacattaat gccacaattt ttgccacacc tacatcgacc gcacttttct ccagcgtgac 6600
aaacaaaggt cgccagttac cagtttctat tgcattttta aaatcagaac caacatcata 6660
tagaaaagat actcgactgg tgattttaag cgactttgat atcttcgtta aattcttaga 6720
taactcatca taattaacag actctaacgc attaaaaata gcatcccgat caaccttact 6780
gaatttctta tccagtacat tcttatactt ttcaaatgct gccagagctt catcaacacc 6840
ttgaattttc tttcctttag acttttccgc taaatcctga gcaatttttg cgtatttttc 6900
tccatattgt tcggttatat attgataaaa tccaaccata gtttcaacag catcttttat 6960
ctggctcttt tcaagagcat cctgagcttc ttttaatttc tgctctgcct ctttaacctc 7020
agcggcctta ccatccctga cactaacagc attcttaatt tcattttcaa ctgcggagta 7080
ctcagcctgc ttagcttcaa gctgacgctg tagtttttc tgaacgtcac gccatcccgg 7140
aaatccggag accttcacgt caacactctt ctgagcgttt tcaagctctc ctgcaactct 7200
ggaaacagta gcttgcttac tctgtacatc actttcagcc ttcgccagtt cagctttcgc 7260
ctcagctaaa cgcttctctg cttccgccac cgcctgtttc tcttcattaa gagtttcatg 7320
ttcagcgacc tctgcatttt cacgagcctt ttcttcagct tccttctgtt tattcacatc 7380
accaatttta ctttgcaatg tatttttata agaattaagt ttgctaatat ctgcatcaag 7440
ctgatttgat tttttttgca actcatcaac atccctctca agatcagtga taccatgata 7500
agaatgatgc ttgaatactt ttttcatctc ctcgattttc ttctgttttt cactaatctg 7560
tgtagcaatt ttattcttct gcttttgttt ttcattaatt acattactca ccaccttcga 7620
actcttatcc atatcactga cctgagcatt cgttggtgca gtattaactg aagcagtgtt 7680
attgttgtta tttcctgagc tttctgcaaa aagtgatggc atatcactaa ttaaagaatt 7740
aagaactctg gagacccctc caaatggatt atcaaccaga gttgaattct cttctgtcat 7800
aacaatacca ttcatcaccg gaaggccatc attattaatg acaacatcac cccacggagt 7860
cagatatgac tcaccggttt tcatcacagt tgatgtagaa ccagatgaat ttgaatttcc 7920
ctgaccacca ttattaccat gcccagagcc accaccccag tgaaccccac tattactatt 7980
attatttcca ccttgctgat tcagattcgc ccctgttccc cccatagact caccagcagt 8040
tggtccatat ccacttagtt ctttagccat aaattcctct ttgataatta aaacaataaa 8100
ttaaaaacaa tatactgtac atataaccac tggttttatg tacagtaaaa acctactact 8160
cagcattgtc catgtcaaga gcatggattt tcatttttgc aataaggatc acactatggg 8220
gaggcaggca ttgagaacgt cgaaacagaa caccggagca aatcaggatg agatataaaa 8280
ctgttggatc atgaaaaaac ggagaacgat gtgagcaaat caccccgcca taaactgaac 8340
aaaacagaca aacgacttct cgacaccctt gttgctgccg gatatgagca tgacaaagcc 8400
cgtgacctca tccagaaaca ggtttacacg ctgacactgg ctgatcagcg tcatgtggtc 8460
agtgaaatca gtaatggtgt gaatcccacc caggcttact cggcggtata ccaggcaaga 8520

-continued

```
cgcattcgcc tcgcccgtaa atatctgaac ggtaaaaagg ttatggaaga aaccggggaa   8580
aatacgcccc catcagcgta aggatttctt ttgccgctcc agagactcca gttttttacg   8640
caaatcctct ctttttggg catctctggt gccagccagc tctgctctca actcatcgat   8700
ctgaagttgt atcttcagtc tattactgaa cattttctgt ctggcattaa catccgcaac   8760
aatgccgttt tttgtcttct cggccttttg ttgaaaaaca ttgctgtccg catgactggc   8820
aaccgaagca gaaagaacac taaaaagcag gactggcaca cattttttca cgggattatt   8880
cctgactcat tgaccatcaa atcacattgg gagtaaaccg acgtatgata agagatactc   8940
ttcggagata taactccctg agtatcaaga ttaaaaacgc aaggagatgt ttatgagatc   9000
tgccgctgcc aggctgcttc tgatacctct gataacagca acaatagctc ttacaggatg   9060
cacaccaaag accagcctgg aacgacatac ccggcattat gtttatgctt cagatgatgg   9120
atttgatcct aacttctaca cccagaaagc agacaccata cgtatgatgc tcccgttctt   9180
tcagcagttc cgggatatgg ggatgaaaga caaagcagcc ggagtatcag cagaaacggc   9240
acagcaacgt gtaaaagaat tccactcaga aaaatttttt cactcactcc ggagcacaac   9300
agcctttgct ggcagaaaat acacaaacag cgatatgcct tcgccgaaaa aaatgaaact   9360
aatggcagac accatttctg cggtttatct cgatggatac gagggcagac agtaagggat   9420
ttaccataat ccccttaattg tacgcaccgc tgaaatgcgt tcagcgcgat cacggctgct   9480
gacaggtaaa aatggcaaca aaccacccga aaagctgccg cgatcgcacc tgataaattt   9540
taaccgtatg catagctatt cagccatgtg aataacgctg gttttgcctg cgtaaacctc   9600
atgacactgt tttttttcca tcttttcagt tgatgacata cgcagacatc gcgggatgag   9660
gctgaggaat gagcgcgatc tggcaaagag gcaaaacaca gcaacaaaaa cgacacgcca   9720
gaatcgcgcc cggatgcgtt tttaacgcgt tccggtacca tctggcaacc tcccggaaca   9780
actcaccgtc acatacctat tgacgggcca cgccataccc gtgcttcccg ttcctgctct   9840
tcatgccagg accgcgcacg ctcccgttcc aggcgtgcct gcctttcctg ttcatccctt   9900
atctgctgtt cgtgataaat aaccgactca agtggtccac ctgcccggct aatctctgca   9960
cctgctgact caagtcgtcg cactgttccc tcagttgccc gttctcctgt cgtgtcagct  10020
cgaacatatg ctgcaaatcc gtgaaggcgc tctcccagtc tttcagccgc tgcatatagt  10080
cctgctgcaa ttgctctaag gcgttcagta agtgcatttc cagctctgtc atactcactt  10140
actccctgac cagtcttact gcgttcttct tctccaccgt ccagttgttt tccccccttca  10200
ccccggacgg caacactaga aatttcccgt tcctgccctc gtgatacgtc acaccccatg  10260
tttttcccg gagtttcgcc agcgtctctt cctggtccct gatagccagg atgttcgccg  10320
caatccggct ttcctgccac tgaatcagcc ccccatgacg ccagaaaaat cccgcccgtg  10380
acgcagagcg ccgtcagcga cgggtacagt atccgccctt tgaccagctt ccagagcagc  10440
tcttcctgcc gccgggccag ttcgttctct gtggcgctga actgcgcgtt cacggcactg  10500
ttcagcgtct ccagttgttc tttcaccgct gctgtgtgtg cgctgatagc gtctctgatt  10560
ttctgcccgt ttaagttcag ttccctgtct acagacgctt cgagcttcct gaactcgctg  10620
ttcagcatgt tctctgtaga gacggcacgc tctttcagtt tcttctcgaa gtctgtcccc  10680
atttgtaaaa gattgctcat acagcgcccc tttcagcctg agattacgcc caccctccgg  10740
gtcggcgata ctgatactgc tcctggttgt cctcacaacc tcaaaacctg ccgctgtaag  10800
cgcctcagtg acatcctgac gcgtttttag cgctccggca tggtaaagag cctccagtcc  10860
cctcgtaatc gcttctgcgg cctcctgttt cgctttcggc agattattcg gggtgacaag  10920
```

tgtccgcctg ttctccggtg cgttcgggtc gtgcagcccg taatggtgat tcaccagtgt 10980
ctgccaggca ttgattcgcg gacggtccgc tcggtcgtaa tagggctgga gccgttttcc 11040
gctcgccagc tccatattcg ggatgacaaa attcagctca agacgcccct tgtcctggtg 11100
ctccacccac aggatgctgt actgattttt ttcaagaccg ggcatcagta cccgctcaaa 11160
gctctccatc accctttcac gctctcccgg tggcagggtc tgctctgcaa aagacagaac 11220
ccccgaggtg tatttttttcg caaacggcgt ggcatcgatg agttcccgca cctcttcggg 11280
agcaccccgc agaactctcg ccccttcccg gttacgctcc cggcccagca ggtaatcaac 11340
cggaccactg ccaccgcctt ttcccctggc atgaaactta actatcatcc cgttctccct 11400
gtttacggac ctcatccctc agctcactca gttcacgtcc gatggccatc agtgcagcca 11460
ccacatgaac ccggtcatgc cccgaccact gtccgctgtt tatcttccgg gctatctgat 11520
tcaggttatt gccgaccgaa gcgaactggc gcaacagcgg cggtgccagt gtcggaagac 11580
ctgacgtttt cgatggcggt gcccccaggc agaccttacg catccatgac gcaagttgtt 11640
ttccctcaca acgtgccagc agccgcgcat gttcctcatc cgtgacccgt atcgtgagca 11700
tcctttcgcg tttcaccggt atcattaaaa acctccgaca gactccccac acatggagaa 11760
acagaactgt gactaaacag gaaaaaaccg cccttaacat ggcccgcttc atcagaagcc 11820
agacgctgac cctgctggaa aaactgaatg aactggacgc cgacgaccag gctgacatct 11880
gcgaagcgct tcacgatcac gctgacgagc tttaccgcag ctgcctcgca cgcttcgggg 11940
ataacggtga aaacctctga cacatgcagc tcccggagac ggtcacagct ggcctgtgag 12000
cggatgccgg gagcagacaa gcccgtcagg gcgcgtcagc gggttttagc gggtgtcggg 12060
gcgcagccat gacccagtca cgtagcgata gcggagtgta tactggctta atcatttggc 12120
atcagtgagg attgtatgaa aagtgcacca tgccgggtgt gaaatgccgc acagatgcgt 12180
aaggagaaaa tgctcgtcca ggcgcttttc cgcttcctcg ctcactgact cgctccgctc 12240
ggtcgttcgg ctgcggcgag cggtatcagc tcactcaaag acggtaatgc ggttatccac 12300
agaatcaggg gataacacca aaagaaacat gtgagcaaaa aacaagaacc cggaaaaggc 12360
cacgcagctg gcgtttttcc ataggctccg cccccttga cgagcatcac aaaaaaccga 12420
cgctcaagtc agaggtggcg aaacccgaca ggacttaaag ataccaggcg tttccccctg 12480
gtggctccct cgtgcgctct cctgttccga ccctgccgct taccggatac ctgtccgcct 12540
ttctcccttt gggaagcgtg gcgctttctc atagctcacg ctgttggtat ctcagttcgg 12600
tgtaggtcgt tcgctccaag ctgggctgtg tgcacgaacc ccccgttcag cccgaccgct 12660
gcgccttatc cggtaactat cgtcttgagt ccaacccggt aagacacgac ttaacgccac 12720
tggcagcagc cattggtaac tggatagtgg atttagatac gcagaactct tgaagttgaa 12780
gccttatagc ggctacactg gaaggacagc atttggtatc tgtgctccac taaagccagt 12840
tacccggtta agcagtcccc aactgactta accttcgact aaaccgcctc cccaggcggt 12900
tttttcgttt acaggcagca gattacgcgc agaaaaaaag gatctcaaga agatcctttg 12960
atcttttcta ctgaaccgcg atccccgtca gttcagaaga cgaagatggt gcaacggttc 13020
ctccttgtac aggggtctga cgctcagtgg aacgaaaact cacgttaagc aacgttttct 13080
acctctgacg cctcttttaa tggtctcaga tgtcctttgg tcaccagttc tgccagcgtg 13140
aaggaataat ggccgagcat attgatatgt ccgtggcaaa gcggggagag gcgtgcgata 13200
tcttcatcat tcagtgtttc accttgcgcc cggagatgat ccagggctgc ctgcatatac 13260

-continued atagtgttcc ataacacgac ggcgttagtg accagcccca gtgcgcccag ttgatcttcc 13320
tgaccgtcgg tatatcgttt tcttatctca cctttttgac cgtgacagat ggctctggca 13380
acggcatggc ggctttctcc ccgattaagc tgggtcagaa tgcgccggcg gtaatcttca 13440
tcatcaatat aattaagcag atacagcgtt ttgttgatgc gccccacttc aatgattgcc 13500
tgagtcagtc cggaaggacg ttcacttttc agcaatgaac ggaccagcac tgaagcctgt 13560
actttgccca gtttcaggga gccagcggtc cggatcattt cgtcccactg aaggactatt 13620
tttcggggat ctgattgccc tctggcaata tcattcagca cgccatagtt ggcatcatgg 13680
cccattcgcc agaaaaccga agcaccggca tcagccaggc gtggagaaaa ctggtatccc 13740
agcagccaga aaaggccaaa gacaagttcg ctggtacctg ctgtatcggt cataatttcg 13800
gttggattca gcccggtctc ctgttccaga aggccttcca gcacaaagat agagtccctc 13860
agcgtccccg gtataacgat gccatgaaag ccggaatact gatcggacac aaagttgtac 13920
caggtgatcc ctctgttatt accaaagtat ttgcggttcg gtccggcatt gattgttctg 13980
actggcgtaa caaagcgcat tccatctgca gtccgcctca gcaatatcgg gatagagcgc 14040
agggtcagga aatccttgga tatcgttcag gtagcccacg ccgcgcttga gcgcatagcg 14100
ctgggtttcc ggttggaagc tgtcgattga aacacggtgc atctgatcgg acagggcgtc 14160
taagagcggc gcaatacgtc tgatctcatc ggccggcgat acaggcctcg cgtccggatg 14220
gctggcggcc ggtccgacat ccacgacgtc tgatccgact cgcagcattt cgatcgccgc 14280
ggtgacagcg ccggcggggt ctagccgccg gctctcatcg aagaaggagt cctcggtgag 14340
attcagaatg ccgaacaccg tcaccatggc gtcggcctcc gcagcgactt ccacgatggg 14400
gatcgggcga gcaaaaaggc agcaattatg agccccatac ctacaaagcc ccacgcatca 14460
agcttttgcc catgaagcaa ccaggcaatg gctgtaatta tgacgacgcc gagtcccgac 14520
cagactgcat aagcaacacc gacagggatg gatttcagaa ccagagaaca tgtcattgta 14580
ctggaaggcg cattacaact gcggctgggg gatgagtggc acaccgtttc tgccggggaa 14640
tccctgcgct tccatgcgga tatcccgcac gcttacgcca atcccggtaa ggccattgtg 14700
acactgcata atctgatcca ttatccgcgc ccggcggaca aataaaaaag cagggtataa 14760
taaatatacc ccgctttgac ttaacggatc gtcttacttt atttgtaaaa taaaaccaaa 14820
ataaatatgt gttcagctta acttattata tatcatcctt ataccaaccg ggatgatatg 14880
tttatactga acagaaaagc atgccattca gaatactatc ttctgttata tatggcggtt 14940
tatttattgt ttaattacac acactcaggc atatcactat gctatcgtga tgttttcact 15000
ggtgttgtta ctactgcctt tacggcattt tggtgttgtt caaaatgact gtcgcagcag 15060
tctttctggt gtcttaaata ctattattat aactgcatct ggtgttgtta atattattgt 15120
tactgcttac tttattatta ttgctgtcag tctttgctgt ttcttttttta ttaagggtat 15180 taccaaactg cgggggcatt atcgtacagt gatcctgaac cagtctgaaa cgaaattaca 15240
gattacggtt aaaatataaa aaaaagccac cattcctgcc ggatacggtg gcttaaatac 15300
agaattaatt aatttatttc agtatgttat cacacatcag ctgaagtgta ttaataaacc 15360
gtgctgcatg aaagccatca cagactgcat gatgaacctg tacagaaaca ggtaataata 15420
cgcggtcacc ttcctgctga aactttgcca tcgtaaaaac cggggcaaaa taatcatcat 15480
ttccggtgat gttcaggtta aatccgtcaa aactcaccca cggtaatgat gatatattca 15540
ggtgattctc cggtaaattt ccctgcggaa acaatctggt atcatgctga tattctgccg 15600
ttaccgcatt ataacctgcc ataaactcac tgagatccgg aaaataacgg caggacagtg 15660

```
cagagaatgt ttcggtttct ttatgaaaga cagtaaagac cgggtctgac tggtcccagt  15720

aaataagttc attgtctttc agtgccatcc ggaactccgg aaactgatta acagcccggg  15780

agatcaggta aatcatcagc ggataaaact tataacctgt ctccgccagt gcggtacgca  15840

aagcggtaat atcgagtttg gtggtcaggc tgaatccgca tttaatctgc tgacgataaa  15900

gggcaaagtg ttccctgcga ttccaggtat tcaggtcaat ccgggtaaaa ttcatggtta  15960

ttccttctga ttaatagtga aaaatattaa taatcagaag gcagtctggt tgtctcaatg  16020

ggtaacattc cgtcctccgt aagctgtttg gtattcagta ataataccct atacgggctt  16080

aatctgtatt aagcccggct ttatttattc cggccaatca tccgcaaaca catagcggat  16140

cagttctgcg gattcacggg gcggtgctct cagcacatcc gccattaaat caatctccat  16200

ctgacaggtt tgcagcttgt cttccgccgg tacatacgga tcatccgtca ggaaactatc  16260

gccgtattta tccatcgacc cctgtatttg tgccgaaaat a                      16301
```

```
<210> SEQ ID NO 9
<211> LENGTH: 12968
<212> TYPE: DNA
<213> ORGANISM: Artificial Sequence
<220> FEATURE:
<223> OTHER INFORMATION: TK225\pABICyano1-6.8_PnirAABICyano1-PDCmax-
      synADHmax-PrbcABICyano 1-Km**-oriVT

<400> SEQUENCE: 9

aatatttttc gtcagatacg caaaccttac aaacataatt aacaactgaa actattgata     60

tgtctaggtt ttagctctat cacaggttgg atctgtcgac aattaataac ttcttcctgt    120

acgggcgaat ggccatttgc tcctaactaa ctccgtactg ctttgcggaa cgagcgtagc    180

gaactctccg aattactaag ccttcatccc tgatagatgc aaaaaacgaa ttaaaattat    240

gtgtaaaaag aaaatgtgtc tttatttagt agtcaaagtt acaaaatatt aagaatcaaa    300

ttaataatgt attgggcagt taagtatata agtctttaaa tatttatttg tattcaatat    360

attaaccgag gacaaattat gaattcttat accgtgggta cttatttagc cgaacgctta    420

gtgcaaattg gtttaaaaca tcattttgcc gtggctgggg actataattt agtgttattg    480

gataacttat tattaaataa aaacatggaa caagtgtatt gttgtaatga attaaattgt    540

ggtttttctg ctgaaggtta tgctagagct aaaggtgcag ctgctgctgt tgttacttat    600

tctgtgggtg ctttatctgc ttttgatgct attggtggtg cttatgccga aaatttaccc    660

gtgattttaa tttctggtgc ccctaataat aatgatcatg ccgctggaca tgttttacat    720

catgccttag gtaaaaccga ttatcattat caattagaaa tggccaaaaa tattactgct    780

gctgccgaag ctatttatac tcctgaagaa gcccctgcca aaattgatca tgtgattaaa    840

accgccttac gcgaaaaaaa acccgtgtat ttagaaattg cctgtaatat tgcttctatg    900

ccttgtgctg ctcctgggcc tgcttctgct ttatttaatg atgaagcctc tgatgaagct    960

agtttaaatg ctgccgtgga agaaacctta aaatttattg ccaatcgcga taaagttgcc   1020

gtgttagttg gttctaaatt aagagctgct ggtgctgaag aagctgctgt taaatttgct   1080

gatgctttag gtggtgcagt tgctactatg gctgctgcca aatctttttt tcccgaagaa   1140

aatccccatt atattggaac tagttgggga gaagtttctt atcctggtgt ggaaaaaact   1200

atgaaagaag ccgacgctgt tattgcttta gcccctgtgt ttaatgatta ttctaccact   1260

ggttggactg atattcccga tcccaaaaaa ttagttttag ccgaacctcg ttctgttgtt   1320

gttaatggtg ttcgctttcc ctctgtgcat ttaaaagatt atttaacccg cttagcccaa   1380
```

```
aaagtttcta aaaaaactgg tgccttagat ttttttaaat ctttaaatgc gggtgaatta   1440
aaaaaagctg ctcctgctga tccttctgct cctttagtta atgctgaaat tgcccgtcaa   1500
gttgaagcct tattaacccc taatactacc gttattgccg aaactggtga ttcttggttt   1560
aatgcccaac gcatgaaatt acctaatggt gcccgtgttg aatatgaaat gcaatggggt   1620
catattggtt ggtctgtacc tgctgctttt ggttatgctg ttggtgctcc tgaacgtcgt   1680
aatattttaa tggtgggtga tggttctttt caattaactg cccaagaagt tgcccaaatg   1740
gttcgcttaa aattacccgt tattattttt ttaataaata attatggtta taccattgaa   1800
gtgatgattc atgatgggcc atataataat attaaaaatt gggattatgc gggtttaatg   1860
gaagtgttta atggtaatgg tggttatgat tctggtgctg gtaaaggttt aaaagccaaa   1920
actggtggtg aattagctga agctattaaa gttgccttag ccaatactga tgggccaacc   1980
ttaattgaat gttttattgg tcgcgaagat tgtaccgaag aattagttaa atggggtaaa   2040
cgtgttgctg ctgctaattc tcgcaaaccc gtgaataaat tattgtaatt tttggggatc   2100
aattcgagct cggtacccaa actagtatgt agggtgaggt tatagctagc gcttttaatt   2160
aatccgcgga tttgtattca atatattaac cgaggacaac atatgattaa agcctatgct   2220
gccttagaag ccaatggtaa attacaaccc tttgaatatg atcctggtgc tttaggtgcc   2280
aatgaagtgg aaattgaagt gcaatattgt ggtgtgtgtc attctgattt atctatgatt   2340
aataatgaat ggggtatttc taattatccc ttagttcctg gtcatgaagt tgttggtact   2400
gttgctgcta tgggtgaagg tgttaatcat gtggaagtgg gtgatttagt tggtttaggt   2460
tggcattctg gttattgtat gacctgtcat tcttgtttat ctggttatca taatttatgt   2520
gccactgccg aatctactat tgtgggtcat tatggtggtt ttggtgatag agttcgtgct   2580
aaaggtgttt ctgtggtgaa attacccaaa ggtattgatt tagcctctgc tgggccttta   2640
ttttgtggtg gtattaccgt tttttctccc atggtggaat tatctttaaa acctaccgcc   2700
aaagttgctg ttattggtat tggtggttta ggtcatttag ccgttcaatt tttaagagcc   2760
tggggttgtg aagttactgc ttttacctct tctgcccgta aacaaaccga agttttagaa   2820
ttaggtgccc atcatatttt agattctacc aatcctgaag ctattgcttc tgccgaaggt   2880
aaatttgatt atattatttc taccgtgaat ttaaaattag attggaattt atatatcagt   2940
accttagccc ctcaaggtca ttttcatttt gttggtgtgg tgttagaacc cttggactta   3000
aacttatttc ccttattaat gggacaacgt tctgtttctg cttctcctgt tggttctcct   3060
gctactattg ccactatgtt agattttgcc gtgcgtcatg atattaaacc cgtggtggaa   3120
caattttctt ttgatcaaat taatgaagcc attgcccatt tagaatctgg taaagcccat   3180
tatcgcgtgg tgttatctca ttctaaaaat taataagatt aacttctaaa ctgaaacaaa   3240
tttgagggta ggcttcattg tctgccctta ttttttttatt taggaaaagt gaacagacta   3300
aagagtgttg gctctattgc tttgagtatg taaattaggc gttgctgaat taaggtatga   3360
tttttgaccc cttctctctt ctgcagttac ctaggatttc tggcgaaagg gggatgtgct   3420
gcaaggcgat taagttgggt aacgccaggg ttttcccagt cacgacgttg taaaacgacg   3480
gccagtgagc gcgacgtaat acgactcact atagggcgaa ttggcggaag gccgtcaagg   3540
ccgcatggcg cgcctacgta gacaattgtc gatgtaatta ttaactatct tattatagat   3600
gaggggagag ggagaaatta gttcggagag aacgctcgag cgctcgttcc gcaaagcggt   3660
acggagttag ttaggggcta atgggcattc tcccgtacag gaaagagtta gaagttatta   3720
```

-continued

```
attatcaaca attctccttt gcctagtgca tcgttacctt tttaattaaa acataaggaa   3780
aactaataat cgtaataatt taacctcaaa gtgtaaagaa atgtgaaatt ctgactttta   3840
taacgttaaa gagggaaaaa ttagcagttt aaaataccta gagaatagtc tggggtaagc   3900
atagagaatt agattagtta agttaatcaa attcagaaaa aataataatc gtaaatagtt   3960
aatctgggtg tatagaaaat gatccccttc atgataagat ttaaactcga aaagcaaaag   4020
ccaaaaaact aacttccatt aaaagaagtt gttacatata acgctataaa gaaaatttat   4080
atatttggag gataccaacc atgtctcata ttcaacgtga aactagttgt tctcgtcctc   4140
gtttaaattc taatatggat gccgatttat atggttataa atgggctcgt gataatgttg   4200
gtcaatctgg tgctactatt tatcgtttat atggtaaacc tgatgctcct gaattattct   4260
tgaaacatgg taaaggttct gttgctaatg atgttactga tgaaatggtt cgtttaaact   4320
ggttgactga atttatgcct ttacctacta ttaaacattt tattcgtact cccgatgatg   4380
cttggttatt aactactgct attcctggta aaactgcttt tcaagtttta gaagaatatc   4440
ctgattctgg tgaaaatatt gttgatgctt tagctgtttt tttacgtcgt ttacattcta   4500
ttcccgtttg taattgtcct tttaattctg atcgtgtttt tcgtttagct caagctcaat   4560
ctcgtatgaa taatggttta gttgatgctt ctgattttga tgatgaacgt aatggttggc   4620
ctgttgaaca agtttggaaa gaaatgcaca aattgttacc tttttctcct gattctgttg   4680
ttactcatgg tgatttttct ttagataatt tgatctttga tgaaggtaaa ttgattggtt   4740
gtattgatgt tggtcgtgtt ggtattgctg atcgttatca agatttagct attttatgga   4800
attgtttagg tgaatttttct ccttctttac agaaacgttt atttcagaaa tatggtattg   4860
ataatcctga tatgaacaag ttacaatttc atttaatgtt ggacgagttc ttttaagaat   4920
taattcatga ccaaaatccc ttaacgtgag ttttcgttcc actgagcgtc agaccccgta   4980
gaaaagatca aaggatcttc ttgagatcct ttttttctgc gcgtaatctg ctgctattta   5040
aattacgtac acgtgttatt actttgttaa cgacaattgt cttaattaac tgggcctcat   5100
gggccttccg ctcactgccc gctttccagt cgggaaacct gtcgtgccag ctctgcagat   5160
gacggtgaaa acctctgaca catgcagctc ccggagacgg tcacagcttg tctgtaagcg   5220
gatgccggga gcagacaagc ccgtcagggc gcgtcagcgg gtgttggcgg gtgtcggggc   5280
gcagccatga cccagtcacg tagcgatagc ggagtgtata ctggcttaac tatgcggcat   5340
cagagcagat tgtactgaga gtgcaccata tgcggtgtga aataccgcac agatgcgtaa   5400
ggagaaaata ccgcatcagg cgctcttccg cttcctcgct cactgactcg ctgcgctcgg   5460
tcgttcggct gcggcgagcg gtatcagctc actcaaaggc ggtaatacgg ttatccacag   5520
aatcagggga taacgcagga aagaacatgt gagcaaaagg ccagcaaaag gccaggaacc   5580
gtaaaaaggc cgcgttgctg gcgtttttcc ataggctccg cccccctgac gagcatcaca   5640
aaaatcgacg ctcaagtcag aggtggcgaa acccgacagg actataaaga taccaggcgt   5700
ttccccctgg aagctccctc gtgcgctctc ctgttccgac cctgccgctt accggatacc   5760
tgtccgcctt tctcccttcg ggaagcgtgg cgctttctca tagctcacgc tgtaggtatc   5820
tcagttcggt gtaggtcgtt cgctccaagc tgggctgtgt gcacgaaccc cccgttcagc   5880
ccgaccgctg cgccttatcc ggtaactatc gtcttgagtc caacccggta agacacgact   5940
tatcgccact ggcagcagcc actggtaaca ggattagcag agcgaggtat gtaggcggtg   6000
ctacagagtt cttgaagtgg tggcctaact acggctacac tagaaggaca gtatttggta   6060
tctgcgctct gctgaagcca gttaccttcg gaaaaagagt tggtagctct tgatccggca   6120
```

-continued

```
aacaaaccac cgctggtagc ggtggttttt ttgtttgcaa gcagcagatt acgcgcagaa   6180
aaaaaggatc tcaagaagat cctttgatct tttctactgc agaagcttgt tagacaccct   6240
gtcatgtatt ttatattatt tatttcacca tacggattaa gtgaaaccta atgaaaatag   6300
tactttcgga gctttaactt taatgaaggt atgttttttt atagacatcg atgtctggtt   6360
taacaatagg aaaaagtagc taaaactccc atgaattaaa gaaataacaa ggtgtctaac   6420
aacctgttat taagaatgtt agaaaagact taacatttgt gttgagtttt tatagacatt   6480
ggtgtctaga catacggtag ataaggtttg ctcaaaaata aaataaaaaa agattggact   6540
aaaaaacatt taatttagta caatttaatt agttattttt tcgtctcaaa ttttgctttg   6600
ttgagcagaa atttagataa aaaaatcccc gtgatcagat tacaatgtcg ttcattgtac   6660
gatgtgtcga aaaatcttta cgacactcta aactgaccac acgggggaaa aagaaaactg   6720
aactaataac atcatgatac tcggaaaacc tagcaattct caacccctaa acaaaagaaa   6780
cttccaaaac cctgaccata taaaggagtg gcaacaatca gcaatcagtc aagatttgat   6840
agcagaaaat cttgtatcgg ttgctaatgg ttttgatgta ctatttatcg gcaataaata   6900
ccgaactaac acgggtgttc tgtcacggca catattaaac tcctattctc atttagaaga   6960
tggtggttcg tatggtagaa catttgaccc atttaccaat aaagaaatgc agtgggttca   7020
atttaaaccg aatagaccaa gaaaaggttc tactggtaag gtaatcaaat atgaatcgcc   7080
aaaaggtgaa cctacaagag ttctaatgcc gtttgtgcct atgaaaatat ggcaacggat   7140
tagcgataag ttcggagtac cgattaatcc gaaaaaaagat actcactttt gggaatgggt   7200
aaagaataat ccatcgatac cgattgccat tacagaagga aataaaaaag ctaattgcct   7260
attatcctat ggctatcctg ctattgcctt tgtaggcatt tggaacggat tagagaaaat   7320
aaatgatttc tcgaaggaaa agcagttaaa agaggatttg aaatggttgt tatccaacgg   7380
caaccgaaat attaatatca tctttgacca agaccagaaa caaaaaactg taattaatgt   7440
aaacaaagct attttcgctt tatcttctct aataagtaga aatggtcata aagttaatat   7500
tgtgcaatgg ttgccgtcaa aaggtaaagg aatagatgat tatttggtag ctttaccttt   7560
tgagaaaaga gaaaatcatt tagacaactt aattaaaatt gcaccatcat ttaatttttg   7620
gtcaactaaa tacttattca agtgtcgtaa accagattta accgtaaatt gccgttattt   7680
gagcgatgca gtaaaagaat tacctcaaga ggatatagca ttaatagcac ctcacggcac   7740
gggtaaaact tcattagtag ctactcacgt taagaatcgg agttatcacg gaaggaaaac   7800
tatttcattg gtgcatcttg aaagtttagc caaagctaat ggcaacgcac ttggattata   7860
ttaccgaacc gaaaataata ttgaaaagca atatcttgga tttagcttat gtgtagatag   7920
ttgccgtgat aagattaacg gcattacaac tgatattatt tcaggtcaag attattgcct   7980
tttcattgat gaaattgacc aagtaattcc acacatcctt aacagtgaaa ctgaagtaag   8040
taagtataga tgcaccatca ttgacacttt ttctgaactg gtgagaaatg ctgaacaggt   8100
cattattgct gatgctgatt tatccgatgt gacgattgac ctaatagaaa acatcagagg   8160
taaaaaacta tatgtaatca agaatgaata tcagtatcag ggaatgactt ttaacgccgt   8220
tggttcacca ttagaaatga tggcaatgat gggaaaatcg gtgtcagaag gcaagaaatt   8280
atttattaac accacatccc aaaaggcaaa aagtaagtac ggcacaatcg ctcttgagtc   8340
ttatattttt ggtctaaata aagaagcaaa gatattaaga atagactctg aaaccactaa   8400
aaaccctgaa catccagcct ataaaatcat tgaccaagac ttaaataata tcctcaaaga   8460
```

-continued

```
ttatgattat gtcattgcct caccttgcct tcaaacaggt gtcagtatta ccttaaaagg   8520
gcattttgac cagcaattta acttttccag tggaaacatt acacctcatt gctttttaca   8580
gcaaatgtgg cggttgaggg atgcagaaat tgaaagattc tattatgtgc cgaactcatc   8640
taacctcaat ctcattggga ataagtcaag ttcaccatca gaccttctaa agagcaataa   8700
caagatggca acggcaacgg ttaacctttt gggtagaatc gactccgaat attccctaga   8760
gtatgaatcg cacggcattt ggcttgagac gtgggcaaaa ttatcagcac ggcataacag   8820
ttcaatgcgt tgttactctg aaattcttac ctatctaatt acgtctcaag ggcataaatt   8880
aaatatcaac attccctcac ctcttgcaga tattaagaag ctaaatgatg aggtaagtag   8940
taacagggaa aaggtaaaaa atgagagata ctctcagagg ttaaactcac cagatattaa   9000
cgatgcagaa gctaccatac tcgaatctaa agagcaaaaa atcggattga ctctcaatga   9060
gagatgcacc ctagaaaagc ataaagttaa gaagcggtat gggaatgtaa agatggatat   9120
tctcaccttt gatgatgatg gactataccc caaactcaga ctattttatt acctcaccat   9180
cggtaaacct catctcaagg ctaatgacag aaaagctatt gccaaaatgg gcaatgacaa   9240
taaaggcaag attctatcaa aagacttagt taataaaact tactccgctc gtgtgaaggt   9300
cttagagatt cttaaactaa ctgactttat cgacaatctt agagatgaac tcttaataac   9360
tcccaataat ccagctatca ccgattttaa taatcttctg ctaagagcta agaaggattt   9420
aagagtatta ggagtcaaca tcggaaaata tccaatggcc aacattaatg ccgtacttac   9480
tctcattggt cacaaacttt ctgtaatgag agatgagttc ggaaaagaga aaaggataaa   9540
agtagatggt aaatcatacc gatgttatca acttgaaaca ttaccagatt ttaccaatga   9600
tactcttgac tactggttag aaaatgatag ccaaaaagaa gtaacagcaa cagaaaatta   9660
ctccgaaaat tttaaccctt caaatagcta caatccagac agtaagacac tttcagaggg   9720
tgcaaatttc ctatatataa ataaagaaga attgcatcca aataaattgc acctagaaat   9780
aaaagaaggt gctgaacttt ttttattcgg ggtaaaggtg attgtgaaag gaatcttgga   9840
cggggcagta actatattct ctatgggtca agaatacgat ttatccctca atgaactaga   9900
ggggatgtta acatcatgaa ctttacaaga atctttttaa agggcgatcg caccatgtta   9960
aatgatggta catttgttca gatatttgat atttaccatg accacgcatt gggagtgacc  10020
cttgacctta agacagaaaa aattatttcc gatgatgtta gggtaattac tgtcaaagac  10080
ttattgttcg atggcactta taaaggggta aaatctttta tgcccgataa tgcccgataa  10140
tgcccgattg atgctacaaa atcccataat cataagcgat aatcccctaa tagcttgtaa  10200
ttcttgaacc gtagcgattt tagagtattc caaaaagaag aaataaacac cgcaaaatgt  10260
cgtatttcac atatataaac caaggttttt tgccctaaaa tctttatgtt tgtagtgtga  10320
tgttgggtca aaatggtcag aaaagttgca aggtttttat ggatgcttac gcgcgcgagg  10380
ggtaagcatc cccaaatagt tactttatcc tagtccatgc ccatttattg ccgtcccgtt  10440
cggctttaaa aaagtgccaa aactcacaag gtgcaataaa aagttctgta cctttcgcaa  10500
ccctagataa tctttcaaca gttacttttt ttcctattat ctcggtacaa agtttggcta  10560
gtttctcttt tccctctttt tcaatcaagc cttcttgtat gcccaactca ttgattaatc  10620
tctctatttt taccattatt tcccgttcag gtagtttatc ccctaaatct tcatcggggg  10680
gcaatgtagg gcattctgaa ggggcttttt cttctgtctg gacattatct aatattgaag  10740
taaccaaact atcttcagtt ttttctattc ctattaattc atattcggtt actgtatccg  10800
tatcaatatc cgaataacta tctttatccg tattagctat tcggttaagt ttatccgtta  10860
```

```
actcagaaac aagactatat agcggtttta gcttttcttc tatcctgtta tctaatacgg  10920
ataagtttat acggttatca ttatccgtat tagtatcatt gggctttttt ggtagttcta  10980
ccccctcata aaccgctttt attcccaatt ccaacagact gataacagta tcctttataa  11040
tgggtttttt gctgatatgg tgaacttttg ccccttccat cattgcgata ctttctatct  11100
cactcatcaa cttatcgctt aagtgaatct cgtatctgtt taatccctta ctggttttat  11160
tcatatccgt ttactttatt cggttaacaa ttctatttta tacgaataaa atattatacg  11220
gttaacttta tacgtttaac tattttatct atacggataa cagtaataag ttattcgtat  11280
tagttatacg tttactttta tccaaataaa attagtgcat ttaaactaaa agaatgattt  11340
tatcggagtt gatagcattg gattaaccta aagatgttta taagctatat ctgataagta  11400
tttaaggtta ttttgttatt ctgtttattg acattatcag aataaaagaa tagaatataa  11460
ttgttgagag ataagaggtt taagtgatta tggttaagaa gttagttggt tatgtcaggg  11520
tcagtagtga atcgcaagag gataacacta gcttacagaa tcagatagag agaattgaag  11580
catattgtat ggcttttggt tatgagttgg taaaaatatt caaagaggtt gccactggta  11640
caaaagcaga tattgaaacc cgtcctattt ttaatgaagc tatagaatac ttgaaacagg  11700
ataatgctaa tggaattatt gccttgaagc tagaccgaat cgcacggaat gctttagatg  11760
tattgcgttt ggttcgtgaa accttagaac cacaaaataa aatgttagtg ttactagata  11820
ttcaggtaga tacttcgaca ccttcaggaa aaatgatttt aactgtaatg agtgccgttg  11880
ctgaactcga aagagacatg atctatgatc gcactcaggg gggtagaaag actaaagccc  11940
aaaagggcgg gtatgcctac gggaaaccta aatttggcta taagactgaa gaaaaggaac  12000
taaaagaaga ttcagcacaa caggaaacta ttaaactaat taagagacac cgtaggtcag  12060
ggaaaagcta ccagaaaata gctgattatc tcaatgccca aagtattccc actaaacaag  12120
gtaagaaatg gagttctagc gtcgtctatc gaatctgtca ggaaaaagct ggttaagtct  12180
gtttatagat atttagaatt tattgaataa aaatagtatg aacaataaat atttatggac  12240
taaccacgct cggaaacgtt taactgaacg atgggaaata aaagaatcat gggttattga  12300
taccatcgaa aatcctgaac gttcagaatt tattgttgat gagtcagggg aaaaatatca  12360
ttactataaa agaatagcta agtttaagaa tagagtgtta gaagtgataa cttctgccaa  12420
ctcaacaccc acaagaataa taacctttta ctttaaccgt aacatgagga aaaatttatg  12480
attgttactt acgataatga agttgacgca atttatttta agttaacgga aaataaaatt  12540
gatagcaccg aacctcaaac agacaggatt atcattgatt acgatgaaag taataatatt  12600
gttggcattg aggtattaga ttttaattat cttgtcaaga aaggtttaac cgttgctgat  12660
ttaccttttt ctgaagatga aagattaaca gcttctcaat attttaattt tcctgttgct  12720
atctaatcca gaaggggcaa taatcccctt ctttcatcga gttagactta atatcacaaa  12780
agtcattttc attttaccgt ttcttttcca cagcgtccgt acgcccctcg ttaaatctca  12840
aaaccgacaa tttatgatgt ttataaaaag ttactcactt taataagtat ttatactcat  12900
taaagggtta ttcttttttt gtagcctgat aggttgggaa ggaatatttc agattatcag  12960
atttgttg                                                           12968
```

<210> SEQ ID NO 10
<211> LENGTH: 13449
<212> TYPE: DNA
<213> ORGANISM: Artificial Sequence
<220> FEATURE:

<223> OTHER INFORMATION: TK293\pABICyano1-6.8_PnirAABICyano1-PDCmax-
PrpsLABICyano1-synADHm ax-PrbcABICyano1-Km**-oriVT

<400> SEQUENCE: 10

```
aatatttttc gtcagatacg caaaccttac aaacataatt aacaactgaa actattgata     60
tgtctaggtt ttagctctat cacaggttgg atctgtcgac aattaataac ttcttcctgt    120
acgggcgaat ggccatttgc tcctaactaa ctccgtactg ctttgcggaa cgagcgtagc    180
gaactctccg aattactaag ccttcatccc tgatagatgc aaaaaacgaa ttaaaattat    240
gtgtaaaaag aaaatgtgtc tttatttagt agtcaaagtt acaaaatatt aagaatcaaa    300
ttaataatgt attgggcagt taagtatata agtctttaaa tatttatttg tattcaatat    360
attaaccgag gacaaattat gaattcttat accgtgggta cttatttagc cgaacgctta    420
gtgcaaattg gtttaaaaca tcattttgcc gtggctgggg actataattt agtgttattg    480
gataacttat tattaaataa aaacatggaa caagtgtatt gttgtaatga attaaattgt    540
ggtttttctg ctgaaggtta tgctagagct aaaggtgcag ctgctgctgt tgttacttat    600
tctgtgggtg ctttatctgc ttttgatgct attggtggtg cttatgccga aaatttaccc    660
gtgattttaa tttctggtgc ccctaataat aatgatcatg ccgctggaca tgttttacat    720
catgccttag gtaaaaccga ttatcattat caattagaaa tggccaaaaa tattactgct    780
gctgccgaag ctatttatac tcctgaagaa gcccctgcca aaattgatca tgtgattaaa    840
accgccttac gcgaaaaaaa acccgtgtat ttagaaattg cctgtaatat tgcttctatg    900
ccttgtgctg ctcctgggcc tgcttctgct ttatttaatg atgaagcctc tgatgaagct    960
agtttaaatg ctgccgtgga agaaacctta aaatttattg ccaatcgcga taaagttgcc   1020
gtgttagttg gttctaaatt aagagctgct ggtgctgaag aagctgctgt taaatttgct   1080
gatgctttag gtggtgcagt tgctactatg gctgctgcca aatctttttt tcccgaagaa   1140
aatccccatt atattggaac tagttgggga gaagtttctt atcctggtgt ggaaaaaact   1200
atgaaagaag ccgacgctgt tattgcttta gcccctgtgt ttaatgatta ttctaccact   1260
ggttggactg atattcccga tcccaaaaaa ttagttttag ccgaacctcg ttctgttgtt   1320
gttaatggtg ttcgctttcc ctctgtgcat ttaaaagatt atttaacccg cttagcccaa   1380
aaagtttcta aaaaaactgg tgccttagat ttttttaaat ctttaaatgc gggtgaatta   1440
aaaaaagctg ctcctgctga tccttctgct cctttagtta atgctgaaat tgcccgtcaa   1500
gttgaagcct tattaacccc taatactacc gttattgccg aaactggtga ttcttggttt   1560
aatgcccaac gcatgaaatt acctaatggt gcccgtgttg aatatgaaat gcaatggggt   1620
catattggtt ggtctgtacc tgctgctttt ggttatgctg ttggtgctcc tgaacgtcgt   1680
aatattttaa tggtgggtga tggttctttt caattaactg cccaagaagt tgcccaaatg   1740
gttcgcttaa aattacccgt tattattttt ttaataaata attatggtta taccattgaa   1800
gtgatgattc atgatgggcc atataataat attaaaaatt gggattatgc gggtttaatg   1860
gaagtgttta atggtaatgg tggttatgat tctggtgctg gtaaaggttt aaaagccaaa   1920
actggtggtg aattagctga agctattaaa gttgccttag ccaatactga tgggccaacc   1980
ttaattgaat gttttattgg tcgcgaagat tgtaccgaag aattagttaa atggggtaaa   2040
cgtgttgctg ctgctaattc tcgcaaaccc gtgaataaat tattgtaatt tttggggatc   2100
aattcgagct cctccgctta aaaaatttca tttttcgatc aaaaaagaca aattattact   2160
aattagctca tggcaataaa taatcagtag taatctgttt tcacatttta ttgttaattt   2220
```

-continued ttattattgc taatatcaac cttttctact tctgcttaat attttattta tgctcaatgg 2280
gaaaatctga aataagattg agaacagtgt taccaataga agtatttaag gtttaaagca 2340
taccttaaag ataacatttt tttttgaaaa gagtcaaatt atttttgaaa ggctgatatt 2400
tttgatattt actaatattt tatttatttc tttttccctt aaaataagag ctaaatctgt 2460
ttttattatc atttatcaag ctctattaat acctcaactt tttcaagaaa aaataataat 2520
aatttttccc tctattctca tgacctttta ggaaaattaa ttttagaaaa actattgaca 2580
aacccataaa aaatgagata agattataga ttgtcactgg tattttatac tagaggcaaa 2640
ttatatttat atatacaaaa atgctgtata aaaaacatct catatgatta aagcctatgc 2700
tgccttagaa gccaatggta aattacaacc ctttgaatat gatcctggtg ctttaggtgc 2760
caatgaagtg gaaattgaag tgcaatattg tggtgtgtgt cattctgatt tatctatgat 2820
taataatgaa tggggtattt ctaattatcc cttagttcct ggtcatgaag ttgttggtac 2880
tgttgctgct atgggtgaag gtgttaatca tgtggaagtg ggtgatttag ttggtttagg 2940
ttggcattct ggttattgta tgacctgtca ttcttgttta tctggttatc ataatttatg 3000
tgccactgcc gaatctacta ttgtgggtca ttatggtggt tttggtgata gagttcgtgc 3060
taaaggtgtt tctgtggtga aattacccaa aggtattgat ttagcctctg ctgggccttt 3120
attttgtggt ggtattaccg ttttttctcc catggtggaa ttatctttaa aacctaccgc 3180
caaagttgct gttattggta ttggtggttt aggtcattta gccgttcaat ttttaagagc 3240
ctggggttgt gaagttactg cttttacctc ttctgcccgt aaacaaaccg aagttttaga 3300
attaggtgcc catcatattt tagattctac caatcctgaa gctattgctt ctgccgaagg 3360
taaatttgat tatattattt ctaccgtgaa tttaaaatta gattggaatt tatatatcag 3420
taccttagcc cctcaaggtc attttcattt tgttggtgtg gtgttagaac ccttggactt 3480
aaacttattt cccttattaa tgggacaacg ttctgtttct gcttctcctg ttggttctcc 3540
tgctactatt gccactatgt tagattttgc cgtgcgtcat gatattaaac ccgtggtgga 3600
acaattttct tttgatcaaa ttaatgaagc cattgcccat ttagaatctg gtaaagccca 3660
ttatcgcgtg gtgttatctc attctaaaaa ttaataagat taacttctaa actgaaacaa 3720
atttgagggt aggcttcatt gtctgccctt attttttat ttaggaaaag tgaacagact 3780
aaagagtgtt ggctctattg ctttgagtat gtaaattagg cgttgctgaa ttaaggtatg 3840
atttttgacc ccttctctct tctgcagtta cctaggattt ctggcgaaag gggatgtgc 3900
tgcaaggcga ttaagttggg taacgccagg gttttcccag tcacgacgtt gtaaaacgac 3960
ggccagtgag cgcgacgtaa tacgactcac tatagggcga attggcggaa ggccgtcaag 4020
gccgcatggc gcgcctacgt agacaattgt cgatgtaatt attaactatc ttattataga 4080
tgaggggaga gggagaaatt agttcggaga gaacgctcga gcgctcgttc cgcaaagcgg 4140
tacggagtta gttaggggct aatgggcatt ctcccgtaca ggaaagagtt agaagttatt 4200
aattatcaac aattctcctt tgcctagtgc atcgttacct tttaattaa aacataagga 4260
aaactaataa tcgtaataat ttaacctcaa agtgtaaaga aatgtgaaat tctgactttt 4320
ataacgttaa agagggaaaa attagcagtt taaaatacct agagaatagt ctggggtaag 4380
catagagaat tagattagtt aagttaatca aattcagaaa aaataataat cgtaaatagt 4440
taatctgggt gtatagaaaa tgatcccctt catgataaga tttaaactcg aaaagcaaaa 4500
gccaaaaaac taacttccat taaaagaagt tgttacatat aacgctataa agaaaattta 4560
tatatttgga ggataccaac catgtctcat attcaacgtg aaactagttg ttctcgtcct 4620

-continued

```
cgtttaaatt ctaatatgga tgccgattta tatggttata aatgggctcg tgataatgtt   4680
ggtcaatctg gtgctactat ttatcgttta tatggtaaac ctgatgctcc tgaattattc   4740
ttgaaacatg gtaaaggttc tgttgctaat gatgttactg atgaaatggt tcgtttaaac   4800
tggttgactg aatttatgcc tttacctact attaaacatt ttattcgtac tcccgatgat   4860
gcttggttat taactactgc tattcctggt aaaactgctt ttcaagtttt agaagaatat   4920
cctgattctg gtgaaaatat tgttgatgct ttagctgttt ttttacgtcg tttacattct   4980
attcccgttt gtaattgtcc ttttaattct gatcgtgttt ttcgtttagc tcaagctcaa   5040
tctcgtatga ataatggttt agttgatgct tctgattttg atgatgaacg taatggttgg   5100
cctgttgaac aagtttggaa agaaatgcac aaattgttac ctttttctcc tgattctgtt   5160
gttactcatg gtgatttttc tttagataat ttgatctttg atgaaggtaa attgattggt   5220
tgtattgatg ttggtcgtgt tggtattgct gatcgttatc aagatttagc tattttatgg   5280
aattgtttag gtgaattttc tccttcttta cagaaacgtt tatttcagaa atatggtatt   5340
gataatcctg atatgaacaa gttacaattt catttaatgt tggacgagtt cttttaagaa   5400
ttaattcatg accaaaatcc cttaacgtga gttttcgttc cactgagcgt cagaccccgt   5460
agaaaagatc aaaggatctt cttgagatcc tttttttctg cgcgtaatct gctgctattt   5520
aaattacgta cacgtgttat tactttgtta acgacaattg tcttaattaa ctgggcctca   5580
tgggccttcc gctcactgcc cgctttccag tcgggaaacc tgtcgtgcca gctctgcaga   5640
tgacggtgaa aacctctgac acatgcagct cccggagacg gtcacagctt gtctgtaagc   5700
ggatgccggg agcagacaag cccgtcaggg cgcgtcagcg ggtgttggcg ggtgtcgggg   5760
cgcagccatg acccagtcac gtagcgatag cggagtgtat actggcttaa ctatgcggca   5820
tcagagcaga ttgtactgag agtgcaccat atgcggtgtg aaataccgca cagatgcgta   5880
aggagaaaat accgcatcag gcgctcttcc gcttcctcgc tcactgactc gctgcgctcg   5940
gtcgttcggc tgcggcgagc ggtatcagct cactcaaagg cggtaatacg gttatccaca   6000
gaatcagggg ataacgcagg aaagaacatg tgagcaaaag gccagcaaaa ggccaggaac   6060
cgtaaaaagg ccgcgttgct ggcgtttttc cataggctcc gcccccctga cgagcatcac   6120
aaaaatcgac gctcaagtca gaggtggcga aacccgacag gactataaag ataccaggcg   6180
tttccccctg gaagctccct cgtgcgctct cctgttccga ccctgccgct taccggatac   6240
ctgtccgcct ttctcccttc gggaagcgtg gcgctttctc atagctcacg ctgtaggtat   6300
ctcagttcgg tgtaggtcgt tcgctccaag ctgggctgtg tgcacgaacc ccccgttcag   6360
cccgaccgct gcgccttatc cggtaactat cgtcttgagt ccaacccggt aagacacgac   6420
ttatcgccac tggcagcagc cactggtaac aggattagca gagcgaggta tgtaggcggt   6480
gctacagagt tcttgaagtg gtggcctaac tacggctaca ctagaaggac agtatttggt   6540
atctgcgctc tgctgaagcc agttaccttc ggaaaaagag ttggtagctc ttgatccggc   6600
aaacaaacca ccgctggtag cggtggtttt tttgtttgca agcagcagat tacgcgcaga   6660
aaaaaaggat ctcaagaaga tcctttgatc ttttctactg cagaagcttg ttagacaccc   6720
tgtcatgtat tttatattat ttatttcacc atacggatta agtgaaacct aatgaaaata   6780
gtactttcgg agctttaact ttaatgaagg tatgtttttt tatagacatc gatgtctggt   6840
ttaacaatag gaaaaagtag ctaaaactcc catgaattaa agaaataaca aggtgtctaa   6900
caacctgtta ttaagaatgt tagaaaagac ttaacatttg tgttgagttt ttatagacat   6960
```

-continued tggtgtctag acatacggta gataaggttt gctcaaaaat aaaataaaaa aagattggac 7020
taaaaaacat ttaatttagt acaatttaat tagttatttt ttcgtctcaa attttgcttt 7080
gttgagcaga aatttagata aaaaaatccc cgtgatcaga ttacaatgtc gttcattgta 7140
cgatgtgtcg aaaaatcttt acgacactct aaactgacca cacgggggaa aaagaaaact 7200
gaactaataa catcatgata ctcggaaaac ctagcaattc tcaaccccta aacaaaagaa 7260
acttccaaaa ccctgaccat ataaaggagt ggcaacaatc agcaatcagt caagatttga 7320
tagcagaaaa tcttgtatcg gttgctaatg gttttgatgt actatttatc ggcaataaat 7380
accgaactaa cacgggtgtt ctgtcacggc acatattaaa ctcctattct catttagaag 7440
atggtggttc gtatggtaga acatttgacc catttaccaa taaagaaatg cagtgggttc 7500
aatttaaacc gaatagacca agaaaaggtt ctactggtaa ggtaatcaaa tatgaatcgc 7560
caaaaggtga acctacaaga gttctaatgc cgtttgtgcc tatgaaaata tggcaacgga 7620
ttagcgataa gttcggagta ccgattaatc cgaaaaaaga tactcacttt tgggaatggg 7680
taaagaataa tccatcgata ccgattgcca ttacagaagg aaataaaaaa gctaattgcc 7740
tattatccta tggctatcct gctattgcct ttgtaggcat ttggaacgga ttagagaaaa 7800
taaatgattt ctcgaaggaa aagcagttaa aagaggattt gaaatggttg ttatccaacg 7860
gcaaccgaaa tattaatatc atctttgacc aagaccagaa acaaaaaact gtaattaatg 7920
taaacaaagc tattttcgct ttatcttctc taataagtag aaatggtcat aaagttaata 7980
ttgtgcaatg gttgccgtca aaaggtaaag gaatagatga ttatttggta gctttacctt 8040
ttgagaaaag agaaaatcat ttagacaact taattaaaat tgcaccatca tttaattttt 8100
ggtcaactaa atacttattc aagtgtcgta aaccagattt aaccgtaaat tgccgttatt 8160
tgagcgatgc agtaaaagaa ttacctcaag aggatatagc attaatagca cctcacggca 8220
cgggtaaaac ttcattagta gctactcacg ttaagaatcg gagttatcac ggaaggaaaa 8280
ctatttcatt ggtgcatctt gaaagtttag ccaaagctaa tggcaacgca cttggattat 8340
attaccgaac cgaaaataat attgaaaagc aatatcttgg atttagctta tgtgtagata 8400
gttgccgtga taagattaac ggcattacaa ctgatattat ttcaggtcaa gattattgcc 8460
ttttcattga tgaaattgac caagtaattc cacacatcct taacagtgaa actgaagtaa 8520
gtaagtatag atgcaccatc attgacactt tttctgaact ggtgagaaat gctgaacagg 8580
tcattattgc tgatgctgat ttatccgatg tgacgattga cctaatagaa aacatcagag 8640
gtaaaaaact atatgtaatc aagaatgaat atcagtatca gggaatgact tttaacgccg 8700
ttggttcacc attagaaatg atggcaatga tgggaaaatc ggtgtcagaa ggcaagaaat 8760
tatttattaa caccacatcc caaaaggcaa aaagtaagta cggcacaatc gctcttgagt 8820
cttatatttt tggtctaaat aaagaagcaa agatattaag aatagactct gaaaccacta 8880
aaaaccctga acatccagcc tataaaatca ttgaccaaga cttaaataat atcctcaaag 8940
attatgatta tgtcattgcc tcaccttgcc ttcaaacagg tgtcagtatt accttaaaag 9000
ggcattttga ccagcaattt aacttttcca gtggaaacat tacacctcat tgctttttac 9060
agcaaatgtg gcggttgagg gatgcagaaa ttgaaagatt ctattatgtg ccgaactcat 9120
ctaacctcaa tctcattggg aataagtcaa gttcaccatc agaccttcta aagagcaata 9180
acaagatggc aacggcaacg gttaaccttt tgggtagaat cgactccgaa tattccctag 9240
agtatgaatc gcacggcatt tggcttgaga cgtgggcaaa attatcagca cggcataaca 9300
gttcaatgcg ttgttactct gaaattctta cctatctaat tacgtctcaa gggcataaat 9360

```
taaatatcaa cattccctca cctcttgcag atattaagaa gctaaatgat gaggtaagta   9420
gtaacaggga aaaggtaaaa aatgagagat actctcagag gttaaactca ccagatatta   9480
acgatgcaga agctaccata ctcgaatcta aagagcaaaa aatcggattg actctcaatg   9540
agagatgcac cctagaaaag cataaagtta agaagcggta tgggaatgta aagatggata   9600
ttctcacctt tgatgatgat ggactatacc ccaaactcag actattttat tacctcacca   9660
tcggtaaacc tcatctcaag gctaatgaca gaaaagctat tgccaaaatg ggcaatgaca   9720
ataaaggcaa gattctatca aaagacttag ttaataaaac ttactccgct cgtgtgaagg   9780
tcttagagat tcttaaacta actgacttta tcgacaatct tagagatgaa ctcttaataa   9840
ctcccaataa tccagctatc accgatttta ataatcttct gctaagagct aagaaggatt   9900
taagagtatt aggagtcaac atcggaaaat atccaatggc caacattaat gccgtactta   9960
ctctcattgg tcacaaactt tctgtaatga gagatgagtt cggaaaagag aaaaggataa  10020
aagtagatgg taaatcatac cgatgttatc aacttgaaac attaccagat tttaccaatg  10080
atactcttga ctactggtta gaaaatgata gccaaaaaga agtaacagca acagaaaatt  10140
actccgaaaa ttttaaccct tcaaatagct acaatccaga cagtaagaca ctttcagagg  10200
gtgcaaattt cctatatata aataaagaag aattgcatcc aaataaattg cacctagaaa  10260
taaaagaagg tgctgaactt tttttattcg gggtaaaggt gattgtgaaa ggaatcttgg  10320
acggggcagt aactatattc tctatgggtc aagaatacga tttatccctc aatgaactag  10380
aggggatgtt aacatcatga actttacaag aatcttttta aagggcgatc gcaccatgtt  10440
aaatgatggt acatttgttc agatatttga tatttaccat gaccacgcat tgggagtgac  10500
ccttgacctt aagacagaaa aaattatttc cgatgatgtt agggtaatta ctgtcaaaga  10560
cttattgttc gatggcactt ataaaggggt aaaatctttt atgcccgata atgcccgata  10620
atgcccgatt gatgctacaa aatcccataa tcataagcga taatccccta atagcttgta  10680
attcttgaac cgtagcgatt ttagagtatt ccaaaaagaa gaaataaaca ccgcaaaatg  10740
tcgtatttca catatataaa ccaaggtttt ttgccctaaa atctttatgt ttgtagtgtg  10800
atgttgggtc aaaatggtca gaaaagttgc aaggttttta tggatgctta cgcgcgcgag  10860
gggtaagcat ccccaaatag ttactttatc ctagtccatg cccatttatt gccgtcccgt  10920
tcggctttaa aaaagtgcca aaactcacaa ggtgcaataa aaagttctgt acctttcgca  10980
accctagata atctttcaac agttactttt tttcctatta tctcggtaca aagtttggct  11040
agtttctctt ttccctcttt ttcaatcaag ccttcttgta tgcccaactc attgattaat  11100
ctctctattt ttaccattat ttcccgttca ggtagtttat cccctaaatc ttcatcgggg  11160
ggcaatgtag ggcattctga aggggctttt tcttctgtct ggacattatc taatattgaa  11220
gtaaccaaac tatcttcagt tttttctatt cctattaatt catattcggt tactgtatcc  11280
gtatcaatat ccgaataact atctttatcc gtattagcta ttcggttaag tttatccgtt  11340
aactcagaaa caagactata tagcggtttt agcttttctt ctatcctgtt atctaatacg  11400
gataagttta tacggttatc attatccgta ttagtatcat tgggcttttt tggtagttct  11460
accccctcat aaaccgcttt tattcccaat tccaacagac tgataacagt atcctttata  11520
atgggttttt tgctgatatg gtgaactttt gccccttcca tcattgcgat actttctatc  11580
tcactcatca acttatcgct taagtgaatc tcgtatctgt ttaatccctt actggtttta  11640
ttcatatccg tttactttat tcggttaaca attctatttt atacgaataa aatattatac  11700
```

```
ggttaacttt atacgtttaa ctattttatc tatacggata acagtaataa gttattcgta  11760

ttagttatac gtttactttt atccaaataa aattagtgca tttaaactaa aagaatgatt  11820

ttatcggagt tgatagcatt ggattaacct aaagatgttt ataagctata tctgataagt  11880

atttaaggtt attttgttat tctgtttatt gacattatca gaataaaaga atagaatata  11940

attgttgaga gataagaggt ttaagtgatt atggttaaga agttagttgg ttatgtcagg  12000

gtcagtagtg aatcgcaaga ggataacact agcttacaga atcagataga gagaattgaa  12060

gcatattgta tggcttttgg ttatgagttg gtaaaaaatat tcaaagaggt tgccactggt  12120

acaaaagcag atattgaaac ccgtcctatt tttaatgaag ctatagaata cttgaaacag  12180

gataatgcta atggaattat tgccttgaag ctagaccgaa tcgcacggaa tgctttagat  12240

gtattgcgtt tggttcgtga aaccttagaa ccacaaaata aaatgttagt gttactagat  12300

attcaggtag atacttcgac accttcagga aaaatgattt taactgtaat gagtgccgtt  12360

gctgaactcg aaagagacat gatctatgat cgcactcagg ggggtagaaa gactaaagcc  12420

caaaagggcg ggtatgccta cgggaaacct aaatttggct ataagactga agaaaaggaa  12480

ctaaaagaag attcagcaca acaggaaact attaaactaa ttaagagaca ccgtaggtca  12540

gggaaaagct accagaaaat agctgattat ctcaatgccc aaagtattcc cactaaacaa  12600

ggtaagaaat ggagttctag cgtcgtctat cgaatctgtc aggaaaaagc tggttaagtc  12660

tgtttataga tatttagaat ttattgaata aaaatagtat gaacaataaa tatttatgga  12720

ctaaccacgc tcggaaacgt ttaactgaac gatgggaaat aaaagaatca tgggttattg  12780

ataccatcga aaatcctgaa cgttcagaat ttattgttga tgagtcaggg gaaaaatatc  12840

attactataa aagaatagct aagtttaaga atagagtgtt agaagtgata acttctgcca  12900

actcaacacc cacaagaata ataacctttt actttaaccg taacatgagg aaaaatttat  12960

gattgttact tacgataatg aagttgacgc aatttatttt aagttaacgg aaaataaaat  13020

tgatagcacc gaacctcaaa cagacaggat tatcattgat tacgatgaaa gtaataatat  13080

tgttggcatt gaggtattag attttaatta tcttgtcaag aaaggtttaa ccgttgctga  13140

tttacctttt tctgaagatg aaagattaac agcttctcaa tattttaatt ttcctgttgc  13200

tatctaatcc agaaggggca ataatcccct tctttcatcg agttagactt aatatcacaa  13260

aagtcatttt cattttaccg tttcttttcc acagcgtccg tacgcccctc gttaaatctc  13320

aaaaccgaca atttatgatg tttataaaaa gttactcact ttaataagta tttatactca  13380

ttaaagggtt attctttttt tgtagcctga taggttggga aggaatattt cagattatca  13440

gatttgttg                                                          13449
```

<210> SEQ ID NO 11
<211> LENGTH: 13033
<212> TYPE: DNA
<213> ORGANISM: Artificial Sequence
<220> FEATURE:
<223> OTHER INFORMATION: TK295\pABICyano1-6.8_PnirAABICyano1-PDCmax-PpsbAABICyano1-synADHmax-PrbcABICyano1-Km**-oriVT

<400> SEQUENCE: 11

```
aatatttttc gtcagatacg caaaccttac aaacataatt aacaactgaa actattgata     60

tgtctaggtt ttagctctat cacaggttgg atctgtcgac aattaataac ttcttcctgt    120

acgggcgaat ggccatttgc tcctaactaa ctccgtactg ctttgcggaa cgagcgtagc    180

gaactctccg aattactaag ccttcatccc tgatagatgc aaaaaacgaa ttaaaattat    240
```

-continued

```
gtgtaaaaag aaaatgtgtc tttatttagt agtcaaagtt acaaaatatt aagaatcaaa    300
ttaataatgt attgggcagt taagtatata agtctttaaa tatttatttg tattcaatat    360
attaaccgag gacaaattat gaattcttat accgtgggta cttatttagc cgaacgctta    420
gtgcaaattg gtttaaaaca tcattttgcc gtggctgggg actataattt agtgttattg    480
gataacttat tattaaataa aaacatggaa caagtgtatt gttgtaatga attaaattgt    540
ggtttttctg ctgaaggtta tgctagagct aaaggtgcag ctgctgctgt tgttacttat    600
tctgtgggtg ctttatctgc ttttgatgct attggtggtg cttatgccga aaatttaccc    660
gtgattttaa tttctggtgc ccctaataat aatgatcatg ccgctggaca tgttttacat    720
catgccttag gtaaaaccga ttatcattat caattagaaa tggccaaaaa tattactgct    780
gctgccgaag ctatttatac tcctgaagaa gcccctgcca aattgatca tgtgattaaa    840
accgccttac gcgaaaaaaa acccgtgtat ttagaaattg cctgtaatat tgcttctatg    900
ccttgtgctg ctcctgggcc tgcttctgct ttatttaatg atgaagcctc tgatgaagct    960
agtttaaatg ctgccgtgga agaaacctta aaatttattg ccaatcgcga taaagttgcc   1020
gtgttagttg gttctaaatt aagagctgct ggtgctgaag aagctgctgt taaatttgct   1080
gatgctttag gtggtgcagt tgctactatg gctgctgcca aatctttttt tcccgaagaa   1140
aatccccatt atattggaac tagttgggga gaagtttctt atcctggtgt ggaaaaaact   1200
atgaaagaag ccgacgctgt tattgcttta gcccctgtgt ttaatgatta ttctaccact   1260
ggttggactg atattcccga tcccaaaaaa ttagttttag ccgaacctcg ttctgttgtt   1320
gttaatggtg ttcgctttcc ctctgtgcat ttaaaagatt atttaacccg cttagcccaa   1380
aaagtttcta aaaaaactgg tgccttagat ttttttaaat ctttaaatgc gggtgaatta   1440
aaaaaagctg ctcctgctga tccttctgct cctttagtta atgctgaaat tgcccgtcaa   1500
gttgaagcct tattaacccc taatactacc gttattgccg aaactggtga ttcttggttt   1560
aatgcccaac gcatgaaatt acctaatggt gcccgtgttg aatatgaaat gcaatggggt   1620
catattggtt ggtctgtacc tgctgctttt ggttatgctg ttggtgctcc tgaacgtcgt   1680
aatattttaa tggtgggtga tggttctttt caattaactg cccaagaagt tgcccaaatg   1740
gttcgcttaa aattacccgt tattattttt ttaataaata attatggtta taccattgaa   1800
gtgatgattc atgatgggcc atataataat attaaaaatt gggattatgc gggtttaatg   1860
gaagtgttta atggtaatgg tggttatgat tctggtgctg gtaaaggttt aaaagccaaa   1920
actggtggtg aattagctga agctattaaa gttgccttag ccaatactga tgggccaacc   1980
ttaattgaat gttttattgg tcgcgaagat tgtaccgaag aattagttaa atggggtaaa   2040
cgtgttgctg ctgctaattc tcgcaaaccc gtgaataaat tattgtaatt tttggggatc   2100
aattcgagct cgccttacta taaacaaaag ttatctgaga aataactata actattctga   2160
aaatatttga caaaacttta caattttgtt atattagtaa gtgaggtgag caaatcaccc   2220
aaaatatata agtacctcga aaaattcata actgaaatca taagcatatg attaaagcct   2280
atgctgcctt agaagccaat ggtaaattac aaccctttga atatgatcct ggtgctttag   2340
gtgccaatga agtggaaatt gaagtgcaat attgtggtgt gtgtcattct gatttatcta   2400
tgattaataa tgaatggggt atttctaatt atcccttagt tcctggtcat gaagttgttg   2460
gtactgttgc tgctatgggt gaaggtgtta atcatgtgga agtgggtgat ttagttggtt   2520
taggttggca ttctggttat tgtatgacct gtcattcttg tttatctggt tatcataatt   2580
tatgtgccac tgccgaatct actattgtgg gtcattatgg tggttttggt gatagagttc   2640
```

```
gtgctaaagg tgtttctgtg gtgaaattac ccaaaggtat tgatttagcc tctgctgggc   2700
ctttattttg tggtggtatt accgtttttt ctcccatggt ggaattatct ttaaaaccta   2760
ccgccaaagt tgctgttatt ggtattggtg gtttaggtca tttagccgtt caatttttaa   2820
gagcctgggg ttgtgaagtt actgctttta cctcttctgc ccgtaaacaa accgaagttt   2880
tagaattagg tgcccatcat attttagatt ctaccaatcc tgaagctatt gcttctgccg   2940
aaggtaaatt tgattatatt atttctaccg tgaatttaaa attagattgg aatttatata   3000
tcagtacctt agcccctcaa ggtcattttc attttgttgg tgtggtgtta gaacccttgg   3060
acttaaactt atttccctta ttaatgggac aacgttctgt ttctgcttct cctgttggtt   3120
ctcctgctac tattgccact atgttagatt ttgccgtgcg tcatgatatt aaacccgtgg   3180
tggaacaatt ttcttttgat caaattaatg aagccattgc ccatttagaa tctggtaaag   3240
cccattatcg cgtggtgtta tctcattcta aaaattaata agattaactt ctaaactgaa   3300
acaaatttga gggtaggctt cattgtctgc ccttattttt ttatttagga aaagtgaaca   3360
gactaaagag tgttggctct attgctttga gtatgtaaat taggcgttgc tgaattaagg   3420
tatgattttt gaccccttct ctcttctgca gttacctagg atttctggcg aaagggggat   3480
gtgctgcaag gcgattaagt tgggtaacgc cagggttttc ccagtcacga cgttgtaaaa   3540
cgacggccag tgagcgcgac gtaatacgac tcactatagg gcgaattggc ggaaggccgt   3600
caaggccgca tggcgcgcct acgtagacaa ttgtcgatgt aattattaac tatcttatta   3660
tagatgaggg gagagggaga aattagttcg gagagaacgc tcgagcgctc gttccgcaaa   3720
gcggtacgga gttagttagg ggctaatggg cattctcccg tacaggaaag agttagaagt   3780
tattaattat caacaattct cctttgccta gtgcatcgtt accttttttaa ttaaaacata   3840
aggaaaacta ataatcgtaa taatttaacc tcaaagtgta aagaaatgtg aaattctgac   3900
ttttataacg ttaaagaggg aaaaattagc agtttaaaat acctagagaa tagtctgggg   3960
taagcataga gaattagatt agttaagtta atcaaattca gaaaaaataa taatcgtaaa   4020
tagttaatct gggtgtatag aaaatgatcc ccttcatgat aagatttaaa ctcgaaaagc   4080
aaaagccaaa aaactaactt ccattaaaag aagttgttac atataacgct ataaagaaaa   4140
tttatatatt tggaggatac caaccatgtc tcatattcaa cgtgaaacta gttgttctcg   4200
tcctcgttta aattctaata tggatgccga tttatatggt tataaatggg ctcgtgataa   4260
tgttggtcaa tctggtgcta ctatttatcg tttatatggt aaacctgatg ctcctgaatt   4320
attcttgaaa catggtaaag gttctgttgc taatgatgtt actgatgaaa tggttcgttt   4380
aaactggttg actgaattta tgcctttacc tactattaaa cattttattc gtactcccga   4440
tgatgcttgg ttattaacta ctgctattcc tggtaaaact gcttttcaag ttttagaaga   4500
atatcctgat tctggtgaaa atattgttga tgctttagct gttttttttac gtcgtttaca   4560
ttctattccc gtttgtaatt gtccttttaa ttctgatcgt gtttttcgtt tagctcaagc   4620
tcaatctcgt atgaataatg gtttagttga tgcttctgat tttgatgatg aacgtaatgg   4680
ttggcctgtt gaacaagttt ggaaagaaat gcacaaattg ttacctttttt ctcctgattc   4740
tgttgttact catggtgatt tttctttaga taatttgatc tttgatgaag gtaaattgat   4800
tggttgtatt gatgttggtc gtgttggtat tgctgatcgt tatcaagatt tagctatttt   4860
atggaattgt ttaggtgaat tttctccttc tttacagaaa cgtttatttc agaaatatgg   4920
tattgataat cctgatatga acaagttaca atttcattta atgttggacg agttctttta   4980
```

-continued

```
agaattaatt catgaccaaa atcccttaac gtgagttttc gttccactga gcgtcagacc   5040
ccgtagaaaa gatcaaagga tcttcttgag atcctttttt tctgcgcgta atctgctgct   5100
atttaaatta cgtacacgtg ttattacttt gttaacgaca attgtcttaa ttaactgggc   5160
ctcatgggcc ttccgctcac tgcccgcttt ccagtcggga aacctgtcgt gccagctctg   5220
cagatgacgg tgaaaacctc tgacacatgc agctcccgga gacggtcaca gcttgtctgt   5280
aagcggatgc cgggagcaga caagcccgtc agggcgcgtc agcgggtgtt ggcgggtgtc   5340
ggggcgcagc catgacccag tcacgtagcg atagcggagt gtatactggc ttaactatgc   5400
ggcatcagag cagattgtac tgagagtgca ccatatgcgg tgtgaaatac cgcacagatg   5460
cgtaaggaga aaataccgca tcaggcgctc ttccgcttcc tcgctcactg actcgctgcg   5520
ctcggtcgtt cggctgcggc gagcggtatc agctcactca aaggcggtaa tacggttatc   5580
cacagaatca ggggataacg caggaaagaa catgtgagca aaaggccagc aaaaggccag   5640
gaaccgtaaa aaggccgcgt tgctggcgtt tttccatagg ctccgccccc ctgacgagca   5700
tcacaaaaat cgacgctcaa gtcagaggtg gcgaaacccg acaggactat aaagatacca   5760
ggcgtttccc cctggaagct ccctcgtgcg ctctcctgtt ccgaccctgc cgcttaccgg   5820
atacctgtcc gcctttctcc cttcgggaag cgtggcgctt tctcatagct cacgctgtag   5880
gtatctcagt tcggtgtagg tcgttcgctc caagctgggc tgtgtgcacg aaccccccgt   5940
tcagcccgac cgctgcgcct tatccggtaa ctatcgtctt gagtccaacc cggtaagaca   6000
cgacttatcg ccactggcag cagccactgg taacaggatt agcagagcga ggtatgtagg   6060
cggtgctaca gagttcttga agtggtggcc taactacggc tacactagaa ggacagtatt   6120
tggtatctgc gctctgctga agccagttac cttcggaaaa agagttggta gctcttgatc   6180
cggcaaacaa accaccgctg gtagcggtgg tttttttgtt tgcaagcagc agattacgcg   6240
cagaaaaaaa ggatctcaag aagatccttt gatcttttct actgcagaag cttgttagac   6300
accctgtcat gtattttata ttatttattt caccatacgg attaagtgaa acctaatgaa   6360
aatagtactt tcggagcttt aactttaatg aaggtatgtt tttttataga catcgatgtc   6420
tggtttaaca ataggaaaaa gtagctaaaa ctcccatgaa ttaaagaaat aacaaggtgt   6480
ctaacaacct gttattaaga atgttagaaa agacttaaca tttgtgttga gtttttatag   6540
acattggtgt ctagacatac ggtagataag gtttgctcaa aataaaaata aaaaaagatt   6600
ggactaaaaa acatttaatt tagtacaatt taattagtta ttttttcgtc tcaaattttg   6660
ctttgttgag cagaaattta gataaaaaaa tccccgtgat cagattacaa tgtcgttcat   6720
tgtacgatgt gtcgaaaaat ctttacgaca ctctaaactg accacacggg ggaaaaagaa   6780
aactgaacta ataacatcat gatactcgga aaacctagca attctcaacc cctaaacaaa   6840
agaaacttcc aaaaccctga ccatataaag gagtggcaac aatcagcaat cagtcaagat   6900
ttgatagcag aaaatcttgt atcggttgct aatggttttg atgtactatt tatcggcaat   6960
aaataccgaa ctaacacggg tgttctgtca cggcacatat taaactccta ttctcattta   7020
gaagatggtg gttcgtatgg tagaacattt gacccattta ccaataaaga aatgcagtgg   7080
gttcaattta aaccgaatag accaagaaaa ggttctactg gtaaggtaat caaatatgaa   7140
tcgccaaaag gtgaacctac aagagttcta atgccgtttg tgcctatgaa aatatggcaa   7200
cggattagcg ataagttcgg agtaccgatt aatccgaaaa aagatactca cttttgggaa   7260
tgggtaaaga ataatccatc gataccgatt gccattacag aaggaaataa aaaagctaat   7320
tgcctattat cctatggcta tcctgctatt gcctttgtag gcatttggaa cggattagag   7380
```

aaaataaatg atttctcgaa ggaaaagcag ttaaaagagg atttgaaatg gttgttatcc 7440
aacggcaacc gaaatattaa tatcatcttt gaccaagacc agaaacaaaa aactgtaatt 7500
aatgtaaaca aagctatttt cgctttatct tctctaataa gtagaaatgg tcataaagtt 7560
aatattgtgc aatggttgcc gtcaaaaggt aaaggaatag atgattattt ggtagcttta 7620
ccttttgaga aaagagaaaa tcatttagac aacttaatta aaattgcacc atcatttaat 7680
ttttggtcaa ctaaatactt attcaagtgt cgtaaaccag atttaaccgt aaattgccgt 7740
tatttgagcg atgcagtaaa agaattacct caagaggata tagcattaat agcacctcac 7800
ggcacgggta aaacttcatt agtagctact cacgttaaga atcggagtta tcacggaagg 7860
aaaactattt cattggtgca tcttgaaagt ttagccaaag ctaatggcaa cgcacttgga 7920
ttatattacc gaaccgaaaa taatattgaa aagcaatatc ttggatttag cttatgtgta 7980
gatagttgcc gtgataagat taacggcatt acaactgata ttatttcagg tcaagattat 8040
tgccttttca ttgatgaaat tgaccaagta attccacaca tccttaacag tgaaactgaa 8100
gtaagtaagt atagatgcac catcattgac actttttctg aactggtgag aaatgctgaa 8160
caggtcatta ttgctgatgc tgatttatcc gatgtgacga ttgacctaat agaaaacatc 8220
agaggtaaaa aactatatgt aatcaagaat gaatatcagt atcagggaat gacttttaac 8280
gccgttggtt caccattaga aatgatggca atgatgggaa aatcggtgtc agaaggcaag 8340
aaattattta ttaacaccac atcccaaaag gcaaaaagta agtacggcac aatcgctctt 8400
gagtcttata tttttggtct aaataaagaa gcaaagatat taagaataga ctctgaaacc 8460
actaaaaacc ctgaacatcc agcctataaa atcattgacc aagacttaaa taatatcctc 8520
aaagattatg attatgtcat tgcctcacct tgccttcaaa caggtgtcag tattacctta 8580
aaagggcatt ttgaccagca atttaacttt tccagtggaa acattacacc tcattgcttt 8640
ttacagcaaa tgtggcggtt gagggatgca gaaattgaaa gattctatta tgtgccgaac 8700
tcatctaacc tcaatctcat tgggaataag tcaagttcac catcagacct tctaaagagc 8760
aataacaaga tggcaacggc aacggttaac cttttgggta gaatcgactc cgaatattcc 8820
ctagagtatg aatcgcacgg catttggctt gagacgtggg caaaattatc agcacggcat 8880
aacagttcaa tgcgttgtta ctctgaaatt cttacctatc taattacgtc tcaagggcat 8940
aaattaaata tcaacattcc ctcacctctt gcagatatta agaagctaaa tgatgaggta 9000
agtagtaaca gggaaaaggt aaaaaatgag agatactctc agaggttaaa ctcaccagat 9060
attaacgatg cagaagctac catactcgaa tctaaagagc aaaaaatcgg attgactctc 9120
aatgagagat gcaccctaga aaagcataaa gttaagaagc ggtatgggaa tgtaaagatg 9180
gatattctca cctttgatga tgatggacta taccccaaac tcagactatt ttattacctc 9240
accatcggta aacctcatct caaggctaat gacagaaaag ctattgccaa aatgggcaat 9300
gacaataaag gcaagattct atcaaaagac ttagttaata aaacttactc cgctcgtgtg 9360
aaggtcttag agattcttaa actaactgac tttatcgaca atcttagaga tgaactctta 9420
ataactccca ataatccagc tatcaccgat tttaataatc ttctgctaag agctaagaag 9480
gatttaagag tattaggagt caacatcgga aaatatccaa tggccaacat taatgccgta 9540
cttactctca ttggtcacaa actttctgta atgagagatg agttcggaaa agagaaaagg 9600
ataaaagtag atggtaaatc ataccgatgt tatcaacttg aaacattacc agattttacc 9660
aatgatactc ttgactactg gttagaaaat gatagccaaa aagaagtaac agcaacagaa 9720

-continued

```
aattactccg aaaattttaa cccttcaaat agctacaatc cagacagtaa gacactttca   9780
gagggtgcaa atttcctata tataaataaa gaagaattgc atccaaataa attgcaccta   9840
gaaataaaag aaggtgctga acttttttta ttcggggtaa aggtgattgt gaaaggaatc   9900
ttggacgggg cagtaactat attctctatg ggtcaagaat acgatttatc cctcaatgaa   9960
ctagagggga tgttaacatc atgaacttta caagaatctt tttaaagggc gatcgcacca  10020
tgttaaatga tggtacattt gttcagatat ttgatattta ccatgaccac gcattgggag  10080
tgacccttga ccttaagaca gaaaaaatta tttccgatga tgttagggta attactgtca  10140
aagacttatt gttcgatggc acttataaag ggtaaaatc ttttatgccc gataatgccc  10200
gataatgccc gattgatgct acaaaatccc ataatcataa gcgataatcc cctaatagct  10260
tgtaattctt gaaccgtagc gattttagag tattccaaaa agaagaaata aacaccgcaa  10320
aatgtcgtat ttcacatata taaaccaagg ttttttgccc taaaatcttt atgtttgtag  10380
tgtgatgttg ggtcaaaatg gtcagaaaag ttgcaaggtt tttatggatg cttacgcgcg  10440
cgaggggtaa gcatccccaa atagttactt tatcctagtc catgcccatt tattgccgtc  10500
ccgttcggct ttaaaaaagt gccaaaactc acaaggtgca ataaaaagtt ctgtaccttt  10560
cgcaacccta gataatcttt caacagttac tttttttcct attatctcgg tacaaagttt  10620
ggctagtttc tcttttccct ctttttcaat caagccttct tgtatgccca actcattgat  10680
taatctctct atttttacca ttatttcccg ttcaggtagt ttatccccta aatcttcatc  10740
ggggggcaat gtagggcatt ctgaaggggc tttttcttct gtctggacat tatctaatat  10800
tgaagtaacc aaactatctt cagtttttttc tattcctatt aattcatatt cggttactgt  10860
atccgtatca atatccgaat aactatcttt atccgtatta gctattcggt taagtttatc  10920
cgttaactca gaaacaagac tatatagcgg ttttagcttt tcttctatcc tgttatctaa  10980
tacggataag tttatacggt tatcattatc cgtattagta tcattgggct tttttggtag  11040
ttctaccccc tcataaaccg cttttattcc caattccaac agactgataa cagtatcctt  11100
tataatgggt tttttgctga tatggtgaac ttttgcccct tccatcattg cgatactttc  11160
tatctcactc atcaacttat cgcttaagtg aatctcgtat ctgtttaatc ccttactggt  11220
tttattcata tccgtttact ttattcggtt aacaattcta ttttatacga ataaaatatt  11280
atacggttaa ctttatacgt ttaactattt tatctatacg gataacagta ataagttatt  11340
cgtattagtt atacgtttac ttttatccaa ataaaattag tgcatttaaa ctaaaagaat  11400
gattttatcg gagttgatag cattggatta acctaaagat gtttataagc tatatctgat  11460
aagtatttaa ggttattttg ttattctgtt tattgacatt atcagaataa aagaatagaa  11520
tataattgtt gagagataag aggtttaagt gattatggtt aagaagttag ttggttatgt  11580
cagggtcagt agtgaatcgc aagaggataa cactagctta cagaatcaga tagagagaat  11640
tgaagcatat tgtatggctt ttggttatga gttggtaaaa atattcaaag aggttgccac  11700
tggtacaaaa gcagatattg aaacccgtcc tatttttaat gaagctatag aatacttgaa  11760
acaggataat gctaatggaa ttattgcctt gaagctagac cgaatcgcac ggaatgcttt  11820
agatgtattg cgtttggttc gtgaaacctt agaaccacaa aataaaatgt tagtgttact  11880
agatattcag gtagatactt cgacaccttc aggaaaaatg attttaactg taatgagtgc  11940
cgttgctgaa ctcgaaagag acatgatcta tgatcgcact caggggggta gaaagactaa  12000
agcccaaaag ggcgggtatg cctacgggaa acctaaattt ggctataaga ctgaagaaaa  12060
ggaactaaaa gaagattcag cacaacagga aactattaaa ctaattaaga gacaccgtag  12120
```

```
gtcagggaaa agctaccaga aaatagctga ttatctcaat gcccaaagta ttcccactaa  12180

acaaggtaag aaatggagtt ctagcgtcgt ctatcgaatc tgtcaggaaa aagctggtta  12240

agtctgttta tagatattta gaatttattg aataaaaata gtatgaacaa taaatattta  12300

tggactaacc acgctcggaa acgtttaact gaacgatggg aaataaaaga atcatgggtt  12360

attgatacca tcgaaaatcc tgaacgttca gaatttattg ttgatgagtc aggggaaaaa  12420

tatcattact ataaaagaat agctaagttt aagaatagag tgttagaagt gataacttct  12480

gccaactcaa cacccacaag aataataacc ttttacttta accgtaacat gaggaaaaat  12540

ttatgattgt tacttacgat aatgaagttg acgcaattta ttttaagtta acggaaaata  12600

aaattgatag caccgaacct caaacagaca ggattatcat tgattacgat gaaagtaata  12660

atattgttgg cattgaggta ttagatttta attatcttgt caagaaaggt ttaaccgttg  12720

ctgatttacc tttttctgaa gatgaaagat taacagcttc tcaatatttt aattttcctg  12780

ttgctatcta atccagaagg ggcaataatc cccttctttc atcgagttag acttaatatc  12840

acaaaagtca ttttcatttt accgtttctt ttccacagcg tccgtacgcc cctcgttaaa  12900

tctcaaaacc gacaatttat gatgtttata aaaagttact cactttaata agtatttata  12960

ctcattaaag ggttattctt tttttgtagc ctgataggtt gggaaggaat atttcagatt  13020

atcagatttg ttg                                                     13033
```

<210> SEQ ID NO 12
<211> LENGTH: 13081
<212> TYPE: DNA
<213> ORGANISM: Artificial Sequence
<220> FEATURE:
<223> OTHER INFORMATION: TK229\pABICyano1-6.8_PpetEABICyano1-PDCmax-synADHmax-PrbcABICyano1-Km**-oriVT

<400> SEQUENCE: 12

```
aatatttttc gtcagatacg caaaccttac aaacataatt aacaactgaa actattgata     60

tgtctaggtt ttagctctat cacaggttgg atctgtcgac gagaagggga acagggaaaa    120

gtatttataa ttgatacaaa ctgtggttca acttatttta aagacatttt tctccattta    180

atgattattt cggggaaaat tttgaggatt tttgattctt aaattgacga tattttgtca    240

ctaacacaac gtgagcggta aatttatata tagacctaaa acctttacta taagtgttat    300

atatttaaat cgctaagtat atagttaaag tgtagccaat aattaacttt taacaagtga    360

ttaccgttaa gtcccttaat ttatcactac aagctaaaac aaatttttca attagatatg    420

acattaggtc aaagttcata gtatgatagt aaaaaataaa atttgacgat ctgtaaaaat    480

aaaaaaacac aatgaattct tataccgtgg gtacttattt agccgaacgc ttagtgcaaa    540

ttggtttaaa acatcatttt gccgtggctg gggactataa tttagtgtta ttggataact    600

tattattaaa taaaaacatg gaacaagtgt attgttgtaa tgaattaaat tgtggttttt    660

ctgctgaagg ttatgctaga gctaaaggtg cagctgctgc tgttgttact tattctgtgg    720

gtgctttatc tgcttttgat gctattggtg gtgcttatgc cgaaaattta cccgtgattt    780

taatttctgg tgcccctaat aataatgatc atgccgctgg acatgtttta catcatgcct    840

taggtaaaac cgattatcat tatcaattag aaatggccaa aaatattact gctgctgccg    900

aagctattta tactcctgaa gaagcccctg ccaaaattga tcatgtgatt aaaaccgcct    960

tacgcgaaaa aaaacccgtg tatttagaaa ttgcctgtaa tattgcttct atgccttgtg   1020

ctgctcctgg gcctgcttct gctttattta atgatgaagc ctctgatgaa gctagtttaa   1080
```

atgctgccgt ggaagaaacc ttaaaattta ttgccaatcg cgataaagtt gccgtgttag 1140
ttggttctaa attaagagct gctggtgctg aagaagctgc tgttaaattt gctgatgctt 1200
taggtggtgc agttgctact atggctgctg ccaaatcttt ttttcccgaa gaaaatcccc 1260
attatattgg aactagttgg ggagaagttt cttatcctgg tgtggaaaaa actatgaaag 1320
aagccgacgc tgttattgct ttagcccctg tgtttaatga ttattctacc actggttgga 1380
ctgatattcc cgatcccaaa aaattagttt tagccgaacc tcgttctgtt gttgttaatg 1440
gtgttcgctt tccctctgtg catttaaaag attatttaac ccgcttagcc caaaaagttt 1500
ctaaaaaaac tggtgcctta gatttttta aatctttaaa tgcgggtgaa ttaaaaaaag 1560
ctgctcctgc tgatccttct gctcctttag ttaatgctga aattgcccgt caagttgaag 1620
ccttattaac ccctaatact accgttattg ccgaaactgg tgattcttgg tttaatgccc 1680
aacgcatgaa attacctaat ggtgcccgtg ttgaatatga aatgcaatgg ggtcatattg 1740
gttggtctgt acctgctgct tttggttatg ctgttggtgc tcctgaacgt cgtaatattt 1800
taatggtggg tgatggttct tttcaattaa ctgcccaaga agttgcccaa atggttcgct 1860
taaaattacc cgttattatt tttttaataa ataattatgg ttataccatt gaagtgatga 1920
ttcatgatgg gccatataat aatattaaaa attgggatta tgcgggttta atggaagtgt 1980
ttaatggtaa tggtggttat gattctggtg ctggtaaagg tttaaaagcc aaaactggtg 2040
gtgaattagc tgaagctatt aaagttgcct tagccaatac tgatgggcca accttaattg 2100
aatgttttat tggtcgcgaa gattgtaccg aagaattagt taaatggggt aaacgtgttg 2160
ctgctgctaa ttctcgcaaa cccgtgaata aattattgta atttttgggg atcaattcga 2220
gctcggtacc caaactagta tgtagggtga ggttatagct agcgctttta attaatccgc 2280
ggatttgtat tcaatatatt aaccgaggac aacatatgat taaagcctat gctgccttag 2340
aagccaatgg taaattacaa ccctttgaat atgatcctgg tgctttaggt gccaatgaag 2400
tggaaattga agtgcaatat tgtggtgtgt gtcattctga tttatctatg attaataatg 2460
aatggggtat ttctaattat cccttagttc ctggtcatga agttgttggt actgttgctg 2520
ctatgggtga aggtgttaat catgtggaag tgggtgattt agttggttta ggttggcatt 2580
ctggttattg tatgacctgt cattcttgtt tatctggtta tcataattta tgtgccactg 2640
ccgaatctac tattgtgggt cattatggtg gttttggtga tagagttcgt gctaaaggtg 2700
tttctgtggt gaaattaccc aaaggtattg atttagcctc tgctgggcct ttattttgtg 2760
gtggtattac cgtttttttct cccatggtgg aattatcttt aaaacctacc gccaaagttg 2820
ctgttattgg tattggtggt ttaggtcatt tagccgttca atttttaaga gcctggggtt 2880
gtgaagttac tgcttttacc tcttctgccc gtaaacaaac cgaagtttta gaattaggtg 2940
cccatcatat tttagattct accaatcctg aagctattgc ttctgccgaa ggtaaatttg 3000
attatattat ttctaccgtg aatttaaaat tagattggaa tttatatatc agtaccttag 3060
cccctcaagg tcattttcat tttgttggtg tggtgttaga acccttggac ttaaacttat 3120
ttcccttatt aatgggacaa cgttctgttt ctgcttctcc tgttggttct cctgctacta 3180
ttgccactat gttagatttt gccgtgcgtc atgatattaa acccgtggtg gaacaatttt 3240
cttttgatca aattaatgaa gccattgccc atttagaatc tggtaaagcc cattatcgcg 3300
tggtgttatc tcattctaaa aattaataag attaacttct aaactgaaac aaatttgagg 3360
gtaggcttca ttgtctgccc ttattttttt atttaggaaa agtgaacaga ctaaagagtg 3420

-continued

```
ttggctctat tgctttgagt atgtaaatta ggcgttgctg aattaaggta tgatttttga   3480
ccccttctct cttctgcagt tacctaggat ttctggcgaa agggggatgt gctgcaaggc   3540
gattaagttg ggtaacgcca gggttttccc agtcacgacg ttgtaaaacg acggccagtg   3600
agcgcgacgt aatacgactc actatagggc gaattggcgg aaggccgtca aggccgcatg   3660
gcgcgcctac gtagacaatt gtcgatgtaa ttattaacta tcttattata gatgagggga   3720
gagggagaaa ttagttcgga gagaacgctc gagcgctcgt tccgcaaagc ggtacggagt   3780
tagttagggg ctaatgggca ttctcccgta caggaaagag ttagaagtta ttaattatca   3840
acaattctcc tttgcctagt gcatcgttac ctttttaatt aaaacataag gaaaactaat   3900
aatcgtaata atttaacctc aaagtgtaaa gaaatgtgaa attctgactt ttataacgtt   3960
aaagagggaa aaattagcag tttaaaatac ctagagaata gtctggggta agcatagaga   4020
attagattag ttaagttaat caaattcaga aaaaataata atcgtaaata gttaatctgg   4080
gtgtatagaa aatgatcccc ttcatgataa gatttaaact cgaaaagcaa aagccaaaaa   4140
actaacttcc attaaaagaa gttgttacat ataacgctat aaagaaaatt tatatatttg   4200
gaggatacca accatgtctc atattcaacg tgaaactagt tgttctcgtc ctcgtttaaa   4260
ttctaatatg gatgccgatt tatatggtta taaatgggct cgtgataatg ttggtcaatc   4320
tggtgctact atttatcgtt tatatggtaa acctgatgct cctgaattat tcttgaaaca   4380
tggtaaaggt tctgttgcta atgatgttac tgatgaaatg gttcgtttaa actggttgac   4440
tgaatttatg cctttaccta ctattaaaca ttttattcgt actcccgatg atgcttggtt   4500
attaactact gctattcctg gtaaaactgc ttttcaagtt ttagaagaat atcctgattc   4560
tggtgaaaat attgttgatg ctttagctgt ttttttacgt cgtttacatt ctattcccgt   4620
ttgtaattgt ccttttaatt ctgatcgtgt tttcgtttta gctcaagctc aatctcgtat   4680
gaataatggt ttagttgatg cttctgattt tgatgatgaa cgtaatggtt ggcctgttga   4740
acaagtttgg aaagaaatgc acaaattgtt accttttttct cctgattctg ttgttactca   4800
tggtgatttt tctttagata atttgatctt tgatgaaggt aaattgattg gttgtattga   4860
tgttggtcgt gttggtattg ctgatcgtta tcaagattta gctattttat ggaattgttt   4920
aggtgaattt tctccttctt tacagaaacg tttatttcag aaatatggta ttgataatcc   4980
tgatatgaac aagttacaat ttcatttaat gttggacgag ttcttttaag aattaattca   5040
tgaccaaaat cccttaacgt gagttttcgt tccactgagc gtcagacccc gtagaaaaga   5100
tcaaaggatc ttcttgagat cctttttttc tgcgcgtaat ctgctgctat ttaaattacg   5160
tacacgtgtt attactttgt taacgacaat tgtcttaatt aactgggcct catgggcctt   5220
ccgctcactg cccgctttcc agtcgggaaa cctgtcgtgc cagctctgca gatgacggtg   5280
aaaacctctg acacatgcag ctcccggaga cggtcacagc ttgtctgtaa gcggatgccg   5340
ggagcagaca agcccgtcag ggcgcgtcag cgggtgttgg cgggtgtcgg ggcgcagcca   5400
tgacccagtc acgtagcgat agcggagtgt atactggctt aactatgcgg catcagagca   5460
gattgtactg agagtgcacc atatgcggtg tgaaataccg cacagatgcg taaggagaaa   5520
ataccgcatc aggcgctctt ccgcttcctc gctcactgac tcgctgcgct cggtcgttcg   5580
gctgcggcga gcggtatcag ctcactcaaa ggcggtaata cggttatcca cagaatcagg   5640
ggataacgca ggaaagaaca tgtgagcaaa aggccagcaa aaggccagga accgtaaaaa   5700
ggccgcgttg ctggcgtttt tccataggct ccgccccccct gacgagcatc acaaaaatcg   5760
acgctcaagt cagaggtggc gaaacccgac aggactataa agataccagg cgtttccccc   5820
```

-continued

```
tggaagctcc ctcgtgcgct ctcctgttcc gaccctgccg cttaccggat acctgtccgc   5880
ctttctccct tcgggaagcg tggcgctttc tcatagctca cgctgtaggt atctcagttc   5940
ggtgtaggtc gttcgctcca agctgggctg tgtgcacgaa ccccccgttc agcccgaccg   6000
ctgcgcctta tccggtaact atcgtcttga gtccaacccg gtaagacacg acttatcgcc   6060
actggcagca gccactggta acaggattag cagagcgagg tatgtaggcg gtgctacaga   6120
gttcttgaag tggtggccta actacggcta cactagaagg acagtatttg gtatctgcgc   6180
tctgctgaag ccagttacct tcggaaaaag agttggtagc tcttgatccg gcaaacaaac   6240
caccgctggt agcggtggtt tttttgtttg caagcagcag attacgcgca gaaaaaaagg   6300
atctcaagaa gatcctttga tcttttctac tgcagaagct tgttagacac cctgtcatgt   6360
attttatatt atttatttca ccatacggat taagtgaaac ctaatgaaaa tagtactttc   6420
ggagctttaa ctttaatgaa ggtatgtttt tttatagaca tcgatgtctg gtttaacaat   6480
aggaaaaagt agctaaaact cccatgaatt aaagaaataa caaggtgtct aacaacctgt   6540
tattaagaat gttagaaaag acttaacatt tgtgttgagt ttttatagac attggtgtct   6600
agacatacgg tagataaggt ttgctcaaaa ataaaataaa aaaagattgg actaaaaaac   6660
atttaattta gtacaattta attagttatt ttttcgtctc aaattttgct ttgttgagca   6720
gaaatttaga taaaaaaatc cccgtgatca gattacaatg tcgttcattg tacgatgtgt   6780
cgaaaaatct ttacgacact ctaaactgac cacacggggg aaaaagaaaa ctgaactaat   6840
aacatcatga tactcggaaa acctagcaat tctcaacccc taaacaaaag aaacttccaa   6900
aaccctgacc atataaagga gtggcaacaa tcagcaatca gtcaagattt gatagcagaa   6960
aatcttgtat cggttgctaa tggttttgat gtactattta tcggcaataa ataccgaact   7020
aacacgggtg ttctgtcacg gcacatatta aactcctatt ctcatttaga agatggtggt   7080
tcgtatggta gaacatttga cccatttacc aataaagaaa tgcagtgggt tcaatttaaa   7140
ccgaatagac caagaaaagg ttctactggt aaggtaatca aatatgaatc gccaaaaggt   7200
gaacctacaa gagttctaat gccgtttgtg cctatgaaaa tatggcaacg gattagcgat   7260
aagttcggag taccgattaa tccgaaaaaa gatactcact tttgggaatg ggtaaagaat   7320
aatccatcga taccgattgc cattacagaa ggaaataaaa aagctaattg cctattatcc   7380
tatggctatc ctgctattgc ctttgtaggc atttggaacg gattagagaa aataaatgat   7440
ttctcgaagg aaaagcagtt aaaagaggat ttgaaatggt tgttatccaa cggcaaccga   7500
aatattaata tcatctttga ccaagaccag aaacaaaaaa ctgtaattaa tgtaaacaaa   7560
gctattttcg ctttatcttc tctaataagt agaaatggtc ataaagttaa tattgtgcaa   7620
tggttgccgt caaaaggtaa aggaatagat gattatttgg tagctttacc ttttgagaaa   7680
agagaaaatc atttagacaa cttaattaaa attgcaccat catttaattt ttggtcaact   7740
aaatacttat tcaagtgtcg taaaccagat ttaaccgtaa attgccgtta tttgagcgat   7800
gcagtaaaag aattacctca agaggatata gcattaatag cacctcacgg cacgggtaaa   7860
acttcattag tagctactca cgttaagaat cggagttatc acggaaggaa aactatttca   7920
ttggtgcatc ttgaaagttt agccaaagct aatggcaacg cacttggatt atattaccga   7980
accgaaaata atattgaaaa gcaatatctt ggatttagct tatgtgtaga tagttgccgt   8040
gataagatta acggcattac aactgatatt atttcaggtc aagattattg ccttttcatt   8100
gatgaaattg accaagtaat tccacacatc cttaacagtg aaactgaagt aagtaagtat   8160
```

-continued

```
agatgcacca tcattgacac tttttctgaa ctggtgagaa atgctgaaca ggtcattatt   8220
gctgatgctg atttatccga tgtgacgatt gacctaatag aaaacatcag aggtaaaaaa   8280
ctatatgtaa tcaagaatga atatcagtat cagggaatga cttttaacgc cgttggttca   8340
ccattagaaa tgatggcaat gatgggaaaa tcggtgtcag aaggcaagaa attatttatt   8400
aacaccacat cccaaaaggc aaaaagtaag tacggcacaa tcgctcttga gtcttatatt   8460
tttggtctaa ataaagaagc aaagatatta agaatagact ctgaaaccac taaaaaccct   8520
gaacatccag cctataaaat cattgaccaa gacttaaata atatcctcaa agattatgat   8580
tatgtcattg cctcaccttg ccttcaaaca ggtgtcagta ttaccttaaa agggcatttt   8640
gaccagcaat ttaacttttc cagtggaaac attacacctc attgcttttt acagcaaatg   8700
tggcggttga gggatgcaga aattgaaaga ttctattatg tgccgaactc atctaacctc   8760
aatctcattg ggaataagtc aagttcacca tcagaccttc taaagagcaa taacaagatg   8820
gcaacggcaa cggttaacct tttgggtaga atcgactccg aatattccct agagtatgaa   8880
tcgcacggca tttggcttga gacgtgggca aaattatcag cacggcataa cagttcaatg   8940
cgttgttact ctgaaattct tacctatcta attacgtctc aagggcataa attaaatatc   9000
aacattccct cacctcttgc agatattaag aagctaaatg atgaggtaag tagtaacagg   9060
gaaaaggtaa aaaatgagag atactctcag aggttaaact caccagatat taacgatgca   9120
gaagctacca tactcgaatc taaagagcaa aaaatcggat tgactctcaa tgagagatgc   9180
accctagaaa agcataaagt taagaagcgg tatgggaatg taaagatgga tattctcacc   9240
tttgatgatg atggactata ccccaaactc agactatttt attacctcac catcggtaaa   9300
cctcatctca aggctaatga cagaaaagct attgccaaaa tgggcaatga caataaaggc   9360
aagattctat caaaagactt agttaataaa acttactccg ctcgtgtgaa ggtcttagag   9420
attcttaaac taactgactt tatcgacaat cttagagatg aactcttaat aactcccaat   9480
aatccagcta tcaccgattt taataatctt ctgctaagag ctaagaagga tttaagagta   9540
ttaggagtca acatcggaaa atatccaatg gccaacatta atgccgtact tactctcatt   9600
ggtcacaaac tttctgtaat gagagatgag ttcggaaaag agaaaaggat aaaagtagat   9660
ggtaaatcat accgatgtta tcaacttgaa acattaccag attttaccaa tgatactctt   9720
gactactggt tagaaaatga tagccaaaaa gaagtaacag caacagaaaa ttactccgaa   9780
aattttaacc cttcaaatag ctacaatcca gacagtaaga cactttcaga gggtgcaaat   9840
ttcctatata taaataaaga agaattgcat ccaaataaat tgcacctaga aataaaagaa   9900
ggtgctgaac tttttttatt cggggtaaag gtgattgtga aaggaatctt ggacggggca   9960
gtaactatat tctctatggg tcaagaatac gatttatccc tcaatgaact agaggggatg  10020
ttaacatcat gaactttaca agaatctttt taaagggcga tcgcaccatg ttaaatgatg  10080
gtacatttgt tcagatattt gatatttacc atgaccacgc attgggagtg acccttgacc  10140
ttaagacaga aaaaattatt tccgatgatg ttagggtaat tactgtcaaa gacttattgt  10200
tcgatggcac ttataaaggg gtaaaatctt ttatgcccga taatgcccga taatgcccga  10260
ttgatgctac aaaatcccat aatcataagc gataatcccc taatagcttg taattcttga  10320
accgtagcga ttttagagta ttccaaaaag aagaaataaa caccgcaaaa tgtcgtattt  10380
cacatatata aaccaaggtt ttttgcccta aaatctttat gtttgtagtg tgatgttggg  10440
tcaaaatggt cagaaaagtt gcaaggtttt tatggatgct tacgcgcgcg aggggtaagc  10500
atccccaaat agttacttta tcctagtcca tgcccattta ttgccgtccc gttcggcttt  10560
```

-continued

```
aaaaaagtgc caaaactcac aaggtgcaat aaaaagttct gtacctttcg caaccctaga  10620
taatctttca acagttactt tttttcctat tatctcggta caaagtttgg ctagtttctc  10680
ttttccctct ttttcaatca agccttcttg tatgcccaac tcattgatta atctctctat  10740
ttttaccatt atttcccgtt caggtagttt atcccctaaa tcttcatcgg ggggcaatgt  10800
agggcattct gaaggggctt tttcttctgt ctggacatta tctaatattg aagtaaccaa  10860
actatcttca gtttttttcta ttcctattaa ttcatattcg gttactgtat ccgtatcaat  10920
atccgaataa ctatctttat ccgtattagc tattcggtta agtttatccg ttaactcaga  10980
aacaagacta tatagcggtt ttagcttttc ttctatcctg ttatctaata cggataagtt  11040
tatacggtta tcattatccg tattagtatc attgggcttt tttggtagtt ctaccccctc  11100
ataaaccgct tttattccca attccaacag actgataaca gtatccttta taatgggttt  11160
tttgctgata tggtgaactt ttgccccttc catcattgcg atactttcta tctcactcat  11220
caacttatcg cttaagtgaa tctcgtatct gtttaatccc ttactggttt tattcatatc  11280
cgtttacttt attcggttaa caattctatt tttatacgaat aaaatattat acggttaact  11340
ttatacgttt aactatttta tctatacgga taacagtaat aagttattcg tattagttat  11400
acgtttactt ttatccaaat aaaattagtg catttaaact aaaagaatga ttttatcgga  11460
gttgatagca ttggattaac ctaaagatgt ttataagcta tatctgataa gtatttaagg  11520
ttattttgtt attctgttta ttgacattat cagaataaaa gaatagaata taattgttga  11580
gagataagag gtttaagtga ttatggttaa gaagttagtt ggttatgtca gggtcagtag  11640
tgaatcgcaa gaggataaca ctagcttaca gaatcagata gagagaattg aagcatattg  11700
tatggctttt ggttatgagt tggtaaaaat attcaaagag gttgccactg gtacaaaagc  11760
agatattgaa acccgtccta tttttaatga agctatagaa tacttgaaac aggataatgc  11820
taatggaatt attgccttga agctagaccg aatcgcacgg aatgctttag atgtattgcg  11880
tttggttcgt gaaaccttag aaccacaaaa taaaatgtta gtgttactag atattcaggt  11940
agatacttcg acaccttcag gaaaaatgat tttaactgta atgagtgccg ttgctgaact  12000
cgaaagagac atgatctatg atcgcactca ggggggtaga aagactaaag cccaaaaggg  12060
cgggtatgcc tacgggaaac ctaaatttgg ctataagact gaagaaaagg aactaaaaga  12120
agattcagca caacaggaaa ctattaaact aattaagaga caccgtaggt cagggaaaag  12180
ctaccagaaa atagctgatt atctcaatgc ccaaagtatt cccactaaac aaggtaagaa  12240
atggagttct agcgtcgtct atcgaatctg tcaggaaaaa gctggttaag tctgtttata  12300
gatatttaga atttattgaa taaaaatagt atgaacaata aatatttatg gactaaccac  12360
gctcggaaac gtttaactga acgatgggaa ataaaagaat catgggttat tgataccatc  12420
gaaaatcctg aacgttcaga atttattgtt gatgagtcag gggaaaaata tcattactat  12480
aaaagaatag ctaagtttaa gaatagagtg ttagaagtga taacttctgc caactcaaca  12540
cccacaagaa taataacctt ttactttaac cgtaacatga ggaaaaattt atgattgtta  12600
cttacgataa tgaagttgac gcaatttatt ttaagttaac ggaaaataaa attgatagca  12660
ccgaacctca aacagacagg attatcattg attacgatga aagtaataat attgttggca  12720
ttgaggtatt agattttaat tatcttgtca agaaaggttt aaccgttgct gatttacctt  12780
tttctgaaga tgaaagatta acagcttctc aatattttaa ttttcctgtt gctatctaat  12840
ccagaagggg caataatccc cttctttcat cgagttagac ttaatatcac aaaagtcatt  12900
```

ttcattttac cgtttctttt ccacagcgtc cgtacgcccc tcgttaaatc tcaaaaccga 12960
caatttatga tgtttataaa aagttactca ctttaataag tatttatact cattaaaggg 13020
ttattctttt tttgtagcct gataggttgg gaaggaatat ttcagattat cagatttgtt 13080
g 13081

<210> SEQ ID NO 13
<211> LENGTH: 13562
<212> TYPE: DNA
<213> ORGANISM: Artificial Sequence
<220> FEATURE:
<223> OTHER INFORMATION: TK368\pABICyano1-6.8_PpetEABICyano1-PDCmax-PrpsLABICyano1-synADHmax-PrbcABICyano1-Km**-oriVT

<400> SEQUENCE: 13
aatatttttc gtcagatacg caaaccttac aaacataatt aacaactgaa actattgata 60
tgtctaggtt ttagctctat cacaggttgg atctgtcgac gagaagggga acagggaaaa 120
gtatttataa ttgatacaaa ctgtggttca acttatttta aagacatttt tctccattta 180
atgattattt cggggaaaat tttgaggatt tttgattctt aaattgacga tattttgtca 240
ctaacacaac gtgagcggta aatttatata tagacctaaa acctttacta taagtgttat 300
atatttaaat cgctaagtat atagttaaag tgtagccaat aattaacttt taacaagtga 360
ttaccgttaa gtcccttaat ttatcactac aagctaaaac aaatttttca attagatatg 420
acattaggtc aaagttcata gtatgatagt aaaaaataaa atttgacgat ctgtaaaaat 480
aaaaaaacac aatgaattct tataccgtgg gtacttattt agccgaacgc ttagtgcaaa 540
ttggtttaaa acatcatttt gccgtggctg gggactataa tttagtgtta ttggataact 600
tattattaaa taaaaacatg gaacaagtgt attgttgtaa tgaattaaat tgtggttttt 660
ctgctgaagg ttatgctaga gctaaaggtg cagctgctgc tgttgttact tattctgtgg 720
gtgctttatc tgcttttgat gctattggtg gtgcttatgc cgaaaattta cccgtgattt 780
taatttctgg tgcccctaat aataatgatc atgccgctgg acatgtttta catcatgcct 840
taggtaaaac cgattatcat tatcaattag aaatggccaa aaatattact gctgctgccg 900
aagctattta tactcctgaa gaagcccctg ccaaaattga tcatgtgatt aaaaccgcct 960
tacgcgaaaa aaaacccgtg tatttagaaa ttgcctgtaa tattgcttct atgccttgtg 1020
ctgctcctgg gcctgcttct gctttattta atgatgaagc ctctgatgaa gctagtttaa 1080
atgctgccgt ggaagaaacc ttaaaattta ttgccaatcg cgataaagtt gccgtgttag 1140
ttggttctaa attaagagct gctggtgctg aagaagctgc tgttaaattt gctgatgctt 1200
taggtggtgc agttgctact atggctgctg ccaaatcttt ttttcccgaa gaaaatcccc 1260
attatattgg aactagttgg ggagaagttt cttatcctgg tgtggaaaaa actatgaaag 1320
aagccgacgc tgttattgct ttagcccctg tgtttaatga ttattctacc actggttgga 1380
ctgatattcc cgatcccaaa aaattagttt tagccgaacc tcgttctgtt gttgttaatg 1440
gtgttcgctt tccctctgtg catttaaaag attatttaac ccgcttagcc caaaaagttt 1500
ctaaaaaaac tggtgcctta gatttttta aatctttaaa tgcgggtgaa ttaaaaaaag 1560
ctgctcctgc tgatccttct gctcctttag ttaatgctga aattgcccgt caagttgaag 1620
ccttattaac ccctaatact accgttattg ccgaaactgg tgattcttgg tttaatgccc 1680
aacgcatgaa attacctaat ggtgcccgtg ttgaatatga aatgcaatgg ggtcatattg 1740
gttggtctgt acctgctgct tttggttatg ctgttggtgc tcctgaacgt cgtaatattt 1800

-continued

```
taatggtggg tgatggttct tttcaattaa ctgcccaaga agttgcccaa atggttcgct   1860
taaaattacc cgttattatt tttttaataa ataattatgg ttataccatt gaagtgatga   1920
ttcatgatgg gccatataat aatattaaaa attgggatta tgcgggttta atggaagtgt   1980
ttaatggtaa tggtggttat gattctggtg ctggtaaagg tttaaaagcc aaaactggtg   2040
gtgaattagc tgaagctatt aaagttgcct tagccaatac tgatgggcca accttaattg   2100
aatgttttat tggtcgcgaa gattgtaccg aagaattagt taaatggggt aaacgtgttg   2160
ctgctgctaa ttctcgcaaa cccgtgaata aattattgta atttttgggg atcaattcga   2220
gctcctccgc ttaaaaaatt tcatttttcg atcaaaaaag acaaattatt actaattagc   2280
tcatggcaat aaataatcag tagtaatctg ttttcacatt ttattgttaa tttttattat   2340
tgctaatatc aacctttttct acttctgctt aatattttat ttatgctcaa tgggaaaatc   2400
tgaaataaga ttgagaacag tgttaccaat agaagtattt aaggtttaaa gcatacctta   2460
aagataacat tttttttga aaagagtcaa attatttttg aaaggctgat atttttgata   2520
tttactaata ttttatttat ttcttttttcc cttaaaataa gagctaaatc tgtttttatt   2580
atcatttatc aagctctatt aatacctcaa ctttttcaag aaaaaataat aataattttt   2640
ccctctattc tcatgacctt ttaggaaaat taattttaga aaaactattg acaaacccat   2700
aaaaaatgag ataagattat agattgtcac tggtatttta tactagaggc aaattatatt   2760
tatatataca aaaatgctgt ataaaaaaca tctcatatga ttaaagccta tgctgcctta   2820
gaagccaatg gtaaattaca accctttgaa tatgatcctg gtgctttagg tgccaatgaa   2880
gtggaaattg aagtgcaata ttgtggtgtg tgtcattctg atttatctat gattaataat   2940
gaatggggta tttctaatta tcccttagtt cctggtcatg aagttgttgg tactgttgct   3000
gctatgggtg aaggtgttaa tcatgtggaa gtgggtgatt tagttggttt aggttggcat   3060
tctggttatt gtatgacctg tcattcttgt ttatctggtt atcataattt atgtgccact   3120
gccgaatcta ctattgtggg tcattatggt ggttttggtg atagagttcg tgctaaaggt   3180
gtttctgtgg tgaaattacc caaaggtatt gatttagcct ctgctgggcc tttattttgt   3240
ggtggtatta ccgtttttttc tcccatggtg gaattatctt taaaacctac cgccaaagtt   3300
gctgttattg gtattggtgg tttaggtcat ttagccgttc aatttttaag agcctggggt   3360
tgtgaagtta ctgcttttac ctcttctgcc cgtaaacaaa ccgaagtttt agaattaggt   3420
gcccatcata ttttagattc taccaatcct gaagctattg cttctgccga aggtaaattt   3480
gattatatta tttctaccgt gaatttaaaa ttagattgga atttatatat cagtacctta   3540
gcccctcaag gtcattttca ttttgttggt gtggtgttag aacccttgga cttaaactta   3600
tttcccttat taatgggaca acgttctgtt tctgcttctc ctgttggttc tcctgctact   3660
attgccacta tgttagattt tgccgtgcgt catgatatta aacccgtggt ggaacaattt   3720
tcttttgatc aaattaatga agccattgcc catttagaat ctggtaaagc ccattatcgc   3780
gtggtgttat ctcattctaa aaattaataa gattaacttc taaactgaaa caaatttgag   3840
ggtaggcttc attgtctgcc cttatttttt tatttaggaa aagtgaacag actaaagagt   3900
gttggctcta ttgctttgag tatgtaaatt aggcgttgct gaattaaggt atgatttttg   3960
accccttctc tcttctgcag ttacctagga tttctggcga aagggggatg tgctgcaagg   4020
cgattaagtt gggtaacgcc agggttttcc cagtcacgac gttgtaaaac gacggccagt   4080
gagcgcgacg taatacgact cactataggg cgaattggcg gaaggccgtc aaggccgcat   4140
ggcgcgccta cgtagacaat tgtcgatgta attattaact atcttattat agatgagggg   4200
```

-continued agagggagaa attagttcgg agagaacgct cgagcgctcg ttccgcaaag cggtacggag 4260
ttagttaggg gctaatgggc attctcccgt acaggaaaga gttagaagtt attaattatc 4320
aacaattctc ctttgcctag tgcatcgtta cctttttaat taaaacataa ggaaaactaa 4380
taatcgtaat aatttaacct caaagtgtaa agaaatgtga aattctgact tttataacgt 4440
taaagaggga aaaattagca gtttaaaata cctagagaat agtctggggt aagcatagag 4500
aattagatta gttaagttaa tcaaattcag aaaaaataat aatcgtaaat agttaatctg 4560
ggtgtataga aaatgatccc cttcatgata agatttaaac tcgaaaagca aaagccaaaa 4620
aactaacttc cattaaaaga agttgttaca tataacgcta taaagaaaat ttatatattt 4680
ggaggatacc aaccatgtct catattcaac gtgaaactag ttgttctcgt cctcgtttaa 4740
attctaatat ggatgccgat ttatatggtt ataaatgggc tcgtgataat gttggtcaat 4800
ctggtgctac tatttatcgt ttatatggta aacctgatgc tcctgaatta ttcttgaaac 4860
atggtaaagg ttctgttgct aatgatgtta ctgatgaaat ggttcgttta aactggttga 4920
ctgaatttat gcctttacct actattaaac attttattcg tactcccgat gatgcttggt 4980
tattaactac tgctattcct ggtaaaactg cttttcaagt tttagaagaa tatcctgatt 5040
ctggtgaaaa tattgttgat gctttagctg ttttttttacg tcgtttacat tctattcccg 5100
tttgtaattg tccttttaat tctgatcgtg tttttcgttt agctcaagct caatctcgta 5160
tgaataatgg tttagttgat gcttctgatt ttgatgatga acgtaatggt tggcctgttg 5220
aacaagtttg gaaagaaatg cacaaattgt tacctttttc tcctgattct gttgttactc 5280
atggtgattt ttctttagat aatttgatct ttgatgaagg taaattgatt ggttgtattg 5340
atgttggtcg tgttggtatt gctgatcgtt atcaagattt agctatttta tggaattgtt 5400
taggtgaatt ttctccttct ttacagaaac gtttatttca gaaatatggt attgataatc 5460
ctgatatgaa caagttacaa tttcatttaa tgttggacga gttcttttaa gaattaattc 5520
atgaccaaaa tcccttaacg tgagttttcg ttccactgag cgtcagaccc cgtagaaaag 5580
atcaaaggat cttcttgaga tcctttttttt ctgcgcgtaa tctgctgcta tttaaattac 5640
gtacacgtgt tattactttg ttaacgacaa ttgtcttaat taactgggcc tcatgggcct 5700
tccgctcact gcccgctttc cagtcgggaa acctgtcgtg ccagctctgc agatgacggt 5760
gaaaacctct gacacatgca gctcccggag acggtcacag cttgtctgta agcggatgcc 5820
gggagcagac aagcccgtca gggcgcgtca gcgggtgttg gcgggtgtcg gggcgcagcc 5880
atgacccagt cacgtagcga tagcggagtg tatactggct taactatgcg gcatcagagc 5940
agattgtact gagagtgcac catatgcggt gtgaaatacc gcacagatgc gtaaggagaa 6000
aataccgcat caggcgctct tccgcttcct cgctcactga ctcgctgcgc tcggtcgttc 6060
ggctgcggcg agcggtatca gctcactcaa aggcggtaat acggttatcc acagaatcag 6120
gggataacgc aggaaagaac atgtgagcaa aaggccagca aaaggccagg aaccgtaaaa 6180
aggccgcgtt gctggcgttt ttccataggc tccgcccccc tgacgagcat cacaaaaatc 6240
gacgctcaag tcagaggtgg cgaaacccga caggactata aagataccag gcgtttcccc 6300
ctggaagctc cctcgtgcgc tctcctgttc cgaccctgcc gcttaccgga tacctgtccg 6360
cctttctccc ttcgggaagc gtggcgcttt ctcatagctc acgctgtagg tatctcagtt 6420
cggtgtaggt cgttcgctcc aagctgggct gtgtgcacga accccccgtt cagcccgacc 6480
gctgcgcctt atccggtaac tatcgtcttg agtccaaccc ggtaagacac gacttatcgc 6540

-continued

```
cactggcagc agccactggt aacaggatta gcagagcgag gtatgtaggc ggtgctacag   6600
agttcttgaa gtggtggcct aactacggct acactagaag gacagtattt ggtatctgcg   6660
ctctgctgaa gccagttacc ttcggaaaaa gagttggtag ctcttgatcc ggcaaacaaa   6720
ccaccgctgg tagcggtggt ttttttgttt gcaagcagca gattacgcgc agaaaaaaag   6780
gatctcaaga agatcctttg atcttttcta ctgcagaagc ttgttagaca ccctgtcatg   6840
tattttatat tatttatttc accatacgga ttaagtgaaa cctaatgaaa atagtacttt   6900
cggagcttta actttaatga aggtatgttt ttttatagac atcgatgtct ggtttaacaa   6960
taggaaaaag tagctaaaac tcccatgaat taaagaaata acaaggtgtc taacaacctg   7020
ttattaagaa tgttagaaaa gacttaacat ttgtgttgag tttttataga cattggtgtc   7080
tagacatacg gtagataagg tttgctcaaa aataaaataa aaaaagattg gactaaaaaa   7140
catttaattt agtacaattt aattagttat tttttcgtct caaattttgc tttgttgagc   7200
agaaatttag ataaaaaaat ccccgtgatc agattacaat gtcgttcatt gtacgatgtg   7260
tcgaaaaatc tttacgacac tctaaactga ccacacgggg gaaaaagaaa actgaactaa   7320
taacatcatg atactcggaa aacctagcaa ttctcaaccc ctaaacaaaa gaaacttcca   7380
aaaccctgac catataaagg agtggcaaca atcagcaatc agtcaagatt tgatagcaga   7440
aaatcttgta tcggttgcta atggttttga tgtactattt atcggcaata aataccgaac   7500
taacacgggt gttctgtcac ggcacatatt aaactcctat tctcatttag aagatggtgg   7560
ttcgtatggt agaacatttg acccatttac caataaagaa atgcagtggg ttcaatttaa   7620
accgaataga ccaagaaaag gttctactgg taaggtaatc aaatatgaat cgccaaaagg   7680
tgaacctaca agagttctaa tgccgtttgt gcctatgaaa atatggcaac ggattagcga   7740
taagttcgga gtaccgatta atccgaaaaa agatactcac ttttgggaat gggtaaagaa   7800
taatccatcg ataccgattg ccattacaga aggaaataaa aaagctaatt gcctattatc   7860
ctatggctat cctgctattg cctttgtagg catttggaac ggattagaga aaataaatga   7920
tttctcgaag gaaaagcagt taaaagagga tttgaaatgg ttgttatcca acggcaaccg   7980
aaatattaat atcatctttg accaagacca gaaacaaaaa actgtaatta atgtaaacaa   8040
agctattttc gctttatctt ctctaataag tagaaatggt cataaagtta atattgtgca   8100
atggttgccg tcaaaaggta aaggaataga tgattatttg gtagctttac cttttgagaa   8160
aagagaaaat catttagaca acttaattaa aattgcacca tcatttaatt tttggtcaac   8220
taaatactta ttcaagtgtc gtaaaccaga tttaaccgta aattgccgtt atttgagcga   8280
tgcagtaaaa gaattacctc aagaggatat agcattaata gcacctcacg gcacgggtaa   8340
aacttcatta gtagctactc acgttaagaa tcggagttat cacggaagga aaactatttc   8400
attggtgcat cttgaaagtt tagccaaagc taatggcaac gcacttggat tatattaccg   8460
aaccgaaaat aatattgaaa agcaatatct tggatttagc ttatgtgtag atagttgccg   8520
tgataagatt aacggcatta caactgatat tatttcaggt caagattatt gcctttttcat   8580
tgatgaaatt gaccaagtaa ttccacacat ccttaacagt gaaactgaag taagtaagta   8640
tagatgcacc atcattgaca ctttttctga actggtgaga aatgctgaac aggtcattat   8700
tgctgatgct gatttatccg atgtgacgat tgacctaata gaaaacatca gaggtaaaaa   8760
actatatgta atcaagaatg aatatcagta tcagggaatg acttttaacg ccgttggttc   8820
accattagaa atgatggcaa tgatgggaaa atcggtgtca gaaggcaaga aattatttat   8880
taacaccaca tcccaaaagg caaaaagtaa gtacggcaca atcgctcttg agtcttatat   8940
```

-continued

```
ttttggtcta aataaagaag caaagatatt aagaatagac tctgaaacca ctaaaaaccc   9000
tgaacatcca gcctataaaa tcattgacca agacttaaat aatatcctca aagattatga   9060
ttatgtcatt gcctcacctt gccttcaaac aggtgtcagt attaccttaa aagggcattt   9120
tgaccagcaa tttaactttt ccagtggaaa cattacacct cattgctttt tacagcaaat   9180
gtggcggttg agggatgcag aaattgaaag attctattat gtgccgaact catctaacct   9240
caatctcatt gggaataagt caagttcacc atcagacctt ctaaagagca ataacaagat   9300
ggcaacggca acggttaacc ttttgggtag aatcgactcc gaatattccc tagagtatga   9360
atcgcacggc atttggcttg agacgtgggc aaaattatca gcacggcata acagttcaat   9420
gcgttgttac tctgaaattc ttacctatct aattacgtct caagggcata aattaaatat   9480
caacattccc tcacctcttg cagatattaa gaagctaaat gatgaggtaa gtagtaacag   9540
ggaaaaggta aaaaatgaga gatactctca gaggttaaac tcaccagata ttaacgatgc   9600
agaagctacc atactcgaat ctaaagagca aaaaatcgga ttgactctca atgagagatg   9660
caccctagaa aagcataaag ttaagaagcg gtatgggaat gtaaagatgg atattctcac   9720
ctttgatgat gatggactat accccaaact cagactattt tattacctca ccatcggtaa   9780
acctcatctc aaggctaatg acagaaaagc tattgccaaa atgggcaatg acaataaagg   9840
caagattcta tcaaaagact tagttaataa aacttactcc gctcgtgtga aggtcttaga   9900
gattcttaaa ctaactgact ttatcgacaa tcttagagat gaactcttaa taactcccaa   9960
taatccagct atcaccgatt ttaataatct tctgctaaga gctaagaagg atttaagagt  10020
attaggagtc aacatcggaa aatatccaat ggccaacatt aatgccgtac ttactctcat  10080
tggtcacaaa ctttctgtaa tgagagatga gttcggaaaa gagaaaagga taaaagtaga  10140
tggtaaatca taccgatgtt atcaacttga aacattacca gattttacca atgatactct  10200
tgactactgg ttagaaaatg atagccaaaa agaagtaaca gcaacagaaa attactccga  10260
aaattttaac ccttcaaata gctacaatcc agacagtaag acactttcag agggtgcaaa  10320
tttcctatat ataaataaag aagaattgca tccaaataaa ttgcacctag aaataaaaga  10380
aggtgctgaa cttttttat tcggggtaaa ggtgattgtg aaaggaatct tggacggggc  10440
agtaactata ttctctatgg gtcaagaata cgatttatcc ctcaatgaac tagaggggat  10500
gttaacatca tgaactttac aagaatcttt ttaaagggcg atcgcaccat gttaaatgat  10560
ggtacatttg ttcagatatt tgatatttac catgaccacg cattgggagt gacccttgac  10620
cttaagacag aaaaaattat ttccgatgat gttagggtaa ttactgtcaa agacttattg  10680
ttcgatggca cttataaagg ggtaaaatct tttatgcccg ataatgcccg ataatgcccg  10740
attgatgcta caaaatccca taatcataag cgataatccc ctaatagctt gtaattcttg  10800
aaccgtagcg attttagagt attccaaaaa gaagaaataa acaccgcaaa atgtcgtatt  10860
tcacatatat aaaccaaggt tttttgccct aaaatcttta tgtttgtagt gtgatgttgg  10920
gtcaaaatgg tcagaaaagt tgcaaggttt ttatggatgc ttacgcgcgc gaggggtaag  10980
catccccaaa tagttacttt atcctagtcc atgcccattt attgccgtcc cgttcggctt  11040
taaaaaagtg ccaaaactca caaggtgcaa taaaaagttc tgtacctttc gcaaccctag  11100
ataatctttc aacagttact ttttttccta ttatctcggt acaaagtttg gctagtttct  11160
cttttccctc tttttcaatc aagccttctt gtatgcccaa ctcattgatt aatctctcta  11220
tttttaccat tatttcccgt tcaggtagtt tatcccctaa atcttcatcg gggggcaatg  11280
```

-continued

```
tagggcattc tgaaggggct ttttcttctg tctggacatt atctaatatt gaagtaacca  11340
aactatcttc agttttttct attcctatta attcatattc ggttactgta tccgtatcaa  11400
tatccgaata actatcttta tccgtattag ctattcggtt aagtttatcc gttaactcag  11460
aaacaagact atatagcggt tttagctttt cttctatcct gttatctaat acggataagt  11520
ttatacggtt atcattatcc gtattagtat cattgggctt ttttggtagt tctacccccct  11580
cataaaccgc ttttattccc aattccaaca gactgataac agtatccttt ataatgggtt  11640
ttttgctgat atggtgaact tttgcccctt ccatcattgc gatactttct atctcactca  11700
tcaacttatc gcttaagtga atctcgtatc tgtttaatcc cttactggtt ttattcatat  11760
ccgtttactt tattcggtta acaattctat tttatacgaa taaaatatta tacggttaac  11820
tttatacgtt taactatttt atctatacgg ataacagtaa taagttattc gtattagtta  11880
tacgtttact tttatccaaa taaaattagt gcatttaaac taaaagaatg attttatcgg  11940
agttgatagc attggattaa cctaaagatg tttataagct atatctgata agtatttaag  12000
gttattttgt tattctgttt attgacatta tcagaataaa agaatagaat ataattgttg  12060
agagataaga ggtttaagtg attatggtta agaagttagt tggttatgtc agggtcagta  12120
gtgaatcgca agaggataac actagcttac agaatcagat agagagaatt gaagcatatt  12180
gtatggcttt tggttatgag ttggtaaaaa tattcaaaga ggttgccact ggtacaaaag  12240
cagatattga aacccgtcct atttttaatg aagctataga atacttgaaa caggataatg  12300
ctaatggaat tattgccttg aagctagacc gaatcgcacg gaatgcttta gatgtattgc  12360
gtttggttcg tgaaacctta gaaccacaaa ataaaatgtt agtgttacta gatattcagg  12420
tagatacttc gacaccttca ggaaaaatga ttttaactgt aatgagtgcc gttgctgaac  12480
tcgaaagaga catgatctat gatcgcactc aggggggtag aaagactaaa gcccaaaagg  12540
gcgggtatgc ctacgggaaa cctaaatttg gctataagac tgaagaaaag gaactaaaag  12600
aagattcagc acaacaggaa actattaaac taattaagag acaccgtagg tcagggaaaa  12660
gctaccagaa aatagctgat tatctcaatg cccaaagtat tcccactaaa caaggtaaga  12720
aatggagttc tagcgtcgtc tatcgaatct gtcaggaaaa agctggttaa gtctgtttat  12780
agatatttag aatttattga ataaaaatag tatgaacaat aaatatttat ggactaacca  12840
cgctcggaaa cgtttaactg aacgatggga aataaaagaa tcatgggtta ttgataccat  12900
cgaaaatcct gaacgttcag aatttattgt tgatgagtca ggggaaaaat atcattacta  12960
taaaagaata gctaagttta agaatagagt gttagaagtg ataacttctg ccaactcaac  13020
acccacaaga ataataacct tttactttaa ccgtaacatg aggaaaaatt tatgattgtt  13080
acttacgata atgaagttga cgcaatttat tttaagttaa cggaaaataa aattgatagc  13140
accgaacctc aaacagacag gattatcatt gattacgatg aaagtaataa tattgttggc  13200
attgaggtat tagattttaa ttatcttgtc aagaaaggtt taaccgttgc tgatttacct  13260
ttttctgaag atgaaagatt aacagcttct caatatttta attttcctgt tgctatctaa  13320
tccagaaggg gcaataatcc ccttctttca tcgagttaga cttaatatca caaaagtcat  13380
tttcatttta ccgtttcttt tccacagcgt ccgtacgccc ctcgttaaat ctcaaaaccg  13440
acaatttatg atgtttataa aaagttactc actttaataa gtatttatac tcattaaagg  13500
gttattcttt ttttgtagcc tgataggttg ggaaggaata tttcagatta tcagatttgt  13560
tg                                                                13562
```

<210> SEQ ID NO 14
<211> LENGTH: 13119
<212> TYPE: DNA
<213> ORGANISM: Artificial Sequence
<220> FEATURE:
<223> OTHER INFORMATION: #1495\pABICyano1-6.8::PnirAABICyano1-
zmPDCABICyano1(opt3)-PrpsLABICyano1-ADHABICyani1(opt3)_ter-
PrbcABICyano1-Km**

<400> SEQUENCE: 14

```
tcgacaatta ataacttctt cctgtacggg cgaatggcca tttgctccta actaactccg     60
tactgctttg cggaacgagc gtagcgaact ctccgaatta ctaagccttc atccctgata    120
gatgcaaaaa acgaattaaa attatgtgta aaaagaaaat gtgtctttat ttagtagtca    180
aagttacaaa atattaagaa tcaaattaat aatgtattgg gcagttaagt atataagtct    240
ttaaatattt atttgtattc aatatattaa ccgaggacaa attatgaatt cttacactgt    300
tggaacctat ttagcagaac gtttagttca aattggtctc aaacaccatt ttgcagtagc    360
tggtgattat aatttagttt tattggataa cttattgtta aataagaata tggaacaagt    420
gtattgttgt aatgaattaa actgtggttt ttctgctgag ggatatgctc gtgcaaaagg    480
tgctgccgca gcagttgtta cttattctgt tggagcatta agtgcttttg acgctattgg    540
aggtgcttat gcagaaaatt tacctgtaat cttaatctct ggtgcaccca ataacaacga    600
tcacgctgct ggtcatgtat tgcatcatgc tttaggtaaa accgattatc attaccaatt    660
agaaatggca aaaaatatta ccgctgccgc agaagctatt tatactcccg aagaagcacc    720
tgctaagatc gatcacgtaa ttaaaaccgc tctccgtgag aaaaaacccg tatatttaga    780
aatcgcttgc aatatcgctt ctatgccttg tgcagctcct ggacctgcta gtgctttatt    840
taacgatgaa gcatctgatg aggctagttt aaatgccgct gttgaagaaa ctttgaaatt    900
tattgctaat cgtgataaag tagctgtttt agttggttct aaactccgtg ccgctggtgc    960
agaagaagcg gctgtaaaat tcgcagatgc cttaggaggt gctgttgcca caatggcagc   1020
cgctaaaagt tttttccccg aagaaaatcc tcattacatt ggtacttctt ggggtgaggt   1080
atcttaccct ggtgtagaaa aaaccatgaa ggaagctgat gcagtaattg cattagctcc   1140
tgttttcaat gattactcta ccactggttg gactgatatt ccagacccca aaaaattagt   1200
tttagcagaa cctcgctctg tagttgtgaa tggtgttaga tttcccagtg tacatctcaa   1260
agattattta actcgtttag ctcaaaaagt gagtaaaaag actggcgcac tcgatttctt   1320
taaatcttta aatgctggtg aattaaagaa agcagctcct gctgatccca gtgctccttt   1380
agtgaatgcc gaaatcgcaa gacaagttga agccttgtta actcctaaca ctaccgttat   1440
tgccgagact ggtgatagtt ggttcaatgc tcaacgcatg aaattaccca atggtgctcg   1500
tgttgagtat gaaatgcaat ggggtcacat tggatggtct gttcctgctg catttggata   1560
tgcagttgga gcacctgagc gtagaaacat tttaatggta ggtgatggtt ctttccaact   1620
cactgctcaa gaagttgcac aaatggtacg tttaaaattg cctgttatta tctttctcat   1680
taacaactat ggttacacca ttgaagttat gattcatgat ggtccttata ataacattaa   1740
gaattgggat tacgcaggtt taatggaggt atttaacggt aatggtggat acgacagtgg   1800
agcaggtaaa ggattaaaag ctaaaacagg aggtgagtta gctgaagcaa ttaaagtagc   1860
tttagccaat acagatggtc ctaccttaat cgaatgtttc attggacgtg aagattgtac   1920
tgaagagtta gttaaatggg gaaagcgtgt tgccgctgca aattctcgta aacctgtaaa   1980
caaactcttg tagttaggat ccgagctcct ccgcttaaaa aatttcattt ttcgatcaaa   2040
```

```
aaagacaaat tattactaat tagctcatgg caataaataa tcagtagtaa tctgttttca   2100
cattttattg ttaattttta ttattgctaa tatcaacctt ttctacttct gcttaatatt   2160
ttatttatgc tcaatgggaa aatctgaaat aagattgaga acagtgttac caatagaagt   2220
atttaaggtt taaagcatac cttaaagata acattttttt ttgaaaagag tcaaattatt   2280
tttgaaaggc tgatattttt gatatttact aatattttat ttatttcttt ttcccttaaa   2340
ataagagcta aatctgtttt tattatcatt tatcaagctc tattaatacc tcaacttttt   2400
caagaaaaaa taataataat ttttccctct attctcatga ccttttagga aaattaattt   2460
tagaaaaact attgacaaac ccataaaaaa tgagataaga ttatagattg tcactggtat   2520
tttatactag aggcaaatta tatttatata tacaaaaatg ctgtataaaa aacatctcat   2580
atgattaagg cttatgctgc attagaagct aatggtaaat tacaaccttt tgaatacgat   2640
cccggtgctt taggtgcaaa tgaagtagaa attgaggttc agtattgtgg tgtatgtcat   2700
tctgatttat ctatgattaa caacgaatgg ggaatttcca attatccctt agttcctgga   2760
cacgaagttg ttggtactgt agcagctatg ggagaaggag ttaatcatgt tgaagtaggt   2820
gacttagtag gtttgggatg gcattctggt tactgtatga cctgtcatag ttgtttatct   2880
ggttatcaca acttatgtgc aactgctgaa agtaccattg ttggtcatta cggtggtttt   2940
ggtgatagag taagagctaa aggagttagt gttgttaaat taccaaaagg tatcgactta   3000
gcaagtgcag gtcctctctt ttgtgggggt attactgttt ttagtcctat ggttgaatta   3060
agtttaaagc caactgcaaa agtagccgtc attggtattg gaggattggg acacttagct   3120
gttcaatttc tccgtgcatg ggatgtgaa gttactgcct ttacttctag tgctcgtaaa   3180
caaaccgagg tattagaatt aggagcacac catatcttag attccaccaa ccctgaagct   3240
atcgctagtg cagagggaaa attcgattat attattagta ctgttaattt gaaattagat   3300
tggaacctct acatctctac tttagctccc caaggtcatt ttcactttgt tggagttgta   3360
ttagaacccc tcgatttaaa cttattccct ttattaatgg gacaacgttc tgttagtgca   3420
tctcctgttg gatctcccgc tactattgct accatgttag attttgcagt acgtcacgat   3480
attaaacctg tagtagaaca attctctttc gatcaaatca acgaagctat tgctcattta   3540
gaaagtggta aggctcatta ccgtgttgtt ttatctcact ctaaaaacta actagatctc   3600
tgcagagaat ataaaaagcc agattattaa tccggctttt ttattattta aatactgtgc   3660
acgatcctgc aggatcatct tgctgaaaaa ctcgagcgct cgttccgcaa agcggtacgg   3720
agttagttag gggctaatgg gcattctccc gtacaggaaa gagttagaag ttattaatta   3780
tcaacaattc tcctttgcct agtgcatcgt tacctttttta attaaaacat aaggaaaact   3840
aataatcgta ataatttaac ctcaaagtgt aaagaaatgt gaaattctga cttttataac   3900
gttaaagagg gaaaaattag cagtttaaaa tacctagaga atagtctggg gtaagcatag   3960
agaattagat tagttaagtt aatcaaattc agaaaaaata ataatcgtaa atagttaatc   4020
tgggtgtata gaaaatgatc cccttcatga taagatttaa actcgaaaag caaaagccaa   4080
aaaactaact tccattaaaa gaagttgtta catataacgc tataaagaaa atttatatat   4140
ttggaggata ccaaccatgt ctcatattca acgtgaaact agttgttctc gccctcgttt   4200
aaattctaat atggatgccg atttatatgg ttataaatgg gctcgtgata atgttggtca   4260
atctggtgct actatttatc gtttatatgg taaacctgat gctcctgaat tattcttgaa   4320
acatggtaaa ggttctgttg ctaatgatgt tactgatgaa atggttcgtt taaactggtt   4380
gactgaattt atgcctttac ctactattaa acattttatt cgtactcccg atgatgcttg   4440
```

```
gttattaact actgctattc ctggtaaaac tgcttttcaa gttttagaag aatatcctga   4500
ttctggtgaa aatattgttg atgctttagc tgttttttta cgtcgtttac attctattcc   4560
cgtttgtaat tgtcctttta attctgatcg tgtttttcgt ttagctcaag ctcaatctcg   4620
tatgaataat ggtttagttg atgcttctga ttttgatgat gaacgtaatg gttggcctgt   4680
tgaacaagtt tggaaagaaa tgcacaaatt gttacctttt tctcctgatt ctgttgttac   4740
tcatggtgat ttttctttag ataatttgat ctttgatgaa ggtaaattga ttggttgtat   4800
tgatgttggt cgtgttggta ttgctgatcg ttatcaagat ttagctattt tatggaattg   4860
tttaggtgaa ttttctcctt ctttacagaa acgtttattt cagaaatatg gtattgataa   4920
tcctgatatg aacaagttac aatttcattt aatgttggac gagttctttt aagaattaat   4980
tcatgaccaa aatcccttaa cgtgagtttt cgttccactg agcgtcagac cccgtagaaa   5040
agatcaaagg atcttcttga gatccttttt ttctgcgcgt aatctgctgc tatttaaatt   5100
acgtacacgt gttattactt tgttaacgac aattgtctta attaactggg cctcatgggc   5160
cttccgctca ctgcccgctt tccagtcggg aaacctgtcg tgccagctct gcagatgacg   5220
gtgaaaacct ctgacacatg cagctcccgg agacggtcac agcttgtctg taagcggatg   5280
ccgggagcag acaagcccgt cagggcgcgt cagcgggtgt tggcgggtgt cggggcgcag   5340
ccatgaccca gtcacgtagc gatagcggag tgtatactgg cttaactatg cggcatcaga   5400
gcagattgta ctgagagtgc accatatgcg gtgtgaaata ccgcacagat gcgtaaggag   5460
aaaataccgc atcaggcgct cttccgcttc ctcgctcact gactcgctgc gctcggtcgt   5520
tcggctgcgg cgagcggtat cagctcactc aaaggcggta atacggttat ccacagaatc   5580
aggggataac gcaggaaaga acatgtgagc aaaaggccag caaaaggcca ggaaccgtaa   5640
aaaggccgcg ttgctggcgt ttttccatag gctccgcccc cctgacgagc atcacaaaaa   5700
tcgacgctca agtcagaggt ggcgaaaccc gacaggacta taaagatacc aggcgtttcc   5760
ccctggaagc tccctcgtgc gctctcctgt tccgaccctg ccgcttaccg gatacctgtc   5820
cgcctttctc ccttcgggaa gcgtggcgct ttctcatagc tcacgctgta ggtatctcag   5880
ttcggtgtag gtcgttcgct ccaagctggg ctgtgtgcac gaaccccccg ttcagcccga   5940
ccgctgcgcc ttatccggta actatcgtct tgagtccaac ccggtaagac acgacttatc   6000
gccactggca gcagccactg gtaacaggat tagcagagcg aggtatgtag gcggtgctac   6060
agagttcttg aagtggtggc ctaactacgg ctacactaga aggacagtat ttggtatctg   6120
cgctctgctg aagccagtta ccttcggaaa aagagttggt agctcttgat ccggcaaaca   6180
aaccaccgct ggtagcggtg gtttttttgt ttgcaagcag cagattacgc gcagaaaaaa   6240
aggatctcaa gaagatcctt tgatcttttc tactgcagaa gcttgttaga caccctgtca   6300
tgtattttat attatttatt tcaccatacg gattaagtga aacctaatga aaatagtact   6360
ttcggagctt taactttaat gaaggtatgt ttttttatag acatcgatgt ctggtttaac   6420
aataggaaaa agtagctaaa actcccatga attaaagaaa taacaaggtg tctaacaacc   6480
tgttattaag aatgttagaa aagacttaac atttgtgttg agtttttata gacattggtg   6540
tctagacata cggtagataa ggtttgctca aaaataaaat aaaaaaagat tggactaaaa   6600
aacatttaat ttagtacaat ttaattagtt attttttcgt ctcaaatttt gctttgttga   6660
gcagaaattt agataaaaaa atccccgtga tcagattaca atgtcgttca ttgtacgatg   6720
tgtcgaaaaa tctttacgac actctaaact gaccacacgg gggaaaaaga aaactgaact   6780
```

-continued

```
aataacatca tgatactcgg aaaacctagc aattctcaac ccctaaacaa aagaaacttc   6840
caaaaccctg accatataaa ggagtggcaa caatcagcaa tcagtcaaga tttgatagca   6900
gaaaatcttg tatcggttgc taatggtttt gatgtactat ttatcggcaa taaataccga   6960
actaacacgg gtgttctgtc acggcacata ttaaactcct attctcattt agaagatggt   7020
ggttcgtatg gtagaacatt tgacccattt accaataaag aaatgcagtg ggttcaattt   7080
aaaccgaata gaccaagaaa aggttctact ggtaaggtaa tcaaatatga atcgccaaaa   7140
ggtgaaccta caagagttct aatgccgttt gtgcctatga aaatatggca acggattagc   7200
gataagttcg gagtaccgat taatccgaaa aaagatactc acttttggga atgggtaaag   7260
aataatccat cgataccgat tgccattaca gaaggaaata aaaaagctaa ttgcctatta   7320
tcctatggct atcctgctat tgcctttgta ggcatttgga acggattaga gaaaataaat   7380
gatttctcga aggaaaagca gttaaaagag gatttgaaat ggttgttatc caacggcaac   7440
cgaaatatta atatcatctt tgaccaagac cagaaacaaa aaactgtaat taatgtaaac   7500
aaagctattt tcgctttatc ttctctaata agtagaaatg gtcataaagt taatattgtg   7560
caatggttgc cgtcaaaagg taaaggaata gatgattatt tggtagcttt accttttgag   7620
aaaagagaaa atcatttaga caacttaatt aaaattgcac catcatttaa tttttggtca   7680
actaaatact tattcaagtg tcgtaaacca gatttaaccg taaattgccg ttatttgagc   7740
gatgcagtaa aagaattacc tcaagaggat atagcattaa tagcacctca cggcacgggt   7800
aaaacttcat tagtagctac tcacgttaag aatcggagtt atcacggaag gaaaactatt   7860
tcattggtgc atcttgaaag tttagccaaa gctaatggca acgcacttgg attatattac   7920
cgaaccgaaa ataatattga aaagcaatat cttggattta gcttatgtgt agatagttgc   7980
cgtgataaga ttaacggcat tacaactgat attatttcag gtcaagatta ttgccttttc   8040
attgatgaaa ttgaccaagt aattccacac atccttaaca gtgaaactga agtaagtaag   8100
tatagatgca ccatcattga cactttttct gaactggtga gaaatgctga acaggtcatt   8160
attgctgatg ctgatttatc cgatgtgacg attgacctaa tagaaaacat cagaggtaaa   8220
aaactatatg taatcaagaa tgaatatcag tatcagggaa tgacttttaa cgccgttggt   8280
tcaccattag aaatgatggc aatgatggga aaatcggtgt cagaaggcaa gaaattattt   8340
attaacacca catcccaaaa ggcaaaaagt aagtacggca caatcgctct tgagtcttat   8400
atttttggtc taaataaaga agcaaagata ttaagaatag actctgaaac cactaaaaac   8460
cctgaacatc cagcctataa aatcattgac caagacttaa ataatatcct caaagattat   8520
gattatgtca ttgcctcacc ttgccttcaa acaggtgtca gtattacctt aaaagggcat   8580
tttgaccagc aatttaactt ttccagtgga aacattacac ctcattgctt tttacagcaa   8640
atgtggcggt tgagggatgc agaaattgaa agattctatt atgtgccgaa ctcatctaac   8700
ctcaatctca ttgggaataa gtcaagttca ccatcagacc ttctaaagag caataacaag   8760
atggcaacgg caacggttaa ccttttgggt agaatcgact ccgaatattc cctagagtat   8820
gaatcgcacg gcatttggct tgagacgtgg gcaaaattat cagcacggca taacagttca   8880
atgcgttgtt actctgaaat tcttacctat ctaattacgt ctcaagggca taaattaaat   8940
atcaacattc cctcacctct tgcagatatt aagaagctaa atgatgaggt aagtagtaac   9000
agggaaaagg taaaaaatga gagatactct cagaggttaa actcaccaga tattaacgat   9060
gcagaagcta ccatactcga atctaaagag caaaaaatcg gattgactct caatgagaga   9120
tgcaccctag aaaagcataa agttaagaag cggtatggga atgtaaagat ggatattctc   9180
```

```
acctttgatg atgatggact ataccccaaa ctcagactat tttattacct caccatcggt   9240
aaacctcatc tcaaggctaa tgacagaaaa gctattgcca aaatgggcaa tgacaataaa   9300
ggcaagattc tatcaaaaga cttagttaat aaaacttact ccgctcgtgt gaaggtctta   9360
gagattctta aactaactga ctttatcgac aatcttagag atgaactctt aataactccc   9420
aataatccag ctatcaccga ttttaataat cttctgctaa gagctaagaa ggatttaaga   9480
gtattaggag tcaacatcgg aaaatatcca atggccaaca ttaatgccgt acttactctc   9540
attggtcaca aactttctgt aatgagagat gagttcggaa aagagaaaag gataaaagta   9600
gatggtaaat cataccgatg ttatcaactt gaaacattac cagattttac caatgatact   9660
cttgactact ggttagaaaa tgatagccaa aaagaagtaa cagcaacaga aaattactcc   9720
gaaaatttta acccttcaaa tagctacaat ccagacagta agacactttc agagggtgca   9780
aatttcctat atataaataa agaagaattg catccaaata aattgcacct agaaataaaa   9840
gaaggtgctg aactttttt attcggggta aaggtgattg tgaaaggaat cttggacggg   9900
gcagtaacta tattctctat gggtcaagaa tacgatttat ccctcaatga actagagggg   9960
atgttaacat catgaacttt acaagaatct ttttaaaggg cgatcgcacc atgttaaatg  10020
atggtacatt tgttcagata tttgatattt accatgacca cgcattggga gtgacccttg  10080
accttaagac agaaaaaatt atttccgatg atgttagggt aattactgtc aaagacttat  10140
tgttcgatgg cacttataaa ggggtaaaat cttttatgcc cgataatgcc cgataatgcc  10200
cgattgatgc tacaaaatcc cataatcata agcgataatc ccctaatagc ttgtaattct  10260
tgaaccgtag cgattttaga gtattccaaa aagaagaaat aaacaccgca aaatgtcgta  10320
tttcacatat ataaaccaag gtttttgcc ctaaaatctt tatgtttgta gtgtgatgtt  10380
gggtcaaaat ggtcagaaaa gttgcaaggt ttttatggat gcttacgcgc gcgaggggta  10440
agcatcccca aatagttact ttatcctagt ccatgcccat ttattgccgt cccgttcggc  10500
tttaaaaaag tgccaaaact cacaaggtgc aataaaaagt tctgtacctt tcgcaaccct  10560
agataatctt tcaacagtta cttttttcc tattatctcg gtacaaagtt tggctagttt  10620
ctcttttccc tctttttcaa tcaagccttc ttgtatgccc aactcattga ttaatctctc  10680
tatttttacc attatttccc gttcaggtag tttatcccct aaatcttcat cgggggggcaa  10740
tgtagggcat tctgaagggg ctttttcttc tgtctggaca ttatctaata ttgaagtaac  10800
caaactatct tcagtttttt ctattcctat taattcatat tcggttactg tatccgtatc  10860
aatatccgaa taactatctt tatccgtatt agctattcgg ttaagtttat ccgttaactc  10920
agaaacaaga ctatatagcg gttttagctt ttcttctatc ctgttatcta atacggataa  10980
gtttatacgg ttatcattat ccgtattagt atcattgggc tttttggta gttctacccc  11040
ctcataaacc gcttttattc ccaattccaa cagactgata acagtatcct ttataatggg  11100
ttttttgctg atatggtgaa cttttgcccc ttccatcatt gcgatacttt ctatctcact  11160
catcaactta tcgcttaagt gaatctcgta tctgtttaat cccttactgg ttttattcat  11220
atccgtttac tttattcggt taacaattct attttatacg aataaaatat tatacggtta  11280
actttatacg tttaactatt ttatctatac ggataacagt aataagttat tcgtattagt  11340
tatacgttta cttttatcca aataaaatta gtgcatttaa actaaaagaa tgattttatc  11400
ggagttgata gcattggatt aacctaaaga tgtttataag ctatatctga taagtattta  11460
aggttatttt gttattctgt ttattgacat tatcagaata aaagaataga atataattgt  11520
```

tgagagataa gaggtttaag tgattatggt taagaagtta gttggttatg tcagggtcag 11580
tagtgaatcg caagaggata acactagctt acagaatcag atagagagaa ttgaagcata 11640
ttgtatggct tttggttatg agttggtaaa aatattcaaa gaggttgcca ctggtacaaa 11700
agcagatatt gaaacccgtc ctatttttaa tgaagctata gaatacttga aacaggataa 11760
tgctaatgga attattgcct tgaagctaga ccgaatcgca cggaatgctt tagatgtatt 11820
gcgtttggtt cgtgaaacct tagaaccaca aaataaaatg ttagtgttac tagatattca 11880
ggtagatact tcgacacctt caggaaaaat gattttaact gtaatgagtg ccgttgctga 11940
actcgaaaga gacatgatct atgatcgcac tcaggggggt agaaagacta aagcccaaaa 12000
gggcgggtat gcctacggga aacctaaatt tggctataag actgaagaaa aggaactaaa 12060
agaagattca gcacaacagg aaactattaa actaattaag agacaccgta ggtcagggaa 12120
aagctaccag aaaatagctg attatctcaa tgcccaaagt attcccacta aacaaggtaa 12180
gaaatggagt tctagcgtcg tctatcgaat ctgtcaggaa aaagctggtt aagtctgttt 12240
atagatattt agaatttatt gaataaaaat agtatgaaca ataaatattt atggactaac 12300
cacgctcgga aacgtttaac tgaacgatgg gaaataaaag aatcatgggt tattgatacc 12360
atcgaaaatc ctgaacgttc agaatttatt gttgatgagt caggggaaaa atatcattac 12420
tataaaagaa tagctaagtt taagaataga gtgttagaag tgataacttc tgccaactca 12480
acacccacaa gaataataac cttttacttt aaccgtaaca tgaggaaaaa tttatgattg 12540
ttacttacga taatgaagtt gacgcaattt attttaagtt aacggaaaat aaaattgata 12600
gcaccgaacc tcaaacagac aggattatca ttgattacga tgaaagtaat aatattgttg 12660
gcattgaggt attagatttt aattatcttg tcaagaaagg tttaaccgtt gctgatttac 12720
ctttttctga agatgaaaga ttaacagctt ctcaatattt taattttcct gttgctatct 12780
aatccagaag ggcaataat ccccttcttt catcgagtta gacttaatat cacaaaagtc 12840
attttcattt taccgtttct tttccacagc gtccgtacgc ccctcgttaa atctcaaaac 12900
cgacaattta tgatgtttat aaaaagttac tcactttaat aagtatttat actcattaaa 12960
gggttattct ttttttgtag cctgataggt tgggaaggaa tatttcagat tatcagattt 13020
gttgaatatt tttcgtcaga tacgcaaacc ttacaaacat aattaacaac tgaaactatt 13080
gatatgtcta ggttttagct ctatcacagg ttggatctg 13119

<210> SEQ ID NO 15
<211> LENGTH: 12648
<212> TYPE: DNA
<213> ORGANISM: Artificial Sequence
<220> FEATURE:
<223> OTHER INFORMATION: #1578\pABICyano1-6.8::PnirAABICyano1-zmPDCABICyano1(opt3)-dsrA-Prbc*(optRBS)-synADH\oop-PrbcABICyano1-Km**

<400> SEQUENCE: 15
cagcaagttt catcccgacc ccctcagggt cgggattttt ttattgtact agttgacata 60
agtaaaggca tcccctgcgt gatataatta ccttcagttt aaggaggtat acacatatga 120
ttaaagccta cgctgccctg gaagccaacg gaaaactcca accctttgaa tacgaccccg 180
gtgccctggg tgctaatgag gtggagattg aggtgcagta ttgtggggtg tgccacagtg 240
atttgtccat gattaataac gaatggggca tttccaatta ccccctagtg ccgggtcatg 300
aggtggtggg tactgtggcc gccatgggcg aaggggtgaa ccatgttgag gtgggggatt 360
tagtggggct gggttggcat tcgggctact gcatgacctg ccatagttgt ttatctggct 420

-continued

```
accacaacct ttgtgccacg gcggaatcga ccattgtggg ccactacggt ggctttggcg    480
atcgggttcg ggccaaggga gtcagcgtgg tgaaattacc taaaggcatt gacctagcca    540
gtgccgggcc ccttttctgt ggaggaatta ccgttttcag tcctatggtg gaactgagtt    600
taaagcccac tgcaaaagtg gcagtgatcg gcattggggg cttgggccat ttagcggtgc    660
aatttctccg ggcctggggc tgtgaagtga ctgcctttac ctccagtgcc aggaagcaaa    720
cggaagtgtt ggaattgggc gctcaccaca tactagattc caccaatcca gaggcgatcg    780
ccagtgcgga aggcaaattt gactatatta tctccactgt gaacctgaag cttgactgga    840
acttatacat cagcaccctg gcgccccagg gacatttcca ctttgttggg gtggtgttgg    900
agcctttgga tctaaatctt tttccccttt tgatgggaca acgctccgtt tctgcctccc    960
cagtgggtag tcccgccacc attgccacca tgttggactt tgctgtgcgc catgacatta   1020
aacccgtggt ggaacaattt agctttgatc agatcaacga ggcgatcgcc catctagaaa   1080
gcggcaaagc ccattatcgg gtagtgctca gccatagtaa aaattagctc tgcaaaggtt   1140
gcttctgggt ccgtggaacg ctcggttgcc gccgggcgtt ttttattcct gcaggatcat   1200
cttgctgaaa aactcgagcg ctcgttccgc aaagcggtac ggagttagtt aggggctaat   1260
gggcattctc ccgtacagga aagagttaga agttattaat tatcaacaat tctcctttgc   1320
ctagtgcatc gttacctttt taattaaaac ataaggaaaa ctaataatcg taataattta   1380
acctcaaagt gtaaagaaat gtgaaattct gacttttata acgttaaaga gggaaaaatt   1440
agcagtttaa aatacctaga gaatagtctg gggtaagcat agagaattag attagttaag   1500
ttaatcaaat tcagaaaaaa taataatcgt aaatagttaa tctgggtgta tagaaaatga   1560
tccccttcat gataagattt aaactcgaaa agcaaaagcc aaaaaactaa cttccattaa   1620
aagaagttgt tacatataac gctataaaga aaatttatat atttggagga taccaaccat   1680
gtctcatatt caacgtgaaa ctagttgttc tcgccctcgt ttaaattcta atatggatgc   1740
cgatttatat ggttataaat gggctcgtga taatgttggt caatctggtg ctactattta   1800
tcgtttatat ggtaaacctg atgctcctga attattcttg aaacatggta aaggttctgt   1860
tgctaatgat gttactgatg aaatggttcg tttaaactgg ttgactgaat ttatgccttt   1920
acctactatt aaacatttta ttcgtactcc cgatgatgct tggttattaa ctactgctat   1980
tcctggtaaa actgcttttc aagttttaga agaatatcct gattctggtg aaaatattgt   2040
tgatgcttta gctgtttttt tacgtcgttt acattctatt cccgtttgta attgtccttt   2100
taattctgat cgtgttttc gtttagctca agctcaatct cgtatgaata atggtttagt   2160
tgatgcttct gattttgatg atgaacgtaa tggttggcct gttgaacaag tttggaaaga   2220
aatgcacaaa ttgttacctt tttctcctga ttctgttgtt actcatggtg atttttcttt   2280
agataatttg atctttgatg aaggtaaatt gattggttgt attgatgttg gtcgtgttgg   2340
tattgctgat cgttatcaag atttagctat tttatggaat tgtttaggtg aattttctcc   2400
ttctttacag aaacgtttat ttcagaaata tggtattgat aatcctgata tgaacaagtt   2460
acaatttcat ttaatgttgg acgagttctt ttaagaatta attcatgacc aaaatccctt   2520
aacgtgagtt ttcgttccac tgagcgtcag accccgtaga aaagatcaaa ggatcttctt   2580
gagatccttt ttttctgcgc gtaatctgct gctatttaaa ttacgtacac gtgttattac   2640
tttgttaacg acaattgtct taattaactg ggcctcatgg gccttccgct cactgcccgc   2700
tttccagtcg ggaaacctgt cgtgccagct ctgcagatga cggtgaaaac ctctgacaca   2760
```

-continued

```
tgcagctccc ggagacggtc acagcttgtc tgtaagcgga tgccgggagc agacaagccc   2820

gtcagggcgc gtcagcgggt gttggcgggt gtcggggcgc agccatgacc cagtcacgta   2880

gcgatagcgg agtgtatact ggcttaacta tgcggcatca gagcagattg tactgagagt   2940

gcaccatatg cggtgtgaaa taccgcacag atgcgtaagg agaaaatacc gcatcaggcg   3000

ctcttccgct tcctcgctca ctgactcgct gcgctcggtc gttcggctgc ggcgagcggt   3060

atcagctcac tcaaaggcgg taatacggtt atccacagaa tcaggggata acgcaggaaa   3120

gaacatgtga gcaaaaggcc agcaaaaggc caggaaccgt aaaaaggccg cgttgctggc   3180

gtttttccat aggctccgcc cccctgacga gcatcacaaa aatcgacgct caagtcagag   3240

gtggcgaaac ccgacaggac tataaagata ccaggcgttt ccccctggaa gctccctcgt   3300

gcgctctcct gttccgaccc tgccgcttac cggatacctg tccgcctttc tcccttcggg   3360

aagcgtggcg ctttctcata gctcacgctg taggtatctc agttcggtgt aggtcgttcg   3420

ctccaagctg ggctgtgtgc acgaaccccc cgttcagccc gaccgctgcg ccttatccgg   3480

taactatcgt cttgagtcca acccggtaag acacgactta tcgccactgg cagcagccac   3540

tggtaacagg attagcagag cgaggtatgt aggcggtgct acagagttct tgaagtggtg   3600

gcctaactac ggctacacta gaaggacagt atttggtatc tgcgctctgc tgaagccagt   3660

taccttcgga aaaagagttg gtagctcttg atccggcaaa caaaccaccg ctggtagcgg   3720

tggttttttt gtttgcaagc agcagattac gcgcagaaaa aaaggatctc aagaagatcc   3780

tttgatcttt tctactgcag aagcttgtta gacaccctgt catgtatttt atattattta   3840

tttcaccata cggattaagt gaaacctaat gaaaatagta ctttcggagc tttaacttta   3900

atgaaggtat gttttttat agacatcgat gtctggttta acaataggaa aaagtagcta   3960

aaactcccat gaattaaaga aataacaagg tgtctaacaa cctgttatta agaatgttag   4020

aaaagactta acatttgtgt tgagttttta tagacattgg tgtctagaca tacggtagat   4080

aaggtttgct caaaaataaa ataaaaaaag attggactaa aaaacattta atttagtaca   4140

atttaattag ttatttttc gtctcaaatt ttgctttgtt gagcagaaat ttagataaaa   4200

aaatccccgt gatcagatta caatgtcgtt cattgtacga tgtgtcgaaa aatctttacg   4260

acactctaaa ctgaccacac gggggaaaaa gaaaactgaa ctaataacat catgatactc   4320

ggaaaaccta gcaattctca accoctaaac aaaagaaact tccaaaaccc tgaccatata   4380

aaggagtggc aacaatcagc aatcagtcaa gatttgatag cagaaaatct tgtatcggtt   4440

gctaatggtt ttgatgtact atttatcggc aataaatacc gaactaacac gggtgttctg   4500

tcacggcaca tattaaactc ctattctcat ttagaagatg gtggttcgta tggtagaaca   4560

tttgacccat ttaccaataa agaaatgcag tgggttcaat ttaaaccgaa tagaccaaga   4620

aaaggttcta ctggtaaggt aatcaaatat gaatcgccaa aaggtgaacc tacaagagtt   4680

ctaatgccgt ttgtgcctat gaaaatatgg caacggatta gcgataagtt cggagtaccg   4740

attaatccga aaaaagatac tcacttttgg gaatgggtaa agaataatcc atcgataccg   4800

attgccatta cagaaggaaa taaaaaagct aattgcctat tatcctatgg ctatcctgct   4860

attgcctttg taggcatttg gaacggatta gagaaaataa atgatttctc gaaggaaaag   4920

cagttaaaag aggatttgaa atggttgtta tccaacggca accgaaatat taatatcatc   4980

tttgaccaag accagaaaca aaaaactgta attaatgtaa acaaagctat tttcgcttta   5040

tcttctctaa taagtagaaa tggtcataaa gttaatattg tgcaatggtt gccgtcaaaa   5100

ggtaaaggaa tagatgatta tttggtagct ttacctttg agaaaagaga aaatcattta   5160
```

gacaacttaa ttaaaattgc accatcattt aatttttggt caactaaata cttattcaag 5220
tgtcgtaaac cagatttaac cgtaaattgc cgttatttga gcgatgcagt aaaagaatta 5280
cctcaagagg atatagcatt aatagcacct cacggcacgg gtaaaacttc attagtagct 5340
actcacgtta agaatcggag ttatcacgga aggaaaacta tttcattggt gcatcttgaa 5400
agtttagcca aagctaatgg caacgcactt ggattatatt accgaaccga aaataatatt 5460
gaaaagcaat atcttggatt tagcttatgt gtagatagtt gccgtgataa gattaacggc 5520
attacaactg atattatttc aggtcaagat tattgccttt tcattgatga aattgaccaa 5580
gtaattccac acatccttaa cagtgaaact gaagtaagta agtatagatg caccatcatt 5640
gacacttttt ctgaactggt gagaaatgct gaacaggtca ttattgctga tgctgattta 5700
tccgatgtga cgattgacct aatagaaaac atcagaggta aaaaactata tgtaatcaag 5760
aatgaatatc agtatcaggg aatgactttt aacgccgttg gttcaccatt agaaatgatg 5820
gcaatgatgg gaaaatcggt gtcagaaggc aagaaattat ttattaacac cacatcccaa 5880
aaggcaaaaa gtaagtacgg cacaatcgct cttgagtctt atatttttgg tctaaataaa 5940
gaagcaaaga tattaagaat agactctgaa accactaaaa accctgaaca tccagcctat 6000
aaaatcattg accaagactt aaataatatc ctcaaagatt atgattatgt cattgcctca 6060
ccttgccttc aaacaggtgt cagtattacc ttaaaagggc attttgacca gcaatttaac 6120
ttttccagtg gaaacattac acctcattgc tttttacagc aaatgtggcg gttgagggat 6180
gcagaaattg aaagattcta ttatgtgccg aactcatcta acctcaatct cattgggaat 6240
aagtcaagtt caccatcaga ccttctaaag agcaataaca agatggcaac ggcaacggtt 6300
aacctttttgg gtagaatcga ctccgaatat tccctagagt atgaatcgca cggcatttgg 6360
cttgagacgt gggcaaaatt atcagcacgg cataacagtt caatgcgttg ttactctgaa 6420
attcttacct atctaattac gtctcaaggg cataaattaa atatcaacat tccctcacct 6480
cttgcagata ttaagaagct aaatgatgag gtaagtagta acagggaaaa ggtaaaaaat 6540
gagagatact ctcagaggtt aaactcacca gatattaacg atgcagaagc taccatactc 6600
gaatctaaag agcaaaaaat cggattgact ctcaatgaga gatgcaccct agaaaagcat 6660
aaagttaaga agcggtatgg gaatgtaaag atggatattc tcacctttga tgatgatgga 6720
ctatacccca aactcagact attttattac ctcaccatcg gtaaacctca tctcaaggct 6780
aatgacagaa aagctattgc caaaatgggc aatgacaata aaggcaagat tctatcaaaa 6840
gacttagtta ataaaactta ctccgctcgt gtgaaggtct tagagattct taaactaact 6900
gactttatcg acaatcttag agatgaactc ttaataactc ccaataatcc agctatcacc 6960
gattttaata atcttctgct aagagctaag aaggatttaa gagtattagg agtcaacatc 7020
ggaaaatatc caatggccaa cattaatgcc gtacttactc tcattggtca caaactttct 7080
gtaatgagag atgagttcgg aaaagagaaa aggataaaag tagatggtaa atcataccga 7140
tgttatcaac ttgaaacatt accagatttt accaatgata ctcttgacta ctggttagaa 7200
aatgatagcc aaaaagaagt aacagcaaca gaaaattact ccgaaaattt taacccttca 7260
aatagctaca atccagacag taagacactt tcagagggtg caaatttcct atatataaat 7320
aaagaagaat tgcatccaaa taaattgcac ctagaaataa aagaaggtgc tgaacttttt 7380
ttattcgggg taaaggtgat tgtgaaagga atcttggacg gggcagtaac tatattctct 7440
atgggtcaag aatacgattt atccctcaat gaactagagg ggatgttaac atcatgaact 7500

-continued

```
ttacaagaat ctttttaaag ggcgatcgca ccatgttaaa tgatggtaca tttgttcaga   7560
tatttgatat ttaccatgac cacgcattgg gagtgaccct tgaccttaag acagaaaaaa   7620
ttatttccga tgatgttagg gtaattactg tcaaagactt attgttcgat ggcacttata   7680
aaggggtaaa atcttttatg cccgataatg cccgataatg cccgattgat gctacaaaat   7740
cccataatca taagcgataa tcccctaata gcttgtaatt cttgaaccgt agcgatttta   7800
gagtattcca aaaagaagaa ataaacaccg caaaatgtcg tatttcacat atataaacca   7860
aggtttttttg ccctaaaatc tttatgtttg tagtgtgatg ttgggtcaaa atggtcagaa   7920
aagttgcaag gtttttatgg atgcttacgc gcgcgagggg taagcatccc caaatagtta   7980
ctttatccta gtccatgccc atttattgcc gtcccgttcg gctttaaaaa agtgccaaaa   8040
ctcacaaggt gcaataaaaa gttctgtacc tttcgcaacc ctagataatc tttcaacagt   8100
tactttttttt cctattatct cggtacaaag tttggctagt ttctcttttc cctctttttc   8160
aatcaagcct tcttgtatgc ccaactcatt gattaatctc tctattttta ccattatttc   8220
ccgttcaggt agtttatccc ctaaatcttc atcggggggc aatgtagggc attctgaagg   8280
ggctttttct tctgtctgga cattatctaa tattgaagta accaaactat cttcagtttt   8340
ttctattcct attaattcat attcggttac tgtatccgta tcaatatccg aataactatc   8400
tttatccgta ttagctattc ggttaagttt atccgttaac tcagaaacaa gactatatag   8460
cggttttagc ttttcttcta tcctgttatc taatacggat aagtttatac ggttatcatt   8520
atccgtatta gtatcattgg gctttttttgg tagttctacc ccctcataaa ccgcttttat   8580
tcccaattcc aacagactga taacagtatc ctttataatg ggtttttttgc tgatatggtg   8640
aacttttgcc ccttccatca ttgcgatact ttctatctca ctcatcaact tatcgcttaa   8700
gtgaatctcg tatctgttta atcccttact ggttttattc atatccgttt actttattcg   8760
gttaacaatt ctattttata cgaataaaat attatacggt taactttata cgtttaacta   8820
ttttatctat acggataaca gtaataagtt attcgtatta gttatacgtt tacttttatc   8880
caaataaaat tagtgcattt aaactaaaag aatgatttta tcggagttga tagcattgga   8940
ttaacctaaa gatgtttata agctatatct gataagtatt taaggttatt ttgttattct   9000
gtttattgac attatcagaa taaaagaata gaatataatt gttgagagat aagaggttta   9060
agtgattatg gttaagaagt tagttggtta tgtcagggtc agtagtgaat cgcaagagga   9120
taacactagc ttacagaatc agatagagag aattgaagca tattgtatgg cttttggtta   9180
tgagttggta aaaatattca aagaggttgc cactggtaca aaagcagata ttgaaacccg   9240
tcctattttt aatgaagcta tagaatactt gaaacaggat aatgctaatg gaattattgc   9300
cttgaagcta gaccgaatcg cacggaatgc tttagatgta ttgcgtttgg ttcgtgaaac   9360
cttagaacca caaaataaaa tgttagtgtt actagatatt caggtagata cttcgacacc   9420
ttcaggaaaa atgattttaa ctgtaatgag tgccgttgct gaactcgaaa gagacatgat   9480
ctatgatcgc actcaggggg gtagaaagac taaagcccaa aagggcgggt atgcctacgg   9540
gaaacctaaa tttggctata agactgaaga aaaggaacta aaagaagatt cagcacaaca   9600
ggaaactatt aaactaatta agagacaccg taggtcaggg aaaagctacc agaaaatagc   9660
tgattatctc aatgcccaaa gtattcccac taaacaaggt aagaaatgga gttctagcgt   9720
cgtctatcga atctgtcagg aaaaagctgg ttaagtctgt ttatagatat ttagaattta   9780
ttgaataaaa atagtatgaa caataaatat ttatggacta accacgctcg gaaacgttta   9840
actgaacgat gggaaataaa agaatcatgg gttattgata ccatcgaaaa tcctgaacgt   9900
```

-continued

```
tcagaattta ttgttgatga gtcaggggaa aaatatcatt actataaaag aatagctaag   9960
tttaagaata gagtgttaga agtgataact tctgccaact caacacccac aagaataata  10020
accttttact ttaaccgtaa catgaggaaa aatttatgat tgttacttac gataatgaag  10080
ttgacgcaat ttattttaag ttaacggaaa ataaaattga tagcaccgaa cctcaaacag  10140
acaggattat cattgattac gatgaaagta ataatattgt tggcattgag gtattagatt  10200
ttaattatct tgtcaagaaa ggtttaaccg ttgctgattt accttttttct gaagatgaaa  10260
gattaacagc ttctcaatat tttaattttc ctgttgctat ctaatccaga aggggcaata  10320
atccccttct ttcatcgagt tagacttaat atcacaaaag tcattttcat tttaccgttt  10380
cttttccaca gcgtccgtac gcccctcgtt aaatctcaaa accgacaatt tatgatgttt  10440
ataaaaagtt actcacttta ataagtattt atactcatta aagggttatt cttttttgt  10500
agcctgatag gttgggaagg aatatttcag attatcagat ttgttgaata tttttcgtca  10560
gatacgcaaa ccttacaaac ataattaaca actgaaacta ttgatatgtc taggttttag  10620
ctctatcaca ggttggatct gtcgacaatt aataacttct tcctgtacgg gcgaatggcc  10680
atttgctcct aactaactcc gtactgcttt gcggaacgag cgtagcgaac tctccgaatt  10740
actaagcctt catccctgat agatgcaaaa aacgaattaa aattatgtgt aaaaagaaaa  10800
tgtgtcttta tttagtagtc aaagttacaa aatattaaga atcaaattaa taatgtattg  10860
ggcagttaag tatataagtc tttaaatatt tatttgtatt caatatatta accgaggaca  10920
aattatgaat tcttacactg ttggaaccta tttagcagaa cgtttagttc aaattggtct  10980
caaacaccat tttgcagtag ctggtgatta taatttagtt ttattggata acttattgtt  11040
aaataagaat atggaacaag tgtattgttg taatgaatta aactgtggtt tttctgctga  11100
gggatatgct cgtgcaaaag gtgctgccgc agcagttgtt acttattctg ttggagcatt  11160
aagtgctttt gacgctattg gaggtgctta tgcagaaaat ttacctgtaa tcttaatctc  11220
tggtgcaccc aataacaacg atcacgctgc tggtcatgta ttgcatcatg ctttaggtaa  11280
aaccgattat cattaccaat tagaaatggc aaaaaatatt accgctgccg cagaagctat  11340
ttatactccc gaagaagcac ctgctaagat cgatcacgta attaaaaccg ctctccgtga  11400
gaaaaaaccc gtatatttag aaatcgcttg caatatcgct tctatgcctt gtgcagctcc  11460
tggacctgct agtgctttat ttaacgatga agcatctgat gaggctagtt taaatgccgc  11520
tgttgaagaa actttgaaat ttattgctaa tcgtgataaa gtagctgttt tagttggttc  11580
taaactccgt gccgctggtg cagaagaagc ggctgtaaaa ttcgcagatg ccttaggagg  11640
tgctgttgcc acaatggcag ccgctaaaag ttttttcccc gaagaaaatc ctcattacat  11700
tggtacttct tggggtgagg tatcttaccc tggtgtagaa aaaaccatga aggaagctga  11760
tgcagtaatt gcattagctc ctgttttcaa tgattactct accactggtt ggactgatat  11820
tccagacccc aaaaaaattag ttttagcaga acctcgctct gtagttgtga atggtgttag  11880
atttcccagt gtacatctca aagattattt aactcgttta gctcaaaaag tgagtaaaaa  11940
gactggcgca ctcgatttct ttaaatcttt aaatgctggt gaattaaaga aagcagctcc  12000
tgctgatccc agtgctcctt tagtgaatgc cgaaatcgca agacaagttg aagccttgtt  12060
aactcctaac actaccgtta ttgccgagac tggtgatagt tggttcaatg ctcaacgcat  12120
gaaattaccc aatggtgctc gtgttgagta tgaaatgcaa tggggtcaca ttggatggtc  12180
tgttcctgct gcatttggat atgcagttgg agcacctgag cgtagaaaca ttttaatggt  12240
```

```
aggtgatggt tctttccaac tcactgctca agaagttgca caaatggtac gtttaaaatt  12300

gcctgttatt atctttctca ttaacaacta tggttacacc attgaagtta tgattcatga  12360

tggtccttat aataacatta agaattggga ttacgcaggt ttaatggagg tatttaacgg  12420

taatggtgga tacgacagtg gagcaggtaa aggattaaaa gctaaaacag gaggtgagtt  12480

agctgaagca attaaagtag ctttagccaa tacagatggt cctaccttaa tcgaatgttt  12540

cattggacgt gaagattgta ctgaagagtt agttaaatgg ggaaagcgtg ttgccgctgc  12600

aaattctcgt aaacctgtaa acaaactctt gtagttagga tccgagct              12648


<210> SEQ ID NO 16
<211> LENGTH: 13165
<212> TYPE: DNA
<213> ORGANISM: Artificial Sequence
<220> FEATURE:
<223> OTHER INFORMATION: #1581\pABICyano1-6.8::PnirAABICyano1-
      zmPDCABICyano1(opt3)-dsrA-PrpsLABICyano1-ADHABICyano1(opt3)_ter-
      PrbcABICyano1-Km**

<400> SEQUENCE: 16

gatccagcaa gtttcatccc gaccccctca gggtcgggat ttttttattg tgagctcctc     60

cgcttaaaaa atttcatttt tcgatcaaaa aagacaaatt attactaatt agctcatggc    120

aataaataat cagtagtaat ctgttttcac attttattgt taatttttat tattgctaat    180

atcaaccttt tctacttctg cttaatattt tatttatgct caatgggaaa atctgaaata    240

agattgagaa cagtgttacc aatagaagta tttaaggttt aaagcatacc ttaaagataa    300

catttttttt tgaaaagagt caaattattt ttgaaaggct gatatttttg atatttacta    360

atattttatt tatttctttt tcccttaaaa taagagctaa atctgttttt attatcattt    420

atcaagctct attaatacct caactttttc aagaaaaaat aataataatt tttccctcta    480

ttctcatgac cttttaggaa aattaatttt agaaaaacta ttgacaaacc cataaaaaat    540

gagataagat tatagattgt cactggtatt ttatactaga ggcaaattat atttatatat    600

acaaaaatgc tgtataaaaa acatctcata tgattaaggc ttatgctgca ttagaagcta    660

atggtaaatt acaacctttt gaatacgatc ccggtgcttt aggtgcaaat gaagtagaaa    720

ttgaggttca gtattgtggt gtatgtcatt ctgatttatc tatgattaac aacgaatggg    780

gaatttccaa ttatccctta gttcctggac acgaagttgt tggtactgta gcagctatgg    840

gagaaggagt taatcatgtt gaagtaggtg acttagtagg tttgggatgg cattctggtt    900

actgtatgac ctgtcatagt tgtttatctg gttatcacaa cttatgtgca actgctgaaa    960

gtaccattgt tggtcattac ggtggttttg gtgatagagt aagagctaaa ggagttagtg   1020

ttgttaaatt accaaaaggt atcgacttag caagtgcagg tcctctcttt tgtgggggta   1080

ttactgtttt tagtcctatg gttgaattaa gtttaaagcc aactgcaaaa gtagccgtca   1140

ttggtattgg aggattggga cacttagctg ttcaatttct ccgtgcatgg ggatgtgaag   1200

ttactgcctt tacttctagt gctcgtaaac aaaccgaggt attagaatta ggagcacacc   1260

atatcttaga ttccaccaac cctgaagcta tcgctagtgc agagggaaaa ttcgattata   1320

ttattagtac tgttaatttg aaattagatt ggaacctcta catctctact ttagctcccc   1380

aaggtcattt tcactttgtt ggagttgtat tagaacccct cgatttaaac ttattccctt   1440

tattaatggg acaacgttct gttagtgcat ctcctgttgg atctcccgct actattgcta   1500

ccatgttaga ttttgcagta cgtcacgata ttaaacctgt agtagaacaa ttctctttcg   1560

atcaaatcaa cgaagctatt gctcatttag aaagtggtaa ggctcattac cgtgttgttt   1620
```

tatctcactc taaaaactaa ctagatctct gcagagaata taaaaagcca gattattaat 1680
ccggcttttt tattatttaa atactgtgca cgatcctgca ggatcatctt gctgaaaaac 1740
tcgagcgctc gttccgcaaa gcggtacgga gttagttagg ggctaatggg cattctcccg 1800
tacaggaaag agttagaagt tattaattat caacaattct cctttgccta gtgcatcgtt 1860
accttttttaa ttaaaacata aggaaaacta ataatcgtaa taatttaacc tcaaagtgta 1920
aagaaatgtg aaattctgac ttttataacg ttaaagaggg aaaaattagc agtttaaaat 1980
acctagagaa tagtctgggg taagcataga gaattagatt agttaagtta atcaaattca 2040
gaaaaaataa taatcgtaaa tagttaatct gggtgtatag aaaatgatcc ccttcatgat 2100
aagatttaaa ctcgaaaagc aaaagccaaa aaactaactt ccattaaaag aagttgttac 2160
atataacgct ataaagaaaa tttatatatt tggaggatac caaccatgtc tcatattcaa 2220
cgtgaaacta gttgttctcg ccctcgttta aattctaata tggatgccga tttatatggt 2280
tataaatggg ctcgtgataa tgttggtcaa tctggtgcta ctatttatcg tttatatggt 2340
aaacctgatg ctcctgaatt attcttgaaa catggtaaag gttctgttgc taatgatgtt 2400
actgatgaaa tggttcgttt aaactggttg actgaattta tgcctttacc tactattaaa 2460
cattttattc gtactcccga tgatgcttgg ttattaacta ctgctattcc tggtaaaact 2520
gcttttcaag ttttagaaga atatcctgat tctggtgaaa atattgttga tgctttagct 2580
gttttttttac gtcgtttaca ttctattccc gtttgtaatt gtccttttaa ttctgatcgt 2640
gtttttcgtt tagctcaagc tcaatctcgt atgaataatg gtttagttga tgcttctgat 2700
tttgatgatg aacgtaatgg ttggcctgtt gaacaagttt ggaaagaaat gcacaaattg 2760
ttaccttttt ctcctgattc tgttgttact catggtgatt tttctttaga taatttgatc 2820
tttgatgaag gtaaattgat tggttgtatt gatgttggtc gtgttggtat tgctgatcgt 2880
tatcaagatt tagctatttt atggaattgt ttaggtgaat tttctccttc tttacagaaa 2940
cgtttatttc agaaatatgg tattgataat cctgatatga acaagttaca atttcattta 3000
atgttggacg agttcttttta agaattaatt catgaccaaa atcccttaac gtgagttttc 3060
gttccactga gcgtcagacc ccgtagaaaa gatcaaagga tcttcttgag atcctttttt 3120
tctgcgcgta atctgctgct atttaaatta cgtacacgtg ttattacttt gttaacgaca 3180
attgtcttaa ttaactgggc ctcatgggcc ttccgctcac tgcccgcttt ccagtcggga 3240
aacctgtcgt gccagctctg cagatgacgg tgaaaacctc tgacacatgc agctcccgga 3300
gacggtcaca gcttgtctgt aagcggatgc cgggagcaga caagcccgtc agggcgcgtc 3360
agcgggtgtt ggcgggtgtc ggggcgcagc catgacccag tcacgtagcg atagcggagt 3420
gtatactggc ttaactatgc ggcatcagag cagattgtac tgagagtgca ccatatgcgg 3480
tgtgaaatac cgcacagatg cgtaaggaga aaataccgca tcaggcgctc ttccgcttcc 3540
tcgctcactg actcgctgcg ctcggtcgtt cggctgcggc gagcggtatc agctcactca 3600
aaggcggtaa tacggttatc cacagaatca ggggataacg caggaaagaa catgtgagca 3660
aaaggccagc aaaaggccag gaaccgtaaa aaggccgcgt tgctggcgtt tttccatagg 3720
ctccgccccc ctgacgagca tcacaaaaat cgacgctcaa gtcagaggtg gcgaaacccg 3780
acaggactat aaagatacca ggcgtttccc cctggaagct ccctcgtgcg ctctcctgtt 3840
ccgaccctgc cgcttaccgg atacctgtcc gcctttctcc cttcgggaag cgtggcgctt 3900
tctcatagct cacgctgtag gtatctcagt tcggtgtagg tcgttcgctc caagctgggc 3960

-continued

```
tgtgtgcacg aacccccccgt tcagcccgac cgctgcgcct tatccggtaa ctatcgtctt   4020
gagtccaacc cggtaagaca cgacttatcg ccactggcag cagccactgg taacaggatt   4080
agcagagcga ggtatgtagg cggtgctaca gagttcttga agtggtggcc taactacggc   4140
tacactagaa ggacagtatt tggtatctgc gctctgctga agccagttac cttcggaaaa   4200
agagttggta gctcttgatc cggcaaacaa accaccgctg gtagcggtgg tttttttgtt   4260
tgcaagcagc agattacgcg cagaaaaaaa ggatctcaag aagatccttt gatcttttct   4320
actgcagaag cttgttagac accctgtcat gtattttata ttatttattt caccatacgg   4380
attaagtgaa acctaatgaa aatagtactt tcggagcttt aactttaatg aaggtatgtt   4440
tttttataga catcgatgtc tggtttaaca ataggaaaaa gtagctaaaa ctcccatgaa   4500
ttaaagaaat aacaaggtgt ctaacaacct gttattaaga atgttagaaa agacttaaca   4560
tttgtgttga gtttttatag acattggtgt ctagacatac ggtagataag gtttgctcaa   4620
aaataaaata aaaaaagatt ggactaaaaa acatttaatt tagtacaatt taattagtta   4680
ttttttcgtc tcaaattttg ctttgttgag cagaaattta gataaaaaaa tccccgtgat   4740
cagattacaa tgtcgttcat tgtacgatgt gtcgaaaaat ctttacgaca ctctaaactg   4800
accacacggg ggaaaaagaa aactgaacta ataacatcat gatactcgga aaacctagca   4860
attctcaacc cctaaacaaa agaaacttcc aaaaccctga ccatataaag gagtggcaac   4920
aatcagcaat cagtcaagat ttgatagcag aaaatcttgt atcggttgct aatggttttg   4980
atgtactatt tatcggcaat aaataccgaa ctaacacggg tgttctgtca cggcacatat   5040
taaactccta ttctcattta gaagatggtg gttcgtatgg tagaacattt gacccattta   5100
ccaataaaga aatgcagtgg gttcaattta aaccgaatag accaagaaaa ggttctactg   5160
gtaaggtaat caaatatgaa tcgccaaaag gtgaacctac aagagttcta atgccgtttg   5220
tgcctatgaa aatatggcaa cggattagcg ataagttcgg agtaccgatt aatccgaaaa   5280
aagatactca cttttgggaa tgggtaaaga ataatccatc gataccgatt gccattacag   5340
aaggaaataa aaaagctaat tgcctattat cctatggcta tcctgctatt gcctttgtag   5400
gcatttggaa cggattagag aaaataaatg atttctcgaa ggaaaagcag ttaaaagagg   5460
atttgaaatg gttgttatcc aacggcaacc gaaatattaa tatcatcttt gaccaagacc   5520
agaaacaaaa aactgtaatt aatgtaaaca aagctatttt cgctttatct tctctaataa   5580
gtagaaatgg tcataaagtt aatattgtgc aatggttgcc gtcaaaaggt aaaggaatag   5640
atgattattt ggtagcttta ccttttgaga aaagagaaaa tcatttagac aacttaatta   5700
aaattgcacc atcatttaat ttttggtcaa ctaaatactt attcaagtgt cgtaaaccag   5760
atttaaccgt aaattgccgt tatttgagcg atgcagtaaa agaattacct caagaggata   5820
tagcattaat agcacctcac ggcacgggta aaacttcatt agtagctact cacgttaaga   5880
atcggagtta tcacggaagg aaaactattt cattggtgca tcttgaaagt ttagccaaag   5940
ctaatggcaa cgcacttgga ttatattacc gaaccgaaaa taatattgaa aagcaatatc   6000
ttggatttag cttatgtgta gatagttgcc gtgataagat taacggcatt acaactgata   6060
ttatttcagg tcaagattat tgccttttca ttgatgaaat tgaccaagta attccacaca   6120
tccttaacag tgaaactgaa gtaagtaagt atagatgcac catcattgac actttttctg   6180
aactggtgag aaatgctgaa caggtcatta ttgctgatgc tgatttatcc gatgtgacga   6240
ttgacctaat agaaaacatc agaggtaaaa aactatatgt aatcaagaat gaatatcagt   6300
atcagggaat gacttttaac gccgttggtt caccattaga aatgatggca atgatgggaa   6360
```

aatcggtgtc agaaggcaag aaattattta ttaacaccac atcccaaaag gcaaaaagta 6420
agtacggcac aatcgctctt gagtcttata tttttggtct aaataaagaa gcaaagatat 6480
taagaataga ctctgaaacc actaaaaacc ctgaacatcc agcctataaa atcattgacc 6540
aagacttaaa taatatcctc aaagattatg attatgtcat tgcctcacct tgccttcaaa 6600
caggtgtcag tattacctta aaagggcatt ttgaccagca atttaacttt tccagtggaa 6660
acattacacc tcattgcttt ttacagcaaa tgtggcggtt gagggatgca gaaattgaaa 6720
gattctatta tgtgccgaac tcatctaacc tcaatctcat tgggaataag tcaagttcac 6780
catcagacct tctaaagagc aataacaaga tggcaacggc aacggttaac cttttgggta 6840
gaatcgactc cgaatattcc ctagagtatg aatcgcacgg catttggctt gagacgtggg 6900
caaaattatc agcacggcat aacagttcaa tgcgttgtta ctctgaaatt cttacctatc 6960
taattacgtc tcaagggcat aaattaaata tcaacattcc ctcacctctt gcagatatta 7020
agaagctaaa tgatgaggta agtagtaaca gggaaaaggt aaaaaatgag agatactctc 7080
agaggttaaa ctcaccagat attaacgatg cagaagctac catactcgaa tctaaagagc 7140
aaaaaatcgg attgactctc aatgagagat gcaccctaga aaagcataaa gttaagaagc 7200
ggtatgggaa tgtaaagatg gatattctca cctttgatga tgatggacta taccccaaac 7260
tcagactatt ttattacctc accatcggta aacctcatct caaggctaat gacagaaaag 7320
ctattgccaa aatgggcaat gacaataaag gcaagattct atcaaaagac ttagttaata 7380
aaacttactc cgctcgtgtg aaggtcttag agattcttaa actaactgac tttatcgaca 7440
atcttagaga tgaactctta ataactccca ataatccagc tatcaccgat tttaataatc 7500
ttctgctaag agctaagaag gatttaagag tattaggagt caacatcgga aaatatccaa 7560
tggccaacat taatgccgta cttactctca ttggtcacaa actttctgta atgagagatg 7620
agttcggaaa agagaaaagg ataaaagtag atggtaaatc ataccgatgt tatcaacttg 7680
aaacattacc agattttacc aatgatactc ttgactactg gttagaaaat gatagccaaa 7740
aagaagtaac agcaacagaa aattactccg aaaattttaa cccttcaaat agctacaatc 7800
cagacagtaa gacactttca gagggtgcaa atttcctata tataaataaa gaagaattgc 7860
atccaaataa attgcaccta gaaataaaag aaggtgctga actttttttta ttcggggtaa 7920
aggtgattgt gaaaggaatc ttggacgggg cagtaactat attctctatg ggtcaagaat 7980
acgatttatc cctcaatgaa ctagagggga tgttaacatc atgaacttta caagaatctt 8040
tttaaagggc gatcgcacca tgttaaatga tggtacattt gttcagatat ttgatattta 8100
ccatgaccac gcattgggag tgacccttga ccttaagaca gaaaaaatta tttccgatga 8160
tgttagggta attactgtca aagacttatt gttcgatggc acttataaag ggtaaaatc 8220
ttttatgccc gataatgccc gataatgccc gattgatgct acaaaatccc ataatcataa 8280
gcgataatcc cctaatagct tgtaattctt gaaccgtagc gattttagag tattccaaaa 8340
agaagaaata aacaccgcaa aatgtcgtat ttcacatata taaaccaagg ttttttgccc 8400
taaaatcttt atgtttgtag tgtgatgttg ggtcaaaatg gtcagaaaag ttgcaaggtt 8460
tttatggatg cttacgcgcg cgaggggtaa gcatccccaa atagttactt tatcctagtc 8520
catgcccatt tattgccgtc ccgttcggct ttaaaaaagt gccaaaactc acaaggtgca 8580
ataaaaagtt ctgtaccttt cgcaacccta gataatcttt caacagttac tttttttcct 8640
attatctcgg tacaaagttt ggctagtttc tcttttccct ctttttcaat caagccttct 8700

-continued

```
tgtatgccca actcattgat taatctctct atttttacca ttatttcccg ttcaggtagt   8760
ttatccccta aatcttcatc ggggggcaat gtagggcatt ctgaaggggc tttttcttct   8820
gtctggacat tatctaatat tgaagtaacc aaactatctt cagtttttc tattcctatt   8880
aattcatatt cggttactgt atccgtatca atatccgaat aactatcttt atccgtatta   8940
gctattcggt taagtttatc cgttaactca gaaacaagac tatatagcgg ttttagcttt   9000
tcttctatcc tgttatctaa tacggataag tttatacggt tatcattatc cgtattagta   9060
tcattgggct tttttggtag ttctaccccc tcataaaccg cttttattcc caattccaac   9120
agactgataa cagtatcctt tataatgggt tttttgctga tatggtgaac ttttgcccct   9180
tccatcattg cgatactttc tatctcactc atcaacttat cgcttaagtg aatctcgtat   9240
ctgtttaatc ccttactggt tttattcata tccgtttact ttattcggtt aacaattcta   9300
ttttatacga ataaaatatt atacggttaa ctttatacgt ttaactattt tatctatacg   9360
gataacagta ataagttatt cgtattagtt atacgtttac ttttatccaa ataaaattag   9420
tgcatttaaa ctaaaagaat gattttatcg gagttgatag cattggatta acctaaagat   9480
gtttataagc tatatctgat aagtatttaa ggttattttg ttattctgtt tattgacatt   9540
atcagaataa aagaatagaa tataattgtt gagagataag aggtttaagt gattatggtt   9600
aagaagttag ttggttatgt cagggtcagt agtgaatcgc aagaggataa cactagctta   9660
cagaatcaga tagagagaat tgaagcatat tgtatggctt ttggttatga gttggtaaaa   9720
atattcaaag aggttgccac tggtacaaaa gcagatattg aaacccgtcc tatttttaat   9780
gaagctatag aatacttgaa acaggataat gctaatggaa ttattgcctt gaagctagac   9840
cgaatcgcac ggaatgcttt agatgtattg cgtttggttc gtgaaacctt agaaccacaa   9900
aataaaatgt tagtgttact agatattcag gtagatactt cgacaccttc aggaaaaatg   9960
attttaactg taatgagtgc cgttgctgaa ctcgaaagag acatgatcta tgatcgcact  10020
cagggggtga gaaagactaa agcccaaaag ggcgggtatg cctacgggaa acctaaattt  10080
ggctataaga ctgaagaaaa ggaactaaaa gaagattcag cacaacagga aactattaaa  10140
ctaattaaga gacaccgtag gtcagggaaa agctaccaga aaatagctga ttatctcaat  10200
gcccaaagta ttcccactaa acaaggtaag aaatggagtt ctagcgtcgt ctatcgaatc  10260
tgtcaggaaa aagctggtta agtctgttta tagatattta gaatttattg aataaaaata  10320
gtatgaacaa taaatattta tggactaacc acgctcggaa acgtttaact gaacgatggg  10380
aaataaaaga atcatgggtt attgatacca tcgaaaatcc tgaacgttca gaatttattg  10440
ttgatgagtc aggggaaaaa tatcattact ataaaagaat agctaagttt aagaatagag  10500
tgttagaagt gataacttct gccaactcaa cacccacaag aataataacc ttttacttta  10560
accgtaacat gaggaaaaat ttatgattgt tacttacgat aatgaagttg acgcaattta  10620
ttttaagtta acggaaaata aaattgatag caccgaacct caaacagaca ggattatcat  10680
tgattacgat gaaagtaata atattgttgg cattgaggta ttagatttta attatcttgt  10740
caagaaaggt ttaaccgttg ctgatttacc tttttctgaa gatgaaagat taacagcttc  10800
tcaatatttt aattttcctg ttgctatcta atccagaagg ggcaataatc cccttctttc  10860
atcgagttag acttaatatc acaaaagtca ttttcatttt accgtttctt ttccacagcg  10920
tccgtacgcc cctcgttaaa tctcaaaacc gacaatttat gatgtttata aaaagttact  10980
cactttaata agtatttata ctcattaaag ggttattctt tttttgtagc ctgataggtt  11040
gggaaggaat atttcagatt atcagatttg ttgaatattt ttcgtcagat acgcaaacct  11100
```

```
tacaaacata attaacaact gaaactattg atatgtctag gttttagctc tatcacaggt  11160

tggatctgtc gacaattaat aacttcttcc tgtacgggcg aatggccatt tgctcctaac  11220

taactccgta ctgctttgcg gaacgagcgt agcgaactct ccgaattact aagccttcat  11280

ccctgataga tgcaaaaaac gaattaaaat tatgtgtaaa aagaaaatgt gtctttattt  11340

agtagtcaaa gttacaaaat attaagaatc aaattaataa tgtattgggc agttaagtat  11400

ataagtcttt aaatatttat ttgtattcaa tatattaacc gaggacaaat tatgaattct  11460

tacactgttg gaacctattt agcagaacgt ttagttcaaa ttggtctcaa acaccatttt  11520

gcagtagctg gtgattataa tttagtttta ttggataact tattgttaaa taagaatatg  11580

gaacaagtgt attgttgtaa tgaattaaac tgtggttttt ctgctgaggg atatgctcgt  11640

gcaaaaggtg ctgccgcagc agttgttact tattctgttg gagcattaag tgcttttgac  11700

gctattggag gtgcttatgc agaaaattta cctgtaatct taatctctgg tgcacccaat  11760

aacaacgatc acgctgctgg tcatgtattg catcatgctt taggtaaaac cgattatcat  11820

taccaattag aaatggcaaa aaatattacc gctgccgcag aagctattta tactcccgaa  11880

gaagcacctg ctaagatcga tcacgtaatt aaaaccgctc tccgtgagaa aaaacccgta  11940

tatttagaaa tcgcttgcaa tatcgcttct atgccttgtg cagctcctgg acctgctagt  12000

gctttattta acgatgaagc atctgatgag gctagtttaa atgccgctgt tgaagaaact  12060

ttgaaattta ttgctaatcg tgataaagta gctgttttag ttggttctaa actccgtgcc  12120

gctggtgcag aagaagcggc tgtaaaattc gcagatgcct taggaggtgc tgttgccaca  12180

atggcagccg ctaaaagttt tttccccgaa gaaaatcctc attacattgg tacttcttgg  12240

ggtgaggtat cttaccctgg tgtagaaaaa accatgaagg aagctgatgc agtaattgca  12300

ttagctcctg ttttcaatga ttactctacc actggttgga ctgatattcc agaccccaaa  12360

aaattagttt tagcagaacc tcgctctgta gttgtgaatg gtgttagatt tcccagtgta  12420

catctcaaag attatttaac tcgtttagct caaaaagtga gtaaaaagac tggcgcactc  12480

gatttcttta aatctttaaa tgctggtgaa ttaaagaaag cagctcctgc tgatcccagt  12540

gctcctttag tgaatgccga aatcgcaaga caagttgaag ccttgttaac tcctaacact  12600

accgttattg ccgagactgg tgatagttgg ttcaatgctc aacgcatgaa attacccaat  12660

ggtgctcgtg ttgagtatga aatgcaatgg ggtcacattg gatggtctgt tcctgctgca  12720

tttggatatg cagttggagc acctgagcgt agaaacattt taatggtagg tgatggttct  12780

ttccaactca ctgctcaaga agttgcacaa atggtacgtt taaaattgcc tgttattatc  12840

tttctcatta acaactatgg ttacaccatt gaagttatga ttcatgatgg tccttataat  12900

aacattaaga attgggatta cgcaggttta atggaggtat ttaacggtaa tggtggatac  12960

gacagtggag caggtaaagg attaaaagct aaaacaggag gtgagttagc tgaagcaatt  13020

aaagtagctt tagccaatac agatggtcct accttaatcg aatgtttcat tggacgtgaa  13080

gattgtactg aagagttagt taaatgggga aagcgtgttg ccgctgcaaa ttctcgtaaa  13140

cctgtaaaca aactcttgta gttag                                          13165
```

<210> SEQ ID NO 17
<211> LENGTH: 12762
<212> TYPE: DNA
<213> ORGANISM: Artificial Sequence
<220> FEATURE:
<223> OTHER INFORMATION: #1606\\pABICyano1::PnirA-zmPDC(opt1)_dsrA-
Prbc*(optRBS)-synADH(opt1)_ter

<400> SEQUENCE: 17

```
tcgacaatta ataacttctt cctgtacggg cgaatggcca tttgctccta actaactccg     60
tactgctttg cggaacgagc gtagcgaact ctccgaatta ctaagccttc atccctgata    120
gatgcaaaaa acgaattaaa attatgtgta aaaagaaaat gtgtctttat ttagtagtca    180
aagttacaaa atattaagaa tcaaattaat aatgtattgg gcagttaagt atataagtct    240
ttaaatattt atttgtattc aatatattaa ccgaggacaa attatgaatt cttataccgt    300
gggtacttat ttagccgaac gcttagtgca aattggttta aaacatcatt ttgccgtggc    360
tggggactat aatttagtgt tattggataa cttattatta aataaaaaca tggaacaagt    420
gtattgttgt aatgaattaa attgtggttt ttctgctgaa ggttatgcta gagctaaagg    480
tgcagctgct gctgttgtta cttattctgt gggtgcttta tctgcttttg atgctattgg    540
tggtgcttat gccgaaaatt tacccgtgat tttaatttct ggtgccccta ataataatga    600
tcatgccgct ggacatgttt tacatcatgc cttaggtaaa accgattatc attatcaatt    660
agaaatggcc aaaaatatta ctgctgctgc cgaagctatt tatactcctg aagaagcccc    720
tgccaaaatt gatcatgtga ttaaaaccgc cttacgcgaa aaaaaacccg tgtatttaga    780
aattgcctgt aatattgctt ctatgccttg tgctgctcct gggcctgctt ctgctttatt    840
taatgatgaa gcctctgatg aagctagttt aaatgctgcc gtggaagaaa ccttaaaatt    900
tattgccaat cgcgataaag ttgccgtgtt agttggttct aaattaagag ctgctggtgc    960
tgaagaagct gctgttaaat ttgctgatgc tttaggtggt gcagttgcta ctatggctgc   1020
tgccaaatct ttttttcccg aagaaaatcc ccattatatt ggaactagtt ggggagaagt   1080
ttcttatcct ggtgtggaaa aaactatgaa agaagccgac gctgttattg ctttagcccc   1140
tgtgtttaat gattattcta ccactggttg gactgatatt cccgatccca aaaaattagt   1200
tttagccgaa cctcgttctg ttgttgttaa tggtgttcgc tttccctctg tgcatttaaa   1260
agattattta acccgcttag cccaaaaagt ttctaaaaaa actggtgcct tagatttttt   1320
taaatcttta aatgcgggtg aattaaaaaa agctgctcct gctgatcctt ctgctccttt   1380
agttaatgct gaaattgccc gtcaagttga agccttatta acccctaata ctaccgttat   1440
tgccgaaact ggtgattctt ggtttaatgc ccaacgcatg aaattaccta atggtgcccg   1500
tgttgaatat gaaatgcaat ggggtcatat tggttggtct gtacctgctg cttttggtta   1560
tgctgttggt gctcctgaac gtcgtaatat tttaatggtg ggtgatggtt cttttcaatt   1620
aactgcccaa gaagttgccc aaatggttcg cttaaaatta cccgttatta ttttttttaat   1680
aaataattat ggttatacca ttgaagtgat gattcatgat gggccatata ataatattaa   1740
aaattgggat tatgcgggtt taatggaagt gtttaatggt aatggtggtt atgattctgg   1800
tgctggtaaa ggtttaaaag ccaaaactgg tggtgaatta gctgaagcta ttaaagttgc   1860
cttagccaat actgatgggc caaccttaat tgaatgtttt attggtcgcg aagattgtac   1920
cgaagaatta gttaaatggg gtaaacgtgt tgctgctgct aattctcgca aacccgtgaa   1980
taaattattg taatttttgg ggatcaattc gagctcagca agtttcatcc cgaccccctc   2040
agggtcggga ttttttttatt gtactagttg acataagtaa aggcatcccc tgcgtgatat   2100
aattaccttc agtttaagga ggtatacaca tatgattaaa gcctatgctg ccttagaagc   2160
caatggtaaa ttacaaccct ttgaatatga tcctggtgct ttaggtgcca atgaagtgga   2220
aattgaagtg caatattgtg gtgtgtgtca ttctgattta tctatgatta ataatgaatg   2280
```

-continued

```
gggtatttct aattatccct tagttcctgg tcatgaagtt gttggtactg ttgctgctat   2340
gggtgaaggt gttaatcatg tggaagtggg tgatttagtt ggtttaggtt ggcattctgg   2400
ttattgtatg acctgtcatt cttgtttatc tggttatcat aatttatgtg ccactgccga   2460
atctactatt gtgggtcatt atggtggttt tggtgataga gttcgtgcta aaggtgtttc   2520
tgtggtgaaa ttacccaaag gtattgattt agcctctgct gggcctttat tttgtggtgg   2580
tattaccgtt ttttctccca tggtggaatt atctttaaaa cctaccgcca aagttgctgt   2640
tattggtatt ggtggtttag gtcatttagc cgttcaattt ttaagagcct ggggttgtga   2700
agttactgct tttacctctt ctgcccgtaa acaaaccgaa gttttagaat taggtgccca   2760
tcatatttta gattctacca atcctgaagc tattgcttct gccgaaggta aatttgatta   2820
tattatttct accgtgaatt taaaattaga ttggaattta tatatcagta ccttagcccc   2880
tcaaggtcat tttcattttg ttggtgtggt gttagaaccc ttggacttaa acttatttcc   2940
cttattaatg ggacaacgtt ctgtttctgc ttctcctgtt ggttctcctg ctactattgc   3000
cactatgtta gattttgccg tgcgtcatga tattaaaccc gtggtggaac aatttttcttt  3060
tgatcaaatt aatgaagcca ttgcccattt agaatctggt aaagcccatt atcgcgtggt   3120
gttatctcat tctaaaaatt aataagatta acttctaaac tgaaacaaat ttgagggtag   3180
gcttcattgt ctgcccttat ttttttattt aggaaaagtg aacagactaa agagtgttgg   3240
ctctattgct ttgagtatgt aaattaggcg ttgctgaatt aaggtatgat ttttgacccc   3300
ttctctcttc tgcaggatca tcttgctgaa aaactcgagc gctcgttccg caaagcggta   3360
cggagttagt taggggctaa tgggcattct cccgtacagg aaagagttag aagttattaa   3420
ttatcaacaa ttctcctttg cctagtgcat cgttaccttt ttaattaaaa cataaggaaa   3480
actaataatc gtaataattt aacctcaaag tgtaaagaaa tgtgaaattc tgacttttat   3540
aacgttaaag agggaaaaat tagcagttta aaatacctag agaatagtct ggggtaagca   3600
tagagaatta gattagttaa gttaatcaaa ttcagaaaaa ataataatcg taaatagtta   3660
atctgggtgt atagaaaatg atccccttca tgataagatt taaactcgaa aagcaaaagc   3720
caaaaaacta acttccatta aaagaagttg ttacatataa cgctataaag aaaatttata   3780
tatttggagg ataccaacca tgtctcatat tcaacgtgaa actagttgtt ctcgccctcg   3840
tttaaattct aatatggatg ccgatttata tggttataaa tgggctcgtg ataatgttgg   3900
tcaatctggt gctactattt atcgtttata tggtaaacct gatgctcctg aattattctt   3960
gaaacatggt aaaggttctg ttgctaatga tgttactgat gaaatggttc gtttaaactg   4020
gttgactgaa tttatgcctt tacctactat taaacatttt attcgtactc ccgatgatgc   4080
ttggttatta actactgcta ttcctggtaa aactgctttt caagttttag aagaatatcc   4140
tgattctggt gaaaatattg ttgatgcttt agctgttttt ttacgtcgtt tacattctat   4200
tcccgtttgt aattgtcctt ttaattctga tcgtgttttt cgtttagctc aagctcaatc   4260
tcgtatgaat aatggtttag ttgatgcttc tgattttgat gatgaacgta atggttggcc   4320
tgttgaacaa gtttggaaag aaatgcacaa attgttacct ttttctcctg attctgttgt   4380
tactcatggt gatttttctt tagataattt gatctttgat gaaggtaaat tgattggttg   4440
tattgatgtt ggtcgtgttg gtattgctga tcgttatcaa gatttagcta ttttatggaa   4500
ttgtttaggt gaattttctc cttctttaca gaaacgttta tttcagaaat atggtattga   4560
taatcctgat atgaacaagt tacaatttca tttaatgttg gacgagttct tttaagaatt   4620
aattcatgac caaaatccct taacgtgagt tttcgttcca ctgagcgtca gaccccgtag   4680
```

```
aaaagatcaa aggatcttct tgagatcctt tttttctgcg cgtaatctgc tgctatttaa   4740
attacgtaca cgtgttatta ctttgttaac gacaattgtc ttaattaact gggcctcatg   4800
ggccttccgc tcactgcccg ctttccagtc gggaaacctg tcgtgccagc tctgcagatg   4860
acggtgaaaa cctctgacac atgcagctcc cggagacggt cacagcttgt ctgtaagcgg   4920
atgccgggag cagacaagcc cgtcagggcg cgtcagcggg tgttggcggg tgtcggggcg   4980
cagccatgac ccagtcacgt agcgatagcg gagtgtatac tggcttaact atgcggcatc   5040
agagcagatt gtactgagag tgcaccatat gcggtgtgaa ataccgcaca gatgcgtaag   5100
gagaaaatac cgcatcaggc gctcttccgc ttcctcgctc actgactcgc tgcgctcggt   5160
cgttcggctg cggcgagcgg tatcagctca ctcaaaggcg gtaatacggt tatccacaga   5220
atcaggggat aacgcaggaa agaacatgtg agcaaaaggc cagcaaaagg ccaggaaccg   5280
taaaaaggcc gcgttgctgg cgtttttcca taggctccgc ccccctgacg agcatcacaa   5340
aaatcgacgc tcaagtcaga ggtggcgaaa cccgacagga ctataaagat accaggcgtt   5400
tccccctgga agctccctcg tgcgctctcc tgttccgacc ctgccgctta ccggatacct   5460
gtccgccttt ctcccttcgg gaagcgtggc gctttctcat agctcacgct gtaggtatct   5520
cagttcggtg taggtcgttc gctccaagct gggctgtgtg cacgaacccc ccgttcagcc   5580
cgaccgctgc gccttatccg gtaactatcg tcttgagtcc aacccggtaa gacacgactt   5640
atcgccactg gcagcagcca ctggtaacag gattagcaga gcgaggtatg taggcggtgc   5700
tacagagttc ttgaagtggt ggcctaacta cggctacact agaaggacag tatttggtat   5760
ctgcgctctg ctgaagccag ttaccttcgg aaaaagagtt ggtagctctt gatccggcaa   5820
acaaaccacc gctggtagcg gtggtttttt tgtttgcaag cagcagatta cgcgcagaaa   5880
aaaaggatct caagaagatc ctttgatctt ttctactgca gaagcttgtt agacaccctg   5940
tcatgtattt tatattattt atttcaccat acggattaag tgaaacctaa tgaaaatagt   6000
actttcggag ctttaacttt aatgaaggta tgttttttta tagacatcga tgtctggttt   6060
aacaatagga aaaagtagct aaaactccca tgaattaaag aaataacaag gtgtctaaca   6120
acctgttatt aagaatgtta gaaaagactt aacatttgtg ttgagttttt atagacattg   6180
gtgtctagac atacggtaga taaggtttgc tcaaaaataa aataaaaaaa gattggacta   6240
aaaaacattt aatttagtac aatttaatta gttatttttt cgtctcaaat tttgctttgt   6300
tgagcagaaa tttagataaa aaaatccccg tgatcagatt acaatgtcgt tcattgtacg   6360
atgtgtcgaa aaatctttac gacactctaa actgaccaca cggggggaaaa agaaaactga   6420
actaataaca tcatgatact cggaaaacct agcaattctc aacccctaaa caaaagaaac   6480
ttccaaaacc ctgaccatat aaaggagtgg caacaatcag caatcagtca agatttgata   6540
gcagaaaatc ttgtatcggt tgctaatggt tttgatgtac tatttatcgg caataaatac   6600
cgaactaaca cgggtgttct gtcacggcac atattaaact cctattctca tttagaagat   6660
ggtggttcgt atggtagaac atttgaccca tttaccaata aagaaatgca gtgggttcaa   6720
tttaaaccga atagaccaag aaaaggttct actggtaagg taatcaaata tgaatcgcca   6780
aaaggtgaac ctacaagagt tctaatgccg tttgtgccta tgaaaatatg gcaacggatt   6840
agcgataagt tcggagtacc gattaatccg aaaaaagata ctcacttttg ggaatgggta   6900
aagaataatc catcgatacc gattgccatt acagaaggaa ataaaaaagc taattgccta   6960
ttatcctatg gctatcctgc tattgccttt gtaggcattt ggaacggatt agagaaaata   7020
```

aatgatttct cgaaggaaaa gcagttaaaa gaggatttga aatggttgtt atccaacggc 7080
aaccgaaata ttaatatcat ctttgaccaa gaccagaaac aaaaaactgt aattaatgta 7140
aacaaagcta ttttcgcttt atcttctcta ataagtagaa atggtcataa agttaatatt 7200
gtgcaatggt tgccgtcaaa aggtaaagga atagatgatt atttggtagc tttacctttt 7260
gagaaaagag aaaatcattt agacaactta attaaaattg caccatcatt taatttttgg 7320
tcaactaaat acttattcaa gtgtcgtaaa ccagatttaa ccgtaaattg ccgttatttg 7380
agcgatgcag taaaagaatt acctcaagag gatatagcat taatagcacc tcacggcacg 7440
ggtaaaactt cattagtagc tactcacgtt aagaatcgga gttatcacgg aaggaaaact 7500
atttcattgg tgcatcttga aagtttagcc aaagctaatg gcaacgcact tggattatat 7560
taccgaaccg aaaataatat tgaaaagcaa tatcttggat ttagcttatg tgtagatagt 7620
tgccgtgata agattaacgg cattacaact gatattattt caggtcaaga ttattgcctt 7680
ttcattgatg aaattgacca agtaattcca cacatcctta acagtgaaac tgaagtaagt 7740
aagtatagat gcaccatcat tgacactttt tctgaactgg tgagaaatgc tgaacaggtc 7800
attattgctg atgctgattt atccgatgtg acgattgacc taatagaaaa catcagaggt 7860
aaaaaactat atgtaatcaa gaatgaatat cagtatcagg gaatgacttt taacgccgtt 7920
ggttcaccat tagaaatgat ggcaatgatg ggaaaatcgg tgtcagaagg caagaaatta 7980
tttattaaca ccacatccca aaaggcaaaa agtaagtacg gcacaatcgc tcttgagtct 8040
tatatttttg gtctaaataa agaagcaaag atattaagaa tagactctga aaccactaaa 8100
aaccctgaac atccagccta taaaatcatt gaccaagact taaataatat cctcaaagat 8160
tatgattatg tcattgcctc accttgcctt caaacaggtg tcagtattac cttaaaaggg 8220
cattttgacc agcaatttaa cttttccagt ggaaacatta cacctcattg ctttttacag 8280
caaatgtggc ggttgaggga tgcagaaatt gaaagattct attatgtgcc gaactcatct 8340
aacctcaatc tcattgggaa taagtcaagt tcaccatcag accttctaaa gagcaataac 8400
aagatggcaa cggcaacggt taaccttttg ggtagaatcg actccgaata ttccctagag 8460
tatgaatcgc acggcatttg gcttgagacg tgggcaaaat tatcagcacg gcataacagt 8520
tcaatgcgtt gttactctga aattcttacc tatctaatta cgtctcaagg gcataaatta 8580
aatatcaaca ttccctcacc tcttgcagat attaagaagc taaatgatga ggtaagtagt 8640
aacagggaaa aggtaaaaaa tgagagatac tctcagaggt taaactcacc agatattaac 8700
gatgcagaag ctaccatact cgaatctaaa gagcaaaaaa tcggattgac tctcaatgag 8760
agatgcaccc tagaaaagca taaagttaag aagcggtatg ggaatgtaaa gatggatatt 8820
ctcacctttg atgatgatgg actatacccc aaactcagac tattttatta cctcaccatc 8880
ggtaaacctc atctcaaggc taatgacaga aaagctattg ccaaaatggg caatgacaat 8940
aaaggcaaga ttctatcaaa agacttagtt aataaaactt actccgctcg tgtgaaggtc 9000
ttagagattc ttaaactaac tgactttatc gacaatctta gagatgaact cttaataact 9060
cccaataatc cagctatcac cgattttaat aatcttctgc taagagctaa gaaggattta 9120
agagtattag gagtcaacat cggaaaatat ccaatggcca acattaatgc cgtacttact 9180
ctcattggtc acaaactttc tgtaatgaga gatgagttcg gaaaagagaa aaggataaaa 9240
gtagatggta aatcataccg atgttatcaa cttgaaacat taccagattt taccaatgat 9300
actcttgact actggttaga aaatgatagc caaaaagaag taacagcaac agaaaattac 9360
tccgaaaatt ttaacccttc aaatagctac aatccagaca gtaagacact ttcagagggt 9420

```
gcaaatttcc tatatataaa taaagaagaa ttgcatccaa ataaattgca cctagaaata   9480
aaagaaggtg ctgaactttt tttattcggg gtaaaggtga ttgtgaaagg aatcttggac   9540
ggggcagtaa ctatattctc tatgggtcaa gaatacgatt tatccctcaa tgaactagag   9600
gggatgttaa catcatgaac tttacaagaa tctttttaaa gggcgatcgc accatgttaa   9660
atgatggtac atttgttcag atatttgata tttaccatga ccacgcattg ggagtgaccc   9720
ttgaccttaa gacagaaaaa attatttccg atgatgttag ggtaattact gtcaaagact   9780
tattgttcga tggcacttat aaaggggtaa aatcttttat gcccgataat gcccgataat   9840
gcccgattga tgctacaaaa tcccataatc ataagcgata atcccctaat agcttgtaat   9900
tcttgaaccg tagcgatttt agagtattcc aaaaagaaga aataaacacc gcaaaatgtc   9960
gtatttcaca tatataaacc aaggtttttt gccctaaaat ctttatgttt gtagtgtgat  10020
gttgggtcaa aatggtcaga aaagttgcaa ggtttttatg gatgcttacg cgcgcgaggg  10080
gtaagcatcc ccaaatagtt actttatcct agtccatgcc catttattgc cgtcccgttc  10140
ggctttaaaa aagtgccaaa actcacaagg tgcaataaaa agttctgtac ctttcgcaac  10200
cctagataat ctttcaacag ttactttttt tcctattatc tcggtacaaa gtttggctag  10260
tttctctttt ccctcttttt caatcaagcc ttcttgtatg cccaactcat tgattaatct  10320
ctctattttt accattattt cccgttcagg tagtttatcc cctaaatctt catcgggggg  10380
caatgtaggg cattctgaag gggctttttc ttctgtctgg acattatcta atattgaagt  10440
aaccaaacta tcttcagttt tttctattcc tattaattca tattcggtta ctgtatccgt  10500
atcaatatcc gaataactat ctttatccgt attagctatt cggttaagtt tatccgttaa  10560
ctcagaaaca agactatata gcggttttag cttttcttct atcctgttat ctaatacgga  10620
taagtttata cggttatcat tatccgtatt agtatcattg ggcttttttg gtagttctac  10680
cccctcataa accgctttta ttcccaattc caacagactg ataacagtat cctttataat  10740
gggttttttg ctgatatggt gaacttttgc cccttccatc attgcgatac tttctatctc  10800
actcatcaac ttatcgctta agtgaatctc gtatctgttt aatcccttac tggttttatt  10860
catatccgtt tactttattc ggttaacaat tctattttat acgaataaaa tattatacgg  10920
ttaactttat acgtttaact attttatcta tacggataac agtaataagt tattcgtatt  10980
agttatacgt ttacttttat ccaaataaaa ttagtgcatt taaactaaaa gaatgatttt  11040
atcggagttg atagcattgg attaacctaa agatgtttat aagctatatc tgataagtat  11100
ttaaggttat tttgttattc tgtttattga cattatcaga ataaaagaat agaatataat  11160
tgttgagaga taagaggttt aagtgattat ggttaagaag ttagttggtt atgtcagggt  11220
cagtagtgaa tcgcaagagg ataacactag cttacagaat cagatagaga gaattgaagc  11280
atattgtatg gcttttggtt atgagttggt aaaaatattc aaagaggttg ccactggtac  11340
aaaagcagat attgaaaccc gtcctatttt taatgaagct atagaatact tgaaacagga  11400
taatgctaat ggaattattg ccttgaagct agaccgaatc gcacggaatg ctttagatgt  11460
attgcgtttg gttcgtgaaa ccttagaacc acaaaataaa atgttagtgt tactagatat  11520
tcaggtagat acttcgacac cttcaggaaa aatgatttta actgtaatga gtgccgttgc  11580
tgaactcgaa agagacatga tctatgatcg cactcagggg ggtagaaaga ctaaagccca  11640
aaagggcggg tatgcctacg ggaaacctaa atttggctat aagactgaag aaaaggaact  11700
aaaagaagat tcagcacaac aggaaactat taaactaatt aagagacacc gtaggtcagg  11760
```

```
gaaaagctac cagaaaatag ctgattatct caatgcccaa agtattccca ctaaacaagg  11820

taagaaatgg agttctagcg tcgtctatcg aatctgtcag gaaaaagctg gttaagtctg  11880

tttatagata tttagaattt attgaataaa aatagtatga acaataaata tttatggact  11940

aaccacgctc ggaaacgttt aactgaacga tgggaaataa aagaatcatg ggttattgat  12000

accatcgaaa atcctgaacg ttcagaattt attgttgatg agtcagggga aaaatatcat  12060

tactataaaa gaatagctaa gtttaagaat agagtgttag aagtgataac ttctgccaac  12120

tcaacaccca caagaataat aaccttttac tttaaccgta acatgaggaa aaatttatga  12180

ttgttactta cgataatgaa gttgacgcaa tttattttaa gttaacggaa aataaaattg  12240

atagcaccga acctcaaaca gacaggatta tcattgatta cgatgaaagt aataatattg  12300

ttggcattga ggtattagat tttaattatc ttgtcaagaa aggtttaacc gttgctgatt  12360

tacctttttc tgaagatgaa agattaacag cttctcaata ttttaatttt cctgttgcta  12420

tctaatccag aaggggcaat aatccccttc tttcatcgag ttagacttaa tatcacaaaa  12480

gtcattttca ttttaccgtt tcttttccac agcgtccgta cgcccctcgt taaatctcaa  12540

aaccgacaat ttatgatgtt tataaaaagt tactcacttt aataagtatt tatactcatt  12600

aaagggttat tctttttttg tagcctgata ggttgggaag gaatatttca gattatcaga  12660

tttgttgaat atttttcgtc agatacgcaa accttacaaa cataattaac aactgaaact  12720

attgatatgt ctaggtttta gctctatcac aggttggatc tg                     12762
```

<210> SEQ ID NO 18
<211> LENGTH: 13354
<212> TYPE: DNA
<213> ORGANISM: Artificial Sequence
<220> FEATURE:
<223> OTHER INFORMATION: TK471\ pABICyano1::pilT-PrbcLABICyano1_Km** pilC-sacB-oriVT

<400> SEQUENCE: 18

```
aatattttc gtcagatacg caaaccttac aaacataatt aacaactgaa actattgata     60

tgtctaggtt ttagctctat cacaggttgg atctgtcgac gatccttttt aacccatcac    120

atatacctgc cgttcactat tatttagtga aatgagatat tatgatattt tctgaattgt    180

gattaaaaag gcaactttat gcccatgcaa cagaaactat aaaaaaatac gagaatgaaa    240

agaaacagat agattttttta gttctttagg cccgtagtct gcaaatcctt ttatgatttt    300

ctatcaaaca aaagaggaaa atagaccagt tgcaatccaa acgagagtct aatagaatga    360

ggtcgaaaag taaatcgcgc gggtttgtta ctgataaagc aggcaagacc taaaatgtgt    420

aaagggcaaa gtgtatactt tggcgtcacc ccttacatat tttaggtctt tttttattgt    480

gcgtaactaa cttgccatct tcaaacagga gggctggaag aagcagaccg ctaacacagt    540

acataaaaaa ggagacatga acgatgaaca tcaaaaagtt tgcaaaacaa gcaacagtat    600

taacctttac taccgcactg ctggcaggag gcgcaactca agcgtttgcg aaagaaacga    660

accaaaagcc atataaggaa acatacggca tttcccatat tacacgccat gatatgctgc    720

aaatccctga acagcaaaaa aatgaaaaat atcaagttcc tgaattcgat tcgtccacaa    780

ttaaaaatat ctcttctgca aaaggcctgg aggtttggga cagctggcca ttacaaaacg    840

ctgacggcac tgtcgcaaac tatcacggct accacatcgt ctttgcatta gccggagatc    900

ctaaaaatgc ggatgacaca tcgatttaca tgttctatca aaaagtcggc gaaacttcta    960

ttgacagctg gaaaaacgct ggccgcgtct ttaaagacag cgacaaattc gatgcaaatg   1020
```

```
attctatcct aaaagaccaa acacaagaat ggtcaggttc agccacattt acatctgacg   1080
gaaaaatccg tttattctac actgatttct ccggtaaaca ttacggcaaa caaacactga   1140
caactgcaca agttaacgta tcagcatcag acagctcttt gaacatcaac ggtgtagagg   1200
attataaatc aatctttgac ggtgacggaa aaacgtatca aaatgtacag cagttcatcg   1260
atgaaggcaa ctacagctca ggcgacaacc atacgctgag agatcctcac tacgtagaag   1320
ataaaggcca caaatactta gtatttgaag caaacactgg aactgaagat ggctaccaag   1380
gcgaagaatc tttatttaac aaagcatact atggcaaaag cacatcattc ttccgtcaag   1440
aaagtcaaaa acttctgcaa agcgataaaa aacgcacggc tgagttagca aacggcgctc   1500
tcggtatgat tgagctaaac gatgattaca cactgaaaaa agtgatgaaa ccgctgattg   1560
catctaacac agtaacagat gaaattgaac gcgcgaacgt ctttaaaatg aacggcaaat   1620
ggtacctgtt cactgactcc cgcggatcaa aaatgacgat tgacggcatt acgtctaacg   1680
atatttacat gcttggttat gtttctaatt ctttaactgg cccatacaag ccgctgaaca   1740
aaactggcct tgtgttaaaa atggatcttg atcctaacga tgtaaccttt acttactcac   1800
acttcgctgt acctcaagcg aaaggaaaca atgtcgtgat tacaagctat atgacaaaca   1860
gaggattcta cgcagacaaa caatcaacgt ttgcgccaag cttcctgctg aacatcaaag   1920
gcaagaaaac atctgttgtc aaagacagca tccttgaaca aggacaatta acagttaaca   1980
aataaaaacg caaaagaaaa tgccgatatc ctattggcat ttcttttat ttcttatcaa    2040
cataaaggtg aatcccatat gaactatgga tcggcgcagc atgctcccgg ccgccatcac   2100
tagtgctcga tgacgctggt taatgcctta actgcttgtt ctacttcatc ttcataaaaa   2160
tctgcaactt tcatcatcat tgcatctaat tcccccgttt cttcaccaat catcatcatt   2220
tgaattgcca tagagggaaa aacctttctt tccgagatcg caacacttaa catacctcct   2280
tctaaaatag aatcttttgc ggcgccaatg gcattagaaa ttactttatt agggatagtc   2340
tcttgagata tttctaaaca ttgtaagata ggcacaccag aacgggttaa agtaccaaaa   2400
atacgacaaa aacgagcaac agcacttttt tcatttaagt ccccaaaaat gggagcttta   2460
agtgcgatcg tatctatttg taaacgtcca gcaggagttt tataatattg acggaaggca   2520
aaaacaaccc caataatcac acccacggga ataattgctt tccagctacg caaaaaatca   2580
ctaagagtaa ccataaattg agtcaaagcc ggcaattctg cacccaattg gtcgaaaata   2640
ccagcaaata caggaatcaa gaaaatggtc atacccaaaa aagcaatgac cgcaaaaata   2700
ccaacagtga caggataagc cattgctgat ttaatttggt tttgcaaacg agcaacatct   2760
tcgagaagtt tagcaagacg attcatgact tcgtctaaaa ccccccctgt ttctcccgct   2820
tctaccatac tcacatatag cctatcaaaa cagtcgggat gctttgccat tgcttcagat   2880
aaattaaccc cctgttgaac atcctctcca atagtagtta gagccttctt aaatttagga   2940
tttcctgatt gctctgccaa tactgacaaa gagcggccgc atttaaatag cagcagatta   3000
cgcgcagaaa aaaaggatct caagaagatc ctttgatctt ttctacgggg tctgacgctc   3060
agtggaacga aaactcacgt taagggattt tggtcatgaa ttaattctta aaagaactcg   3120
tccaacatta aatgaaattg taacttgttc atatcaggat tatcaatacc atatttctga   3180
aataaacgtt tctgtaaaga aggagaaaat tcacctaaac aattccataa aatagctaaa   3240
tcttgataac gatcagcaat accaacacga ccaacatcaa tacaaccaat caatttacct   3300
tcatcaaaga tcaaattatc taaagaaaaa tcaccatgag taacaacaga atcaggagaa   3360
aaaggtaaca atttgtgcat ttctttccaa acttgttcaa caggccaacc attacgttca   3420
```

```
tcatcaaaat cagaagcatc aactaaacca ttattcatac gagattgagc ttgagctaaa   3480
cgaaaaacac gatcagaatt aaaaggacaa ttacaaacgg gaatagaatg taaacgacgt   3540
aaaaaaacag ctaaagcatc aacaatattt tcaccagaat caggatattc ttctaaaact   3600
tgaaaagcag ttttaccagg aatagcagta gttaataacc aagcatcatc gggagtacga   3660
ataaaatgtt taatagtagg taaaggcata aattcagtca accagtttaa acgaaccatt   3720
tcatcagtaa catcattagc aacagaacct ttaccatgtt tcaagaataa ttcaggagca   3780
tcaggtttac catataaacg ataaatagta gcaccagatt gaccaacatt atcacgagcc   3840
catttataac catataaatc ggcatccata ttagaattta aacgaggacg agaacaacta   3900
gtttcacgtt gaatatgaga catggttggt atcctccaaa tatataaatt ttctttatag   3960
cgttatatgt aacaacttct tttaatggaa gttagttttt tggcttttgc ttttcgagtt   4020
taaatcttat catgaagggg atcattttct atacacccag attaactatt tacgattatt   4080
atttttctg aatttgatta acttaactaa tctaattctc tatgcttacc ccagactatt   4140
ctctaggtat tttaaactgc taatttttcc ctctttaacg ttataaaagt cagaatttca   4200
catttcttta cactttgagg ttaaattatt acgattatta gttttcctta tgttttaatt   4260
aaaaaggtaa cgatgcacta ggcaaaggag aattgttgat aattaataac ttctaactct   4320
ttcctgtacg ggagaatgcc cattagcccc taactaactc cgtaccgctt tgcggaacga   4380
gcgctcgagc gttctctccg aactaatttc tccctctccc ctcatctata ataagatagt   4440
taataattac atcgacaatt gtctacgtag gcgcgccatg cggccttgac ggccttccgc   4500
caattcgccc tatagtgagt cgtattacgt cgcgctcact ggccgtcgtt ttacaacgtc   4560
gtgactggga aaaccctggc gttacccaac ttaatcgcct tgcagcacat ccccctttcg   4620
ccagctgcgc cggatccctg caggtcgacg atcgcaggtg tcacaatcat gatttcttga   4680
gccattgccc taccaaattc gcccggtttg ggatttttct ttttagccaa agtttgagca   4740
aatactgcca ataaagagtt agataacatt gctctaattt gggcttgttc tgccgaagga   4800
aatacatcaa taatacgatc aattgttccc gccgcagagc tagtatgtaa agtaccaaag   4860
acaaggtgtc cagtttccgc cgccgtaatc gccaaagaaa tggtttctaa gtcgcgcatc   4920
tcacccacta gaataatatc tggatcttcc cttaacgccg cttttaaggc attggcaaaa   4980
cttttagtat cttctccttt ttgacgttgg tgaaatagac tgttaatatt gggaaaaaca   5040
tactcgatcg gatcttctac tgttaagatg tgttctgcac gagtgcggtt aattaagtcc   5100
aacattgccg ctaaagtagt agtttttcca gaacctgtct gccctgtcac taaaatcata   5160
cccctagggc gttcggacat ctccttgaca atatctggta agcctaattg atcaaaattg   5220
ggaattttgg aagataaagc ccttaaacaa gcggcataac aaccccttc cttataaaca   5280
tttacacgaa atcgagccaa gccttttacc ccgtaggaac agtctaactc ccattcttgc   5340
tctaatgttt tacgttgagt attattgagc atactaaaaa ttaatttttg gcactcttga   5400
gcattaaggg gttcatctcc aatgcaaaat tacgtacacg tgttattact ttgttaacga   5460
caattgtctt aattaactgg cctcatgggc cttccgctca ctgcccgctt tccagtcggg   5520
aaacctgtcg tgccagctct gcagatgacg gtgaaaacct ctgacacatg cagctcccgg   5580
agacggtcac agcttgtctg taagcggatg ccgggagcag acaagcccgt cagggcgcgt   5640
cagcgggtgt tggcgggtgt cggggcgcag ccatgaccca gtcacgtagc gatagcggag   5700
tgtatactgg cttaactatg cggcatcaga gcagattgta ctgagagtgc accatatgcg   5760
```

-continued gtgtgaaata ccgcacagat gcgtaaggag aaaataccgc atcaggcgct cttccgcttc 5820
ctcgctcact gactcgctgc gctcggtcgt tcggctgcgg cgagcggtat cagctcactc 5880
aaaggcggta atacggttat ccacagaatc aggggataac gcaggaaaga acatgtgagc 5940
aaaaggccag caaaaggcca ggaaccgtaa aaaggccgcg ttgctggcgt ttttccatag 6000
gctccgcccc cctgacgagc atcacaaaaa tcgacgctca agtcagaggt ggcgaaaccc 6060
gacaggacta taaagatacc aggcgtttcc ccctggaagc tccctcgtgc gctctcctgt 6120
tccgaccctg ccgcttaccg gatacctgtc cgcctttctc ccttcgggaa gcgtggcgct 6180
ttctcaatgc tcacgctgta ggtatctcag ttcggtgtag gtcgttcgct ccaagctggg 6240
ctgtgtgcac gaaccccccg ttcagcccga ccgctgcgcc ttatccggta actatcgtct 6300
tgagtccaac ccggtaagac acgacttatc gccactggca gcagccactg gtaacaggat 6360
tagcagagcg aggtatgtag gcggtgctac agagttcttg aagtggtggc ctaactacgg 6420
ctacactaga aggacagtat ttggtatctg cgctctgctg aagccagtta ccttcggaaa 6480
aagagttggt agctcttgat ccggcaaaca aaccaccgct ggtagcggtg gtttttttgt 6540
ttgcaagcag cagattacgc gcagaaaaaa aggatctcaa gaagatcctt tgatcttttc 6600
tactgcagaa gcttgttaga caccctgtca tgtattttat attatttatt tcaccatacg 6660
gattaagtga aacctaatga aaatagtact ttcggagctt taactttaat gaaggtatgt 6720
tttttatag acatcgatgt ctggtttaac aataggaaaa agtagctaaa actcccatga 6780
attaaagaaa taacaaggtg tctaacaacc tgttattaag aatgttagaa aagacttaac 6840
atttgtgttg agtttttata gacattggtg tctagacata cggtagataa ggtttgctca 6900
aaaataaaat aaaaaaagat tggactaaaa aacatttaat ttagtacaat ttaattagtt 6960
atttttcgt ctcaaatttt gctttgttga gcagaaattt agataaaaaa atccccgtga 7020
tcagattaca atgtcgttca ttgtacgatg tgtcgaaaaa tctttacgac actctaaact 7080
gaccacacgg gggaaaaaga aaactgaact aataacatca tgatactcgg aaaacctagc 7140
aattctcaac ccctaaacaa aagaaacttc caaaaccctg accatataaa ggagtggcaa 7200
caatcagcaa tcagtcaaga tttgatagca gaaaatcttg tatcggttgc taatggtttt 7260
gatgtactat ttatcggcaa taaataccga actaacacgg gtgttctgtc acggcacata 7320
ttaaactcct attctcattt agaagatggt ggttcgtatg gtagaacatt tgacccattt 7380
accaataaag aaatgcagtg ggttcaattt aaaccgaata gaccaagaaa aggttctact 7440
ggtaaggtaa tcaaatatga atcgccaaaa ggtgaaccta caagagttct aatgccgttt 7500
gtgcctatga aaatatggca acggattagc gataagttcg gagtaccgat taatccgaaa 7560
aaagatactc acttttggga atgggtaaag aataatccat cgataccgat tgccattaca 7620
gaaggaaata aaaaagctaa ttgcctatta tcctatggct atcctgctat tgcctttgta 7680
ggcatttgga acggattaga gaaaataaat gatttctcga aggaaaagca gttaaaagag 7740
gatttgaaat ggttgttatc caacggcaac cgaaatatta atatcatctt tgaccaagac 7800
cagaaacaaa aaactgtaat taatgtaaac aaagctattt tcgctttatc ttctctaata 7860
agtagaaatg gtcataaagt taatattgtg caatggttgc cgtcaaaagg taaaggaata 7920
gatgattatt tggtagcttt acctttgag aaaagagaaa atcatttaga caacttaatt 7980
aaaattgcac catcatttaa tttttggtca actaaatact tattcaagtg tcgtaaacca 8040
gatttaaccg taaattgccg ttatttgagc gatgcagtaa aagaattacc tcaagaggat 8100
atagcattaa tagcacctca cggcacgggt aaaacttcat tagtagctac tcacgttaag 8160

-continued

```
aatcggagtt atcacggaag gaaaactatt tcattggtgc atcttgaaag tttagccaaa   8220
gctaatggca acgcacttgg attatattac cgaaccgaaa ataatattga aaagcaatat   8280
cttggattta gcttatgtgt agatagttgc cgtgataaga ttaacggcat tacaactgat   8340
attatttcag gtcaagatta ttgccttttc attgatgaaa ttgaccaagt aattccacac   8400
atccttaaca gtgaaactga agtaagtaag tatagatgca ccatcattga cacttttttct   8460
gaactggtga gaaatgctga acaggtcatt attgctgatg ctgatttatc cgatgtgacg   8520
attgacctaa tagaaaacat cagaggtaaa aaactatatg taatcaagaa tgaatatcag   8580
tatcagggaa tgacttttaa cgccgttggt tcaccattag aaatgatggc aatgatggga   8640
aaatcggtgt cagaaggcaa gaaattattt attaacacca catcccaaaa ggcaaaaagt   8700
aagtacggca caatcgctct tgagtcttat atttttggtc taaataaaga agcaaagata   8760
ttaagaatag actctgaaac cactaaaaac cctgaacatc cagcctataa aatcattgac   8820
caagacttaa ataatatcct caaagattat gattatgtca ttgcctcacc ttgccttcaa   8880
acaggtgtca gtattacctt aaaagggcat tttgaccagc aatttaactt ttccagtgga   8940
aacattacac ctcattgctt tttacagcaa atgtggcggt tgagggatgc agaaattgaa   9000
agattctatt atgtgccgaa ctcatctaac ctcaatctca ttgggaataa gtcaagttca   9060
ccatcagacc ttctaaagag caataacaag atggcaacgg caacggttaa ccttttgggt   9120
agaatcgact ccgaatattc cctagagtat gaatcgcacg gcatttggct tgagacgtgg   9180
gcaaaattat cagcacggca taacagttca atgcgttgtt actctgaaat tcttacctat   9240
ctaattacgt ctcaagggca taaattaaat atcaacattc cctcacctct tgcagatatt   9300
aagaagctaa atgatgaggt aagtagtaac agggaaaagg taaaaaatga gagatactct   9360
cagaggttaa actcaccaga tattaacgat gcagaagcta ccatactcga atctaaagag   9420
caaaaaatcg gattgactct caatgagaga tgcaccctag aaaagcataa agttaagaag   9480
cggtatggga atgtaaagat ggatattctc acctttgatg atgatggact ataccccaaa   9540
ctcagactat tttattacct caccatcggt aaacctcatc tcaaggctaa tgacagaaaa   9600
gctattgcca aaatgggcaa tgacaataaa ggcaagattc tatcaaaaga cttagttaat   9660
aaaacttact ccgctcgtgt gaaggtctta gagattctta aactaactga ctttatcgac   9720
aatcttagag atgaactctt aataactccc aataatccag ctatcaccga ttttaataat   9780
cttctgctaa gagctaagaa ggatttaaga gtattaggag tcaacatcgg aaaatatcca   9840
atggccaaca ttaatgccgt acttactctc attggtcaca aactttctgt aatgagagat   9900
gagttcggaa aagagaaaag gataaaagta gatggtaaat cataccgatg ttatcaactt   9960
gaaacattac cagattttac caatgatact cttgactact ggttagaaaa tgatagccaa  10020
aaagaagtaa cagcaacaga aaattactcc gaaaatttta acccttcaaa tagctacaat  10080
ccagacagta agacactttc agagggtgca aatttcctat atataaataa agaagaattg  10140
catccaaata aattgcacct agaaataaaa gaaggtgctg aacttttttt attcggggta  10200
aaggtgattg tgaaaggaat cttggacggg gcagtaacta tattctctat gggtcaagaa  10260
tacgatttat ccctcaatga actagagggg atgttaacat catgaacttt acaagaatct  10320
ttttaaaggg cgatcgcacc atgttaaatg atggtacatt tgttcagata tttgatattt  10380
accatgacca cgcattggga gtgacccttg accttaagac agaaaaaatt atttccgatg  10440
atgttagggt aattactgtc aaagacttat tgttcgatgg cacttataaa ggggtaaaat  10500
```

-continued

```
cttttatgcc cgataatgcc cgataatgcc cgattgatgc tacaaaatcc cataatcata  10560
agcgataatc ccctaatagc ttgtaattct tgaaccgtag cgattttaga gtattccaaa  10620
aagaagaaat aaacaccgca aaatgtcgta tttcacatat ataaaccaag gtttttgcc  10680
ctaaaatctt tatgtttgta gtgtgatgtt gggtcaaaat ggtcagaaaa gttgcaaggt  10740
ttttatggat gcttacgcgc gcgaggggta agcatcccca aatagttact ttatcctagt  10800
ccatgcccat ttattgccgt cccgttcggc tttaaaaaag tgccaaaact cacaaggtgc  10860
aataaaaagt tctgtacctt tcgcaaccct agataatctt tcaacagtta cttttttcc  10920
tattatctcg gtacaaagtt tggctagttt ctcttttccc tctttttcaa tcaagccttc  10980
ttgtatgccc aactcattga ttaatctctc tatttttacc attatttccc gttcaggtag  11040
tttatcccct aaatcttcat cggggggcaa tgtagggcat tctgaagggg ctttttcttc  11100
tgtctggaca ttatctaata ttgaagtaac caaactatct tcagtttttt ctattcctat  11160
taattcatat tcggttactg tatccgtatc aatatccgaa taactatctt tatccgtatt  11220
agctattcgg ttaagtttat ccgttaactc agaaacaaga ctatatagcg gttttagctt  11280
ttcttctatc ctgttatcta atacggataa gtttatacgg ttatcattat ccgtattagt  11340
atcattgggc tttttggta gttctacccc ctcataaacc gcttttattc ccaattccaa  11400
cagactgata acagtatcct ttataatggg tttttgctg atatggtgaa cttttgcccc  11460
ttccatcatt gcgatacttt ctatctcact catcaactta tcgcttaagt gaatctcgta  11520
tctgtttaat cccttactgg ttttattcat atccgtttac tttattcggt taacaattct  11580
attttatacg aataaaatat tatacggtta actttatacg tttaactatt ttatctatac  11640
ggataacagt aataagttat tcgtattagt tatacgttta cttttatcca aataaaatta  11700
gtgcatttaa actaaaagaa tgattttatc ggagttgata gcattggatt aacctaaaga  11760
tgtttataag ctatatctga taagtattta aggttatttt gttattctgt ttattgacat  11820
tatcagaata aaagaataga atataattgt tgagagataa gaggtttaag tgattatggt  11880
taagaagtta gttggttatg tcagggtcag tagtgaatcg caagaggata acactagctt  11940
acagaatcag atagagagaa ttgaagcata ttgtatggct tttggttatg agttggtaaa  12000
aatattcaaa gaggttgcca ctggtacaaa agcagatatt gaaacccgtc ctatttttaa  12060
tgaagctata gaatacttga aacaggataa tgctaatgga attattgcct tgaagctaga  12120
ccgaatcgca cggaatgctt tagatgtatt gcgtttggtt cgtgaaacct tagaaccaca  12180
aaataaaatg ttagtgttac tagatattca ggtagatact tcgacacctt caggaaaaat  12240
gattttaact gtaatgagtg ccgttgctga actcgaaaga gacatgatct atgatcgcac  12300
tcagggggt agaaagacta aagcccaaaa gggcgggtat gcctacggga aacctaaatt  12360
tggctataag actgaagaaa aggaactaaa agaagattca gcacaacagg aaactattaa  12420
actaattaag agacaccgta ggtcagggaa aagctaccag aaaatagctg attatctcaa  12480
tgcccaaagt attcccacta aacaaggtaa gaaatggagt tctagcgtcg tctatcgaat  12540
ctgtcaggaa aaagctggtt aagtctgttt atagatattt agaatttatt gaataaaaat  12600
agtatgaaca ataaatattt atggactaac cacgctcgga aacgtttaac tgaacgatgg  12660
gaaataaaag aatcatgggt tattgatacc atcgaaaatc ctgaacgttc agaatttatt  12720
gttgatgagt caggggaaaa atatcattac tataaaagaa tagctaagtt taagaataga  12780
gtgttagaag tgataacttc tgccaactca acacccacaa gaataataac cttttacttt  12840
aaccgtaaca tgaggaaaaa tttatgattg ttacttacga taatgaagtt gacgcaattt  12900
```

```
attttaagtt aacggaaaat aaaattgata gcaccgaacc tcaaacagac aggattatca  12960
ttgattacga tgaaagtaat aatattgttg gcattgaggt attagatttt aattatcttg  13020
tcaagaaagg tttaaccgtt gctgatttac ctttttctga agatgaaaga ttaacagctt  13080
ctcaatattt taattttcct gttgctatct aatccagaag ggcaataat  cccttcttt   13140
catcgagtta gacttaatat cacaaaagtc attttcattt taccgtttct tttccacagc  13200
gtccgtacgc ccctcgttaa atctcaaaac cgacaattta tgatgtttat aaaaagttac  13260
tcactttaat aagtatttat actcattaaa gggttattct ttttttgtag cctgataggt  13320
tgggaaggaa tatttcagat tatcagattt gttg                              13354
```

<210> SEQ ID NO 19
<211> LENGTH: 12763
<212> TYPE: DNA
<213> ORGANISM: Artificial Sequence
<220> FEATURE:
<223> OTHER INFORMATION: #1629\\pABICyano1::PnirA(opt2)-
zmPDC(opt1)_dsrA-Prbc*(optRBS)-synADH(opt1)_ter

<400> SEQUENCE: 19

```
tcgacaatta ataacttctt cctgtacggg cgaatggcca tttgctccta actaactccg     60
tactgctttg cggaacgagc gtagcgaact ctccgaatta ctaagccttc atccctgata    120
gatgcaaaaa acgaattaaa attatgtgta aaaagaaaat gtgtctttat ttagtagtca    180
aagttacaaa atattaagaa tcaaattaat aatgtattgg gcagttaagt atataagtct    240
ttaaatattt atttgtattc aatatattaa ggaggatcag ccttatgaat tcttataccg    300
tgggtactta tttagccgaa cgcttagtgc aaattggttt aaaacatcat tttgccgtgg    360
ctggggacta taatttagtg ttattggata acttattatt aaataaaaac atggaacaag    420
tgtattgttg taatgaatta aattgtggtt tttctgctga aggttatgct agagctaaag    480
gtgcagctgc tgctgttgtt acttattctg tgggtgcttt atctgctttt gatgctattg    540
gtggtgctta tgccgaaaat ttacccgtga ttttaatttc tggtgcccct aataataatg    600
atcatgccgc tggacatgtt ttacatcatg ccttaggtaa aaccgattat cattatcaat    660
tagaaatggc caaaaatatt actgctgctg ccgaagctat ttatactcct gaagaagccc    720
ctgccaaaat tgatcatgtg attaaaaccg ccttacgcga aaaaaaaccc gtgtatttag    780
aaattgcctg taatattgct tctatgcctt gtgctgctcc tgggcctgct tctgctttat    840
ttaatgatga agcctctgat gaagctagtt taaatgctgc cgtggaagaa accttaaaat    900
ttattgccaa tcgcgataaa gttgccgtgt tagttggttc taaattaaga gctgctggtg    960
ctgaagaagc tgctgttaaa tttgctgatg ctttaggtgg tgcagttgct actatggctg   1020
ctgccaaatc ttttttcccc gaagaaaatc cccattatat tggaactagt tggggagaag   1080
tttcttatcc tggtgtggaa aaaactatga aagaagccga cgctgttatt gctttagccc   1140
ctgtgtttaa tgattattct accactggtt ggactgatat tcccgatccc aaaaaaattag  1200
ttttagccga acctcgttct gttgttgtta atggtgttcg ctttccctct gtgcatttaa   1260
aagattattt aacccgctta gcccaaaaag tttctaaaaa aactggtgcc ttagattttt   1320
ttaaatcttt aaatgcgggt gaattaaaaa aagctgctcc tgctgatcct tctgctcctt   1380
tagttaatgc tgaaattgcc cgtcaagttg aagccttatt aacccctaat actaccgtta   1440
ttgccgaaac tggtgattct tggtttaatg cccaacgcat gaaattacct aatggtgccc   1500
gtgttgaata tgaaatgcaa tggggtcata ttggttggtc tgtacctgct gcttttggtt   1560
```

```
atgctgttgg tgctcctgaa cgtcgtaata ttttaatggt gggtgatggt tcttttcaat   1620
taactgccca agaagttgcc caaatggttc gcttaaaatt acccgttatt attttttttaa   1680
taaataatta tggttatacc attgaagtga tgattcatga tgggccatat aataatatta   1740
aaaattggga ttatgcgggt ttaatggaag tgtttaatgg taatggtggt tatgattctg   1800
gtgctggtaa aggtttaaaa gccaaaactg gtggtgaatt agctgaagct attaaagttg   1860
ccttagccaa tactgatggg ccaaccttaa ttgaatgttt tattggtcgc gaagattgta   1920
ccgaagaatt agttaaatgg ggtaaacgtg ttgctgctgc taattctcgc aaacccgtga   1980
ataaattatt gtaattttttg gggatcaatt cgagctcagc aagtttcatc ccgacccccct   2040
cagggtcggg atttttttat tgtactagtt gacataagta aaggcatccc ctgcgtgata   2100
taattacctt cagtttaagg aggtatacac atatgattaa agcctatgct gccttagaag   2160
ccaatggtaa attacaaccc tttgaatatg atcctggtgc tttaggtgcc aatgaagtgg   2220
aaattgaagt gcaatattgt ggtgtgtgtc attctgattt atctatgatt aataatgaat   2280
ggggtatttc taattatccc ttagttcctg gtcatgaagt tgttggtact gttgctgcta   2340
tgggtgaagg tgttaatcat gtggaagtgg gtgatttagt tggtttaggt tggcattctg   2400
gttattgtat gacctgtcat tcttgtttat ctggttatca taatttatgt gccactgccg   2460
aatctactat tgtgggtcat tatggtggtt ttggtgatag agttcgtgct aaaggtgttt   2520
ctgtggtgaa attacccaaa ggtattgatt tagcctctgc tgggccttta ttttgtggtg   2580
gtattaccgt tttttctccc atggtggaat tatctttaaa acctaccgcc aaagttgctg   2640
ttattggtat tggtggttta ggtcatttag ccgttcaatt tttaagagcc tggggttgtg   2700
aagttactgc ttttacctct tctgcccgta aacaaaccga agttttagaa ttaggtgccc   2760
atcatatttt agattctacc aatcctgaag ctattgcttc tgccgaaggt aaatttgatt   2820
atattatttc taccgtgaat ttaaaattag attggaattt atatatcagt accttagccc   2880
ctcaaggtca ttttcatttt gttggtgtgg tgttagaacc cttggactta aacttatttc   2940
ccttattaat gggacaacgt tctgtttctg cttctcctgt tggttctcct gctactattg   3000
ccactatgtt agattttgcc gtgcgtcatg atattaaacc cgtggtggaa caattttctt   3060
ttgatcaaat taatgaagcc attgcccatt tagaatctgg taaagcccat tatcgcgtgg   3120
tgttatctca ttctaaaaat taataagatt aacttctaaa ctgaaacaaa tttgagggta   3180
ggcttcattg tctgccctta ttttttttatt taggaaaagt gaacagacta aagagtgttg   3240
gctctattgc tttgagtatg taaattaggc gttgctgaat taaggtatga tttttgaccc   3300
cttctctctt ctgcaggatc atcttgctga aaaactcgag cgctcgttcc gcaaagcggt   3360
acggagttag ttaggggcta atgggcattc tcccgtacag gaaagagtta gaagttatta   3420
attatcaaca attctccttt gcctagtgca tcgttacctt tttaattaaa acataaggaa   3480
aactaataat cgtaataatt taacctcaaa gtgtaaagaa atgtgaaatt ctgactttta   3540
taacgttaaa gagggaaaaa ttagcagttt aaaataccta gagaatagtc tggggtaagc   3600
atagagaatt agattagtta agttaatcaa attcagaaaa aataataatc gtaaatagtt   3660
aatctgggtg tatagaaaat gatccccttc atgataagat ttaaactcga aaagcaaaag   3720
ccaaaaaact aacttccatt aaaagaagtt gttacatata acgctataaa gaaaatttat   3780
atatttggag gataccaacc atgtctcata ttcaacgtga aactagttgt tctcgccctc   3840
gtttaaattc taatatggat gccgatttat atggttataa atgggctcgt gataatgttg   3900
```

```
gtcaatctgg tgctactatt tatcgtttat atggtaaacc tgatgctcct gaattattct   3960
tgaaacatgg taaaggttct gttgctaatg atgttactga tgaaatggtt cgtttaaact   4020
ggttgactga atttatgcct ttacctacta ttaaacattt tattcgtact cccgatgatg   4080
cttggttatt aactactgct attcctggta aaactgcttt tcaagtttta gaagaatatc   4140
ctgattctgg tgaaaatatt gttgatgctt tagctgtttt tttacgtcgt ttacattcta   4200
ttcccgtttg taattgtcct tttaattctg atcgtgtttt tcgtttagct caagctcaat   4260
ctcgtatgaa taatggttta gttgatgctt ctgattttga tgatgaacgt aatggttggc   4320
ctgttgaaca agtttggaaa gaaatgcaca aattgttacc tttttctcct gattctgttg   4380
ttactcatgg tgattttcct ttagataatt tgatctttga tgaaggtaaa ttgattggtt   4440
gtattgatgt tggtcgtgtt ggtattgctg atcgttatca agatttagct attttatgga   4500
attgtttagg tgaattttct ccttctttac agaaacgttt atttcagaaa tatggtattg   4560
ataatcctga tatgaacaag ttacaatttc atttaatgtt ggacgagttc ttttaagaat   4620
taattcatga ccaaaatccc ttaacgtgag ttttcgttcc actgagcgtc agaccccgta   4680
gaaaagatca aaggatcttc ttgagatcct ttttttctgc gcgtaatctg ctgctattta   4740
aattacgtac acgtgttatt actttgttaa cgacaattgt cttaattaac tgggcctcat   4800
gggccttccg ctcactgccc gctttccagt cgggaaacct gtcgtgccag ctctgcagat   4860
gacggtgaaa acctctgaca catgcagctc ccggagacgg tcacagcttg tctgtaagcg   4920
gatgccggga gcagacaagc ccgtcagggc gcgtcagcgg gtgttggcgg gtgtcggggc   4980
gcagccatga cccagtcacg tagcgatagc ggagtgtata ctggcttaac tatgcggcat   5040
cagagcagat tgtactgaga gtgcaccata tgcggtgtga aataccgcac agatgcgtaa   5100
ggagaaaata ccgcatcagg cgctcttccg cttcctcgct cactgactcg ctgcgctcgg   5160
tcgttcggct gcggcgagcg gtatcagctc actcaaaggc ggtaatacgg ttatccacag   5220
aatcagggga taacgcagga aagaacatgt gagcaaaagg ccagcaaaag gccaggaacc   5280
gtaaaaaggc cgcgttgctg gcgtttttcc ataggctccg cccccctgac gagcatcaca   5340
aaaatcgacg ctcaagtcag aggtggcgaa acccgacagg actataaaga taccaggcgt   5400
ttccccctgg aagctccctc gtgcgctctc ctgttccgac cctgccgctt accggatacc   5460
tgtccgcctt tctcccttcg ggaagcgtgg cgctttctca tagctcacgc tgtaggtatc   5520
tcagttcggt gtaggtcgtt cgctccaagc tgggctgtgt gcacgaaccc cccgttcagc   5580
ccgaccgctg cgccttatcc ggtaactatc gtcttgagtc caacccggta agacacgact   5640
tatcgccact ggcagcagcc actggtaaca ggattagcag agcgaggtat gtaggcggtg   5700
ctacagagtt cttgaagtgg tggcctaact acggctacac tagaaggaca gtatttggta   5760
tctgcgctct gctgaagcca gttaccttcg gaaaaagagt tggtagctct tgatccggca   5820
aacaaaccac cgctggtagc ggtggttttt ttgtttgcaa gcagcagatt acgcgcagaa   5880
aaaaaggatc tcaagaagat cctttgatct tttctactgc agaagcttgt tagacaccct   5940
gtcatgtatt ttatattatt tatttcacca tacggattaa gtgaaaccta atgaaaatag   6000
tactttcgga gctttaactt taatgaaggt atgttttttt atagacatcg atgtctggtt   6060
taacaatagg aaaaagtagc taaaactccc atgaattaaa gaaataacaa ggtgtctaac   6120
aacctgttat taagaatgtt agaaaagact taacatttgt gttgagtttt tatagacatt   6180
ggtgtctaga catacggtag ataaggtttg ctcaaaaata aaataaaaaa agattggact   6240
aaaaaacatt taatttagta caatttaatt agttattttt tcgtctcaaa ttttgctttg   6300
```

```
ttgagcagaa atttagataa aaaaatcccc gtgatcagat tacaatgtcg ttcattgtac   6360
gatgtgtcga aaaatcttta cgacactcta aactgaccac acgggggaaa aagaaaactg   6420
aactaataac atcatgatac tcggaaaacc tagcaattct caacccctaa acaaaagaaa   6480
cttccaaaac cctgaccata taaaggagtg gcaacaatca gcaatcagtc aagatttgat   6540
agcagaaaat cttgtatcgg ttgctaatgg ttttgatgta ctatttatcg gcaataaata   6600
ccgaactaac acgggtgttc tgtcacggca catattaaac tcctattctc atttagaaga   6660
tggtggttcg tatggtagaa catttgaccc atttaccaat aaagaaatgc agtgggttca   6720
atttaaaccg aatagaccaa gaaaaggttc tactggtaag gtaatcaaat atgaatcgcc   6780
aaaaggtgaa cctacaagag ttctaatgcc gtttgtgcct atgaaaatat ggcaacggat   6840
tagcgataag ttcggagtac cgattaatcc gaaaaaagat actcactttt gggaatgggt   6900
aaagaataat ccatcgatac cgattgccat tacagaagga aataaaaaag ctaattgcct   6960
attatcctat ggctatcctg ctattgcctt tgtaggcatt tggaacggat tagagaaaat   7020
aaatgatttc tcgaaggaaa agcagttaaa agaggatttg aaatggttgt tatccaacgg   7080
caaccgaaat attaatatca tctttgacca agaccagaaa caaaaaactg taattaatgt   7140
aaacaaagct attttcgctt tatcttctct aataagtaga aatggtcata aagttaatat   7200
tgtgcaatgg ttgccgtcaa aaggtaaagg aatagatgat tatttggtag ctttaccttt   7260
tgagaaaaga gaaaatcatt tagacaactt aattaaaatt gcaccatcat ttaatttttg   7320
gtcaactaaa tacttattca agtgtcgtaa accagattta accgtaaatt gccgttattt   7380
gagcgatgca gtaaaagaat tacctcaaga ggatatagca ttaatagcac ctcacggcac   7440
gggtaaaact tcattagtag ctactcacgt taagaatcgg agttatcacg gaaggaaaac   7500
tatttcattg gtgcatcttg aaagtttagc caaagctaat ggcaacgcac ttggattata   7560
ttaccgaacc gaaaataata ttgaaaagca atatcttgga tttagcttat gtgtagatag   7620
ttgccgtgat aagattaacg gcattacaac tgatattatt tcaggtcaag attattgcct   7680
tttcattgat gaaattgacc aagtaattcc acacatcctt aacagtgaaa ctgaagtaag   7740
taagtataga tgcaccatca ttgacacttt ttctgaactg gtgagaaatg ctgaacaggt   7800
cattattgct gatgctgatt tatccgatgt gacgattgac ctaatagaaa acatcagagg   7860
taaaaaacta tatgtaatca agaatgaata tcagtatcag ggaatgactt ttaacgccgt   7920
tggttcacca ttagaaatga tggcaatgat gggaaaatcg gtgtcagaag gcaagaaatt   7980
atttattaac accacatccc aaaaggcaaa aagtaagtac ggcacaatcg ctcttgagtc   8040
ttatattttt ggtctaaata aagaagcaaa gatattaaga atagactctg aaaccactaa   8100
aaaccctgaa catccagcct ataaaatcat tgaccaagac ttaaataata tcctcaaaga   8160
ttatgattat gtcattgcct caccttgcct tcaaacaggt gtcagtatta ccttaaaagg   8220
gcattttgac cagcaattta acttttccag tggaaacatt acacctcatt gctttttaca   8280
gcaaatgtgg cggttgaggg atgcagaaat tgaaagattc tattatgtgc cgaactcatc   8340
taacctcaat ctcattggga ataagtcaag ttcaccatca gaccttctaa agagcaataa   8400
caagatggca acggcaacgg ttaacctttt gggtagaatc gactccgaat attccctaga   8460
gtatgaatcg cacggcattt ggcttgagac gtgggcaaaa ttatcagcac ggcataacag   8520
ttcaatgcgt tgttactctg aaattcttac ctatctaatt acgtctcaag ggcataaatt   8580
aaatatcaac attccctcac ctcttgcaga tattaagaag ctaaatgatg aggtaagtag   8640
```

```
taacagggaa aaggtaaaaa atgagagata ctctcagagg ttaaactcac cagatattaa   8700
cgatgcagaa gctaccatac tcgaatctaa agagcaaaaa atcggattga ctctcaatga   8760
gagatgcacc ctagaaaagc ataaagttaa gaagcggtat gggaatgtaa agatggatat   8820
tctcaccttt gatgatgatg gactataccc caaactcaga ctattttatt acctcaccat   8880
cggtaaacct catctcaagg ctaatgacag aaaagctatt gccaaaatgg gcaatgacaa   8940
taaaggcaag attctatcaa aagacttagt taataaaact tactccgctc gtgtgaaggt   9000
cttagagatt cttaaactaa ctgactttat cgacaatctt agagatgaac tcttaataac   9060
tcccaataat ccagctatca ccgattttaa taatcttctg ctaagagcta agaaggattt   9120
aagagtatta ggagtcaaca tcggaaaata tccaatggcc aacattaatg ccgtacttac   9180
tctcattggt cacaaacttt ctgtaatgag agatgagttc ggaaaagaga aaaggataaa   9240
agtagatggt aaatcatacc gatgttatca acttgaaaca ttaccagatt ttaccaatga   9300
tactcttgac tactggttag aaaatgatag ccaaaaagaa gtaacagcaa cagaaaatta   9360
ctccgaaaat tttaaccctt caaatagcta caatccagac agtaagacac tttcagaggg   9420
tgcaaatttc ctatatataa ataaagaaga attgcatcca aataaattgc acctagaaat   9480
aaaagaaggt gctgaacttt ttttattcgg ggtaaaggtg attgtgaaag gaatcttgga   9540
cggggcagta actatattct ctatgggtca agaatacgat ttatccctca atgaactaga   9600
ggggatgtta acatcatgaa ctttacaaga atctttttaa agggcgatcg caccatgtta   9660
aatgatggta catttgttca gatatttgat atttaccatg accacgcatt gggagtgacc   9720
cttgacctta agacagaaaa aattatttcc gatgatgtta gggtaattac tgtcaaagac   9780
ttattgttcg atggcactta taaaggggta aaatctttta tgcccgataa tgcccgataa   9840
tgcccgattg atgctacaaa atcccataat cataagcgat aatcccctaa tagcttgtaa   9900
ttcttgaacc gtagcgattt tagagtattc caaaaagaag aaataaacac cgcaaaatgt   9960
cgtatttcac atatataaac caaggttttt tgccctaaaa tctttatgtt tgtagtgtga  10020
tgttgggtca aaatggtcag aaaagttgca aggtttttat ggatgcttac gcgcgcgagg  10080
ggtaagcatc cccaaatagt tactttatcc tagtccatgc ccatttattg ccgtcccgtt  10140
cggctttaaa aaagtgccaa aactcacaag gtgcaataaa aagttctgta cctttcgcaa  10200
ccctagataa tctttcaaca gttacttttt ttcctattat ctcggtacaa agtttggcta  10260
gtttctcttt tccctctttt tcaatcaagc cttcttgtat gcccaactca ttgattaatc  10320
tctctatttt taccattatt tcccgttcag gtagtttatc ccctaaatct tcatcggggg  10380
gcaatgtagg gcattctgaa ggggcttttt cttctgtctg gacattatct aatattgaag  10440
taaccaaact atcttcagtt ttttctattc ctattaattc atattcggtt actgtatccg  10500
tatcaatatc cgaataacta tctttatccg tattagctat tcggttaagt ttatccgtta  10560
actcagaaac aagactatat agcggtttta gcttttcttc tatcctgtta tctaatacgg  10620
ataagtttat acggttatca ttatccgtat tagtatcatt gggctttttt ggtagttcta  10680
ccccctcata aaccgctttt attcccaatt ccaacagact gataacagta tcctttataa  10740
tgggtttttt gctgatatgg tgaacttttg ccccttccat cattgcgata ctttctatct  10800
cactcatcaa cttatcgctt aagtgaatct cgtatctgtt taatccctta ctggttttat  10860
tcatatccgt ttactttatt cggttaacaa ttctatttta tacgaataaa atattatacg  10920
gttaacttta tacgtttaac tattttatct atacggataa cagtaataag ttattcgtat  10980
tagttatacg tttactttta tccaaataaa attagtgcat ttaaactaaa agaatgattt  11040
```

```
tatcggagtt gatagcattg gattaaccta aagatgttta taagctatat ctgataagta  11100

tttaaggtta ttttgttatt ctgtttattg acattatcag aataaaagaa tagaatataa  11160

ttgttgagag ataagaggtt taagtgatta tggttaagaa gttagttggt tatgtcaggg  11220

tcagtagtga atcgcaagag gataacacta gcttacagaa tcagatagag agaattgaag  11280

catattgtat ggcttttggt tatgagttgg taaaaatatt caaagaggtt gccactggta  11340

caaaagcaga tattgaaacc cgtcctattt ttaatgaagc tatagaatac ttgaaacagg  11400

ataatgctaa tggaattatt gccttgaagc tagaccgaat cgcacggaat gctttagatg  11460

tattgcgttt ggttcgtgaa accttagaac cacaaaataa aatgttagtg ttactagata  11520

ttcaggtaga tacttcgaca ccttcaggaa aaatgatttt aactgtaatg agtgccgttg  11580

ctgaactcga aagagacatg atctatgatc gcactcaggg gggtagaaag actaaagccc  11640

aaaagggcgg gtatgcctac gggaaaccta aatttggcta taagactgaa gaaaaggaac  11700

taaaagaaga ttcagcacaa caggaaacta ttaaactaat taagagacac cgtaggtcag  11760

ggaaaagcta ccagaaaata gctgattatc tcaatgccca aagtattccc actaaacaag  11820

gtaagaaatg gagttctagc gtcgtctatc gaatctgtca ggaaaaagct ggttaagtct  11880

gtttatagat atttagaatt tattgaataa aaatagtatg aacaataaat atttatggac  11940

taaccacgct cggaaacgtt taactgaacg atgggaaata aaagaatcat gggttattga  12000

taccatcgaa aatcctgaac gttcagaatt tattgttgat gagtcagggg aaaaatatca  12060

ttactataaa agaatagcta agtttaagaa tagagtgtta gaagtgataa cttctgccaa  12120

ctcaacaccc acaagaataa taacctttta ctttaaccgt aacatgagga aaaatttatg  12180

attgttactt acgataatga agttgacgca atttatttta agttaacgga aaataaaatt  12240

gatagcaccg aacctcaaac agacaggatt atcattgatt acgatgaaag taataatatt  12300

gttggcattg aggtattaga ttttaattat cttgtcaaga aaggtttaac cgttgctgat  12360

ttaccttttt ctgaagatga aagattaaca gcttctcaat attttaattt tcctgttgct  12420

atctaatcca gaaggggcaa taatcccctt ctttcatcga gttagactta atatcacaaa  12480

agtcattttc attttaccgt ttcttttcca cagcgtccgt acgcccctcg ttaaatctca  12540

aaaccgacaa tttatgatgt ttataaaaag ttactcactt taataagtat ttatactcat  12600

taaagggtta ttcttttttt gtagcctgat aggttgggaa ggaatatttc agattatcag  12660

atttgttgaa tatttttcgt cagatacgca aaccttacaa acataattaa caactgaaac  12720

tattgatatg tctaggtttt agctctatca caggttggat ctg                   12763
```

```
<210> SEQ ID NO 20
<211> LENGTH: 12762
<212> TYPE: DNA
<213> ORGANISM: Artificial Sequence
<220> FEATURE:
<223> OTHER INFORMATION: #1636\\pABICyano1::PnirA(opt3)-
      zmPDC(opt1)_dsrA-Prbc*(optRBS)-synADH(opt1)_ter

<400> SEQUENCE: 20

tcgacaatta ataacttctt cctgtacggg cgaatggcca tttgctccta actaactccg     60

tactgctttg cggaacgagc gtagcgaact ctccgaatta ctaagccttc atccctgata    120

gatgcaaaaa acgcattaaa attatgcgta aaaagcatat ttgtctttat ttagtaatca    180

aagttacaaa ttattaagaa tcaaattaat aatatattgg gcagttaagt atataagtct    240

ttaaatattt atttgtattc aatatattaa ccgaggacaa attatgaatt cttataccgt    300
```

```
gggtacttat ttagccgaac gcttagtgca aattggttta aaacatcatt ttgccgtggc    360
tggggactat aatttagtgt tattggataa cttattatta aataaaaaca tggaacaagt    420
gtattgttgt aatgaattaa attgtggttt ttctgctgaa ggttatgcta gagctaaagg    480
tgcagctgct gctgttgtta cttattctgt gggtgcttta tctgcttttg atgctattgg    540
tggtgcttat gccgaaaatt tacccgtgat tttaatttct ggtgccccta ataataatga    600
tcatgccgct ggacatgttt tacatcatgc cttaggtaaa accgattatc attatcaatt    660
agaaatggcc aaaaatatta ctgctgctgc cgaagctatt tatactcctg aagaagcccc    720
tgccaaaatt gatcatgtga ttaaaaccgc cttacgcgaa aaaaaacccg tgtatttaga    780
aattgcctgt aatattgctt ctatgccttg tgctgctcct gggcctgctt ctgctttatt    840
taatgatgaa gcctctgatg aagctagttt aaatgctgcc gtggaagaaa ccttaaaatt    900
tattgccaat cgcgataaag ttgccgtgtt agttggttct aaattaagag ctgctggtgc    960
tgaagaagct gctgttaaat ttgctgatgc tttaggtggt gcagttgcta ctatggctgc   1020
tgccaaatct ttttttcccg aagaaaatcc ccattatatt ggaactagtt ggggagaagt   1080
ttcttatcct ggtgtggaaa aaactatgaa agaagccgac gctgttattg ctttagcccc   1140
tgtgtttaat gattattcta ccactggttg gactgatatt cccgatccca aaaaattagt   1200
tttagccgaa cctcgttctg ttgttgttaa tggtgttcgc tttccctctg tgcatttaaa   1260
agattattta acccgcttag cccaaaaagt ttctaaaaaa actggtgcct tagatttttt   1320
taaatcttta aatgcgggtg aattaaaaaa agctgctcct gctgatcctt ctgctccttt   1380
agttaatgct gaaattgccc gtcaagttga agccttatta acccctaata ctaccgttat   1440
tgccgaaact ggtgattctt ggtttaatgc ccaacgcatg aaattaccta atggtgcccg   1500
tgttgaatat gaaatgcaat ggggtcatat tggttggtct gtacctgctg cttttggtta   1560
tgctgttggt gctcctgaac gtcgtaatat tttaatggtg ggtgatggtt cttttcaatt   1620
aactgcccaa gaagttgccc aaatggttcg cttaaaatta cccgttatta ttttttttaat   1680
aaataattat ggttatacca ttgaagtgat gattcatgat gggccatata ataatattaa   1740
aaattgggat tatgcgggtt taatggaagt gtttaatggt aatggtggtt atgattctgg   1800
tgctggtaaa ggtttaaaag ccaaaactgg tggtgaatta gctgaagcta ttaaagttgc   1860
cttagccaat actgatgggc caaccttaat tgaatgtttt attggtcgcg aagattgtac   1920
cgaagaatta gttaaatggg gtaaacgtgt tgctgctgct aattctcgca aacccgtgaa   1980
taaattattg taatttttgg ggatcaattc gagctcagca agtttcatcc cgacccccctc   2040
agggtcggga ttttttttatt gtactagttg acataagtaa aggcatcccc tgcgtgatat   2100
aattaccttc agtttaagga ggtatacaca tatgattaaa gcctatgctg ccttagaagc   2160
caatggtaaa ttacaaccct ttgaatatga tcctggtgct ttaggtgcca atgaagtgga   2220
aattgaagtg caatattgtg gtgtgtgtca ttctgattta tctatgatta ataatgaatg   2280
ggtatttct aattatccct tagttcctgg tcatgaagtt gttggtactg ttgctgctat   2340
gggtgaaggt gttaatcatg tggaagtggg tgatttagtt ggtttaggtt ggcattctgg   2400
ttattgtatg acctgtcatt cttgtttatc tggttatcat aatttatgtg ccactgccga   2460
atctactatt gtgggtcatt atggtggttt tggtgataga gttcgtgcta aaggtgtttc   2520
tgtggtgaaa ttacccaaag gtattgattt agcctctgct gggcctttat tttgtggtgg   2580
tattaccgtt ttttctccca tggtggaatt atctttaaaa cctaccgcca aagttgctgt   2640
```

-continued

```
tattggtatt ggtggtttag gtcatttagc cgttcaattt ttaagagcct ggggttgtga   2700
agttactgct tttacctctt ctgcccgtaa acaaaccgaa gttttagaat taggtgccca   2760
tcatatttta gattctacca atcctgaagc tattgcttct gccgaaggta aatttgatta   2820
tattatttct accgtgaatt taaaattaga ttggaattta tatatcagta ccttagcccc   2880
tcaaggtcat tttcatttgg ttggtgtggt gttagaaccc ttggacttaa acttatttcc   2940
cttattaatg ggacaacgtt ctgtttctgc ttctcctgtt ggttctcctg ctactattgc   3000
cactatgtta gattttgccg tgcgtcatga tattaaaccc gtggtggaac aattttcttt   3060
tgatcaaatt aatgaagcca ttgcccattt agaatctggt aaagcccatt atcgcgtggt   3120
gttatctcat tctaaaaatt aataagatta acttctaaac tgaaacaaat ttgagggtag   3180
gcttcattgt ctgcccttat ttttttattt aggaaaagtg aacagactaa agagtgttgg   3240
ctctattgct ttgagtatgt aaattaggcg ttgctgaatt aaggtatgat ttttgacccc   3300
ttctctcttc tgcaggatca tcttgctgaa aaactcgagc gctcgttccg caaagcggta   3360
cggagttagt taggggctaa tggcattctc cccgtacagg aaagagttag aagttattaa   3420
ttatcaacaa ttctcctttg cctagtgcat cgttaccttt ttaattaaaa cataaggaaa   3480
actaataatc gtaataattt aacctcaaag tgtaaagaaa tgtgaaattc tgacttttat   3540
aacgttaaag agggaaaaat tagcagttta aaatacctag agaatagtct ggggtaagca   3600
tagagaatta gattagttaa gttaatcaaa ttcagaaaaa ataataatcg taaatagtta   3660
atctgggtgt atagaaaatg atccccttca tgataagatt taaactcgaa aagcaaaagc   3720
caaaaaacta acttccatta aaagaagttg ttacatataa cgctataaag aaaatttata   3780
tatttggagg ataccaacca tgtctcatat tcaacgtgaa actagttgtt ctcgccctcg   3840
tttaaattct aatatggatg ccgatttata tggttataaa tgggctcgtg ataatgttgg   3900
tcaatctggt gctactattt atcgtttata tggtaaacct gatgctcctg aattattctt   3960
gaaacatggt aaaggttctg ttgctaatga tgttactgat gaaatggttc gtttaaactg   4020
gttgactgaa tttatgcctt tacctactat taaacatttt attcgtactc ccgatgatgc   4080
ttggttatta actactgcta ttcctggtaa aactgctttt caagttttag aagaatatcc   4140
tgattctggt gaaaatattg ttgatgcttt agctgttttt ttacgtcgtt tacattctat   4200
tcccgtttgt aattgtcctt ttaattctga tcgtgttttt cgtttagctc aagctcaatc   4260
tcgtatgaat aatggtttag ttgatgcttc tgattttgat gatgaacgta atggttggcc   4320
tgttgaacaa gtttggaaag aaatgcacaa attgttacct ttttctcctg attctgttgt   4380
tactcatggt gatttttctt tagataattt gatctttgat gaaggtaaat tgattggttg   4440
tattgatgtt ggtcgtgttg gtattgctga tcgttatcaa gatttagcta ttttatggaa   4500
ttgtttaggt gaattttctc cttctttaca gaaacgttta tttcagaaat atggtattga   4560
taatcctgat atgaacaagt tacaatttca tttaatgttg gacgagttct tttaagaatt   4620
aattcatgac caaaatccct taacgtgagt tttcgttcca ctgagcgtca gaccccgtag   4680
aaaagatcaa aggatcttct tgagatcctt tttttctgcg cgtaatctgc tgctatttaa   4740
attacgtaca cgtgttatta ctttgttaac gacaattgtc ttaattaact gggcctcatg   4800
ggccttccgc tcactgcccg ctttccagtc gggaaacctg tcgtgccagc tctgcagatg   4860
acggtgaaaa cctctgacac atgcagctcc cggagacggt cacagcttgt ctgtaagcgg   4920
atgccgggag cagacaagcc cgtcagggcg cgtcagcggg tgttggcggg tgtcggggcg   4980
cagccatgac ccagtcacgt agcgatagcg gagtgtatac tggcttaact atgcggcatc   5040
```

```
agagcagatt gtactgagag tgcaccatat gcggtgtgaa ataccgcaca gatgcgtaag   5100
gagaaaatac cgcatcaggc gctcttccgc ttcctcgctc actgactcgc tgcgctcggt   5160
cgttcggctg cggcgagcgg tatcagctca ctcaaaggcg gtaatacggt tatccacaga   5220
atcaggggat aacgcaggaa agaacatgtg agcaaaaggc cagcaaaagg ccaggaaccg   5280
taaaaaggcc gcgttgctgg cgtttttcca taggctccgc ccccctgacg agcatcacaa   5340
aaatcgacgc tcaagtcaga ggtggcgaaa cccgacagga ctataaagat accaggcgtt   5400
tccccctgga agctccctcg tgcgctctcc tgttccgacc ctgccgctta ccggatacct   5460
gtccgccttt ctcccttcgg gaagcgtggc gctttctcat agctcacgct gtaggtatct   5520
cagttcggtg taggtcgttc gctccaagct gggctgtgtg cacgaacccc ccgttcagcc   5580
cgaccgctgc gccttatccg gtaactatcg tcttgagtcc aacccggtaa gacacgactt   5640
atcgccactg gcagcagcca ctggtaacag gattagcaga gcgaggtatg taggcggtgc   5700
tacagagttc ttgaagtggt ggcctaacta cggctacact agaaggacag tatttggtat   5760
ctgcgctctg ctgaagccag ttaccttcgg aaaaagagtt ggtagctctt gatccggcaa   5820
acaaaccacc gctggtagcg gtggtttttt tgtttgcaag cagcagatta cgcgcagaaa   5880
aaaaggatct caagaagatc ctttgatctt ttctactgca gaagcttgtt agacaccctg   5940
tcatgtattt tatattattt atttcaccat acggattaag tgaaacctaa tgaaaatagt   6000
actttcggag ctttaacttt aatgaaggta tgttttttta tagacatcga tgtctggttt   6060
aacaatagga aaaagtagct aaaactccca tgaattaaag aaataacaag gtgtctaaca   6120
acctgttatt aagaatgtta gaaaagactt aacatttgtg ttgagttttt atagacattg   6180
gtgtctagac atacggtaga taaggtttgc tcaaaaataa aataaaaaaa gattggacta   6240
aaaaacattt aatttagtac aatttaatta gttatttttt cgtctcaaat tttgctttgt   6300
tgagcagaaa tttagataaa aaaatccccg tgatcagatt acaatgtcgt tcattgtacg   6360
atgtgtcgaa aaatctttac gacactctaa actgaccaca cgggggaaaa agaaaactga   6420
actaataaca tcatgatact cggaaaacct agcaattctc aacccctaaa caaaagaaac   6480
ttccaaaacc ctgaccatat aaaggagtgg caacaatcag caatcagtca agatttgata   6540
gcagaaaatc ttgtatcggt tgctaatggt tttgatgtac tatttatcgg caataaatac   6600
cgaactaaca cgggtgttct gtcacggcac atattaaact cctattctca tttagaagat   6660
ggtggttcgt atggtagaac atttgaccca tttaccaata aagaaatgca gtgggttcaa   6720
tttaaaccga atagaccaag aaaaggttct actggtaagg taatcaaata tgaatcgcca   6780
aaaggtgaac ctacaagagt tctaatgccg tttgtgccta tgaaaatatg gcaacggatt   6840
agcgataagt tcggagtacc gattaatccg aaaaaagata ctcacttttg ggaatgggta   6900
aagaataatc catcgatacc gattgccatt acagaaggaa ataaaaaagc taattgccta   6960
ttatcctatg gctatcctgc tattgccttt gtaggcattt ggaacggatt agagaaaata   7020
aatgatttct cgaaggaaaa gcagttaaaa gaggatttga aatggttgtt atccaacggc   7080
aaccgaaata ttaatatcat ctttgaccaa gaccagaaac aaaaaactgt aattaatgta   7140
aacaaagcta ttttcgcttt atcttctcta ataagtagaa atggtcataa agttaatatt   7200
gtgcaatggt tgccgtcaaa aggtaaagga atagatgatt atttggtagc tttacctttt   7260
gagaaaagag aaaatcattt agacaactta attaaaattg caccatcatt taatttttgg   7320
tcaactaaat acttattcaa gtgtcgtaaa ccagatttaa ccgtaaattg ccgttatttg   7380
```

agcgatgcag taaaagaatt acctcaagag gatatagcat taatagcacc tcacggcacg 7440
ggtaaaactt cattagtagc tactcacgtt aagaatcgga gttatcacgg aaggaaaact 7500
atttcattgg tgcatcttga aagtttagcc aaagctaatg gcaacgcact tggattatat 7560
taccgaaccg aaaataatat tgaaaagcaa tatcttggat ttagcttatg tgtagatagt 7620
tgccgtgata agattaacgg cattacaact gatattattt caggtcaaga ttattgcctt 7680
ttcattgatg aaattgacca agtaattcca cacatcctta acagtgaaac tgaagtaagt 7740
aagtatagat gcaccatcat tgacactttt tctgaactgg tgagaaatgc tgaacaggtc 7800
attattgctg atgctgattt atccgatgtg acgattgacc taatagaaaa catcagaggt 7860
aaaaaactat atgtaatcaa gaatgaatat cagtatcagg gaatgacttt taacgccgtt 7920
ggttcaccat tagaaatgat ggcaatgatg ggaaaatcgg tgtcagaagg caagaaatta 7980
tttattaaca ccacatccca aaaggcaaaa agtaagtacg gcacaatcgc tcttgagtct 8040
tatatttttg gtctaaataa agaagcaaag atattaagaa tagactctga aaccactaaa 8100
aaccctgaac atccagccta taaaatcatt gaccaagact taaataatat cctcaaagat 8160
tatgattatg tcattgcctc accttgcctt caaacaggtg tcagtattac cttaaaaggg 8220
cattttgacc agcaatttaa cttttccagt ggaaacatta cacctcattg ctttttacag 8280
caaatgtggc ggttgaggga tgcagaaatt gaaagattct attatgtgcc gaactcatct 8340
aacctcaatc tcattgggaa taagtcaagt tcaccatcag accttctaaa gagcaataac 8400
aagatggcaa cggcaacggt taaccttttg ggtagaatcg actccgaata ttccctagag 8460
tatgaatcgc acggcatttg gcttgagacg tgggcaaaat tatcagcacg gcataacagt 8520
tcaatgcgtt gttactctga aattcttacc tatctaatta cgtctcaagg gcataaatta 8580
aatatcaaca ttccctcacc tcttgcagat attaagaagc taaatgatga ggtaagtagt 8640
aacagggaaa aggtaaaaaa tgagagatac tctcagaggt taaactcacc agatattaac 8700
gatgcagaag ctaccatact cgaatctaaa gagcaaaaaa tcggattgac tctcaatgag 8760
agatgcaccc tagaaaagca taaagttaag aagcggtatg ggaatgtaaa gatggatatt 8820
ctcacctttg atgatgatgg actatacccc aaactcagac tattttatta cctcaccatc 8880
ggtaaacctc atctcaaggc taatgacaga aaagctattg ccaaaatggg caatgacaat 8940
aaaggcaaga ttctatcaaa agacttagtt aataaaactt actccgctcg tgtgaaggtc 9000
ttagagattc ttaaactaac tgactttatc gacaatctta gagatgaact cttaataact 9060
cccaataatc cagctatcac cgattttaat aatcttctgc taagagctaa gaaggattta 9120
agagtattag gagtcaacat cggaaaatat ccaatggcca acattaatgc cgtacttact 9180
ctcattggtc acaaactttc tgtaatgaga gatgagttcg gaaaagagaa aaggataaaa 9240
gtagatggta aatcataccg atgttatcaa cttgaaacat taccagattt taccaatgat 9300
actcttgact actggttaga aaatgatagc caaaaagaag taacagcaac agaaaattac 9360
tccgaaaatt ttaacccttc aaatagctac aatccagaca gtaagacact ttcagagggt 9420
gcaaatttcc tatatataaa taaagaagaa ttgcatccaa ataaattgca cctagaaata 9480
aaagaaggtg ctgaactttt tttattcggg gtaaaggtga ttgtgaaagg aatcttggac 9540
ggggcagtaa ctatattctc tatgggtcaa gaatacgatt tatccctcaa tgaactagag 9600
gggatgttaa catcatgaac tttacaagaa tctttttaaa gggcgatcgc accatgttaa 9660
atgatggtac atttgttcag atatttgata tttaccatga ccacgcattg ggagtgaccc 9720
ttgaccttaa gacagaaaaa attatttccg atgatgttag ggtaattact gtcaaagact 9780

```
tattgttcga tggcacttat aaaggggtaa aatcttttat gcccgataat gcccgataat   9840
gcccgattga tgctacaaaa tcccataatc ataagcgata atcccctaat agcttgtaat   9900
tcttgaaccg tagcgatttt agagtattcc aaaaagaaga aataaacacc gcaaaatgtc   9960
gtatttcaca tatataaacc aaggtttttt gccctaaaat ctttatgttt gtagtgtgat  10020
gttgggtcaa aatggtcaga aaagttgcaa ggtttttatg gatgcttacg cgcgcgaggg  10080
gtaagcatcc ccaaatagtt actttatcct agtccatgcc catttattgc cgtcccgttc  10140
ggctttaaaa aagtgccaaa actcacaagg tgcaataaaa agttctgtac ctttcgcaac  10200
cctagataat ctttcaacag ttactttttt tcctattatc tcggtacaaa gtttggctag  10260
tttctctttt ccctcttttt caatcaagcc ttcttgtatg cccaactcat tgattaatct  10320
ctctattttt accattattt cccgttcagg tagtttatcc cctaaatctt catcgggggg  10380
caatgtaggg cattctgaag gggctttttc ttctgtctgg acattatcta atattgaagt  10440
aaccaaacta tcttcagttt tttctattcc tattaattca tattcggtta ctgtatccgt  10500
atcaatatcc gaataactat ctttatccgt attagctatt cggttaagtt tatccgttaa  10560
ctcagaaaca agactatata gcggttttag cttttcttct atcctgttat ctaatacgga  10620
taagtttata cggttatcat tatccgtatt agtatcattg ggcttttttg gtagttctac  10680
cccctcataa accgctttta ttcccaattc caacagactg ataacagtat cctttataat  10740
gggtttttttg ctgatatggt gaacttttgc cccttccatc attgcgatac tttctatctc  10800
actcatcaac ttatcgctta agtgaatctc gtatctgttt aatcccttac tggttttatt  10860
catatccgtt tactttattc ggttaacaat tctattttat acgaataaaa tattatacgg  10920
ttaactttat acgtttaact attttatcta tacggataac agtaataagt tattcgtatt  10980
agttatacgt ttacttttat ccaaataaaa ttagtgcatt taaactaaaa gaatgatttt  11040
atcggagttg atagcattgg attaacctaa agatgtttat aagctatatc tgataagtat  11100
ttaaggttat tttgttattc tgtttattga cattatcaga ataaaagaat agaatataat  11160
tgttgagaga taagaggttt aagtgattat ggttaagaag ttagttggtt atgtcagggt  11220
cagtagtgaa tcgcaagagg ataacactag cttacagaat cagatagaga gaattgaagc  11280
atattgtatg gcttttggtt atgagttggt aaaaaatattc aaagaggttg ccactggtac  11340
aaaagcagat attgaaaccc gtcctatttt taatgaagct atagaatact tgaaacagga  11400
taatgctaat ggaattattg ccttgaagct agaccgaatc gcacggaatg ctttagatgt  11460
attgcgtttg gttcgtgaaa ccttagaacc acaaaataaa atgttagtgt tactagatat  11520
tcaggtagat acttcgacac cttcaggaaa aatgatttta actgtaatga gtgccgttgc  11580
tgaactcgaa agagacatga tctatgatcg cactcagggg ggtagaaaga ctaaagccca  11640
aaagggcggg tatgcctacg ggaaacctaa atttggctat aagactgaag aaaaggaact  11700
aaaagaagat tcagcacaac aggaaactat taaactaatt aagagacacc gtaggtcagg  11760
gaaaagctac cagaaaatag ctgattatct caatgcccaa agtattccca ctaaacaagg  11820
taagaaatgg agttctagcg tcgtctatcg aatctgtcag gaaaaagctg gttaagtctg  11880
tttatagata tttagaattt attgaataaa aatagtatga acaataaata tttatggact  11940
aaccacgctc ggaaacgttt aactgaacga tgggaaataa aagaatcatg ggttattgat  12000
accatcgaaa atcctgaacg ttcagaattt attgttgatg agtcagggga aaaatatcat  12060
tactataaaa gaatagctaa gtttaagaat agagtgttag aagtgataac ttctgccaac  12120
```

tcaacaccca caagaataat aaccttttac tttaaccgta acatgaggaa aaatttatga 12180
ttgttactta cgataatgaa gttgacgcaa tttattttaa gttaacggaa aataaaattg 12240
atagcaccga acctcaaaca gacaggatta tcattgatta cgatgaaagt aataatattg 12300
ttggcattga ggtattagat tttaattatc ttgtcaagaa aggtttaacc gttgctgatt 12360 taccttttc tgaagatgaa agattaacag cttctcaata ttttaatttt cctgttgcta 12420
tctaatccag aaggggcaat aatccccttc tttcatcgag ttagacttaa tatcacaaaa 12480
gtcattttca ttttaccgtt tcttttccac agcgtccgta cgcccctcgt taaatctcaa 12540
aaccgacaat ttatgatgtt tataaaaagt tactcacttt aataagtatt tatactcatt 12600
aaagggttat tcttttttttg tagcctgata ggttgggaag gaatatttca gattatcaga 12660
tttgttgaat atttttcgtc agatacgcaa accttacaaa cataattaac aactgaaact 12720
attgatatgt ctaggtttta gctctatcac aggttggatc tg 12762

<210> SEQ ID NO 21
<211> LENGTH: 13726
<212> TYPE: DNA
<213> ORGANISM: Artificial Sequence
<220> FEATURE:
<223> OTHER INFORMATION: #1630\\pABICyano1::corR-PcorT*1-
zmPDC(opt1)_dsrA-Prbc*(optRBS)-synADH(opt1)_ter

<400> SEQUENCE: 21
tcgaccatgc gtccaaaact ttcaccatcc tttccctatc aacctttact gcactaaaga 60
caagtgagat agcagtggca atctggcttt gcaatcaatg tttccactaa agcgtttagc 120
gttactgcgg ctagaagtcc tccaccgagg ctcccctgaa tggtgatatg gggaatggga 180
ctggtcatca gtcgtcgttt tgcccccgga gcatgactaa aaccgatcgg cattccgatc 240
acaagagccg gctgaatatg ttgttgctct atcagcttac aggcagtgag taaaacagaa 300
ggggcatagc cgatcgccag cacacatcct tggggaatct gttgtaaccg ctgttgccaa 360
tggtcatggt gccaaaaagc ttgctcggct tccctaagcc ctgtgatgtg agggtcgtca 420
atcagcgttt taaccgtaca tcctaaatga gctaaccgag tttgatcaag agccgcagcc 480
acaaccggaa catcggtgac gactggacac cctgctttca gtgcatctcg tgccgaggcg 540
atcgctccct gactcaatcg aacggcgttt accaagctaa catcaccaca ggccagcact 600
aattgatgta gtaagtgaat ggtaatttca gagtaagccg ataaatccgg tagcaggtgt 660
ttgagggatt cctgaaaggc ttctggatga gttgttgtct ccgcatctag gttcgtccac 720
aactgatcga gttttcctaa cccctcctgg acatccacat caagctgttt cagttgggcc 780
agagcttccg cttgggtaat ctggcaactc tggtcgcgtc ccagtaatcc ttctaaagca 840
gatgcggttt ggcggagtcg agtaatctgc tgaatcacag cctgatattg ctgttgcaac 900
tgcaccatta gggtgggatc aaggctctct tcagaatggc tatccagcag ttgccgaata 960
tgagacaact gaaagccctg ctgtttgagg gcaatgactc gttggagccg ttgtacgtcc 1020
tgctgagtat aaaggcggta gttgccctct gagcgttgaa cgggggggaag caatcccagg 1080 gtgtggtaat ggcgcaccat gcgaggcgta acgccacctc ccactgcatc tgtgagttct 1140
ttaatcgtta agtgattagt cttcatgact ttagtttact caaaaccttg acattgacac 1200
taatgttaag gtttaggctg agaaggtaaa aatcgaggat aaaaagcatg aattcttata 1260
ccgtgggtac ttatttagcc gaacgcttag tgcaaattgg tttaaaacat cattttgccg 1320
tggctgggga ctataattta gtgttattgg ataacttatt attaaataaa aacatggaac 1380

-continued

```
aagtgtattg ttgtaatgaa ttaaattgtg gtttttctgc tgaaggttat gctagagcta   1440
aaggtgcagc tgctgctgtt gttacttatt ctgtgggtgc tttatctgct tttgatgcta   1500
ttggtggtgc ttatgccgaa aatttacccg tgattttaat ttctggtgcc cctaataata   1560
atgatcatgc cgctggacat gttttacatc atgccttagg taaaaccgat tatcattatc   1620
aattagaaat ggccaaaaat attactgctg ctgccgaagc tatttatact cctgaagaag   1680
cccctgccaa aattgatcat gtgattaaaa ccgccttacg cgaaaaaaaa cccgtgtatt   1740
tagaaattgc ctgtaatatt gcttctatgc cttgtgctgc tcctgggcct gcttctgctt   1800
tatttaatga tgaagcctct gatgaagcta gtttaaatgc tgccgtggaa gaaaccttaa   1860
aatttattgc caatcgcgat aaagttgccg tgttagttgg ttctaaatta agagctgctg   1920
gtgctgaaga agctgctgtt aaatttgctg atgctttagg tggtgcagtt gctactatgg   1980
ctgctgccaa atcttttttt cccgaagaaa atccccatta tattggaact agttggggag   2040
aagtttctta tcctggtgtg gaaaaaacta tgaaagaagc cgacgctgtt attgctttag   2100
cccctgtgtt taatgattat tctaccactg gttggactga tattcccgat cccaaaaaat   2160
tagttttagc cgaacctcgt tctgttgttg ttaatggtgt tcgctttccc tctgtgcatt   2220
taaaagatta tttaacccgc ttagcccaaa aagtttctaa aaaaactggt gccttagatt   2280
tttttaaatc tttaaatgcg ggtgaattaa aaaaagctgc tcctgctgat ccttctgctc   2340
ctttagttaa tgctgaaatt gcccgtcaag ttgaagcctt attaacccct aatactaccg   2400
ttattgccga aactggtgat tcttggttta atgcccaacg catgaaatta cctaatggtg   2460
cccgtgttga atatgaaatg caatggggtc atattggttg gtctgtacct gctgcttttg   2520
gttatgctgt tggtgctcct gaacgtcgta atattttaat ggtgggtgat ggttcttttc   2580
aattaactgc ccaagaagtt gcccaaatgg ttcgcttaaa attacccgtt attatttttt   2640
taataaataa ttatggttat accattgaag tgatgattca tgatgggcca tataataata   2700
ttaaaaattg ggattatgcg ggtttaatgg aagtgtttaa tggtaatggt ggttatgatt   2760
ctggtgctgg taaaggttta aaagccaaaa ctggtggtga attagctgaa gctattaaag   2820
ttgccttagc caatactgat gggccaacct taattgaatg ttttattggt cgcgaagatt   2880
gtaccgaaga attagttaaa tggggtaaac gtgttgctgc tgctaattct cgcaaacccg   2940
tgaataaatt attgtaattt ttggggatca attcgagctc agcaagtttc atcccgaccc   3000
cctcagggtc gggatttttt tattgtacta gttgacataa gtaaaggcat cccctgcgtg   3060
atataattac cttcagttta aggaggtata cacatatgat taaagcctat gctgccttag   3120
aagccaatgg taaattacaa ccctttgaat atgatcctgg tgctttaggt gccaatgaag   3180
tggaaattga agtgcaatat tgtggtgtgt gtcattctga tttatctatg attaataatg   3240
aatggggtat ttctaattat cccttagttc ctggtcatga agttgttggt actgttgctg   3300
ctatgggtga aggtgttaat catgtggaag tgggtgattt agttggttta ggttggcatt   3360
ctggttattg tatgacctgt cattcttgtt tatctggtta tcataattta tgtgccactg   3420
ccgaatctac tattgtgggt cattatggtg gttttggtga tagagttcgt gctaaaggtg   3480
tttctgtggt gaaattaccc aaaggtattg atttagcctc tgctgggcct ttattttgtg   3540
gtggtattac cgtttttttct cccatggtgg aattatcttt aaaacctacc gccaaagttg   3600
ctgttattgg tattggtggt ttaggtcatt tagccgttca atttttaaga gcctggggtt   3660
gtgaagttac tgcttttacc tcttctgccc gtaaacaaac cgaagtttta gaattaggtg   3720
cccatcatat tttagattct accaatcctg aagctattgc ttctgccgaa ggtaaatttg   3780
```

attatattat ttctaccgtg aatttaaaat tagattggaa tttatatatc agtaccttag 3840
cccctcaagg tcattttcat tttgttggtg tggtgttaga acccttggac ttaaacttat 3900
ttcccttatt aatgggacaa cgttctgttt ctgcttctcc tgttggttct cctgctacta 3960
ttgccactat gttagatttt gccgtgcgtc atgatattaa acccgtggtg gaacaatttt 4020
cttttgatca aattaatgaa gccattgccc atttagaatc tggtaaagcc cattatcgcg 4080
tggtgttatc tcattctaaa aattaataag attaacttct aaactgaaac aaatttgagg 4140
gtaggcttca ttgtctgccc ttattttttt atttaggaaa agtgaacaga ctaaagagtg 4200
ttggctctat tgctttgagt atgtaaatta ggcgttgctg aattaaggta tgatttttga 4260
ccccttctct cttctgcagg atcatcttgc tgaaaaactc gagcgctcgt tccgcaaagc 4320
ggtacggagt tagttagggg ctaatgggca ttctcccgta caggaaagag ttagaagtta 4380
ttaattatca acaattctcc tttgcctagt gcatcgttac ctttttaatt aaaacataag 4440
gaaaactaat aatcgtaata atttaacctc aaagtgtaaa gaaatgtgaa attctgactt 4500
ttataacgtt aaagagggaa aaattagcag tttaaaatac ctagagaata gtctggggta 4560
agcatagaga attagattag ttaagttaat caaattcaga aaaaataata atcgtaaata 4620
gttaatctgg gtgtatagaa aatgatcccc ttcatgataa gatttaaact cgaaaagcaa 4680
aagccaaaaa actaacttcc attaaaagaa gttgttacat ataacgctat aaagaaaatt 4740
tatatatttg gaggatacca accatgtctc atattcaacg tgaaactagt tgttctcgcc 4800
ctcgtttaaa ttctaatatg gatgccgatt tatatggtta taaatgggct cgtgataatg 4860
ttggtcaatc tggtgctact atttatcgtt tatatggtaa acctgatgct cctgaattat 4920
tcttgaaaca tggtaaaggt tctgttgcta atgatgttac tgatgaaatg gttcgtttaa 4980
actggttgac tgaatttatg cctttaccta ctattaaaca ttttattcgt actcccgatg 5040
atgcttggtt attaactact gctattcctg gtaaaactgc ttttcaagtt ttagaagaat 5100
atcctgattc tggtgaaaat attgttgatg ctttagctgt ttttttacgt cgtttacatt 5160
ctattcccgt ttgtaattgt ccttttaatt ctgatcgtgt tttcgtttta gctcaagctc 5220
aatctcgtat gaataatggt ttagttgatg cttctgattt tgatgatgaa cgtaatggtt 5280
ggcctgttga acaagtttgg aaagaaatgc acaaattgtt accttttttct cctgattctg 5340
ttgttactca tggtgatttt tctttagata atttgatctt tgatgaaggt aaattgattg 5400
gttgtattga tgttggtcgt gttggtattg ctgatcgtta tcaagattta gctattttat 5460
ggaattgttt aggtgaattt tctccttctt tacagaaacg tttatttcag aaatatggta 5520
ttgataatcc tgatatgaac aagttacaat ttcatttaat gttggacgag ttcttttaag 5580
aattaattca tgaccaaaat cccttaacgt gagttttcgt tccactgagc gtcagacccc 5640
gtagaaaaga tcaaaggatc ttcttgagat cctttttttc tgcgcgtaat ctgctgctat 5700
ttaaattacg tacacgtgtt attactttgt taacgacaat tgtcttaatt aactgggcct 5760
catgggcctt ccgctcactg cccgctttcc agtcgggaaa cctgtcgtgc cagctctgca 5820
gatgacggtg aaaacctctg acacatgcag ctcccggaga cggtcacagc ttgtctgtaa 5880
gcggatgccg ggagcagaca agcccgtcag ggcgcgtcag cgggtgttgg cgggtgtcgg 5940
ggcgcagcca tgacccagtc acgtagcgat agcggagtgt atactggctt aactatgcgg 6000
catcagagca gattgtactg agagtgcacc atatgcggtg tgaaataccg cacagatgcg 6060
taaggagaaa ataccgcatc aggcgctctt ccgcttcctc gctcactgac tcgctgcgct 6120

-continued

```
cggtcgttcg gctgcggcga gcggtatcag ctcactcaaa ggcggtaata cggttatcca   6180

cagaatcagg ggataacgca ggaaagaaca tgtgagcaaa aggccagcaa aaggccagga   6240

accgtaaaaa ggccgcgttg ctggcgtttt tccataggct ccgcccccct gacgagcatc   6300

acaaaaatcg acgctcaagt cagaggtggc gaaacccgac aggactataa agataccagg   6360

cgtttccccc tggaagctcc ctcgtgcgct ctcctgttcc gaccctgccg cttaccggat   6420

acctgtccgc ctttctccct tcgggaagcg tggcgctttc tcatagctca cgctgtaggt   6480

atctcagttc ggtgtaggtc gttcgctcca agctgggctg tgtgcacgaa ccccccgttc   6540

agcccgaccg ctgcgcctta tccggtaact atcgtcttga gtccaacccg gtaagacacg   6600

acttatcgcc actggcagca gccactggta acaggattag cagagcgagg tatgtaggcg   6660

gtgctacaga gttcttgaag tggtggccta actacggcta cactagaagg acagtatttg   6720

gtatctgcgc tctgctgaag ccagttacct tcggaaaaag agttggtagc tcttgatccg   6780

gcaaacaaac caccgctggt agcggtggtt tttttgtttg caagcagcag attacgcgca   6840

gaaaaaaagg atctcaagaa gatcctttga tcttttctac tgcagaagct tgttagacac   6900

cctgtcatgt attttatatt atttatttca ccatacggat taagtgaaac ctaatgaaaa   6960

tagtactttc ggagctttaa ctttaatgaa ggtatgtttt tttatagaca tcgatgtctg   7020

gtttaacaat aggaaaaagt agctaaaact cccatgaatt aaagaaataa caaggtgtct   7080

aacaacctgt tattaagaat gttagaaaag acttaacatt tgtgttgagt ttttatagac   7140

attggtgtct agacatacgg tagataaggt ttgctcaaaa ataaaataaa aaaagattgg   7200

actaaaaaac atttaattta gtacaattta attagttatt ttttcgtctc aaattttgct   7260

ttgttgagca gaaatttaga taaaaaaatc cccgtgatca gattacaatg tcgttcattg   7320

tacgatgtgt cgaaaaatct ttacgacact ctaaactgac cacacggggg aaaaagaaaa   7380

ctgaactaat aacatcatga tactcggaaa acctagcaat tctcaacccc taaacaaaag   7440

aaacttccaa aaccctgacc atataaagga gtggcaacaa tcagcaatca gtcaagattt   7500

gatagcagaa aatcttgtat cggttgctaa tggttttgat gtactattta tcggcaataa   7560

ataccgaact aacacgggtg ttctgtcacg gcacatatta aactcctatt ctcatttaga   7620

agatggtggt tcgtatggta gaacatttga cccatttacc aataaagaaa tgcagtgggt   7680

tcaatttaaa ccgaatagac caagaaaagg ttctactggt aaggtaatca aatatgaatc   7740

gccaaaaggt gaacctacaa gagttctaat gccgtttgtg cctatgaaaa tatggcaacg   7800

gattagcgat aagttcggag taccgattaa tccgaaaaaa gatactcact tttgggaatg   7860

ggtaaagaat aatccatcga taccgattgc cattacagaa ggaaataaaa aagctaattg   7920

cctattatcc tatggctatc ctgctattgc ctttgtaggc atttggaacg gattagagaa   7980

aataaatgat ttctcgaagg aaaagcagtt aaaagaggat ttgaaatggt tgttatccaa   8040

cggcaaccga aatattaata tcatctttga ccaagaccag aaacaaaaaa ctgtaattaa   8100

tgtaaacaaa gctattttcg ctttatcttc tctaataagt agaaatggtc ataaagttaa   8160

tattgtgcaa tggttgccgt caaaaggtaa aggaatagat gattatttgg tagctttacc   8220

ttttgagaaa agagaaaatc atttagacaa cttaattaaa attgcaccat catttaattt   8280

ttggtcaact aaatacttat tcaagtgtcg taaaccagat ttaaccgtaa attgccgtta   8340

tttgagcgat gcagtaaaag aattacctca agaggatata gcattaatag cacctcacgg   8400

cacgggtaaa acttcattag tagctactca cgttaagaat cggagttatc acggaaggaa   8460

aactatttca ttggtgcatc ttgaaagttt agccaaagct aatggcaacg cacttggatt   8520
```

-continued

```
atattaccga accgaaaata atattgaaaa gcaatatctt ggatttagct tatgtgtaga   8580
tagttgccgt gataagatta acggcattac aactgatatt atttcaggtc aagattattg   8640
ccttttcatt gatgaaattg accaagtaat tccacacatc cttaacagtg aaactgaagt   8700
aagtaagtat agatgcacca tcattgacac tttttctgaa ctggtgagaa atgctgaaca   8760
ggtcattatt gctgatgctg atttatccga tgtgacgatt gacctaatag aaaacatcag   8820
aggtaaaaaa ctatatgtaa tcaagaatga atatcagtat cagggaatga cttttaacgc   8880
cgttggttca ccattagaaa tgatggcaat gatgggaaaa tcggtgtcag aaggcaagaa   8940
attatttatt aacaccacat cccaaaaggc aaaaagtaag tacggcacaa tcgctcttga   9000
gtcttatatt tttggtctaa ataaagaagc aaagatatta agaatagact ctgaaaccac   9060
taaaaaccct gaacatccag cctataaaat cattgaccaa gacttaaata atatcctcaa   9120
agattatgat tatgtcattg cctcaccttg ccttcaaaca ggtgtcagta ttaccttaaa   9180
agggcatttt gaccagcaat ttaacttttc cagtggaaac attacacctc attgcttttt   9240
acagcaaatg tggcggttga gggatgcaga aattgaaaga ttctattatg tgccgaactc   9300
atctaacctc aatctcattg ggaataagtc aagttcacca tcagaccttc taaagagcaa   9360
taacaagatg gcaacggcaa cggttaacct tttgggtaga atcgactccg aatattccct   9420
agagtatgaa tcgcacggca tttggcttga gacgtgggca aaattatcag cacggcataa   9480
cagttcaatg cgttgttact ctgaaattct tacctatcta attacgtctc aagggcataa   9540
attaaatatc aacattccct cacctcttgc agatattaag aagctaaatg atgaggtaag   9600
tagtaacagg gaaaaggtaa aaaatgagag atactctcag aggttaaact caccagatat   9660
taacgatgca gaagctacca tactcgaatc taaagagcaa aaaatcggat tgactctcaa   9720
tgagagatgc accctagaaa agcataaagt taagaagcgg tatgggaatg taaagatgga   9780
tattctcacc tttgatgatg atggactata ccccaaactc agactatttt attacctcac   9840
catcggtaaa cctcatctca aggctaatga cagaaaagct attgccaaaa tgggcaatga   9900
caataaaggc aagattctat caaaagactt agttaataaa acttactccg ctcgtgtgaa   9960
ggtcttagag attcttaaac taactgactt tatcgacaat cttagagatg aactcttaat  10020
aactcccaat aatccagcta tcaccgattt taataatctt ctgctaagag ctaagaagga  10080
tttaagagta ttaggagtca acatcggaaa atatccaatg gccaacatta atgccgtact  10140
tactctcatt ggtcacaaac tttctgtaat gagagatgag ttcggaaaag agaaaaggat  10200
aaaagtagat ggtaaatcat accgatgtta tcaacttgaa acattaccag attttaccaa  10260
tgatactctt gactactggt tagaaaatga tagccaaaaa gaagtaacag caacagaaaa  10320
ttactccgaa aattttaacc cttcaaatag ctacaatcca gacagtaaga cactttcaga  10380
gggtgcaaat ttcctatata taaataaaga agaattgcat ccaaataaat tgcacctaga  10440
aataaaagaa ggtgctgaac ttttttttatt cggggtaaag gtgattgtga aaggaatctt  10500
ggacggggca gtaactatat tctctatggg tcaagaatac gatttatccc tcaatgaact  10560
agaggggatg ttaacatcat gaactttaca agaatctttt taaagggcga tcgcaccatg  10620
ttaaatgatg gtacatttgt tcagatattt gatatttacc atgaccacgc attgggagtg  10680
acccttgacc ttaagacaga aaaaattatt tccgatgatg ttagggtaat tactgtcaaa  10740
gacttattgt tcgatggcac ttataaaggg gtaaaatctt ttatgcccga taatgcccga  10800
taatgcccga ttgatgctac aaaatcccat aatcataagc gataatcccc taatagcttg  10860
```

-continued

```
taattcttga accgtagcga ttttagagta ttccaaaaag aagaaataaa caccgcaaaa  10920
tgtcgtattt cacatatata aaccaaggtt ttttgcccta aaatctttat gtttgtagtg  10980
tgatgttggg tcaaaatggt cagaaaagtt gcaaggtttt tatggatgct tacgcgcgcg  11040
aggggtaagc atccccaaat agttacttta tcctagtcca tgcccattta ttgccgtccc  11100
gttcggcttt aaaaaagtgc caaaactcac aaggtgcaat aaaaagttct gtacctttcg  11160
caaccctaga taatctttca acagttactt tttttcctat tatctcggta caaagtttgg  11220
ctagtttctc ttttccctct ttttcaatca agccttcttg tatgcccaac tcattgatta  11280
atctctctat ttttaccatt atttcccgtt caggtagttt atcccctaaa tcttcatcgg  11340
ggggcaatgt agggcattct gaaggggctt tttcttctgt ctggacatta tctaatattg  11400
aagtaaccaa actatcttca gttttttcta ttcctattaa ttcatattcg gttactgtat  11460
ccgtatcaat atccgaataa ctatctttat ccgtattagc tattcggtta agtttatccg  11520
ttaactcaga aacaagacta tatagcggtt ttagcttttc ttctatcctg ttatctaata  11580
cggataagtt tatacggtta tcattatccg tattagtatc attgggcttt tttggtagtt  11640
ctacccccctc ataaaccgct tttattccca attccaacag actgataaca gtatccttta  11700
taatgggttt tttgctgata tggtgaactt ttgccccttc catcattgcg atactttcta  11760
tctcactcat caacttatcg cttaagtgaa tctcgtatct gtttaatccc ttactggttt  11820
tattcatatc cgtttacttt attcggttaa caattctatt ttatacgaat aaaatattat  11880
acggttaact ttatacgttt aactatttta tctatacgga taacagtaat aagttattcg  11940
tattagttat acgtttactt ttatccaaat aaaattagtg catttaaact aaaagaatga  12000
ttttatcgga gttgatagca ttggattaac ctaaagatgt ttataagcta tatctgataa  12060
gtatttaagg ttattttgtt attctgttta ttgacattat cagaataaaa gaatagaata  12120
taattgttga gagataagag gtttaagtga ttatggttaa gaagttagtt ggttatgtca  12180
gggtcagtag tgaatcgcaa gaggataaca ctagcttaca gaatcagata gagagaattg  12240
aagcatattg tatggctttt ggttatgagt tggtaaaaat attcaaagag gttgccactg  12300
gtacaaaagc agatattgaa acccgtccta tttttaatga agctatagaa tacttgaaac  12360
aggataatgc taatggaatt attgccttga agctagaccg aatcgcacgg aatgctttag  12420
atgtattgcg tttggttcgt gaaaccttag aaccacaaaa taaaatgtta gtgttactag  12480
atattcaggt agatacttcg acaccttcag gaaaaatgat tttaactgta atgagtgccg  12540
ttgctgaact cgaaagagac atgatctatg atcgcactca ggggggtaga aagactaaag  12600
cccaaaaggg cgggtatgcc tacgggaaac ctaaatttgg ctataagact gaagaaaagg  12660
aactaaaaga agattcagca caacaggaaa ctattaaact aattaagaga caccgtaggt  12720
cagggaaaag ctaccagaaa atagctgatt atctcaatgc ccaaagtatt cccactaaac  12780
aaggtaagaa atggagttct agcgtcgtct atcgaatctg tcaggaaaaa gctggttaag  12840
tctgtttata gatatttaga atttattgaa taaaaatagt atgaacaata aatatttatg  12900
gactaaccac gctcggaaac gtttaactga acgatgggaa ataaaagaat catgggttat  12960
tgataccatc gaaaatcctg aacgttcaga atttattgtt gatgagtcag gggaaaaata  13020
tcattactat aaaagaatag ctaagtttaa gaatagagtg ttagaagtga taacttctgc  13080
caactcaaca cccacaagaa taataacctt ttactttaac cgtaacatga ggaaaaattt  13140
atgattgtta cttacgataa tgaagttgac gcaatttatt ttaagttaac ggaaaataaa  13200
attgatagca ccgaacctca aacagacagg attatcattg attacgatga aagtaataat  13260
```

```
attgttggca ttgaggtatt agattttaat tatcttgtca agaaaggttt aaccgttgct  13320

gatttacctt tttctgaaga tgaaagatta acagcttctc aatattttaa ttttcctgtt  13380

gctatctaat ccagaagggg caataatccc cttctttcat cgagttagac ttaatatcac  13440

aaaagtcatt ttcattttac cgtttctttt ccacagcgtc cgtacgcccc tcgttaaatc  13500

tcaaaaccga caatttatga tgtttataaa aagttactca ctttaataag tatttatact  13560

cattaaaggg ttattctttt tttgtagcct gataggttgg gaaggaatat ttcagattat  13620

cagatttgtt gaatattttt cgtcagatac gcaaacctta caaacataat taacaactga  13680

aactattgat atgtctaggt tttagctcta tcacaggttg gatctg                13726
```

<210> SEQ ID NO 22
<211> LENGTH: 13726
<212> TYPE: DNA
<213> ORGANISM: Artificial Sequence
<220> FEATURE:
<223> OTHER INFORMATION: #1631\\pABICyano1::corR-PcorT*2-zmPDC(opt1)_dsrA-Prbc*(optRBS)-synADH(opt1)_ter

<400> SEQUENCE: 22

```
tcgaccatgc gtccaaaact ttcaccatcc tttccctatc aacctttact gcactaaaga     60

caagtgagat agcagtggca atctggcttt gcaatcaatg tttccactaa agcgtttagc    120

gttactgcgg ctagaagtcc tccaccgagg ctcccctgaa tggtgatatg gggaatggga    180

ctggtcatca gtcgtcgttt tgcccccgga gcatgactaa aaccgatcgg cattccgatc    240

acaagagccg gctgaatatg ttgttgctct atcagcttac aggcagtgag taaaacagaa    300

ggggcatagc cgatcgccag cacacatcct tggggaatct gttgtaaccg ctgttgccaa    360

tggtcatggt gccaaaaagc ttgctcggct tccctaagcc ctgtgatgtg agggtcgtca    420

atcagcgttt taaccgtaca tcctaaatga gctaaccgag tttgatcaag agccgcagcc    480

acaaccggaa catcggtgac gactggacac cctgctttca gtgcatctcg tgccgaggcg    540

atcgctccct gactcaatcg aacggcgttt accaagctaa catcaccaca ggccagcact    600

aattgatgta gtaagtgaat ggtaatttca gagtaagccg ataaatccgg tagcaggtgt    660

ttgagggatt cctgaaaggc ttctggatga gttgttgtct ccgcatctag gttcgtccac    720

aactgatcga gttttcctaa cccctcctgg acatccacat caagctgttt cagttgggcc    780

agagcttccg cttgggtaat ctggcaactc tggtcgcgtc ccagtaatcc ttctaaagca    840

gatgcggttt ggcggagtcg agtaatctgc tgaatcacag cctgatattg ctgttgcaac    900

tgcaccatta gggtgggatc aaggctctct tcagaatggc tatccagcag ttgccgaata    960

tgagacaact gaaagccctg ctgtttgagg gcaatgactc gttggagccg ttgtacgtcc   1020

tgctgagtat aaaggcggta gttgccctct gagcgttgaa cgggggggaag caatcccagg   1080

gtgtggtaat ggcgcaccat gcgaggcgta acgccacctc ccactgcatc tgtgagttct   1140

ttaatcgtta agtgattagt cttcatgact ttagtttact caaaaccttg acattgacac   1200

taatgttaag gtttagaatg agaaggtaaa aatccaagtt aaaaagcatg aattcttata   1260

ccgtgggtac ttatttagcc gaacgcttag tgcaaattgg tttaaaacat cattttgccg   1320

tggctgggga ctataattta gtgttattgg ataacttatt attaaataaa aacatggaac   1380

aagtgtattg ttgtaatgaa ttaaattgtg gtttttctgc tgaaggttat gctagagcta   1440

aaggtgcagc tgctgctgtt gttacttatt ctgtgggtgc tttatctgct tttgatgcta   1500

ttggtggtgc ttatgccgaa aatttacccg tgattttaat ttctggtgcc cctaataata   1560
```

-continued

```
atgatcatgc cgctggacat gttttacatc atgccttagg taaaaccgat tatcattatc   1620
aattagaaat ggccaaaaat attactgctg ctgccgaagc tatttatact cctgaagaag   1680
cccctgccaa aattgatcat gtgattaaaa ccgccttacg cgaaaaaaaa cccgtgtatt   1740
tagaaattgc ctgtaatatt gcttctatgc cttgtgctgc tcctgggcct gcttctgctt   1800
tatttaatga tgaagcctct gatgaagcta gtttaaatgc tgccgtggaa gaaaccttaa   1860
aatttattgc caatcgcgat aaagttgccg tgttagttgg ttctaaatta agagctgctg   1920
gtgctgaaga agctgctgtt aaatttgctg atgctttagg tggtgcagtt gctactatgg   1980
ctgctgccaa atcttttttt cccgaagaaa atccccatta tattggaact agttggggag   2040
aagtttctta tcctggtgtg gaaaaaacta tgaaagaagc cgacgctgtt attgctttag   2100
cccctgtgtt taatgattat tctaccactg gttggactga tattcccgat cccaaaaaat   2160
tagttttagc cgaacctcgt tctgttgttg ttaatggtgt tcgctttccc tctgtgcatt   2220
taaaagatta tttaacccgc ttagcccaaa aagtttctaa aaaaactggt gccttagatt   2280
tttttaaatc tttaaatgcg ggtgaattaa aaaaagctgc tcctgctgat ccttctgctc   2340
ctttagttaa tgctgaaatt gcccgtcaag ttgaagcctt attaacccct aatactaccg   2400
ttattgccga aactggtgat tcttggttta atgcccaacg catgaaatta cctaatggtg   2460
cccgtgttga atatgaaatg caatggggtc atattggttg gtctgtacct gctgcttttg   2520
gttatgctgt tggtgctcct gaacgtcgta atattttaat ggtgggtgat ggttcttttc   2580
aattaactgc ccaagaagtt gcccaaatgg ttcgcttaaa attacccgtt attatttttt   2640
taataaataa ttatggttat accattgaag tgatgattca tgatgggcca tataataata   2700
ttaaaaattg ggattatgcg ggtttaatgg aagtgtttaa tggtaatggt ggttatgatt   2760
ctggtgctgg taaaggttta aaagccaaaa ctggtggtga attagctgaa gctattaaag   2820
ttgccttagc caatactgat gggccaacct taattgaatg ttttattggt cgcgaagatt   2880
gtaccgaaga attagttaaa tggggtaaac gtgttgctgc tgctaattct cgcaaacccg   2940
tgaataaatt attgtaattt ttggggatca attcgagctc agcaagtttc atcccgaccc   3000
cctcagggtc gggatttttt tattgtacta gttgacataa gtaaaggcat cccctgcgtg   3060
atataattac cttcagttta aggaggtata cacatatgat taaagcctat gctgccttag   3120
aagccaatgg taaattacaa ccctttgaat atgatcctgg tgctttaggt gccaatgaag   3180
tggaaattga agtgcaatat tgtggtgtgt gtcattctga tttatctatg attaataatg   3240
aatggggtat ttctaattat cccttagttc ctggtcatga agttgttggt actgttgctg   3300
ctatgggtga aggtgttaat catgtggaag tgggtgattt agttggttta ggttggcatt   3360
ctggttattg tatgacctgt cattcttgtt tatctggtta tcataattta tgtgccactg   3420
ccgaatctac tattgtgggt cattatggtg gttttggtga tagagttcgt gctaaaggtg   3480
tttctgtggt gaaattaccc aaaggtattg atttagcctc tgctgggcct ttattttgtg   3540
gtggtattac cgtttttttct cccatggtgg aattatcttt aaaacctacc gccaaagttg   3600
ctgttattgg tattggtggt ttaggtcatt tagccgttca atttttaaga gcctggggtt   3660
gtgaagttac tgcttttacc tcttctgccc gtaaacaaac cgaagtttta gaattaggtg   3720
cccatcatat tttagattct accaatcctg aagctattgc ttctgccgaa ggtaaatttg   3780
attatattat ttctaccgtg aatttaaaat tagattggaa tttatatatc agtaccttag   3840
cccctcaagg tcattttcat tttgttggtg tggtgttaga acccttggac ttaaacttat   3900
```

-continued

```
ttcccttatt aatgggacaa cgttctgttt ctgcttctcc tgttggttct cctgctacta   3960
ttgccactat gttagatttt gccgtgcgtc atgatattaa acccgtggtg gaacaatttt   4020
cttttgatca aattaatgaa gccattgccc atttagaatc tggtaaagcc cattatcgcg   4080
tggtgttatc tcattctaaa aattaataag attaacttct aaactgaaac aaatttgagg   4140
gtaggcttca ttgtctgccc ttattttttt atttaggaaa agtgaacaga ctaaagagtg   4200
ttggctctat tgctttgagt atgtaaatta ggcgttgctg aattaaggta tgatttttga   4260
ccccttctct cttctgcagg atcatcttgc tgaaaaactc gagcgctcgt tccgcaaagc   4320
ggtacggagt tagttagggg ctaatgggca ttctcccgta caggaaagag ttagaagtta   4380
ttaattatca acaattctcc tttgcctagt gcatcgttac ctttttaatt aaaacataag   4440
gaaaactaat aatcgtaata atttaacctc aaagtgtaaa gaaatgtgaa attctgactt   4500
ttataacgtt aaagagggaa aaattagcag tttaaaatac ctagagaata gtctggggta   4560
agcatagaga attagattag ttaagttaat caaattcaga aaaaataata atcgtaaata   4620
gttaatctgg gtgtatagaa aatgatcccc ttcatgataa gatttaaact cgaaaagcaa   4680
aagccaaaaa actaacttcc attaaaagaa gttgttacat ataacgctat aaagaaaatt   4740
tatatatttg gaggatacca accatgtctc atattcaacg tgaaactagt tgttctcgcc   4800
ctcgtttaaa ttctaatatg gatgccgatt tatatggtta taaatgggct cgtgataatg   4860
ttggtcaatc tggtgctact atttatcgtt tatatggtaa acctgatgct cctgaattat   4920
tcttgaaaca tggtaaaggt tctgttgcta atgatgttac tgatgaaatg gttcgtttaa   4980
actggttgac tgaatttatg cctttaccta ctattaaaca ttttattcgt actcccgatg   5040
atgcttggtt attaactact gctattcctg gtaaaactgc ttttcaagtt ttagaagaat   5100
atcctgattc tggtgaaaat attgttgatg ctttagctgt ttttttacgt cgtttacatt   5160
ctattcccgt ttgtaattgt ccttttaatt ctgatcgtgt ttttcgttta gctcaagctc   5220
aatctcgtat gaataatggt ttagttgatg cttctgattt tgatgatgaa cgtaatggtt   5280
ggcctgttga acaagtttgg aaagaaatgc acaaattgtt accttttict cctgattctg   5340
ttgttactca tggtgatttt tctttagata atttgatctt tgatgaaggt aaattgattg   5400
gttgtattga tgttggtcgt gttggtattg ctgatcgtta tcaagattta gctattttat   5460
ggaattgttt aggtgaattt tctccttctt tacagaaacg tttatttcag aaatatggta   5520
ttgataatcc tgatatgaac aagttacaat ttcatttaat gttggacgag ttcttttaag   5580
aattaattca tgaccaaaat cccttaacgt gagttttcgt tccactgagc gtcagacccc   5640
gtagaaaaga tcaaaggatc ttcttgagat cctttttttc tgcgcgtaat ctgctgctat   5700
ttaaattacg tacacgtgtt attactttgt taacgacaat tgtcttaatt aactgggcct   5760
catgggcctt ccgctcactg cccgctttcc agtcgggaaa cctgtcgtgc cagctctgca   5820
gatgacggtg aaaacctctg acacatgcag ctcccggaga cggtcacagc ttgtctgtaa   5880
gcggatgccg ggagcagaca agcccgtcag ggcgcgtcag cgggtgttgg cgggtgtcgg   5940
ggcgcagcca tgacccagtc acgtagcgat agcggagtgt atactggctt aactatgcgg   6000
catcagagca gattgtactg agagtgcacc atatgcggtg tgaaataccg cacagatgcg   6060
taaggagaaa ataccgcatc aggcgctctt ccgcttcctc gctcactgac tcgctgcgct   6120
cggtcgttcg gctgcggcga gcggtatcag ctcactcaaa ggcggtaata cggttatcca   6180
cagaatcagg ggataacgca ggaaagaaca tgtgagcaaa aggccagcaa aaggccagga   6240
accgtaaaaa ggccgcgttg ctggcgtttt tccataggct ccgcccccct gacgagcatc   6300
```

```
acaaaaatcg acgctcaagt cagaggtggc gaaacccgac aggactataa agataccagg   6360
cgtttccccc tggaagctcc ctcgtgcgct ctcctgttcc gaccctgccg cttaccggat   6420
acctgtccgc ctttctccct tcgggaagcg tggcgctttc tcatagctca cgctgtaggt   6480
atctcagttc ggtgtaggtc gttcgctcca agctgggctg tgtgcacgaa ccccccgttc   6540
agcccgaccg ctgcgcctta tccggtaact atcgtcttga gtccaacccg gtaagacacg   6600
acttatcgcc actggcagca gccactggta acaggattag cagagcgagg tatgtaggcg   6660
gtgctacaga gttcttgaag tggtggccta actacggcta cactagaagg acagtatttg   6720
gtatctgcgc tctgctgaag ccagttacct tcggaaaaag agttggtagc tcttgatccg   6780
gcaaacaaac caccgctggt agcggtggtt tttttgtttg caagcagcag attacgcgca   6840
gaaaaaaagg atctcaagaa gatcctttga tcttttctac tgcagaagct tgttagacac   6900
cctgtcatgt attttatatt atttatttca ccatacggat taagtgaaac ctaatgaaaa   6960
tagtactttc ggagctttaa ctttaatgaa ggtatgtttt tttatagaca tcgatgtctg   7020
gtttaacaat aggaaaaagt agctaaaact cccatgaatt aaagaaataa caaggtgtct   7080
aacaacctgt tattaagaat gttagaaaag acttaacatt tgtgttgagt ttttatagac   7140
attggtgtct agacatacgg tagataaggt ttgctcaaaa ataaaataaa aaaagattgg   7200
actaaaaaac atttaattta gtacaattta attagttatt ttttcgtctc aaattttgct   7260
ttgttgagca gaaatttaga taaaaaaatc cccgtgatca gattacaatg tcgttcattg   7320
tacgatgtgt cgaaaaatct ttacgacact ctaaactgac cacacggggg aaaaagaaaa   7380
ctgaactaat aacatcatga tactcggaaa acctagcaat tctcaacccc taaacaaaag   7440
aaacttccaa aaccctgacc atataaagga gtggcaacaa tcagcaatca gtcaagattt   7500
gatagcagaa aatcttgtat cggttgctaa tggttttgat gtactattta tcggcaataa   7560
ataccgaact aacacgggtg ttctgtcacg gcacatatta aactcctatt ctcatttaga   7620
agatggtggt tcgtatggta gaacatttga cccatttacc aataaagaaa tgcagtgggt   7680
tcaatttaaa ccgaatagac caagaaaagg ttctactggt aaggtaatca aatatgaatc   7740
gccaaaaggt gaacctacaa gagttctaat gccgtttgtg cctatgaaaa tatggcaacg   7800
gattagcgat aagttcggag taccgattaa tccgaaaaaa gatactcact tttgggaatg   7860
ggtaaagaat aatccatcga taccgattgc cattacagaa ggaaataaaa aagctaattg   7920
cctattatcc tatggctatc ctgctattgc ctttgtaggc atttggaacg gattagagaa   7980
aataaatgat ttctcgaagg aaaagcagtt aaaagaggat ttgaaatggt tgttatccaa   8040
cggcaaccga aatattaata tcatctttga ccaagaccag aaacaaaaaa ctgtaattaa   8100
tgtaaacaaa gctattttcg ctttatcttc tctaataagt agaaatggtc ataaagttaa   8160
tattgtgcaa tggttgccgt caaaaggtaa aggaatagat gattatttgg tagctttacc   8220
ttttgagaaa agagaaaatc atttagacaa cttaattaaa attgcaccat catttaattt   8280
ttggtcaact aaatacttat tcaagtgtcg taaaccagat ttaaccgtaa attgccgtta   8340
tttgagcgat gcagtaaaag aattacctca agaggatata gcattaatag cacctcacgg   8400
cacgggtaaa acttcattag tagctactca cgttaagaat cggagttatc acggaaggaa   8460
aactatttca ttggtgcatc ttgaaagttt agccaaagct aatggcaacg cacttggatt   8520
atattaccga accgaaaata atattgaaaa gcaatatctt ggatttagct tatgtgtaga   8580
tagttgccgt gataagatta acggcattac aactgatatt atttcaggtc aagattattg   8640
```

cctttttcatt gatgaaattg accaagtaat tccacacatc cttaacagtg aaactgaagt 8700
aagtaagtat agatgcacca tcattgacac tttttctgaa ctggtgagaa atgctgaaca 8760
ggtcattatt gctgatgctg atttatccga tgtgacgatt gacctaatag aaaacatcag 8820
aggtaaaaaa ctatatgtaa tcaagaatga atatcagtat cagggaatga cttttaacgc 8880
cgttggttca ccattagaaa tgatggcaat gatgggaaaa tcggtgtcag aaggcaagaa 8940
attatttatt aacaccacat cccaaaaggc aaaaagtaag tacggcacaa tcgctcttga 9000
gtcttatatt tttggtctaa ataaagaagc aaagatatta agaatagact ctgaaaccac 9060
taaaaaccct gaacatccag cctataaaat cattgaccaa gacttaaata atatcctcaa 9120
agattatgat tatgtcattg cctcaccttg ccttcaaaca ggtgtcagta ttaccttaaa 9180
agggcatttt gaccagcaat ttaacttttc cagtggaaac attacacctc attgcttttt 9240
acagcaaatg tggcggttga gggatgcaga aattgaaaga ttctattatg tgccgaactc 9300
atctaacctc aatctcattg ggaataagtc aagttcacca tcagaccttc taaagagcaa 9360
taacaagatg gcaacggcaa cggttaacct tttgggtaga atcgactccg aatattccct 9420
agagtatgaa tcgcacggca tttggcttga gacgtgggca aaattatcag cacggcataa 9480
cagttcaatg cgttgttact ctgaaattct tacctatcta attacgtctc aagggcataa 9540
attaaatatc aacattccct cacctcttgc agatattaag aagctaaatg atgaggtaag 9600
tagtaacagg gaaaaggtaa aaaatgagag atactctcag aggttaaact caccagatat 9660
taacgatgca gaagctacca tactcgaatc taaagagcaa aaaatcggat tgactctcaa 9720
tgagagatgc accctagaaa agcataaagt taagaagcgg tatgggaatg taaagatgga 9780
tattctcacc tttgatgatg atggactata ccccaaactc agactatttt attacctcac 9840
catcggtaaa cctcatctca aggctaatga cagaaaagct attgccaaaa tgggcaatga 9900
caataaaggc aagattctat caaaagactt agttaataaa acttactccg ctcgtgtgaa 9960
ggtcttagag attcttaaac taactgactt tatcgacaat cttagagatg aactcttaat 10020
aactcccaat aatccagcta tcaccgattt taataatctt ctgctaagag ctaagaagga 10080
tttaagagta ttaggagtca acatcggaaa atatccaatg gccaacatta atgccgtact 10140
tactctcatt ggtcacaaac tttctgtaat gagagatgag ttcggaaaag agaaaaggat 10200
aaaagtagat ggtaaatcat accgatgtta tcaacttgaa acattaccag attttaccaa 10260
tgatactctt gactactggt tagaaaatga tagccaaaaa gaagtaacag caacagaaaa 10320
ttactccgaa aattttaacc cttcaaatag ctacaatcca gacagtaaga cactttcaga 10380
gggtgcaaat ttcctatata taaataaaga agaattgcat ccaaataaat tgcacctaga 10440
aataaaagaa ggtgctgaac tttttttatt cggggtaaag gtgattgtga aaggaatctt 10500
ggacggggca gtaactatat tctctatggg tcaagaatac gatttatccc tcaatgaact 10560
agaggggatg ttaacatcat gaactttaca agaatctttt taaagggcga tcgcaccatg 10620
ttaaatgatg gtacatttgt tcagatattt gatatttacc atgaccacgc attgggagtg 10680
acccttgacc ttaagacaga aaaaattatt tccgatgatg ttagggtaat tactgtcaaa 10740
gacttattgt tcgatggcac ttataaaggg gtaaaatctt ttatgcccga taatgcccga 10800
taatgcccga ttgatgctac aaaatcccat aatcataagc gataatcccc taatagcttg 10860
taattcttga accgtagcga ttttagagta ttccaaaaag aagaaataaa caccgcaaaa 10920
tgtcgtattt cacatatata aaccaaggtt ttttgcccta aaatctttat gtttgtagtg 10980
tgatgttggg tcaaaatggt cagaaaagtt gcaaggtttt tatggatgct tacgcgcgcg 11040

```
aggggtaagc atccccaaat agttacttta tcctagtcca tgcccattta ttgccgtccc  11100
gttcggcttt aaaaaagtgc caaaactcac aaggtgcaat aaaaagttct gtacctttcg  11160
caaccctaga taatctttca acagttactt tttttcctat tatctcggta caaagtttgg  11220
ctagtttctc ttttccctct ttttcaatca agccttcttg tatgcccaac tcattgatta  11280
atctctctat ttttaccatt atttcccgtt caggtagttt atcccctaaa tcttcatcgg  11340
ggggcaatgt agggcattct gaaggggctt tttcttctgt ctggacatta tctaatattg  11400
aagtaaccaa actatcttca gttttttcta ttcctattaa ttcatattcg gttactgtat  11460
ccgtatcaat atccgaataa ctatctttat ccgtattagc tattcggtta agtttatccg  11520
ttaactcaga aacaagacta tatagcggtt ttagcttttc ttctatcctg ttatctaata  11580
cggataagtt tatacggtta tcattatccg tattagtatc attgggcttt tttggtagtt  11640
ctaccccctc ataaaccgct tttattccca attccaacag actgataaca gtatccttta  11700
taatgggttt tttgctgata tggtgaactt ttgccccttc catcattgcg atactttcta  11760
tctcactcat caacttatcg cttaagtgaa tctcgtatct gtttaatccc ttactggttt  11820
tattcatatc cgtttacttt attcggttaa caattctatt ttatacgaat aaaatattat  11880
acggttaact ttatacgttt aactatttta tctatacgga taacagtaat aagttattcg  11940
tattagttat acgtttactt ttatccaaat aaaattagtg catttaaact aaaagaatga  12000
ttttatcgga gttgatagca ttggattaac ctaaagatgt ttataagcta tatctgataa  12060
gtatttaagg ttattttgtt attctgttta ttgacattat cagaataaaa gaatagaata  12120
taattgttga gagataagag gtttaagtga ttatggttaa gaagttagtt ggttatgtca  12180
gggtcagtag tgaatcgcaa gaggataaca ctagcttaca gaatcagata gagagaattg  12240
aagcatattg tatggctttt ggttatgagt tggtaaaaat attcaaagag gttgccactg  12300
gtacaaaagc agatattgaa acccgtccta tttttaatga agctatagaa tacttgaaac  12360
aggataatgc taatggaatt attgccttga agctagaccg aatcgcacgg aatgctttag  12420
atgtattgcg tttggttcgt gaaaccttag aaccacaaaa taaaatgtta gtgttactag  12480
atattcaggt agatacttcg acaccttcag gaaaaatgat tttaactgta atgagtgccg  12540
ttgctgaact cgaaagagac atgatctatg atcgcactca ggggggtaga aagactaaag  12600
cccaaaaggg cgggtatgcc tacgggaaac ctaaatttgg ctataagact gaagaaaagg  12660
aactaaaaga agattcagca caacaggaaa ctattaaact aattaagaga caccgtaggt  12720
cagggaaaag ctaccagaaa atagctgatt atctcaatgc ccaaagtatt cccactaaac  12780
aaggtaagaa atggagttct agcgtcgtct atcgaatctg tcaggaaaaa gctggttaag  12840
tctgtttata gatatttaga atttattgaa taaaaatagt atgaacaata aatatttatg  12900
gactaaccac gctcggaaac gtttaactga acgatgggaa ataaaagaat catgggttat  12960
tgataccatc gaaaatcctg aacgttcaga atttattgtt gatgagtcag gggaaaaata  13020
tcattactat aaaagaatag ctaagtttaa gaatagagtg ttagaagtga taacttctgc  13080
caactcaaca cccacaagaa taataacctt ttactttaac cgtaacatga ggaaaaattt  13140
atgattgtta cttacgataa tgaagttgac gcaatttatt ttaagttaac ggaaaataaa  13200
attgatagca ccgaacctca aacagacagg attatcattg attacgatga aagtaataat  13260
attgttggca ttgaggtatt agattttaat tatcttgtca agaaaggttt aaccgttgct  13320
gatttacctt tttctgaaga tgaaagatta acagcttctc aatattttaa ttttcctgtt  13380
```

gctatctaat ccagaagggg caataatccc cttctttcat cgagttagac ttaatatcac 13440
aaaagtcatt ttcattttac cgtttctttt ccacagcgtc cgtacgcccc tcgttaaatc 13500
tcaaaaccga caatttatga tgtttataaa aagttactca ctttaataag tatttatact 13560
cattaaaggg ttattctttt tttgtagcct gataggttgg gaaggaatat ttcagattat 13620
cagatttgtt gaatattttt cgtcagatac gcaaacctta caaacataat taacaactga 13680
aactattgat atgtctaggt tttagctcta tcacaggttg gatctg 13726

<210> SEQ ID NO 23
<211> LENGTH: 13726
<212> TYPE: DNA
<213> ORGANISM: Artificial Sequence
<220> FEATURE:
<223> OTHER INFORMATION: #1632\\pABICyano1::corR-PcorT*3-
zmPDCABICyano1(opt1)_dsrA-Prbc*(optRBS)-synADH(opt1)_ter

<400> SEQUENCE: 23
tcgaccatgc gtccaaaact ttcaccatcc tttccctatc aacctttact gcactaaaga 60
caagtgagat agcagtggca atctggcttt gcaatcaatg tttccactaa agcgtttagc 120
gttactgcgg ctagaagtcc tccaccgagg ctcccctgaa tggtgatatg gggaatggga 180
ctggtcatca gtcgtcgttt tgcccccgga gcatgactaa aaccgatcgg cattccgatc 240
acaagagccg gctgaatatg ttgttgctct atcagcttac aggcagtgag taaaacagaa 300
ggggcatagc cgatcgccag cacacatcct tggggaatct gttgtaaccg ctgttgccaa 360
tggtcatggt gccaaaaagc ttgctcggct tccctaagcc ctgtgatgtg agggtcgtca 420
atcagcgttt taaccgtaca tcctaaatga gctaaccgag tttgatcaag agccgcagcc 480
acaaccggaa catcggtgac gactggacac cctgctttca gtgcatctcg tgccgaggcg 540
atcgctccct gactcaatcg aacggcgttt accaagctaa catcaccaca ggccagcact 600
aattgatgta gtaagtgaat ggtaatttca gagtaagccg ataaatccgg tagcaggtgt 660
ttgagggatt cctgaaaggc ttctggatga gttgttgtct ccgcatctag gttcgtccac 720
aactgatcga gttttcctaa cccctcctgg acatccacat caagctgttt cagttgggcc 780
agagcttccg cttgggtaat ctggcaactc tggtcgcgtc ccagtaatcc ttctaaagca 840
gatgcggttt ggcggagtcg agtaatctgc tgaatcacag cctgatattg ctgttgcaac 900
tgcaccatta gggtgggatc aaggctctct tcagaatggc tatccagcag ttgccgaata 960
tgagacaact gaaagccctg ctgtttgagg gcaatgactc gttggagccg ttgtacgtcc 1020
tgctgagtat aaaggcggta gttgccctct gagcgttgaa cggggggaag caatcccagg 1080
gtgtggtaat ggcgcaccat gcgaggcgta acgccacctc ccactgcatc tgtgagttct 1140
ttaatcgtta agtgattagt cttcatgact ttagtttact caaaaccttg acattgacac 1200
taatgttaag gtttagaatg agaaggtaaa aatcgaggat aaaaagcatg aattcttata 1260
ccgtgggtac ttatttagcc gaacgcttag tgcaaattgg tttaaaacat catttttgccg 1320 tggctgggga ctataattta gtgttattgg ataacttatt attaaataaa aacatggaac 1380
aagtgtattg ttgtaatgaa ttaaattgtg gtttttctgc tgaaggttat gctagagcta 1440
aaggtgcagc tgctgctgtt gttacttatt ctgtgggtgc tttatctgct tttgatgcta 1500
ttggtggtgc ttatgccgaa aatttacccg tgattttaat ttctggtgcc cctaataata 1560
atgatcatgc cgctggacat gttttacatc atgccttagg taaaaccgat tatcattatc 1620
aattagaaat ggccaaaaat attactgctg ctgccgaagc tatttatact cctgaagaag 1680

-continued

```
ccccctgccaa aattgatcat gtgattaaaa ccgccttacg cgaaaaaaaa cccgtgtatt   1740
tagaaattgc ctgtaatatt gcttctatgc cttgtgctgc tcctgggcct gcttctgctt   1800
tatttaatga tgaagcctct gatgaagcta gtttaaatgc tgccgtggaa gaaaccttaa   1860
aatttattgc caatcgcgat aaagttgccg tgttagttgg ttctaaatta agagctgctg   1920
gtgctgaaga agctgctgtt aaatttgctg atgctttagg tggtgcagtt gctactatgg   1980
ctgctgccaa atcttttttt cccgaagaaa atccccatta tattggaact agttggggag   2040
aagtttctta tcctggtgtg gaaaaaacta tgaaagaagc cgacgctgtt attgctttag   2100
cccctgtgtt taatgattat tctaccactg gttggactga tattcccgat cccaaaaaat   2160
tagttttagc cgaacctcgt tctgttgttg ttaatggtgt tcgctttccc tctgtgcatt   2220
taaaagatta tttaacccgc ttagcccaaa aagtttctaa aaaaactggt gccttagatt   2280
tttttaaatc tttaaatgcg ggtgaattaa aaaaagctgc tcctgctgat ccttctgctc   2340
ctttagttaa tgctgaaatt gcccgtcaag ttgaagcctt attaacccct aatactaccg   2400
ttattgccga aactggtgat tcttggttta atgcccaacg catgaaatta cctaatggtg   2460
cccgtgttga atatgaaatg caatggggtc atattggttg gtctgtacct gctgcttttg   2520
gttatgctgt tggtgctcct gaacgtcgta atattttaat ggtgggtgat ggttcttttc   2580
aattaactgc ccaagaagtt gcccaaatgg ttcgcttaaa attacccgtt attatttttt   2640
taataaataa ttatggttat accattgaag tgatgattca tgatgggcca tataataata   2700
ttaaaaattg ggattatgcg ggtttaatgg aagtgtttaa tggtaatggt ggttatgatt   2760
ctggtgctgg taaaggttta aaagccaaaa ctggtggtga attagctgaa gctattaaag   2820
ttgccttagc caatactgat gggccaacct taattgaatg ttttattggt cgcgaagatt   2880
gtaccgaaga attagttaaa tggggtaaac gtgttgctgc tgctaattct cgcaaacccg   2940
tgaataaatt attgtaattt ttggggatca attcgagctc agcaagtttc atcccgaccc   3000
cctcagggtc gggatttttt tattgtacta gttgacataa gtaaaggcat cccctgcgtg   3060
atataattac cttcagttta aggaggtata cacatatgat taaagcctat gctgccttag   3120
aagccaatgg taaattacaa ccctttgaat atgatcctgg tgctttaggt gccaatgaag   3180
tggaaattga agtgcaatat tgtggtgtgt gtcattctga tttatctatg attaataatg   3240
aatggggtat ttctaattat cccttagttc ctggtcatga agttgttggt actgttgctg   3300
ctatgggtga aggtgttaat catgtggaag tgggtgattt agttggttta ggttggcatt   3360
ctggttattg tatgacctgt cattcttgtt tatctggtta tcataattta tgtgccactg   3420
ccgaatctac tattgtgggt cattatggtg gttttggtga tagagttcgt gctaaaggtg   3480
tttctgtggt gaaattaccc aaaggtattg atttagcctc tgctgggcct ttattttgtg   3540
gtggtattac cgtttttttct cccatggtgg aattatcttt aaaacctacc gccaaagttg   3600
ctgttattgg tattggtggt ttaggtcatt tagccgttca atttttaaga gcctggggtt   3660
gtgaagttac tgcttttacc tcttctgccc gtaaacaaac cgaagtttta gaattaggtg   3720
cccatcatat tttagattct accaatcctg aagctattgc ttctgccgaa ggtaaatttg   3780
attatattat ttctaccgtg aatttaaaat tagattggaa tttatatatc agtaccttag   3840
cccctcaagg tcattttcat tttgttggtg tggtgttaga acccttggac ttaaacttat   3900
ttccccttatt aatgggacaa cgttctgttt ctgcttctcc tgttggttct cctgctacta   3960
ttgccactat gttagatttt gccgtgcgtc atgatattaa acccgtggtg gaacaatttt   4020
cttttgatca aattaatgaa gccattgccc atttagaatc tggtaaagcc cattatcgcg   4080
```

-continued

```
tggtgttatc tcattctaaa aattaataag attaacttct aaactgaaac aaatttgagg   4140
gtaggcttca ttgtctgccc ttattttttt atttaggaaa agtgaacaga ctaaagagtg   4200
ttggctctat tgctttgagt atgtaaatta ggcgttgctg aattaaggta tgatttttga   4260
ccccttctct cttctgcagg atcatcttgc tgaaaaactc gagcgctcgt tccgcaaagc   4320
ggtacggagt tagttagggg ctaatgggca ttctcccgta caggaaagag ttagaagtta   4380
ttaattatca acaattctcc tttgcctagt gcatcgttac ctttttaatt aaaacataag   4440
gaaaactaat aatcgtaata atttaacctc aaagtgtaaa gaaatgtgaa attctgactt   4500
ttataacgtt aaagagggaa aaattagcag tttaaaatac ctagagaata gtctggggta   4560
agcatagaga attagattag ttaagttaat caaattcaga aaaaataata atcgtaaata   4620
gttaatctgg gtgtatagaa aatgatcccc ttcatgataa gatttaaact cgaaaagcaa   4680
aagccaaaaa actaacttcc attaaaagaa gttgttacat ataacgctat aaagaaaatt   4740
tatatatttg gaggatacca accatgtctc atattcaacg tgaaactagt tgttctcgcc   4800
ctcgtttaaa ttctaatatg gatgccgatt tatatggtta taaatgggct cgtgataatg   4860
ttggtcaatc tggtgctact atttatcgtt tatatggtaa acctgatgct cctgaattat   4920
tcttgaaaca tggtaaaggt tctgttgcta atgatgttac tgatgaaatg gttcgtttaa   4980
actggttgac tgaatttatg cctttaccta ctattaaaca ttttattcgt actcccgatg   5040
atgcttggtt attaactact gctattcctg gtaaaactgc ttttcaagtt ttagaagaat   5100
atcctgattc tggtgaaaat attgttgatg ctttagctgt ttttttacgt cgtttacatt   5160
ctattcccgt ttgtaattgt ccttttaatt ctgatcgtgt tttcgttta gctcaagctc   5220
aatctcgtat gaataatggt ttagttgatg cttctgattt tgatgatgaa cgtaatggtt   5280
ggcctgttga acaagtttgg aaagaaatgc acaaattgtt accttttttct cctgattctg   5340
ttgttactca tggtgatttt tctttagata atttgatctt tgatgaaggt aaattgattg   5400
gttgtattga tgttggtcgt gttggtattg ctgatcgtta tcaagattta gctattttat   5460
ggaattgttt aggtgaattt tctccttctt tacagaaacg tttatttcag aaatatggta   5520
ttgataatcc tgatatgaac aagttacaat ttcatttaat gttggacgag ttcttttaag   5580
aattaattca tgaccaaaat cccttaacgt gagttttcgt tccactgagc gtcagacccc   5640
gtagaaaaga tcaaaggatc ttcttgagat cctttttttc tgcgcgtaat ctgctgctat   5700
ttaaattacg tacacgtgtt attactttgt taacgacaat tgtcttaatt aactgggcct   5760
catgggcctt ccgctcactg cccgctttcc agtcgggaaa cctgtcgtgc cagctctgca   5820
gatgacggtg aaaacctctg acacatgcag ctcccggaga cggtcacagc ttgtctgtaa   5880
gcggatgccg ggagcagaca agcccgtcag ggcgcgtcag cgggtgttgg cgggtgtcgg   5940
ggcgcagcca tgacccagtc acgtagcgat agcggagtgt atactggctt aactatgcgg   6000
catcagagca gattgtactg agagtgcacc atatgcggtg tgaaataccg cacagatgcg   6060
taaggagaaa ataccgcatc aggcgctctt ccgcttcctc gctcactgac tcgctgcgct   6120
cggtcgttcg gctgcggcga gcggtatcag ctcactcaaa ggcggtaata cggttatcca   6180
cagaatcagg ggataacgca ggaaagaaca tgtgagcaaa aggccagcaa aaggccagga   6240
accgtaaaaa ggccgcgttg ctggcgtttt tccataggct ccgcccccct gacgagcatc   6300
acaaaaatcg acgctcaagt cagaggtggc gaaacccgac aggactataa agataccagg   6360
cgtttccccc tggaagctcc ctcgtgcgct ctcctgttcc gaccctgccg cttaccggat   6420
```

-continued

```
acctgtccgc ctttctccct tcgggaagcg tggcgctttc tcatagctca cgctgtaggt   6480
atctcagttc ggtgtaggtc gttcgctcca agctgggctg tgtgcacgaa ccccccgttc   6540
agcccgaccg ctgcgcctta tccggtaact atcgtcttga gtccaacccg gtaagacacg   6600
acttatcgcc actggcagca gccactggta acaggattag cagagcgagg tatgtaggcg   6660
gtgctacaga gttcttgaag tggtggccta actacggcta cactagaagg acagtatttg   6720
gtatctgcgc tctgctgaag ccagttacct tcggaaaaag agttggtagc tcttgatccg   6780
gcaaacaaac caccgctggt agcggtggtt tttttgtttg caagcagcag attacgcgca   6840
gaaaaaaagg atctcaagaa gatcctttga tcttttctac tgcagaagct tgttagacac   6900
cctgtcatgt attttatatt atttatttca ccatacggat taagtgaaac ctaatgaaaa   6960
tagtactttc ggagctttaa ctttaatgaa ggtatgtttt tttatagaca tcgatgtctg   7020
gtttaacaat aggaaaaagt agctaaaact cccatgaatt aaagaaataa caaggtgtct   7080
aacaacctgt tattaagaat gttagaaaag acttaacatt tgtgttgagt ttttatagac   7140
attggtgtct agacatacgg tagataaggt ttgctcaaaa ataaaataaa aaaagattgg   7200
actaaaaaac atttaattta gtacaattta attagttatt ttttcgtctc aaattttgct   7260
ttgttgagca gaaatttaga taaaaaaatc cccgtgatca gattacaatg tcgttcattg   7320
tacgatgtgt cgaaaaatct ttacgacact ctaaactgac cacacggggg aaaaagaaaa   7380
ctgaactaat aacatcatga tactcggaaa acctagcaat tctcaacccc taaacaaaag   7440
aaacttccaa aaccctgacc atataaagga gtggcaacaa tcagcaatca gtcaagattt   7500
gatagcagaa aatcttgtat cggttgctaa tggttttgat gtactattta tcggcaataa   7560
ataccgaact aacacgggtg ttctgtcacg gcacatatta aactcctatt ctcatttaga   7620
agatggtggt tcgtatggta gaacatttga cccatttacc aataaagaaa tgcagtgggt   7680
tcaatttaaa ccgaatagac caagaaaagg ttctactggt aaggtaatca aatatgaatc   7740
gccaaaaggt gaacctacaa gagttctaat gccgtttgtg cctatgaaaa tatggcaacg   7800
gattagcgat aagttcggag taccgattaa tccgaaaaaa gatactcact tttgggaatg   7860
ggtaaagaat aatccatcga taccgattgc cattacagaa ggaaataaaa aagctaattg   7920
cctattatcc tatggctatc ctgctattgc ctttgtaggc atttggaacg gattagagaa   7980
aataaatgat ttctcgaagg aaaagcagtt aaaagaggat ttgaaatggt tgttatccaa   8040
cggcaaccga aatattaata tcatctttga ccaagaccag aaacaaaaaa ctgtaattaa   8100
tgtaaacaaa gctattttcg ctttatcttc tctaataagt agaaatggtc ataaagttaa   8160
tattgtgcaa tggttgccgt caaaaggtaa aggaatagat gattatttgg tagctttacc   8220
ttttgagaaa agagaaaatc atttagacaa cttaattaaa attgcaccat catttaattt   8280
ttggtcaact aaatacttat tcaagtgtcg taaaccagat ttaaccgtaa attgccgtta   8340
tttgagcgat gcagtaaaag aattacctca agaggatata gcattaatag cacctcacgg   8400
cacgggtaaa acttcattag tagctactca cgttaagaat cggagttatc acggaaggaa   8460
aactatttca ttggtgcatc ttgaaagttt agccaaagct aatggcaacg cacttggatt   8520
atattaccga accgaaaata atattgaaaa gcaatatctt ggatttagct tatgtgtaga   8580
tagttgccgt gataagatta acggcattac aactgatatt atttcaggtc aagattattg   8640
ccttttcatt gatgaaattg accaagtaat tccacacatc cttaacagtg aaactgaagt   8700
aagtaagtat agatgcacca tcattgacac tttttctgaa ctggtgagaa atgctgaaca   8760
ggtcattatt gctgatgctg atttatccga tgtgacgatt gacctaatag aaaacatcag   8820
```

-continued

```
aggtaaaaaa ctatatgtaa tcaagaatga atatcagtat cagggaatga cttttaacgc   8880
cgttggttca ccattagaaa tgatggcaat gatgggaaaa tcggtgtcag aaggcaagaa   8940
attatttatt aacaccacat cccaaaaggc aaaaagtaag tacggcacaa tcgctcttga   9000
gtcttatatt tttggtctaa ataaagaagc aaagatatta agaatagact ctgaaaccac   9060
taaaaaccct gaacatccag cctataaaat cattgaccaa gacttaaata atatcctcaa   9120
agattatgat tatgtcattg cctcaccttg ccttcaaaca ggtgtcagta ttaccttaaa   9180
agggcatttt gaccagcaat ttaacttttc cagtggaaac attacacctc attgcttttt   9240
acagcaaatg tggcggttga gggatgcaga aattgaaaga ttctattatg tgccgaactc   9300
atctaacctc aatctcattg ggaataagtc aagttcacca tcagaccttc taaagagcaa   9360
taacaagatg gcaacggcaa cggttaacct tttgggtaga atcgactccg aatattccct   9420
agagtatgaa tcgcacggca tttggcttga gacgtgggca aaattatcag cacggcataa   9480
cagttcaatg cgttgttact ctgaaattct tacctatcta attacgtctc aagggcataa   9540
attaaatatc aacattccct cacctcttgc agatattaag aagctaaatg atgaggtaag   9600
tagtaacagg gaaaaggtaa aaaatgagag atactctcag aggttaaact caccagatat   9660
taacgatgca gaagctacca tactcgaatc taaagagcaa aaaatcggat tgactctcaa   9720
tgagagatgc accctagaaa agcataaagt taagaagcgg tatgggaatg taaagatgga   9780
tattctcacc tttgatgatg atggactata ccccaaactc agactatttt attacctcac   9840
catcggtaaa cctcatctca aggctaatga cagaaaagct attgccaaaa tgggcaatga   9900
caataaaggc aagattctat caaaagactt agttaataaa acttactccg ctcgtgtgaa   9960
ggtcttagag attcttaaac taactgactt tatcgacaat cttagagatg aactcttaat  10020
aactcccaat aatccagcta tcaccgattt taataatctt ctgctaagag ctaagaagga  10080
tttaagagta ttaggagtca acatcggaaa atatccaatg gccaacatta atgccgtact  10140
tactctcatt ggtcacaaac tttctgtaat gagagatgag ttcggaaaag agaaaaggat  10200
aaaagtagat ggtaaatcat accgatgtta tcaacttgaa acattaccag attttaccaa  10260
tgatactctt gactactggt tagaaaatga tagccaaaaa gaagtaacag caacagaaaa  10320
ttactccgaa aattttaacc cttcaaatag ctacaatcca gacagtaaga cactttcaga  10380
gggtgcaaat ttcctatata taaataaaga agaattgcat ccaaataaat tgcacctaga  10440
aataaaagaa ggtgctgaac ttttttttatt cggggtaaag gtgattgtga aaggaatctt  10500
ggacggggca gtaactatat tctctatggg tcaagaatac gatttatccc tcaatgaact  10560
agaggggatg ttaacatcat gaactttaca agaatctttt taaagggcga tcgcaccatg  10620
ttaaatgatg gtacatttgt tcagatattt gatatttacc atgaccacgc attgggagtg  10680
acccttgacc ttaagacaga aaaaattatt tccgatgatg ttagggtaat tactgtcaaa  10740
gacttattgt tcgatggcac ttataaaggg gtaaaatctt ttatgcccga taatgcccga  10800
taatgcccga ttgatgctac aaaatcccat aatcataagc gataatcccc taatagcttg  10860
taattcttga accgtagcga ttttagagta ttccaaaaag aagaaataaa caccgcaaaa  10920
tgtcgtattt cacatatata aaccaaggtt ttttgcccta aaatctttat gtttgtagtg  10980
tgatgttggg tcaaaatggt cagaaaagtt gcaaggtttt tatggatgct tacgcgcgcg  11040
aggggtaagc atccccaaat agttacttta tcctagtcca tgcccattta ttgccgtccc  11100
gttcggcttt aaaaaagtgc caaaactcac aaggtgcaat aaaaagttct gtacctttcg  11160
```

-continued caaccctaga taatctttca acagttactt tttttcctat tatctcggta caaagtttgg 11220
ctagtttctc ttttccctct ttttcaatca agccttcttg tatgcccaac tcattgatta 11280
atctctctat ttttaccatt atttcccgtt caggtagttt atcccctaaa tcttcatcgg 11340
ggggcaatgt agggcattct gaaggggctt tttcttctgt ctggacatta tctaatattg 11400
aagtaaccaa actatcttca gttttttcta ttcctattaa ttcatattcg gttactgtat 11460
ccgtatcaat atccgaataa ctatctttat ccgtattagc tattcggtta agtttatccg 11520
ttaactcaga aacaagacta tatagcggtt ttagcttttc ttctatcctg ttatctaata 11580
cggataagtt tatacggtta tcattatccg tattagtatc attgggcttt tttggtagtt 11640
ctacccccctc ataaaccgct tttattccca attccaacag actgataaca gtatccttta 11700
taatgggttt tttgctgata tggtgaactt ttgccccttc catcattgcg atactttcta 11760
tctcactcat caacttatcg cttaagtgaa tctcgtatct gtttaatccc ttactggttt 11820
tattcatatc cgtttacttt attcggttaa caattctatt tttatacgaat aaaatattat 11880
acggttaact ttatacgttt aactatttta tctatacgga taacagtaat aagttattcg 11940
tattagttat acgtttactt ttatccaaat aaaattagtg catttaaact aaaagaatga 12000
ttttatcgga gttgatagca ttggattaac ctaaagatgt ttataagcta tatctgataa 12060
gtatttaagg ttattttgtt attctgttta ttgacattat cagaataaaa gaatagaata 12120
taattgttga gagataagag gtttaagtga ttatggttaa gaagttagtt ggttatgtca 12180
gggtcagtag tgaatcgcaa gaggataaca ctagcttaca gaatcagata gagagaattg 12240
aagcatattg tatggctttt ggttatgagt tggtaaaaat attcaaagag gttgccactg 12300
gtacaaaagc agatattgaa acccgtccta tttttaatga agctatagaa tacttgaaac 12360
aggataatgc taatggaatt attgccttga agctagaccg aatcgcacgg aatgctttag 12420
atgtattgcg tttggttcgt gaaaccttag aaccacaaaa taaaatgtta gtgttactag 12480
atattcaggt agatacttcg acaccttcag gaaaaatgat tttaactgta atgagtgccg 12540
ttgctgaact cgaaagagac atgatctatg atcgcactca ggggggtaga aagactaaag 12600
cccaaaaggg cgggtatgcc tacgggaaac ctaaatttgg ctataagact gaagaaaagg 12660
aactaaaaga agattcagca caacaggaaa ctattaaact aattaagaga caccgtaggt 12720
cagggaaaag ctaccagaaa atagctgatt atctcaatgc ccaaagtatt cccactaaac 12780
aaggtaagaa atggagttct agcgtcgtct atcgaatctg tcaggaaaaa gctggttaag 12840
tctgtttata gatatttaga atttattgaa taaaaatagt atgaacaata aatatttatg 12900
gactaaccac gctcggaaac gtttaactga acgatgggaa ataaaagaat catgggttat 12960
tgataccatc gaaaatcctg aacgttcaga atttattgtt gatgagtcag gggaaaaata 13020
tcattactat aaaagaatag ctaagtttaa gaatagagtg ttagaagtga taacttctgc 13080
caactcaaca cccacaagaa taataacctt ttactttaac cgtaacatga ggaaaaattt 13140
atgattgtta cttacgataa tgaagttgac gcaatttatt ttaagttaac ggaaaataaa 13200
attgatagca ccgaacctca aacagacagg attatcattg attacgatga aagtaataat 13260
attgttggca ttgaggtatt agattttaat tatcttgtca agaaaggttt aaccgttgct 13320
gatttacctt tttctgaaga tgaaagatta acagcttctc aatattttaa ttttcctgtt 13380
gctatctaat ccagaagggg caataatccc cttctttcat cgagttagac ttaatatcac 13440
aaaagtcatt ttcattttac cgtttctttt ccacagcgtc cgtacgcccc tcgttaaatc 13500
tcaaaaccga caatttatga tgtttataaa aagttactca ctttaataag tatttatact 13560

```
cattaaaggg ttattctttt tttgtagcct gataggttgg gaaggaatat ttcagattat  13620

cagatttgtt gaatattttt cgtcagatac gcaaacctta caaacataat taacaactga  13680

aactattgat atgtctaggt tttagctcta tcacaggttg gatctg                 13726
```

<210> SEQ ID NO 24
<211> LENGTH: 12973
<212> TYPE: DNA
<213> ORGANISM: Artificial Sequence
<220> FEATURE:
<223> OTHER INFORMATION: #1635\pABICyano1::smtB-PsmtA-zmPDC(opt1)_dsrA-Prbc*(optRBS)-synADH(opt1)_ter

<400> SEQUENCE: 24

```
tcgtcagata cgcaaacctt acaaacataa ttaacaactg aaactattga tatgtctagg     60

ttttagctct atcacaggtt ggatctgtcg acgggcaaac tttatgaagc agatcaagcc    120

tatatccgcc aagcaaccgg cagccgcgtt gattagtggg tgtgtccatc ctctggttcg    180

tctaggtgct ccgaagcgtc acgatagaga ttaagaatgt ggtgatcctt gaggcgataa    240

atcacattcc gcccttcctt gcgatagctc actaaacgtg ctgtgcgcag ggttcttagt    300

tggtgagaga cagccgattc actcatttca acggcggcgg cgagttcccc cacccgcatc    360

tctccagtgg ccagggccga aagaatacgc cagcggttgg catcccccaa gacaccaaaa    420

aattcggcca tccgttgggc cttggcttgg ttcaagattt tgccactgtg gtctgtcatt    480

gttcgctgat ctaaacaata cctgaataat tgttcatgtg ttaatctaaa aatgtgaaca    540

atcgttcaac tatttaagac aataccttgg aggtttaaac catgaattct tataccgtgg    600

gtacttattt agccgaacgc ttagtgcaaa ttggtttaaa acatcatttt gccgtggctg    660

gggactataa tttagtgtta ttggataact tattattaaa taaaaacatg gaacaagtgt    720

attgttgtaa tgaattaaat tgtggttttt ctgctgaagg ttatgctaga gctaaaggtg    780

cagctgctgc tgttgttact tattctgtgg gtgctttatc tgcttttgat gctattggtg    840

gtgcttatgc cgaaaattta cccgtgattt taatttctgg tgccccctaat aataatgatc    900

atgccgctgg acatgtttta catcatgcct taggtaaaac cgattatcat tatcaattag    960

aaatggccaa aaatattact gctgctgccg aagctattta tactcctgaa gaagcccctg   1020

ccaaaattga tcatgtgatt aaaaccgcct tacgcgaaaa aaaacccgtg tatttagaaa   1080

ttgcctgtaa tattgcttct atgccttgtg ctgctcctgg gcctgcttct gctttattta   1140

atgatgaagc ctctgatgaa gctagtttaa atgctgccgt ggaagaaacc ttaaaattta   1200

ttgccaatcg cgataaagtt gccgtgttag ttggttctaa attaagagct gctggtgctg   1260

aagaagctgc tgttaaattt gctgatgctt taggtggtgc agttgctact atggctgctg   1320

ccaaatcttt ttttcccgaa gaaaatcccc attatattgg aactagttgg ggagaagttt   1380

cttatcctgg tgtggaaaaa actatgaaag aagccgacgc tgttattgct ttagcccctg   1440

tgtttaatga ttattctacc actggttgga ctgatattcc cgatcccaaa aaattagttt   1500

tagccgaacc tcgttctgtt gttgttaatg gtgttcgctt tccctctgtg catttaaaag   1560

attatttaac ccgcttagcc caaaaagttt ctaaaaaaac tggtgcctta gatttttttta   1620

aatctttaaa tgcgggtgaa ttaaaaaaag ctgctcctgc tgatccttct gctcctttag   1680

ttaatgctga aattgcccgt caagttgaag ccttattaac ccctaatact accgttattg   1740

ccgaaactgg tgattcttgg tttaatgccc aacgcatgaa attacctaat ggtgcccgtg   1800

ttgaatatga aatgcaatgg ggtcatattg gttggtctgt acctgctgct tttggttatg   1860
```

```
ctgttggtgc tcctgaacgt cgtaatattt taatggtggg tgatggttct tttcaattaa   1920
ctgcccaaga agttgcccaa atggttcgct taaaattacc cgttattatt tttttaataa   1980
ataattatgg ttataccatt gaagtgatga ttcatgatgg gccatataat aatattaaaa   2040
attgggatta tgcgggttta atggaagtgt ttaatggtaa tggtggttat gattctggtg   2100
ctggtaaagg tttaaaagcc aaaactggtg gtgaattagc tgaagctatt aaagttgcct   2160
tagccaatac tgatgggcca accttaattg aatgttttat tggtcgcgaa gattgtaccg   2220
aagaattagt taaatggggt aaacgtgttg ctgctgctaa ttctcgcaaa cccgtgaata   2280
aattattgta atttttgggg atcaattcga gctcagcaag tttcatcccg accccctcag   2340
ggtcgggatt tttttattgt actagttgac ataagtaaag gcatcccctg cgtgatataa   2400
ttaccttcag tttaaggagg tatacacata tgattaaagc ctatgctgcc ttagaagcca   2460
atggtaaatt acaacccttt gaatatgatc ctggtgcttt aggtgccaat gaagtggaaa   2520
ttgaagtgca atattgtggt gtgtgtcatt ctgatttatc tatgattaat aatgaatggg   2580
gtatttctaa ttatccctta gttcctggtc atgaagttgt tggtactgtt gctgctatgg   2640
gtgaaggtgt taatcatgtg gaagtgggtg atttagttgg tttaggttgg cattctggtt   2700
attgtatgac ctgtcattct tgtttatctg gttatcataa tttatgtgcc actgccgaat   2760
ctactattgt gggtcattat ggtggttttg gtgatagagt tcgtgctaaa ggtgtttctg   2820
tggtgaaatt acccaaaggt attgatttag cctctgctgg gcctttattt tgtggtggta   2880
ttaccgtttt ttctcccatg gtggaattat ctttaaaacc taccgccaaa gttgctgtta   2940
ttggtattgg tggtttaggt catttagccg ttcaattttt aagagcctgg ggttgtgaag   3000
ttactgcttt tacctcttct gcccgtaaac aaaccgaagt tttagaatta ggtgcccatc   3060
atattttaga ttctaccaat cctgaagcta ttgcttctgc cgaaggtaaa tttgattata   3120
ttatttctac cgtgaattta aaattagatt ggaatttata tatcagtacc ttagcccctc   3180
aaggtcattt tcattttgtt ggtgtggtgt tagaaccctt ggacttaaac ttatttccct   3240
tattaatggg acaacgttct gtttctgctt ctcctgttgg ttctcctgct actattgcca   3300
ctatgttaga ttttgccgtg cgtcatgata ttaaacccgt ggtggaacaa ttttcttttg   3360
atcaaattaa tgaagccatt gcccatttag aatctggtaa agcccattat cgcgtggtgt   3420
tatctcattc taaaaattaa taagattaac ttctaaactg aaacaaattt gagggtaggc   3480
ttcattgtct gcccttattt ttttatttag gaaaagtgaa cagactaaag agtgttggct   3540
ctattgcttt gagtatgtaa attaggcgtt gctgaattaa ggtatgattt ttgacccctt   3600
ctctcttctg caggatcatc ttgctgaaaa actcgagcgc tcgttccgca aagcggtacg   3660
gagttagtta ggggctaatg ggcattctcc cgtacaggaa agagttagaa gttattaatt   3720
atcaacaatt ctcctttgcc tagtgcatcg ttaccttttt aattaaaaca taaggaaaac   3780
taataatcgt aataatttaa cctcaaagtg taaagaaatg tgaaattctg acttttataa   3840
cgttaaagag ggaaaaatta gcagtttaaa atacctagag aatagtctgg ggtaagcata   3900
gagaattaga ttagttaagt taatcaaatt cagaaaaaat aataatcgta aatagttaat   3960
ctgggtgtat agaaaatgat ccccttcatg ataagattta aactcgaaaa gcaaaagcca   4020
aaaaactaac ttccattaaa agaagttgtt acatataacg ctataaagaa aatttatata   4080
tttggaggat accaaccatg tctcatattc aacgtgaaac tagttgttct cgccctcgtt   4140
taaattctaa tatggatgcc gatttatatg gttataaatg ggctcgtgat aatgttggtc   4200
```

-continued

```
aatctggtgc tactatttat cgtttatatg gtaaacctga tgctcctgaa ttattcttga   4260
aacatggtaa aggttctgtt gctaatgatg ttactgatga aatggttcgt ttaaactggt   4320
tgactgaatt tatgccttta cctactatta aacattttat tcgtactccc gatgatgctt   4380
ggttattaac tactgctatt cctggtaaaa ctgcttttca agttttagaa gaatatcctg   4440
attctggtga aaatattgtt gatgctttag ctgttttttt acgtcgttta cattctattc   4500
ccgtttgtaa ttgtcctttt aattctgatc gtgtttttcg tttagctcaa gctcaatctc   4560
gtatgaataa tggtttagtt gatgcttctg attttgatga tgaacgtaat ggttggcctg   4620
ttgaacaagt ttggaaagaa atgcacaaat tgttaccttt ttctcctgat tctgttgtta   4680
ctcatggtga tttttcttta gataatttga tctttgatga aggtaaattg attggttgta   4740
ttgatgttgg tcgtgttggt attgctgatc gttatcaaga tttagctatt ttatggaatt   4800
gtttaggtga attttctcct tctttacaga aacgtttatt tcagaaatat ggtattgata   4860
atcctgatat gaacaagtta caatttcatt taatgttgga cgagttcttt taagaattaa   4920
ttcatgacca aaatccctta acgtgagttt tcgttccact gagcgtcaga ccccgtagaa   4980
aagatcaaag gatcttcttg agatcctttt tttctgcgcg taatctgctg ctatttaaat   5040
tacgtacacg tgttattact ttgttaacga caattgtctt aattaactgg gcctcatggg   5100
ccttccgctc actgcccgct ttccagtcgg gaaacctgtc gtgccagctc tgcagatgac   5160
ggtgaaaacc tctgacacat gcagctcccg gagacggtca cagcttgtct gtaagcggat   5220
gccgggagca gacaagcccg tcagggcgcg tcagcgggtg ttggcgggtg tcggggcgca   5280
gccatgaccc agtcacgtag cgatagcgga gtgtatactg gcttaactat gcggcatcag   5340
agcagattgt actgagagtg caccatatgc ggtgtgaaat accgcacaga tgcgtaagga   5400
gaaaataccg catcaggcgc tcttccgctt cctcgctcac tgactcgctg cgctcggtcg   5460
ttcggctgcg gcgagcggta tcagctcact caaaggcggt aatacggtta tccacagaat   5520
caggggataa cgcaggaaag aacatgtgag caaaaggcca gcaaaaggcc aggaaccgta   5580
aaaaggccgc gttgctggcg tttttccata ggctccgccc ccctgacgag catcacaaaa   5640
atcgacgctc aagtcagagg tggcgaaacc cgacaggact ataaagatac caggcgtttc   5700
cccctggaag ctccctcgtg cgctctcctg ttccgaccct gccgcttacc ggatacctgt   5760
ccgcctttct cccttcggga agcgtggcgc tttctcatag ctcacgctgt aggtatctca   5820
gttcggtgta ggtcgttcgc tccaagctgg gctgtgtgca cgaacccccc gttcagcccg   5880
accgctgcgc cttatccggt aactatcgtc ttgagtccaa cccggtaaga cacgacttat   5940
cgccactggc agcagccact ggtaacagga ttagcagagc gaggtatgta ggcggtgcta   6000
cagagttctt gaagtggtgg cctaactacg gctacactag aaggacagta tttggtatct   6060
gcgctctgct gaagccagtt accttcggaa aaagagttgg tagctcttga tccggcaaac   6120
aaaccaccgc tggtagcggt ggtttttttg tttgcaagca gcagattacg cgcagaaaaa   6180
aaggatctca agaagatcct ttgatctttt ctactgcaga agcttgttag acaccctgtc   6240
atgtatttta tattatttat ttcaccatac ggattaagtg aaacctaatg aaaatagtac   6300
tttcggagct ttaactttaa tgaaggtatg ttttttttata gacatcgatg tctggtttaa   6360
caataggaaa aagtagctaa aactcccatg aattaaagaa ataacaaggt gtctaacaac   6420
ctgttattaa gaatgttaga aaagacttaa catttgtgtt gagtttttat agacattggt   6480
gtctagacat acggtagata aggtttgctc aaaaataaaa taaaaaaaga ttggactaaa   6540
aaacatttaa tttagtacaa tttaattagt tatttttttcg tctcaaattt tgctttgttg   6600
```

-continued

```
agcagaaatt tagataaaaa aatccccgtg atcagattac aatgtcgttc attgtacgat   6660
gtgtcgaaaa atctttacga cactctaaac tgaccacacg ggggaaaaag aaaactgaac   6720
taataacatc atgatactcg gaaaacctag caattctcaa cccctaaaca aaagaaactt   6780
ccaaaaccct gaccatataa aggagtggca acaatcagca atcagtcaag atttgatagc   6840
agaaaatctt gtatcggttg ctaatggttt tgatgtacta tttatcggca ataaataccg   6900
aactaacacg ggtgttctgt cacggcacat attaaactcc tattctcatt tagaagatgg   6960
tggttcgtat ggtagaacat ttgacccatt taccaataaa gaaatgcagt gggttcaatt   7020
taaaccgaat agaccaagaa aaggttctac tggtaaggta atcaaatatg aatcgccaaa   7080
aggtgaacct acaagagttc taatgccgtt tgtgcctatg aaaatatggc aacggattag   7140
cgataagttc ggagtaccga ttaatccgaa aaaagatact cacttttggg aatgggtaaa   7200
gaataatcca tcgataccga ttgccattac agaaggaaat aaaaaagcta attgcctatt   7260
atcctatggc tatcctgcta ttgcctttgt aggcatttgg aacggattag agaaaataaa   7320
tgatttctcg aaggaaaagc agttaaaaga ggatttgaaa tggttgttat ccaacggcaa   7380
ccgaaatatt aatatcatct ttgaccaaga ccagaaacaa aaaactgtaa ttaatgtaaa   7440
caaagctatt ttcgctttat cttctctaat aagtagaaat ggtcataaag ttaatattgt   7500
gcaatggttg ccgtcaaaag gtaaaggaat agatgattat ttggtagctt taccttttga   7560
gaaaagagaa aatcatttag acaacttaat taaaattgca ccatcattta atttttggtc   7620
aactaaatac ttattcaagt gtcgtaaacc agatttaacc gtaaattgcc gttatttgag   7680
cgatgcagta aaagaattac ctcaagagga tatagcatta atagcacctc acggcacggg   7740
taaaacttca ttagtagcta ctcacgttaa gaatcggagt tatcacggaa ggaaaactat   7800
ttcattggtg catcttgaaa gtttagccaa agctaatggc aacgcacttg gattatatta   7860
ccgaaccgaa aataatattg aaaagcaata tcttggattt agcttatgtg tagatagttg   7920
ccgtgataag attaacggca ttacaactga tattatttca ggtcaagatt attgcctttt   7980
cattgatgaa attgaccaag taattccaca catccttaac agtgaaactg aagtaagtaa   8040
gtatagatgc accatcattg acactttttc tgaactggtg agaaatgctg aacaggtcat   8100
tattgctgat gctgatttat ccgatgtgac gattgaccta atagaaaaca tcagaggtaa   8160
aaaactatat gtaatcaaga atgaatatca gtatcaggga atgactttta acgccgttgg   8220
ttcaccatta gaaatgatgg caatgatggg aaaatcggtg tcagaaggca agaaattatt   8280
tattaacacc acatcccaaa aggcaaaaag taagtacggc acaatcgctc ttgagtctta   8340
tatttttggt ctaaataaag aagcaaagat attaagaata gactctgaaa ccactaaaaa   8400
ccctgaacat ccagcctata aaatcattga ccaagactta aataatatcc tcaaagatta   8460
tgattatgtc attgcctcac cttgccttca aacaggtgtc agtattacct taaaagggca   8520
ttttgaccag caatttaact tttccagtgg aaacattaca cctcattgct ttttacagca   8580
aatgtggcgg ttgagggatg cagaaattga aagattctat tatgtgccga actcatctaa   8640
cctcaatctc attgggaata agtcaagttc accatcagac cttctaaaga gcaataacaa   8700
gatggcaacg gcaacggtta accttttggg tagaatcgac tccgaatatt ccctagagta   8760
tgaatcgcac ggcatttggc ttgagacgtg ggcaaaatta tcagcacggc ataacagttc   8820
aatgcgttgt tactctgaaa ttcttaccta tctaattacg tctcaagggc ataaattaaa   8880
tatcaacatt ccctcacctc ttgcagatat taagaagcta aatgatgagg taagtagtaa   8940
```

```
cagggaaaag gtaaaaaatg agagatactc tcagaggtta aactcaccag atattaacga   9000
tgcagaagct accatactcg aatctaaaga gcaaaaaatc ggattgactc tcaatgagag   9060
atgcacccta gaaaagcata aagttaagaa gcggtatggg aatgtaaaga tggatattct   9120
cacctttgat gatgatggac tataccccaa actcagacta ttttattacc tcaccatcgg   9180
taaacctcat ctcaaggcta atgacagaaa agctattgcc aaaatgggca atgacaataa   9240
aggcaagatt ctatcaaaag acttagttaa taaaacttac tccgctcgtg tgaaggtctt   9300
agagattctt aaactaactg actttatcga caatcttaga gatgaactct taataactcc   9360
caataatcca gctatcaccg attttaataa tcttctgcta agagctaaga aggatttaag   9420
agtattagga gtcaacatcg gaaaatatcc aatggccaac attaatgccg tacttactct   9480
cattggtcac aaactttctg taatgagaga tgagttcgga aaagagaaaa ggataaaagt   9540
agatggtaaa tcataccgat gttatcaact tgaaacatta ccagatttta ccaatgatac   9600
tcttgactac tggttagaaa atgatagcca aaaagaagta acagcaacag aaaattactc   9660
cgaaaatttt aacccttcaa atagctacaa tccagacagt aagacacttt cagagggtgc   9720
aaatttccta tatataaata aagaagaatt gcatccaaat aaattgcacc tagaaataaa   9780
agaaggtgct gaactttttt tattcggggt aaaggtgatt gtgaaaggaa tcttggacgg   9840
ggcagtaact atattctcta tgggtcaaga atacgattta tccctcaatg aactagaggg   9900
gatgttaaca tcatgaactt tacaagaatc tttttaaagg gcgatcgcac catgttaaat   9960
gatggtacat ttgttcagat atttgatatt taccatgacc acgcattggg agtgaccctt  10020
gaccttaaga cagaaaaaat tatttccgat gatgttaggg taattactgt caaagactta  10080
ttgttcgatg gcacttataa aggggtaaaa tcttttatgc ccgataatgc ccgataatgc  10140
ccgattgatg ctacaaaatc ccataatcat aagcgataat cccctaatag cttgtaattc  10200
ttgaaccgta gcgattttag agtattccaa aaagaagaaa taaacaccgc aaaatgtcgt  10260
atttcacata tataaaccaa ggttttttgc cctaaaatct ttatgtttgt agtgtgatgt  10320
tgggtcaaaa tggtcagaaa agttgcaagg tttttatgga tgcttacgcg cgcgaggggt  10380
aagcatcccc aaatagttac tttatcctag tccatgccca tttattgccg tcccgttcgg  10440
ctttaaaaaa gtgccaaaac tcacaaggtg caataaaaag ttctgtacct ttcgcaaccc  10500
tagataatct ttcaacagtt actttttttc ctattatctc ggtacaaagt ttggctagtt  10560
tctcttttcc ctctttttca atcaagcctt cttgtatgcc caactcattg attaatctct  10620
ctatttttac cattatttcc cgttcaggta gtttatcccc taaatcttca tcgggggggca  10680
atgtagggca ttctgaaggg gctttttctt ctgtctggac attatctaat attgaagtaa  10740
ccaaactatc ttcagttttt tctattccta ttaattcata ttcggttact gtatccgtat  10800
caatatccga ataactatct ttatccgtat tagctattcg gttaagttta tccgttaact  10860
cagaaacaag actatatagc ggttttagct tttcttctat cctgttatct aatacggata  10920
agtttatacg gttatcatta tccgtattag tatcattggg ctttttttggt agttctaccc  10980
cctcataaac cgcttttatt cccaattcca acagactgat aacagtatcc tttataatgg  11040
gtttttgct gatatggtga acttttgccc cttccatcat tgcgatactt tctatctcac  11100
tcatcaactt atcgcttaag tgaatctcgt atctgtttaa tcccttactg gttttattca  11160
tatccgttta ctttattcgg ttaacaattc tattttatac gaataaaata ttatacggtt  11220
aactttatac gtttaactat tttatctata cggataacag taataagtta ttcgtattag  11280
ttatacgttt acttttatcc aaataaaatt agtgcattta aactaaaaga atgattttat  11340
```

```
cggagttgat agcattggat taacctaaag atgtttataa gctatatctg ataagtattt  11400
aaggttattt tgttattctg tttattgaca ttatcagaat aaaagaatag aatataattg  11460
ttgagagata agaggtttaa gtgattatgg ttaagaagtt agttggttat gtcagggtca  11520
gtagtgaatc gcaagaggat aacactagct tacagaatca gatagagaga attgaagcat  11580
attgtatggc ttttggttat gagttggtaa aaatattcaa agaggttgcc actggtacaa  11640
aagcagatat tgaaacccgt cctattttta atgaagctat agaatacttg aaacaggata  11700
atgctaatgg aattattgcc ttgaagctag accgaatcgc acggaatgct ttagatgtat  11760
tgcgtttggt tcgtgaaacc ttagaaccac aaaataaaat gttagtgtta ctagatattc  11820
aggtagatac ttcgacacct tcaggaaaaa tgattttaac tgtaatgagt gccgttgctg  11880
aactcgaaag agacatgatc tatgatcgca ctcagggggg tagaaagact aaagcccaaa  11940
agggcgggta tgcctacggg aaacctaaat ttggctataa gactgaagaa aaggaactaa  12000
aagaagattc agcacaacag gaaactatta aactaattaa gagacaccgt aggtcaggga  12060
aaagctacca gaaaatagct gattatctca atgcccaaag tattcccact aaacaaggta  12120
agaaatggag ttctagcgtc gtctatcgaa tctgtcagga aaaagctggt taagtctgtt  12180
tatagatatt tagaatttat tgaataaaaa tagtatgaac aataaatatt tatggactaa  12240
ccacgctcgg aaacgtttaa ctgaacgatg ggaaataaaa gaatcatggg ttattgatac  12300
catcgaaaat cctgaacgtt cagaatttat tgttgatgag tcaggggaaa aatatcatta  12360
ctataaaaga atagctaagt ttaagaatag agtgttagaa gtgataactt ctgccaactc  12420
aacacccaca agaataataa ccttttactt taaccgtaac atgaggaaaa atttatgatt  12480
gttacttacg ataatgaagt tgacgcaatt tattttaagt taacggaaaa taaaattgat  12540
agcaccgaac ctcaaacaga caggattatc attgattacg atgaaagtaa taatattgtt  12600
ggcattgagg tattagattt taattatctt gtcaagaaag gtttaaccgt tgctgattta  12660
ccttttttctg aagatgaaag attaacagct tctcaatatt ttaattttcc tgttgctatc  12720
taatccagaa ggggcaataa tccccttctt tcatcgagtt agacttaata tcacaaaagt  12780
cattttcatt ttaccgtttc ttttccacag cgtccgtacg cccctcgtta aatctcaaaa  12840
ccgacaattt atgatgttta taaaaagtta ctcactttaa taagtattta tactcattaa  12900
agggttattc ttttttgta gcctgatagg ttgggaagga atatttcaga ttatcagatt  12960
tgttgaatat ttt                                                    12973
```

```
<210> SEQ ID NO 25
<211> LENGTH: 12973
<212> TYPE: DNA
<213> ORGANISM: Artificial Sequence
<220> FEATURE:
<223> OTHER INFORMATION: #1639\\pABICyano1::smtB-PsmtA*1-
      zmPDC(opt1)_dsrA-Prbc*(optRBS)-synADH(opt1)_ter

<400> SEQUENCE: 25
```

```
tcgacgggca aactttatga agcagatcaa gcctatatcc gccaagcaac cggcagccgc     60
gttgattagt gggtgtgtcc atcctctggt tcgtctaggt gctccgaagc gtcacgatag    120
agattaagaa tgtggtgatc cttgaggcga taaatcacat tccgcccttc cttgcgatag    180
ctcactaaac gtgctgtgcg cagggttctt agttggtgag agacagccga ttcactcatt    240
tcaacggcgg cggcgagttc ccccacccgc atctctccag tggccagggc cgaaagaata    300
cgccagcggt tggcatcccc caagacacca aaaaattcgg ccatccgttg ggccttggct    360
```

```
tggttcaaga ttttgccact gtggtctgtc attgttcgct gatctaaaca atacctgaat    420
aattgttcat gtgttaatct aaaaatgtga acaatcgttc aactatttaa gacaatacca    480
aggaggtgat aaccatgaat tcttataccg tgggtactta tttagccgaa cgcttagtgc    540
aaattggttt aaaacatcat tttgccgtgg ctggggacta taatttagtg ttattggata    600
acttattatt aaataaaaac atggaacaag tgtattgttg taatgaatta aattgtggtt    660
tttctgctga aggttatgct agagctaaag gtgcagctgc tgctgttgtt acttattctg    720
tgggtgcttt atctgctttt gatgctattg gtggtgctta tgccgaaaat ttacccgtga    780
ttttaatttc tggtgcccct aataataatg atcatgccgc tggacatgtt ttacatcatg    840
ccttaggtaa aaccgattat cattatcaat tagaaatggc caaaaatatt actgctgctg    900
ccgaagctat ttatactcct gaagaagccc ctgccaaaat tgatcatgtg attaaaaccg    960
ccttacgcga aaaaaaaccc gtgtatttag aaattgcctg taatattgct tctatgcctt   1020
gtgctgctcc tgggcctgct tctgctttat ttaatgatga agcctctgat gaagctagtt   1080
taaatgctgc cgtggaagaa accttaaaat ttattgccaa tcgcgataaa gttgccgtgt   1140
tagttggttc taaattaaga gctgctggtg ctgaagaagc tgctgttaaa tttgctgatg   1200
ctttaggtgg tgcagttgct actatggctg ctgccaaatc ttttttccc gaagaaaatc   1260
cccattatat tggaactagt tggggagaag tttcttatcc tggtgtggaa aaaactatga   1320
aagaagccga cgctgttatt gctttagccc ctgtgtttaa tgattattct accactggtt   1380
ggactgatat tcccgatccc aaaaaattag ttttagccga acctcgttct gttgttgtta   1440
atggtgttcg ctttccctct gtgcatttaa aagattattt aacccgctta gcccaaaaag   1500
tttctaaaaa aactggtgcc ttagattttt ttaaatcttt aaatgcgggt gaattaaaaa   1560
aagctgctcc tgctgatcct tctgctcctt tagttaatgc tgaaattgcc cgtcaagttg   1620
aagccttatt aacccctaat actaccgtta ttgccgaaac tggtgattct tggtttaatg   1680
cccaacgcat gaaattacct aatggtgccc gtgttgaata tgaaatgcaa tggggtcata   1740
ttggttggtc tgtacctgct gcttttggtt atgctgttgg tgctcctgaa cgtcgtaata   1800
ttttaatggt gggtgatggt tcttttcaat taactgccca agaagttgcc caaatggttc   1860
gcttaaaatt acccgttatt atttttttaa taaataatta tggttatacc attgaagtga   1920
tgattcatga tgggccatat aataatatta aaaattggga ttatgcgggt ttaatggaag   1980
tgtttaatgg taatggtggt tatgattctg gtgctggtaa aggtttaaaa gccaaaactg   2040
gtggtgaatt agctgaagct attaaagttg ccttagccaa tactgatggg ccaaccttaa   2100
ttgaatgttt tattggtcgc gaagattgta ccgaagaatt agttaaatgg ggtaaacgtg   2160
ttgctgctgc taattctcgc aaacccgtga ataaattatt gtaatttttg gggatcaatt   2220
cgagctcagc aagtttcatc ccgaccccct cagggtcggg atttttttat tgtactagtt   2280
gacataagta aaggcatccc ctgcgtgata taattacctt cagtttaagg aggtatacac   2340
atatgattaa agcctatgct gccttagaag ccaatggtaa attacaaccc tttgaatatg   2400
atcctggtgc tttaggtgcc aatgaagtgg aaattgaagt gcaatattgt ggtgtgtgtc   2460
attctgattt atctatgatt aataatgaat ggggtatttc taattatccc ttagttcctg   2520
gtcatgaagt tgttggtact gttgctgcta tgggtgaagg tgttaatcat gtggaagtgg   2580
gtgatttagt tggtttaggt tggcattctg gttattgtat gacctgtcat tcttgtttat   2640
ctggttatca taatttatgt gccactgccg aatctactat tgtgggtcat tatggtggtt   2700
```

-continued

```
ttggtgatag agttcgtgct aaaggtgttt ctgtggtgaa attacccaaa ggtattgatt   2760
tagcctctgc tgggccttta ttttgtggtg gtattaccgt tttttctccc atggtggaat   2820
tatctttaaa acctaccgcc aaagttgctg ttattggtat tggtggttta ggtcatttag   2880
ccgttcaatt tttaagagcc tggggttgtg aagttactgc ttttacctct tctgcccgta   2940
aacaaaccga agttttagaa ttaggtgccc atcatatttt agattctacc aatcctgaag   3000
ctattgcttc tgccgaaggt aaatttgatt atattatttc taccgtgaat ttaaaattag   3060
attggaattt atatatcagt accttagccc ctcaaggtca ttttcatttt gttggtgtgg   3120
tgttagaacc cttggactta aacttatttc ccttattaat gggacaacgt tctgtttctg   3180
cttctcctgt tggttctcct gctactattg ccactatgtt agattttgcc gtgcgtcatg   3240
atattaaacc cgtggtggaa caattttctt ttgatcaaat taatgaagcc attgcccatt   3300
tagaatctgg taaagcccat tatcgcgtgg tgttatctca ttctaaaaat taataagatt   3360
aacttctaaa ctgaaacaaa tttgagggta ggcttcattg tctgccctta ttttttttatt   3420
taggaaaagt gaacagacta aagagtgttg gctctattgc tttgagtatg taaattaggc   3480
gttgctgaat taaggtatga tttttgaccc cttctctctt ctgcaggatc atcttgctga   3540
aaaactcgag cgctcgttcc gcaaagcggt acggagttag ttaggggcta atgggcattc   3600
tcccgtacag gaaagagtta gaagttatta attatcaaca attctccttt gcctagtgca   3660
tcgttacctt tttaattaaa acataaggaa aactaataat cgtaataatt taacctcaaa   3720
gtgtaaagaa atgtgaaatt ctgactttta taacgttaaa gagggaaaaa ttagcagttt   3780
aaaataccta gagaatagtc tggggtaagc atagagaatt agattagtta agttaatcaa   3840
attcagaaaa aataataatc gtaaatagtt aatctgggtg tatagaaaat gatccccttc   3900
atgataagat ttaaactcga aaagcaaaag ccaaaaaact aacttccatt aaaagaagtt   3960
gttacatata acgctataaa gaaaatttat atatttggag gataccaacc atgtctcata   4020
ttcaacgtga aactagttgt tctcgccctc gtttaaattc taatatggat gccgatttat   4080
atggttataa atgggctcgt gataatgttg gtcaatctgg tgctactatt tatcgtttat   4140
atggtaaacc tgatgctcct gaattattct tgaaacatgg taaaggttct gttgctaatg   4200
atgttactga tgaaatggtt cgtttaaact ggttgactga atttatgcct ttacctacta   4260
ttaaacattt tattcgtact cccgatgatg cttggttatt aactactgct attcctggta   4320
aaactgcttt tcaagtttta gaagaatatc ctgattctgg tgaaaatatt gttgatgctt   4380
tagctgtttt tttacgtcgt ttacattcta ttcccgtttg taattgtcct tttaattctg   4440
atcgtgtttt tcgtttagct caagctcaat ctcgtatgaa taatggttta gttgatgctt   4500
ctgattttga tgatgaacgt aatggttggc ctgttgaaca agtttggaaa gaaatgcaca   4560
aattgttacc tttttctcct gattctgttg ttactcatgg tgatttttct ttagataatt   4620
tgatctttga tgaaggtaaa ttgattggtt gtattgatgt tggtcgtgtt ggtattgctg   4680
atcgttatca agatttagct attttatgga attgtttagg tgaattttct ccttctttac   4740
agaaacgttt atttcagaaa tatggtattg ataatcctga tatgaacaag ttacaatttc   4800
atttaatgtt ggacgagttc ttttaagaat taattcatga ccaaaatccc ttaacgtgag   4860
ttttcgttcc actgagcgtc agaccccgta gaaaagatca aaggatcttc ttgagatcct   4920
tttttctgc gcgtaatctg ctgctattta aattacgtac acgtgttatt actttgttaa   4980
cgacaattgt cttaattaac tgggcctcat gggccttccg ctcactgccc gctttccagt   5040
cgggaaacct gtcgtgccag ctctgcagat gacggtgaaa acctctgaca catgcagctc   5100
```

-continued

```
ccggagacgg tcacagcttg tctgtaagcg gatgccggga gcagacaagc ccgtcagggc   5160
gcgtcagcgg gtgttggcgg gtgtcggggc gcagccatga cccagtcacg tagcgatagc   5220
ggagtgtata ctggcttaac tatgcggcat cagagcagat tgtactgaga gtgcaccata   5280
tgcggtgtga aataccgcac agatgcgtaa ggagaaaata ccgcatcagg cgctcttccg   5340
cttcctcgct cactgactcg ctgcgctcgg tcgttcggct gcggcgagcg gtatcagctc   5400
actcaaaggc ggtaatacgg ttatccacag aatcagggga taacgcagga aagaacatgt   5460
gagcaaaagg ccagcaaaag gccaggaacc gtaaaaaggc cgcgttgctg gcgtttttcc   5520
ataggctccg cccccctgac gagcatcaca aaaatcgacg ctcaagtcag aggtggcgaa   5580
acccgacagg actataaaga taccaggcgt ttccccctgg aagctccctc gtgcgctctc   5640
ctgttccgac cctgccgctt accggatacc tgtccgcctt tctcccttcg ggaagcgtgg   5700
cgctttctca tagctcacgc tgtaggtatc tcagttcggt gtaggtcgtt cgctccaagc   5760
tgggctgtgt gcacgaaccc cccgttcagc ccgaccgctg cgccttatcc ggtaactatc   5820
gtcttgagtc caacccggta agacacgact tatcgccact ggcagcagcc actggtaaca   5880
ggattagcag agcgaggtat gtaggcggtg ctacagagtt cttgaagtgg tggcctaact   5940
acggctacac tagaaggaca gtatttggta tctgcgctct gctgaagcca gttaccttcg   6000
gaaaaagagt tggtagctct tgatccggca aacaaaccac cgctggtagc ggtggttttt   6060
ttgtttgcaa gcagcagatt acgcgcagaa aaaaaggatc tcaagaagat cctttgatct   6120
tttctactgc agaagcttgt tagacaccct gtcatgtatt ttatattatt tatttcacca   6180
tacggattaa gtgaaaccta atgaaaatag tactttcgga gctttaactt taatgaaggt   6240
atgttttttt atagacatcg atgtctggtt taacaatagg aaaaagtagc taaaactccc   6300
atgaattaaa gaaataacaa ggtgtctaac aacctgttat taagaatgtt agaaaagact   6360
taacatttgt gttgagtttt tatagacatt ggtgtctaga catacggtag ataaggtttg   6420
ctcaaaaata aaataaaaaa agattggact aaaaaacatt taatttagta caatttaatt   6480
agttattttt tcgtctcaaa ttttgctttg ttgagcagaa atttagataa aaaaatcccc   6540
gtgatcagat tacaatgtcg ttcattgtac gatgtgtcga aaaatcttta cgacactcta   6600
aactgaccac acgggggaaa aagaaaactg aactaataac atcatgatac tcggaaaacc   6660
tagcaattct caacccctaa acaaaagaaa cttccaaaac cctgaccata taaaggagtg   6720
gcaacaatca gcaatcagtc aagatttgat agcagaaaat cttgtatcgg ttgctaatgg   6780
ttttgatgta ctatttatcg gcaataaata ccgaactaac acgggtgttc tgtcacggca   6840
catattaaac tcctattctc atttagaaga tggtggttcg tatggtagaa catttgaccc   6900
atttaccaat aaagaaatgc agtgggttca atttaaaccg aatagaccaa gaaaaggttc   6960
tactggtaag gtaatcaaat atgaatcgcc aaaaggtgaa cctacaagag ttctaatgcc   7020
gtttgtgcct atgaaaatat ggcaacggat tagcgataag ttcggagtac cgattaatcc   7080
gaaaaaagat actcactttt gggaatgggt aaagaataat ccatcgatac cgattgccat   7140
tacagaagga aataaaaaag ctaattgcct attatcctat ggctatcctg ctattgcctt   7200
tgtaggcatt tggaacggat tagagaaaat aaatgatttc tcgaaggaaa agcagttaaa   7260
agaggatttg aaatggttgt tatccaacgg caaccgaaat attaatatca tctttgacca   7320
agaccagaaa caaaaaactg taattaatgt aaacaaagct attttcgctt tatcttctct   7380
aataagtaga aatggtcata aagttaatat tgtgcaatgg ttgccgtcaa aaggtaaagg   7440
```

-continued

```
aatagatgat tatttggtag ctttaccttt tgagaaaaga gaaaatcatt tagacaactt   7500
aattaaaatt gcaccatcat ttaatttttg gtcaactaaa tacttattca agtgtcgtaa   7560
accagattta accgtaaatt gccgttattt gagcgatgca gtaaaagaat tacctcaaga   7620
ggatatagca ttaatagcac ctcacggcac gggtaaaact tcattagtag ctactcacgt   7680
taagaatcgg agttatcacg gaaggaaaac tatttcattg gtgcatcttg aaagtttagc   7740
caaagctaat ggcaacgcac ttggattata ttaccgaacc gaaaataata ttgaaaagca   7800
atatcttgga tttagcttat gtgtagatag ttgccgtgat aagattaacg gcattacaac   7860
tgatattatt tcaggtcaag attattgcct tttcattgat gaaattgacc aagtaattcc   7920
acacatcctt aacagtgaaa ctgaagtaag taagtataga tgcaccatca ttgacacttt   7980
ttctgaactg gtgagaaatg ctgaacaggt cattattgct gatgctgatt tatccgatgt   8040
gacgattgac ctaatagaaa acatcagagg taaaaaacta tatgtaatca agaatgaata   8100
tcagtatcag ggaatgactt ttaacgccgt tggttcacca ttagaaatga tggcaatgat   8160
gggaaaatcg gtgtcagaag gcaagaaatt atttattaac accacatccc aaaaggcaaa   8220
aagtaagtac ggcacaatcg ctcttgagtc ttatattttt ggtctaaata aagaagcaaa   8280
gatattaaga atagactctg aaaccactaa aaaccctgaa catccagcct ataaaatcat   8340
tgaccaagac ttaaataata tcctcaaaga ttatgattat gtcattgcct caccttgcct   8400
tcaaacaggt gtcagtatta ccttaaaagg gcattttgac cagcaattta acttttccag   8460
tggaaacatt acacctcatt gctttttaca gcaaatgtgg cggttgaggg atgcagaaat   8520
tgaaagattc tattatgtgc cgaactcatc taacctcaat ctcattggga ataagtcaag   8580
ttcaccatca gaccttctaa agagcaataa caagatggca acggcaacgg ttaacctttt   8640
gggtagaatc gactccgaat attccctaga gtatgaatcg cacggcattt ggcttgagac   8700
gtgggcaaaa ttatcagcac ggcataacag ttcaatgcgt tgttactctg aaattcttac   8760
ctatctaatt acgtctcaag ggcataaatt aaatatcaac attccctcac ctcttgcaga   8820
tattaagaag ctaaatgatg aggtaagtag taacagggaa aaggtaaaaa atgagagata   8880
ctctcagagg ttaaactcac cagatattaa cgatgcagaa gctaccatac tcgaatctaa   8940
agagcaaaaa atcggattga ctctcaatga gagatgcacc ctagaaaagc ataaagttaa   9000
gaagcggtat gggaatgtaa agatggatat tctcaccttt gatgatgatg gactataccc   9060
caaactcaga ctattttatt acctcaccat cggtaaacct catctcaagg ctaatgacag   9120
aaaagctatt gccaaaatgg gcaatgacaa taaaggcaag attctatcaa aagacttagt   9180
taataaaact tactccgctc gtgtgaaggt cttagagatt cttaaactaa ctgactttat   9240
cgacaatctt agagatgaac tcttaataac tcccaataat ccagctatca ccgattttaa   9300
taatcttctg ctaagagcta agaaggattt aagagtatta ggagtcaaca tcggaaaata   9360
tccaatggcc aacattaatg ccgtacttac tctcattggt cacaaacttt ctgtaatgag   9420
agatgagttc ggaaaaagaga aaaggataaa agtagatggt aaatcatacc gatgttatca   9480
acttgaaaca ttaccagatt ttaccaatga tactcttgac tactggttag aaaatgatag   9540
ccaaaaagaa gtaacagcaa cagaaaatta ctccgaaaat tttaaccctt caaatagcta   9600
caatccagac agtaagacac tttcagaggg tgcaaatttc ctatatataa ataaagaaga   9660
attgcatcca aataaattgc acctagaaat aaaagaaggt gctgaacttt ttttattcgg   9720
ggtaaaggtg attgtgaaag gaatcttgga cggggcagta actatattct ctatgggtca   9780
agaatacgat ttatccctca atgaactaga ggggatgtta acatcatgaa ctttacaaga   9840
```

-continued

```
atctttttaa agggcgatcg caccatgtta aatgatggta catttgttca gatatttgat   9900
atttaccatg accacgcatt gggagtgacc cttgacctta agacagaaaa aattatttcc   9960
gatgatgtta gggtaattac tgtcaaagac ttattgttcg atggcactta taaaggggta  10020
aaatctttta tgcccgataa tgcccgataa tgcccgattg atgctacaaa atcccataat  10080
cataagcgat aatcccctaa tagcttgtaa ttcttgaacc gtagcgattt tagagtattc  10140
caaaaagaag aaataaacac cgcaaaatgt cgtatttcac atatataaac caaggttttt  10200
tgccctaaaa tctttatgtt tgtagtgtga tgttgggtca aaatggtcag aaaagttgca  10260
aggtttttat ggatgcttac gcgcgcgagg ggtaagcatc cccaaatagt tactttatcc  10320
tagtccatgc ccatttattg ccgtcccgtt cggctttaaa aaagtgccaa aactcacaag  10380
gtgcaataaa aagttctgta cctttcgcaa ccctagataa tctttcaaca gttacttttt  10440
ttcctattat ctcggtacaa agtttggcta gtttctcttt tccctctttt tcaatcaagc  10500
cttcttgtat gcccaactca ttgattaatc tctctatttt taccattatt tcccgttcag  10560
gtagtttatc ccctaaatct tcatcggggg gcaatgtagg gcattctgaa ggggcttttt  10620
cttctgtctg gacattatct aatattgaag taaccaaact atcttcagtt ttttctattc  10680
ctattaattc atattcggtt actgtatccg tatcaatatc cgaataacta tctttatccg  10740
tattagctat tcggttaagt ttatccgtta actcagaaac aagactatat agcggtttta  10800
gcttttcttc tatcctgtta tctaatacgg ataagtttat acggttatca ttatccgtat  10860
tagtatcatt gggctttttt ggtagttcta ccccctcata aaccgctttt attcccaatt  10920
ccaacagact gataacagta tcctttataa tgggtttttt gctgatatgg tgaacttttg  10980
ccccttccat cattgcgata ctttctatct cactcatcaa cttatcgctt aagtgaatct  11040
cgtatctgtt taatccctta ctggttttat tcatatccgt ttactttatt cggttaacaa  11100
ttctatttta tacgaataaa atattatacg gttaacttta tacgtttaac tattttatct  11160
atacggataa cagtaataag ttattcgtat tagttatacg tttactttta tccaaataaa  11220
attagtgcat ttaaactaaa agaatgattt tatcggagtt gatagcattg gattaaccta  11280
aagatgttta taagctatat ctgataagta tttaaggtta ttttgttatt ctgtttattg  11340
acattatcag aataaaagaa tagaatataa ttgttgagag ataagaggtt taagtgatta  11400
tggttaagaa gttagttggt tatgtcaggg tcagtagtga atcgcaagag gataacacta  11460
gcttacagaa tcagatagag agaattgaag catattgtat ggcttttggt tatgagttgg  11520
taaaaatatt caaagaggtt gccactggta caaaagcaga tattgaaacc cgtcctattt  11580
ttaatgaagc tatagaatac ttgaaacagg ataatgctaa tggaattatt gccttgaagc  11640
tagaccgaat cgcacggaat gctttagatg tattgcgttt ggttcgtgaa accttagaac  11700
cacaaaataa aatgttagtg ttactagata ttcaggtaga tacttcgaca ccttcaggaa  11760
aaatgatttt aactgtaatg agtgccgttg ctgaactcga aagagacatg atctatgatc  11820
gcactcaggg gggtagaaag actaaagccc aaaagggcgg gtatgcctac gggaaaccta  11880
aatttggcta taagactgaa gaaaaggaac taaaagaaga ttcagcacaa caggaaacta  11940
ttaaactaat taagagacac cgtaggtcag ggaaaagcta ccagaaaata gctgattatc  12000
tcaatgccca aagtattccc actaaacaag gtaagaaatg gagttctagc gtcgtctatc  12060
gaatctgtca ggaaaaagct ggttaagtct gtttatagat atttagaatt tattgaataa  12120
aaatagtatg aacaataaat atttatggac taaccacgct cggaaacgtt taactgaacg  12180
```

-continued atgggaaata aaagaatcat gggttattga taccatcgaa aatcctgaac gttcagaatt 12240
tattgttgat gagtcagggg aaaaatatca ttactataaa agaatagcta agtttaagaa 12300
tagagtgtta gaagtgataa cttctgccaa ctcaacaccc acaagaataa taacctttta 12360
ctttaaccgt aacatgagga aaaatttatg attgttactt acgataatga agttgacgca 12420
atttatttta agttaacgga aaataaaatt gatagcaccg aacctcaaac agacaggatt 12480
atcattgatt acgatgaaag taataatatt gttggcattg aggtattaga ttttaattat 12540
cttgtcaaga aaggtttaac cgttgctgat ttaccttttt ctgaagatga aagattaaca 12600
gcttctcaat attttaattt tcctgttgct atctaatcca gaaggggcaa taatcccctt 12660
ctttcatcga gttagactta atatcacaaa agtcattttc attttaccgt ttcttttcca 12720
cagcgtccgt acgcccctcg ttaaatctca aaaccgacaa tttatgatgt ttataaaaag 12780
ttactcactt taataagtat ttatactcat taaagggtta ttcttttttt gtagcctgat 12840
aggttgggaa ggaatatttc agattatcag atttgttgaa tatttttcgt cagatacgca 12900
aaccttacaa acataattaa caactgaaac tattgatatg tctaggtttt agctctatca 12960
caggttggat ctg 12973

<210> SEQ ID NO 26
<211> LENGTH: 12973
<212> TYPE: DNA
<213> ORGANISM: Artificial Sequence
<220> FEATURE:
<223> OTHER INFORMATION: #1640\pABICyano1::smtB-PsmtA*2-
zmPDC(opt1)_dsrA-Prbc*(optRBS)-synADH(opt1)_ter

<400> SEQUENCE: 26
tcgacgggca aactttatga agcagatcaa gcctatatcc gccaagcaac cggcagccgc 60
gttgattagt gggtgtgtcc atcctctggt tcgtctaggt gctccgaagc gtcacgatag 120
agattaagaa tgtggtgatc cttgaggcga taaatcacat tccgcccttc cttgcgatag 180
ctcactaaac gtgctgtgcg cagggttctt agttggtgag agacagccga ttcactcatt 240
tcaacggcgg cggcgagttc ccccacccgc atctctccag tggccagggc cgaaagaata 300
cgccagcggt tggcatcccc caagacacca aaaaattcgg ccatccgttg ggccttggct 360
tggttcaaga ttttgccact gtggtctgtc attgttcgct gatctaaaca atacctgaat 420
aattgttcat gtgttaatct aaaaatgtga acaatcgttc aactatttaa gacaatacca 480
aggaggtata aaccatgaat tcttataccg tgggtactta tttagccgaa cgcttagtgc 540
aaattggttt aaaacatcat tttgccgtgg ctggggacta taatttagtg ttattggata 600
acttattatt aaataaaaac atggaacaag tgtattgttg taatgaatta aattgtggtt 660
tttctgctga aggttatgct agagctaaag gtgcagctgc tgctgttgtt acttattctg 720
tgggtgcttt atctgctttt gatgctattg gtggtgctta tgccgaaaat ttacccgtga 780
ttttaatttc tggtgcccct aataataatg atcatgccgc tggacatgtt ttacatcatg 840
ccttaggtaa aaccgattat cattatcaat tagaaatggc caaaaatatt actgctgctg 900
ccgaagctat ttatactcct gaagaagccc ctgccaaaat tgatcatgtg attaaaaccg 960
ccttacgcga aaaaaaaccc gtgtatttag aaattgcctg taatattgct tctatgcctt 1020
gtgctgctcc tgggcctgct tctgctttat ttaatgatga agcctctgat gaagctagtt 1080
taaatgctgc cgtggaagaa accttaaaat ttattgccaa tcgcgataaa gttgccgtgt 1140
tagttggttc taaattaaga gctgctggtg ctgaagaagc tgctgttaaa tttgctgatg 1200

-continued

```
ctttaggtgg tgcagttgct actatggctg ctgccaaatc ttttttttccc gaagaaaatc   1260
cccattatat tggaactagt tggggagaag tttcttatcc tggtgtggaa aaaactatga   1320
aagaagccga cgctgttatt gctttagccc ctgtgtttaa tgattattct accactggtt   1380
ggactgatat tcccgatccc aaaaaattag ttttagccga acctcgttct gttgttgtta   1440
atggtgttcg ctttccctct gtgcatttaa aagattattt aacccgctta gcccaaaaag   1500
tttctaaaaa aactggtgcc ttagattttt ttaaatcttt aaatgcgggt gaattaaaaa   1560
aagctgctcc tgctgatcct tctgctcctt tagttaatgc tgaaattgcc cgtcaagttg   1620
aagccttatt aacccctaat actaccgtta ttgccgaaac tggtgattct tggtttaatg   1680
cccaacgcat gaaattacct aatggtgccc gtgttgaata tgaaatgcaa tggggtcata   1740
ttggttggtc tgtacctgct gcttttggtt atgctgttgg tgctcctgaa cgtcgtaata   1800
ttttaatggt gggtgatggt tcttttcaat taactgccca agaagttgcc caaatggttc   1860
gcttaaaatt acccgttatt atttttttaa taaataatta tggttatacc attgaagtga   1920
tgattcatga tgggccatat aataatatta aaaattggga ttatgcgggt ttaatggaag   1980
tgtttaatgg taatggtggt tatgattctg gtgctggtaa aggtttaaaa gccaaaactg   2040
gtggtgaatt agctgaagct attaaagttg ccttagccaa tactgatggg ccaaccttaa   2100
ttgaatgttt tattggtcgc gaagattgta ccgaagaatt agttaaatgg ggtaaacgtg   2160
ttgctgctgc taattctcgc aaacccgtga ataaattatt gtaatttttg ggatcaatt    2220
cgagctcagc aagtttcatc ccgacccccct cagggtcggg atttttttat tgtactagtt   2280
gacataagta aaggcatccc ctgcgtgata taattacctt cagtttaagg aggtatacac   2340
atatgattaa agcctatgct gccttagaag ccaatggtaa attacaaccc tttgaatatg   2400
atcctggtgc tttaggtgcc aatgaagtgg aaattgaagt gcaatattgt ggtgtgtgtc   2460
attctgattt atctatgatt aataatgaat ggggtatttc taattatccc ttagttcctg   2520
gtcatgaagt tgttggtact gttgctgcta tgggtgaagg tgttaatcat gtggaagtgg   2580
gtgatttagt tggtttaggt tggcattctg gttattgtat gacctgtcat tcttgtttat   2640
ctggttatca taatttatgt gccactgccg aatctactat tgtgggtcat tatggtggtt   2700
ttggtgatag agttcgtgct aaaggtgttt ctgtggtgaa attacccaaa ggtattgatt   2760
tagcctctgc tgggcctttta ttttgtggtg gtattaccgt tttttctccc atggtggaat   2820
tatctttaaa acctaccgcc aaagttgctg ttattggtat tggtggttta ggtcatttag   2880
ccgttcaatt tttaagagcc tggggttgtg aagttactgc ttttacctct tctgcccgta   2940
aacaaaccga agttttagaa ttaggtgccc atcatatttt agattctacc aatcctgaag   3000
ctattgcttc tgccgaaggt aaatttgatt atattatttc taccgtgaat ttaaaattag   3060
attggaattt atatatcagt accttagccc ctcaaggtca ttttcatttt gttggtgtgg   3120
tgttagaacc cttggactta aacttatttc ccttattaat gggacaacgt tctgtttctg   3180
cttctcctgt tggttctcct gctactattg ccactatgtt agattttgcc gtgcgtcatg   3240
atattaaacc cgtggtggaa caattttctt ttgatcaaat taatgaagcc attgcccatt   3300
tagaatctgg taaagcccat tatcgcgtgg tgttatctca ttctaaaaat taataagatt   3360
aacttctaaa ctgaaacaaa tttgagggta ggcttcattg tctgccctta ttttttttatt   3420
taggaaaagt gaacagacta aagagtgttg gctctattgc tttgagtatg taaattaggc   3480
gttgctgaat taaggtatga tttttgaccc cttctctctt ctgcaggatc atcttgctga   3540
aaaactcgag cgctcgttcc gcaaagcggt acggagttag ttaggggcta atgggcattc   3600
```

```
tcccgtacag gaaagagtta gaagttatta attatcaaca attctccttt gcctagtgca   3660
tcgttacctt tttaattaaa acataaggaa aactaataat cgtaataatt taacctcaaa   3720
gtgtaaagaa atgtgaaatt ctgactttta taacgttaaa gagggaaaaa ttagcagttt   3780
aaaataccta gagaatagtc tggggtaagc atagagaatt agattagtta agttaatcaa   3840
attcagaaaa aataataatc gtaaatagtt aatctgggtg tatagaaaat gatccccttc   3900
atgataagat ttaaactcga aaagcaaaag ccaaaaaact aacttccatt aaaagaagtt   3960
gttacatata acgctataaa gaaaatttat atatttggag gataccaacc atgtctcata   4020
ttcaacgtga aactagttgt tctcgccctc gtttaaattc taatatggat gccgatttat   4080
atggttataa atgggctcgt gataatgttg gtcaatctgg tgctactatt tatcgtttat   4140
atggtaaacc tgatgctcct gaattattct tgaaacatgg taaaggttct gttgctaatg   4200
atgttactga tgaaatggtt cgtttaaact ggttgactga atttatgcct ttacctacta   4260
ttaaacattt tattcgtact cccgatgatg cttggttatt aactactgct attcctggta   4320
aaactgcttt tcaagtttta gaagaatatc ctgattctgg tgaaaatatt gttgatgctt   4380
tagctgtttt tttacgtcgt ttacattcta ttcccgtttg taattgtcct tttaattctg   4440
atcgtgtttt tcgtttagct caagctcaat ctcgtatgaa taatggttta gttgatgctt   4500
ctgattttga tgatgaacgt aatggttggc ctgttgaaca agtttggaaa gaaatgcaca   4560
aattgttacc tttttctcct gattctgttg ttactcatgg tgatttttct ttagataatt   4620
tgatctttga tgaaggtaaa ttgattggtt gtattgatgt tggtcgtgtt ggtattgctg   4680
atcgttatca agatttagct attttatgga attgtttagg tgaattttct ccttctttac   4740
agaaacgttt atttcagaaa tatggtattg ataatcctga tatgaacaag ttacaatttc   4800
atttaatgtt ggacgagttc ttttaagaat taattcatga ccaaaatccc ttaacgtgag   4860
ttttcgttcc actgagcgtc agaccccgta gaaaagatca aaggatcttc ttgagatcct   4920
tttttctgc gcgtaatctg ctgctattta aattacgtac acgtgttatt actttgttaa    4980
cgacaattgt cttaattaac tggcctcat gggccttccg ctcactgccc gctttccagt    5040
cgggaaacct gtcgtgccag ctctgcagat gacggtgaaa acctctgaca catgcagctc   5100
ccggagacgg tcacagcttg tctgtaagcg gatgccggga gcagacaagc ccgtcagggc   5160
gcgtcagcgg gtgttggcgg gtgtcggggc gcagccatga cccagtcacg tagcgatagc   5220
ggagtgtata ctggcttaac tatgcggcat cagagcagat tgtactgaga gtgcaccata   5280
tgcggtgtga aataccgcac agatgcgtaa ggagaaaata ccgcatcagg cgctcttccg   5340
cttcctcgct cactgactcg ctgcgctcgg tcgttcggct gcggcgagcg gtatcagctc   5400
actcaaaggc ggtaatacgg ttatccacag aatcagggga taacgcagga aagaacatgt   5460
gagcaaaagg ccagcaaaag gccaggaacc gtaaaaaggc cgcgttgctg gcgtttttcc   5520
ataggctccg cccccctgac gagcatcaca aaaatcgacg ctcaagtcag aggtggcgaa   5580
acccgacagg actataaaga taccaggcgt ttccccctgg aagctccctc gtgcgctctc   5640
ctgttccgac cctgccgctt accggatacc tgtccgcctt tctcccttcg ggaagcgtgg   5700
cgctttctca tagctcacgc tgtaggtatc tcagttcggt gtaggtcgtt cgctccaagc   5760
tgggctgtgt gcacgaaccc cccgttcagc ccgaccgctg cgccttatcc ggtaactatc   5820
gtcttgagtc caacccggta agacacgact tatcgccact ggcagcagcc actggtaaca   5880
ggattagcag agcgaggtat gtaggcggtg ctacagagtt cttgaagtgg tggcctaact   5940
```

-continued acggctacac tagaaggaca gtatttggta tctgcgctct gctgaagcca gttaccttcg 6000
gaaaaagagt tggtagctct tgatccggca aacaaaccac cgctggtagc ggtggttttt 6060
ttgtttgcaa gcagcagatt acgcgcagaa aaaaaggatc tcaagaagat cctttgatct 6120
tttctactgc agaagcttgt tagacaccct gtcatgtatt ttatattatt tatttcacca 6180
tacggattaa gtgaaaccta atgaaaatag tactttcgga gctttaactt taatgaaggt 6240
atgttttttt atagacatcg atgtctggtt taacaatagg aaaaagtagc taaaactccc 6300
atgaattaaa gaaataacaa ggtgtctaac aacctgttat taagaatgtt agaaaagact 6360
taacatttgt gttgagtttt tatagacatt ggtgtctaga catacggtag ataaggtttg 6420
ctcaaaaata aaataaaaaa agattggact aaaaaacatt taatttagta caatttaatt 6480
agttattttt tcgtctcaaa ttttgctttg ttgagcagaa atttagataa aaaaatcccc 6540
gtgatcagat tacaatgtcg ttcattgtac gatgtgtcga aaatctttta cgacactcta 6600
aactgaccac acgggggaaa aagaaaactg aactaataac atcatgatac tcggaaaacc 6660
tagcaattct caacccctaa acaaaagaaa cttccaaaac cctgaccata taaaggagtg 6720
gcaacaatca gcaatcagtc aagatttgat agcagaaaat cttgtatcgg ttgctaatgg 6780
ttttgatgta ctatttatcg gcaataaata ccgaactaac acgggtgttc tgtcacggca 6840
catattaaac tcctattctc atttagaaga tggtggttcg tatggtagaa catttgaccc 6900
atttaccaat aaagaaatgc agtgggttca atttaaaccg aatagaccaa gaaaaggttc 6960
tactggtaag gtaatcaaat atgaatcgcc aaaaggtgaa cctacaagag ttctaatgcc 7020
gtttgtgcct atgaaaatat ggcaacggat tagcgataag ttcggagtac cgattaatcc 7080
gaaaaaagat actcactttt gggaatgggt aaagaataat ccatcgatac cgattgccat 7140
tacagaagga aataaaaaag ctaattgcct attatcctat ggctatcctg ctattgcctt 7200
tgtaggcatt tggaacggat tagagaaaat aaatgatttc tcgaaggaaa agcagttaaa 7260
agaggatttg aaatggttgt tatccaacgg caaccgaaat attaatatca tctttgacca 7320
agaccagaaa caaaaaactg taattaatgt aaacaaagct attttcgctt tatcttctct 7380
aataagtaga aatggtcata aagttaatat tgtgcaatgg ttgccgtcaa aaggtaaagg 7440
aatagatgat tatttggtag ctttaccttt tgagaaaaga gaaaatcatt tagacaactt 7500
aattaaaatt gcaccatcat ttaatttttg gtcaactaaa tacttattca agtgtcgtaa 7560
accagattta accgtaaatt gccgttattt gagcgatgca gtaaaagaat tacctcaaga 7620
ggatatagca ttaatagcac ctcacggcac gggtaaaact tcattagtag ctactcacgt 7680
taagaatcgg agttatcacg gaaggaaaac tatttcattg gtgcatcttg aaagtttagc 7740
caaagctaat ggcaacgcac ttggattata ttaccgaacc gaaaataata ttgaaaagca 7800
atatcttgga tttagcttat gtgtagatag ttgccgtgat aagattaacg gcattacaac 7860
tgatattatt tcaggtcaag attattgcct tttcattgat gaaattgacc aagtaattcc 7920
acacatcctt aacagtgaaa ctgaagtaag taagtataga tgcaccatca ttgacacttt 7980
ttctgaactg gtgagaaatg ctgaacaggt cattattgct gatgctgatt tatccgatgt 8040
gacgattgac ctaatagaaa acatcagagg taaaaaacta tatgtaatca agaatgaata 8100
tcagtatcag ggaatgactt ttaacgccgt tggttcacca ttagaaatga tggcaatgat 8160
gggaaaatcg gtgtcagaag gcaagaaatt atttattaac accacatccc aaaaggcaaa 8220
aagtaagtac ggcacaatcg ctcttgagtc ttatattttt ggtctaaata aagaagcaaa 8280
gatattaaga atagactctg aaaccactaa aaaccctgaa catccagcct ataaaatcat 8340
tgaccaagac ttaaataata tcctcaaaga ttatgattat gtcattgcct caccttgcct 8400
tcaaacaggt gtcagtatta ccttaaaagg gcattttgac cagcaattta acttttccag 8460
tggaaacatt acacctcatt gctttttaca gcaaatgtgg cggttgaggg atgcagaaat 8520
tgaaagattc tattatgtgc cgaactcatc taacctcaat ctcattggga ataagtcaag 8580
ttcaccatca gaccttctaa agagcaataa caagatggca acggcaacgg ttaacctttt 8640
gggtagaatc gactccgaat attccctaga gtatgaatcg cacggcattt ggcttgagac 8700
gtgggcaaaa ttatcagcac ggcataacag ttcaatgcgt tgttactctg aaattcttac 8760
ctatctaatt acgtctcaag ggcataaatt aaatatcaac attccctcac ctcttgcaga 8820
tattaagaag ctaaatgatg aggtaagtag taacagggaa aaggtaaaaa atgagagata 8880
ctctcagagg ttaaactcac cagatattaa cgatgcagaa gctaccatac tcgaatctaa 8940
agagcaaaaa atcggattga ctctcaatga gagatgcacc ctagaaaagc ataaagttaa 9000
gaagcggtat gggaatgtaa agatggatat tctcaccttt gatgatgatg gactataccc 9060
caaactcaga ctattttatt acctcaccat cggtaaacct catctcaagg ctaatgacag 9120
aaaagctatt gccaaaatgg gcaatgacaa taaaggcaag attctatcaa aagacttagt 9180
taataaaact tactccgctc gtgtgaaggt cttagagatt cttaaactaa ctgactttat 9240
cgacaatctt agagatgaac tcttaataac tcccaataat ccagctatca ccgattttaa 9300
taatcttctg ctaagagcta agaaggattt aagagtatta ggagtcaaca tcggaaaata 9360
tccaatggcc aacattaatg ccgtacttac tctcattggt cacaaacttt ctgtaatgag 9420
agatgagttc ggaaaagaga aaaggataaa agtagatggt aaatcatacc gatgttatca 9480
acttgaaaca ttaccagatt ttaccaatga tactcttgac tactggttag aaaatgatag 9540
ccaaaaagaa gtaacagcaa cagaaaatta ctccgaaaat tttaaccctt caaatagcta 9600
caatccagac agtaagacac tttcagaggg tgcaaatttc ctatatataa ataaagaaga 9660
attgcatcca aataaattgc acctagaaat aaaagaaggt gctgaacttt ttttattcgg 9720
ggtaaaggtg attgtgaaag gaatcttgga cggggcagta actatattct ctatgggtca 9780
agaatacgat ttatccctca atgaactaga ggggatgtta acatcatgaa ctttacaaga 9840
atctttttaa agggcgatcg caccatgtta aatgatggta catttgttca gatatttgat 9900
atttaccatg accacgcatt gggagtgacc cttgacctta agacagaaaa aattatttcc 9960
gatgatgtta gggtaattac tgtcaaagac ttattgttcg atggcactta taaaggggta 10020
aaatctttta tgcccgataa tgcccgataa tgcccgattg atgctacaaa atcccataat 10080
cataagcgat aatcccctaa tagcttgtaa ttcttgaacc gtagcgattt tagagtattc 10140
caaaaagaag aaataaacac cgcaaaatgt cgtatttcac atatataaac caaggttttt 10200
tgccctaaaa tctttatgtt tgtagtgtga tgttgggtca aaatggtcag aaaagttgca 10260
aggtttttat ggatgcttac gcgcgcgagg ggtaagcatc cccaaatagt tactttatcc 10320
tagtccatgc ccatttattg ccgtcccgtt cggctttaaa aaagtgccaa aactcacaag 10380
gtgcaataaa aagttctgta cctttcgcaa ccctagataa tctttcaaca gttacttttt 10440
ttcctattat ctcggtacaa agtttggcta gtttctcttt tccctctttt tcaatcaagc 10500
cttcttgtat gcccaactca ttgattaatc tctctatttt taccattatt tcccgttcag 10560
gtagtttatc ccctaaatct tcatcggggg gcaatgtagg gcattctgaa ggggcttttt 10620
cttctgtctg gacattatct aatattgaag taaccaaact atcttcagtt ttttctattc 10680

-continued

```
ctattaattc atattcggtt actgtatccg tatcaatatc cgaataacta tctttatccg  10740
tattagctat tcggttaagt ttatccgtta actcagaaac aagactatat agcggtttta  10800
gcttttcttc tatcctgtta tctaatacgg ataagtttat acggttatca ttatccgtat  10860
tagtatcatt gggctttttt ggtagttcta ccccctcata aaccgctttt attcccaatt  10920
ccaacagact gataacagta tcctttataa tgggtttttt gctgatatgg tgaacttttg  10980
ccccttccat cattgcgata ctttctatct cactcatcaa cttatcgctt aagtgaatct  11040
cgtatctgtt taatccctta ctggttttat tcatatccgt ttactttatt cggttaacaa  11100
ttctatttta tacgaataaa atattatacg gttaacttta tacgtttaac tattttatct  11160
atacggataa cagtaataag ttattcgtat tagttatacg tttactttta tccaaataaa  11220
attagtgcat ttaaactaaa agaatgattt tatcggagtt gatagcattg gattaaccta  11280
aagatgttta taagctatat ctgataagta tttaaggtta ttttgttatt ctgtttattg  11340
acattatcag aataaaagaa tagaatataa ttgttgagag ataagaggtt taagtgatta  11400
tggttaagaa gttagttggt tatgtcaggg tcagtagtga atcgcaagag gataacacta  11460
gcttacagaa tcagatagag agaattgaag catattgtat ggcttttggt tatgagttgg  11520
taaaaatatt caaagaggtt gccactggta caaaagcaga tattgaaacc cgtcctattt  11580
ttaatgaagc tatagaatac ttgaaacagg ataatgctaa tggaattatt gccttgaagc  11640
tagaccgaat cgcacggaat gctttagatg tattgcgttt ggttcgtgaa accttagaac  11700
cacaaaataa aatgttagtg ttactagata ttcaggtaga tacttcgaca ccttcaggaa  11760
aaatgatttt aactgtaatg agtgccgttg ctgaactcga aagagacatg atctatgatc  11820
gcactcaggg gggtagaaag actaaagccc aaaagggcgg gtatgcctac gggaaaccta  11880
aatttggcta taagactgaa gaaaaggaac taaaagaaga ttcagcacaa caggaaacta  11940
ttaaactaat taagagacac cgtaggtcag ggaaaagcta ccagaaaata gctgattatc  12000
tcaatgccca aagtattccc actaaacaag gtaagaaatg gagttctagc gtcgtctatc  12060
gaatctgtca ggaaaaagct ggttaagtct gtttatagat atttagaatt tattgaataa  12120
aaatagtatg aacaataaat atttatggac taaccacgct cggaaacgtt taactgaacg  12180
atgggaaata aaagaatcat gggttattga taccatcgaa aatcctgaac gttcagaatt  12240
tattgttgat gagtcagggg aaaaatatca ttactataaa agaatagcta agtttaagaa  12300
tagagtgtta gaagtgataa cttctgccaa ctcaacaccc acaagaataa taacctttta  12360
ctttaaccgt aacatgagga aaaatttatg attgttactt acgataatga agttgacgca  12420
atttatttta agttaacgga aaataaaatt gatagcaccg aacctcaaac agacaggatt  12480
atcattgatt acgatgaaag taataatatt gttggcattg aggtattaga ttttaattat  12540
cttgtcaaga aaggtttaac cgttgctgat ttaccttttt ctgaagatga aagattaaca  12600
gcttctcaat attttaattt tcctgttgct atctaatcca gaaggggcaa taatcccctt  12660
ctttcatcga gttagactta atatcacaaa agtcattttc attttaccgt ttcttttcca  12720
cagcgtccgt acgcccctcg ttaaatctca aaaccgacaa tttatgatgt ttataaaaag  12780
ttactcactt taataagtat ttatactcat taaagggtta ttcttttttt gtagcctgat  12840
aggttgggaa ggaatatttc agattatcag atttgttgaa tatttttcgt cagatacgca  12900
aaccttacaa acataattaa caactgaaac tattgatatg tctaggtttt agctctatca  12960
caggttggat ctg                                                     12973
```

<210> SEQ ID NO 27
<211> LENGTH: 359
<212> TYPE: DNA
<213> ORGANISM: Cyanobacterium sp. ABICyano1

<400> SEQUENCE: 27

```
cctcaactac aagttctttt atatattact ttaacctgag ttttggataa gctgaaagca     60
ttattttctc gtagtcagaa aaccttatag cttcttagaa ataacgataa aattacctta    120
atccgaactg acgttaaata tattcacccc tatcacccca aaaccctaag cccctacttc    180
ccccttccc ttcatcacct catcccccca tcccctaaca cttaacctta ttctttattc     240
ttaaaccgaa ctgaggtgaa gttgcagaat acccatgggg ggttacagca ttgtagaaaa    300
ataaatattc tttcattatt aaggttgttt ggtaaaaata tgtgaaaacc ctaataatt     359
```

<210> SEQ ID NO 28
<211> LENGTH: 239
<212> TYPE: DNA
<213> ORGANISM: Cyanobacterium sp. ABICyano1

<400> SEQUENCE: 28

```
ggggacagac atatttttat cataatggta aattcataat aattttagac tttttttgc      60
aaaaattaat ctcactctct tctttcccta tctcccattg tttcttatat cccaatgccc    120
caatacccaa agctcagaaa ataggtatta gcgaagaggt gttgatcccc tcccctagca    180
aaatatactc ctatatagta aagtgagaaa gtgaagaaat aagatcaagt tcgcaattt     239
```

<210> SEQ ID NO 29
<211> LENGTH: 496
<212> TYPE: DNA
<213> ORGANISM: Cyanobacterium sp. ABICyano1

<400> SEQUENCE: 29

```
caaatcacga gaatttatgt agggactatt ttgggttgac ggtggagagt atgtcgccct     60
tgaattatga cccgaagatg aagatgtcgg ggaggtggaa ggacggtctt taagaggttt    120
aacatcaaag ttggtcataa tctctgtccc tgtttgataa ctactattta attttgagtt    180
gttttaggta catcaaaata cccaaatcct tactctcccc tcaatataca acaaaaaaaa    240
ctttttgatt cactttagtc ataaaaatta gaatttatct accgaaatat tacataaatg    300
taatgtatat attttctgat ttattccgtg tgagccatga ttcataattt ataattcata    360
atttctaaat atgcccctac aatggatata gaatgtcatt ttaattatag gtatcataat    420
cgtggtagtt actccggaaa aaactattga atcaaattca gtctcacctg ctacagatag    480
agtagccgtt attctt                                                    496
```

<210> SEQ ID NO 30
<211> LENGTH: 290
<212> TYPE: DNA
<213> ORGANISM: Cyanobacterium sp. ABICyano1

<400> SEQUENCE: 30

```
ttgacgattg tattgactta cgccaaatgg cttaccctca tagtgaatag ttgataatta     60
agaattaaaa atcccgttca cgacagaagg gagtgtaaga gccttcggtg cgaactctca    120
tcttccctga aacctgacac ctgaaacctg acacctgaaa cctgacacct catctcccta    180
atcccctaat tttaatgaaa aaataccctg agtgggcatt gaaaaaaaag aaaagttgtt    240
cgactatgaa ataagaattc tgcacttcgt gagaaaaaag gaaatgaaat                290
```

<210> SEQ ID NO 31
<211> LENGTH: 355
<212> TYPE: DNA
<213> ORGANISM: Cyanobacterium sp. ABICyano1

<400> SEQUENCE: 31
ctatttaact aggaaaaggt aaagttaaaa ggacaagggt aaataattaa aaattaagaa 60
ttaagaactt ctaactctca ttactcatta cttatttcct cctctcaccc cttctcctga 120
tcacctcttc tcctcaatac tcggaactca tttccccatg gtgtgacact caaatcaaaa 180
gtctgttatt gactttcaga tgaaatatta ctatgataac aatatccccc ctatgggtat 240
ataaaaatat gagcgatatt agttaaaaat caaatttgga tttttttct gaaaatattt 300 taagattaag taaagataag taaagaaatt ataagcaatt ttgttaaatc atacc 355

<210> SEQ ID NO 32
<211> LENGTH: 619
<212> TYPE: DNA
<213> ORGANISM: Cyanobacterium sp. ABICyano1

<400> SEQUENCE: 32
ctcacactga aaatattgcc acaagaaata aagatcaagc aataatcctg actaaaaagg 60
aataaagtaa ttatcctttt cctgatatgt tatctgactt gttgtttctt agtcatgttc 120
cttccatttt tatttttgtt tttatcattt ttattacaaa aatttcttaa tagggctaaa 180
gcatttagtt agttttttag ctctcaacaa gttgactaat caatataatg ccctaagtta 240
atttgccctt ggtttgacgg aggatattgg aaaaaagaaa cttctcgttg tatttcacag 300
ggaaaagggg gaaattttat taataactaa acaatagaaa ataattattt atttatatta 360
ttttgtgaac aaatgttcaa gaattaaagt gtaataagaa aatttatttt tttatattta 420
tttaaaactt agatataagc ctaaaggtct gaaattatta ttagacaatc aattgattca 480
gaggtaatag ttttttactt aaaaatattt tttcaaaatt atcccctatt tgggtattga 540
aaaataaata aattcaagta ataatataca gaataaagga aaatctaatc ttaaaaattt 600
tgtgtgtgag gaattgaaa 619

<210> SEQ ID NO 33
<211> LENGTH: 190
<212> TYPE: DNA
<213> ORGANISM: Cyanobacterium sp. ABICyano1

<400> SEQUENCE: 33
tatcaccatt gtagaaaagc cagaaaatca attaacacaa atttcctgta aattattatg 60
tatgattttc cccttctccc cttaaaagga gaaataaaaa actatatccc ccaaccaccg 120
ataagcattg tgagagaaaa atcatttagg taggatcaat gctgtaaccg ataaagataa 180
ataaataatt 190

<210> SEQ ID NO 34
<211> LENGTH: 536
<212> TYPE: DNA
<213> ORGANISM: Cyanobacterium sp. ABICyano1

<400> SEQUENCE: 34
attctgtgaa ttgattagat ttgaggtttt ttaagaggtt gattaccttg cctccaaaaa 60
aatcataaca cactaatgct ctatatgaaa gggctttaga cccataggtt tttgagaaaa 120
aaacttgcta actctcggac aatgtcagca taactaaagt caattctttt cgtactttat 180

-continued

```
aattgtctat aatttaatat acaactgttc tgaaactagt ttttctctac attccttagt    240

tttatctgag taaggttgct tgtaacttaa cttcggttgg gcctaaaaat atccgattag    300

gagcaggtgt cagactttaa ttaattatta attattaatt gcttattgcc aaccctcggc    360

gacaccactt tttcatcagc cccagataaa gattgatgtt ttagttttgt ttcttttat     420

cccctaattc aactaataca agtaaaacta aggttgttta tcaaaaatga tggttgatgt    480

ttgggtaaat tttaagatat tatgaaaaga aaatgaataa aaaatgaaaa atcttt        536


<210> SEQ ID NO 35
<211> LENGTH: 283
<212> TYPE: DNA
<213> ORGANISM: Cyanobacterium sp. ABICyano1

<400> SEQUENCE: 35

ctacaggggc aagatttggc ggaaatctat atgtggattc tctttcaagt gaagaaggtg     60

cagtgccgac ttatctggac ttattagaat acgatattcg cactattact aatggtttgt    120

tagcaggagt gaacaattaa aaattttttc ctaattgacg aataaaaaat caatgtcaac    180

taatagttaa caatactctc tgaaaaccaa aaattgtcaa ccaaaacata acataatttt    240

tacccaaaaa cctcatttat aaactttaag gataaaatca atg                      283


<210> SEQ ID NO 36
<211> LENGTH: 299
<212> TYPE: DNA
<213> ORGANISM: Cyanobacterium sp. ABICyano1

<400> SEQUENCE: 36

gggattagag agttcaaagt taggaatgag gtgtcaggtt ttaggtttca ggtttagggg     60

agcaatgaga aagaggtttc aggtttcagg tgtcaggttg caggtgtcac aggtgatgag    120

gggatggggg atgaggggga aacaagtaag taataagtgt tcggagtttt taattcttaa    180

ttcttaattt ttcctttgcc tcttgccttt tgccttgtct taattactaa tttctaatta    240

aaatgattgt gttttctagt ttagtctcat ggttacttga acccttacag catagtttt     299


<210> SEQ ID NO 37
<211> LENGTH: 414
<212> TYPE: DNA
<213> ORGANISM: Cyanobacterium sp. ABICyano1

<400> SEQUENCE: 37

ttacaaacgg cgggaattat tatggtagta gcgatgttag taaccccggg tgcgatcgca     60

tatttactta cagatcgttt tgatcaaatg ttaatcttat caatagttag tagtgttcta    120

tcttgtgttt taggcactta tttaagttat cattttgatg tttctacggg gggaagtatt    180

gtcgttttaa tgaccataat ttttatttta gcgatgattt ttgctcctaa atatggcatc    240

atcaatcaaa ataccaaaat atattctgct taacttgttt actgatactt caaataatca    300

tataacctat cttccgagtt aaaaaataatg gatattatcc aactgaggtc gagaatagag    360

tttcttttttt gatagaattt ttttacacca gttattcatt actatcatgg gata          414


<210> SEQ ID NO 38
<211> LENGTH: 412
<212> TYPE: DNA
<213> ORGANISM: Cyanobacterium sp. ABICyano1

<400> SEQUENCE: 38
```

```
taatatagtg attattataa atgcaatgtg aatcaaacct atattttacc gtacattgac     60

catggaactt aatttgaggt gattagtaga gggtgcgatc gccctatttg tcaaataata    120

aagataacat ttgacattgc tgattgaaga cataaaacac agaaaaaatc aggtaaaaat    180

ataaagctaa agtctaaata tggtttactt ttgccttcga cttacaacaa aaaatcatag    240

ctagaatcac caacgcctaa tattttattt agctgaaatt ttgggatgaa ctttttgtaa    300

aaatcggggg tctaaaaata tagcaaccac gatattaaat aactgagtga ttattttaat    360

ctattggggg cttattaact aaatacttgc atttttatgg agggttttaa tt            412


<210> SEQ ID NO 39
<211> LENGTH: 364
<212> TYPE: DNA
<213> ORGANISM: Cyanobacterium sp. ABICyano1

<400> SEQUENCE: 39

aaagattatt ttctacagaa gcaacccttt catcttccga attttcagga atttcctgct     60

tttgtttctg aatattagca taggcggctt ttgcccactc taaagaaggt tgagactgaa    120

tttctgaggt ttcagaagga gcattagatt gtttatcttc aacaacagga ggtttttgtt    180

caatattttc cttattctct tttttacggc gaaaccaatt aaacataatg attgtgcata    240

aatattcgtt aatatattgt aaccctagaa aggaatcggt ttcaggttta tccccagaga    300

atgtgaacct ttacagaaag taaaaagtct aaaatcgtag caacaataaa tcacagaaat    360

tgag                                                                 364


<210> SEQ ID NO 40
<211> LENGTH: 234
<212> TYPE: DNA
<213> ORGANISM: Cyanobacterium sp. ABICyano1

<400> SEQUENCE: 40

atctagtaat aatcatcaag agttgttaaa acttcactat caagaattgg tagcaagagg     60

attacaacat ctgagtttag atcatcgagc agttattgtt cttcatgatt tggaagattt    120

accacaacag gaaatagcgg aaatattatc tattcccctt ggtacggtca aatctcgttt    180

attcaaagcc agaaaaaatt tgcgtcaatt tttagaactt gaaggtatta gctt          234


<210> SEQ ID NO 41
<211> LENGTH: 246
<212> TYPE: DNA
<213> ORGANISM: Cyanobacterium sp. ABICyano1

<400> SEQUENCE: 41

ccaatatctt gtcatacata cttatttgcc tcactattag ccctatatgt ctctattgta     60

tttttctttt tctcctattc ctagatcttg taatgaatca ttactctctg aaatatagct    120

actaatttta tggttgtttg taaaatatat taacaaatga acaataaatc atattttgtg    180

ttaatctaat tattagacaa ctactgaatt tatattcaga tattcacaga taggagaatt    240

ttgatt                                                               246


<210> SEQ ID NO 42
<211> LENGTH: 346
<212> TYPE: DNA
<213> ORGANISM: Cyanobacterium sp. ABICyano1

<400> SEQUENCE: 42

attctattac cctccgaggg tggctatctc cttttatttg gtggctgata aaaccctatt     60
```

ctattaaagt agccaatgag ttagttaatg cggcggctaa atgtcactaa aatttcatct 120
taggttcaca tcaaagtcat atcggttgtt tatagtatta agtgtcaggg agaaagatag 180
gttttcctct ttagctcctt cgcaccttta atccctgact ttttttattt ttttgttcgt 240
gtgattaatc tatttgtgta gcaattattt ttatcttatt ttcttttcag tctagtaatt 300
aattattttt atattttgta ttatttttag agaggtttga gctgtt 346

<210> SEQ ID NO 43
<211> LENGTH: 320
<212> TYPE: DNA
<213> ORGANISM: Cyanobacterium sp. ABICyano1

<400> SEQUENCE: 43
gaatatctca tccttagctt ctacttatac cttcagcata gttaaaaatc atccctttat 60
tgatggtaat aaaagaacag gttttattag tggagtaacc tttttaatgc tcaatggttc 120
tcactttact gcttctgaag tggaagtagt acatatcatc caaaccttag ctagtggcag 180
aattaccgag gaagaattac aacaatggtt cgtaaggaaa agtaagcaga tgaataatta 240
aagcatcatt tcatcctcat ttcatattct cctgtcacca tggtatggaa gattaggtaa 300
aaatgaggaa aaagtttatt 320

<210> SEQ ID NO 44
<211> LENGTH: 304
<212> TYPE: DNA
<213> ORGANISM: Cyanobacterium sp. ABICyano1

<400> SEQUENCE: 44
gcgattatca accacgaaaa catacaatta ttatcaaacc tgctgagaaa ttatccacag 60
aaatagatgt ttctgcgaag ggaaaatggg cttttcattg ccatttaatg tatcacatgg 120
atgtgggaat gtttcggact attaatgtta tttcctaaaa aataatagta ttaaagccta 180
aaatttttat aaaaaaattc atgtctttta ttagggtgag cattcttcct ttatgtctcc 240
ttattttacc tctttagagg taactacaaa cttaatcaaa aaatttagat aattaattat 300
atca 304

<210> SEQ ID NO 45
<211> LENGTH: 309
<212> TYPE: DNA
<213> ORGANISM: Cyanobacterium sp. ABICyano1

<400> SEQUENCE: 45
atacatggtt ggttcactga cttttacccc agttttctct ttgaacaatt ggcataactc 60
tgaaaaaatc agatcgggct tttgttgaat tatttgttca atcaaagcaa aaccgtgatt 120
gtctattttc tttttttcc caccactcat agataaaaat ttatcccgaa ctcaggttat 180
attaagttcg gatgatcact taagataatt gatcagattg gttaagatag agaaaaattc 240
tttttcatag tgatttcata attgatagtt acaataacga ttattattta gtaaaaagat 300
tttcaaatc 309

<210> SEQ ID NO 46
<211> LENGTH: 330
<212> TYPE: DNA
<213> ORGANISM: Cyanobacterium sp. ABICyano1

<400> SEQUENCE: 46

-continued

```
tggtcaagtt actatatgtt tagaaacaac aaaaaaagaa gtcattataa aaataattga     60

tacaggaatt ggcattaata aagaagaaca aaaattaatt tttaatcgtt tttatcgaat    120

caataaagca agaaatagag agaaaggcag ttgcggatta ggtttagcta ttgcaaatgc    180

gatcgcgctt aatcatggtg gtagaataat tttagaaagt caagaaaatc aaggcagtat    240

ttttaccgtt tatttaccga aaatcatttc atcctaattt catattcttt tgacagaatc    300

aaaggtaaag ataaaaagag agaaacagtc                                     330
```

<210> SEQ ID NO 47
<211> LENGTH: 490
<212> TYPE: DNA
<213> ORGANISM: Cyanobacterium sp. ABICyano1

<400> SEQUENCE: 47

```
catctttact tttgactaac atttcatagg tatcatgacg aaaatttttt agtctgttat     60

atttgttcat gtagagagat tttaatttgt gattatttta ttttctctct atttttcttt    120

tttgtcttgt ccttcctcat ttttctctac atttagtcta aactacagct ctttaatctt    180

cagtttctct ttcctcctct tcctcatcaa ggtaatcatc ccaattaata tcttcttctt    240

gttctaattt gggttgagat tgttgtttat caatcatatt tcatactcct aaaactttct    300

tacttattta tcagttactt tttacccatt tatgcaatag tgtagaaatt tttttcgatc    360

gagttaatta atttttattt caaccatatc taaataattc ttgatggaca ttctagttaa    420

ctagaaggtt taagctaaaa ataattattg atattgcctt cggtataact aactatatcc    480

agagaaaaag                                                           490
```

<210> SEQ ID NO 48
<211> LENGTH: 433
<212> TYPE: DNA
<213> ORGANISM: Cyanobacterium sp. ABICyano1

<400> SEQUENCE: 48

```
tttatatata aactcgaata aaattatcaa tataaagtca aactatatct atcctatttt     60

aactgctatt ggtaagtccc ttaattagtg ttggggtgaa tagattttaa aagggcaaac    120

ccccctttat cctccctcga gagggggggag ggcaaaaggc aaggggcaag ggaaaaatta    180

agaattaaga attaaaaact ccgaacacct gtaggggcga atagccattc gcttcccctc    240

atccccccat ctccccaaca ccctaagccc ctactcgtta ctcatttatt tacatcattt    300

atttacatca ttaagaaaag taacaaattt tgacaagtag tcttttgaca ggaaaaagca    360

aattctcgaa gatgaaaaca atagaaaaaa attcaatctt acagtaacga tgaaaaaact    420

tttaggctta att                                                       433
```

<210> SEQ ID NO 49
<211> LENGTH: 306
<212> TYPE: DNA
<213> ORGANISM: Cyanobacterium sp. ABICyano1

<400> SEQUENCE: 49

```
ctcaagagat agttaaaaaa caaatagctt tagtctatca attaatcgaa ttatttttac     60

aaacaaattt tcataaaccc atagaactag aggaggaagt tatttatgtt taaaaatcta    120

aaagagtttt atattcccct aaaaccccct tagtaagagt gacttttttc atcatttgcc    180

tgtaaattct cctcttttaa taagagagct agggtgtttt aaaagaggat tttattgctt    240

tccaattcta actacttcaa aaacttattt tatactcaat aatttattaa tcaagaggaa    300
```

attacc 306

<210> SEQ ID NO 50
<211> LENGTH: 13604
<212> TYPE: DNA
<213> ORGANISM: Artificial Sequence
<220> FEATURE:
<223> OTHER INFORMATION: TK441\pABICyano:PpetJABICyano1-PDCmax-
PrpsLABICyano-synADHmax-PrbcABICyano-Km**-oriVT

<400> SEQUENCE: 50
aatatttttc gtcagatacg caaaccttac aaacataatt aacaactgaa actattgata 60
tgtctaggtt ttagctctat cacaggttgg atctgtcgac tttatatata aactcgaata 120
aaattatcaa tataaagtca aactatatct atcctatttt aactgctatt ggtaagtccc 180
ttaattagtg ttggggtgaa tagattttaa aagggcaaac ccccctttat cctccctcga 240
gaggggggag ggcaaaaggc aaggggcaag ggaaaaatta agaattaaga attaaaaact 300
ccgaacacct gtaggggcga atagccattc gcttcccctc atccccccat ctccccaaca 360
ccctaagccc ctactcgtta ctcatttatt tacatcattt atttacatca ttaagaaaag 420
taacaaattt tgacaagtag tcttttgaca ggaaaaagca aattctcgaa gatgaaaaca 480
atagaaaaaa attcaatctt acagtaacga tgaaaaaact tttaggctta attatgaatt 540
cttataccgt gggtacttat ttagccgaac gcttagtgca aattggttta aaacatcatt 600
ttgccgtggc tggggactat aatttagtgt tattggataa cttattatta aataaaaaca 660
tggaacaagt gtattgttgt aatgaattaa attgtggttt ttctgctgaa ggttatgcta 720
gagctaaagg tgcagctgct gctgttgtta cttattctgt gggtgcttta tctgcttttg 780
atgctattgg tggtgcttat gccgaaaatt tacccgtgat tttaatttct ggtgccccta 840
ataataatga tcatgccgct ggacatgttt tacatcatgc cttaggtaaa accgattatc 900
attatcaatt agaaatggcc aaaaatatta ctgctgctgc cgaagctatt tatactcctg 960
aagaagcccc tgccaaaatt gatcatgtga ttaaaaccgc cttacgcgaa aaaaaacccg 1020
tgtatttaga aattgcctgt aatattgctt ctatgccttg tgctgctcct gggcctgctt 1080
ctgctttatt taatgatgaa gcctctgatg aagctagttt aaatgctgcc gtggaagaaa 1140
ccttaaaatt tattgccaat cgcgataaag ttgccgtgtt agttggttct aaattaagag 1200
ctgctggtgc tgaagaagct gctgttaaat ttgctgatgc tttaggtggt gcagttgcta 1260
ctatggctgc tgccaaatct ttttttcccg aagaaaatcc ccattatatt ggaactagtt 1320
ggggagaagt ttcttatcct ggtgtggaaa aaactatgaa agaagccgac gctgttattg 1380
ctttagcccc tgtgtttaat gattattcta ccactggttg gactgatatt cccgatccca 1440
aaaaattagt tttagccgaa cctcgttctg ttgttgttaa tggtgttcgc tttccctctg 1500
tgcatttaaa agattattta acccgcttag cccaaaaagt ttctaaaaaa actggtgcct 1560
tagatttttt taaatcttta aatgcgggtg aattaaaaaa agctgctcct gctgatcctt 1620
ctgctccttt agttaatgct gaaattgccc gtcaagttga agccttatta acccctaata 1680
ctaccgttat tgccgaaact ggtgattctt ggtttaatgc ccaacgcatg aaattaccta 1740
atggtgcccg tgttgaatat gaaatgcaat ggggtcatat tggttggtct gtacctgctg 1800
cttttggtta tgctgttggt gctcctgaac gtcgtaatat tttaatggtg ggtgatggtt 1860
cttttcaatt aactgcccaa gaagttgccc aaatggttcg cttaaaatta cccgttatta 1920
tttttttaat aaataattat ggttatacca ttgaagtgat gattcatgat gggccatata 1980

-continued

```
ataatattaa aaattgggat tatgcgggtt taatggaagt gtttaatggt aatggtggtt   2040
atgattctgg tgctggtaaa ggtttaaaag ccaaaactgg tggtgaatta gctgaagcta   2100
ttaaagttgc cttagccaat actgatgggc caaccttaat tgaatgtttt attggtcgcg   2160
aagattgtac cgaagaatta gttaaatggg gtaaacgtgt tgctgctgct aattctcgca   2220
aacccgtgaa taaattattg taatttttgg ggatcaattc gagctcctcc gcttaaaaaa   2280
tttcattttt cgatcaaaaa agacaaatta ttactaatta gctcatggca ataaataatc   2340
agtagtaatc tgttttcaca ttttattgtt aatttttatt attgctaata tcaacctttt   2400
ctacttctgc ttaatatttt atttatgctc aatgggaaaa tctgaaataa gattgagaac   2460
agtgttacca atagaagtat ttaaggttta aagcatacct taaagataac attttttttt   2520
gaaaagagtc aaattatttt tgaaaggctg atatttttga tatttactaa tattttattt   2580
atttcttttt cccttaaaat aagagctaaa tctgttttta ttatcattta tcaagctcta   2640
ttaatacctc aactttttca agaaaaaata ataataattt ttccctctat tctcatgacc   2700
ttttaggaaa attaatttta gaaaaactat tgacaaaccc ataaaaaatg agataagatt   2760
atagattgtc actggtattt tatactagag gcaaattata tttatatata caaaaatgct   2820
gtataaaaaa catctcatat gattaaagcc tatgctgcct tagaagccaa tggtaaatta   2880
caaccctttg aatatgatcc tggtgcttta ggtgccaatg aagtggaaat tgaagtgcaa   2940
tattgtggtg tgtgtcattc tgatttatct atgattaata atgaatgggg tatttctaat   3000
tatcccttag ttcctggtca tgaagttgtt ggtactgttg ctgctatggg tgaaggtgtt   3060
aatcatgtgg aagtgggtga tttagttggt ttaggttggc attctggtta ttgtatgacc   3120
tgtcattctt gtttatctgg ttatcataat ttatgtgcca ctgccgaatc tactattgtg   3180
ggtcattatg gtggttttgg tgatagagtt cgtgctaaag gtgtttctgt ggtgaaatta   3240
cccaaaggta ttgatttagc ctctgctggg cctttatttt gtggtggtat taccgttttt   3300
tctcccatgg tggaattatc tttaaaacct accgccaaag ttgctgttat tggtattggt   3360
ggtttaggtc atttagccgt tcaattttta agagcctggg gttgtgaagt tactgctttt   3420
acctcttctg cccgtaaaca aaccgaagtt ttagaattag gtgcccatca tattttagat   3480
tctaccaatc ctgaagctat tgcttctgcc gaaggtaaat ttgattatat tatttctacc   3540
gtgaatttaa aattagattg gaatttatat atcagtacct tagcccctca aggtcatttt   3600
cattttgttg gtgtggtgtt agaacccttg gacttaaact tatttccctt attaatggga   3660
caacgttctg tttctgcttc tcctgttggt tctcctgcta ctattgccac tatgttagat   3720
tttgccgtgc gtcatgatat taaacccgtg gtggaacaat tttcttttga tcaaattaat   3780
gaagccattg cccatttaga atctggtaaa gcccattatc gcgtggtgtt atctcattct   3840
aaaaattaat aagattaact tctaaactga aacaaatttg agggtaggct tcattgtctg   3900
cccttatttt tttatttagg aaaagtgaac agactaaaga gtgttggctc tattgctttg   3960
agtatgtaaa ttaggcgttg ctgaattaag gtatgatttt tgaccccttc tctcttctgc   4020
agttacctag gatttctggc gaaaggggga tgtgctgcaa ggcgattaag ttgggtaacg   4080
ccagggtttt cccagtcacg acgttgtaaa acgacggcca gtgagcgcga cgtaatacga   4140
ctcactatag ggcgaattgg cggaaggccg tcaaggccgc atggcgcgcc tacgtagaca   4200
attgtcgatg taattattaa ctatcttatt atagatgagg ggagagggag aaattagttc   4260
ggagagaacg ctcgagcgct cgttccgcaa agcggtacgg agttagttag ggctaatgg    4320
```

-continued

```
gcattctccc gtacaggaaa gagttagaag ttattaatta tcaacaattc tcctttgcct   4380
agtgcatcgt taccttttta attaaaacat aaggaaaact aataatcgta ataatttaac   4440
ctcaaagtgt aaagaaatgt gaaattctga cttttataac gttaaagagg gaaaaattag   4500
cagtttaaaa tacctagaga atagtctggg gtaagcatag agaattagat tagttaagtt   4560
aatcaaattc agaaaaaata ataatcgtaa atagttaatc tgggtgtata gaaaatgatc   4620
cccttcatga taagatttaa actcgaaaag caaaagccaa aaaactaact tccattaaaa   4680
gaagttgtta catataacgc tataaagaaa atttatatat ttggaggata ccaaccatgt   4740
ctcatattca acgtgaaact agttgttctc gtcctcgttt aaattctaat atggatgccg   4800
atttatatgg ttataaatgg gctcgtgata atgttggtca atctggtgct actatttatc   4860
gtttatatgg taaacctgat gctcctgaat tattcttgaa acatggtaaa ggttctgttg   4920
ctaatgatgt tactgatgaa atggttcgtt taaactggtt gactgaattt atgcctttac   4980
ctactattaa acattttatt cgtactcccg atgatgcttg gttattaact actgctattc   5040
ctggtaaaac tgcttttcaa gttttagaag aatatcctga ttctggtgaa aatattgttg   5100
atgctttagc tgttttttta cgtcgtttac attctattcc cgtttgtaat tgtcctttta   5160
attctgatcg tgtttttcgt ttagctcaag ctcaatctcg tatgaataat ggtttagttg   5220
atgcttctga ttttgatgat gaacgtaatg gttggcctgt tgaacaagtt tggaaagaaa   5280
tgcacaaatt gttacctttt tctcctgatt ctgttgttac tcatggtgat ttttctttag   5340
ataatttgat ctttgatgaa ggtaaattga ttggttgtat tgatgttggt cgtgttggta   5400
ttgctgatcg ttatcaagat ttagctattt tatggaattg tttaggtgaa ttttctcctt   5460
ctttacagaa acgtttattt cagaaatatg gtattgataa tcctgatatg aacaagttac   5520
aatttcattt aatgttggac gagttctttt aagaattaat tcatgaccaa aatcccttaa   5580
cgtgagtttt cgttccactg agcgtcagac cccgtagaaa agatcaaagg atcttcttga   5640
gatccttttt ttctgcgcgt aatctgctgc tatttaaatt acgtacacgt gttattactt   5700
tgttaacgac aattgtctta attaactggg cctcatgggc cttccgctca ctgcccgctt   5760
tccagtcggg aaacctgtcg tgccagctct gcagatgacg gtgaaaacct ctgacacatg   5820
cagctcccgg agacggtcac agcttgtctg taagcggatg ccgggagcag acaagcccgt   5880
cagggcgcgt cagcgggtgt tggcgggtgt cggggcgcag ccatgaccca gtcacgtagc   5940
gatagcggag tgtatactgg cttaactatg cggcatcaga gcagattgta ctgagagtgc   6000
accatatgcg gtgtgaaata ccgcacagat gcgtaaggag aaaataccgc atcaggcgct   6060
cttccgcttc ctcgctcact gactcgctgc gctcggtcgt tcggctgcgg cgagcggtat   6120
cagctcactc aaaggcggta atacggttat ccacagaatc aggggataac gcaggaaaga   6180
acatgtgagc aaaaggccag caaaaggcca ggaaccgtaa aaaggccgcg ttgctggcgt   6240
ttttccatag gctccgcccc cctgacgagc atcacaaaaa tcgacgctca agtcagaggt   6300
ggcgaaaccc gacaggacta taaagatacc aggcgtttcc ccctggaagc tccctcgtgc   6360
gctctcctgt tccgaccctg ccgcttaccg gatacctgtc cgcctttctc ccttcgggaa   6420
gcgtggcgct ttctcatagc tcacgctgta ggtatctcag ttcggtgtag gtcgttcgct   6480
ccaagctggg ctgtgtgcac gaaccccccg ttcagcccga ccgctgcgcc ttatccggta   6540
actatcgtct tgagtccaac ccggtaagac acgacttatc gccactggca gcagccactg   6600
gtaacaggat tagcagagcg aggtatgtag gcggtgctac agagttcttg aagtggtggc   6660
ctaactacgg ctacactaga aggacagtat ttggtatctg cgctctgctg aagccagtta   6720
```

```
ccttcggaaa aagagttggt agctcttgat ccggcaaaca aaccaccgct ggtagcggtg   6780
gtttttttgt ttgcaagcag cagattacgc gcagaaaaaa aggatctcaa gaagatcctt   6840
tgatcttttc tactgcagaa gcttgttaga caccctgtca tgtattttat attatttatt   6900
tcaccatacg gattaagtga aacctaatga aaatagtact ttcggagctt taactttaat   6960
gaaggtatgt ttttttatag acatcgatgt ctggtttaac aataggaaaa agtagctaaa   7020
actcccatga attaaagaaa taacaaggtg tctaacaacc tgttattaag aatgttagaa   7080
aagacttaac atttgtgttg agtttttata gacattggtg tctagacata cggtagataa   7140
ggtttgctca aaaataaaat aaaaaaagat tggactaaaa aacatttaat ttagtacaat   7200
ttaattagtt attttttcgt ctcaaatttt gctttgttga gcagaaattt agataaaaaa   7260
atccccgtga tcagattaca atgtcgttca ttgtacgatg tgtcgaaaaa tctttacgac   7320
actctaaact gaccacacgg gggaaaaaga aaactgaact aataacatca tgatactcgg   7380
aaaacctagc aattctcaac ccctaaacaa aagaaacttc caaaaccctg accatataaa   7440
ggagtggcaa caatcagcaa tcagtcaaga tttgatagca gaaaatcttg tatcggttgc   7500
taatggtttt gatgtactat ttatcggcaa taaataccga actaacacgg gtgttctgtc   7560
acggcacata ttaaactcct attctcattt agaagatggt ggttcgtatg gtagaacatt   7620
tgacccattt accaataaag aaatgcagtg ggttcaattt aaaccgaata gaccaagaaa   7680
aggttctact ggtaaggtaa tcaaatatga atcgccaaaa ggtgaaccta caagagttct   7740
aatgccgttt gtgcctatga aaatatggca acggattagc gataagttcg gagtaccgat   7800
taatccgaaa aagatactc acttttggga atgggtaaag aataatccat cgataccgat   7860
tgccattaca gaaggaaata aaaaagctaa ttgcctatta tcctatggct atcctgctat   7920
tgcctttgta ggcatttgga acggattaga gaaaataaat gatttctcga aggaaaagca   7980
gttaaaagag gatttgaaat ggttgttatc caacggcaac cgaaatatta atatcatctt   8040
tgaccaagac cagaaacaaa aaactgtaat taatgtaaac aaagctattt tcgctttatc   8100
ttctctaata agtagaaatg gtcataaagt taatattgtg caatggttgc cgtcaaaagg   8160
taaaggaata gatgattatt tggtagcttt accttttgag aaaagagaaa atcatttaga   8220
caacttaatt aaaattgcac catcatttaa tttttggtca actaaatact tattcaagtg   8280
tcgtaaacca gatttaaccg taaattgccg ttatttgagc gatgcagtaa aagaattacc   8340
tcaagaggat atagcattaa tagcacctca cggcacgggt aaaacttcat tagtagctac   8400
tcacgttaag aatcggagtt atcacggaag gaaaactatt tcattggtgc atcttgaaag   8460
tttagccaaa gctaatggca acgcacttgg attatattac cgaaccgaaa ataatattga   8520
aaagcaatat cttggattta gcttatgtgt agatagttgc cgtgataaga ttaacggcat   8580
tacaactgat attatttcag gtcaagatta ttgccttttc attgatgaaa ttgaccaagt   8640
aattccacac atccttaaca gtgaaactga agtaagtaag tatagatgca ccatcattga   8700
cactttttct gaactggtga gaaatgctga acaggtcatt attgctgatg ctgatttatc   8760
cgatgtgacg attgacctaa tagaaaacat cagaggtaaa aaactatatg taatcaagaa   8820
tgaatatcag tatcagggaa tgacttttaa cgccgttggt tcaccattag aaatgatggc   8880
aatgatggga aaatcggtgt cagaaggcaa gaaattattt attaacacca catcccaaaa   8940
ggcaaaaagt aagtacggca caatcgctct tgagtcttat atttttggtc taaataaaga   9000
agcaaagata ttaagaatag actctgaaac cactaaaaac cctgaacatc cagcctataa   9060
```

-continued

```
aatcattgac caagacttaa ataatatcct caaagattat gattatgtca ttgcctcacc   9120
ttgccttcaa acaggtgtca gtattacctt aaaagggcat tttgaccagc aatttaactt   9180
ttccagtgga aacattacac ctcattgctt tttacagcaa atgtggcggt tgagggatgc   9240
agaaattgaa agattctatt atgtgccgaa ctcatctaac ctcaatctca ttgggaataa   9300
gtcaagttca ccatcagacc ttctaaagag caataacaag atggcaacgg caacggttaa   9360
ccttttgggt agaatcgact ccgaatattc cctagagtat gaatcgcacg gcatttggct   9420
tgagacgtgg gcaaaattat cagcacggca taacagttca atgcgttgtt actctgaaat   9480
tcttacctat ctaattacgt ctcaagggca taaattaaat atcaacattc cctcacctct   9540
tgcagatatt aagaagctaa atgatgaggt aagtagtaac agggaaaagg taaaaaatga   9600
gagatactct cagaggttaa actcaccaga tattaacgat gcagaagcta ccatactcga   9660
atctaaagag caaaaaatcg gattgactct caatgagaga tgcaccctag aaaagcataa   9720
agttaagaag cggtatggga atgtaaagat ggatattctc acctttgatg atgatggact   9780
ataccccaaa ctcagactat tttattacct caccatcggt aaacctcatc tcaaggctaa   9840
tgacagaaaa gctattgcca aaatgggcaa tgacaataaa ggcaagattc tatcaaaaga   9900
cttagttaat aaaacttact ccgctcgtgt gaaggtctta gagattctta aactaactga   9960
ctttatcgac aatcttagag atgaactctt aataactccc aataatccag ctatcaccga  10020
ttttaataat cttctgctaa gagctaagaa ggatttaaga gtattaggag tcaacatcgg  10080
aaaatatcca atggccaaca ttaatgccgt acttactctc attggtcaca aactttctgt  10140
aatgagagat gagttcggaa aagagaaaag gataaaagta gatggtaaat cataccgatg  10200
ttatcaactt gaaacattac cagattttac caatgatact cttgactact ggttagaaaa  10260
tgatagccaa aaagaagtaa cagcaacaga aaattactcc gaaaatttta acccttcaaa  10320
tagctacaat ccagacagta agacactttc agagggtgca aatttcctat atataaataa  10380
agaagaattg catccaaata aattgcacct agaaataaaa gaaggtgctg aacttttttt  10440
attcggggta aaggtgattg tgaaaggaat cttggacggg gcagtaacta tattctctat  10500
gggtcaagaa tacgatttat ccctcaatga actagagggg atgttaacat catgaacttt  10560
acaagaatct ttttaaaggg cgatcgcacc atgttaaatg atggtacatt tgttcagata  10620
tttgatattt accatgacca cgcattggga gtgacccttg accttaagac agaaaaaatt  10680
atttccgatg atgttagggt aattactgtc aaagacttat tgttcgatgg cacttataaa  10740
ggggtaaaat cttttatgcc cgataatgcc cgataatgcc cgattgatgc tacaaaatcc  10800
cataatcata agcgataatc ccctaatagc ttgtaattct tgaaccgtag cgattttaga  10860
gtattccaaa aagaagaaat aaacaccgca aaatgtcgta tttcacatat ataaaccaag  10920
gttttttgcc ctaaaatctt tatgtttgta gtgtgatgtt gggtcaaaat ggtcagaaaa  10980
gttgcaaggt ttttatggat gcttacgcgc gcgaggggta agcatcccca aatagttact  11040
ttatcctagt ccatgcccat ttattgccgt cccgttcggc tttaaaaaag tgccaaaact  11100
cacaaggtgc aataaaaagt tctgtacctt tcgcaaccct agataatctt tcaacagtta  11160
ctttttttcc tattatctcg gtacaaagtt tggctagttt ctcttttccc tctttttcaa  11220
tcaagccttc ttgtatgccc aactcattga ttaatctctc tatttttacc attatttccc  11280
gttcaggtag tttatcccct aaatcttcat cggggggcaa tgtagggcat tctgaagggg  11340
ctttttcttc tgtctggaca ttatctaata ttgaagtaac caaactatct tcagtttttt  11400
ctattcctat taattcatat tcggttactg tatccgtatc aatatccgaa taactatctt  11460
```

-continued tatccgtatt agctattcgg ttaagtttat ccgttaactc agaaacaaga ctatatagcg 11520
gttttagctt ttcttctatc ctgttatcta atacggataa gtttatacgg ttatcattat 11580
ccgtattagt atcattgggc ttttttggta gttctacccc ctcataaacc gcttttattc 11640
ccaattccaa cagactgata acagtatcct ttataatggg ttttttgctg atatggtgaa 11700
cttttgcccc ttccatcatt gcgatacttt ctatctcact catcaactta tcgcttaagt 11760
gaatctcgta tctgtttaat cccttactgg ttttattcat atccgtttac tttattcggt 11820
taacaattct attttatacg aataaaatat tatacggtta actttatacg tttaactatt 11880
ttatctatac ggataacagt aataagttat tcgtattagt tatacgttta cttttatcca 11940
aataaaatta gtgcatttaa actaaaagaa tgattttatc ggagttgata gcattggatt 12000
aacctaaaga tgtttataag ctatatctga taagtattta aggttatttt gttattctgt 12060
ttattgacat tatcagaata aaagaataga atataattgt tgagagataa gaggtttaag 12120
tgattatggt taagaagtta gttggttatg tcagggtcag tagtgaatcg caagaggata 12180
acactagctt acagaatcag atagagagaa ttgaagcata ttgtatggct tttggttatg 12240
agttggtaaa aatattcaaa gaggttgcca ctggtacaaa agcagatatt gaaacccgtc 12300
ctatttttaa tgaagctata gaatacttga aacaggataa tgctaatgga attattgcct 12360
tgaagctaga ccgaatcgca cggaatgctt tagatgtatt gcgtttggtt cgtgaaacct 12420
tagaaccaca aaataaaatg ttagtgttac tagatattca ggtagatact tcgacacctt 12480
caggaaaaat gattttaact gtaatgagtg ccgttgctga actcgaaaga gacatgatct 12540
atgatcgcac tcagggggt agaaagacta aagcccaaaa gggcgggtat gcctacggga 12600
aacctaaatt tggctataag actgaagaaa aggaactaaa agaagattca gcacaacagg 12660
aaactattaa actaattaag agacaccgta ggtcagggaa aagctaccag aaaatagctg 12720
attatctcaa tgcccaaagt attcccacta aacaaggtaa gaaatggagt tctagcgtcg 12780
tctatcgaat ctgtcaggaa aaagctggtt aagtctgttt atagatattt agaatttatt 12840
gaataaaaat agtatgaaca ataaatattt atggactaac cacgctcgga aacgtttaac 12900
tgaacgatgg gaaataaaag aatcatgggt tattgatacc atcgaaaatc ctgaacgttc 12960
agaatttatt gttgatgagt caggggaaaa atatcattac tataaaagaa tagctaagtt 13020
taagaataga gtgttagaag tgataacttc tgccaactca acacccacaa gaataataac 13080
cttttacttt aaccgtaaca tgaggaaaaa tttatgattg ttacttacga taatgaagtt 13140
gacgcaattt attttaagtt aacggaaaat aaaattgata gcaccgaacc tcaaacagac 13200
aggattatca ttgattacga tgaaagtaat aatattgttg gcattgaggt attagatttt 13260
aattatcttg tcaagaaagg tttaaccgtt gctgatttac ctttttctga agatgaaaga 13320
ttaacagctt ctcaatattt taattttcct gttgctatct aatccagaag gggcaataat 13380
ccccttcttt catcgagtta gacttaatat cacaaaagtc attttcattt taccgtttct 13440
tttccacagc gtccgtacgc ccctcgttaa atctcaaaac cgacaattta tgatgtttat 13500
aaaaagttac tcactttaat aagtatttat actcattaaa gggttattct ttttttgtag 13560
cctgataggt tgggaaggaa tatttcagat tatcagattt gttg 13604

<210> SEQ ID NO 51
<211> LENGTH: 205
<212> TYPE: DNA
<213> ORGANISM: Cyanobacterium sp. ABICyano1

<400> SEQUENCE: 51
tagagtatga taaaatgaca aggaaaggat tattttctct tgtttaaatt ctcaagattc 60
ttatgcttat ttattttatg taagtgtctc ttttccttga aatagaaaga aaaaagtggc 120
taattttgag aaaagctaac aacgctttgg ttaactaaaa atcaaaagtg agattactga 180
tcgcttaaga aatggagtat tgatt 205

<210> SEQ ID NO 52
<211> LENGTH: 327
<212> TYPE: DNA
<213> ORGANISM: Cyanobacterium sp. ABICyano1

<400> SEQUENCE: 52
tgagaaaaag tgtaaacaaa tattaagaaa aagatcagaa aaatttaaca acacgtaata 60
aaaaaatgcg tcactacggg ttataaattt acatgaaagg ttaaaacact tttctgagac 120
gattttgata aaaaagttgt caaaaaatta agtttcttta caaatgctta acaaaaactt 180
ggttttaagc acaaaataag agagactaat ttgcagaagt tttacaagga aatcttgaag 240
aaaaagatct aagtaaaacg actctgttta accaaaattt aacaaattta acaaaacaaa 300
ctaaatctat taggagatta actaagc 327

<210> SEQ ID NO 53
<211> LENGTH: 214
<212> TYPE: DNA
<213> ORGANISM: Cyanobacterium sp. ABICyano1

<400> SEQUENCE: 53
agagttatat ttacatagtg tgtgcgagta agggcaactt ttgtaggtag atgaataaac 60
ctcaaattac tcatcttaaa agacgatatt tttaatctat tcttctgtaa taaaatactt 120
ctttcgatag agatatttaa tacttttgag agatgaaaat aatttcaata attgtcatga 180
tagagagtaa gtgcaaataa gaaaaaattg attt 214

<210> SEQ ID NO 54
<211> LENGTH: 338
<212> TYPE: DNA
<213> ORGANISM: Cyanobacterium sp. ABICyano1

<400> SEQUENCE: 54
gcagttagat aaataagtaa tgagcgggag aaataggggc aaatggccat tcgcccctac 60
agggaggtgg caggtgttag ggtgtttagg ggatgaggtg atgagggtag agggagataa 120
ggtgtcgggt ttcagatttc aggttttaga agaaagtaac gagtaattat caactattca 180
ctattcacta ttgcctgttg cccttctctc cttgaaatat aaaaaaatgt aaaaatatca 240
ttaagaaaag taacaaaata aacagaaagg ttgacaaagt tgacgcttta atatccgtat 300
gttagcttta taacaacgaa atcaacggag gagtgaaa 338

<210> SEQ ID NO 55
<211> LENGTH: 408
<212> TYPE: DNA
<213> ORGANISM: Cyanobacterium sp. ABICyano1

<400> SEQUENCE: 55
cttgaaaaag ttgaggtatt aatagagctt gataaatgat aataaaaaca gatttagctc 60
ttattttaag ggaaaaagaa ataaataaaa tattagtaaa tatcaaaaat atcagccttt 120
caaaaataat ttgactcttt tcaaaaaaaa atgttatctt taaggtatgc tttaaacctt 180
aaatacttct attggtaaca ctgttctcaa tcttatttca gattttccca ttgagcataa 240
ataaaatatt aagcagaagt agaaaaggtt gatattagca ataataaaaa ttaacaataa 300
aatgtgaaaa cagattacta ctgattattt attgccatga gctaattagt aataatttgt 360 ctttttgat cgaaaaatga aattttttaa gcggaggaac tgaaaatt 408

<210> SEQ ID NO 56
<211> LENGTH: 411
<212> TYPE: DNA
<213> ORGANISM: Cyanobacterium sp. ABICyano1

<400> SEQUENCE: 56
tatttatata taaactcgaa taaaattatc aatataaagt caaactatat ctatcctatt 60
ttaactgcta ttggtaagtc ccttaattag tgttggggtg aatagatttt aaaagggcaa 120
accccccttt atcctccctc gagagggggg agggcaaaag gcaaggggca agggaaaaat 180
taagaattaa gaattaaaaa ctccgaacac ctgtaggggc gaatagccat tcgcttcccc 240
tcatcccccc atctccccaa caccctaagc ccctactcgt tactcattta tttacatcat 300
ttatttacat cattaagaaa agtaacaaat tttgacaagt agtcttttga caggaaaaag 360
caaattctcg aagatgaaaa caatagaaaa aaattcaatc ttacagtaac g 411

<210> SEQ ID NO 57
<211> LENGTH: 211
<212> TYPE: DNA
<213> ORGANISM: Cyanobacterium sp. ABICyano1

<400> SEQUENCE: 57
gtgatatttg gtttattcta tattttcctt aagtaaaaat tcagtcatga gggaaacttt 60
tgttaaaatt tgctttaaat taataggaag atcattaaga aaatcttaaa aagattgagt 120
ttttagatcg aaattattga agaaaaatta acaggggttc tgctcaaaat tttattaaat 180
tactctactg tagtaaagga gaaattttat t 211

<210> SEQ ID NO 58
<211> LENGTH: 542
<212> TYPE: DNA
<213> ORGANISM: Cyanobacterium sp. ABICyano1

<400> SEQUENCE: 58
gaatagttga taattactcg ttactcatta ctcacttaaa cctgccacct gatacctgcc 60
acctctcccc ccatcacctc atcccctcaa cattccgaac cccttgacac tttgaactaa 120
aattgtatta aagtgcaaat ctggacgggg ttaaccagtg tgacttataa tagtaaacgc 180
tgttttttat aataaataag ctaaatattt aaaaactatg agtaaatata cactaaatgg 240
tactagacgt aagcagaaaa gaacctccgg tttccgcgcc cgtatgagaa ccaaaaatgg 300
tagaaaagta attcaagctc gtcgtaataa gggtagaaaa agattagcag tataaaatta 360
ctgttaaata aggaagctaa gtttagcatt ttaagtttga tattactaat cattaaattt 420
actgtgaaat ataggtggga ctaccatcaa agcatcgact gaaacggcgt ttaaatttcc 480
aatctgttta tcaacagggt attcgccgct ctagtcgtta ttttattgtc cgagggttac 540
gg 542

<210> SEQ ID NO 59
<211> LENGTH: 380
<212> TYPE: DNA

<213> ORGANISM: Cyanobacterium sp. ABICyano1

<400> SEQUENCE: 59

```
ataaccaatg ggacttgaat tttagatcca tttatttaat tctatttttg ttacatttct     60
ttatattaat cagaattatg ttactttgtt ttgttttatg tcgttacctt attgaagaaa    120
gagtggatga gaaggtaaat gacggggcat aaatatcgat tcgttgtcag aataagctgt    180
tttattcact taactggttg tttgccaatt tctccctaat tcccataact tgtataacta    240
aatttaataa tcaattttag taaattaaga ataggttaaa agtagtattt agaattaagt    300
taactttaat aaatttcctg tattttttta tagaaaaaag tataaaataa aaacatatca    360
aaaaagtttg aaatgacaat                                                380
```

<210> SEQ ID NO 60
<211> LENGTH: 1252
<212> TYPE: DNA
<213> ORGANISM: Cyanobacterium sp. MBIC10216

<400> SEQUENCE: 60

```
acctgcctca aggtcgggga caacagttgg aaacgactgc taataccgga tgagccgaat     60
aggtaaaaga tttatcgcct tgagaggggc tcgcgtctga ttagctagat ggtgaggtaa    120
aggcttacca tggcgacgat cagtagctgg tctgagagga tgagcagcca cactgggact    180
gagacacggc ccagactcct acgggaggca gcagtgggga attttccgca atgggcgaaa    240
gcctgacgga gcaataccgc gtgagggagg aaggctcttg ggttgtaaac ctcaaaactt    300
agggaagaaa aaaatgacgg tacctaatgt aagcatcggc taactccgtg ccagcagccg    360
cggtaatacg gaggatgcaa gcgttatccg gaatcattgg gcgtaaagag tccgtaggtg    420
gcacttcaag tctgctttca aagaccgaag ctcaacttcg gaaagggagt ggaaactgaa    480
gagctagagt atagtagggg tagagggaat tcctagtgta gcggtgaaat gcgtagagat    540
taggaagaac accagtggcg aaggcgctct actgggcata tactgacact gagggacgaa    600
agctagggga gcgaaaggga ttagataccc ctgtagtcct agcggtaaac gatggatact    660
aggcgtagtg ctgtaaaagg gactgtgccg aagctaacgc gttaagtatc ccgcctgggg    720
agtacgcacg caagtgtgaa actcaaagga attgacgggg acccgcacaa gcggtggagt    780
atgtggttta attcgatgca acgcgaagaa ccttaccaag gcttgacatc ctgcgaatct    840
tgatgaaagt tgagagtgcc taagggaacg cagagacagg tggtgcatgg ctgtcgtcag    900
ctcgtgtcgt gagatgttgg gttaagtccc gcaacgagcg caaccctcgt ccttagttgc    960
cagcattaag ttggggactc tagggagacc gccggggaga actcggagga aggtggggat   1020
gacgtcaagt cagcatgccc cttacgtctt gggctacaca cgtactacaa tggttgggac   1080
aaaggggagc gaagccgcga ggtggagcga atctcatcaa acccagccac agttcagatt   1140
gcaggctgaa actcgcctgc atgaaggagg aatcgctagt aatcgcaggt cagcatactg   1200
cggtgaatcc gttcccgggt cttgtacaca ccgcccgtca caccatggaa gt           1252
```

<210> SEQ ID NO 61
<211> LENGTH: 1390
<212> TYPE: DNA
<213> ORGANISM: Cyanobacterium aponinum ETS-03

<400> SEQUENCE: 61

```
gcagctacac atgcaagtcg aacgggctct tcggagctag tggcggacgg gtgaggaacg     60
cgtgagaacc tgcctcaagg tcggggacaa cagttggaaa cgactgctaa taccggatga    120
```

gccgaatagg taaaagattt atcgcctaga gaggggctcg cgtctgatta gctagatggt 180
gaggtaaagg cttaccatgg cgacgatcag tagctggtct gagaggatga gcagccacac 240
tgggactgag acacggccca gactcctacg ggaggcagca gtggggaatt ttccgcaatg 300
ggcgaaagcc tgacggagca ataccgcgtg agggaggaag gctcttgggt tgtaaacctc 360
aaaacttagg gaagaaaaaa atgacggtac ctaatgtaag catcggctaa ctccgtgcca 420
gcagccgcgg taatacggag gatgcaagcg ttatccggaa tcattgggcg taaagagtcc 480
gtaggtggca cttcaagtct gctttcaaag accgaagctc aacttcggaa agggagtgga 540
aactgaagag ctagagtata gtagggggta ggaggggaat tcctagtgta gcggtgaaat 600
gcgtagagat taggaagaac accagtggcg aaggcgctct actgggcata tactgacact 660
gagggacgaa agctagggga gcgaaaggga ttagataccc ctgtagtcct agcggtaaac 720
gatggatact aggcgtagtg ctgttagaag gactgtgccg aagctaacgc gttaagtatc 780
ccgcctgggg agtacgcacg caagtgtgaa actcaaagga attgacgggg acccgcacaa 840
gcggtggagt atgtggttta attcgatgca acgcgaagaa ccttaccaag gcttgacatc 900
ctgcgaatct tggagaaatc tgagagtgcc taagggaacg cagagacagg tggtgcatgg 960
ctgtcgtcag ctcgtgtcgt gagatgttgg gttaagtccc gcaacgagcg caaccctcgt 1020
ccttagttgc cagcattaag ttggggactc tagggagacc gccggggaga actcggagga 1080
aggtggggat gacgtcaagt cagcatgccc cttacgtctt gggctacaca cgtactacaa 1140
tggttgggac aaaggggagc gaaaccgcga ggtggagcga atctcatcaa acccagccac 1200
agttcagatt gcaggctgaa actcgcctgc atgaaggagg aatcgctagt aatcgcaggt 1260
cagcatactg cggtgaatcc gttcccgggt cttgtacaca ccgcccgtca caccatggaa 1320
gttggtcacg cccgaagtcg ttattctaac ccaagggaag agacgccaag tgggactagt 1380
gactggggtg 1390

<210> SEQ ID NO 62
<211> LENGTH: 1474
<212> TYPE: DNA
<213> ORGANISM: Cyanobacterium sp. ABICyano2

<400> SEQUENCE: 62
agagtttgat cctggctcag gatgaacgct ggcggtatgc ctaacacatg caagtcgaac 60
gggctcttcg gagctagtgg cggacgggtg aggaacgcgt gagaacctgc ctcaaggtcg 120
gggacaacag ttggaaacga ctgctaatac cggatgagcc gaataggtaa aagatttatc 180
gccttgagag gggctcgcgt ctgattagct agatggtgag gtaaaggctt accatggcga 240
cgatcagtag ctggtctgag aggatgagca gccacactgg gactgagaca cggcccagac 300
tcctacggga ggcagcagtg gggaattttc cgcaatgggc gaaagcctga cggagcaata 360
ccgcgtgagg gaggaaggct cttgggttgt aaacctcaaa acttagggaa gaaaaaaatg 420
acggtaccta atgtaagcat cggctaactc cgtgccagca gccgcggtaa tacggaggat 480
gcaagcgtta tccggaatca ttgggcgtaa agagtccgta ggtggcactt caagtctgct 540
ttcaaagacc gaagctcaac ttcggaaagg gagtggaaac tgaagagcta gagtatagta 600
ggggtagagg gaattcctag tgtagcggtg aaatgcgtag agattaggaa gaacaccagt 660
ggcgaaggcg ctctactggg catatactga cactgaggga cgaaagctag gggagcgaaa 720
gggattagat acccctgtag tcctagcggt aaacgatgga tactaggcgt agtgctgtaa 780

```
aagggactgt gccgaagcta acgcgttaag tatcccgcct ggggagtacg cacgcaagtg    840

tgaaactcaa aggaattgac ggggacccgc acaagcggtg gagtatgtgg tttaattcga    900

tgcaacgcga agaaccttac caaggcttga catcctgcga atcttgatga aagttgagag    960

tgcctaaggg aacgcagaga caggtggtgc atggctgtcg tcagctcgtg tcgtgagatg   1020

ttgggttaag tcccgcaacg agcgcaaccc tcgtccttag ttgccagcat taagttgggg   1080

actctaggga gaccgccggg gagaactcgg aggaaggtgg ggatgacgtc aagtcagcat   1140

gccccttacg tcttgggcta cacacgtact acaatggttg ggacaaaggg gagcgaagcc   1200

gcgaggtgga gcgaatctca tcaaacccag ccacagttca gattgcaggc tgaaactcgc   1260

ctgcatgaag gaggaatcgc tagtaatcgc aggtcagcat actgcggtga atccgttccc   1320

gggtcttgta cacaccgccc gtcacaccat ggaagttggt cacgcccgaa gtcgttattc   1380

taacccaagt ggaaggagac gccgaaggtg ggactagtga ctggggtgaa gtcgtaacaa   1440

ggtagccgta ccggaaggtg tggctggatc acct                               1474


<210> SEQ ID NO 63
<211> LENGTH: 1474
<212> TYPE: DNA
<213> ORGANISM: Cyanobacterium sp. ABICyano1

<400> SEQUENCE: 63

agagtttgat cctggctcag gatgaacgct ggcggtatgc ctaacacatg caagtcgaac     60

ggtctcttcg gagatagtgg cggacgggtg aggaacgcgt gagaacctgc ctcaaggtcg    120

gggacaacag ttggaaacga ctgctaatac cggatgagcc gaataggtaa aagatttatc    180

gcctagagag ggctcgcgt ctgattagct agatggtgag gtaaaggctt accatggcga    240

cgatcagtag ctggtctgag aggatgagca gccacactgg gactgagaca cggcccagac    300

tcctacggga ggcagcagtg gggaattttc cgcaatgggc gaaagcctga cggagcaata    360

ccgcgtgagg gaggaaggct cttgggttgt aaacctcaaa acttagggaa gaaaaaaatg    420

acggtaccta atgtaagcat cggctaactc cgtgccagca gccgcggtaa tacggaggat    480

gcaagcgtta tccggaatca ttgggcgtaa agagtccgta ggtggcactt caagtctgct    540

ttcaaagacc gaagctcaac ttcggaaagg gagtggaaac tgaagagcta gagtatagta    600

ggggtagagg gaattcctag tgtagcggtg aaatgcgtag agattaggaa gaacaccagt    660

ggcgaaggcg ctctactggg catatactga cactgaggga cgaaagctag gggagcgaaa    720

gggattagat acccctgtag tcctagcggt aaacgatgga tactaggcgt agtgctgtta    780

gaaggactgt gccgaagcta acgcgttaag tatcccgcct ggggagtacg cacgcaagtg    840

tgaaactcaa aggaattgac ggggacccgc acaagcggtg gagtatgtgg tttaattcga    900

tgcaacgcga agaaccttac caaggcttga catcctgcga atcttggaga aatctgagag    960

tgcctaaggg aacgcagaga caggtggtgc atggctgtcg tcagctcgtg tcgtgagatg   1020

ttgggttaag tcccgcaacg agcgcaaccc tcgtccttag ttgccagcat taagttgggg   1080

actctaggga gaccgccggg gagaactcgg aggaaggtgg ggatgacgtc aagtcagcat   1140

gccccttacg tcttgggcta cacacgtact acaatggttg ggacaaaggg gagcgaaacc   1200

gcgaggtgga gcgaatctca tcaaacccag ccacagttca gattgcaggc tgaaactcgc   1260

ctgcatgaag gaggaatcgc tagtaatcgc aggtcagcat actgcggtga atccgttccc   1320

gggtcttgta cacaccgccc gtcacaccat ggaagttggt cacgcccgaa gtcgttattc   1380

taacccaagt ggaaggagac gccgaaggtg ggactagtga ctggggtgaa gtcgtaacaa   1440
```

ggtagccgta ccggaaggtg tggctggatc acct 1474

<210> SEQ ID NO 64
<211> LENGTH: 1460
<212> TYPE: DNA
<213> ORGANISM: Cyanobacterium sp. LLi5

<400> SEQUENCE: 64
gatgaacgct ggcggtatgc ttaacacatg caagtcgaac gggcacttcg gtgatagtgg 60
cgcacgggtg aggaacacgt gagaatctgc ctcaaagtcg ggacaacag ttggaaacga 120 ctgctaatac cggatgagcc gcaaggtaaa agatttatcg ctttgagagg agctcgcgtc 180
tgattagcta gatggtgagg taaaggctta ccatggcgac gatcagtagc tggtctgaga 240
ggatgagcag ccacactggg actgagacac ggcccagact cctacgggag gcagcagtgg 300
ggaattttcc gcaatgggcg aaagcctgac ggagcaatac cgcgtgaggg aggaaggctc 360
ttgggttgta aacctcaaaa cttagggaag aagcaagtga cggtacctaa tataagcatc 420
ggctaactcc gtgccagcag ccgcggtaat acggaggatg caagcgttat ccggaatcat 480
tgggcgtaaa gcgtccgtag gtggcatttc aagtctgctg tcaaagaccg aagctcaact 540
tcgggccggc ggtggaaact gaaaagctag agtgaagtag ggtagagggg aattcctagt 600
gtagcggtga aatgcgtaga gattaggaag aacaccagtg gcgaaggcgc tctactggac 660
ttaaactgac actgagggac gaaagctaag ggagcgaaag ggattagata cccctgtagt 720
cttagcggta aacgatggat actaggtgtt gtctgtatcg acccggacag tgccgaagca 780
aacgcgttaa gtatcccgcc tggggagtac gcacgcaagt gtgaaactca aaggaattga 840
cggggacccg cacaagcggt ggagtatgtg gtttaattcg atgcaacgcg aagaacctta 900
ccaaggcttg acatcctgtg aatctcgatg aaagttgaga gtgccttagg gaacacagag 960
acaggtggtg catggctgtc gtcagctcgt gtcgtgagat gttgggttaa gtcccgcaac 1020
gagcgcaacc ctcgtcctta gttgccagca ttaagttggg gactctaggg agactgccgg 1080
ggagaactcg gaggaaggtg gggatgacgt caagtcagca tgccccttac gtcttgggct 1140
acacacgtac tacaatggta gggacaaagg gaggcgaaac tgcgaagtgg agcgaatcct 1200
gtcaaaccct gccccagttc agattgtagg ctgaaactcg cctacatgaa ggaggaatcg 1260
ctagtaatcg caggtcagca tactgcggtg aatccgttcc cgggtcttgt acacaccgcc 1320
cgtcacacca tggaagttgg taacatccga agtcgttact ccaacccgca aggggggagg 1380
atgccgaagg tgggactagt gactggggtg aagtcgtaac aaggtagccg taccggaagg 1440
tgtggctgga tcacctcctt 1460

<210> SEQ ID NO 65
<211> LENGTH: 1476
<212> TYPE: DNA
<213> ORGANISM: Cyanobacterium stanieri PCC 7202

<400> SEQUENCE: 65
agagtttgat cctggctcag gatgaacgct ggcggtatgc ctaacacatg caagtcgaac 60
ggtcacttcg gtgatagtgg cggacgggtg agtaacacgt gagaatctgc ccttaggtcg 120
gggacaacag ttggaaacga ctgctaatac cggatgagct gaaaagtaaa agatttatcg 180
cctagggaag agctcgcggc tgattagcta gttggtgatg taaaggatca ccaaggcaac 240
gatcagtagc tggtctgaga ggatgagcag ccacactggg actgagacac ggcccagact 300

-continued

```
cctacgggag gcagcagtgg ggaattttcc gcaatgggcg aaagcctgac ggagcaatac    360

cgcgtgaggg aggaaggctc ttgggttgta aacctcaaaa ctcagggaag aagaaagtga    420

cggtacctga tataagcatc ggctaactcc gtgccagcag ccgcggtaat acggaggatg    480

caagcgttat ccggaatcat tgggcgtaaa gcgtccgtag gtggcatttc aagtctgcat    540

tcaaagaccg aggctcaacc tcgggcaggg tgtggaaact gaaaagctag agtacaggag    600

gggtagaggg aattcctagt gtagcggtga aatgcgtaga gattaggaag aacaccagtg    660

gcgaaggcgc tctactggac atgtactgac actgagggac gaaagctagg gtagcgaaag    720

ggattagata cccctgtagt cttagctgta aacgatggat actaagtgta gcgggtataa    780

actccggctg tgctgaagcg aacgcgttaa gtatcccgcc tggggagtac gcacgcaagt    840

gtgaaactca aaggaattga cggggacccg cacaagcggt ggagtatgtg gtttaattcg    900

atgcaacgcg aagaacctta ccaagacttg acatccgatg aatctttttg aaagaagaga    960

gtgccttagg gaacatcgtg acaggtggtg catggctgtc gtcagctcgt gtcgtgagat   1020

gttgggttaa gtcccgcaac gagcgcaacc ctcgtcctta gttgccagca ttaagttggg   1080

gactctaggg agaccgccgg ggagaactcg gaggaaggtg gggatgacgt caagtcagca   1140

tgccccttac gtcttgggct acacacgtac tacaatggtt gggacaaagg gatgcgagac   1200

cgcaaggtgg agcgaaaccc atcaaaccca gccccagttc agatcgtcgg ctgaaactcg   1260

ccgacgtgaa ggaggaatcg ctagtaatcg caggtcagca tactgcggtg aatccgttcc   1320

cgggtcttgt acacaccgcc cgtcacacca tggaagttgg taacatccga agtcgttact   1380

ccaaccattt atggaggagg acgccgaagg tgggactagt gactggggtg aagtcgtaac   1440

aaggtagccg taccggaagg tgtggctgga tcacct                             1476
```

<210> SEQ ID NO 66
<211> LENGTH: 292
<212> TYPE: DNA
<213> ORGANISM: Cyanobacterium sp. ABICyano1

<400> SEQUENCE: 66

```
gtcgacaatt aataacttct tcctgtacgg gcgaatggcc atttgctcct aactaactcc     60

gtactgcttt gcggaacgag cgtagcgaac tctccgaatt actaagcctt catccctgat    120

agatgcaaaa aacgaattaa aattatgtgt aaaaagaaaa tgtgtcttta tttagtagtc    180

aaagttacaa aatattaaga atcaaattaa taatgtattg ggcagttaag tatataagtc    240

tttaaatatt tatttgtatt caatatatta accgaggaca aattatgaat tc            292
```

<210> SEQ ID NO 67
<211> LENGTH: 293
<212> TYPE: DNA
<213> ORGANISM: Artificial Sequence
<220> FEATURE:
<223> OTHER INFORMATION: Promoter nirA*2

<400> SEQUENCE: 67

```
gtcgacaatt aataacttct tcctgtacgg gcgaatggcc atttgctcct aactaactcc     60

gtactgcttt gcggaacgag cgtagcgaac tctccgaatt actaagcctt catccctgat    120

agatgcaaaa aacgaattaa aattatgtgt aaaaagaaaa tgtgtcttta tttagtagtc    180

aaagttacaa aatattaaga atcaaattaa taatgtattg ggcagttaag tatataagtc    240

tttaaatatt tatttgtatt caatatatta aggaggatca gccttatgaa ttc           293
```

<210> SEQ ID NO 68
<211> LENGTH: 196
<212> TYPE: DNA
<213> ORGANISM: Artificial Sequence
<220> FEATURE:
<223> OTHER INFORMATION: Promoter nirA*3

<400> SEQUENCE: 68
gtcgactaag ccttcatccc tgatagatgc aaaaaacgca ttaaaattat gcgtaaaaag 60
catatgtgtc tttatttagt aatcaaagtt acaaattatt aagaatcaaa ttaataatat 120
attgggcagt taagtatata agtctttaaa tatttatttg tattcaatat attaaccgag 180
gacaaattat gaattc 196

<210> SEQ ID NO 69
<211> LENGTH: 197
<212> TYPE: DNA
<213> ORGANISM: Artificial Sequence
<220> FEATURE:
<223> OTHER INFORMATION: Promoter nirA*4

<400> SEQUENCE: 69
gtcgactaag ccttcatccc tgatagatgc aaaaaacgca ttaaaattat gcgtaaaaag 60
catatgtgtc tttatttagt aatcaaagtt acaaattatt aagaatcaaa ttaataatat 120
attgggcagt taagtatata agtctttaaa tatttatttg tattcaatat attaaggagg 180
atcagcctta tgaattc 197

<210> SEQ ID NO 70
<211> LENGTH: 93
<212> TYPE: DNA
<213> ORGANISM: Synechocystis PCC6803

<400> SEQUENCE: 70
tcatgacttt agtttactca aaaccttgac attgacacta atgttaaggt ttaggctgag 60
aaggtaaaaa tccaagttaa aaagcatgaa ttc 93

<210> SEQ ID NO 71
<211> LENGTH: 93
<212> TYPE: DNA
<213> ORGANISM: Artificial Sequence
<220> FEATURE:
<223> OTHER INFORMATION: promoter corT*1

<400> SEQUENCE: 71
tcatgacttt agtttactca aaaccttgac attgacacta atgttaaggt ttaggctgag 60
aaggtaaaaa tcgaggataa aaagcatgaa ttc 93

<210> SEQ ID NO 72
<211> LENGTH: 93
<212> TYPE: DNA
<213> ORGANISM: Artificial Sequence
<220> FEATURE:
<223> OTHER INFORMATION: Promoter corT*2

<400> SEQUENCE: 72
tcatgacttt agtttactca aaaccttgac attgacacta atgttaaggt ttagaatgag 60
aaggtaaaaa tccaagttaa aaagcatgaa ttc 93

<210> SEQ ID NO 73
<211> LENGTH: 93
<212> TYPE: DNA

<213> ORGANISM: Artificial Sequence
<220> FEATURE:
<223> OTHER INFORMATION: Promoter corT*3

<400> SEQUENCE: 73
tcatgacttt agtttactca aaaccttgac attgacacta atgttaaggt ttagaatgag 60
aaggtaaaaa tcgaggataa aaagcatgaa ttc 93

<210> SEQ ID NO 74
<211> LENGTH: 93
<212> TYPE: DNA
<213> ORGANISM: Artificial Sequence
<220> FEATURE:
<223> OTHER INFORMATION: Promoter corT*4

<400> SEQUENCE: 74
tcatgacttt agtttactca aaaccttgac attgacacta atgttaaggt ttagaatgag 60
aaggtaaaaa aggaggtgat caagcatgaa ttc 93

<210> SEQ ID NO 75
<211> LENGTH: 101
<212> TYPE: DNA
<213> ORGANISM: Synechococcus PCC7002

<400> SEQUENCE: 75
atctaaacaa tacctgaata attgttcatg tgttaatcta aaaatgtgaa caatcgttca 60
actatttaag acaatacctt ggaggtttaa accatgaatt c 101

<210> SEQ ID NO 76
<211> LENGTH: 101
<212> TYPE: DNA
<213> ORGANISM: Artificial Sequence
<220> FEATURE:
<223> OTHER INFORMATION: Promoter smtA*1

<400> SEQUENCE: 76
atctaaacaa tacctgaata attgttcatg tgttaatcta aaaatgtgaa caatcgttca 60
actatttaag acaataccaa ggaggtgata accatgaatt c 101

<210> SEQ ID NO 77
<211> LENGTH: 101
<212> TYPE: DNA
<213> ORGANISM: Artificial Sequence
<220> FEATURE:
<223> OTHER INFORMATION: Promoter smtA*2

<400> SEQUENCE: 77
atctaaacaa tacctgaata attgttcatg tgttaatcta aaaatgtgaa caatcgttca 60
actatttaag acaataccaa ggaggtataa accatgaatt c 101

<210> SEQ ID NO 78
<211> LENGTH: 281
<212> TYPE: DNA
<213> ORGANISM: Artificial Sequence
<220> FEATURE:
<223> OTHER INFORMATION: Generalized sequence of nirA promoter
<220> FEATURE:
<221> NAME/KEY: misc_feature
<222> LOCATION: (1)..(116)
<223> OTHER INFORMATION: n is a, c, g, or t
<220> FEATURE:
<221> NAME/KEY: misc_feature
<222> LOCATION: (132)..(138)
<223> OTHER INFORMATION: n is a, c, g, or t
<220> FEATURE:
<221> NAME/KEY: misc_feature
<222> LOCATION: (154)..(168)
<223> OTHER INFORMATION: n is a, c, g, or t
<220> FEATURE:
<221> NAME/KEY: misc_feature
<222> LOCATION: (183)..(204)
<223> OTHER INFORMATION: n is a, c, g, or t
<220> FEATURE:
<221> NAME/KEY: misc_feature
<222> LOCATION: (211)..(265)
<223> OTHER INFORMATION: n is a, c, g, or t
<220> FEATURE:
<221> NAME/KEY: misc_feature
<222> LOCATION: (277)..(278)
<223> OTHER INFORMATION: n is a, c, g, or t

<400> SEQUENCE: 78
nnnnnnnnnn nnnnnnnnnn nnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnatgc 120
aaaaaacgaa tnnnnnnnat gtgtaaaaag aaannnnnnn nnnnnnnngt agtcaaagtt 180
acnnnnnnnn nnnnnnnnnn nnnntaatgt nnnnnnnnnn nnnnnnnnnn nnnnnnnnnn 240
nnnnnnnnnn nnnnnnnnnn nnnnnccgag gacaaannat g 281

<210> SEQ ID NO 79
<211> LENGTH: 282
<212> TYPE: DNA
<213> ORGANISM: Artificial Sequence
<220> FEATURE:
<223> OTHER INFORMATION: Generalized sequence for nirA promoter
<220> FEATURE:
<221> NAME/KEY: misc_feature
<222> LOCATION: (1)..(116)
<223> OTHER INFORMATION: n is a, c, g, or t
<220> FEATURE:
<221> NAME/KEY: misc_feature
<222> LOCATION: (132)..(138)
<223> OTHER INFORMATION: n is a, c, g, or t
<220> FEATURE:
<221> NAME/KEY: misc_feature
<222> LOCATION: (154)..(168)
<223> OTHER INFORMATION: n is a, c, g, or t
<220> FEATURE:
<221> NAME/KEY: misc_feature
<222> LOCATION: (183)..(204)
<223> OTHER INFORMATION: n is a, c, g, or t
<220> FEATURE:
<221> NAME/KEY: misc_feature
<222> LOCATION: (211)..(265)
<223> OTHER INFORMATION: n is a, c, g, or t
<220> FEATURE:
<221> NAME/KEY: misc_feature
<222> LOCATION: (278)..(279)
<223> OTHER INFORMATION: n is a, c, g, or t

<400> SEQUENCE: 79
nnnnnnnnnn nnnnnnnnnn nnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnatgc 120
aaaaaacgaa tnnnnnnnat gtgtaaaaag aaannnnnnn nnnnnnnngt agtcaaagtt 180
acnnnnnnnn nnnnnnnnnn nnnntaatgt nnnnnnnnnn nnnnnnnnnn nnnnnnnnnn 240
nnnnnnnnnn nnnnnnnnnn nnnnnggagg atcagccnna tg 282

<210> SEQ ID NO 80
<211> LENGTH: 281
<212> TYPE: DNA
<213> ORGANISM: Artificial Sequence
<220> FEATURE:

```
<223> OTHER INFORMATION: Variation on a generalized nirA promoter with
      changes to the operator region and the TATA box
<220> FEATURE:
<221> NAME/KEY: misc_feature
<222> LOCATION: (1)..(116)
<223> OTHER INFORMATION: n is a, c, g, or t
<220> FEATURE:
<221> NAME/KEY: misc_feature
<222> LOCATION: (132)..(138)
<223> OTHER INFORMATION: n is a, c, g, or t
<220> FEATURE:
<221> NAME/KEY: misc_feature
<222> LOCATION: (154)..(168)
<223> OTHER INFORMATION: n is a, c, g, or t
<220> FEATURE:
<221> NAME/KEY: misc_feature
<222> LOCATION: (183)..(204)
<223> OTHER INFORMATION: n is a, c, g, or t
<220> FEATURE:
<221> NAME/KEY: misc_feature
<222> LOCATION: (211)..(265)
<223> OTHER INFORMATION: n is a, c, g, or t
<220> FEATURE:
<221> NAME/KEY: misc_feature
<222> LOCATION: (277)..(278)
<223> OTHER INFORMATION: n is a, c, g, or t

<400> SEQUENCE: 80

nnnnnnnnnn nnnnnnnnnn nnnnnnnnnn nnnnnnnnnn nnnnnnnnnn nnnnnnnnnn     60

nnnnnnnnnn nnnnnnnnnn nnnnnnnnnn nnnnnnnnnn nnnnnnnnnn nnnnnnatgc    120

aaaaaacgca tnnnnnnnat gcgtaaaaag catnnnnnnn nnnnnnnngt aatcaaagtt    180

acnnnnnnnn nnnnnnnnnn nnnntaatat nnnnnnnnnn nnnnnnnnnn nnnnnnnnnn    240

nnnnnnnnnn nnnnnnnnnn nnnnnccgag gacaaannat g                         281


<210> SEQ ID NO 81
<211> LENGTH: 280
<212> TYPE: DNA
<213> ORGANISM: Artificial Sequence
<220> FEATURE:
<223> OTHER INFORMATION: Variation of generalized nirA promoter
<220> FEATURE:
<221> NAME/KEY: misc_feature
<222> LOCATION: (1)..(116)
<223> OTHER INFORMATION: n is a, c, g, or t
<220> FEATURE:
<221> NAME/KEY: misc_feature
<222> LOCATION: (132)..(138)
<223> OTHER INFORMATION: n is a, c, g, or t
<220> FEATURE:
<221> NAME/KEY: misc_feature
<222> LOCATION: (154)..(168)
<223> OTHER INFORMATION: n is a, c, g, or t
<220> FEATURE:
<221> NAME/KEY: misc_feature
<222> LOCATION: (183)..(204)
<223> OTHER INFORMATION: n is a, c, g, or t
<220> FEATURE:
<221> NAME/KEY: misc_feature
<222> LOCATION: (211)..(265)
<223> OTHER INFORMATION: n is a, c, g, or t
<220> FEATURE:
<221> NAME/KEY: misc_feature
<222> LOCATION: (276)..(277)
<223> OTHER INFORMATION: n is a, c, g, or t

<400> SEQUENCE: 81

nnnnnnnnnn nnnnnnnnnn nnnnnnnnnn nnnnnnnnnn nnnnnnnnnn nnnnnnnnnn     60

nnnnnnnnnn nnnnnnnnnn nnnnnnnnnn nnnnnnnnnn nnnnnnnnnn nnnnnnatgc    120

aaaaaacgca tnnnnnnnat gcgtaaaaag catnnnnnnn nnnnnnnngt aatcaaagtt    180
```

acnnnnnnnn nnnnnnnnnn nnnntaatat nnnnnnnnnn nnnnnnnnnn nnnnnnnnnn 240
nnnnnnnnnn nnnnnnnnnn nnnnnggagt cagccnnatg 280

<210> SEQ ID NO 82
<211> LENGTH: 87
<212> TYPE: DNA
<213> ORGANISM: Artificial Sequence
<220> FEATURE:
<223> OTHER INFORMATION: Generalized sequence of promoter corT
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 82
catnnnnnnn gtttactcaa aaccttgaca ttgacactaa tgttaaggtt taggctnnnn 60
nnnnnnnnnn ncaagttaaa aagcatg 87

<210> SEQ ID NO 83
<211> LENGTH: 87
<212> TYPE: DNA
<213> ORGANISM: Artificial Sequence
<220> FEATURE:
<223> OTHER INFORMATION: A generalized corT promoter sequence with changes to the ribosomal binding site
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 83
catnnnnnnn gtttactcaa aaccttgaca ttgacactaa tgttaaggtt taggctnnnn 60
nnnnnnnnnn ngaggataaa aagcatg 87

<210> SEQ ID NO 84
<211> LENGTH: 87
<212> TYPE: DNA
<213> ORGANISM: Artificial Sequence
<220> FEATURE:
<223> OTHER INFORMATION: Generalized sequence of corT promoter having changes in the TATA box
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 84
catnnnnnnn gtttactcaa aaccttgaca ttgacactaa tgttaaggtt tagaatnnnn 60
nnnnnnnnnn ncaagttaaa aagcatg 87

<210> SEQ ID NO 85
<211> LENGTH: 87
<212> TYPE: DNA
<213> ORGANISM: Artificial Sequence
<220> FEATURE:
<223> OTHER INFORMATION: A generalized corT promoter sequence with changes to the ribosomal binding site and the TATA box
<220> FEATURE:
<221> NAME/KEY: misc_feature
<222> LOCATION: (4)..(10)
<223> OTHER INFORMATION: n is a, c, g, or t
<220> FEATURE:
<221> NAME/KEY: misc_feature
<222> LOCATION: (57)..(71)
<223> OTHER INFORMATION: n is a, c, g, or t

<400> SEQUENCE: 85
catnnnnnnn gtttactcaa aaccttgaca ttgacactaa tgttaaggtt tagaatnnnn 60
nnnnnnnnnn ngaggataaa aagcatg 87

<210> SEQ ID NO 86
<211> LENGTH: 96
<212> TYPE: DNA
<213> ORGANISM: Artificial Sequence
<220> FEATURE:
<223> OTHER INFORMATION: A generalized smtA promoter sequence
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (35)..(38)
<223> OTHER INFORMATION: n is a, c, g, or t
<220> FEATURE:
<221> NAME/KEY: misc_feature
<222> LOCATION: (69)..(80)
<223> OTHER INFORMATION: n is a, c, g, or t
<220> FEATURE:
<221> NAME/KEY: misc_feature
<222> LOCATION: (87)..(93)
<223> OTHER INFORMATION: n is a, c, g, or t

<400> SEQUENCE: 86
nnnnnnnnaa tacctgaata attgttcatg tgttnnnnta aaaatgtgaa caatcgttca 60
actatttann nnnnnnnnnn ggaggtnnnn nnnatg 96

<210> SEQ ID NO 87
<211> LENGTH: 96
<212> TYPE: DNA
<213> ORGANISM: Artificial Sequence
<220> FEATURE:
<223> OTHER INFORMATION: A generalized sequence for smtA promoter having
changes in the ribosomal binding site
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (35)..(38)
<223> OTHER INFORMATION: n is a, c, g, or t
<220> FEATURE:
<221> NAME/KEY: misc_feature
<222> LOCATION: (69)..(78)
<223> OTHER INFORMATION: n is a, c, g, or t
<220> FEATURE:
<221> NAME/KEY: misc_feature
<222> LOCATION: (90)..(93)
<223> OTHER INFORMATION: n is a, c, g, or t

<400> SEQUENCE: 87
nnnnnnnnaa tacctgaata attgttcatg tgttnnnnta aaaatgtgaa caatcgttca 60
actatttann nnnnnnnnaa ggaggtgatn nnnatg 96

<210> SEQ ID NO 88

-continued

```
<211> LENGTH: 96
<212> TYPE: DNA
<213> ORGANISM: Artificial Sequence
<220> FEATURE:
<223> OTHER INFORMATION: A generalized sequence of smtA promoter having
      changes to the ribosomal binding site
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (35)..(38)
<223> OTHER INFORMATION: n is a, c, g, or t
<220> FEATURE:
<221> NAME/KEY: misc_feature
<222> LOCATION: (69)..(78)
<223> OTHER INFORMATION: n is a, c, g, or t
<220> FEATURE:
<221> NAME/KEY: misc_feature
<222> LOCATION: (89)..(93)
<223> OTHER INFORMATION: n is a, c, g, or t

<400> SEQUENCE: 88

nnnnnnnnaa tacctgaata attgttcatg tgttnnnnta aaaatgtgaa caatcgttca     60

actatttann nnnnnnnnaa ggaggtatnn nnnatg                               96
```